US007511145B2

(12) United States Patent
Schmitz et al.

(10) Patent No.: US 7,511,145 B2
(45) Date of Patent: Mar. 31, 2009

(54) BICYCLIC HETEROARYL DERIVATIVES

(75) Inventors: Franz Ulrich Schmitz, Mill Valley, CA (US); Christopher Don Roberts, Belmont, CA (US); Ronald Conrad Griffith, Escondido, CA (US); Janos Botyanszki, Fremont, CA (US); Mikail Hakan Gezginci, Foster City, CA (US); Joshua Michael Gralapp, Sunnyvale, CA (US); Dong-Fang Shi, Fremont, CA (US); Sebastian Johannes Reinhard Liehr, East Palo Alto, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 497 days.

(21) Appl. No.: 10/909,758

(22) Filed: Jul. 30, 2004

(65) Prior Publication Data

US 2005/0187390 A1    Aug. 25, 2005

Related U.S. Application Data

(60) Provisional application No. 60/492,108, filed on Aug. 1, 2003.

(51) Int. Cl.
*A61K 31/4375* (2006.01)
*C07D 401/04* (2006.01)
(52) U.S. Cl. ..................... 546/167; 514/314
(58) Field of Classification Search ................ 546/167
See application file for complete search history.

(56) References Cited

U.S. PATENT DOCUMENTS

| 3,644,382 | A | 2/1972 | Clemence et al. |
| 3,778,504 | A | 12/1973 | Clemence et al. |
| 4,250,317 | A | 2/1981 | Meyer et al. |
| 4,329,459 | A | 5/1982 | McCall |
| 4,360,679 | A | 11/1982 | Meyer et al. |
| 5,280,030 | A | 1/1994 | Jegham et al. |
| 5,434,150 | A | 7/1995 | Austel et al. |
| 5,563,143 | A | 10/1996 | Cohan et al. |
| 5,633,388 | A | 5/1997 | Diana et al. |
| 5,814,651 | A | 9/1998 | Duplantier et al. |
| 5,892,114 | A | 4/1999 | Goddmann et al. |
| 5,932,743 | A | 8/1999 | Collini et al. |
| 6,166,219 | A | 12/2000 | Yamasaki et al. |
| 6,207,679 | B1 | 3/2001 | Cuny et al. |
| 6,211,177 | B1 | 4/2001 | Sperl et al. |
| 6,310,212 | B1 | 10/2001 | Yuan et al. |
| 6,358,986 | B1 | 3/2002 | Schneider |
| 6,358,992 | B1 | 3/2002 | Pamukcu et al. |
| 6,426,344 | B2 | 7/2002 | Jones et al. |
| 6,448,281 | B1 | 9/2002 | Beaulieu et al. |
| 6,479,508 | B1 | 11/2002 | Beaulieu et al. |
| 6,605,615 | B2 | 8/2003 | Medina et al. |
| 6,670,388 | B1 | 12/2003 | Daines et al. |
| 6,730,794 | B2 | 5/2004 | Jones et al. |
| 6,770,666 | B2 | 8/2004 | Hashimoto et al. |
| 6,794,404 | B2 | 9/2004 | Beaulieu et al. |
| 6,864,265 | B2 | 3/2005 | Bridger et al. |
| 7,112,600 | B1 * | 9/2006 | Hashimoto et al. .......... 514/394 |
| 2001/0039286 | A1 | 11/2001 | Dinnell et al. |
| 2002/0151575 | A1 | 10/2002 | LaVoie et al. |
| 2002/0161022 | A1 | 10/2002 | Reich et al. |
| 2003/0018053 | A1 | 1/2003 | Jones et al. |
| 2003/0050320 | A1 | 3/2003 | Hashimoto et al. |
| 2003/0130331 | A1 | 7/2003 | Donsbach et al. |
| 2003/0171353 | A1 | 9/2003 | Cole et al. |
| 2004/0077851 | A1 | 4/2004 | Makriyannis et al. |
| 2004/0082635 | A1 | 4/2004 | Hashimoto et al. |
| 2004/0082637 | A1 | 4/2004 | LaVoie et al. |
| 2004/0097438 | A1 | 5/2004 | Hashimoto et al. |
| 2004/0147759 | A1 | 7/2004 | Hofgen et al. |
| 2004/0224955 | A1 | 11/2004 | Beaulieu et al. |
| 2005/0009894 | A1 | 1/2005 | Babin et al. |
| 2005/0014810 | A1 | 1/2005 | Streicher et al. |
| 2005/0020654 | A1 | 1/2005 | Pershadsingh et al. |
| 2005/0038022 | A1 | 2/2005 | Morris et al. |
| 2005/0038095 | A1 | 2/2005 | Farina et al. |
| 2005/0075331 | A1 | 4/2005 | Pratt et al. |
| 2005/0075334 | A1 | 4/2005 | King et al. |

FOREIGN PATENT DOCUMENTS

| CA | 2115737 | 8/1994 |
| CA | 2363274 | 7/2001 |
| CA | 2 423 800 B2 | 3/2003 |
| DE | 4304650 | 8/1994 |
| EP | 0010063 | 12/1982 |
| EP | 0 694 535 | 1/1996 |

(Continued)

OTHER PUBLICATIONS

Giangaspero, et al. "Serological and antigenical findings indicating pestivirus in man" *Arch. Virol. Suppl.*, 7:53-62 (1993).
Giangaspero, et al. "Anti-bovine viral diarrhea virus antibodies in adult Zambian patients infected with the human immunodeficiency virus" *Int. J. STD. AIDS*, 4(5):300-302 (1993).
Yolken, "Infantile Gastroenteritis Associated with Excretion of Pestivirus Antigens" et al., *Lancet*, 1(8637):517-520 (1989).
Wilks, et al. "Bovine Pestivirus and Human Infection" *Lancet* 1(8629):107 (1989).
Giangaspero, et al. "Bovine Viral Diarrhoea" *Lancet*, 2:110 (1988).
Potts, et al. "Possible Role of Pestiviruses in Microcephaly" *Lancet*, 1(8539):972-973 (1987).
Comberg, et al. "Heptatiis C: therapeutic perspectives." *Forum (Genova)*, 11(2):154-162 (2001).
Dymock, et al. Novel approaches to the treatment of hepatitis C virus infection: *Antivir. chem. Chemother.* 11(2):79-96 (2000).

(Continued)

*Primary Examiner*—Laura L Stockton
(74) *Attorney, Agent, or Firm*—Foley & Lardner LLP; Junrui Yang

(57) ABSTRACT

Disclosed are compounds, compositions and methods for treating Flaviviridae family virus infections.

11 Claims, No Drawings

FOREIGN PATENT DOCUMENTS

| | | |
|---|---|---|
| EP | 0507650 | 5/1996 |
| JP | 03-031264 | 2/1991 |
| WO | WO 96/35713 | 11/1996 |
| WO | WO 97/25316 | 7/1997 |
| WO | WO 97/36866 | 10/1997 |
| WO | WO 97/46237 | 12/1997 |
| WO | WO 99/09007 | 2/1999 |
| WO | WO 99/51619 | 10/1999 |
| WO | WO 01/21634 | 3/2001 |
| WO | WO 01/90121 | 5/2001 |
| WO | WO 01/47883 | 7/2001 |
| WO | WO 02/04425 B1 | 1/2002 |
| WO | WO 02/18404 | 3/2002 |
| WO | WO 02/051837 | 7/2002 |
| WO | WO 02/057287 | 7/2002 |
| WO | WO 02/057425 | 7/2002 |
| WO | WO 03/000254 | 1/2003 |
| WO | WO 03/007945 | 1/2003 |
| WO | WO 03/010140 | 2/2003 |
| WO | WO 03/010141 | 2/2003 |
| WO | WO 03/014377 | 2/2003 |
| WO | WO 03/024899 | 3/2003 |
| WO | WO 03/026587 | 4/2003 |
| WO | WO 03/053938 | 7/2003 |
| WO | WO 03/101993 | 12/2003 |
| WO | WO 2004/005286 | 1/2004 |
| WO | WO 2004/064925 | 8/2004 |
| WO | WO 2004/065367 | 8/2004 |
| WO | WO 2004/087714 | 10/2004 |
| WO | WO 2004/098494 | 11/2004 |
| WO | WO 2004/099241 | 11/2004 |
| WO | WO 2005/012288 | 2/2005 |
| WO | WO 2005/014543 | 2/2005 |
| WO | WO 2005/023819 | 3/2005 |
| WO | WO 2005/034941 | 4/2005 |

OTHER PUBLICATIONS

Herr, R. Jason "5-Substituted-1$H$-tetrazoles as carboxylic Acid Isosteres: Medicinal Chemistry and Synthetic Methods" *Biorg. Med. Chem.* 10:3379-3393 (2002).

Andersen, K.E., et al. "Oxadiazoles as bioisosteric transformations of carboxylic functionalities II" *Eur. J. Med. Chem* 31:417-425 (1996).

Thornber, C. W. "Isosterism and Molecular Modification in Drug Design" *Chem. Soc. Rev.I* 8:563-580 (1979).

Lipinski, Christopher A. "Bioisosterism in Drug Design" *Annual reports in Med. Chem.* 12:283-297 (1986).

Wissner et al. "Prostaglandins and Congeners. 25. Inhibition of Gastric Acid Secretion. Replacement of the Carboxylate Moiety of a Prostaglandin with a Hydroxymethylketo Functional Group" *J. Med. Chem.* 23:715-717 (1980).

Patani et al. "Bioisosterism: A Rational Approach in Drug Design" *Chem. Rev.* 96:3147-3176 (1996).

Beaulieu, P.L., et al., "A practical Oxone-mediated, high-throughput, solution-phase synthesis of benzimidazoles from 1,2-phenylenediamines and aldehydes and its application to preparative scale synthesis" Synthesis 11:1683-1692 (2003).

Haskell, T.H., et al, "Neuraminidase inhibition and viral chemotherapy" J. Med. Chem. 15(4):697-704 (1970).

Hori, M., et al, "Design and syntheses of a series of novel serotonin$_3$ antagonists" Chem. Pharm. Bull. 41(10): 1832-1841 (1993).

Kataev, V.A., et al, "Synthesis and immunostimulating activity of 1-(thietan-3-yl)benzimidazoles" Pharmaceutical Chemistry Journal, 30(7):448-450 (1996), and equivalent article in Russian.

Von Angerer, E., "2-Phenylindoles. Effect of N-benzylation on estrogen receptor affinity, estrogenic properties, and mammary tumor inhibiting activity" J. Med. Chem., 30:131-136 (1987).

Zhang, H.-C., et al, "Efficient synthesis of 3-substituted 2-arylindoles via Suzuki coupling reactions on the solid phase" Tet. Lett. 42:4751-4754 (2001).

\* cited by examiner

BICYCLIC HETEROARYL DERIVATIVES

CROSS-REFERENCE TO RELATED APPLICATIONS

This application claims the benefit under 35 U.S.C. § 119 (e) of U.S. Provisional Application Ser. No. 60/492,108 which application is incorporated herein by reference in its entirety.

BACKGROUND OF THE INVENTION

1. Field of the Invention

The invention relates to the field of pharmaceutical chemistry, in particular to compounds, compositions and methods for treating viral infections in mammals mediated, at least in part, by a virus in the Flaviviridae family of viruses.

REFERENCES

The following publications are cited in this application as superscript numbers:
1. Giangaspero, et al., Arch. Virol. Suppl., 7: 53-62 (1993);
2. Giangaspero, et al., Int. J. STD. AIDS, 4(5): 300-302 (1993);
3. Yolken, et al., Lancet, 1(8637): 517-20 (1989);
4. Wilks, et al., Lancet, 1(8629): 107 (1989);
5. Giangaspero, et al., Lancet, 2: 110 (1988);
6. Potts, et al., Lancet, 1(8539): 972-973 (1987);
7. Cornberg, et al., "Hepatitis C: therapeutic perspectives." Forum (Genova), 11(2):154-62 (2001);
8. Dymock, et al., Antivir. Chem. Chemother. 11(2):79-96 (2000);
9. Devos, et al., International Patent Application Publication No. WO 02/18404 A2, published 7 Mar., 2002;
10. Sommadossi, et al., International Patent Application Publication No. WO 01/90121, published 23 May, 2001;
11. Carroll, S. S., et al., International Patent Application Publication No. WO 02057287, published 25 Jul., 2002;
12. Carroll, S. S., et al., International Patent Application Publication No. WO 02057425, published 25 Jul., 2002;
13. Herr, J. R., Bioorg. Med. Chem., 10: 3379-3393 (2002);
14. Andersen, K. E. et al., Eur. J. Med. Chem, 31: 417-425 (1996);
15. Thomber, C. W. Chem. Soc. Rev. 8: 563-580 (1979);
16. Lipinski, C. A. Annual Reports in Med. Chem. 21: 283-297 (1986);
17. Wissner, A. et al., J. Med. Chem. 23: 715-717 (1980);
18. Patani, G. A. et al., Chem. Rev. 96: 3147-3176 (1996).

All of the above publications applications are herein incorporated by reference in their entirety to the same extent as if each individual publication was specifically and individually indicated to be incorporated by reference in its entirety.

2. State of the Art

The Flaviviridae family of viruses is composed of three genera: pestivirus, flavivirus and hepacivirus (hepatitis C virus). Of these genera, flaviviruses and hepaciviruses represent important pathogens of man and are prevalent throughout the world. There are 38 flaviviruses associated with human disease, including the dengue fever viruses, yellow fever virus and Japanese encephalitis virus. Flaviviruses cause a range of acute febrile illnesses and encephalitic and hemorrhagic diseases. Hepaciviruses currently infect approximately 2 to 3% of the world population and cause persistent infections leading to chronic liver disease, cirrhosis, hepatocellular carcinoma and liver failure. Human pestiviruses have not been as extensively characterized as the animal pestiviruses. However, serological surveys indicate considerable pestivirus exposure in humans. Pestivirus infections in man have been implicated in several diseases including, but not likely limited to, congenital brain injury, infantile gastroenteritis and chronic diarrhea in human immunodeficiency virus (HIV) positive patients.[1-6]

Currently, there are no antiviral pharmaceutical drugs to prevent or treat pestivirus or flavivirus infections. For hepacivirus, i.e., hepatitis C virus (HCV) infections, interferon alpha (IFN) is currently the only approved drug in the United States. HCV is a major causative agent for post-transfusion and for sporadic non-A, non-B hepatitis. Infection by HCV is insidious in a high proportion of chronically infected (and infectious) carriers who may not experience clinical symptoms for many years.

At present, the only acceptable treatment for chronic HCV is interferon (IFN-alpha) and this requires at least six (6) months of treatment and/or ribavirin, which can inhibit viral replication in infected cells and also improve liver function in some people.

IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon, however, has limited long term efficacy with a response rate about 25%. In addition, treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Ribavirin (1-β-D-ribofuranosyl-1H-1,2,-4-triazole-3-carboxamide), an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of PEG-IFN plus ribavirin. However, a number of patients still have significant side effects, primarily related to ribaviran. Ribavirin causes significant hemolysis in 10-20% of patients treated at currently recommended doses, and the drug is both teratogenic and embryotoxic.

Other approaches are being taken to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. NS3/4A serine protease, ribonucleic acid (RNA) helicase, RNA-dependent RNA polymerase are considered as potential targets for new drugs.[7,8]

Devos, et al.[9] describes purine and pyrimidine nucleoside derivatives and their use as inhibitors of HCV RNA replication. Sommadossi, et al.[10] describes 1', 2' or 3'-modified nucleosides and their use for treating a host infected with HCV. Carroll, et al.[11,12], describes nucleosides as inhibitors of RNA-dependent RNA viral polymerase. Given the fact of the worldwide epidemic level of HCV and other members of the Flaviviridae family of viruses, there is a strong need for new effective drugs for treatment of Flaviviridae family viruses. The present invention provides compounds for treating such infections.

SUMMARY OF THE INVENTION

This invention is directed to novel compounds that are useful in the treatment of viral infections in mammals mediated at least in part by a member of the Flaviviridae family viruses such as HCV. Specifically, the compounds of this invention are represented by formula I:

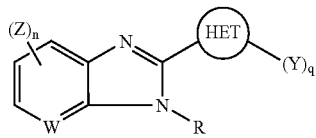

wherein:
W is CH or N;
R is selected from the group consisting of hydrogen, ($C_1$-$C_{10}$)alkyl, substituted ($C_1$-$C_{10}$)alkyl, ($C_3$-$C_{10}$)cycloalkyl, substituted ($C_3$-$C_{10}$)cycloalkyl, ($C_2$-$C_{10}$)alkenyl, substituted ($C_2$-$C_{10}$)alkenyl, ($C_2$-$C_{10}$)alkynyl, substituted ($C_2$-$C_{10}$)alkynyl, heterocyclic, substituted heterocyclic, aryl, substituted aryl, heteroaryl, substituted heteroaryl, and —$NR^{12}R^{13}$,
where each of $R^{12}$ and $R^{13}$ is independently selected from the group consisting of ($C_1$-$C_{10}$)alkyl, substituted ($C_1$-$C_{10}$)alkyl, ($C_3$-$C_{10}$)cycloalkyl, substituted ($C_3$-$C_{10}$)cycloalkyl, ($C_2$-$C_{10}$)alkenyl, substituted ($C_2$-$C_{10}$)alkenyl, ($C_2$-$C_{10}$)alkynyl, substituted ($C_2$-$C_{10}$)alkynyl, heterocyclic, substituted heterocyclic, aryl, substituted aryl, heteroaryl, and substituted heteroaryl; or $R^{12}$ and $R^{13}$ may optionally be joined together with the nitrogen atom bound thereto to form a heterocyclic, substituted heterocyclic, heteroaryl or substituted heteroaryl;
Z is selected from the group consisting of
a) —C(=O)$OR^7$, wherein $R^7$ is selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic;
b) —C(=O)$NR^8R^9$, wherein $R^8$ and $R^9$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocycle or, alternatively, $R^8$ and $R^9$ together with the nitrogen atom pendent thereto, form a heterocyclic, a substituted heterocyclic, a heteroaryl or a substituted heteroaryl ring group;
c) tetrazolyl or —C(O)NHS(O)$_2R^4$, wherein $R^4$ is selected from the group consisting of alkyl, substituted alkyl, aryl, substituted aryl, heteroaryl, substituted heteroaryl, heterocyclic and substituted heterocyclic;
d) —C(X)—N($R^3$)$CR^2R^{2'}$C(=O)$R^1$, wherein X is selected from the group consisting of =O, =S, and =$NR^{11}$, where $R^{11}$ is hydrogen or alkyl, $R^1$ is selected from the group consisting of —$OR^7$ and —$NR^8R^9$; wherein $R^7$, $R^8$ and $R^9$ are as defined above;
each $R^2$ and $R^{2'}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic,
or, alternatively, $R^2$ and $R^{2'}$ as defined are taken together with the carbon atom pendent thereto to form a cycloalkyl, substituted cycloalkyl, heterocyclic or substituted heterocyclic group,
or, still further alternatively, one or $R^2$ or $R^{2'}$ is hydrogen, alkyl or substituted alkyl, and the other is joined, together with the carbon atom pendent thereto, with either the $R^7$ and the oxygen atom pendent thereto or $R^8$ and the nitrogen atom pendent thereto to form a heterocyclic or substituted heterocyclic group;
$R^3$ is selected from the group consisting of hydrogen and alkyl or, when $R^2$ and $R^{2'}$ are not taken together to form a ring and when $R^2/R^{2'}$ and $R^7$ or $R^8$ are not joined to form a heterocyclic or substituted heterocyclic group, then $R^3$, together with the nitrogen atom pendent thereto, may be taken together with one of $R^2$ or $R^{2'}$ to form a heterocyclic or substituted heterocyclic ring group;
HET is a fused 6,6-bicycle provided by the fused linkage of any two 6-membered rings selected from aryl, cycloalkyl, cycloalkenyl, heterocyclic, or heteroaryl rings that are optionally substituted with (Y)$_q$; with the proviso that at least one 6-membered ring in the bicycle is heterocyclic or heteroaryl or the bicycle is naphthyl;
each Y is independently selected from the group consisting of halo, cyano, nitro, ($C_1$-$C_{10}$)alkyl, substituted ($C_1$-$C_{10}$)alkyl, acyl, acyloxy, guanidino, substituted guanidino, oxycarbonylamino, aminocarbonyloxy, aminocarbonylamino, oxycarbonyloxy, ($C_3$-$C_{10}$)cycloalkyl, substituted ($C_3$-$C_{10}$)cycloalkyl, ($C_2$-$C_{10}$)alkenyl, substituted ($C_2$-$C_{10}$)alkenyl, ($C_2$-$C_{10}$)alkynyl, substituted ($C_2$-$C_{10}$)alkynyl, heterocyclic, substituted heterocyclic, aryl, substituted aryl, heteroaryl, substituted heteroaryl, —$CO_2R^7$, —$NR^{14}R^{15}$, —$NHNR^{14}R^{15}$, —C(X)$NR^{14}R^{15}$, —$OR^{14}$, $SR^{14}$, —S(O)$R^{14}$, —S(O)$_2R^{14}$, and —S(O)$_2NR^{14}R^{15}$; where X is as defined above;
where $R^7$ is as defined above and each of $R^{14}$ and $R^{15}$ is independently selected from the group consisting of hydrogen, ($C_1$-$C_{10}$)alkyl, substituted ($C_1$-$C_{10}$)alkyl, ($C_3$-$C_{10}$)cycloalkyl, substituted ($C_3$-$C_{10}$)cycloalkyl, ($C_2$-$C_{10}$)alkenyl, substituted ($C_2$-$C_{10}$)alkenyl, ($C_2$-$C_{10}$)alkynyl, substituted ($C_2$-$C_{10}$)alkynyl, heterocyclic, substituted heterocyclic, aryl, substituted aryl, heteroaryl, and substituted heteroaryl; or $R^{14}$ and $R^{15}$ may optionally be joined together with the nitrogen atom bound thereto to form a heterocyclic, substituted heterocyclic, heteroaryl or substituted heteroaryl;
n is an integer equal to 0, 1 or 2;
q is an integer equal to 1, 2 or 3;
and pharmaceutically acceptable salts or tautomers thereof.

In one preferred embodiment, n is zero (i.e., Z=hydrogen).
In another preferred embodiment, n is one or two; more preferably, n is one.
When n is not zero, preferred Z groups fall into several embodiments. For example, in one preferred embodiment, Z is 1H-tetrazol-5-yl or —$COOR^7$ where $R^7$ is as defined above. In a particularly preferred aspect of this embodiment, Z is selected from the group consisting of 1H-tetrazol-5-yl, —C(=O)OH, and —C(=O)OR" where R" is ($C_1$-$C_6$)alkyl and especially ($C_1$-$C_2$)alkyl. Further with regard to this embodiment, Z is most preferably —C(=O)OH.
In another preferred embodiment, Z is —C(=O)$NR^8R^9$ where $R^8$ and $R^9$ are as defined above. In one particularly preferred aspect of this embodiment, $R^8$ is hydrogen and $R^9$ is as defined above. Even more preferably, in this aspect, $R^9$ is selected from the group consisting of alkyl, substituted alkyl, aryl, substituted aryl, heteroaryl, substituted heteroaryl, heterocyclic and substituted heterocyclic.

Preferred $R^9$ substituted alkyl groups comprise 1 to 2 substituents selected from the group consisting of sulfonic acid, carboxy and carboxy ester. Particularly preferred $R^9$ substituted alkyl groups include, by way of example, —$CH_2CH_2SO_3H$ and —$CH_2CH_2COOH$.

Preferred $R^9$ aryl and substituted aryl groups include, for example, 7-hydroxynaphth-1-yl, 6-hydroxynaphth-1-yl, 5-hydroxynaphth-1-yl, 4-methyl-2-oxo-2H-chromen-7yl, 6-carboxynaphth-2-yl, (4-HOOCCH$_2$-)phenyl, (3,4-dicarboxy)phenyl, 3-carboxyphenyl, 3-carboxy-4-hydroxyphenyl, 2-carboxy-naphthen-6-yl, (4-carboxymethyl)phenyl, (3,4-dicarboxy)phenyl, 4-hydroxy-3-carboxyphenyl and 3-carboxyphenyl.

Preferred $R^9$ heteroaryl and substituted heteroaryl groups include, for example, 1-phenyl-4-carboxy-1H-pyrazol-5-yl, 5-carboxypyrid-2-yl, 2-carboxypyrazin-3-yl, and 3-carboxythien-2-yl.

In Another preferred embodiement, $R^9$ is heterocyclic, more preferably, N-morpholino.

In another particularly preferred aspect of this embodiment, $R^8$ and $R^9$, together with the nitrogen atom pendent thereto, form a heterocyclic or substituted heterocyclic ring. Preferred heterocyclic and substituted heterocyclic rings include 4 to 8 membered rings containing 1 to 3 heteroatoms and particularly 1 to 2 nitrogen atoms including, for example, piperidine, substituted piperidine, piperazine, substituted piperazine, morpholino, substituted morpholino, thiomorpholino and substituted thiomorpholino wherein the sulfur atom of the thiomorpholino or substituted thiomorpholino ring is optionally oxidized to provide for sulfoxide and sulfones. Particularly preferred heterocyclic and substituted heterocyclic groups include, by way of example, 4-hydroxypiperidin-1-yl, 1,2,3,4-tetrahydro-3-carboxy-isoquinolin-2-yl, 4-methylpiperizin-1-yl, morpholin-4-yl, and thiomorpholin-4-yl.

In still another preferred embodiment, Z is —C(X)—N($R^3$)—$CR^2R^{2'}$—C(=O)$R^1$.

In one aspect of this embodiment, Z is —C(O)NHCH$R^2$C(=O)$R^1$. In this aspect, preferred $R^2$ groups include hydrogen, alkyl, substituted alkyl, cycloalkyl, substituted cycloalkyl, aryl, substituted aryl, heteroaryl and substituted heteroaryl. Particularly preferred $R^2$ groups include hydrogen, alkyl, substituted alkyl, and cycloalkyl including, for example, hydrogen, methyl, 1-methylprop-1-yl, sec-butyl, hydroxymethyl, 1-hydroxyeth-1-yl, 4-amino-n-butyl, 2-carboxyeth-1-yl, carboxymethyl, benzyl, (1H-imidazol-4-yl)methyl, (4-phenyl)benzyl, (4-phenylcarbonyl)benzyl, cyclohexylmethyl, cyclohexyl, 5-hydroxy-1H-indol-3-yl, 2-methylthioeth-1-yl, iso-propyl, carbamoylmethyl, 2-carbamoyleth-1-yl, (4-hydroxy)benzyl and 3-guanidino-n-propyl.

In this aspect, preferred R1 groups include, for example, hydroxy, amino, and amino(N-morpholino).

In another aspect of the above embodiment, Z is —C(O)N($R^3$)CH$R^2$C(=O)$R^1$ where $R^2$ and $R^3$, together with the carbon atom and nitrogen atom bound thereto respectively, are joined to form a heterocyclic or substituted heterocyclic group. In this aspect, preferred heterocyclic and substituted heterocyclic groups include, by way of example, pyrrolidinyl, 2-carboxypyrrolidinyl, 2-carboxy-4-hydroxypyrrolidinyl, and 3-carboxy-1,2,3,4-tetrahydroisoquinolin-3-yl.

In still another preferred embodiment, Z is —C(O)NHS(O)$_2R^4$. In this preferred aspect, $R^4$ is preferably alkyl, substituted alkyl, aryl and substituted aryl. More preferably, $R^4$ is exemplified by methyl, trifluoromethyl, phenyl, 4-bromophenyl, 4-nitrophenyl or 4-methylphenyl.

In another preferred embodiment, Z is a carboxylic acid isostere such as those recited in references 13 to 18 as listed: Herr, J. R., Bioorg. Med. Chem., 10: 3379-3393 (2002)[13]; Andersen, K. E. et al., Eur. J. Med. Chem, 31: 417-425 (1996)[14]; Thornber, C. W. Chem. Soc. Rev. 8: 563-580 (1979)[15]; Lipinski, C. A. Annual Reports in Med. Chem. 21: 283-297 (1986)[16]; Wissner, A. et al., J. Med. Chem. 23: 715-717 (1980)[17]; and, Patani, G. A. et al., Chem. Rev. 96: 3147-3176 (1996)[18].

In another preferred embodiment, R is selected from the group consisting of hydrogen, ($C_1$-$C_{10}$)alkyl, substituted ($C_1$-$C_{10}$)alkyl, ($C_3$-$C_{10}$)cycloalkyl, -substituted ($C_3$-$C_{10}$)cycloalkyl, ($C_2$-$C_{10}$)alkenyl, substituted ($C_2$-$C_{10}$)alkenyl, ($C_2$-$C_{10}$)alkynyl, substituted ($C_2$-$C_{10}$)alkynyl, heterocyclic, substituted heterocyclic, aryl, substituted aryl, heteroaryl, and substituted heteroaryl.

Particularly preferred R groups include hydrogen, alkyl, substituted alkyl, cycloalkyl and substituted cycloalkyl which are exemplified by, for example, hydrogen, ethyl, iso-propyl, sec-butyl, 3-methyl-n-butyl, cyclopropyl, cyclopentyl, cyclohexyl, cyclopropylmethyl, 2-(N,N-dimethylamino)eth-1-yl. Most preferably, R is cyclohexyl.

In one embodiment, W is N. Preferably, however, W is CH.

In one preferred embodiment, the HET group is a fused bicyclic nitrogen-containing heterocyclic or heteroaryl ring. More preferably, the HET group contains a total of 1 to 4 nitrogen ring atoms in one or both ring groups and optionally 1 to 2 hetero ring atoms selected from the group consisting of —O—, —S—, —S(O)— and —S(O)$_2$— again, in one or both ring groups. Preferably, there are no more than 3 nitrogen ring atoms in any one of the fused rings and, even more preferably, there are no more than 2 nitrogen ring atoms in any one of the fused rings.

In a particularly preferred aspect of this embodiment, the HET group is selected from the group consisting of quinolinyl, isoquinolinyl, quinoxalinyl, quinazolinyl, pteridinyl, cinnolinyl, [1,8]naphthyridinyl, [1,5]naphthyridinyl, 1,2,3,4-tetrahydroquinolinyl, 1,2,3,4-tetrahydroisoquinolinyl, 1,4-dioxo-1,4-dihydrophthalazinyl, 4-oxo-1,4-dihydroquinolinyl, 4-oxo-1,4-dihydroquinazolinyl, 1,1-dioxo-1,4-dihydro-1λ6-benzo[1,2,4]thiadiazinyl, and 1,4-dihydroisoquinolinyl which groups are exemplified by, for example, quinolin-6-yl, isoquinolin-6-yl, quinolin-7-yl, quinoxalin-6-yl, quinazolin-7-yl, pteridin-6-yl, cinnolin-3-yl, [1,8]naphthyridin-3-yl, [1,5]naphthyridin-2-yl, 1,2,3,4-tetrahydroquinolin-6-yl, 1,4-dioxo-1,4-dihydrophthalazin-6-yl, 4-oxo-1,4-dihydroquinolin-6-yl, 4-oxo-1,4-dihydroquinazolin-6-yl, 1,1-dioxo-1,4-dihydro-1λ6-benzo[1,2,4]thiadiazin-7-yl, and 1,4-dihydroisoquinolin-6-yl.

In another preferred embodiment, the heterocyclic or heteroaryl ring of the HET group is an oxygen-containing heterocyclic or heteroaryl ring. Preferably, the HET group contains 1 to 2 oxygen ring atoms and optionally 1 to 2 hetero ring atoms selected from the group consisting of —S—, —S(O)— and —S(O)$_2$—.

In a particularly preferred aspect of this embodiment, the HET group is selected from the group consisting of 2-oxo-2H-chromenyl, 4-oxo-2H-chromenyl, and 4-oxo-4H-chromen-6-yl which groups are exemplified, for example, by 2-oxo-2H-chromen-7-yl, 4-oxo-2H-chromen-6-yl, 4-oxo-2H-chromen-7-yl, and 4-oxo-4H-chromen-6-yl.

In another particularly preferred embodiment, the HET group is naphthyl.

Preferably, Y is selected from the group consisting of ($C_1$-$C_{10}$)alkyl, substituted ($C_1$-$C_{10}$)alkyl, amino, substituted amino, aryl, substituted aryl, cycloalkyl, substituted cycloalkyl, halo, heteroaryl, substituted heteroaryl, substituted heterocyclic, —C(O)NR$^{14}$R$^{15}$, —OR$^{14}$, and —SR$^{14}$.

One set of preferred Y groups, for example, amino substituted amino (hydrazine) and mono- and disubstituted amino groups. Mono-substituted amino groups include alkylamino, substituted alkylamino, arylamino, substituted arylamino. Disubstituted amino groups include substituents independently selected from alkyl, substituted alkyl, aryl and substituted aryl groups. Examples of preferred amino Y groups include, for instance, amino, phenylamino, [2-(t-butoxycarbonylaminoethyl]amino, N-(4-chlorophenyl)amino, N,N-dimethylamino, 4-hydroxybutylamino, 3-imidazol-1-yl-propylamino, and hydrazino.

Another set of preferred Y groups include ($C_1$-$C_{10}$) alkyl, substituted ($C_1$-$C_{10}$) alkyl, cycloalkyl, and substituted cycloalkyl. Preferred substituents for substituted ($C_1$-$C_{10}$) alkyl Y groups include, for example, hydroxy, amino, substituted amino, aryl, substituted aryl, heteroaryl and substituted heteroaryl. Preferred substituents for substituted cycloalkyl include, for example, carboxymethyl and methyl. Examples of preferred alkyl, substituted alkyl and substituted cycloalkyl Y groups include, for instance, methyl, 3-hydroxypropyl, (N,N-di-n-propyl)aminomethyl, diphenylmethyl (benzhydryl), and 2-(pyrazol-1-yl)eth-1-yl and 3-carboxymethyl-2,2-dimethylcyclobutyl.

Another set of preferred Y groups include carboxy, carboxy esters, halo (particularly fluoro), cyano, and nitro.

Another set of preferred Y groups include —C(O)NR$^{14}$R$^{15}$ where each of R$^{14}$ and R$^{15}$ is independently selected from the group consisting of hydrogen, alkyl, substituted alkyl, aryl and substituted aryl or where R$^{14}$ and R$^{15}$, together with the nitrogen atom pendent thereto, form a heterocyclic and substituted heterocyclic group. Preferred substituents on the substituted alkyl and substituted aryl include, for example, halo, hydroxy, carbamoyl, and the like. These preferred Y groups are exemplified by, for instance, 1-carbamoylethyl-carbamoyl, 1-carbamoyl-2-(1H-imidazol-2-yl)ethylcarbamoyl, 1-carbamoyl-2-hydroxyethylcarbamoyl, 1-carbamoyl-2-methylpropylcarbamoyl, 4-chlorophenylcarbamoyl, and pyrrolidin-1-ylcarbonyl.

Another set of preferred Y groups include aryl groups which are exemplified by, for instance, phenyl, naphthalen-1-yl, and 5,6,7,8-tetrahydronaphthalen-2-yl.

Another set of preferred Y groups include substituted aryl. In one embodiment, the substituted aryls are substituted with non-aryl groups. In another embodiment, the substituted aryl is substituted with an aryl or substituted aryl to form, e.g., a biphenyl group.

Preferred substituents for substituted aryl Y groups include, for example, acylamino, amino, substituted amino, alkyl, substituted alkyl, alkoxy, substituted alkoxy, aryl, substituted aryl, aryloxy, substituted aryloxy, cycloalkyl, substituted cycloalkyl, halo, heterocyclic, substituted heterocyclic, heteroaryl, substituted heteroaryl, hydroxy, nitro and —C(O)NR$^{14}$R$^{15}$ where each of R$^{14}$ and R$^{15}$ is independently selected from the group consisting of hydrogen, alkyl, substituted alkyl, aryl and substituted aryl or where R$^{14}$ and R$^{15}$, together with the nitrogen atom pendent thereto, form a heterocyclic and substituted heterocyclic group.

Substituted aryl Y groups which are not substituted by an aryl or substituted aryl group are, for example, 4-acetylaminophenyl, 4-aminophenyl, 4-amino-3-bromophenyl, 4-amino-3,5-dichlorophenyl, 4-benzyloxy-2-hydroxy-3-methylphenyl, 2-bromophenyl, 3-bromophenyl, 4-bromophenyl, 5-bromo-2-hydroxyphenyl, 3-carbamoyl-4-hydroxyphenyl, 3-carboxymethoxyphenyl, 2-cyclohexyl-5-methoxyphenyl, 3,4-dichlorophenyl, 2,4-dihydroxyphenyl, 3,5-dihydroxyphenyl, 4-(N,N-dimethylamino)phenyl, 4-fluorophenyl, 2-furan-2-yl-5-methoxyphenyl, 3-hydroxyphenyl, 2-hydroxy-4-,6-dimethoxyphenyl, 2-hydroxynaphthalen-1-yl, 2-hydroxy-6-methoxyphenyl, 2-hydroxy-5-methyl-3-nitrophenyl, 4-(imidazol-1-yl)phenyl, 3-(2-methoxyethoxy)phenyl, 2-methoxy-5-nitrophenyl, 3-methoxyphenyl, 4-methoxyphenyl, 5-methoxy-2-thiophen-2-ylphenyl, 4-methylphenyl, 4-morpholinophenyl, 6-methylnaphthalen-2-yl, 2-nitrophenyl, 3-(2-oxo-2-pyrrolidin-1-ylethoxy)phenyl, 4-phenoxyphenyl, (4-piperazin-1-yl)phenyl, 3-[pyrrolidin-1-ylcarbonyl]-phenyl, 3-[3-(pyrrolidin-1-yl)propoxy)]phenyl. 2-(2,4-dimethoxypyrimidin-5-yl)-4-methoxyphenyl, and 2-(pyrid-4-yl)phenyl.

Substituted aryl Y groups which are substituted by an aryl or substituted aryl group are exemplified, for example, by biphen-2-yl, biphen-4-yl, 4-amino-4'-chlorobiphen-2-yl, 4'-aminomethyl-4-methoxybiphen-2-yl, 4-carbamoyl-4'-methoxybiphen-2-yl, 4-carbamoyl-4'-fluorobiphen-2-yl, 4-carbamoyl-4'-methoxybiphen-2-yl, 4-carbamoyl-4'-nitro-biphen-2-yl, 4-(carbamoylmethylcarbamoyl)biphen-2-yl, 4-(carbamoylmethylcarbamoyl)-4'-chlorobiphen-2-yl, 4-carboxy-4'-chlorobiphen-2-yl, 3-carboxy-4'-methoxybiphen-2-yl, 4-carboxy-4'-methoxybiphen-2-yl, 4'-carboxy-4-(pyrrolidin-1-ylcarbonyl)biphen-2-yl, 4-carboxymethoxybiphen-2-yl, 4-carboxymethoxy-4'-chlorobiphen-2-yl, 4'-chlorobiphen-2-yl, 4'-chloro-4-chlorobiphen-2-yl, 4'-chloro-4-(dimethylaminoethylcarbamoylbiphen-2-yl, 4'-chloro-4-(2-ethoxyethoxy)biphen-2-yl, 3'-chloro-4'-fluoro-4-methoxybiphen-2-yl, 4'-chloro-4-fluorobiphen-2-yl, 4'-chloro-4-hydroxybiphen-2-yl, 3'-chloro-4-methoxybiphen-2-yl, 4'-chloro-4-methylcarbamoylbiphen-2-yl, 4'-chloro-4-methoxybiphen-2-yl, 4'-chloro-4-(2-methoxyethoxy)biphen-2-yl, 4'-chloro-4-nitrobiphen-2-yl, 4'-chloro-4-(2-oxo-2-pyrrolidin-1-ylethoxy)biphen-2-yl, 4'-chloro-4-(pyrrolidin-1-ylcarbonyl)biphen-2-yl, 4'-chloro-4-(3-pyrrolidin-1-ylpropoxy)biphen-2-yl, 4'-cyano-4-methoxybiphen-2-yl, 3',4'-dichloro-4-methoxybiphen-2-yl, 4,4'-dimethoxybiphen-2-yl, 3',4'-dimethoxy-4-(pyrrolidin-1-ylcarbonyl)biphen-2-yl, 4'-dimethylamino-4-methoxybiphen-2-yl, 4-(2-dimethylaminoethylcarbamoyl)biphen-2-yl, 4'-ethoxy-4-methoxybiphen-2-yl, 4'-fluoro-4-methoxybiphen-2-yl, 4-hydroxybiphenyl, 4-methoxybiphenyl, 4-methoxy-4'-hydroxybiphen-2-yl, 4-(2-methoxyethoxy)biphen-2-yl, 4-methoxy-4'-methylbiphen-2-yl, 4-methoxy-3'-nitrobiphen-2-yl, 4-methoxy-4'-nitrobiphen-2-yl, 4-methylcarbamoylbiphen-2-yl, 3'-methyl-4-methoxybiphen-2-yl, 4'-nitro-4-(pyrrolidin-1-ylcarbonyl)biphen-2-yl, 4-(2-oxo-2-pyrrolidin-1-ylethoxy)biphen-2-yl, 4-(3-pyrrolidin-1-ylpropoxy)biphen-2-yl, and 4'-trifluoromethyl-4-methoxybiphen-2-yl.

Another set of preferred Y groups include heteroaryl groups which are exemplified by, for instance, benzo[1,3]dioxol-5-yl, benzofuran-2-yl, 2,3-dihydrobenzofuran-5-yl, pyrazin-2-yl, pyrid-2-yl, pyrid-3-yl, pyrid-4-yl, 1H-pyrrol-2-yl, 1H-pyrrol-3-yl, quinolin-4-yl, 3-oxo-3,4-dihydro-2H-benzo[1,4]oxazin-6-yl, and thien-2-yl.

Another set of preferred Y groups include substituted heteroaryl. Preferred substituents on the substituted heteroaryl Y groups include amino, substituted amino, alkyl, substituted alkyl, aryl, substituted aryl, alkoxy, substituted alkoxy, halo, heteroaryl, substituted heteroaryl, hydroxy, nitro and cyano. Such groups are exemplified by, for example, 2-amino-4- methylthiazol-5-yl, 3-amino-5-phenylthiophen-2-yl, 5-benzyloxy-2-methylbenzofuran-3-yl, 7-bromo-5-methoxybenzofuran-2-yl, 6-chloro-9-methyl-9H-carbazol-3-yl, 5-(4-chlorophenyl)-2-methylfuran-2-yl, 3-(4-chlorophenyl)-5-methylisoxazol-4-yl, 2-(4-chlorophenyl)-4-methylthiazol-5-yl, 1-(2-chloropyrid-3-yl)-2,4-dioxo-1,2,3,4-tetrahydropyrimidin-5-yl, 3-(3,4-dichlorophenyl)isoxazol-5-yl, 7-hydroxybenzofuran-2-yl, 5-methoxybenzofuran-3-yl, 3,5-dimethyl-1-phenyl-1H-pyrazol-4-yl, 2,4-dimethylthiazol-5-yl, 5-methyl-2-phenyl-thiophen-3-yl, and 1-phenyl-1H-pyrazol-4-yl.

Another set of preferred Y groups include alkoxy, thioalkyl, substituted alkoxy, substituted thioalkyl, aryloxy and substituted aryloxy group. Such groups are exemplified by, for example, 2-chloro-4-(4-chlorophenyl)phenoxy, ethoxy, 7-hydroxynaphthalen-2-oxy, phenoxy, and phenylsulfanyl.

A particularly preferred class of compounds of this invention are set forth in formula II below:

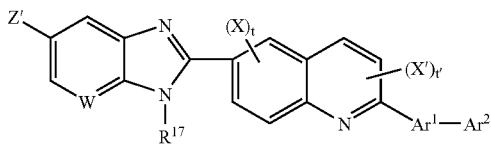

II wherein:
W is CH or N;
Z' is selected from the group consisting of carboxy, carboxy ester, and tetrazolyl,
$R^{17}$ is selected from the group consisting of cycloalkyl, cycloalkyl substituted with 1 to 3 alkyl groups, heterocyclic and heterocyclic substituted with 1 to 3 alkyl groups;
X and X' are independently selected from the group consisting of alkyl, substituted alkyl, alkoxy, substituted alkoxy, halo, hydroxy, and nitro;
$Ar^1$ and $Ar^2$ are independently selected from the group consisting of aryl, substituted aryl, cycloalkyl, substituted cycloalkyl, heteroaryl, substituted heteroaryl, heterocyclic and substituted heterocyclic;
t is an integer equal to 0, 1 or 2;
t' is an integer equal to 0 or 1;
and pharmaceutically acceptable salts thereof.
Preferably, W is CH.
Preferably, $R^{17}$ is cycloalkyl and, more preferably, is cyclohexyl.

In one preferred embodiment, —$Ar^1$—$Ar^2$— are selected from the group consisting of -aryl-aryl, -aryl-substituted aryl, -substituted aryl-aryl, and -substituted aryl-substituted aryl. Examples of such preferred embodiments include, for instance, biphen-2-yl, biphen-4-yl, 4-amino-4'-chlorobiphen-2-yl, 4'-aminomethyl-4-methoxybiphen-2-yl, 4-carbamoyl-4'-methoxybiphen-2-yl, 4-carbamoyl-4'-fluorobiphen-2-yl, 4-carbamoyl-4'-methoxybiphen-2-yl, 4-carbamoyl-4'-nitrobiphen-2-yl, 4-(carbamoylmethylcarbamoyl)-biphen-2-yl, 4-(carbamoylmethylcarbamoyl)-4'-chlorobiphen-2-yl, 4-carboxy-4'-chlorobiphen-2-yl, 3-carboxy-4'-methoxybiphen-2-yl, 4-carboxy-4'-methoxybiphen-2-yl, 4'-carboxy-4-(pyrrolidin-1-ylcarbonyl)biphen-2-yl, 4-carboxymethoxybiphen-2-yl, 4-carboxymethoxy-4'-chlorobiphen-2-yl, 4'-chlorobiphen-2-yl, 4'-chloro-4-chlorobiphen-2-yl, 4'-chloro-4-(dimethylaminoethylcarbamoyl)biphen-2-yl, 4'-chloro-4-(2-ethoxyethoxy)biphen-2-yl, 3'-chloro-4'-fluoro-4-methoxybiphen-2-yl, 4'-chloro-4-fluorobiphen-2-yl, 4'-chloro-4-hydroxybiphen-2-yl, 3'-chloro-4-methoxybiphen-2-yl, 4'-chloro-4-methylcarbamoylbiphen-2-yl, 4'-chloro-4-methoxybiphen-2-yl, 4'-chloro-4-(2-methoxyethoxy)biphen-2-yl, 4'-chloro-4-nitrobiphen-2-yl, 4'-chloro-4-(2-oxo-2-pyrrolidin-1-ylethoxy)biphen-2-yl, 4'-chloro-4-(pyrrolidin-1-ylcarbonyl)biphen-2-yl, 4'-chloro-4-(3-pyrrolidin-1-ylpropoxy)biphen-2-yl, 4'-cyano-4-methoxybiphen-2-yl, 3',4'-dichloro-4-methoxybiphen-2-yl, 4,4'-dimethoxybiphen-2-yl, 3',4'-dimethoxy-4-(pyrrolidin-1-ylcarbonyl)biphen-2-yl, 4'-dimethylamino-4-methoxybiphen-2-yl, 4-(2-dimethylaminoethylcarbamoyl)biphen-2-yl, 4'-ethoxy-4-methoxybiphen-2-yl, 4'-fluoro-4-methoxybiphen-2-yl, 4-hydroxybiphenyl, 4-methoxybiphenyl, 4-methoxy-4'-hydroxybiphen-2-yl, 4-(2-methoxyethoxy)biphen-2-yl, 4-methoxy-4'-methylbiphen-2-yl, 4-methoxy-3'-nitrobiphen-2-yl, 4-methoxy-4'-nitrobiphen-2-yl, 4-methylcarbamoylbiphen-2-yl, 3'-methyl-4-methoxybiphen-2-yl, 4'-nitro-4-(pyrrolidin-1-ylcarbonyl)biphen-2-yl, 4-(2-oxo-2-pyrrolidin-1-ylethoxy)biphen-2-yl, 4-(3-pyrrolidin-1-ylpropoxy)biphen-2-yl, and 4'-trifluoromethyl-4-methoxybiphen-2-yl.

In another preferred embodiment, —$Ar^1$—$Ar^2$— are selected from the group consisting of -aryl-heteroaryl, -aryl-substituted heteroaryl, -substituted aryl-heteroaryl, -substituted aryl-substituted heteroaryl, heteroaryl-aryl, heteroaryl-substituted aryl, substituted heteroaryl-aryl, and substituted heteroaryl-substituted aryl. Examples of such preferred embodiments include, for instance, 2-furan-2-yl-5-methoxyphenyl, 4-(imidazol-1-yl)phenyl, 5-methoxy-2-thiophen-2-ylphenyl, 2-(2,4-dimethoxypyrimidin-5-yl)-4-methoxyphenyl, 2-(pyrid-4-yl)phenyl, 3-amino-5-phenylthiophen-2-yl, 5-(4-chlorophenyl)-2-methylfuran-2-yl, 3-(4-chlorophenyl)-5-methylisoxazol-4-yl, 2-(4-chlorophenyl)-4-methylthiazol-5-yl, 3-(3,4-dichloro-phenyl)isoxazol-5-yl, 3,5-dimethyl-1-phenyl-1H-pyrazol-4-yl, 5-methyl-2-phenylthiophen-3-yl, and 1-phenyl-1H-pyrazol-4-yl.

In another preferred embodiment, —$Ar^1$—$Ar^2$— are selected from the group consisting of -aryl-cycloalkyl, -aryl-substituted cycloalkyl, -substituted aryl-cycloalkyl, -substituted aryl-substituted cycloalkyl, -aryl-heterocyclic, aryl-substituted heterocyclic, substituted aryl-heterocyclic, and substituted aryl-substituted heterocyclic. Examples of such preferred embodiments include, (4-piperazin-1-yl)phenyl, 2-cyclohexyl-5-methoxyphenyl, and 4-morpholinophenyl.

In another embodiment of the invention, the compounds are represented by formula III:

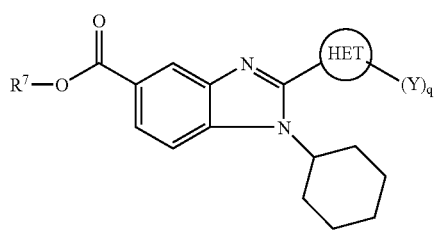

III wherein:
q is an integer equal to 1, 2 or 3;
$R^7$ is selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic;
HET is a fused 6,6-bicycle provided by the fused linkage of any two 6-membered rings selected from aryl, cycloalkyl, cycloalkenyl, heterocyclic, or heteroaryl rings that are optionally substituted with $(Y)_q$; with the proviso that at least one 6-membered ring in the bicycle is heterocyclic or heteroaryl or the bicycle is naphthyl;
each Y is independently selected from the group consisting of halo, cyano, nitro, $(C_1-C_{10})$alkyl, substituted $(C_1-C_{10})$alkyl, acyl, acyloxy, guanidino, substituted guanidino, oxycarbonylamino, aminocarbonyloxy, aminocarbonylamino, oxycarbonyloxy, $(C_3$-$C_{10})$cycloalkyl, substituted $(C_3$-$C_{10})$cycloalkyl, $(C_2$-$C_{10})$alkenyl, substituted $(C_2$-$C_{10})$alkenyl, $(C_2$-$C_{10})$alkynyl, substituted $(C_2$-$C_{10})$alkynyl, heterocyclic, substituted heterocyclic, aryl, substituted aryl, heteroaryl, substituted heteroaryl, —$CO_2R^7$, —$NR^{14}R^{15}$, —$NHNR^{14}R^{15}$, —$C(X)NR^{14}R^{15}$, —$OR^{14}$, —$SR^{14}$, —$S(O)R^{14}$, —$S(O)_2R^{14}$, and —$S(O)_2NR^{14}R^{15}$; where X is as defined above;

where $R^7$ is as defined above and each of $R^{14}$ and $R^{15}$ is independently selected from the group consisting of hydrogen, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_2$-$C_{10})$alkenyl, substituted $(C_2$-$C_{10})$alkenyl, $(C_2$-$C_{10})$alkynyl, substituted $(C_2$-$C_{10})$alkynyl, heterocyclic, substituted heterocyclic, aryl, substituted aryl, heteroaryl, and substituted heteroaryl; or $R^{14}$ and $R^{15}$ may optionally be joined together with the nitrogen atom bound thereto to form a heterocyclic, substituted heterocyclic, heteroaryl or substituted heteroaryl;

and pharmaceutically acceptable salts and/or tautomers thereof.

Preferred $R^7$, HET and Y groups are as defined above.

In another embodiment of the invention, the compounds are represented by formula IV:

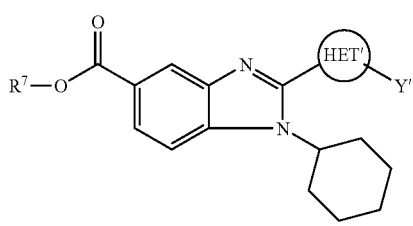

IV wherein:
$R^7$ is selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic;

HET' is a fused 6,6-bicycle provided by the fused linkage of any two 6-membered rings selected from aryl, substituted aryl, heterocyclic, substituted heterocyclic, heteroaryl, or substituted heteroaryl rings that are optionally substituted with Y; with the proviso that at least one 6-membered ring in the bicycle is aromatic;

Y' is independently selected from the group consisting of alkyl, aryl, heteroaryl, substituted aryl, and substituted heteroaryl; and pharmaceutically acceptable salts and/or tautomers thereof.

In another embodiment of the invention, the compounds are represented by formula V:

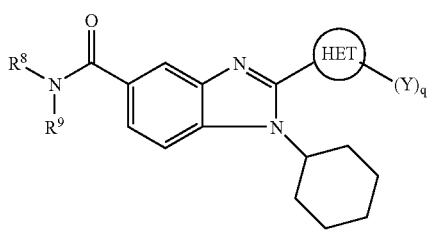

V wherein:
$R^8$ and $R^9$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocycle or, alternatively, $R^8$ and $R^9$ together with the nitrogen atom pendent thereto, form a heterocyclic, a substituted heterocyclic, a heteroaryl or a substituted heteroaryl ring group;

HET' is a fused 6,6-bicycle provided by the fused linkage of any two 6-membered rings selected from aryl, cycloalkyl, cycloalkenyl, heterocyclic, or heteroaryl rings that are optionally substituted with $(Y)_q$; with the proviso that at least one 6-membered ring in the bicycle is heterocyclic or heteroaryl or the bicycle is naphthyl;

each Y is independently selected from the group consisting of halo, cyano, nitro, $(C_1$-$C_{10})$alkyl, substituted $(C_1$-$C_{10})$alkyl, acyl, acyloxy, guanidino, oxycarbonylamino, aminocarbonyloxy, aminocarbonylamino, oxycarbonyloxy, $(C_3$-$C_{10})$cycloalkyl, substituted $(C_3$-$C_{10})$cycloalkyl, $(C_2$-$C_{10})$alkenyl, substituted $(C_2$-$C_{10})$alkenyl, $(C_2$-$C_{10})$alkynyl, substituted $(C_2$-$C_{10})$alkynyl, heterocyclic, substituted heterocyclic, aryl, substituted aryl, heteroaryl, substituted heteroaryl, —$CO_2R^7$, —$NR^{14}R^{15}$, —$NHNR^{14}R^{15}$, —$C(X)NR^{14}R^{15}$, —$OR^{14}$, $SR^{14}$, —$S(O)R^{14}$, —$S(O)_2R^{14}$, and —$S(O)_2NR^{14}R^{15}$; where X is as defined above;

where $R^7$ is as defined above and each of $R^{14}$ and $R^{15}$ is independently selected from the group consisting of hydrogen, $(C_1$-$C_{10})$alkyl, substituted $(C_1$-$C_{10})$alkyl, $(C_3$-$C_{10})$cycloalkyl, substituted $(C_3$-$C_{10})$cycloalkyl, $(C_2$-$C_{10})$alkenyl, substituted $(C_2$-$C_{10})$alkenyl, $(C_2$-$C_{10})$alkynyl, substituted $(C_2$-$C_{10})$alkynyl, heterocyclic, substituted heterocyclic, aryl, substituted aryl, heteroaryl, and substituted heteroaryl; or $R^{14}$ and $R^{15}$ may optionally be joined together with the nitrogen atom bound thereto to form a heterocyclic, substituted heterocyclic, heteroaryl or substituted heteroaryl;

q is an integer equal to 1, 2 or 3; and pharmaceutically acceptable salts or tautomers thereof.

In yet another embodiment, the compounds are represented by the formula VI:

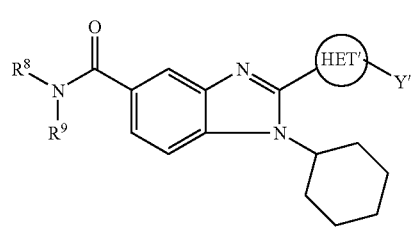

VI wherein:
$R^8$ and $R^9$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocycle or, alternatively, $R^8$ and $R^9$ together with the nitrogen atom pendent thereto, form a heterocyclic, a substituted heterocyclic, a heteroaryl or a substituted heteroaryl ring group;

HET' is a fused 6,6-bicycle provided by the fused linkage of any two 6-membered rings selected from aryl, substituted aryl, heterocyclic, substituted heterocyclic, heteroaryl, or substituted heteroaryl rings that are optionally substituted with Y; with the proviso that at least one 6-membered ring in the bicycle is aromatic;

Y' is independently selected from the group consisting of alkyl, aryl, heteroaryl, substituted aryl, and substituted heteroaryl; and pharmaceutically acceptable salts and/or tautomers thereof.

In yet another embodiment, the compounds are represented by the formula VII:

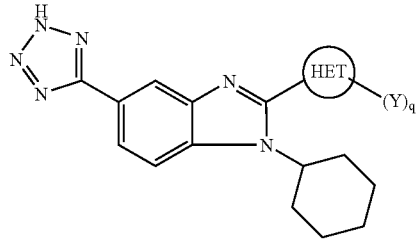

VII wherein:
HET is a fused 6,6-bicycle provided by the fused linkage of any two 6-membered rings selected from aryl, cycloalkyl, cycloalkenyl, heterocyclic, or heteroaryl rings that are optionally substituted with $(Y)_q$; with the proviso that at least one 6-membered ring in the bicycle is heterocyclic or heteroaryl or the bicycle is naphthyl;

each Y is independently selected from the group consisting of halo, cyano, nitro, $(C_1-C_{10})$alkyl, substituted $(C_1-C_{10})$alkyl, acyl, acyloxy, guanidino, substituted guanidino, oxycarbonylamino, aminocarbonyloxy, aminocarbonylamino, oxycarbonyloxy, $(C_3-C_{10})$cycloalkyl, substituted $(C_3-C_{10})$cycloalkyl, $(C_2-C_{10})$alkenyl, substituted $(C_2-C_{10})$alkenyl, $(C_2-C_{10})$alkynyl, substituted $(C_2-C_{10})$alkynyl, heterocyclic, substituted heterocyclic, aryl, substituted aryl, heteroaryl, substituted heteroaryl, —$CO_2R^7$, —$NR^{14}R^{15}$, —$NHNR^{14}R^{15}$, —$C(X)NR^{14}R^{15}$, —$OR^{14}$, $SR^{14}$, —$S(O)R^{14}$, —$S(O)_2R^{14}$, and —$S(O)_2NR^{14}R^{15}$; where X is as defined above;

where $R^7$ is as defined above and each of $R^{14}$ and $R^{15}$ is independently selected from the group consisting of hydrogen, $(C_1-C_{10})$alkyl, substituted $(C_1-C_{10})$alkyl, $(C_3-C_{10})$cycloalkyl, substituted $(C_3-C_{10})$cycloalkyl, $(C_2-C_{10})$alkenyl, substituted $(C_2-C_{10})$alkenyl, $(C_2-C_{10})$alkynyl, substituted $(C_2-C_{10})$alkynyl, heterocyclic, substituted heterocyclic, aryl, substituted aryl, heteroaryl, and substituted heteroaryl; or $R^{14}$ and $R^{15}$ may optionally be joined together with the nitrogen atom bound thereto to form a heterocyclic, substituted heterocyclic, heteroaryl or substituted heteroaryl;

q is an integer equal to 1, 2 or 3; and pharmaceutically acceptable salts or tautomers thereof.

In yet another embodiment, the compounds are represented by the formula VIII:

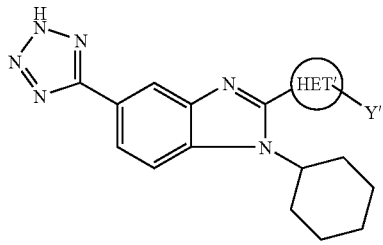

VIII wherein:
HET' is a fused 6,6-bicycle provided by the fused linkage of any two 6-membered rings selected from aryl, substituted aryl, heterocyclic, substituted heterocyclic, heteroaryl, or substituted heteroaryl rings that are optionally substituted with Y; with the proviso that at least one 6-membered ring in the bicycle is aromatic;

Y' is independently selected from the group consisting of alkyl, aryl, heteroaryl, substituted aryl, and substituted heteroaryl; and pharmaceutically acceptable salts and/or tautomers thereof.

In yet another embodiment, the compounds are represented by the formula IX:

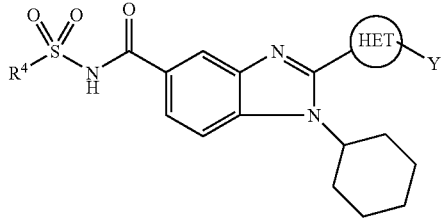

IX wherein:
$R^4$ is selected from the group consisting of alkyl, substituted alkyl, aryl, substituted aryl, heteroaryl, substituted heteroaryl, heterocyclic and substituted heterocyclic;

HET is a fused 6,6-bicycle provided by the fused linkage of any two 6-membered rings selected from aryl, cycloalkyl, cycloalkenyl, heterocyclic, or heteroaryl rings that are optionally substituted with $(Y)_q$; with the proviso that at least one 6-membered ring in the bicycle is heterocyclic or heteroaryl or the bicycle is naphthyl;

each Y is independently selected from the group consisting of halo, cyano, nitro, $(C_1-C_{10})$alkyl, substituted $(C_1-C_{10})$alkyl, acyl, acyloxy, guanidino, substituted guanidino, oxycarbonylamino, aminocarbonyloxy, aminocarbonylamino, oxycarbonyloxy, $(C_3-C_{10})$cycloalkyl, substituted $(C_3-C_{10})$cycloalkyl, $(C_2-C_{10})$alkenyl, substituted $(C_2-C_{10})$alkenyl, $(C_2-C_{10})$alkynyl, substituted $(C_2-C_{10})$alkynyl, heterocyclic, substituted heterocyclic, aryl, substituted aryl, heteroaryl, substituted heteroaryl, —$CO_2R^7$, —$NR^{14}R^{15}$, —$NHNR^{14}R^{15}$, —$C(X)NR^{14}R^{15}$, —$OR^{14}$, $SR^{14}$, —$S(O)R^{14}$, —$S(O)_2R^{14}$, and —$S(O)_2NR^{14}R^{15}$; where X is as defined above;

where $R^7$ is as defined above and each of $R^{14}$ and $R^{15}$ is independently selected from the group consisting of hydrogen, $(C_1-C_{10})$alkyl, substituted $(C_1-C_{10})$alkyl, $(C_3-C_{10})$cycloalkyl, substituted $(C_3-C_{10})$cycloalkyl, $(C_2-C_{10})$alkenyl, substituted $(C_2-C_{10})$alkenyl, $(C_2-C_{10})$alkynyl, substituted $(C_2-C_{10})$alkynyl, heterocyclic, substituted heterocyclic, aryl, substituted aryl, heteroaryl, and substituted heteroaryl; or $R^{14}$ and $R^{15}$ may optionally be joined together with the nitrogen atom bound thereto to form a heterocyclic, substituted heterocyclic, heteroaryl or substituted heteroaryl;

q is an integer equal to 1, 2 or 3; and pharmaceutically acceptable salts or tautomers thereof.

In yet another embodiment, the compounds are represented by the formula X:

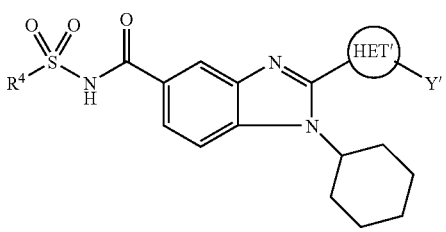

X wherein:

R[4] is selected from the group consisting of alkyl, substituted alkyl, aryl, substituted aryl, heteroaryl, substituted heteroaryl, heterocyclic and substituted heterocyclic;

HET' is a fused 6,6-bicycle provided by the fused linkage of any two 6-membered rings selected from aryl, substituted aryl, heterocyclic, substituted heterocyclic, heteroaryl, or substituted heteroaryl rings that are optionally substituted with Y; with the proviso that at least one 6-membered ring in the bicycle is aromatic;

Y' is independently selected from the group consisting of alkyl, aryl, heteroaryl, substituted aryl, and substituted heteroaryl; and pharmaceutically acceptable salts and/or tautomers thereof.

In yet another embodiment, the compounds are represented by the formula XI:

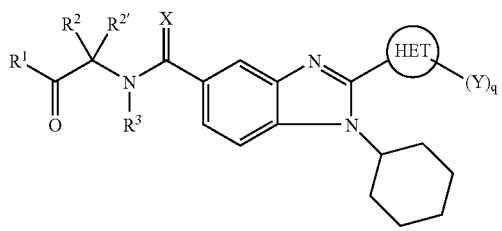

XI wherein X is selected from the group consisting of =O, =S, and =NR[11], where R[11] is hydrogen or alkyl, R[1] is selected from the group consisting of —OR[7] and —NR[8]R[9] where R[7] is selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic; R[8] and R[9] are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocycle or, alternatively, R[8] and R[9] together with the nitrogen atom pendent thereto, form a heterocyclic, a substituted heterocyclic, a heteroaryl or a substituted heteroaryl ring group;

each R[2] and R[2'] is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, or, alternatively, R[2] and R[2'] as defined are taken together with the carbon atom pendent thereto to form a cycloalkyl, substituted cycloalkyl, heterocyclic or substituted heterocyclic group, or, still further alternatively, one or R[2] or R[2'] is hydrogen, alkyl or substituted alkyl, and the other is joined, together with the carbon atom pendent thereto, with either the R[7] and the oxygen atom pendent thereto or R[8] and the nitrogen atom pendent thereto to form a heterocyclic or substituted heterocyclic group;

R[3] is selected from the group consisting of hydrogen and alkyl or, when R[2] and R[2'] are not taken together to form a ring and when R[2]/R[2'] and R[7] or R[8] are not joined to form a heterocyclic or substituted heterocyclic group, then R[3], together with the nitrogen atom pendent thereto, may be taken together with one of R[2] and R[2'] to form a heterocyclic or substituted heterocyclic ring group;

HET is a fused 6,6-bicycle provided by the fused linkage of any two 6-membered rings selected from aryl, cycloalkyl, cycloalkenyl, heterocyclic, or heteroaryl rings that are optionally substituted with (Y)$_q$; with the proviso that at least one 6-membered ring in the bicycle is heterocyclic or heteroaryl or the bicycle is naphthyl;

each Y is independently selected from the group consisting of halo, cyano, nitro, $(C_1-C_{10})$alkyl, substituted $(C_1-C_{10})$alkyl, acyl, acyloxy, guanidino, substituted guanidino, oxycarbonylamino, aminocarbonyloxy, aminocarbonylamino, oxycarbonyloxy, $(C_3-C_{10})$cycloalkyl, substituted $(C_3-C_{10})$cycloalkyl, $(C_2-C_{10})$alkenyl, substituted $(C_2-C_{10})$alkenyl, $(C_2-C_{10})$alkynyl, substituted $(C_2-C_{10})$alkynyl, heterocyclic, substituted heterocyclic, aryl, substituted aryl, heteroaryl, substituted heteroaryl, —CO$_2$R[7], —NR[14]R[15], —NHNR[14]R[15], —C(X)NR[14]R[15], —OR[14], SR[14], —S(O)R[14], —S(O)$_2$R[14], and —S(O)$_2$NR[14]R[15]; where X is as defined above;

where R[7] is selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic; s as defined above and each of R[14] and R[15] is independently selected from the group consisting of hydrogen, $(C_1-C_{10})$alkyl, substituted $(C_1-C_{10})$alkyl, $(C_3-C_{10})$cycloalkyl, substituted $(C_3-C_{10})$cycloalkyl, $(C_2-C_{10})$alkenyl, substituted $(C_2-C_{10})$alkenyl, $(C_2-C_{10})$alkynyl, substituted $(C_2-C_{10})$alkynyl, heterocyclic, substituted heterocyclic, aryl, substituted aryl, heteroaryl, and substituted heteroaryl; or R[14] and R[15] may optionally be joined together with the nitrogen atom bound thereto to form a heterocyclic, substituted heterocyclic, heteroaryl or substituted heteroaryl;

q is an integer equal to 1, 2 or 3; and pharmaceutically acceptable salts or tautomers thereof.

In yet another embodiment, the compounds are represented by the formula XII:

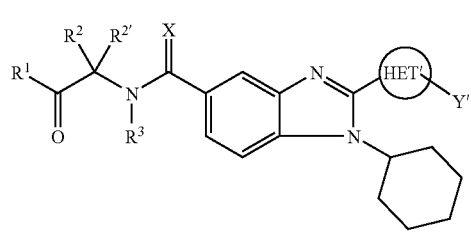

XII wherein X is selected from the group consisting of =O, =S, and =NR[11], where R[11] is hydrogen or alkyl, R[1] is selected from the group consisting of —OR[7] and —NR[8]R[9] where R[7] is selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic; R[8] and R[9] are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocycle or, alternatively, R[8] and R[9] together with the nitrogen atom pendent thereto, form a heterocyclic, a substituted heterocyclic, a heteroaryl or a substituted heteroaryl ring group;

each $R^2$ and $R^{2'}$ is independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic, and substituted heterocyclic, or, alternatively, $R^2$ and $R^{2'}$ as defined are taken together with the carbon atom pendent thereto to form a ring group, $R^3$ is selected from the group consisting of hydrogen and alkyl or, when $R^2$ and $R^{2'}$ are not taken together to form a ring then $R^3$ may be taken together with one of $R^2$ and $R^{2'}$ to form a heterocyclic or substituted heterocyclic ring group;

HET' is a fused 6,6-bicycle provided by the fused linkage of any two 6-membered rings selected from aryl, substituted aryl, heterocyclic, substituted heterocyclic, heteroaryl, or substituted heteroaryl rings that are optionally substituted with Y; with the proviso that at least one 6-membered ring in the bicycle is aromatic;

Y' is independently selected from the group consisting of alkyl, aryl, heteroaryl, substituted aryl, and substituted heteroaryl; and pharmaceutically acceptable salts and/or tautomers thereof.

Compounds within the scope of this invention include those of Formula I as set forth in Tables I-VIII as follows:

TABLE I

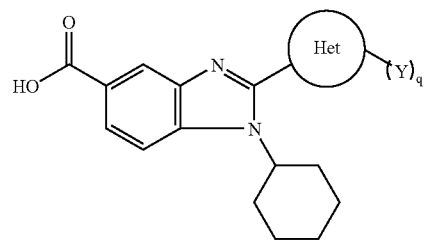

| Cmpd # | Structure | q | Y | Het | Name |
|---|---|---|---|---|---|
| 201 | 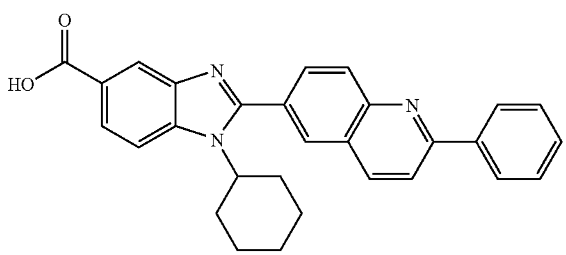 | 1 | phenyl | quinolin-6-yl | 1-cyclohexyl-2-(2-phenyl-quinolin-6-yl)-1H-benzoimidazole-5-carboxylic-acid |
| 203 | 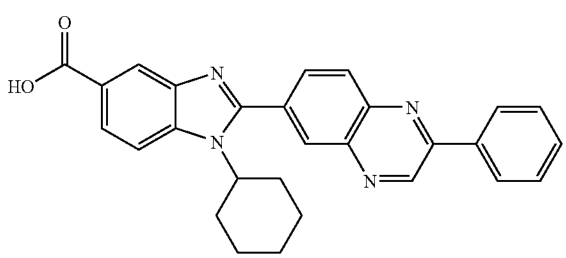 | 1 | phenyl | quinoxalin-6-yl | 1-cyclohexyl-2-(2-phenyl-quinoxalin-6-yl)-1H-benzoimidazole-5-carboxylic acid |
| 204 | 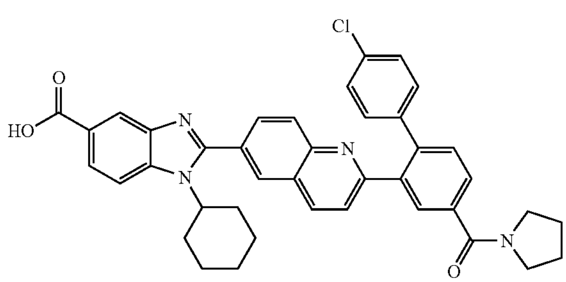 | 1 | 4'-chloro-4-(pyrrolidine-1-carbonyl)-biphen-2-yl | quinolin-6-yl | 2-{2-[4'-chloro-4-(pyrrolidinyl-1-carbonyl)-biphen-2-yl]-quinolin-6-yl}-1-cyclohexyl-1H benzoimidazole-5-carboxylic acid |

TABLE I-continued

| Cmpd # | Structure | q | Y | Het | Name |
|---|---|---|---|---|---|
| 205 | 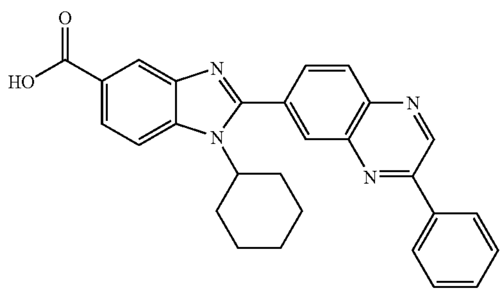 | 1 | phenyl | quinoxalin-6-yl | 1-cyclohexyl-2-(3-phenyl-quinoxalin-6-yl)-1H-benzoimidazole-5-carboxylic acid |
| 206 | 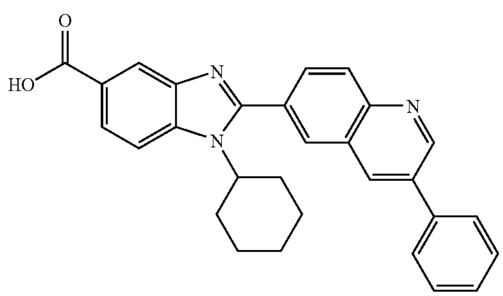 | 1 | phenyl | quinolin-6-yl | 1-cyclohexyl-2-(3-phenyl-quinolin-6-yl)-1H-benzoimidazole-5-carboxylic acid |
| 207 | 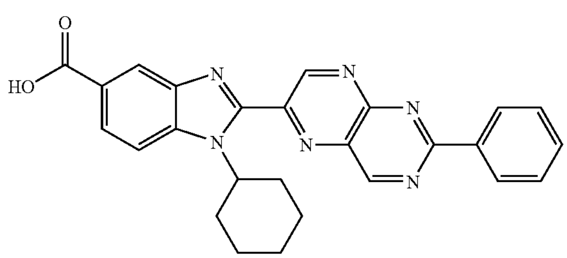 | 1 | phenyl | pteridin-6-yl | 1-cyclohexyl-2-(2-phenyl-pteridin-6-yl)-1H-benzoimidazole-carboxylic acid |
| 208 | 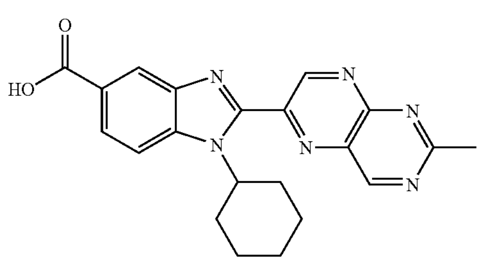 | 1 | methyl | pteridin-6-yl | 1-cyclohexyl-2-(2-methyl-pteridin-6-yl)-1H-benzoimidazole-5-carboxylic acid |

TABLE I-continued

| Cmpd # | Structure | q | Y | Het | Name |
|---|---|---|---|---|---|
| 209 | 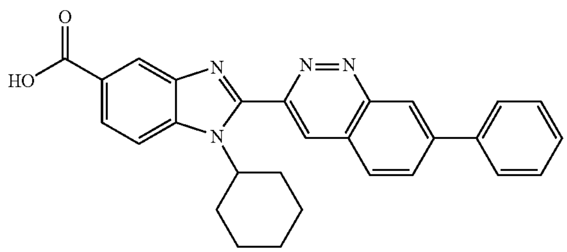 | 1 | Phenyl | cinnolin-3-yl | 1-cyclohexyl-2-(7-phenyl-cinnolin-3-yl)-1H-benzoimidazole-5-carboxylic acid |
| 210 | 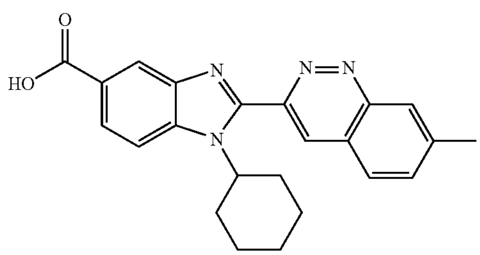 | 1 | Methyl | cinnolin-3-yl | 1-cyclohexyl-2-(7-methyl-cinnolin-3-yl)-1H-benzoimidazole-5-carboxylic acid |
| 211 | 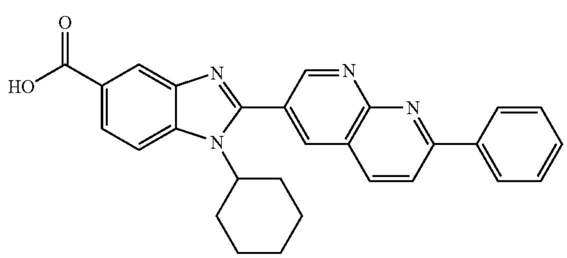 | 1 | Phenyl | [1,8]naph-thyridin-3-yl | 1-cyclohexyl-2-(7-phenyl[1,8]-naphthyridin-3-yl)-1H-benzoimidazole-5-carboxylic acid |
| 212 | 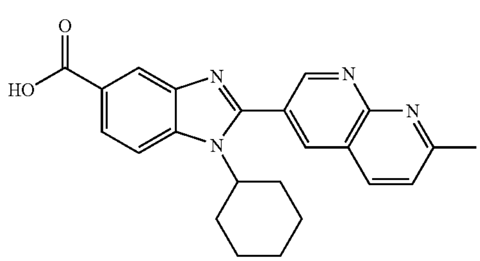 | 1 | Methyl | [1,8]naph-thyridin-3-yl | 1-cyclohexyl-2-(7-methyl-[1,8]naphthyridin-3-yl)-1H-benzoimidazole-5-carboxylic acid |
| 213 | 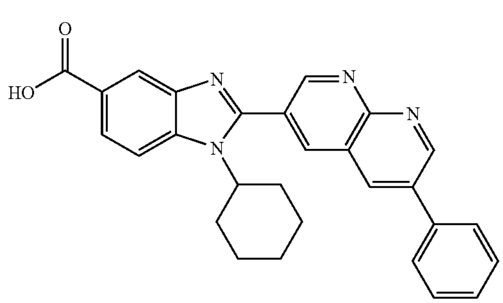 | 1 | Phenyl | [1,8]naph-thyridin-3-yl | 1-cyclohexyl-2-(6-phenyl-[1,8]naphthyridin-3-yl)-1H-benzoimidazole-5-carboxylic acid |

TABLE I-continued

| Cmpd # | Structure | q | Y | Het | Name |
|---|---|---|---|---|---|
| 214 | 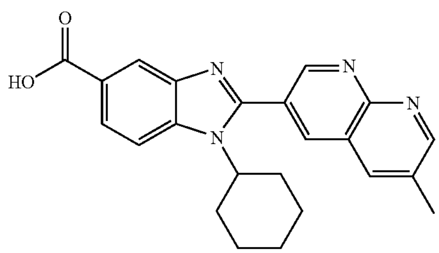 | 1 | Methyl | [1,8]naph-thyridin-3-yl | 1-cyclohexyl-2-(6-methyl-[1,8]naphthyridin-3-yl)-1H-benzoimidazole-5-carboxylic acid |
| 215 | 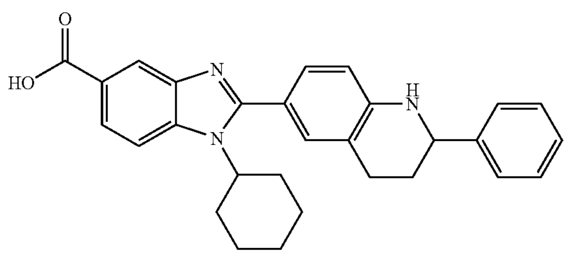 | 1 | Phenyl | 1,2,3,4-tetrahydro-quinolin-6-yl | 1-cyclohexyl-2-(2-phenyl-1,2,3,4-tetrahydro-quinolin-6-yl)-1H-benzoimidazole-5-carboxylic acid |
| 216 | 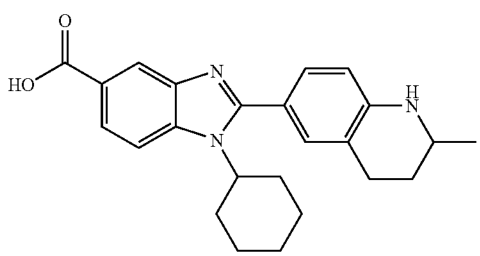 | 1 | Methyl | 1,2,3,4-tetrahydro-quinolin-6-yl | 1-cyclohexyl-2-(2-methyl-1,2,3,4-tetrahydroquinolin-6-yl)-1H-benzoimidazole-5-carboxylic acid |
| 217 | 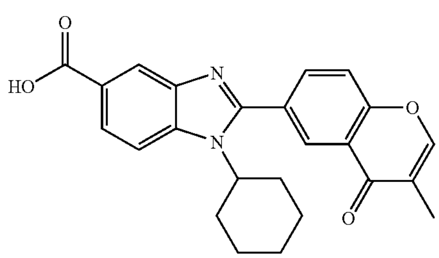 | 1 | Methyl | 4-oxo-2H-chromen-6-yl | 1-cyclohexyl-2-(3-methyl-4-oxo-chromen-6-yl)-1H-benzoimidazole-5-carboxylic acid |
| 218 | 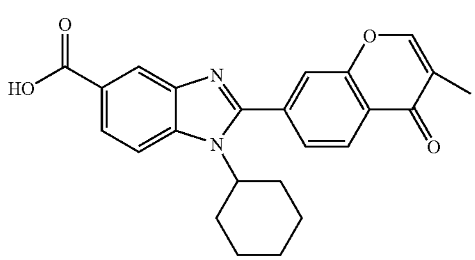 | 1 | Methyl | 4-oxo-2H-chromen-7-yl | 1-cyclohexyl-2-(3-methyl-4-oxo-chromen-7-yl)-1H-benzoimidazole-5-carboxylic acid |

TABLE I-continued

| Cmpd # | Structure | q | Y | Het | Name |
|---|---|---|---|---|---|
| 219 | 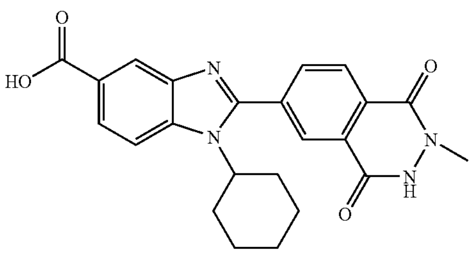 | 1 | Methyl | 1,4-dioxo-1,2,3,4-tetrahydro-phthalazin-6-yl | 1-cyclohexyl-2-(2-methyl-1,4-dioxo-1,2,3,4-tetrahydro-phthalazin-6-yl)-1H-benzoimidazole-5-carboxylic acid |
| 220 | 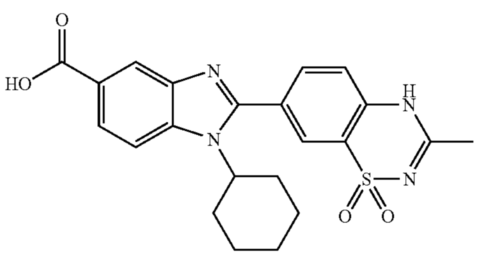 | 1 | Methyl | 1,1-dioxo-1,4-dihydro-1λ16-benzo[1,2,4]thiadiazin-7-yl | 1-cyclohexyl-2-(3-methyl-1,1-dioxo-1,4-dihydro-1λ6-benzo[1,2,4]thiadiazin-7-yl)-1H-benzoimidazole-5-carboxylic acid |
| 221 | 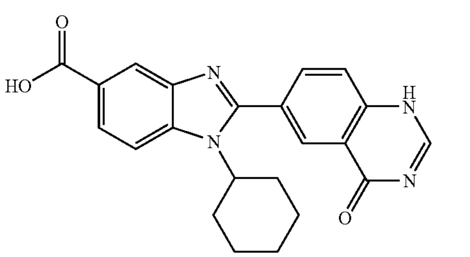 | 0 | | 4-oxo-1,4-dihydro-quinazolin-6-yl | 1-cyclohexyl-2-(4-oxo-1,4-dihydro-quinazolin-6-yl)-1H-benzoimidazole-5-carboxylic acid |
| 222 | 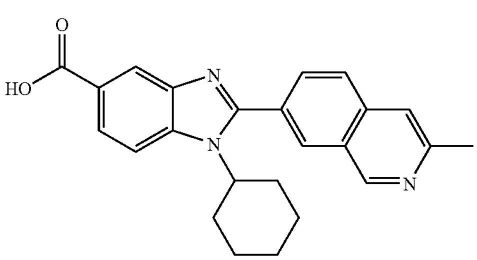 | 1 | Methyl | Isoquinolin-6-yl | 1-cyclohexyl-2-(3-methyl-isoquinolin-6-yl)-1H-benzoimidazole-5-carboxylic acid |
| 223 | 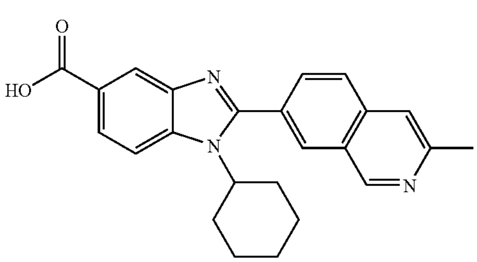 | 1 | Methyl | 1,4-dihydro-isoquinolin-6-yl | 1-cyclohexyl-2-(3-methyl-1,4-dihydro-isoquinolin-6-yl)-1H-benzoimidazole-5-carboxylic acid |

TABLE I-continued

| Cmpd # | Structure | q | Y | Het | Name |
|---|---|---|---|---|---|
| 224 | 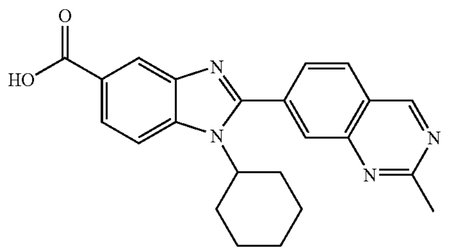 | 1 | Methyl | quinazolin-7-yl | 1-cyclohexyl-2-(2-methyl-quinazolin-7-yl)-1H-benzoimidazole-5-carboxylic acid |
| 225 | 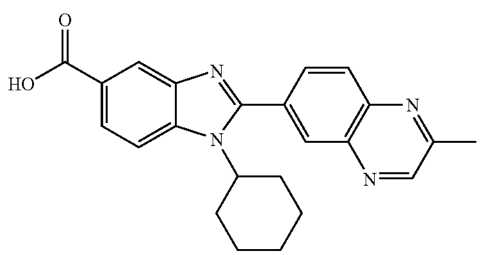 | 1 | Methyl | quinoxolin-6-yl | 1-cyclohexyl-2-(2-methyl-quinoxalin-6-yl)-1H-benzoimidazole-5-carboxylic acid |
| 226 | 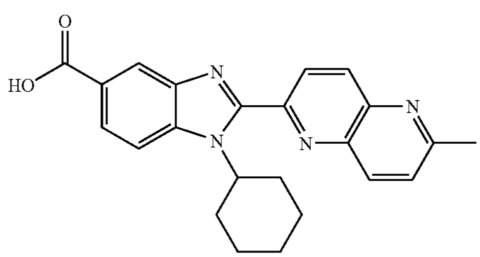 | 1 | Methyl | [1,5]naphthyridin-2-yl | 1-cyclohexyl-2-(6-methyl-[1,5]naphthyridin-2-yl)-1H-benzoimidazole-5-carboxylic acid |
| 227 | 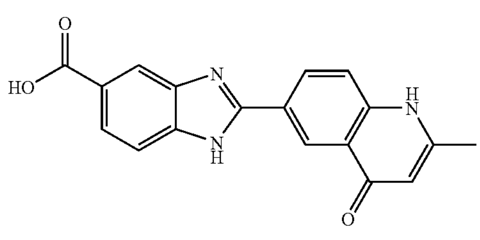 | 1 | Methyl | 4-oxo-1,4-dihydro-quinolin-6-yl | 1-cyclohexyl-2-(2-methyl-4-oxo-1,4-dihydro-quinolin-6-yl)-1H-benzoimidazole-5-carboxylic acid |
| 228 | 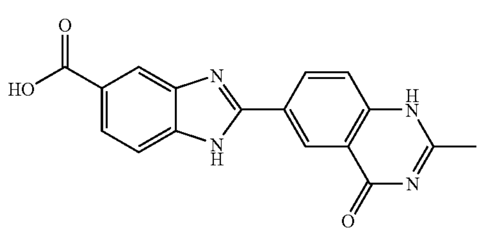 | 1 | Methyl | 4-oxo-1,4-dihydro-quinazolin-6-yl | 1-cyclohexyl-2-(2-methyl-4-oxo-1,4-dihydro-quinazolin-6-yl)-1H-benzoimidazole-5-carboxylic acid |

TABLE I-continued

| Cmpd # | Structure | q | Y | Het | Name |
|---|---|---|---|---|---|
| 351 | 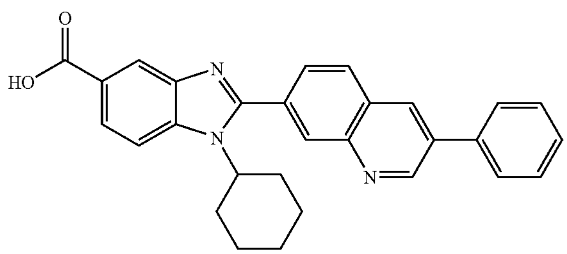 | 1 | Phenyl | quinolin-7-yl | 1-cyclohexyl-2-(3-phenyl-quinolin-7-yl)-1H-benzoimidazale-5-carboxylic-acid |
| 352 | 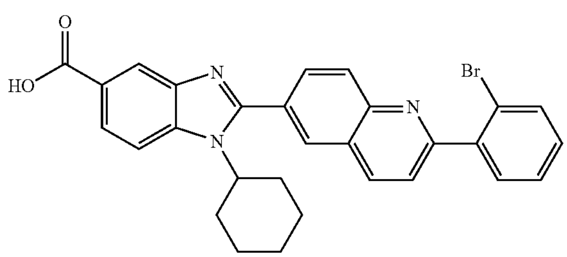 | 1 | 2-bromo-phenyl | quinolin-6-yl | 2-[2-(2-bromo-phenyl)-quinolin-6-yl]-1-cyclohexyl-1H-benzoimidazole-5-carboxylic acid |
| 353 | 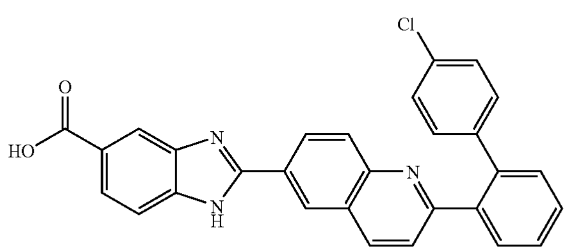 | 1 | 4'-chloro-biphen-2-yl | quinolin-6-yl | 2-[2-(4'-chloro-biphen-2-yl)-quinolin-6-yl]-1H-benzoimidazole-5-carboxylic acid |
| 354 | 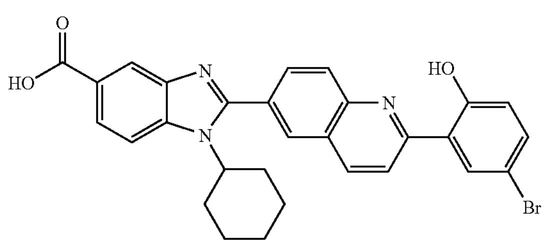 | 1 | 5-bromo-2-hydroxy-phenyl | quinolin-6-yl | 2-[2-(5-bromo-2-hydroxy-phenyl)-quinolin-6-yl]-1-cyclohexyl-1H-benzoimidazole-5-carboxylic acid |
| 355 | 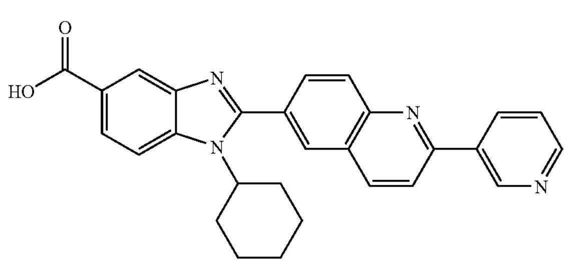 | 1 | pyridin-3-yl | quinolin-6-yl | 1-cyclohexyl-2-(2-pyridin-3-yl-quinolin-6-yl)-1H-benzoimidazole-5-carboxylic acid |

TABLE I-continued

| Cmpd # | Structure | q | Y | Het | Name |
|---|---|---|---|---|---|
| 356 | 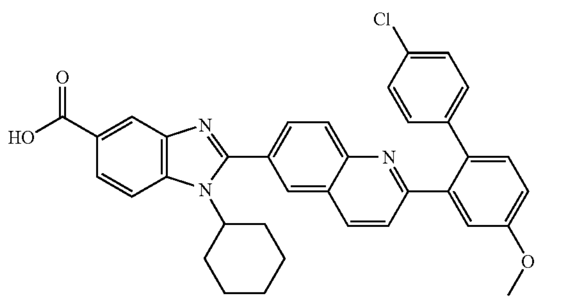 | 1 | 4'-chloro-4-methoxy-biphen-2-yl | quinolin-6-yl | 2-[2-(4'-chloro-4-methoxy-biphen-2-yl)-quinolin-6-yl]-1-cyclohexyl-1H-benzoimidazole-5-carboxylic acid |
| 357 | 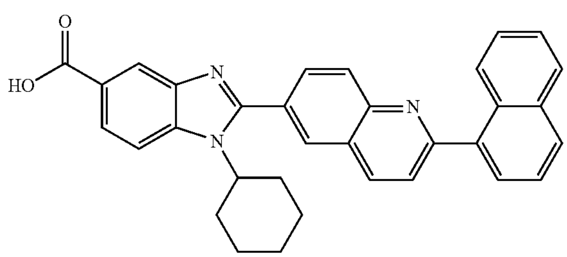 | 1 | naphthalen-1-yl- | quinolin-6-yl | 1-cyclohexyl-2-(2-naphthalen-1-yl-quinolin-6-yl)-1H-benzoimidazole-5-carboxylic acid |
| 358 | 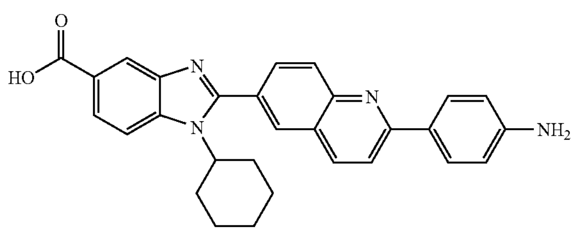 | 1 | 4-amino-phenyl | quinolin-6-yl | 2-[2-(4-amino-phenyl)-quinolin-6-yl]-1-cyclohexyl-1H-benzoimidazole-5-carboxylic acid |
| 359 | 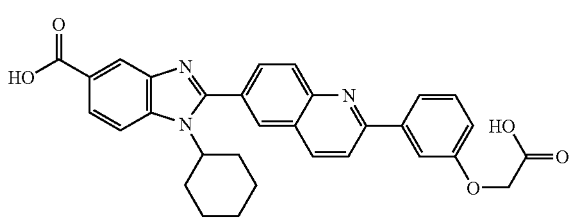 | 1 | 3-carboxy-methoxy-phenyl | quinolin-6-yl | 2-[2-(3-carboxymethoxy-phenyl)-quinolin-6-yl]-1-cyclohexyl-1H-benzoimidazole-5-carboxylic acid |
| 360 | 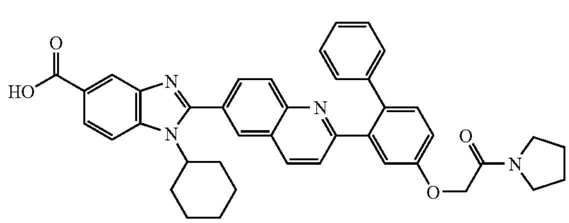 | 1 | 4-(2-oxo-2-pyrrolidin-1-yl-ethoxy)-biphen-2-yl | quinolin-6-yl | 1-cyclohexyl-2-{2-[4-(2-oxo-2-pyrrolidin-1-yl-ethoxy)-biphen-2-yl]-quinolin-6-yl}-1H-benzoimidazole-5-carboxylic acid |

TABLE I-continued

| Cmpd # Structure | q | Y | Het | Name |
|---|---|---|---|---|
| 361 | 1 | 4-(carbamoyl methyl-carbamoyl)-4'-chloro-biphen-2-yl | quinolin-6-yl | 2-{2-[4-(carbamoylmethyl-carbamoyl)-4'-chloro-biphen-2-yl]-quinolin-6-yl}-1-cyclohexyl-1H-benzoimidazole-5-carboxylic acid |
| 362 | 1 | 4-methyl-carbamoyl-biphen-2-yl | quinolin-6-yl | 1-cyclohexyl-2-[2-(4-methylcarbamoyl-biphen-2-yl)-quinolin-6-yl]-1H-benzoimidazole-5-carboxylic acid |
| 363 | 1 | 4-amino-3,5-dichloro-phenyl | quinolin-6-yl | 2-[2-(4-amino-3,5-dichloro-phenyl)-quinolin-6-yl]-1-cyclohexyl-1H-benzoimidazole-5-carboxylic acid |
| 364 | 1 | 2,4-dihydroxy-phenyl | quinolin-6-yl | 1-cyclohexyl-2-[2-(2,4-dihydroxy-phenyl)-quinolin-6-yl]-1H-benzoimidazole-5-carboxylic acid |
| 365 | 1 | 4'-cyano-4-methoxy-biphen-2-yl | quinolin-6-yl | 2-[2-(4'-cyano-4-methoxy-biphen-2-yl)-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 366 | 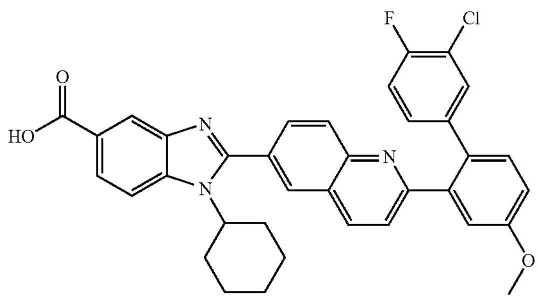 | 1 | 3'-chloro-4'-fluoro-4-methoxy-biphen-2-yl | quinolin-6-yl | 2-[2-(3'-chloro-4'-fluoro-4-methoxy-biphen-2-yl)-quinolin-6-yl]-1-cyclohexyl-1H-benzoimidazole-5-carboxylic acid |
| 367 | 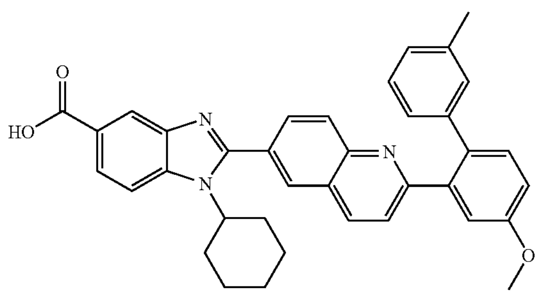 | 1 | 4-methoxy-3'-methyl-biphen-2-yl | quinolin-6-yl | 1-cyclohexyl-2-[2-(4-methoxy-3'-methyl-biphen-2-yl)-quinolin-6-yl]-1H-benzoimidazole-5-carboxylic acid |
| 368 | 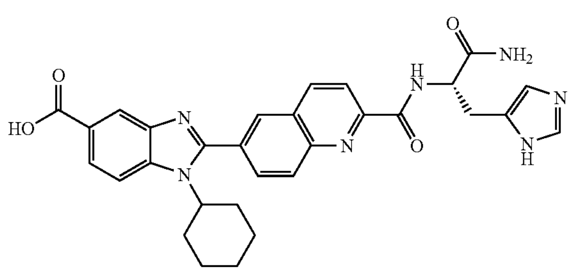 | 1 | 1-carbamoyl-2-(1H-imidazol-2-yl)ethyl-carbamoyl | quinolin-6-yl | 2-{2-[1-carbamoyl-2-(1H-imidazol-2-yl)ethylcarbamoyl]-quinolin-6-yl}-1-cyclohexyl-1H-benzimidazole-5-carboxylic acid |
| 369 | 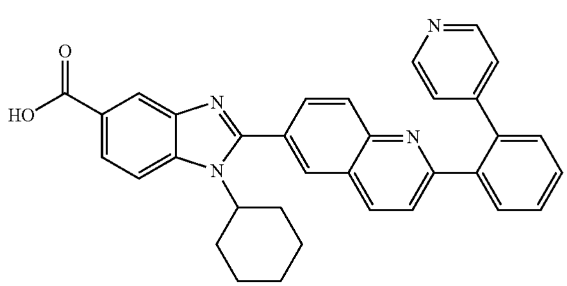 | 1 | 2-pyridin-4-yl-phenyl | quinolin-6-yl | 1-cyclohexyl-2-[2-(2-pyridin-4-yl-phenyl)-quinolin-6-yl]-1H-benzoimidazole-5-carboxylic acid |

TABLE I-continued

| Cmpd # | Structure | q | Y | Het | Name |
|---|---|---|---|---|---|
| 370 | 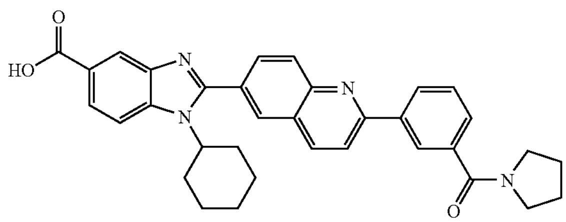 | 1 | 3-(pyrrolidinyl-1-carbonyl)-phenyl | quinolin-6-yl | 1-cyclohexyl-2-{2-[3-(pyrrolidinyl-1-carbonyl)-phenyl]-quinolin-6-yl}-1H-benzoimidazole-5-carboxylic acid |
| 371 | 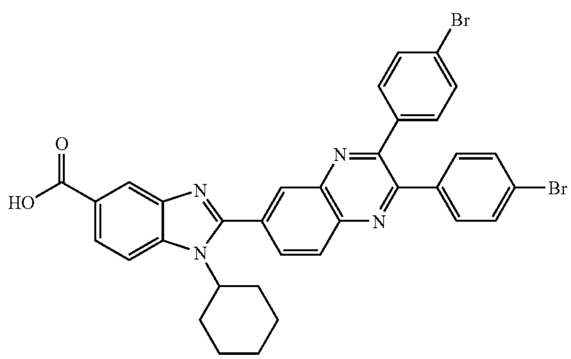 | 2 | 4-bromo-phenyl AND 4-bromo-phenyl | quinoxalin-6-yl | 2-[2,3-bis-(4-bromophenyl)quinoxalin-6-yl]-1-cyclohexyl-1H-benzimidazole-5-carboxylic acid |
| 372 | 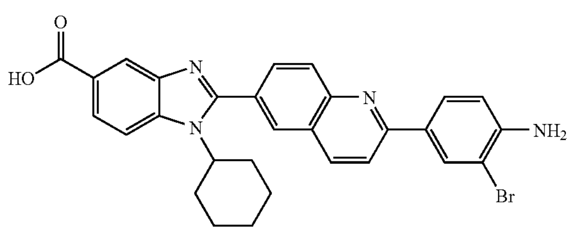 | 1 | 4-amino-3-bromo-phenyl | quinolin-6-yl | 2-[2-(4-amino-3-bromo-phenyl)-quinolin-6-yl]-1-cyclohexyl-1H-benzoimidazole-5-carboxylic acid |
| 373 | 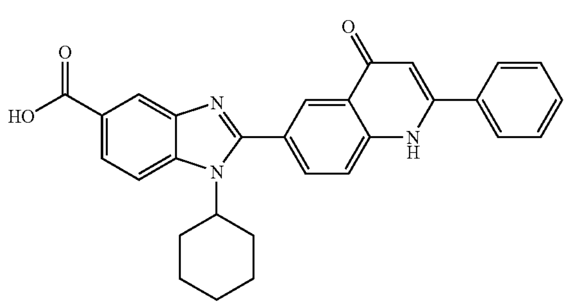 | 1 | Phenyl | 4-oxo-1,4-dihydro-quinolin-6-yl | 1-cyclohexyl-2-(4-oxo-2-phenyl-1,4-dihydro-quinolin-6-yl)-1H-benzoimidazole-5-carboxylic acid |

TABLE I-continued

| Cmpd # | Structure | q | Y | Het | Name |
|---|---|---|---|---|---|
| 374 | 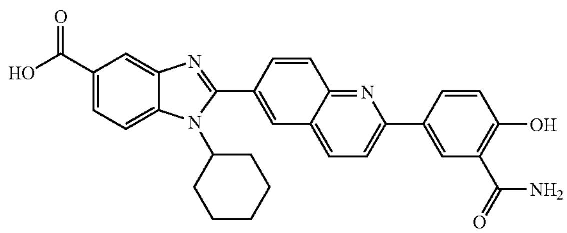 | 1 | 3-carbamoyl-4-hydroxy-phenyl | quinolin-6-yl | 2-[2-(3-carbamoyl-4-hydroxy-phenyl)-quinolin-6-yl]-1-cyclohexyl-1H-benzoimidazole-5-carboxylic acid |
| 375 | 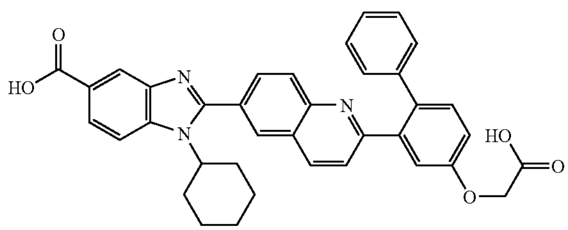 | 1 | 4-carboxy-methoxy-biphen-2-yl | quinolin-6-yl | 2-[2-(4-carboxymethoxy-biphen-2-yl)-quinolin-6-yl]-1-cyclohexyl-1H-benzoimidazole-5-carboxylic acid |
| 376 | 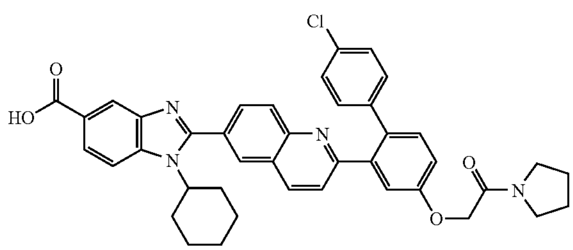 | 1 | 4'-chloro-4-(2-oxo-2-pyrrolidin-1-yl-ethoxy)-biphen-2-yl | quinolin-6-yl | 2-{2-[4'-chloro-4-(2-oxo-2-pyrrolidin-1-yl-ethoxy)-biphen-2-yl]-quinolin-6-yl}-1-cyclohexyl-1H-benzoimidazole-5-carboxylic acid |
| 377 | 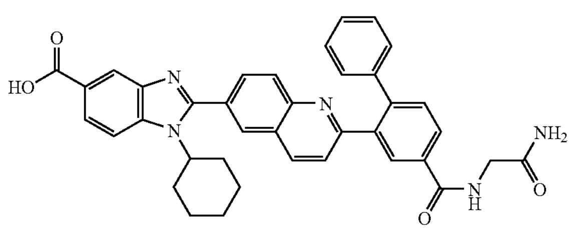 | 1 | 4-(carbamoyl methyl-carbamoyl)-biphen-2-yl | 2-[4-(carbamoyl-methyl-carbamoyl)-biphen-2-yl]-quinolin-6-yl | 2-{2-[4-(carbamoylmethyl-carbamoyl)-biphen-2-yl]-quinolin-6-yl}-1-cyclohexyl-1H-benzoimidazole-5-carboxylic acid |
| 378 | 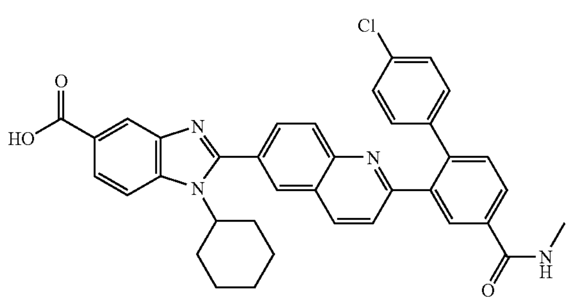 | 1 | 4'-chloro-4-methyl-carbamoyl-biphen-2-yl | quinolin-6-yl | 2-[2-(4'-chloro-4-methylcarbamoyl-biphen-2-yl)-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 379 | 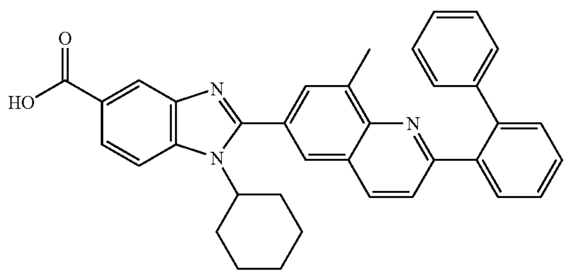 | 2 | biphen-2-yl AND methyl | quinolin-6-yl | 2-(2-biphen-2-yl-8-methyl-quinolin-6-yl)-1-cyclohexyl-1H-benzoimidazole-5-carboxylic acid |
| 380 | 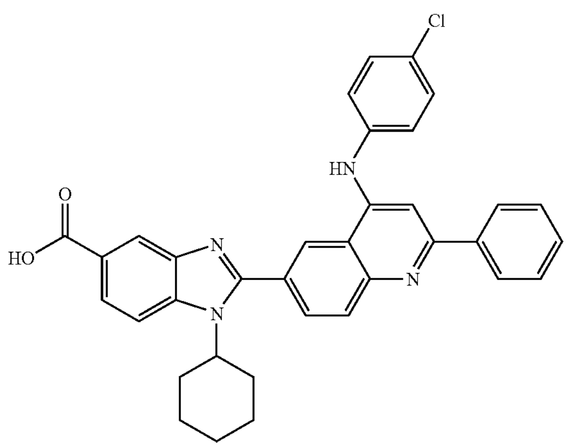 | 2 | (4-chloro-phenyl)-amino AND phenyl | quinolin-6-yl | 2-[4-(4-chloro-phenylamino)-2-phenyl-quinolin-6-yl]-1-cyclohexyl-1H-benzoimidazole-5-carboxylic acid |
| 381 | 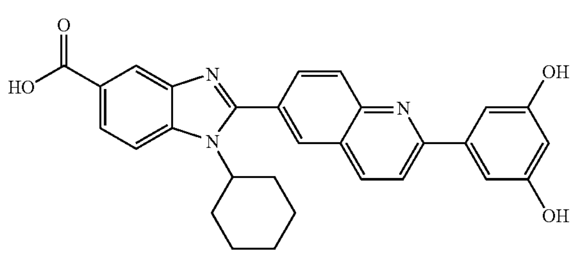 | 1 | 3,5-dihydroxy-phenyl | quinolin-6-yl | 1-cyclohexyl-2-[2-(3,5-dihydroxy-phenyl)-quinolin-6-yl]-1H-benzoimidazole-5-carboxylic acid |
| 382 | 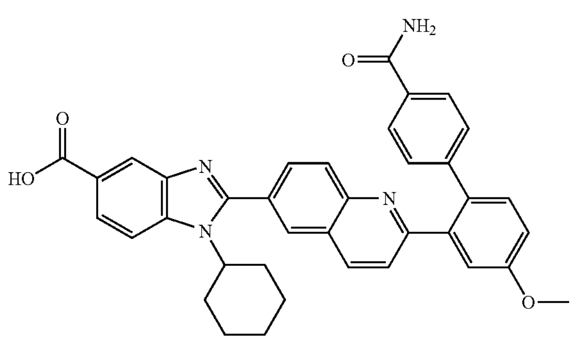 | 1 | 4'-carbamoyl-4-methoxy-biphen-2-yl | quinolin-6-yl | 2-[2-(4'-carbamoyl-4-methoxy-biphen-2-yl)-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 383 | 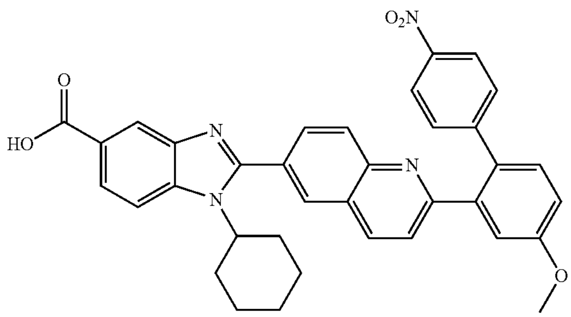 | 1 | 4-methoxy-4'-nitro-biphen-2-yl | quinolin-6-yl | 1-cyclohexyl-2-[2-(4-methoxy-4'-nitro-biphen-2-yl)-quinolin-6-yl]-1H-benzoimidazole-5-carboxylic acid |
| 384 | 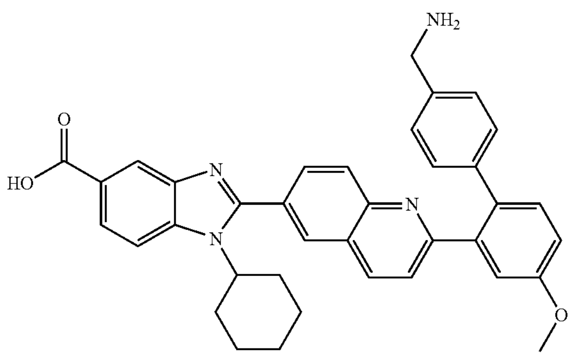 | 1 | 4'-amino-methyl-4-methoxy-biphen-2-yl | quinolin-6-yl | 2-[2-[4'-aminomethyl-4-methoxy-biphen-2-yl]-quinolin-6-yl]-1-cyclohexyl-1H-benzoimidazole-5-carboxylic acid |
| 385 | 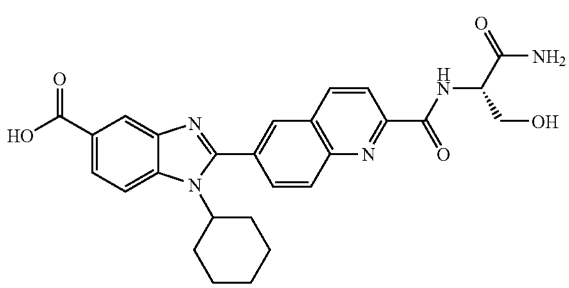 | 1 | 1-carbamoyl-2-hydroxy-ethyl-carbamoyl | quinolin-6-yl | 2-[2-(1-carbamoyl-2-hydroxyethylcarbamoyl)-quinolin-6-yl]-1-cyclohexyl-1H-benzoimidazole-5-carboxylic acid |
| 386 | 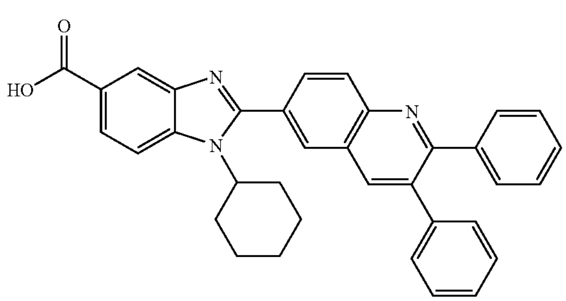 | 2 | Phenyl AND phenyl | quinolin-6-yl | 1-cyclohexyl-2-(2,3-diphenyl-quinolin-6-yl)-1H-benzoimidazole-5-carboxylic acid |

TABLE I-continued

| Cmpd # Structure | q | Y | Het | Name |
|---|---|---|---|---|
| 387 | 1 | 4'-chloro-biphen-2-yl | quinolin-6-yl | 2-[2-(4'-chloro-biphen-2-yl)-quinolin-6-yl]-1-cyclohexyl-1H-benzoimidazole-5-carboxylic acid |
| 388 | 2 | biphen-2-yl AND fluoro | quinolin-6-yl | 2-(2-biphen-2-yl-7-fluoro-quinolin-6-yl)-1-cyclohexyl-1H-benzoimidazole-5-carboxylic acid |
| 389 | 2 | p-tolyl AND p-tolyl | quinoxalin-6-yl | 1-cyclohexyl-2-(2,3-di-p-tolylquinoxalin-6-yl)-1H-benzoimidazole-5-carboxylic acid |
| 390 | 1 | biphen-4-yl | quinolin-6-yl | 2-(2-biphen-4-yl-quinolin-6-yl)-1-cyclohexyl-1H-benzoimidazole-5-carboxylic acid |

TABLE I-continued

| Cmpd # | q | Y | Het | Name |
| --- | --- | --- | --- | --- |
| 391 | 1 | 2-amino-4-methyl-thiazol-5-yl | quinolin-6-yl | 2-[2-(2-amino-4-methyl-thiazol-5-yl)-quinolin-6-yl]-1-cyclohexyl-1H-benzoimidazole-5-carboxylic acid |
| 392 | 1 | 3-hydroxy-propyl | quinolin-6-yl | 1-cyclohexyl-2-[2-(3-hydroxy-propyl)-quinolin-6-yl]-1H-benzoimidazole-5-carboxylic acid |
| 393 | 1 | 4-carboxy-methoxy-4'-chloro-biphen-2-yl | quinolin-6-yl | 2-[2-(4-carboxymethyl-4'-chloro-biphen-2-yl)-quinolin-6-yl]-1-cyclohexyl-1H-benzoimidazole-5-carboxylic acid |
| 394 | 1 | 7-bromo-5-methoxy-benzofuran-2-yl | quinolin-6-yl | 2-[2-(7-bromo-5-methoxy-benzofuran-2-yl)-quinolin-6-yl]-1-cyclohexyl-1H-benzoimidazole-5-carboxylic acid |
| 395 | 1 | biphen-2-yl | quinolin-6-yl | 2-(2-biphen-2-yl-quinolin-6-yl)-1-cyclohexyl-1H-benzoimidazole-5-carboxylic acid |

TABLE I-continued

| Cmpd # | Structure | q | Y | Het | Name |
|---|---|---|---|---|---|
| 396 | 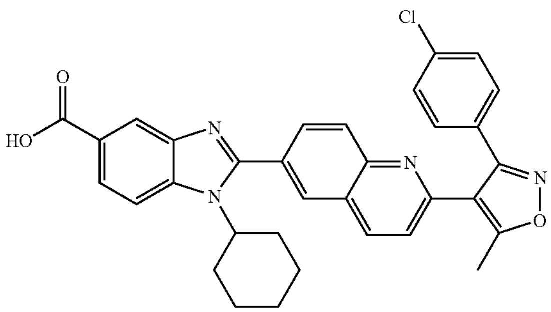 | 1 | 3-(4-chloro-phenyl)-5-methyl-isoxazol-4-yl | quinolin-6-yl | 2-{2-(3-(4-chloro-phenyl)-5-methyl-isoxazol-4-yl]-quinolin-6-yl}-1-cyclohexyl-1H-benzoimidazole-5-carboxylic acid |
| 397 | 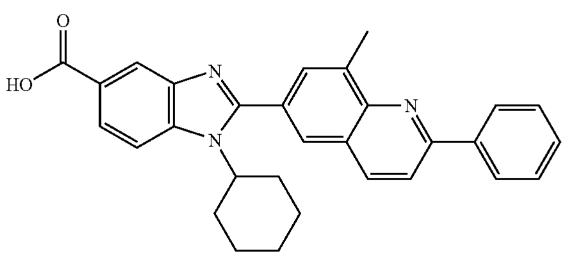 | 2 | Methyl AND phenyl | quinolin-6-yl)- | 1-cyclohexyl-2-(8-methyl-2-phenyl-quinolin-6-yl)-1H-benzoimidazole-5-carboxylic acid |
| 398 | 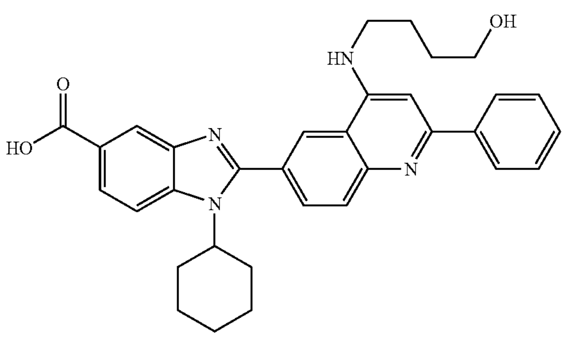 | 2 | 4-hydroxy-butylamino AND phenyl | quinolin-6-yl | 1-cyclohexyl-2-[4-(4-hydroxy-butylamino)-2-phenyl-quinolin-6-yl]-1H-benzoimidazole-5-carboxylic acid |
| 399 | 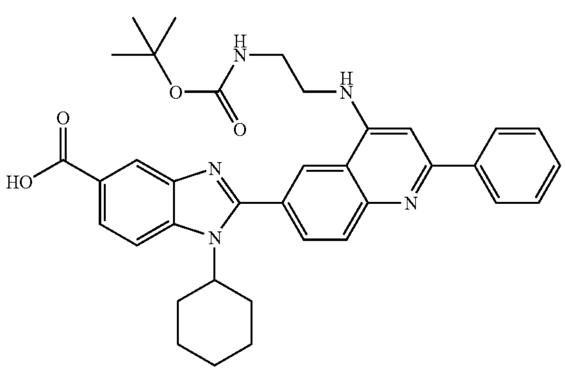 | 2 | 2-tert-butoxy-carbonyl-carbonyl-aminoethyl-amino AND phenyl | quinolin-6-yl | 2-[4-(2-tert-butoxycarbonylamino-ethylamino)-2-phenyl-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 400 | 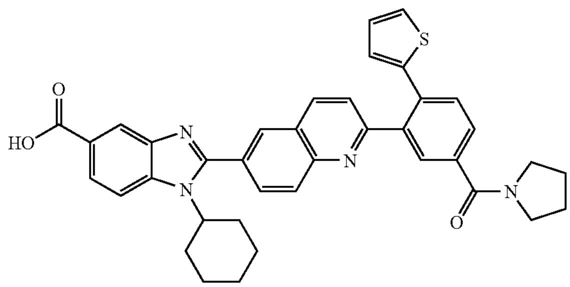 | 1 | 5-(pyrrolidinyl-1-carbonyl)-2-thiophen-2-yl | quinolin-6-yl | 1-cyclohexyl-2-{2-[5-(pyrrolidinyl-1-carbonyl)-2-thiophen-2-yl]quinolin-6-yl}-1H-benzoimidazole-5-carboxylic acid |
| 401 | 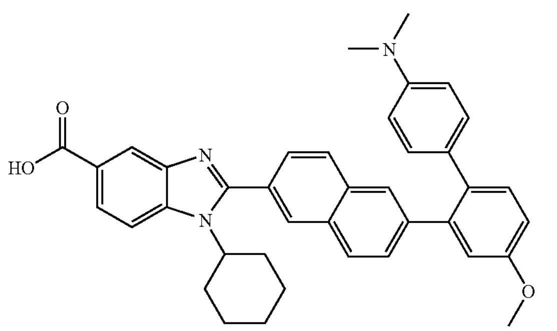 | 1 | 4'-dimethyl-amino-4-methoxy-biphen-2-yl | quinolin-6-yl | 1-cyclohexyl-2-[2-(4'-dimethylamino-4-methoxy-biphen-2-yl)-quinolin-6-yl]-1H-benzoimidazole-5-carboxylic acid |
| 402 | 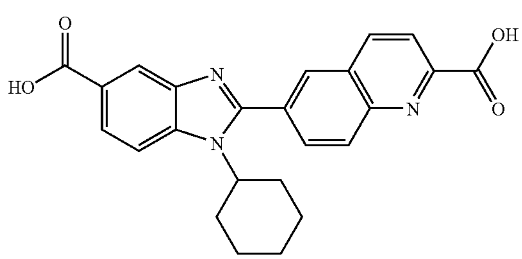 | 1 | carboxyl | quinolin-6-yl | 6-(5-carboxy-1-cyclohexyl-1H-benzimidazol-2-yl)quinoline-2-carboxylic acid |
| 403 | 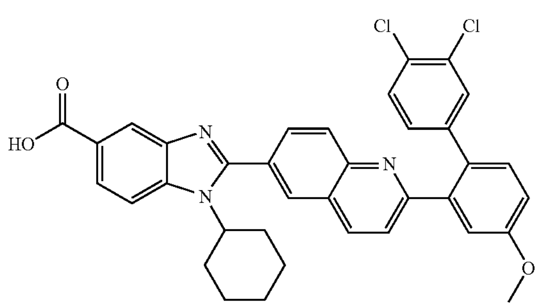 | 1 | 3',4'-dichloro-4-methoxy-biphen-2-yl | quinolin-6-yl | 1-cyclohexyl-2-[2-(3',4'-dichloro-4-methoxy-biphen-2-yl)-quinolin-6-yl]-1H-benzoimidazole-5-carboxylic acid |

TABLE I-continued

| Cmpd # | Structure | q | Y | Het | Name |
|---|---|---|---|---|---|
| 404 | 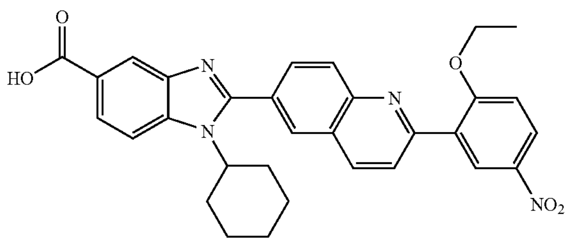 | 1 | 2-ethoxy-5-nitrophenyl | quinolin-6-yl | 1-cyclohexyl-2-[2-(2-ethoxy-5-nitrophenyl)-quinolin-6-yl]-1H-benzoimidazole-5-carboxylic acid |
| 405 | 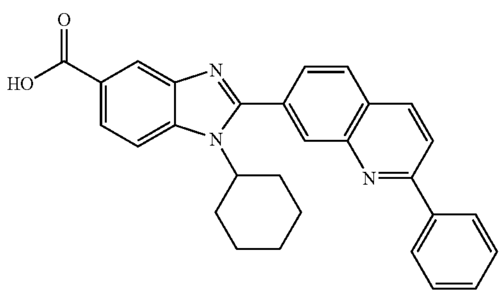 | 1 | Phenyl | quinolin-7-yl | 1-cyclohexyl-2-(2-phenyl-quinolin-7-yl)-1H-benzoimidazole-5-carboxylic acid |
| 406 | 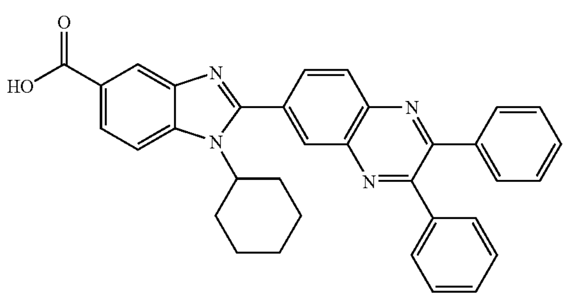 | 2 | Phenyl AND phenyl | quinoxalin-6-yl | cyclohexyl-2-(2,3-diphenylquinoxalin-6-yl)-1H-benzimidazole-5-carboxylic acid |
| 407 | 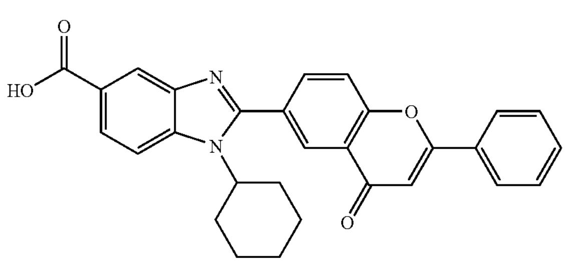 | 1 | Phenyl | 4-oxo-4H-chromen-6-yl | cyclohexyl-2-(4-oxo-2-phenyl-4H-chromen-6-yl)-1H-benzoimidazole-5-carboxylic acid |

TABLE I-continued

| Cmpd # Structure | q | Y | Het | Name |
|---|---|---|---|---|
| 408 | 2 | 4'-chloro-biphen-2-yl AND fluoro | quinolin-6-yl | 2-[2-(4'-chloro-biphen-2-yl)-7-fluoro-quinolin-6-yl]-1-cyclohexyl-1H-benzoimidazole-5-carboxylic acid |
| 409 | 2 | 4-fluoro-phenyl AND 4-fluoro-phenyl | quinoxalin-6-yl | 2-[2,3-bis-(4-fluorophenyl)quinoxalin-6-yl]-1-cyclohexyl-1H-benzoimidazole-5-carboxylic acid |
| 410 | 2 | biphen-2-yl AND fluoro | quinolin-6-yl | 2-(2-biphen-2-yl-7-fluoro-quinolin-6-yl)-1-cyclohexyl-1H-benzoimidazole-5-yl]-(4-hydroxy-piperidin-1-yl)-methanone |
| 411 | 1 | 7-hydroxy-benzofuran-2-yl | quinolin-6-yl | 1-cyclohexyl-2-[2-(7-hydroxy-benzofuran-2-yl)-quinolin-6-yl]-1H-benzoimidazole-5-carboxylic acid |

TABLE I-continued

| Cmpd # | Structure | q | Y | Het | Name |
|---|---|---|---|---|---|
| 412 | 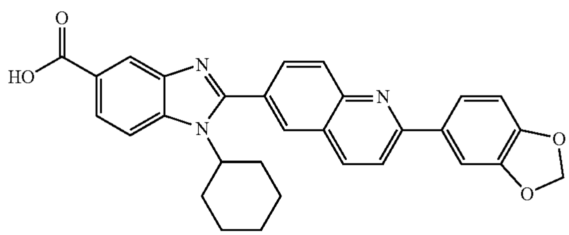 | 1 | benzo[1,3]-dioxol-5-yl | quinolin-6-yl | 2-(2-benzo[1,3]dioxol-5-yl-quinolin-6-yl)-1-cyclohexyl-1H-benzoimidazole-5-carboxylic acid |
| 413 | 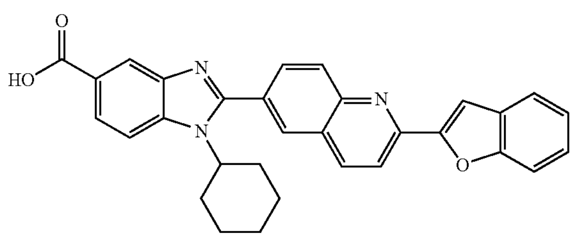 | 1 | benzofuran-2-yl | quinolin-6-yl | 2-(2-benzofuran-2-yl-quinolin-6-yl)-1-cyclohexyl-1H-benzoimidazole-5-carboxylic acid |
| 414 | 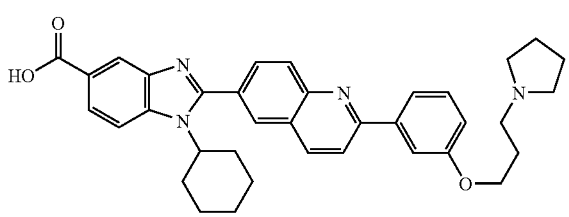 | 1 | 3-(3-pyrrolidin-1-yl-propoxy)phenyl | quinolin-6-yl | 1-cyclohexyl-2-{2-[3-(3-pyrrolidin-1-yl-propoxy)-phenyl]-quinolin-6-yl}-1H-benzoimidazole-5-carboxylic acid |
| 415 | 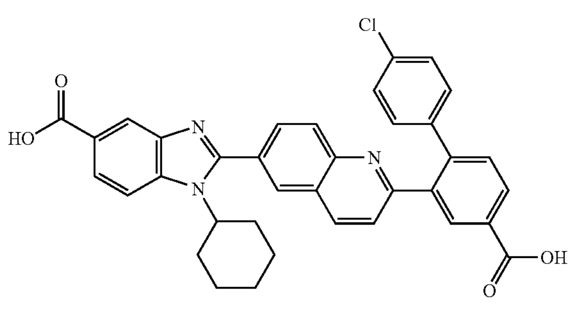 | 1 | 4-carboxy-4'-chloro-biphen-2-yl | quinolin-6-yl | 2-[2-(4-carboxy-4'-chloro-biphen-2-yl)-quinolin-6-yl]-1-cyclohexyl-1H-benzoimidazole-5-carboxylic acid |
| 416 | 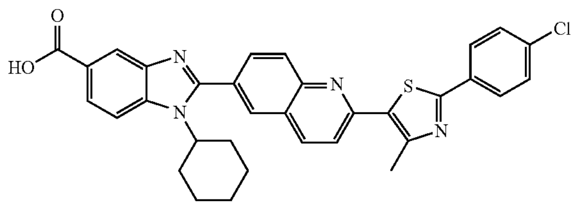 | 1 | 2-(4-chloro-phenyl)-4-methyl-thiazol-5-yl | quinolin-6-yl | 2-{2-[2-(4-chloro-phenyl)-4-methyl-thiazol-4-yl]-quinolin-6-yl}-1-cyclohexyl-1H-benzoimidazole-5-carboxylic acid |

TABLE I-continued

| Cmpd # | Structure | q | Y | Het | Name |
|---|---|---|---|---|---|
| 417 | 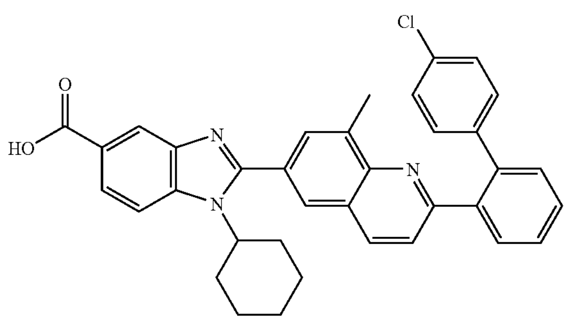 | 2 | 4'-chloro-biphen-2-yl AND methyl | quinolin-6-yl | 2-[2-(4'-chloro-biphen-2-yl)-8-methyl-quinolin-6-yl]-1-cyclohexyl-1H-benzoimidazole-5-carboxylic acid |
| 418 | 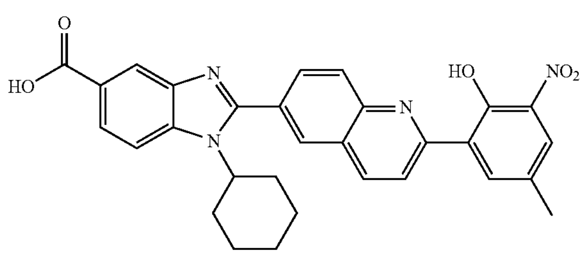 | 1 | 2-hydroxy-5-methyl-3-nitrophenyl | quinolin-6-yl | 1-cyclohexyl-2-[2-(2-hydroxy-5-methyl-3-nitro-phenyl)-quinolin-6-yl]-1H-benzoimidazole-5-carboxylic acid |
| 419 | 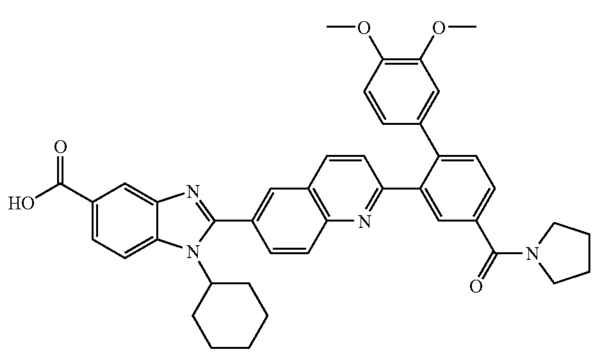 | 1 | 3',4'-dimethoxy-4-(pyrrolidinyl-1-carbonyl)-biphen-2-yl | quinolin-6-yl | 1-cyclohexyl-2-{2-(3',4'-dimethoxy-4-(pyrrolidine-1-carbonyl)biphen-2-yl]-quinolin-6-yl}-1H-benzoimidazole-5-carboxylic acid |
| 420 | 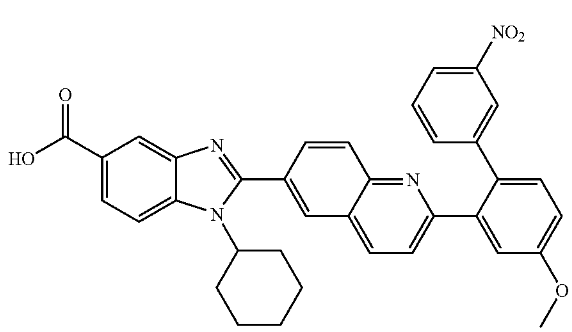 | 1 | 4-methoxy-3'-nitro-biphen-2-yl | quinolin-6-yl | 1-cyclohexyl-2-[2-(4-methoxy-3'-nitro-biphen-2-yl)-quinolin-6-yl]-1H-benzoimidazole-5-carboxylic acid |

TABLE I-continued

| Cmpd # | Structure | q | Y | Het | Name |
|---|---|---|---|---|---|
| 421 | 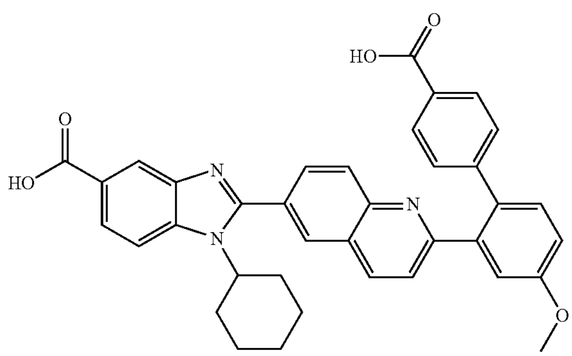 | 1 | 4'-carboxy-4-methoxy-biphen-2-yl | quinolin-6-yl | 2-[2-(4'-carboxy-4-methoxy-biphen-2-yl)-quinolin-6-yl]-1-cyclohexyl-1H-benzoimidazole-5-carboxylic acid |
| 422 | 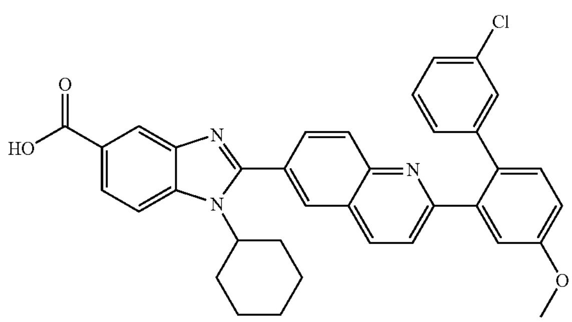 | 1 | 3'-chloro-4-methoxy-biphen-2-yl | quinolin-6-yl | 2-[2-(3'-chloro-4-methoxy-biphen-2-yl)-quinolin-6-yl]-1-cyclohexyl-1H-benzoimidazole-5-carboxylic acid |
| 423 | 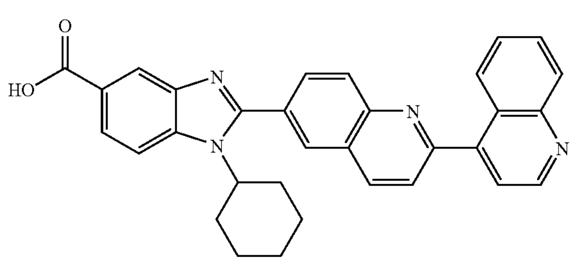 | 1 | quinolin-4-yl | quinolin-6-yl | 2-[2,4']biquinolinyl-6-yl-1-cyclohexyl-1H-benzoimidazole-5-carboxylic acid |
| 424 | 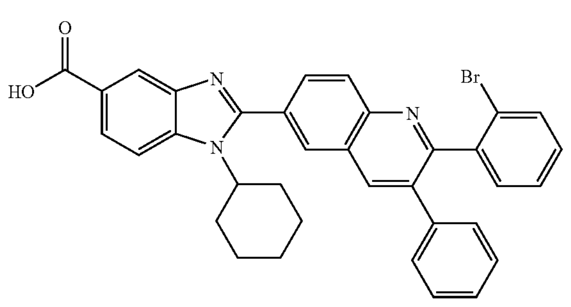 | 2 | 2-bromo-phenyl AND phenyl | quinolin-6-yl | 2-[2-(2-bromo-phenyl)-3-phenyl-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 425 | 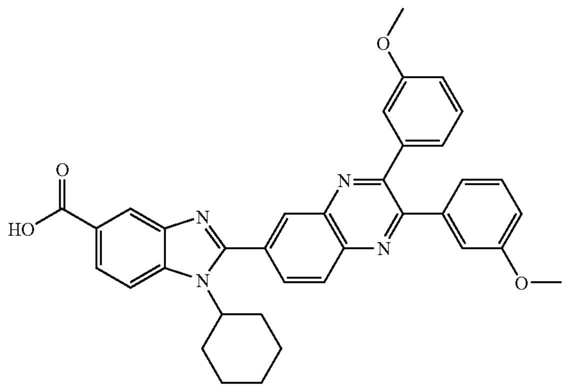 | 2 | 3-methoxy-phenyl AND 3-methoxy-phenyl | quinoxalin-6-yl | 2-[2,3-bis-(3-methoxyphenyl)quinoxalin-6-yl]-1-cyclohexyl-1H-benzoimidazole-5-carboxylic acid |
| 426 | 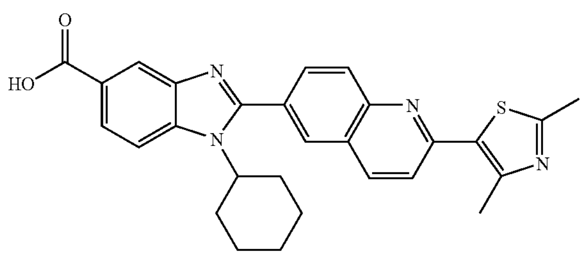 | 1 | 2,4-dimethyl-thiazol-5-yl | quinolin-6-yl | 1-cyclohexyl-2-[2-(2,4-dimethyl-thiazol-5-yl)-quinolin-6-yl]-1H-benzoimidazole-5-carboxylic acid |
| 427 | 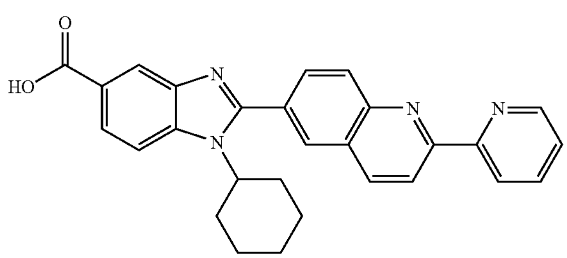 | 1 | pyridin-2-yl | quinolin-6-yl | 1-cyclohexyl-2-(2-pyridin-2-yl-quinolin-6-yl)-1H-benzoimidazole-5-carboxylic acid |
| 428 | 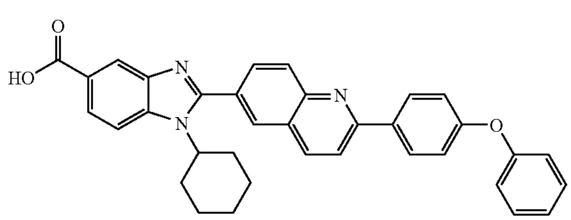 | 1 | 4-phenoxy-phenyl | quinolin-6-yl | 1-cyclohexyl-2-[2-(4-phenoxy-phenyl)-quinolin-6-yl]-1H-benzoimidazole-5-carboxylic acid |
| 429 | 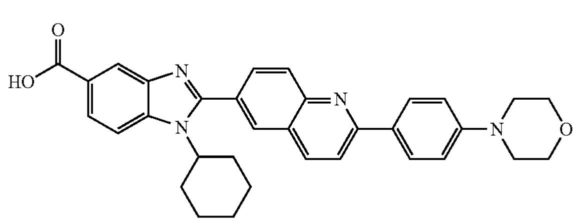 | 1 | 4-morph-olin-4-yl-phenyl | quinolin-6-yl | 1-cyclohexyl-2-[2-(4-morpholin-4-yl-phenyl)-quinolin-6-yl]-1H-benzoimidazole-5-carboxylic acid |

TABLE I-continued

| Cmpd # | Structure | q | Y | Het | Name |
|---|---|---|---|---|---|
| 430 | 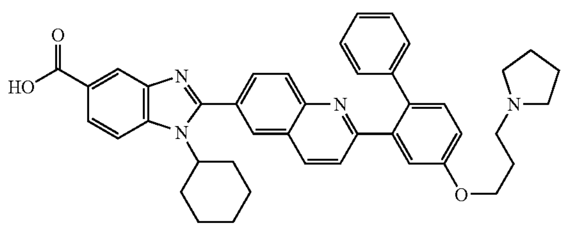 | 1 | 4-(3-pyrrolidin-1-yl-propoxy)-biphen-2-yl | quinolin-6-yl | 1-cyclohexyl-2-{2-[4-(3-pyrrolidin-1-yl-propoxy)-biphen-2-yl]-quinolin-6-yl}-1H-benzoimidazole-5-carboxylic acid |
| 431 | 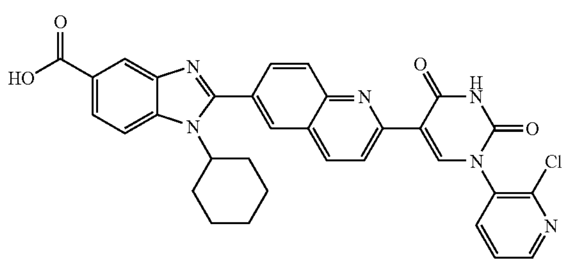 | 1 | 1-(2-chloro-pyridin-3-yl)-2,4-dioxo-1,2,3,4-tetrahydro-pyrimidin-5-yl | quinolin-6-yl | 2-{2-[1-(2-chloro-pyridin-3-yl)-2,4-dioxo-1,2,3,4-tetrahydro-pyrimidin-5-yl]-quinolin-6-yl}-1-cyclohexyl-1H-benzoimidazole-5-carboxylic acid |
| 432 | 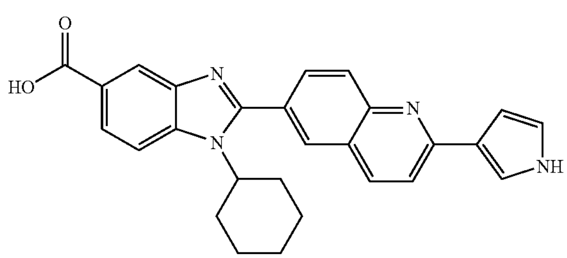 | 1 | 1H-pyrrol-3-yl | quinolin-6-yl | 1-cyclohexyl-2-[2-(1H-pyrrol-3-yl)-quinolin-6-yl]-1H-benzoimidazole-5-carboxylic acid |
| 433 | 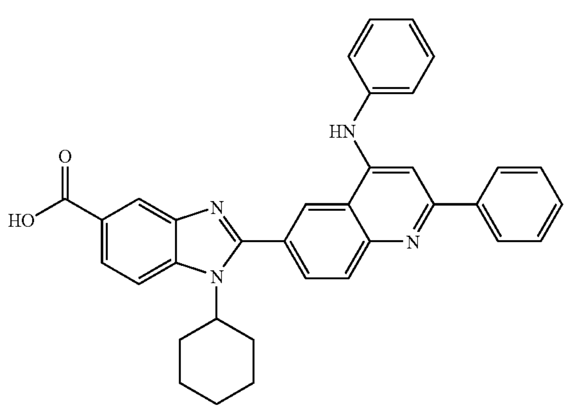 | 2 | Phenyl AND Phenyl-amino | quinolin-6-yl | 1-cyclohexyl-2-(2-phenyl-4-phenylamino-quinolin-6-yl)-1H-benzoimidazole-5-carboxylic acid |

TABLE I-continued

| Cmpd # | Structure | q | Y | Het | Name |
|---|---|---|---|---|---|
| 434 | 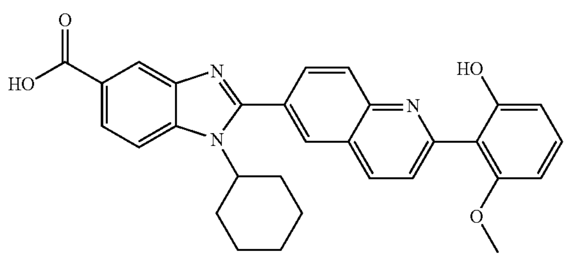 | 1 | 2-hydroxy-6-methoxy-phenyl | quinolin-6-yl | 1-cyclohexyl-2-[2-(2-hydroxy-6-methoxy-phenyl)-quinolin-6-yl]-1H-benzoimidazole-5-carboxylic acid |
| 435 | 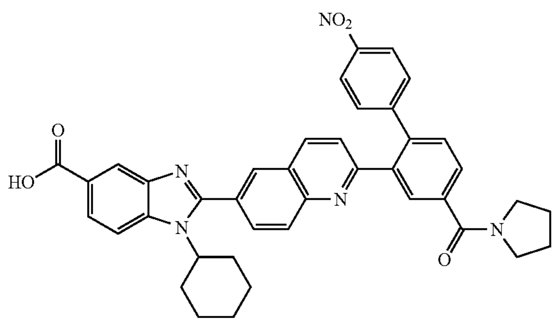 | 1 | 2-[4'-nitro-4-pyrrolidinyl-1-carbonyl)-biphen-2-yl) | quinolin-6-yl | 1-cyclohexyl-2-{2-[4'-nitro-4-(pyrrolidinyl-1-carbonyl)biphen-2-yl]quinolin-6-yl}-1H-benzimidazole-5-carboxylic acid |
| 436 | 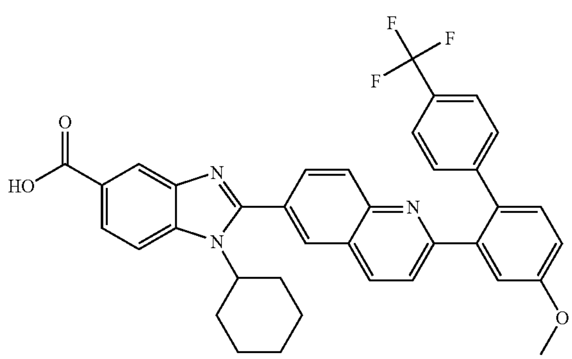 | 1 | 4-methoxy-4'-trifluoro-methyl-biphen-2-yl | quinolin-6-yl | 1-cyclohexyl-2-[2-(4-methoxy-4'-trifluoromethyl-biphen-2-yl)-quinolin-6-yl]-1H-benzoimidazole-5-carboxylic acid |
| 437 | 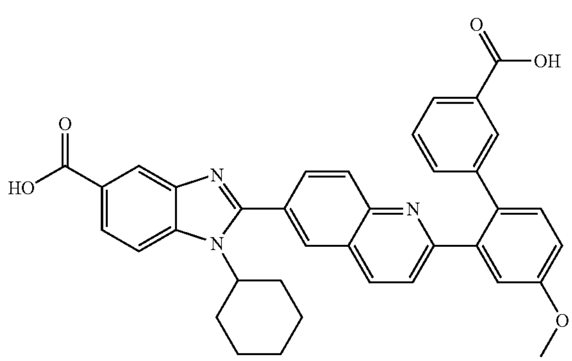 | 1 | 3'-carboxy-4-methoxy-biphen-2-yl | quinolin-6-yl | 2-[2-(3'-carboxy-4-methoxy-biphen-2-yl)-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 438 | 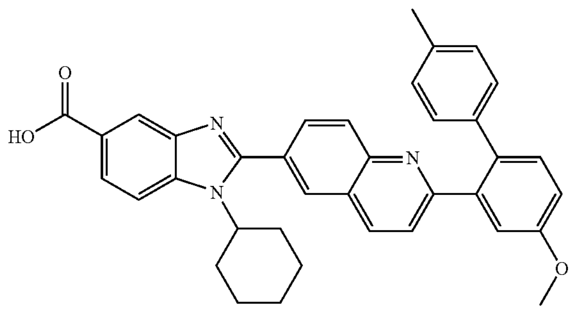 | 1 | 4-methoxy-4'-methyl-biphen-2-yl | quinolin-6-yl | 1-cyclohexyl-2-[2-(4-methoxy-4'-methyl-biphen-2-yl)-quinolin-6-yl]-1H-benzoimidazole-5-carboxylic acid |
| 439 | 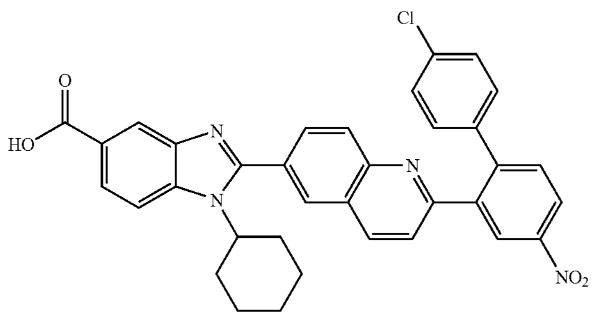 | 1 | 4'-chloro-4-nitrobiphen-2-yl | quinolin-6-yl | 2-[2-(4'-chloro-4-nitro-biphen-2-yl)-quinolin-6-yl]-1-cyclohexyl-1H-benzoimidazole-5-carboxylic acid |
| 440 | 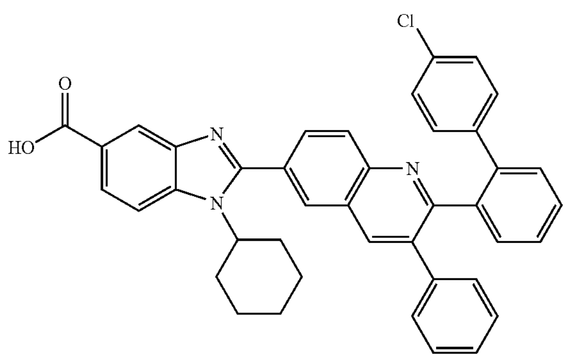 | 2 | 4'-chloro-biphen-2-yl AND phenyl | quinolin-6-yl | 2-[2-(4'-chloro-biphen-2-yl)-3-phenyl-quinolin-6-yl]-1-cyclohexyl-1H-benzoimidazole-5-carboxylic acid |
| 441 | 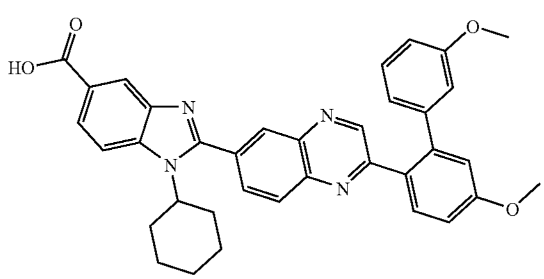 | 2 | 4-methoxy-phenyl AND 4-methoxy-phenyl | quinoxalin-6-yl | 2-[2,3-bis-(4-methoxyphenyl)quinoxalin-6-yl]-1-cyclohexyl-1H-benzoimidazole-5-carboxylic acid |

TABLE I-continued

| Cmpd # | Structure | q | Y | Het | Name |
|---|---|---|---|---|---|
| 442 | 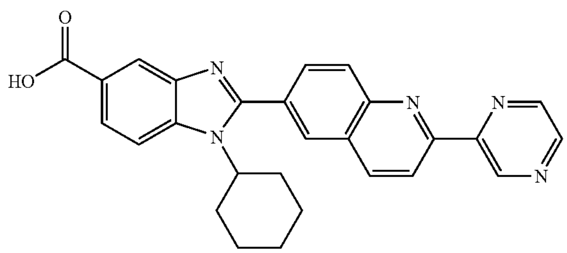 | 1 | pyrazin-2-yl | quinolin-6-yl | 1-cyclohexyl-2-(2-pyrazin-2-yl-quinolin-6-yl)-1H-benzoimidazole-5-carboxylic acid |
| 443 | 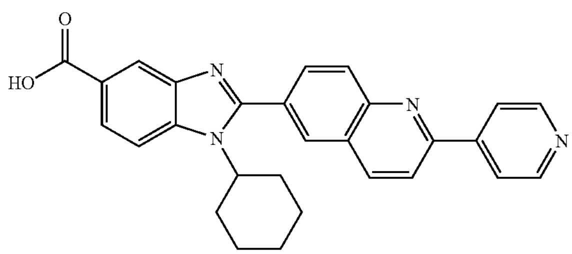 | 1 | pyridin-4-yl | quinolin-6-yl | 1-cyclohexyl-2-(2-pyridin-4-yl-quinolin-6-yl)-1H-benzoimidazole-5-carboxylic acid |
| 444 | 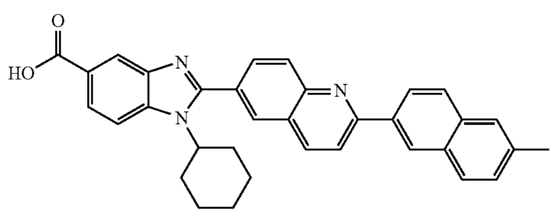 | 1 | 6-methyl-naphthalen-2-yl | quinolin-6-yl | 1-cyclohexyl-2-[2-(6-methyl-naphthalen-2-yl)-quinolin-6-yl]-1H-benzoimidazole-5-carboxylic acid |
| 445 | 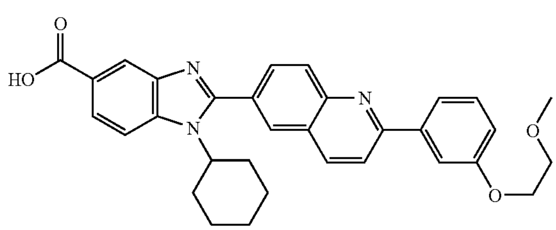 | 1 | 3-(2-methoxy-ethoxy)-phenyl | quinolin-6-yl | 1-cyclohexyl-2-{2-[3-(2-methoxy-ethoxy)-phenyl]-quinolin-6-yl}-1H-benzoimidazole-5-carboxylic acid |
| 446 | 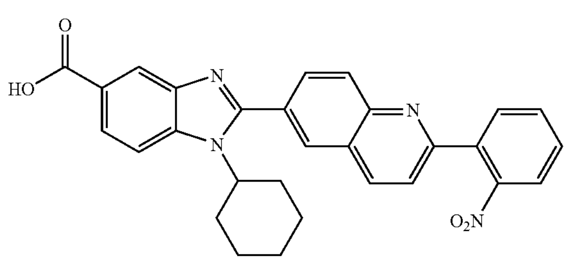 | 1 | 2-nitro-phenyl | quinolin-6-yl | 2-[6-(2-nitrophenyl)-quinolin-6-yl]-1H-benzoimidazole-5-carboxylic acid |

TABLE I-continued

| Cmpd # | Structure | q | Y | Het | Name |
|---|---|---|---|---|---|
| 447 | 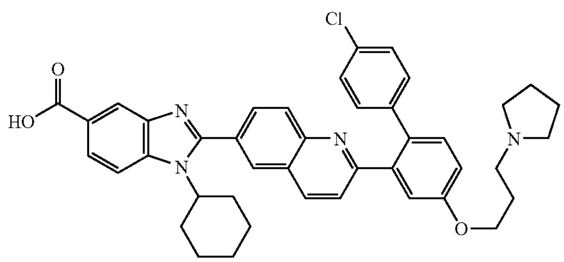 | 1 | 4'-chloro-4-(3-pyrrolidin-1-yl-propoxy)-biphen-2-yl | quinolin-6-yl | 2-{2-[4'-chloro-4-(3-pyrrolidin-1-yl-propoxy)-biphen-2-yl]-quinolin-6-yl}-1-cyclohexyl-1H-benzoimidazole-5-carboxylic acid |
| 448 | 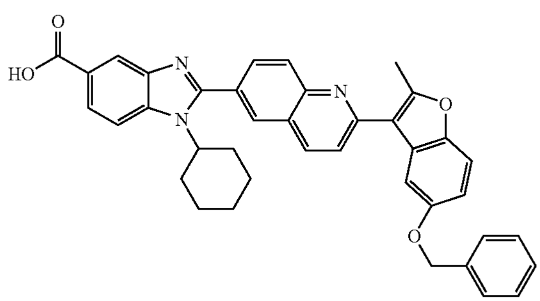 | 1 | 5-benzyl-oxy-2-methyl-benzofuran-3-yl | quinolin-6-yl | 2-[2-(5-benzyloxy-2-methyl-benzofuran-3-yl)quinolin-6-yl]-1-cyclohexyl-1H-benzoimidazole-5-carboxylic acid |
| 449 | 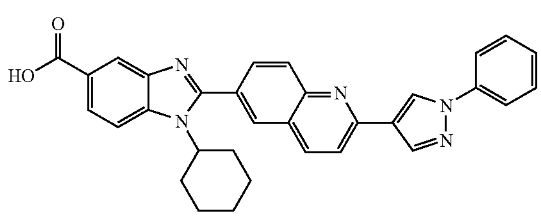 | 1 | 1-phenyl-1H-pyrazol-4-yl | quinolin-6-yl | 1-cyclohexyl-2-[2-(1-phenyl-1H-pyrazol-4-yl)-quinolin-6-yl]-1H-benzoimidazole-5-carboxylic acid |
| 450 | 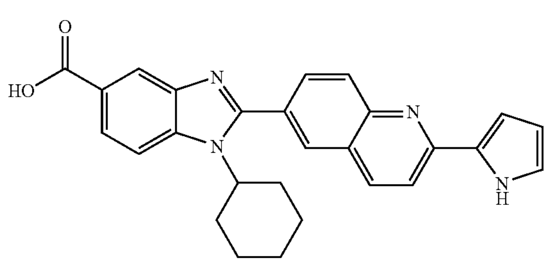 | 1 | 1H-pyrrol-2-yl | quinolin-6-yl | 1-cyclohexyl-2-[2-(1H-pyrrol-2-yl)-quinolin-6-yl]-1H-benzoimidazole-5-carboxylic acid |

TABLE I-continued

| Cmpd # | Structure | q | Y | Het | Name |
|---|---|---|---|---|---|
| 451 | 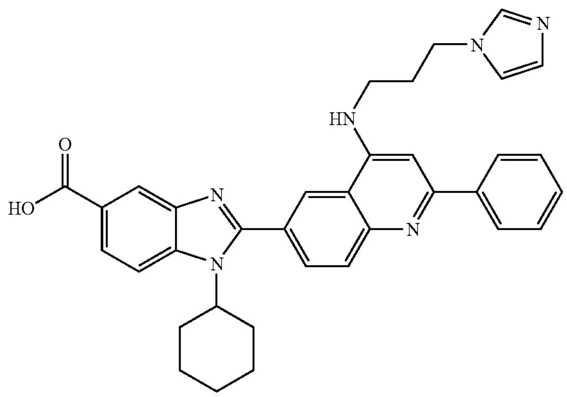 | 1 | (3-imidazol-1-yl-propyl-amino-2-phenyl | quinolin-6-yl | 1-cyclohexyl-2-[4-(3-imidazol-1-yl-propylamino)-2-phenyl)-quinolin-6-yl]-1H-benzoimidazole-5-carboxylic acid |
| 452 | 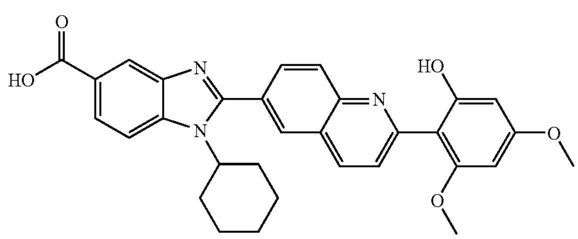 | 1 | 2-hydroxy-4,6-dimethoxy-phenyl | quinolin-6-yl | 1-cyclohexyl-2-[2-(2-hydroxy-4,6-dimethoxy-phenyl)-quinolin-6-yl]-1H-benzoimidazole-5-carboxylic acid |
| 453 | 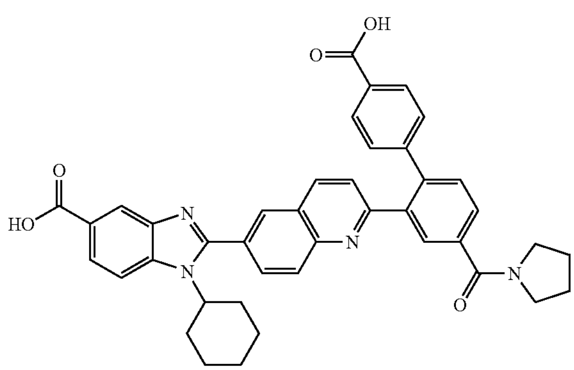 | 1 | 4'-carboxy-4-(pyrrolidine-1-carbonyl)-biphen-2-yl | quinolin-6-yl | 2-{2-[4'-carboxy-4-[(pyrrolidine-1-carbonyl)biphen-2-yl]quinolin-6-yl}-1-cyclohexyl-1H-benzimidazole-5-carboxylic acid |
| 454 | 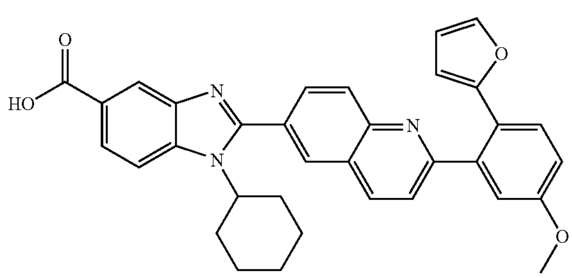 | 1 | 2-furan-2-yl-5-methoxy-phenyl | quinolin-6-yl | 1-cyclohexyl-2-[2-(2-furan-2-yl-5-methoxy-phenyl)-quinolin-6-yl]-1H-benzoimidazole-5-carboxylic acid |

TABLE I-continued

| Cmpd # | Structure | q | Y | Het | Name |
|---|---|---|---|---|---|
| 455 | 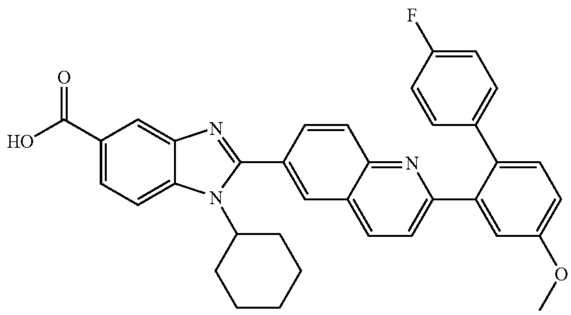 | 1 | 4'-fluoro-4-methoxy-biphen-2-yl | quinolin-6-yl | 1-cylcohexyl-2-[2-(4'-fluoro-4-methoxy-biphen-2-yl)-quinolin-6-yl]-1-benzoimidazole-5-carboxylic acid |
| 456 | 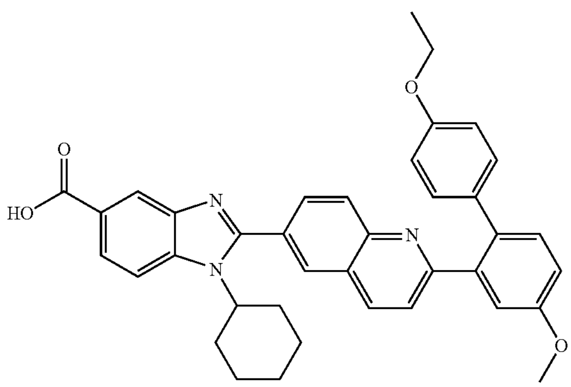 | 1 | 4'-ethoxy-4-methoxy-biphen-2-yl | quinolin-6-yl | 1-cylcohexyl-2-[4'-ethoxy-4-methoxybiphen-2-yl]-1H-benzoimidazole-5-carboxylic acid |
| 457 | 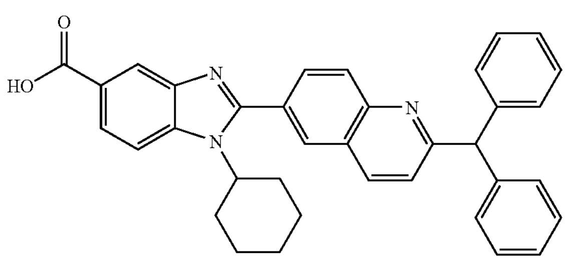 | 1 | Diphenyl-methyl | quinolin-6-yl | 2-(2-dimethylphenyl-quinolin-6-yl)-1-cyclohexyl-1H-benzoimidazole-5-carboxylic acid |
| 458 | 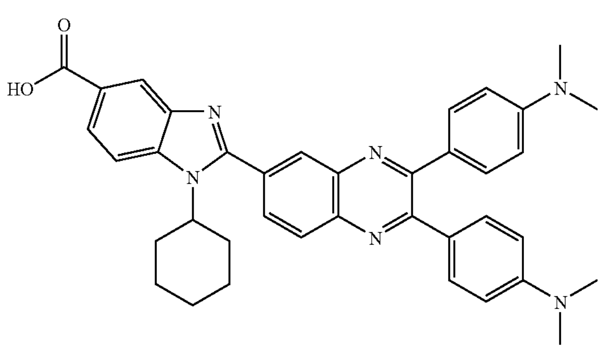 | 2 | 4-dimethyl-amino-phenyl AND 4-dimethyl-amino-phenyl | quinoxalin-6-yl | 2-[2,3-bis-(4-dimethyl-aminophenyl)quinoxalin-6-yl]-1-cyclohexyl-1H-benzoimidazole-5-carboxylic acid |

TABLE I-continued

| Cmpd # | Structure | q | Y | Het | Name |
|---|---|---|---|---|---|
| 459 | 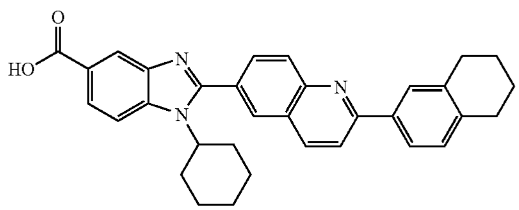 | 1 | 5,6,7,8-tetrahydro-naphthalen-2-yl | quinolin-6-yl | 1-cyclohexyl-2-[5,6,7,8-tetrahydronaphthalen-2-yl]-1H-benzoimidazole-5-carboxylic acid |
| 460 | 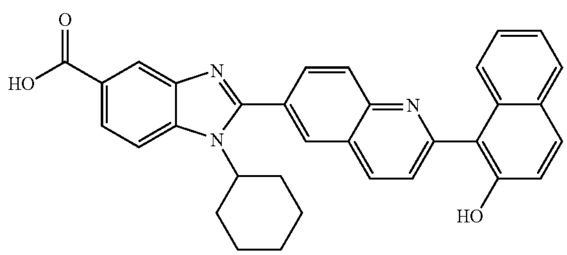 | 1 | 2-hydroxy-naphthalen-1-yl | quinolin-6-yl | 1-cyclohexyl-2-[2-(2-hydroxy-naphthalen-1-yl)-quinolin-6-yl]-1H-benzoimidazole-5-carboxylic acid |
| 461 | 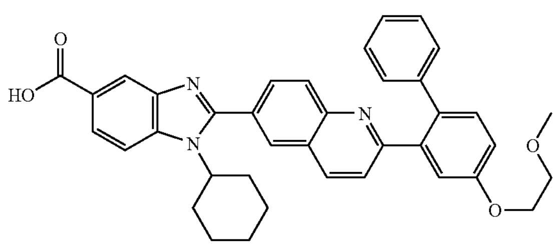 | 1 | 4-(2-methoxy-ethoxy)-biphen-2-yl | quinolin-6-yl | 1-cyclohexyl-2-{2-[4-(2-methoxy-ethoxy)-biphen-2-yl]-quinolin-6-yl}-1H-benzoimidazole-5-carboxylic acid |
| 462 | 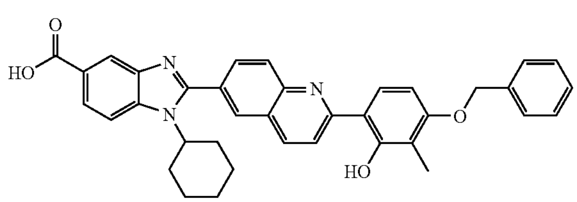 | 1 | 2-(4-benzyloxy-2-hydroxy-3-methyl-phenyl)- | quinolin-6-yl | 2-[2-(4-benzyloxy-2-hydroxy-3-methyl-phenyl)-quinolin-6-yl]-1-cyclohexyl-1H-benzoimidazole-5-carboxylic acid |
| 463 | 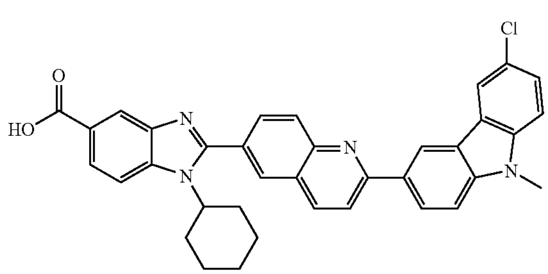 | 1 | 6-chloro-9-methyl-9H-carbazol-3-yl | quinolin-6-yl | 2-[2-(6-chloro-9-methyl-9H-carbazol-3-yl)-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 464 | 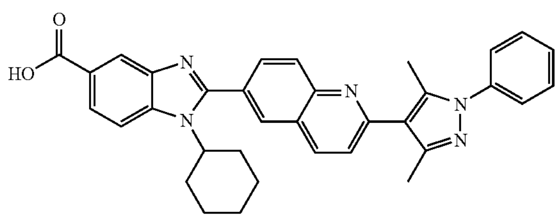 | 1 | 3,5-dimethyl-1-phenyl-1H-pyrazol-4-yl | quinolin-6-yl | 1-cyclohexyl-2-[2-(3,5-dimethyl-1-phenyl-1H-pyrazol-4-yl)-quinolin-6-yl]-1H-benzoimidazole 5-carboxylic aciD |
| 465 | 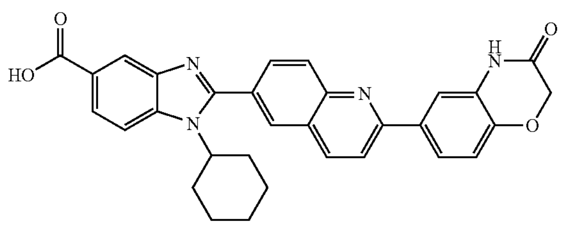 | 1 | 3-oxo-3,4-dihydro-2H-benzo[1,4]-oxazin-6-yl | quinolin-6-yl | 1-cyclohexyl-2-[2-(3-oxo-3,4-dihydro-2H-benzo[1,4]oxazin-6-yl)-quinolin-6-yl]-1H-benzoimidazole-5-carboxylic acid |
| 466 | 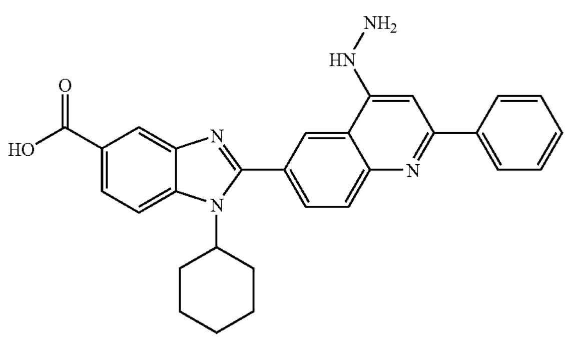 | 2 | hydrazino AND phenyl | quinolin-6-yl | 1-cyclohexyl-2-(4-hydrazino-2-phenyl-quinolin-6-yl)-1H-benzoimidazole-5-carboxylic acid |
| 467 | 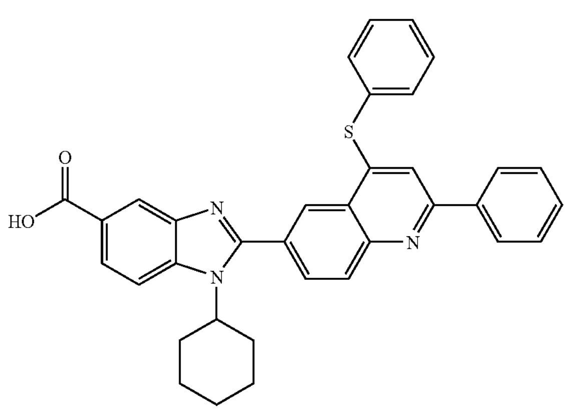 | 2 | phenyl AND Phenyl-sulfanyl | quinolin-6-yl | 1-cyclohexyl-2-(2-phenyl-4-phenylsulfanyl-quinolin-6-yl)-1H-benzoimidazole-5-carboxylic acid |

TABLE I-continued

| Cmpd # | Structure | q | Y | Het | Name |
|---|---|---|---|---|---|
| 468 | 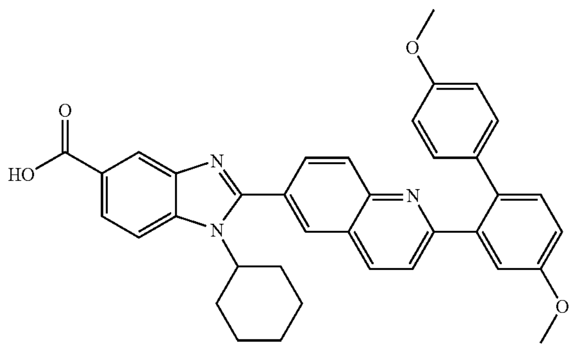 | 1 | 4,4'-dimethoxy-biphen-2-yl | quinolin-6-yl | 1-cyclohexyl-2-[2-(4,4'-dimethoxy-biphen-2-yl)-quinolin-6-yl]-1H-benzoimidazole-5-carboxylic acid |
| 469 | 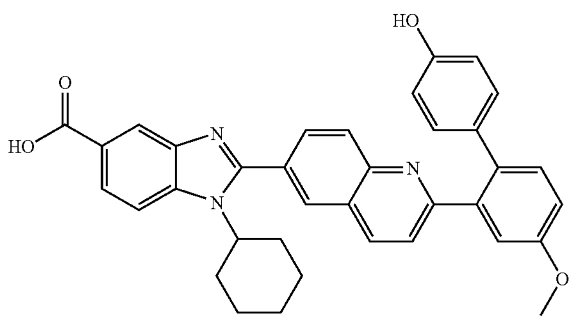 | 1 | 4'-hydroxy-4-methoxy-biphen-2-yl | quinolin-6-yl | 1-cyclohexyl-2-[2-(4'-hydroxy-4-methoxy-biphen-2-yl)-quinolin-6-yl]-1H-benzoimidazole-5-carboxylic acid |
| 470 | 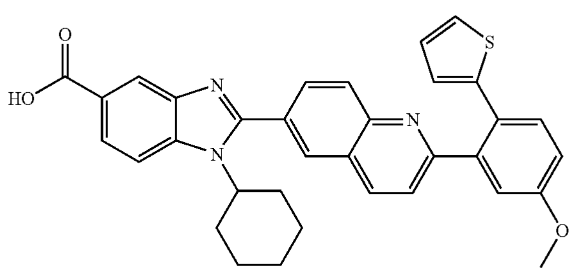 | 1 | 5-methoxy-2-thiophen-2-yl-phenyl | quinolin-6-yl | 1-cyclohexyl-2-[2-(5-methoxy-2-thiophen-2-yl-phenyl)-quinolin-6-yl]-1H-benzoimidazole-5-carboxylic acid |
| 471 | 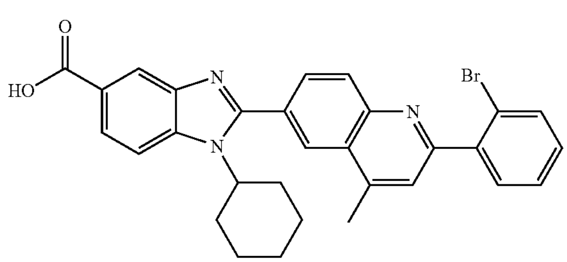 | 2 | 2-bromo-phenyl AND methyl | quinolin-6-yl | 2-[2-(2-bromo-phenyl)-4-methyl-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 472 | 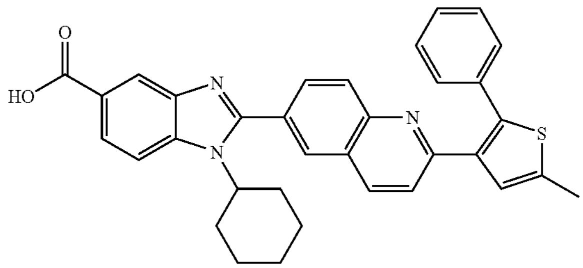 | 1 | 5-methyl-2-phenyl-thiophen-3-yl | quinolin-6-yl | 1-cyclohexyl-2-[2-(5-methyl-2-phenyl-thiophen-3-yl)-quinolin-6-yl]-1H-benzoimidazole-5-carboxylic acid |
| 473 | 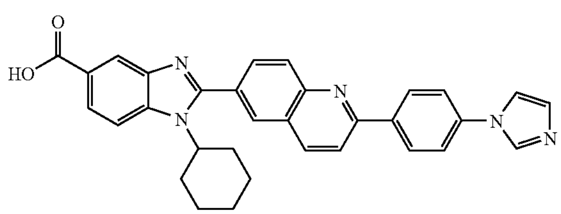 | 1 | 4-imidazol-1-yl-phenyl | quinolin-6-yl | 1-cyclohexyl-2-[2-(4-imidazol-1-yl phenyl)-quinolin-6-yl]-1H-benzoimidazole-5-carboxylic acid |
| 474 | 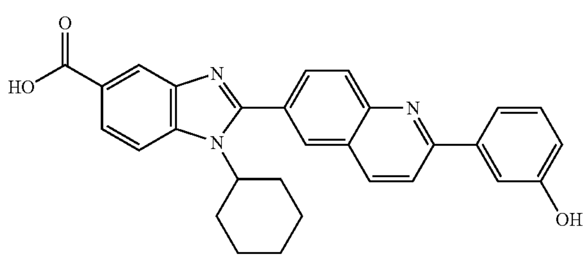 | 1 | 3-hydroxy-phenyl | quinolin-6-yl | 1-cyclohexyl-2-[2-(3-hydroxy-phenyl)-quinolin-6-yl]-1H-benzoimidazole-5-carboxylic acid |
| 475 | 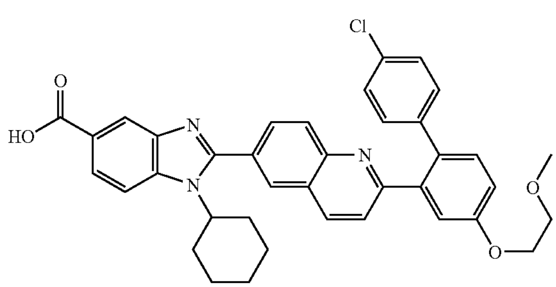 | 1 | 4'-chloro-4-(2-methoxy-ethoxy)-biphen-2-yl | quinolin-6-yl | 2-{2-[4'-chloro-4-(2-methoxy-ethoxy)-biphen-2-yl]-quinolin-6-yl}-1-cyclohexyl-1H-benzoimidazole-5-carboxylic acid |
| 476 | 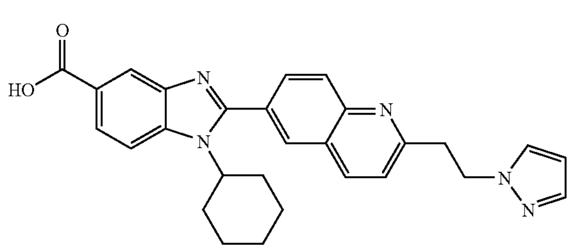 | 1 | 2-pyrazol-1-yl-eth-1-yl | quinolin-6-yl | 1-cyclohexyl-2-[2-(2-pyrazol-1-yl-eth-1-yl)-quinolin-6-yl]-1H-benzoimidazole-5-carboxylic acid |

TABLE I-continued

| Cmpd # | Structure | q | Y | Het | Name |
|---|---|---|---|---|---|
| 477 | 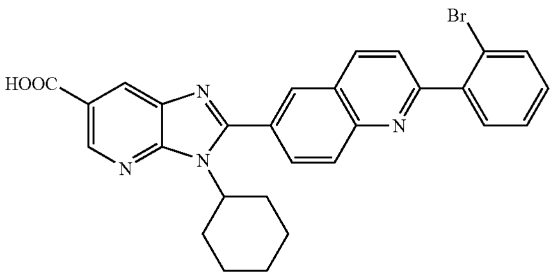 | 1 | 2-bromo-phenyl | quinolin-6-yl | 2-[2-(2-bromo-phenyl)-quinolin-6-yl]-3-cyclohexyl-3H-imidazo[4,5-b]pyridine-6-carboxylic |
| 478 | 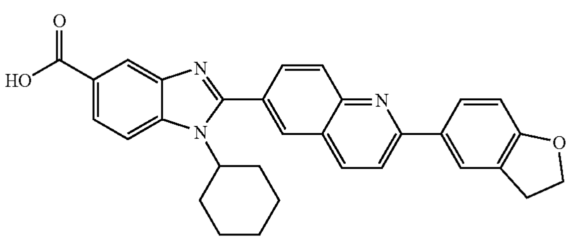 | 1 | 2,3-dihydro-benzofuran-5-yl | quinolin-6-yl | 1-cyclohexyl-2-[2-(2,3-dihydro-benzofuran-5-yl)-quinolin-6-yl]-1H-benzoimidazole-5-carboxylic acid |
| 479 | 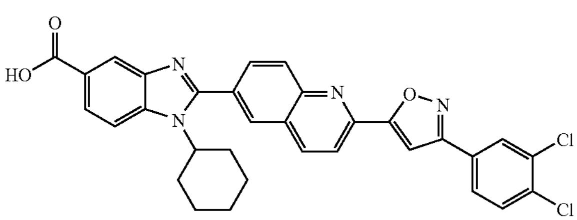 | 1 | 3-(3,4-dichloro-phenyl)-isoxazol-5-yl | quinolin-6-yl | 1-cyclohexyl-2-{2-[3-(3,4-dichloro-phenyl)-isoxazol-5-yl]-quinolin-6-yl}-1H-benzoimidazole-5-carboxylic acid |
| 480 | 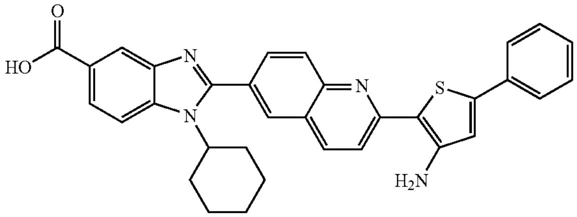 | 1 | 3-amino-5-phenyl-thiophen-2-yl | quinolin-6-yl | 2-[2-(3-amino-5-phenyl-thiophen-2-yl)-quinolin-6-yl]-1-cyclohexyl-1H-benzoimidazole-5-carboxylic acid |
| 481 | 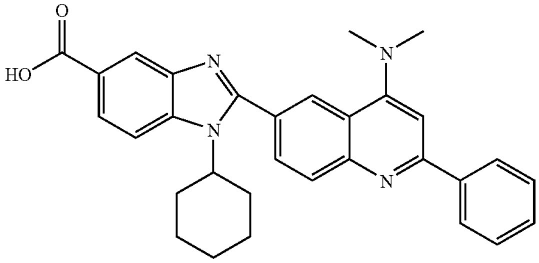 | 2 | Dimethyl-amino AND phenyl | quinolin-6-yl | 1-cyclohexyl-2-(4-dimethylamino-2-phenyl-quinolin-6-yl)-1H-benzoimidazole-5-carboxylic acid |

TABLE I-continued

| Cmpd # | Structure | q | Y | Het | Name |
|---|---|---|---|---|---|
| 482 | 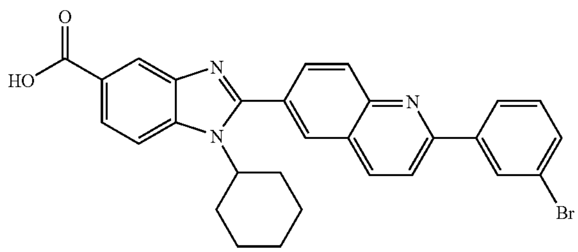 | 1 | 3-bromo-phenyl | quinolin-6-yl | 2-[2-(3-bromo-phenyl)-quinolin-6-yl]-1-cyclohexyl-1H-benzoimidazole-5-carboxylic acid |
| 483 | 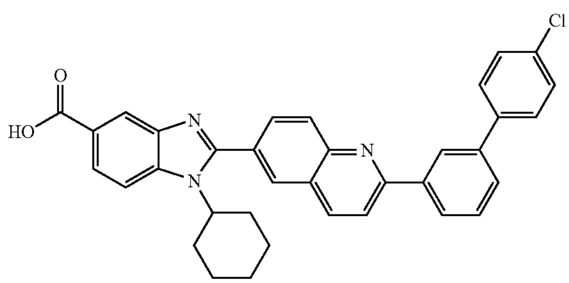 | 1 | 4'-chloro-4-biphen-3-yl | quinolin-6-yl | 2-[2-(4'-chloro-biphen-3-yl)-quinolin-6-yl]-1-cyclohexyl-1H-benzoimidazole-5-carboxylic acid |
| 484 | 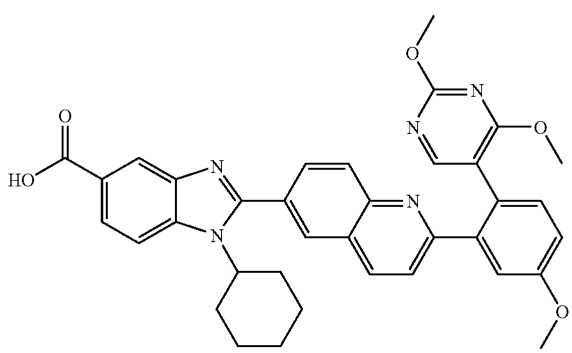 | 1 | 2-(2,4-dimethoxy-pyrimidin-5-yl)-5-methoxy-phenyl | quinolin-6-yl | 1-cyclohexyl-2-{2-[2-(2,4-dimethoxy-pyrimidin-5-yl)-5-methoxy-phenyl]-quinolin-6-yl}-1H-benzoimidazole-5-carboxylic acid |
| 485 | 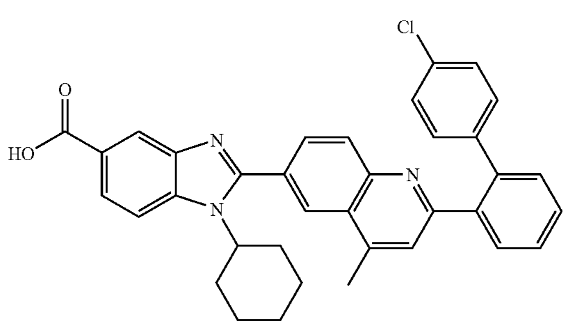 | 2 | 2-(4'-chloro-biphen-2-yl) AND methyl | quinolin-6-yl | 2-[2-(4'-chloro-biphen-2-yl)-4-methyl-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 486 | 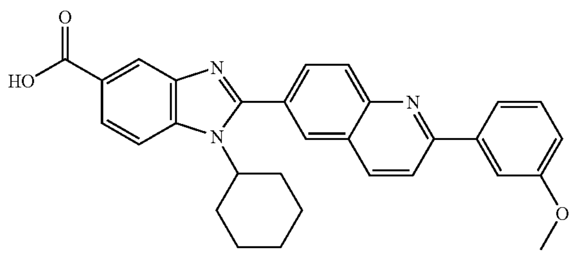 | 1 | 3-methoxy-phenyl | quinolin-6-yl | 1-cyclohexyl-2-[2-(3-methoxy-phenyl)-quinolin-6-yl]-1H-benzoimidazole-5-carboxylic acid |
| 487 | 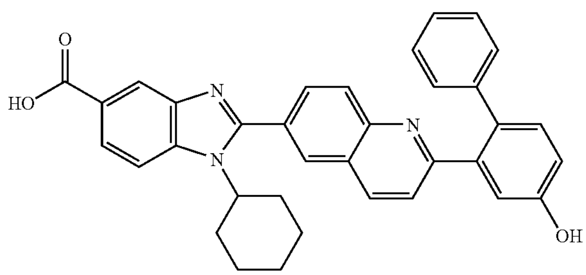 | 1 | 4-hydroxy-biphen-2-yl | quinolin-6-yl | 1-cyclohexyl-2-[2-(4-hydroxy-biphen-2-yl)-quinolin-6-yl]-1H-benzoimidazole-5-carboxylic acid |
| 488 | 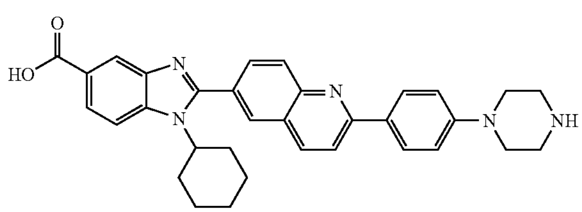 | 1 | 4-piperazin-1-yl-phenyl | quinolin-6-yl | 1-cyclohexyl-2-[2-(4-piperazin-1-yl phenyl)-quinolin-6-yl]-1H-benzoimidazole-5-carboxylic acid |
| 489 | 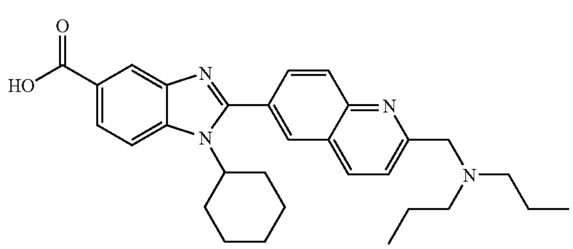 | 1 | Dipropyl-amino-methyl | quinolin-6-yl | 1-cyclohexyl-2-(2-dipropylaminomethyl-quinolin-6-yl]-1H-benzoimidazole-5-carboxylic acid |

TABLE I-continued

| Cmpd # | Structure | q | Y | Het | Name |
|---|---|---|---|---|---|
| 490 | 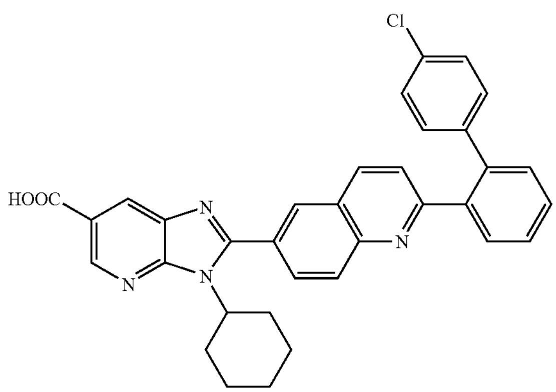 | 1 | 4'-chloro-biphen-2-yl | quinolin-6-yl | 2-[2-(4'-chlorobiphen-2-yl)-quinolin-6-yl]-3-cyclohexyl-3H-imidazo[4,5-b]pyridine-6-carboxylic acid |
| 491 | 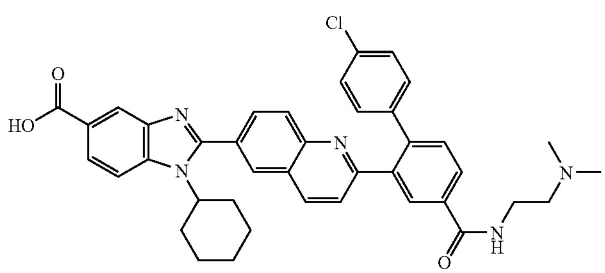 | 1 | 4'-chloro-4-(2-dimethyl-aminoethyl-carbamoyl)-biphen-2-yl | quinolin-6-yl | 2-{2-[4'-chloro-4-(2-dimethylamino-ethylcarbamoyl)-biphen-2-yl]-quinolin-6-yl}-1-cyclohexyl-1H-benzoimidazole-5-carboxylic acid |
| 492 | 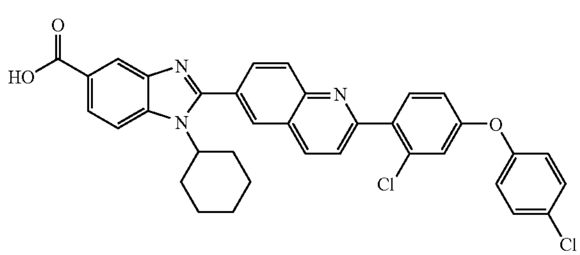 | 1 | 2-chloro-4-(4-chloro-phenoxy)-phenyl | quinolin-6-yl | 2-{2-[2-chloro-4-(4-chloro-phenoxy)-phenyl-quinolin-6-yl]-1-cyclohexyl-1H-benzoimidazole-5-carboxylic acid |
| 493 | 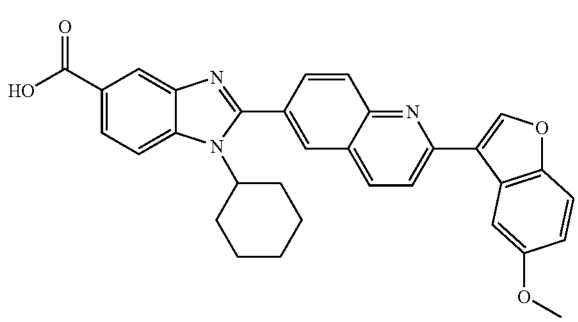 | 1 | 5-methoxy-benzofuran-3-yl | quinolin-6-yl | 1-cyclohexyl-2-[2-(5-methoxy-benzofuran-3-yl)-quinolin-6-yl]-1H-benzoimidazole-5-carboxylic acid |

TABLE I-continued

| Cmpd # | Structure | q | Y | Het | Name |
|---|---|---|---|---|---|
| 494 | 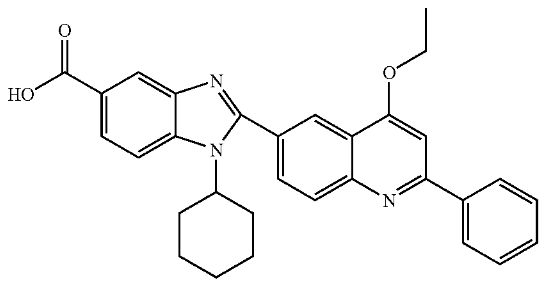 | 2 | ethoxy AND phenyl | quinolin-6-yl | 1-cyclohexyl-2-(4-ethoxy-2-phenyl-quinolin-6-yl)-1H-benzoimidazole-5-carboxylic acid |
| 495 | 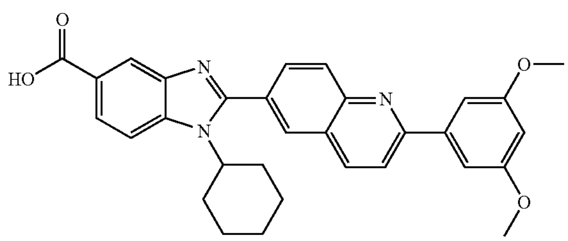 | 1 | 3,5-dimethoxy-phenyl | quinolin-6-yl | 1-cyclohexyl-2-[2-(3,5-dimethoxy-phenyl)-quinolin-6-yl]-1H-benzoimidazole-5-carboxylic acid |
| 496 | 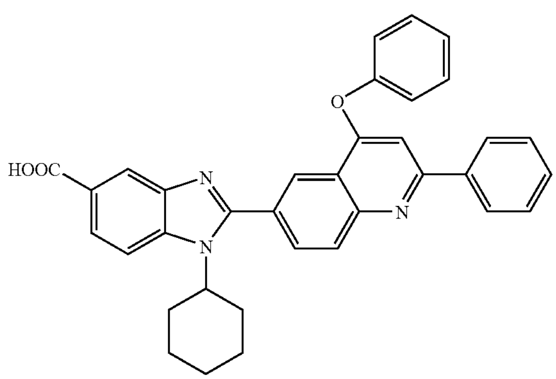 | 2 | phenoxy AND phenyl | quinolin-6-yl | 1-cyclohexyl-2-(4-phenoxy-2-phenyl-quinolin-6-yl)-1H-benzoimidazole-5-carboxylic acid |
| 497 | 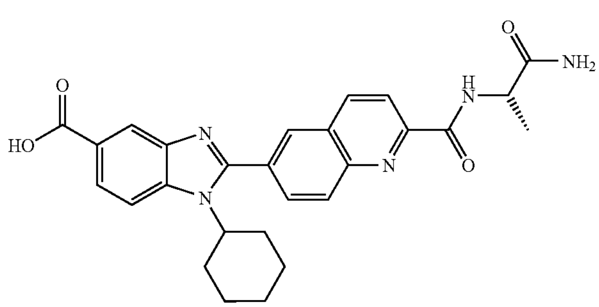 | 1 | 1-carbamoyl-ethyl-carbamoyl | quinolin-6-yl | 2-[2-(1-carbamoylethylcarbamoyl)-quinolin-6-yl]-1-cyclohexyl-1H-benzimidazole-5-carboxylic acid |

TABLE I-continued

| Cmpd # | Structure | q | Y | Het | Name |
|---|---|---|---|---|---|
| 498 | 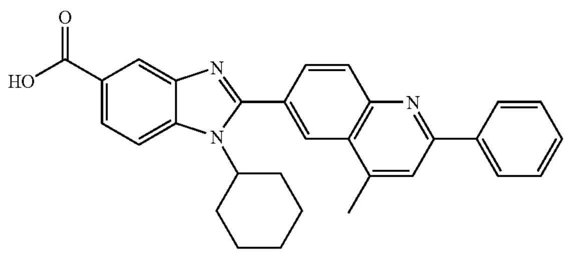 | 2 | methyl AND phenyl | quinolin-6-yl | 1-cyclohexyl-2-(4-methyl-2-phenyl-quinolin-6-yl)-1H-benzoimidazole-5-carboxylic acid |
| 499 | 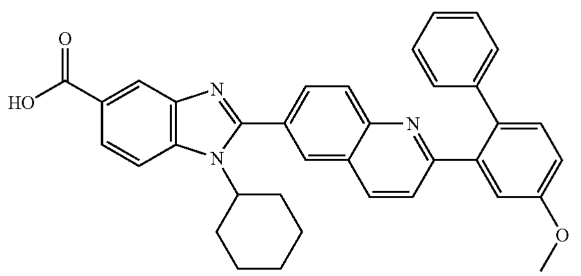 | 1 | 4-methoxy-biphen-2-yl | quinolin-6-yl | 1-cyclohexyl-2-[2-(4-methoxy-biphen-2-yl)-quinolin-6-yl]-1H-benzoimidazole-5-carboxylic acid |
| 500 | 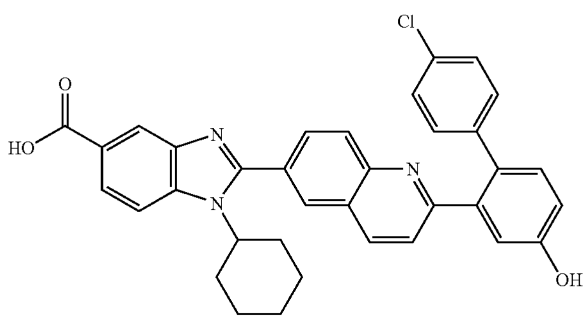 | 1 | 4'-chloro-4-hydroxy-biphen-2-yl | quinolin-6-yl | 2-[2-(4'-chloro-4-hydroxy-biphen-2-yl)-quinolin-6-yl]-1-cyclohexyl-1H-benzoimidazole-5-carboxylic acid |
| 501 | 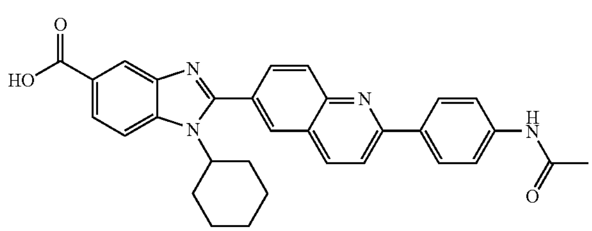 | 1 | 4-acetylamino phenyl | quinolin-6-yl | 2-[2-(4-acetylamino-phenyl)-quinolin-6-yl]-1-cyclohexyl-1H-benzoimidazole-5-carboxylic acid |
| 502 | 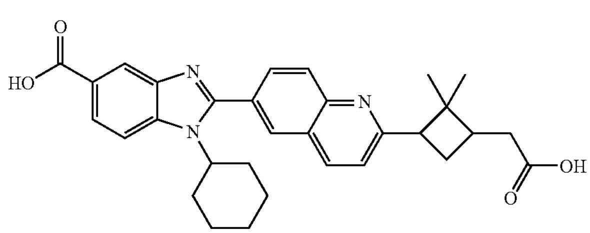 | 1 | 3-carboxy-methyl-2,2-dimethyl-cyclobutyl | quinolin-6-yl | 2-[2-(3-carboxymethyl-2,2-dimethyl-cyclobutyl)-quinolin-6-yl]-1-cyclohexyl-1H-benzoimidazole-5-carboxylic acid |

TABLE I-continued

| Cmpd # | Structure | q | Y | Het | Name |
|---|---|---|---|---|---|
| 503 | 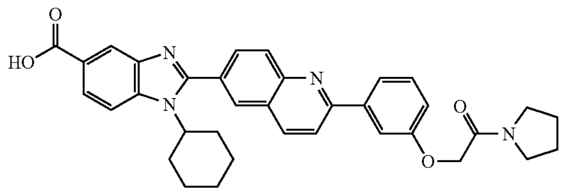 | 1 | 3-(2-oxo-2-pyrrolidin-1-yl-ethoxy)-phenyl | quinolin-6-yl | 1-cyclohexyl-2-{2-[3-(2-oxo-2-pyrrolidin-1-yl-ethoxy)-phenyl]-quinolin-6-yl}-1H-benzoimidazole-5-carboxylic acid |
| 504 | 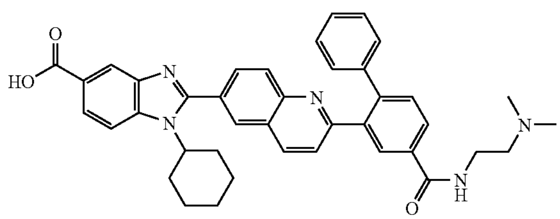 | 1 | 4-(2-dimethyl-aminoethyl-carbamoyl)-biphen-2-yl]- | quinolin-6-yl | 1-cyclohexyl-2-{2-[4-(2-dimethylamino-ethylcarbamoyl)-biphen-2-yl]-quinolin-6-yl}-1H-benzoimidazole-5-carboxylic acid |
| 505 | 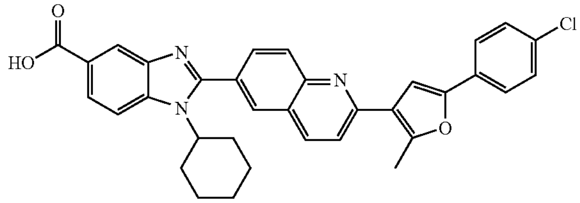 | 1 | 5-(4-chloro-phenyl)-2-methyl-furan-3-yl | quinolin-6-yl | 2-{2-[5-(4-chloro-phenyl)-2-methyl-furan-3-yl]-quinolin-6-yl}-1-cyclohexyl-1H-benzoimidazole-5-carboxylic acid |
| 507 | 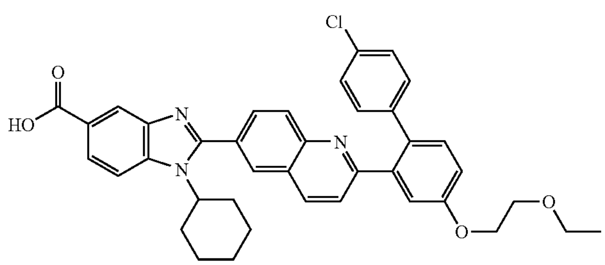 | 1 | 4'-chloro-4-(2-ethoxy-ethoxy)-biphen-2-yl | quinolin-6-yl | 2-{2-[4'-chloro-4-(2-ethoxy-ethoxy)-biphen-2-yl]-quinolin-6-yl}-1-cyclohexyl-1H-benzoimidazole-5-carboxylic acid |
| 508 | 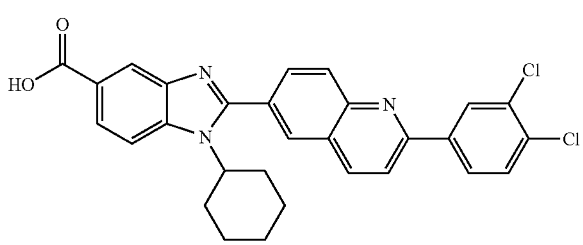 | 1 | 3,4-dichloro-phenyl | quinolin-6-yl | 1-cyclohexyl-2-[2-(3,4-dichloro-phenyl)-quinolin-6-yl]-1H-benzoimidazole-5-carboxylic acid |

TABLE I-continued

| Cmpd # | Structure | q | Y | Het | Name |
|---|---|---|---|---|---|
| 509 | 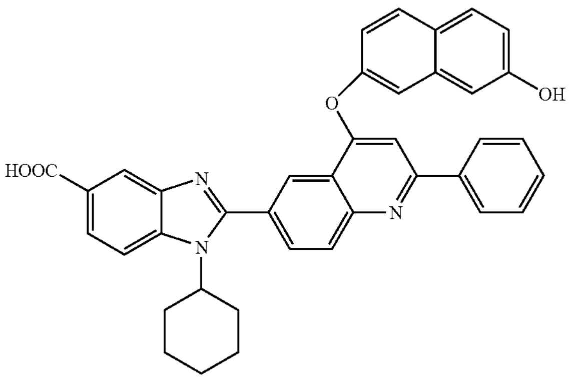 | 2 | 7-hydroxy-naphthalen-2-oxy AND phenyl | quinolin-6-yl | 1-cyclohexyl-2-[4-(7-hydroxy-naphthalen-2-yloxy)-2-phenyl-quinolin-6-yl]-1H-benzoimidazole-5-carboxylic acid |
| 510 | 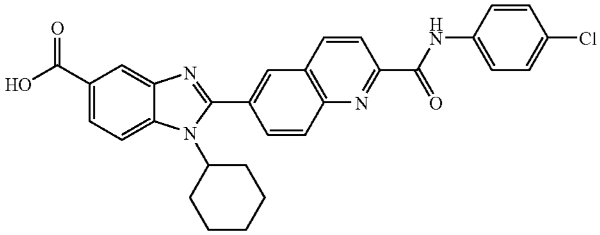 | 1 | 4-chloro-phenyl-carbamoyl | quinolin-6-yl | 2-[2-(4-chlorophenylcarbamoyl)quinolin-6-yl]-1-cyclohexyl-1H-benzimidazole-5-carboxylic acid |
| 511 | 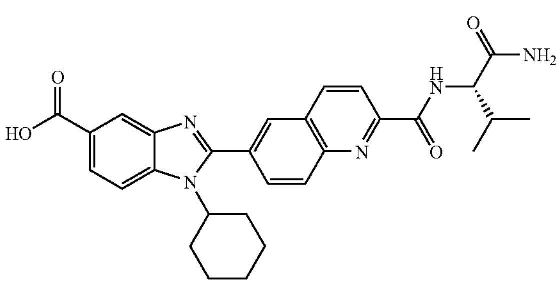 | 1 | 1-carbamoyl-2-methyl-propyl-carbamoyl | quinolin-6-yl | 2-[2-(1-carbamoyl-2-methylpropylcarbamoyl)quinolin-6-yl]-1-cyclohexyl-1H-benzimidazole-5-carboxylic acid |
| 542 | 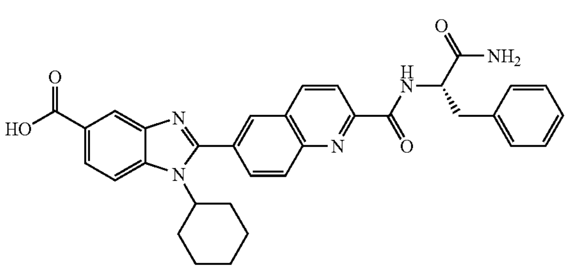 | 1 | 1-carbamoyl-2-phenyl-ethyl-carbamoyl | quinolin-6-yl | 2-[2-(1-carbamoyl-2-phenylethylcarbamoyl)quinolin-6-yl]-1-cyclohexyl-1H-benzimidazole-5-carboxylic acid |

TABLE I-continued

| Cmpd # | Structure | q | Y | Het | Name |
|---|---|---|---|---|---|
| 543 | Isomer A | 1 | 4'-chloro-4-methoxy-biphen-2-yl | quinolin-6-yl | 2-[2-(4'-chloro-4-methoxy-biphen-2-yl)-quinolin-6-yl]-1-(4-methyl-cyclohexyl-1H-benzoimidazole-5-carboxylic acid |
| 544 | 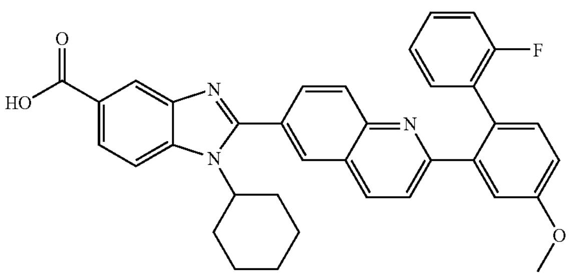 | 1 | 2'-fluoro-4-methoxy-biphen-2-yl | quinolin-6-yl | 1-cylcohexyl-2-[2-(2'-fluoro-4-methoxy-biphen-2-yl)-quinolin-6-yl]-1-benzoimidazole-5-carboxylic acid |
| 545 | 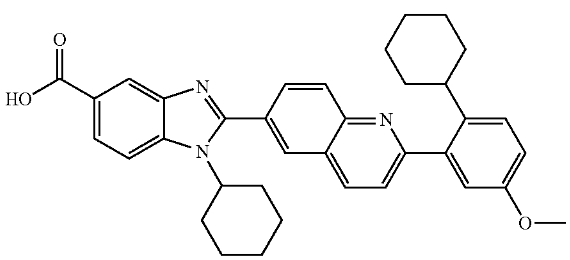 | 1 | 2-cylcohexyl-5-methoxy-phenyl | quinolin-6-yl | 1-cyclohexyl-2-[2-(2-cyclohexyl-5-methoxy-phenyl)-quinolin-6-yl]-1H-benzoimidazole-5-carboxylic acid |
| 546 | 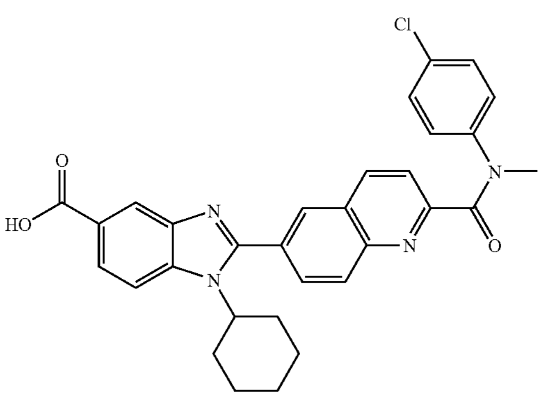 | 1 | (4-chloro-phenyl)methyl carbamoyl | quinolin-6-yl | 2-{2-[(4-chlorophenyl)methyl carbamoyl]quinolin-6-yl}-1-cyclohexyl-1H-benzimidazole-5-carboxylic acid |

TABLE I-continued

| Cmpd # | Structure | q | Y | Het | Name |
|---|---|---|---|---|---|
| 547 | Isomer B | 1 | 4'-chloro-4-methoxy-biphen-2-yl | quinolin-6-yl | 2-[2-(4'-chloro-4-(2-methoxy-biphen-2-yl)-quinolin-6-yl]-1-(4-methyl-cyclohexyl-1H-benzoimidazole-5-carboxylic acid |
| 548 | 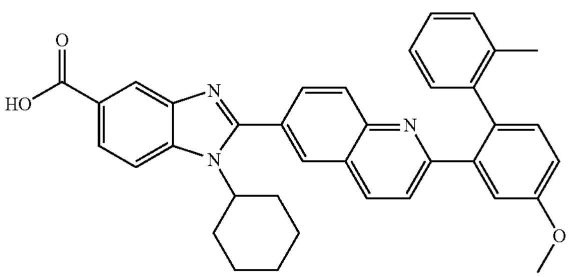 | 1 | biphen-4-yl- | quinolin-6-yl | 2-(2-biphen-4-yl-quinolin-6-yl)-1-cyclohexyl-1H-benzoimidazole-5-carboxylic acid |
| 549 | 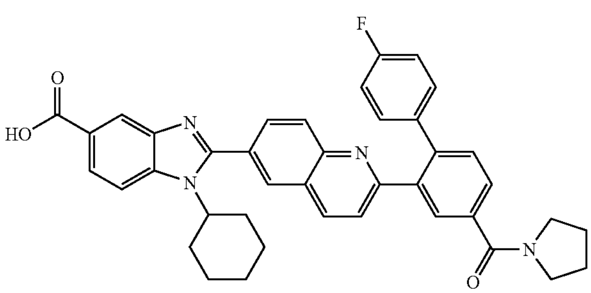 | 1 | 4'-fluoro-4-(pyrrolidin-1-ylcarbonyl)-biphen-2-yl | quinolin-6-yl | 1-cyclohexyl-2-{2-[4'-fluoro-4-(pyrrolidin-1-carbonyl-biphen-2-yl]-quinolin-6-yl}-1H-benzoimidazole-5-carboxylic acid |
| 550 | 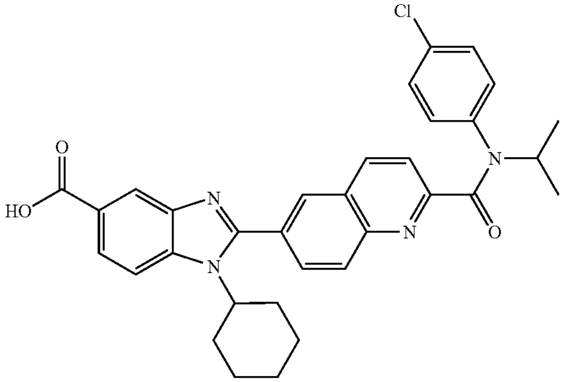 | 1 | (4-chloro-phenyl) isopropyl carbamoyl | quinolin-6-yl | 2-{2-[(4-chlorophenyl) isopropyl carbamoyl]quinolin-6-yl}-1-cyclohexyl-1H-benzimidazole-5-carboxylic acid |

TABLE I-continued

| Cmpd # | Structure | q | Y | Het | Name |
|---|---|---|---|---|---|
| 551 | 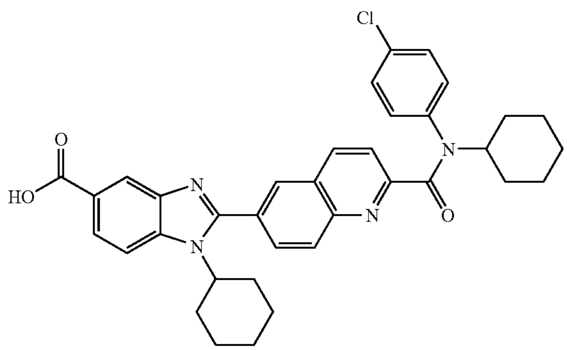 | 1 | (4-chlorophenyl) cyclohexyl carbamoyl | quinolin-6-yl | 2-{2-[(4-chlorophenyl) cyclohexyl carbamoyl]quinolin-6-yl}-1-cyclohexyl-1H-benzimidazole-5-carboxylic acid |
| 552 | 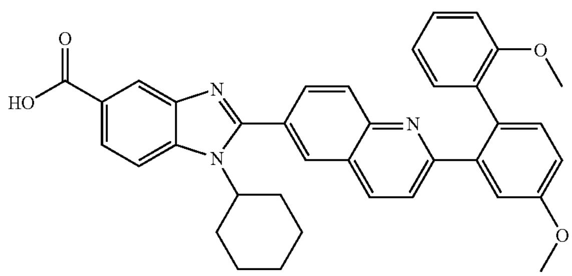 | 1 | 4,2'-dimethoxy-biphen-2-yl | quinolin-6-yl | 1-cyclohexyl-2-[2-(4,2'-dimethoxy-biphen-2-yl)-quinolin-6-yl]-1H-benzoimidazole-5-carboxylic acid |
| 554 | 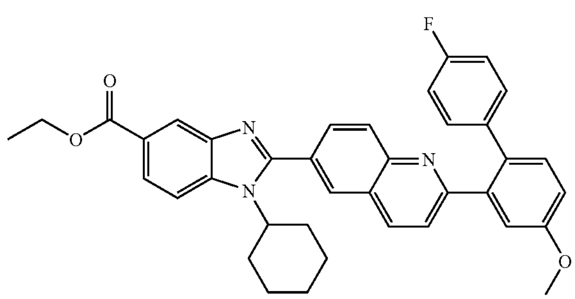 | 1 | 4'-fluoro-4-methoxy-biphen-2-yl | quinolin-6-yl | Ethyl 1-cylcohexyl-2-[2-(4'-fluoro-4-methoxy-biphen-2-yl)-quinolin-6-yl]-1H-benzimidazole-5-carboxylic acid |
| 555 | 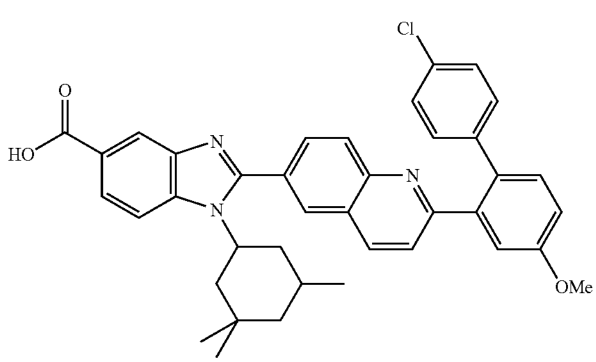 | 1 | 4'-chloro-4-methoxy-biphen-2-yl | quinolin-6-yl | 2-[2-(4'-chloro-4-methoxybiphen-2-yl)-quinolin-6-yl]-1-(3,3,5-trimethyl-cyclohexyl-1H-benzoimidazole-5-carboxylic acid |

TABLE I-continued

| Cmpd # | Structure | q | Y | Het | Name |
|---|---|---|---|---|---|
| 556 | 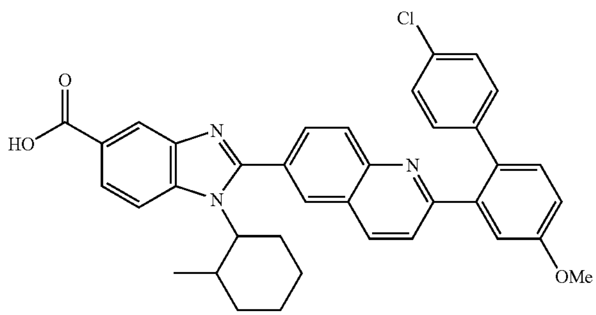 | 1 | 4'-chloro-4-methoxy-biphen-2-yl | quinolin-6-yl | 2-[2-(4'-chloro-4-methoxy-biphen-2-yl)-quinolin-6-yl]-1-(2-methyl-cyclohexyl-1H-benzoimidazole-5-carboxylic acid |
| 557 | 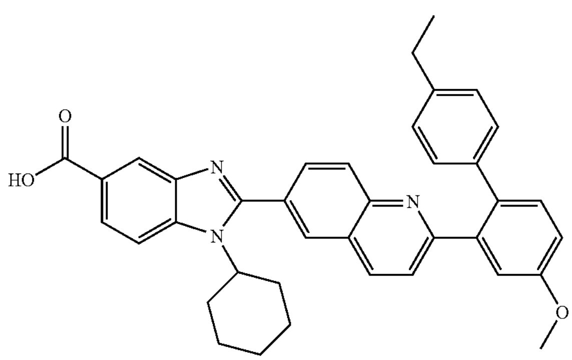 | 1 | 4'-ethyl-4-methoxy-biphen-2-yl | quinolin-6-yl | 1-cyclohexyl-2-[2-(4'-ethyl-4-methoxy-biphen-2-yl)-quinolin-6-yl]-1H-benzoimidazole-5-carboxylic acid |
| 558 | 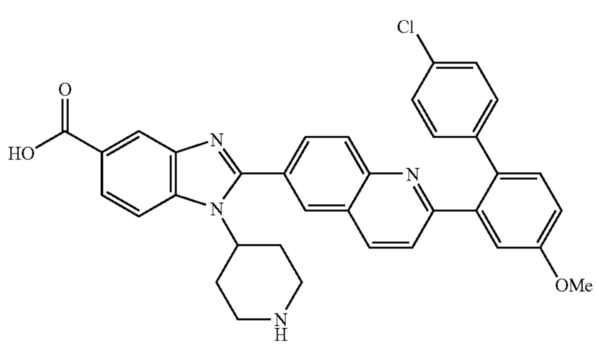 | 1 | 4'-chloro-4-methoxy-biphen-2-yl | quinolin-6-yl | 2-[2-(4'-chloro-4-methoxy-biphen-2-yl)-quinolin-6-yl]-1-piperidin-4-yl-1H-benzoimidazole-5-carboxylic acid |

TABLE I-continued

| Cmpd # | Structure | q | Y | Het | Name |
|---|---|---|---|---|---|
| 559 | 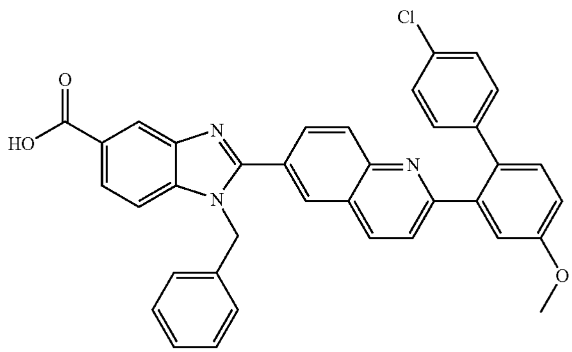 | 1 | 4'-chloro-4-methoxy-biphen-2-yl | quinolin-6-yl | 1-benzyl-2-[2-(4'-chloro-4-methoxy-biphen-2-yl)-quinolin-6-yl]-1H-benzoimidazole-5-carboxylic acid |
| 560 | 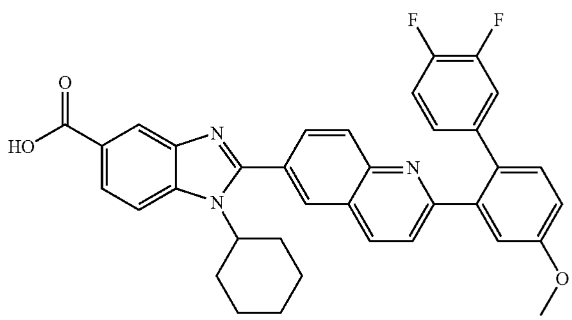 | 1 | 3',4'-difluoro-4-methoxy-biphen-2-yl | quinolin-6-yl | 1-cyclohexyl-2-[2-(3',4'-dichloro-4-methoxy-biphen-2-yl)-quinolin-6-yl]-1H-benzoimidazole-5-carboxylic acid |
| 561 | 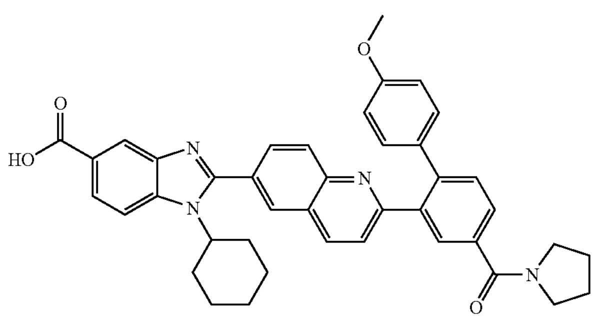 | 1 | 4'-methoxy-4-(pyrrolidin-1-ylcarbonyl)-biphen-2-yl) | quinolin-6-yl | 1-cyclohexyl-2-{2-[4'-methoxy-4-(pyrrolidinyl-1-ylcarbonyl)biphen-2-yl]quinolin-6-yl}-1H-benzimidazole-5-carboxylic acid |
| 562 | 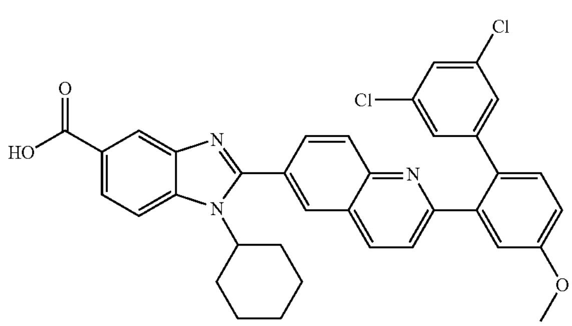 | 1 | 3',5'-dichloro-4-methoxy-biphen-2-yl | quinolin-6-yl | 1-cyclohexyl-2-[2-(3',5'-dichloro-4-methoxy-biphen-2-yl)-quinolin-6-yl]-1H-benzoimidazole-5-carboxylic acid |

TABLE I-continued

| Cmpd # | Structure | q | Y | Het | Name |
|---|---|---|---|---|---|
| 563 | 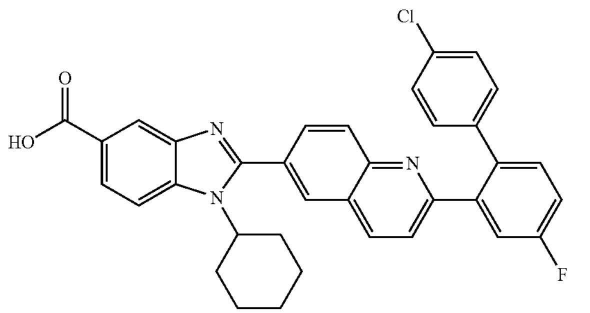 | 1 | 4'-chloro-4-fluoro-biphen-2-yl | quinolin-6-yl | 2-[2-(4'-chloro-4-fluoro-biphen-2-yl)-quinolin-6-yl]-1-cyclohexyl-1H-benzoimidazole-5-carboxylic acid |
| 564 | 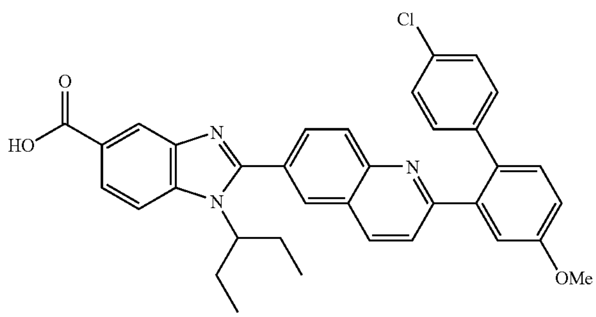 | 1 | 4'-chloro-4-methoxy-biphen-2-yl | quinolin-6-yl | 2-[2-(4'-chloro-4-methoxy-biphen-2-yl)-quinolin-6-yl]-1-(1-ethyl-propyl)-1H-benzoimidazole-5-carboxylic acid |
| 565 | 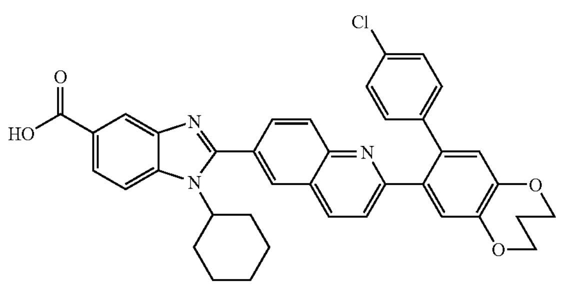 | 1 | 8-(4-chloro-phenyl)-3,4-dihydro-2H-benzo[b][1,4]dioxepin-7-yl | quinolin-6-yl | 2-{2-[8-(4-chloro-phenyl)-3,4-dihydro-2H-benzo[b][1,4]dioxepin-7-yl]-quinolin-6-yl}-1-cylcohexyl-1H-benzoimidazole-5-carboxylic acid |
| 566 | 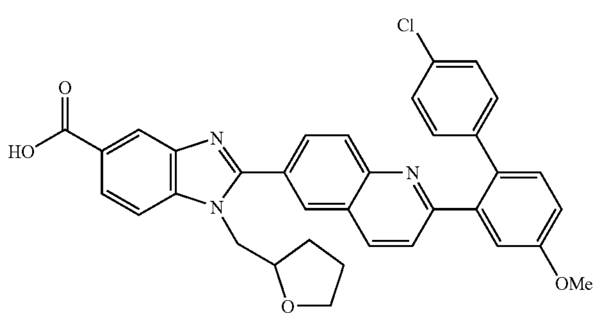 | 1 | 4'-chloro-4-methoxy-biphen-2-yl | quinolin-6-yl | 2-[2-(4'-chloro-4-methoxy-biphen-2-yl)-quinolin-6-yl]-1-(tetrahydrofuran-2-yl-methyl)-1H-benzoimidazole-5-carboxylic acid |

TABLE I-continued

| Cmpd # | Structure | q | Y | Het | Name |
|---|---|---|---|---|---|
| 567 | 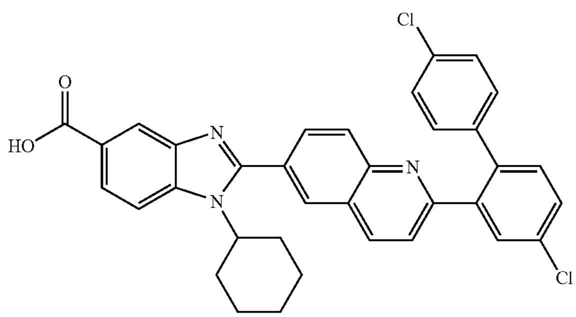 | 1 | 4,4'-dichloro-biphen-2-yl | quinolin-6-yl | 1-cyclohexyl-2-[2-(4,4'-dichloro-biphen-2-yl)-quinolin-6-yl]-1H-benzoimidazole-5-carboxylic acid |
| 568 | 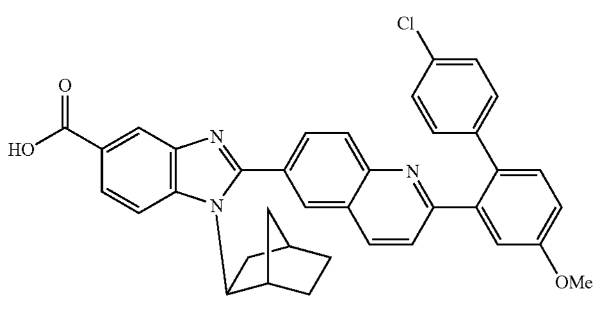 | 1 | 4'-chloro-4-methoxy-biphen-2-yl | quinolin-6-yl | 1-bicyclo[2.2.1]hept-2-yl-2-[2-(4'-chloro-4-methoxy-biphen-2-yl)-quinolin-6-yl]1H-benzoimidazole-5-carboxylic acid |
| 569 | 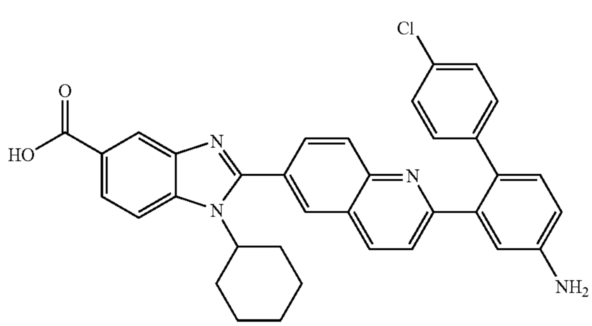 | 1 | 4-amino-4'-chloro-biphen-2-yl | quinolin-6-yl | 2-[2-(4-amino-4'-chlorobiphen-2-yl)-quinolin-6-yl]-1-cyclohexyl-1H-benzoimidazole-5-carboxylic acid |

TABLE I-continued
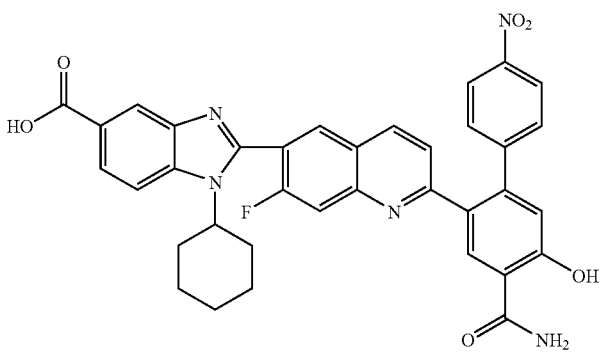
| Cmpd # | Structure | q | Y | Het | Name |
|---|---|---|---|---|---|
| | 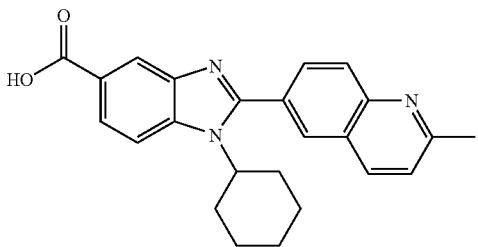 | 2 | fluoro AND 4-carbamoyl-5-hydroxy-4'-nitrobiphen-2-yl | quinolin-6-yl | 2-[2-(4-carbamoyl-5-hydroxy-4'-nitro-biphen-2-yl)-7-fluoro-quinolin-6-yl]-1-cyclohexyl-1H-benzoimidazole-5-carboxylic acid |
| 573 | 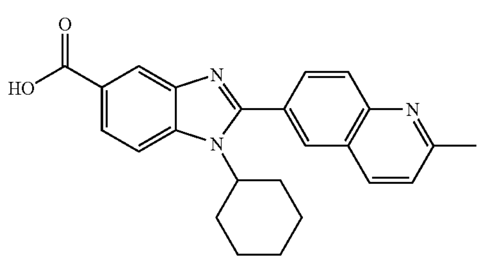 | 1 | methyl | quinolin-6-yl | 1-cyclohexyl-2-(2-phenyl-quinolin-6-yl)-1H-benzoimidazole-5-carboxylic acid |

TABLE II

| Cmpd # | Structure | R⁸ | R⁹ | Y | Het | Name |
|---|---|---|---|---|---|---|
| 229 | 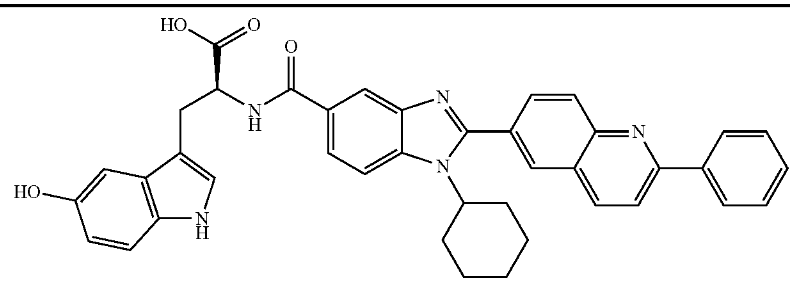 | H | 3-(5-hydroxy-1H-indol-3-yl)-propionic acid | phenyl | Quinolin-6-yl | 2-{[1-cyclohexyl-2-(2-phenyl-quinolin-6-yl)-1H-benzoimidazole-5-carbonyl]-amino}-3-(5-hydroxy-1H-indol-3-yl)-propionic acid |
| 230 | 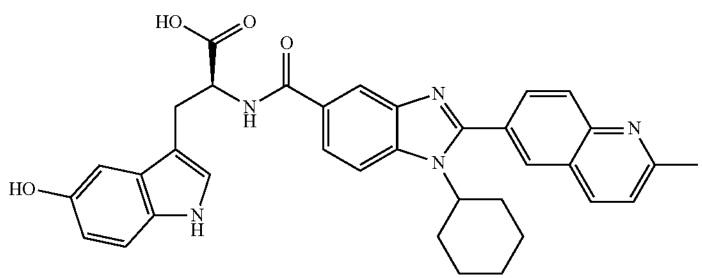 | H | 3-(5-hydroxy-1H-indol-3-yl)-propionic acid | methyl | Quinolin-6-yl | 2-{[1-cyclohexyl-2-(2-methyl-quinolin-6-yl)-1H-benzoimidazol-5-carbonyl]-amino}-3-(5-hydroxy-1H-indol-3-yl)-propionic acid |

TABLE II-continued
| Cmpd # | Structure | R⁸ | R⁹ | Y | Het | Name |
|---|---|---|---|---|---|---|
| 231 | 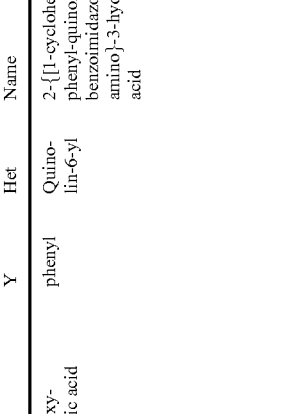 | H | 3-hydroxy-propionic acid | phenyl | Quinolin-6-yl | 2-{[1-cyclohexyl-2-(2-phenyl-quinolin-6-yl)-1H-benzoimidazole-5-carbonyl]-amino}-3-hydroxy-propionic acid |
| 232 | 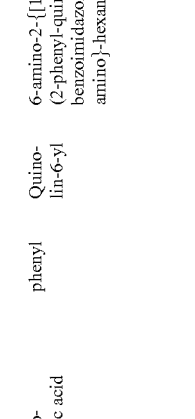 | H | 6-amino-hexanoic acid | phenyl | Quinolin-6-yl | 6-amino-2-{[1-cyclohexyl-2-(2-phenyl-quinolin-6-yl)-1H-benzoimidazole-5-carbonyl]-amino}-hexanoic acid |

TABLE II-continued

| Cmpd # | Structure | R⁸ | R⁹ | Y | Het | Name |
|---|---|---|---|---|---|---|
| 233 | 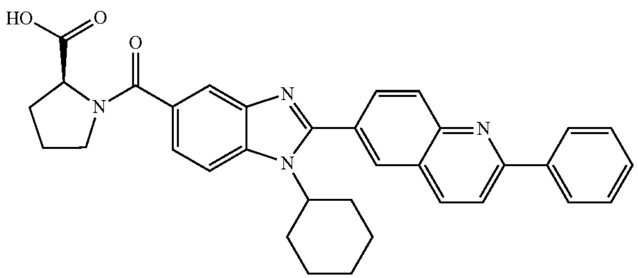 | | pyrrolidine-2-carboxylic acid | phenyl | Quinolin-6-yl | 1-[1-cyclohexyl-2-(2-phenyl-quinolin-6-yl)-1H-benzoimidazole-5-carbonyl]-pyrrolidine-2-carboxylic acid |
| 234 | 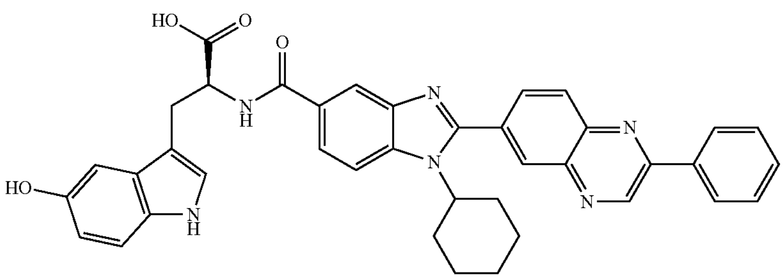 | H | 3-(5-hydroxy-1H-indol-3-yl)-propionic acid | phenyl | Quinoxalin-6-yl | 2-{[1-cyclohexyl-2-(2-phenyl-quinoxalin-6-yl)-1H-benzoimidazole-5-carbonyl]-amino}-3-(5-hydroxy-1H-indol-3-yl)-propionic acid |

TABLE II-continued

| Cmpd # | Structure | R8 | R9 | Y | Het | Name |
|---|---|---|---|---|---|---|
| 235 | 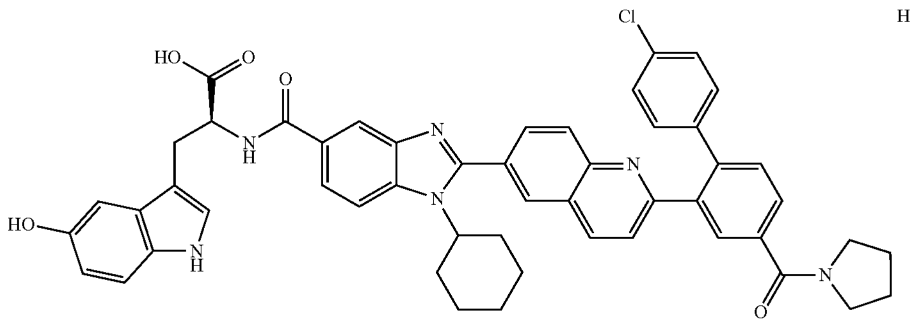 | H | 3-(5-hydroxy-1H-indol-3-yl)-propionic acid | 4'-chloro-4-(pyrrolidine-1-carbonyl)-biphen-2-yl | Quinolin-6-yl | 2-[(2-{2-[4'-chloro-4-(pyrrolidine-1-carbonyl)-biphen-2-yl]-quinolin-6-yl}-1-cyclohexyl-1H-benzoimidazole-5-carbonyl)-amino]-3-(5-hydroxy-1H-indol-3-yl)-propionic acid |
| 236 | 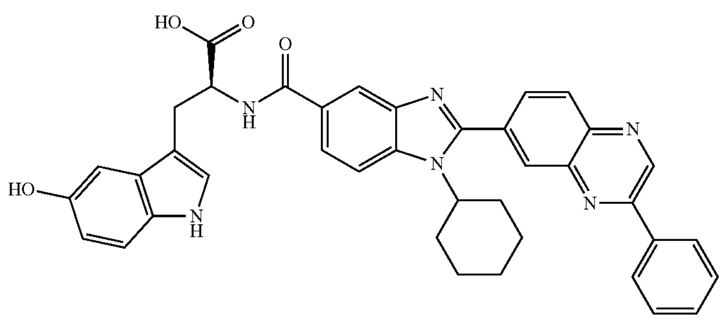 | H | 3-(5-hydroxy-1H-indol-3-yl)-propionic acid | phenyl | Quinoxalin-6-yl | 2-{[1-cyclohexyl-2-(3-phenyl-quinoxalin-6-yl)-1H-benzoimidazole-5-carbonyl]-amino}-3-(5-hydroxy-1H-indol-3-yl)-propionic acid |

TABLE II-continued

| Cmpd # | Structure | R⁸ | R⁹ | Y | Het | Name |
|---|---|---|---|---|---|---|
| 237 | 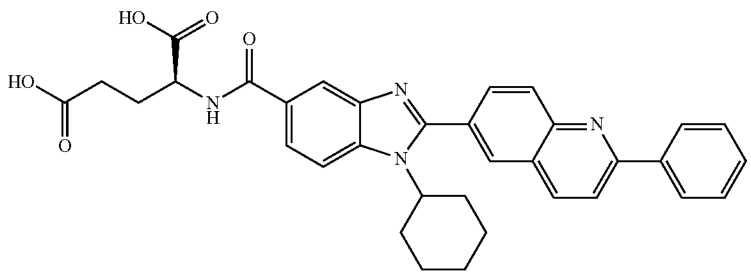 | H | pentanedioic acid | phenyl | Quinolin-6-yl | 2-{[1-cyclohexyl-2-(2-phenyl-quinolin-6-yl)-1H-benzoimidazole-5-carbonyl]-amino}-pentanedioic acid |
| 238 | 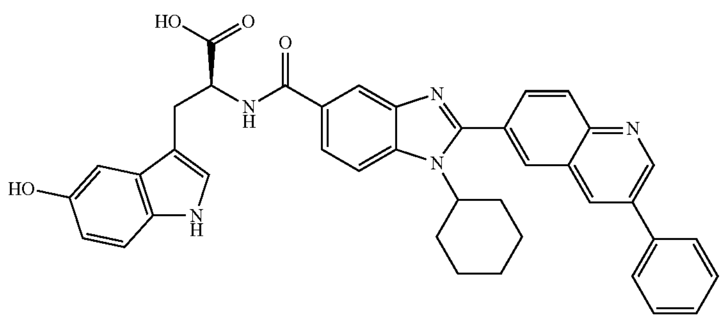 | H | 3-(5-hydroxy-1H-indol-3-yl)-propionic acid | phenyl | Quinolin-6-yl | 2-{[1-cyclohexyl-2-(3-phenyl-quinolin-6-yl)-1H-benzoimidazole-5-carbonyl]-amino}-3-(5-hydroxy-1H-indol-3-yl)-propionic acid |

TABLE II-continued

| Cmpd # | Structure | R⁸ | R⁹ | Y | Het | Name |
|---|---|---|---|---|---|---|
| 239 | 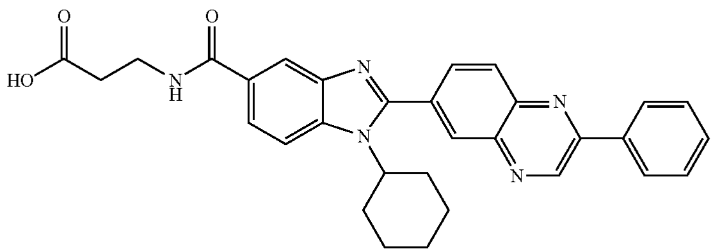 | H | propionic acid | phenyl | Quinoxalin-6-yl | 3-{[1-cyclohexyl-2-(2-phenyl-quinoxalin-6-yl)-1H-benzoimidazole-5-carbonyl]-amino}-propionic acid |
| 240 | 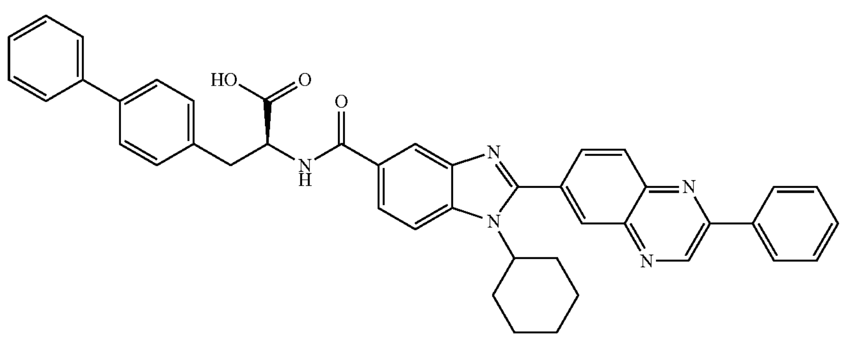 | H | 3-biphenyl-4-yl propionic acid | phenyl | Quinoxalin-6-yl | 3-biphenyl-4-yl-2-{[1-cyclohexyl-2-(2-phenyl-quinoxalin-6-yl)-1H-benzoimidazole-5-carbonyl]-amino}-propionic acid |

TABLE II-continued

| Cmpd # | Structure | R[8] | R[9] | Y | Het | Name |
|---|---|---|---|---|---|---|
| 241 | 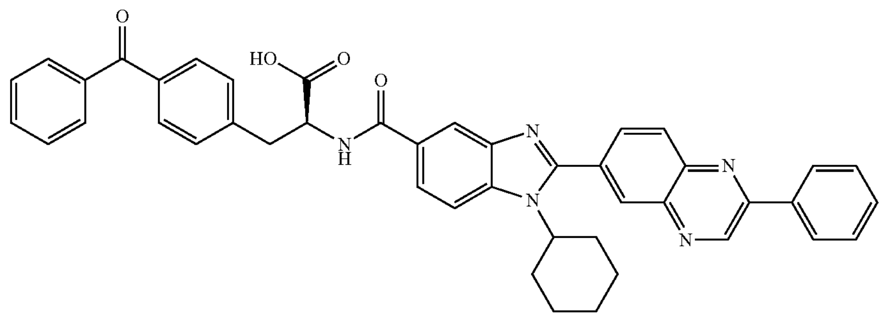 | H | 3-(4-benzoyl-phenyl)-propionic acid | phenyl | Quinoxalin-6-yl | 3-(4-benzoyl-phenyl)-2-{[1-cyclohexyl-2-(2-phenyl-quinoxalin-6-yl)-1H-benzoimidazole-5-carbonyl]-amino}-propionic acid |
| 242 | 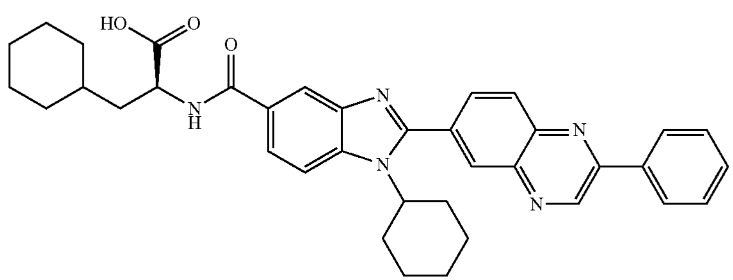 | H | 3-cyclohexyl-propionic acid | phenyl | Quinoxalin-6-yl | 3-cyclohexyl-2-{[1-cyclohexyl-2-(2-phenyl-quinoxalin-6-yl)-1H-benzoimidazole-5-carbonyl]-amino}-propionic acid |

TABLE II-continued

| Cmpd # | Structure | R[8] | R[9] | Y | Het | Name |
|---|---|---|---|---|---|---|
| 243 | 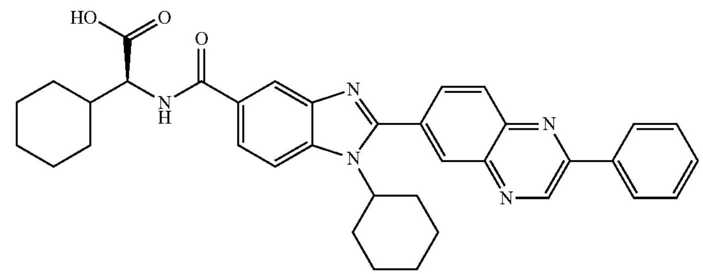 | H | cyclohexyl-acetic acid | phenyl | Quinoxalin-6-yl | cyclohexyl-{[1-cyclohexyl-2-(2-phenyl-quinoxalin-6-yl)-1H-benzoimidazole-5-carbonyl]-amino}-acetic acid |
| 244 | 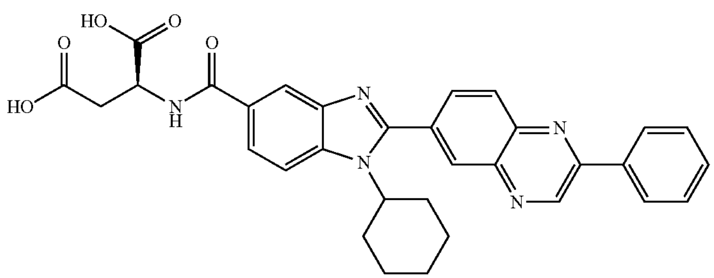 | H | succinic acid | phenyl | Quinoxalin-6-yl | 2-{[1-cyclohexyl-2-(2-phenyl-quinoxalin-6-yl)-1H-benzoimdazole-5-carbonyl]-amino}-succinic acid |

TABLE II-continued

| Cmpd # | Structure | R⁸ | R⁹ | Y | Het | Name |
|---|---|---|---|---|---|---|
| 245 | 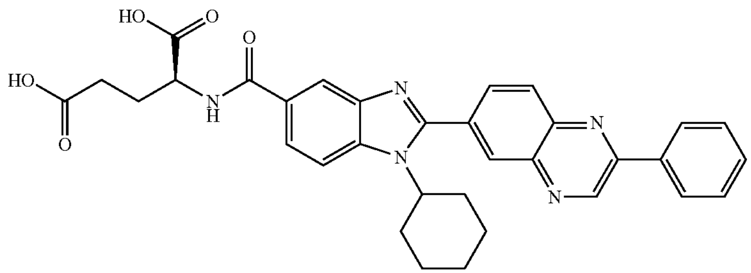 | H | pentanedioic acid | phenyl | Quinoxalin-6-yl | 2-{[1-cyclohexyl-2-(2-phenyl-quinoxalin-6-yl)-1H-benzoimidazole-5-carbonyl]-amino}-pentanedioic acid |
| 246 | 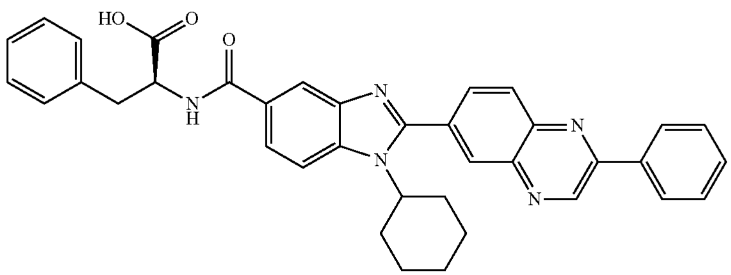 | H | 3-phenyl-propionic acid | phenyl | Quinoxalin-6-yl | 2-{[1-cyclohexyl-2-(2-phenyl-quinoxalin-6-yl)-1H-benzoimidazole-5-carbonyl]-amino}-3-phenyl-propionic acid |

TABLE II-continued

| Cmpd # | Structure | R⁸ | R⁹ | Y | Het | Name |
|---|---|---|---|---|---|---|
| 247 | 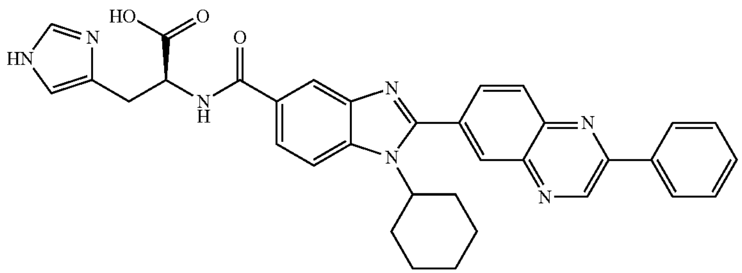 | H | 3-(1H-imidazol-4-yl)-propionic acid | phenyl | Quinoxalin-6-yl | 2-{[1-cyclohexyl-2-(2-phenyl-quinoxalin-6-yl)-1H-benzoimidazole-5-carbonyl]-amino}-3-(1H-imidazol-4-yl)-propionic acid |
| 248 | 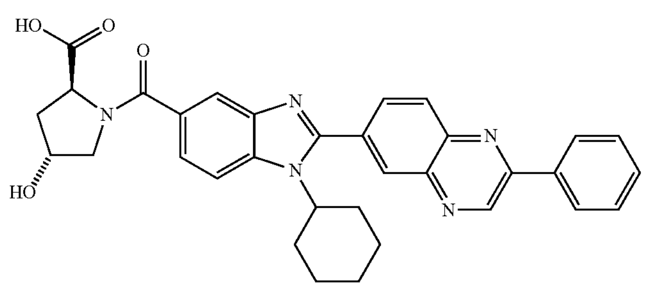 | | -pyrrolidine-2-carboxylic acid | phenyl | Quinoxalin-6-yl | 1-[1-cyclohexyl-2-(2-phenyl-quinoxalin-6-yl)-1H-benzoimidazole-5-carbonyl]-4-hydroxy-pyrrolidine-2-carboxylic acid |

TABLE II-continued

| Cmpd # | Structure | R⁸ | R⁹ | Y | Het | Name |
|---|---|---|---|---|---|---|
| 249 | 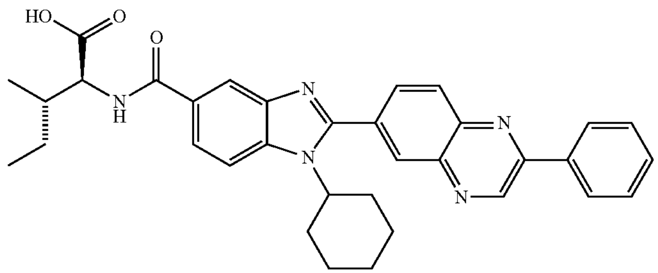 | H | 3-methyl-pentanoic acid | phenyl | Quinoxalin-6-yl | 2-{[1-cyclohexyl-2-(2-phenyl-quinoxalin-6-yl)-1H-benzoimidazole-5-carbonyl]-amino}-3-methyl-pentanoic acid |
| 512 | 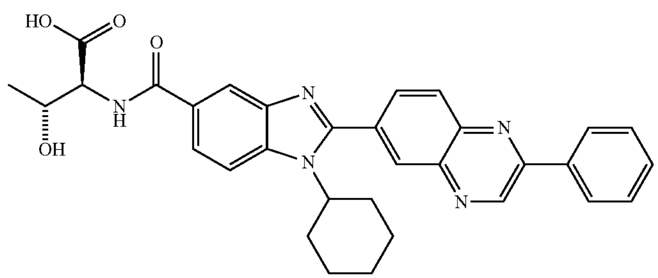 | H | 3-hydroxy-butyric acid | phenyl | Quinoxalin-6-yl | 2-{[1-cyclohexyl-2-(2-phenyl-quinoxalin-6-yl)-1H-benzoimidazole-5-carbonyl]-amino}-3-hydroxy-butyric acid |

TABLE II-continued

| Cmpd # | Structure | R⁸ | R⁹ | Y | Het | Name |
|---|---|---|---|---|---|---|
| 513 | 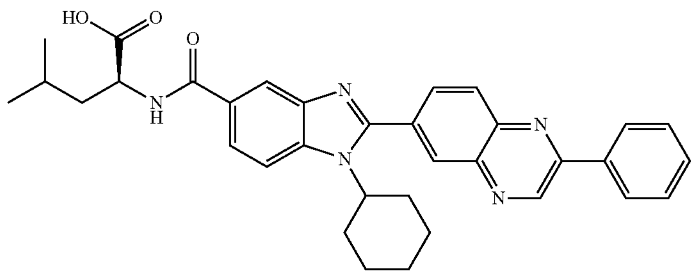 | H | 4-methyl-pentanoic acid | phenyl | Quinoxalin-6-yl | 2-{[1-cyclohexyl-2-(2-phenyl-quinoxalin-6-yl)-1H-benzoimidazole-5-carbonyl]-amino}-4-methyl-pentanoic acid |
| 514 | 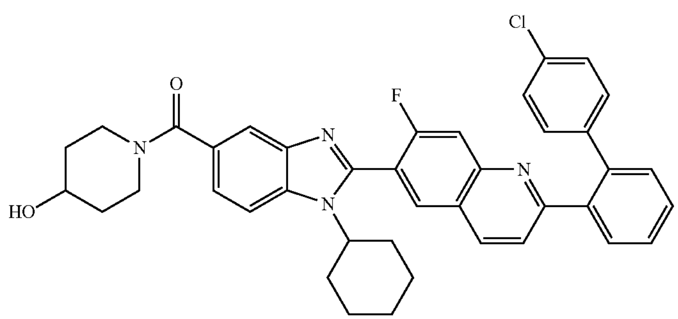 | | 4-hydroxy-piperidin-1-y | 2-(4'-chloro-biphen-2-yl)-7-fluoro- | Quinolin-6-yl | {2-[2-(4'-chloro-biphen-2-yl)-7-fluoro-quinolin-6-yl]-1-cyclohexyl-1H-benzoimidazole-5-yl}-(4-hydroxy-piperidin-1-yl)-methanone |

TABLE II-continued

| Cmpd # | Structure | R[8] | R[9] | Y | Het | Name |
|---|---|---|---|---|---|---|
| 515 | 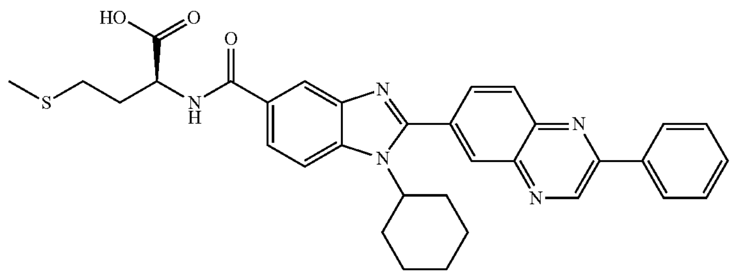 | H | 4-methylsulfanyl-butyric acid | 2-phenyl- | Quinoxalin-6-yl | 2-{[1-cyclohexyl-2-(2-phenyl-quinoxalin-6-yl)-1H-benzoimidazole-5-carbonyl]-amino}-4-methylsulfanyl-butyric acid |
| 516 | 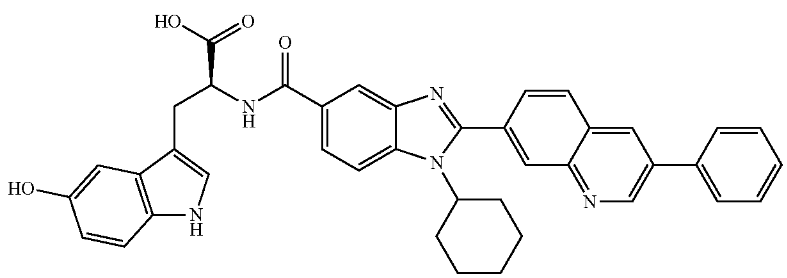 | H | 3-(5-hydroxy-1H-indol-3-yl)-propionic acid | 3-phenyl | Quinolin-7-yl | 2-{[1-cyclohexyl-2-(3-phenyl-quinolin-7-yl)-1H-benzoimidazole-5-carbonyl]-amino}-3-(5-hydroxy-1H-indol-3-yl)-propionic acid |

TABLE II-continued

| Cmpd # | Structure | R⁸ | R⁹ | Y | Het | Name |
|---|---|---|---|---|---|---|
| 517 | 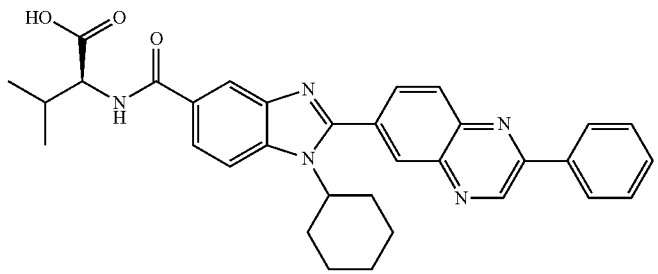 | H | 3-methyl-butyric acid | 2-phenyl- | Quinoxalin-6-yl | 2-{[1-cyclohexyl-2-(2-phenyl-quinoxalin-6-yl)-1H-benzoimidazole-5-carbonyl]-amino}-3-methyl-butryric acid |
| 518 | 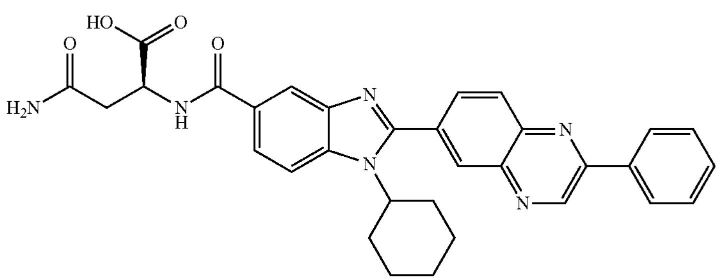 | H | succinic acid | 2-phenyl- | Quinoxalin-6-yl | 2-{[1-cyclohexyl-2-(2-phenyl-quinoxalin-6-yl)-1H-benzoimidazole-5-carbonyl]-amino}-succinamic acid |

TABLE II-continued

| Cmpd # | Structure | R[8] | R[9] | Y | Het | Name |
|---|---|---|---|---|---|---|
| 519 | 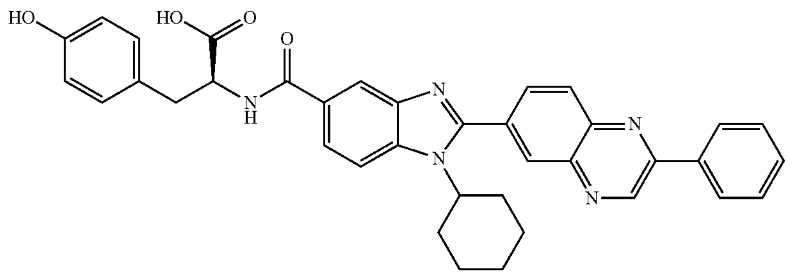 | H | 3-(4-hydroxy-phenyl)-propionic acid | 2-phenyl- | Quinoxalin-6-yl | 2-{[1-cyclohexyl-2-(2-phenyl-quinoxalin-6-yl)-1H-benzoimidazole-5-carbonyl]-amino}-3-(4-hydroxy-phenyl)-propionic acid |
| 520 | | \multicolumn{2}{|c|}{1,2,3,4-tetrahydro-isoquinoline-3-carboxylic acid} | 2-phenyl- | Quinoxalin-6-yl | 2-[1-cyclohexyl-2-(2-phenyl-quinoxalin-6-yl)-1H-benzoimidazole-5-carbonyl]-1,2,3,4-tetrahydro-isoquinoline-3-carboxylic acid |

TABLE II-continued

| Cmpd # | Structure | R⁸ | R⁹ | Y | Het | Name |
|---|---|---|---|---|---|---|
| 521 | 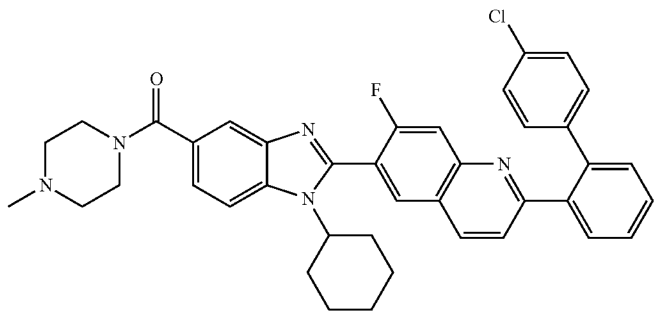 | 4-methyl-piperiazin-1-yl | | 4'-chloro-biphen-2-yl-fluoro | Quinolin-6-yl | {2-[2-(4'-chloro-biphen-2-yl)-7-fluoro-quinolin-6-yl]-1-cyclohexyl-1H-benzoimidazole-5-yl}-(4-methyl-piperazin-1-yl)-methanone |
| 522 | 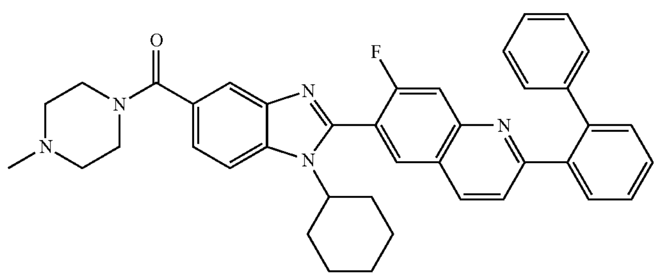 | 4-methyl-piperiazin-1-yl | | biphen-2-yl-fluoro | Quinolin-6-yl | [2-(2-biphen-2-yl-7-fluoro-quinolin-6-yl)-1-cyclohexyl-1H-benzoimidazol-5-yl]-(4-methyl-piperazin-1-yl)-methanone |

TABLE II-continued

| Cmpd # | Structure | R8 | R9 | Y | Het | Name |
|---|---|---|---|---|---|---|
| 523 | 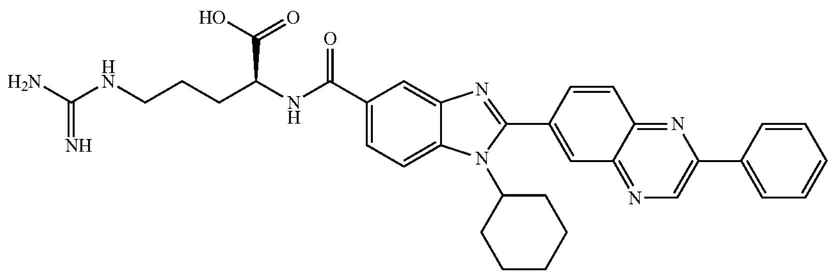 | H | 5-guanidino-pentanoic acid | phenyl | Quinoxalin-6-yl | 2-{[1-cyclohexyl-2-(2-phenyl-quinoxalin-6-yl)-1H-benzoimidazole-5-carbonyl]-amino}-5-guanidino-pentanoic acid |
| 524 | 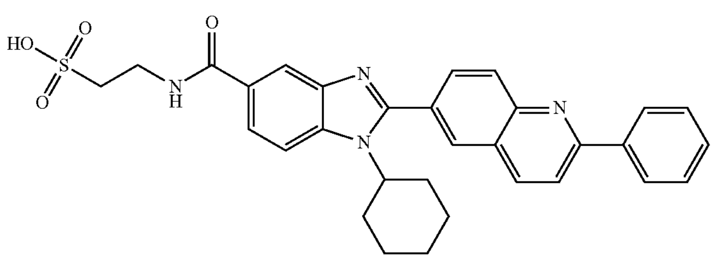 | H | ethanesulfonic acid | phenyl | Quinoxalin-6-yl | 2-{[1-cyclohexyl-2-(2-phenyl-quinoxalin-6-yl)-1H-benzoimidazole-5-carbonyl]-amino}-ethanesulfonic acid |

TABLE II-continued

| Cmpd # | Structure | R⁸ | R⁹ | Y | Het | Name |
|---|---|---|---|---|---|---|
| 541 | 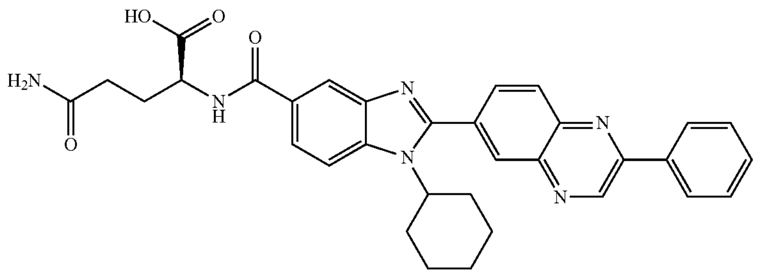 | H | butyric acid | phenyl | Quinoxalin-6-yl | 4-carbamoyl-2-{[1-cyclohexyl-2-(2-phenyl-quinoxalin-6-yl)-1H-benzoimidazole-5-carbonyl]-amino}-butyric acid |
| 250 | 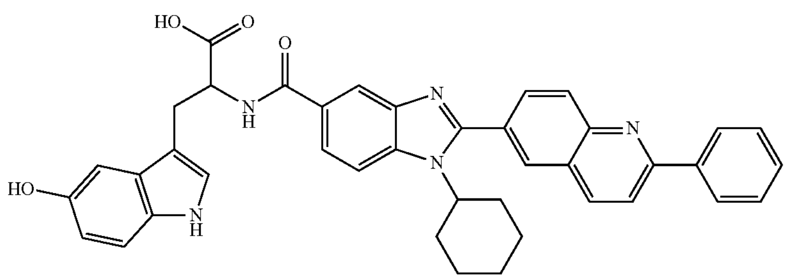 | H | 3-(5-Hydroxy-1H-indol-3-yl)-2-propionic acid | phenyl | Quinolin-6-yl | 2-{[1-cyclohexyl-2-(2-phenyl-quinolin-6-yl)-1H-benzoimidazole-5-carbonyl]-amino}-3-(5-hydroxy-1H-indol-3-yl)-propionic acid |

TABLE II-continued

| Cmpd # | Structure | R[8] | R[9] | Y | Het | Name |
|---|---|---|---|---|---|---|
| 251 | 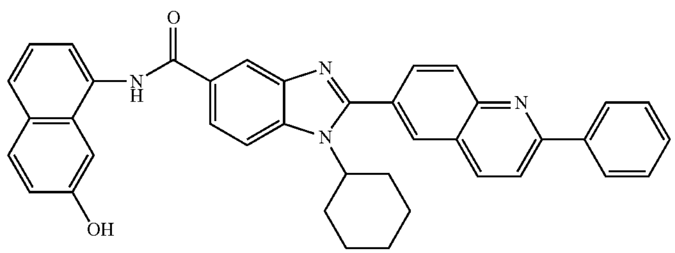 | H | 7-hydroxy-naphthalen-1-yl | phenyl | Quinolin-6-yl | 1-{[1-cyclohexyl-2-(2-phenyl-quinolin-6-yl)-1H-benzoimidazole-5-carbonyl]-amino}-7-hydroxy-naphthalene |
| 252 | 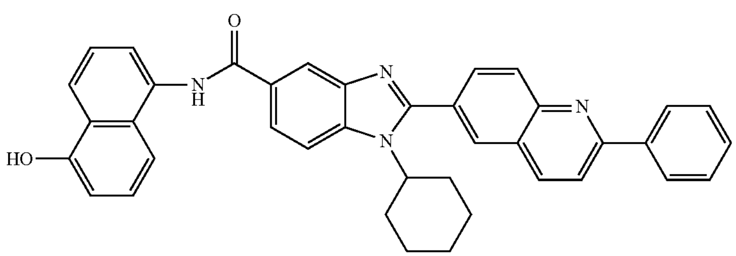 | H | 5-hydroxy-naphthalen-1-yl | phenyl | Quinolin-6-yl | 1-[[1-cyclohexyl-2-(2-phenyl-quinolin-6-yl)-1H-benzoimidazole-5-carbonyl]-amino}-5-hydroxy-naphthalene |

TABLE II-continued

| Cmpd # | Structure | R[8] | R[9] | Y | Het | Name |
|---|---|---|---|---|---|---|
| 253 | 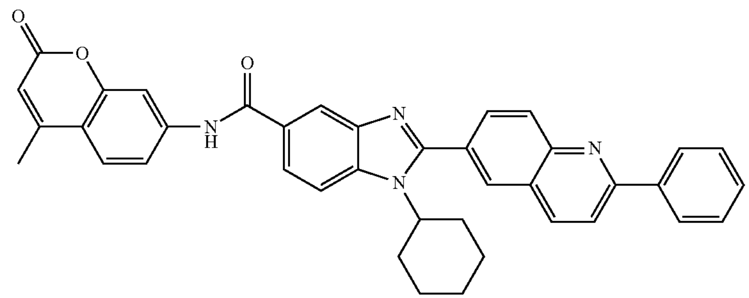 | H | 4-methyl-2-oxo-chromen-7-yl | phenyl | Quinolin-6-yl | 7-{[1-cyclohexyl-2-(2-phenyl-quinolin-6-yl)-1H-benzoimidazole-5-carbonyl]-amino}-4-methyl-2-oxo-chromene |
| 254 | 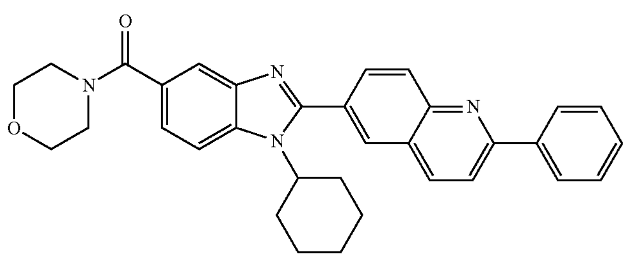 | H | morpholin-4-yl | phenyl | Quinolin-6-yl | {2-[2-phenyl-quinolin-6-yl]-1-cyclohexyl-1H-benzoimidazol-5-yl}-(morpholin-4-yl)-methanone |

TABLE II-continued

| Cmpd # | Structure | R[8] | R[9] | Y | Het | Name |
|---|---|---|---|---|---|---|
| 255 | 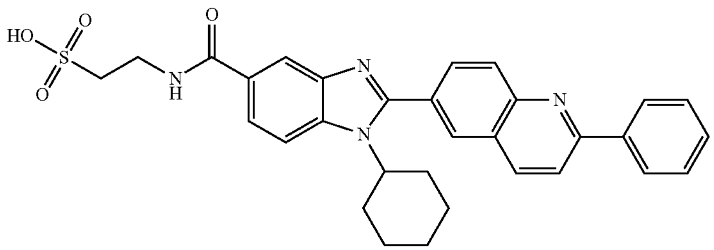 | H | Ethanesulfonic acid-1-yl | phenyl | Quinolin-6-yl | 2-{[1-cyclohexyl-2-(2-phenyl-quinolin-6-yl)-1H-benzoimidazole-5-carbonyl]-amino}-ethanesulfonic acid |
| 570 | 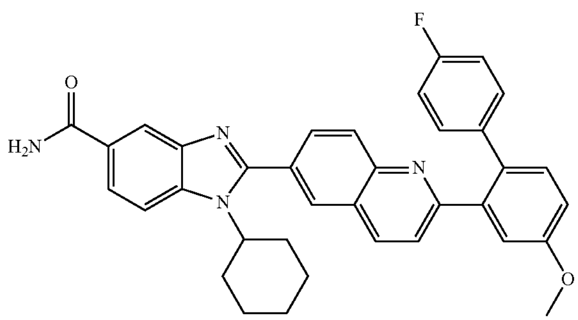 | H | H | 4'-fluoro-4-methoxy-biphen-2-yl | Quinolin-6-yl | 1-cyclohexyl-2-[2-(4'-fluoro-4-methoxy-biphen-2-yl)-quinolin-6-yl]-1H-benzoimidazole-5-carboxylic acid amide |

TABLE II-continued

| Cmpd # | Structure | R⁸ | R⁹ | Y | Het | Name |
|---|---|---|---|---|---|---|
| 574 | 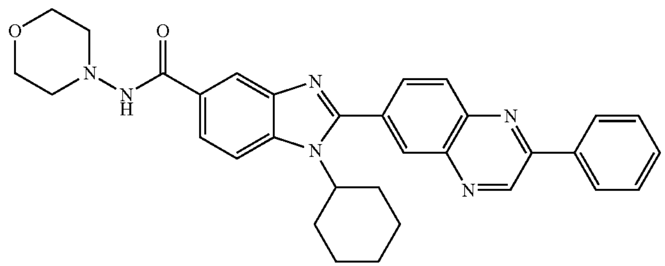 | H | morpholin-4-yl | phenyl | Quinoxalin-6-yl | 1-cyclohexyl-2-(2-phenyl-quinoxalin-6-yl)-1H-benzoimidazole-5-carboxylic acid morpholin-4-ylamide |
| 575 | 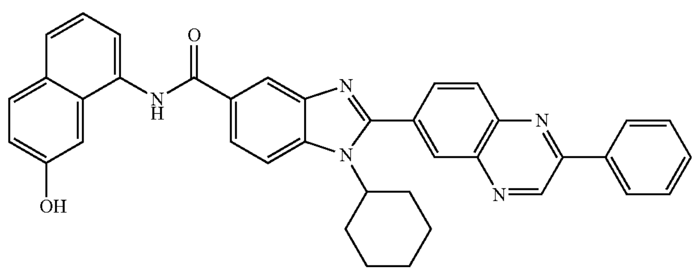 | H | 7-hydroxy-naphthalen-1-yl | phenyl | Quinoxalin-6-yl | 1-cyclohexyl-2-(2-phenyl-quinoxalin-6-yl)-1H-benzoimidazole-5-carboxylic acid (7-hydroxy-naphthalen-1-yl)-amide |

TABLE II-continued

| Cmpd # | Structure | R⁸ | R⁹ | Y | Het | Name |
|---|---|---|---|---|---|---|
| 576 | 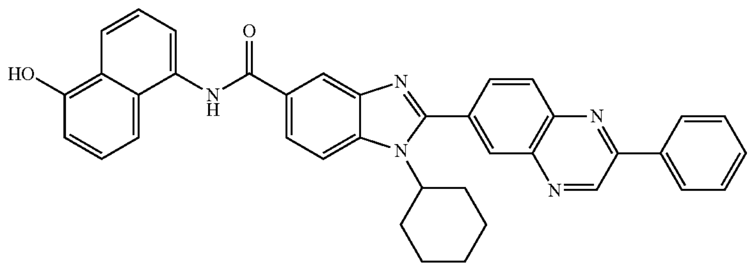 | H | 5-hydroxy-naphthalen-1-yl | phenyl | Quinoxalin-6-yl | 1-cyclohexyl-2-(2-phenyl-quinoxalin-6-yl)-1H-benzoimidazole-5-carboxylic acid (5-hydroxy-naphthalen-1-yl)-amide |
| 577 | 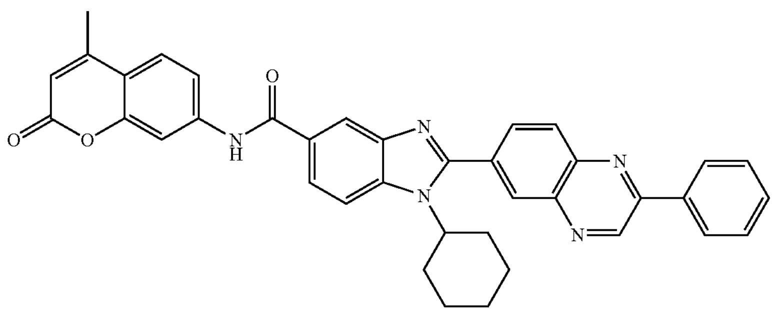 | H | 4-methyl-2-oxo-2H-chromen-7-yl | phenyl | Quinoxalin-6-yl | 1-cyclohexyl-2-(2-phenyl-quinoxalin-6-yl)-1H-benzoimidazole-5-carboxylic acid (4-methyl-2-oxo-2H-chromen-7-yl)-amide |

TABLE III

| Cmpd # | Structure | Y | Het | Name |
|---|---|---|---|---|
| 256 | 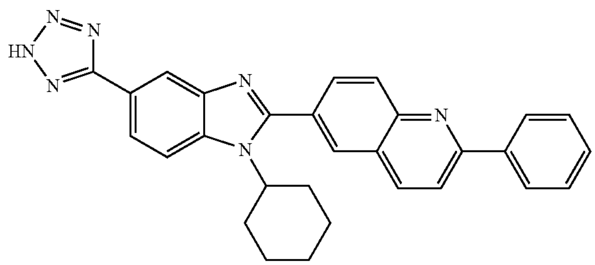 | phenyl | quinolin-6-yl | 6-[1-cyclohexyl-5-(1H-tetrazol-5-yl)-1H-benzimidazol-2-yl]-2-phenylquinoline |
| 257 | 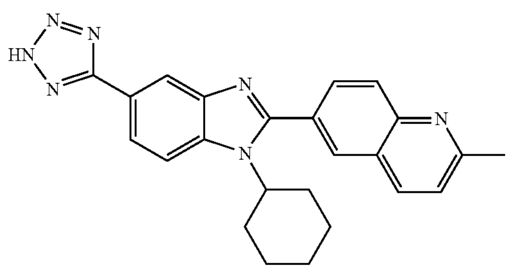 | methyl | quinolin-6-yl | 6-[1-cyclohexyl-5-(1H-tetrazol-5-yl)-1H-benzimidazol-2-yl]-22-methylquinoline |
| 258 | 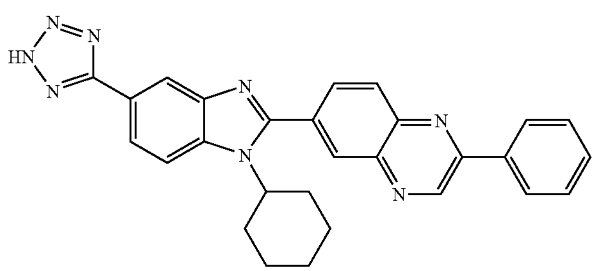 | phenyl | quinoxalin-6-yl | 6-[1-cyclohexyl-5-(1H-tetrazol-5-yl)-1H-benzimidazol-2-yl]-2-phenylquinoxaline |
| 259 | 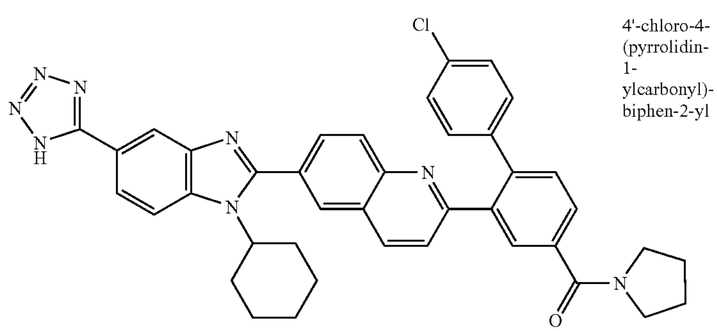 | 4'-chloro-4-(pyrrolidin-1-ylcarbonyl)-biphen-2-yl | quinoxalin-6-yl | (4'-chloro-2-{6-[1-cyclohexyl-5-(1H-tetrazol-5-yl)-1H-benzimidazol-2-yl]-quinolin-2-yl}-biphen-4-yl)-pyrrolidin-1-yl-methanone |

TABLE III-continued

| Cmpd # | Structure | Y | Het | Name |
|---|---|---|---|---|
| 260 | 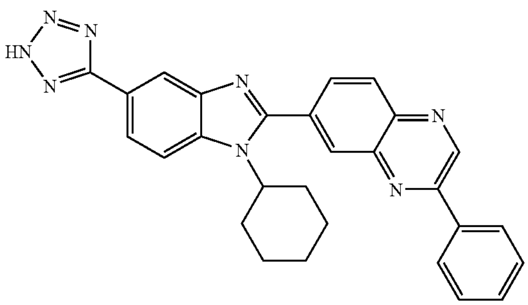 | phenyl | quinoxalin-6-yl | 6-[1-cyclohexyl-5-(1-H-tetrazol-5-yl)-1H-benzimidazol-2-yl]-3-phenylquinoxaline |
| 261 | 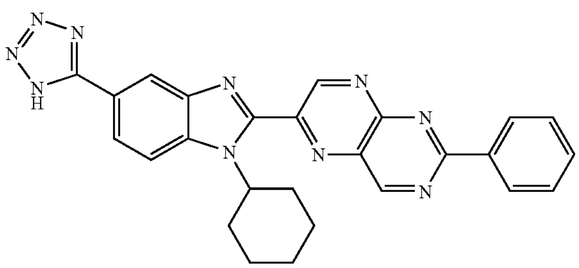 | phenyl | pteridin-6-yl | 6-[1-cyclohexyl-5-(1H-tetrazol-5-yl)-1H-benzimidazol-2-yl]-phenylpteridine |
| 262 | 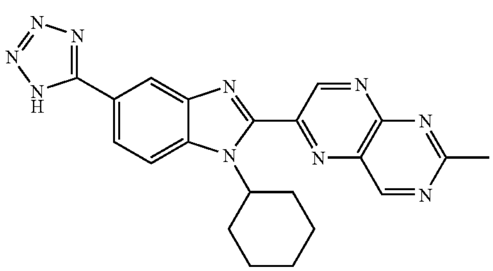 | methyl | pteridin-6-yl | 6-[1-cyclohexyl-5-(1H-tetrazol-5-yl)-1H-benzimidazol-2-yl]-2-methylpteridine |
| 263 | 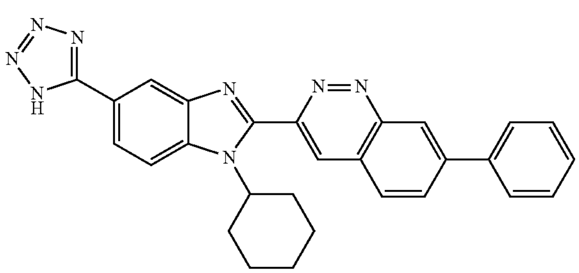 | phenyl | cinnolin-3-yl | 3-[1-cyclohexyl-5-(1H-tetrazol-5-yl)-1H-benzimidazol-2-yl]-7-phenylcinnoline |

TABLE III-continued

| Cmpd # | Structure | Y | Het | Name |
|---|---|---|---|---|
| 264 | 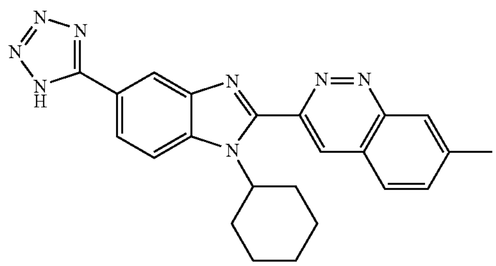 | methyl | cinnolin-3-yl | 3-[1-cyclohexyl-5-(1H-tetrazol-5-yl)-1H-benzimidazol-2-yl]-7-methylcinnoline |
| 265 | 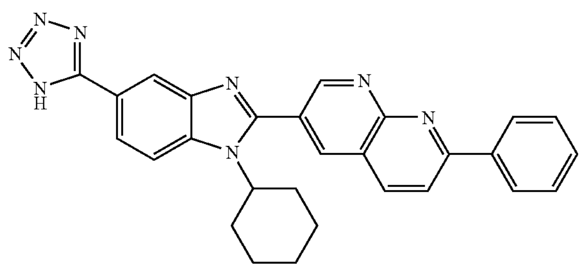 | phenyl | [1,8]naph-thyridin-3-yl | 3-[1-cyclohexyl-5-(1H-tetrazol-5-yl)-1H-benzimidazol-2-yl]-7-phenyl[1,8]naphthyridine |
| 266 | 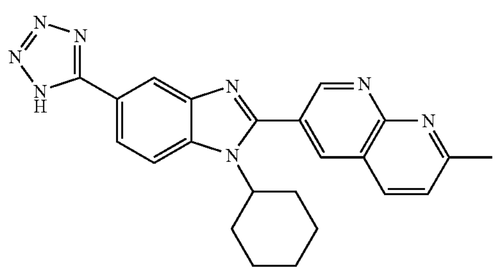 | methyl | [1,8]naph-thyridin-3-yl | 3-[1-cyclohexyl-5-(1H-tetrazol-5-yl)-1H-benzimidazol-2-yl]-7-methyl[1,8]naphthyridine |
| 267 | 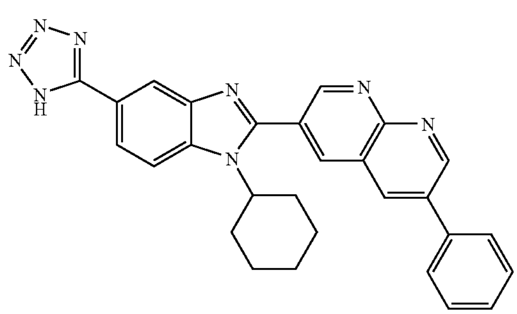 | phenyl | [1,8]naph-thyridin-3-yl | 3-[1-cyclohexyl-5-(1H-tetrazol-5-yl)-1H-benzimidazol-2-yl]-6-phenyl[1,8]naphthyridine |

TABLE III-continued

| Cmpd # | Structure | Y | Het | Name |
|---|---|---|---|---|
| 268 | 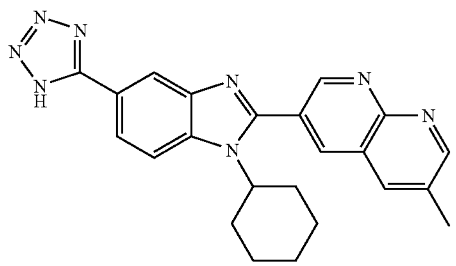 | methyl | [1,8]naph-thyridin-3-yl | 3-[1-cyclohexyl-5-(1H-tetrazol-5-yl)-1H-benzimidazol-2-yl]-6-methyl[1,8]naphthyridine |
| 269 | 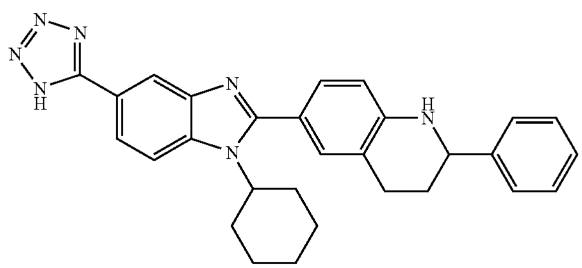 | phenyl | 1,2,3,4-tetrahydro-quinolin-6-yl | 6-[1-cyclohexyl-5-(1H-tetrazol-5-yl)-1H-benzimidazol-2-yl]-2-phenyl-1,2,3,4-tetrahydroquinoline |
| 270 | 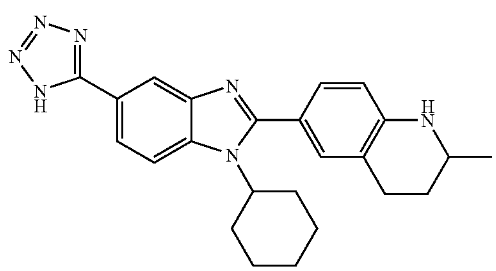 | methyl | 1,2,3,4-tetrahydro-quinolin-6-yl | 6-[1-cyclohexyl-5-(1H-tetrazol-5-yl)-1H-benzimidazol-2-yl]-2-methyl-1,2,3,4-tetrahydroquinoline |
| 271 | 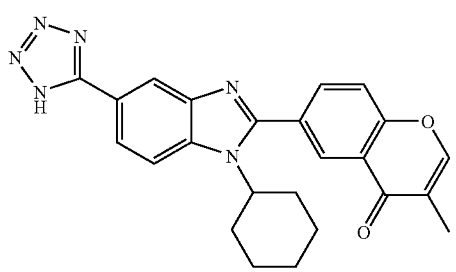 | methyl | 4-oxo-2H-chromen-6-yl | 6-[1-cyclohexyl-5-(1H-tetrazol-5-yl)-1H-benzimidazol-2-yl]-3-methyl-4-oxo-2H-chromene |

TABLE III-continued

| Cmpd # | Structure | Y | Het | Name |
|---|---|---|---|---|
| 272 | 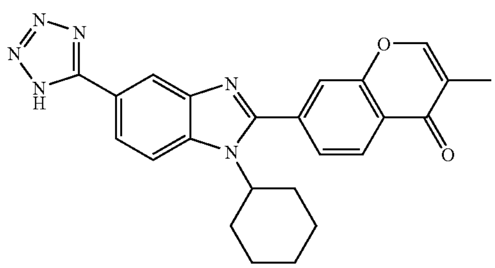 | methyl | 2-oxo-2H-chromen-7-yl | 7-[1-cyclohexyl-5-(1H-tetrazol-5-yl)-1H-benzimidazol-2-yl]-3-methyl-2-oxo-2H-chromene |
| 273 | 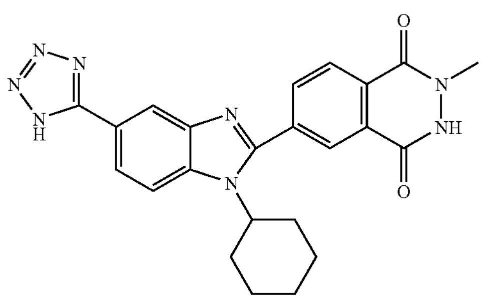 | methyl | 1,4-dioxo-1,2,3,4-tetrahydro-phthalazin-6-yl | 6-[1-cyclohexyl-5-(1H-tetrazol-5-yl)-1H-benzimidazol-2-yl]-2-methyl-1,4-dioxo-1,2,3,4-tetrahydro-phthalazine |
| 274 | 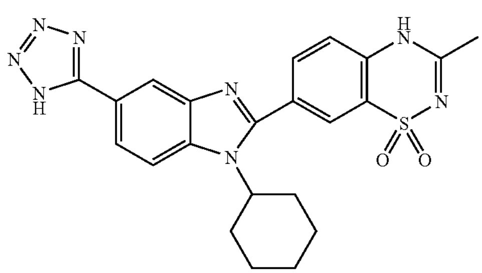 | methyl | 1,1-dioxo-1,4-dihydro-1λ6-benzo-[1,2,4]thiadiazin-7-yl | 7-[1-cyclohexyl-5-(1H-tetrazol-5-yl)-1H-benzimidazol-2-yl]-3-methyl-1,1-dioxo-1,4-dihydro-1λ6-benzo[1,2,4]thiadiazine |
| 275 | 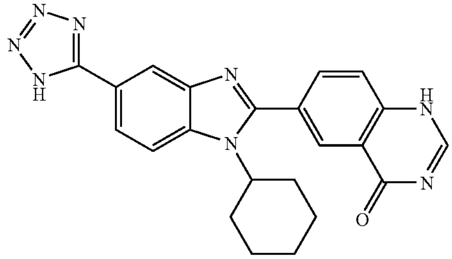 | | 4-oxo-1,4-dihydro-quinazolin-6-yl | 6-[1-cyclohexyl-5-(1H-tetrazol-5-yl)-1H-benzimidazol-2-yl]-4-oxo-1,4-dihydro-quinazoline |

TABLE III-continued

| Cmpd # | Structure | Y | Het | Name |
|---|---|---|---|---|
| 276 | 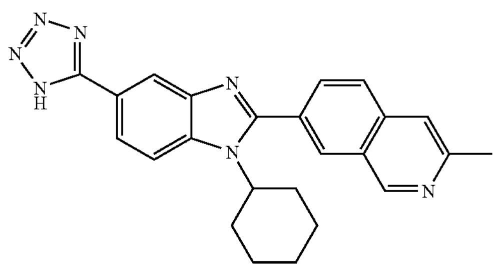 | methyl | Isoquinolin-6-yl | 6-[1-cyclohexyl-5-(1H-tetrazol-5-yl)-1H-benzimidazol-2-yl]-3-methyl-isoquinoline |
| 277 | 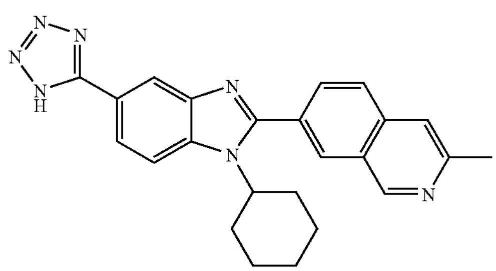 | methyl | 1,4-dihydro-isoquinolin-6-yl | 6-[1-cyclohexyl-5-(1H-tetrazol-5-yl)-1H-benzimidazol-2-yl]-3-methyl-1,4-dihydro-isoquinoline |
| 278 | 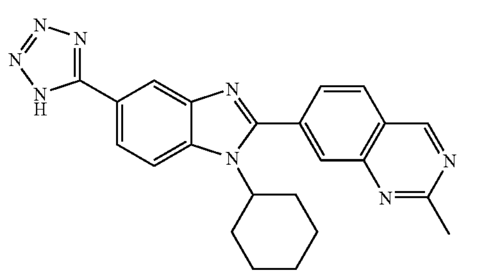 | methyl | quinazolin-7-yl | 7-[1-ccyclohexyl-5-(1H-tetrazol-5-yl)-1H-benzimidazol-2-yl]-2-methyl-quinazoline |
| 279 | 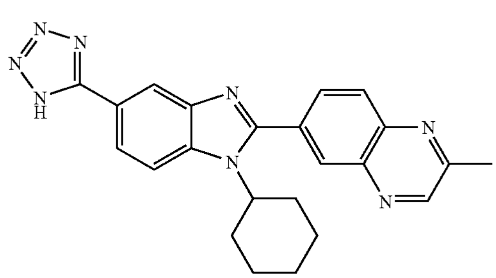 | methyl | quinoxalin-6-yl | 6-[1-cyclohexyl-5-(1H-tetrazol-5-yl)-1H-benzimidazol-2-yl]-2-methyl-quinoxaline |

TABLE III-continued

| Cmpd # | Structure | Y | Het | Name |
|---|---|---|---|---|
| 280 | 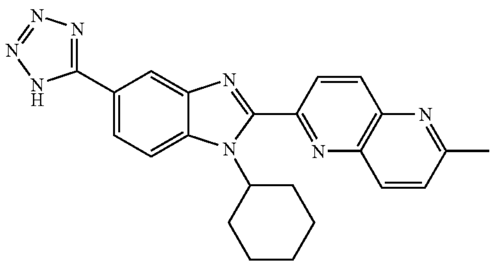 | methyl | [1,5]naph-thyridin-2-yl | 2-[1-cyclohexyl-5-(1H-tetrazol-5-yl)-1H-benzimidazol-2-yl]-6-methyl-[1,5]naphthyridine |
| 281 | 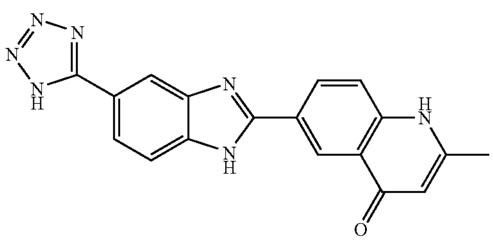 | methyl | 4-oxo-1,4-dihydro-quinolin-6-yl | 6-[1-cyclohexyl-5-(1H-tetrazol-5-yl)-1H-benzimidazol-2-yl]-2-methyl-4-oxo-1,4-dihydro-quinoline |
| 282 | 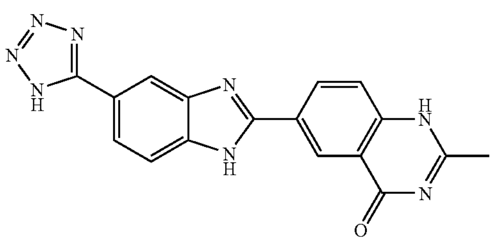 | methyl | 4-oxo-1,4-dihydro-quinazolin-6-yl | 6-[1-cyclohexyl-5-(1H-tetrazol-5-yl)-1H-benzimidazol-2-yl]-2-methyl-4-oxo-1,4-dihydro-quinazoline |
| 525 | 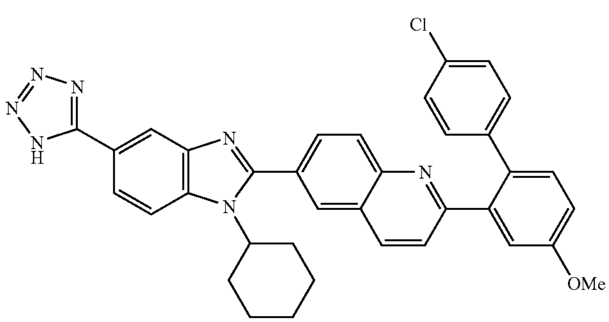 | 4'-chloro-4-methoxy-biphen-2-yl | quinolin-6-yl | 2-(4'-chloro-4-methoxy-biphen-2-yl)-6-[1-cyclohexyl-5-(1H-tetrazol-5-yl)-1H-benzoimidazol-2-yl]-quinoline |

TABLE IV

| Cmpd # | Structure | R⁴ | Y | Het | Name |
|---|---|---|---|---|---|
| 283 | 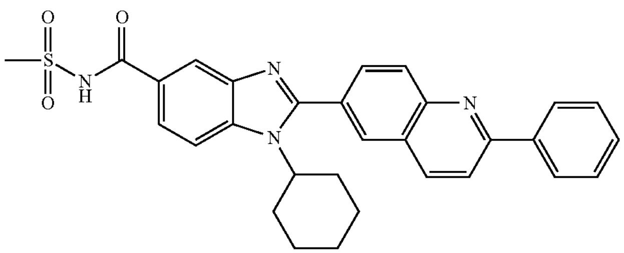 | methyl | Phenyl | quinolin-6-yl | N-[1-cyclohexyl-2-(2-phenyl-quinolin-6-yl)-1H-benzimidazol-5-ylcarbonyl]-N-(methylsulfonyl)amine |
| 284 | 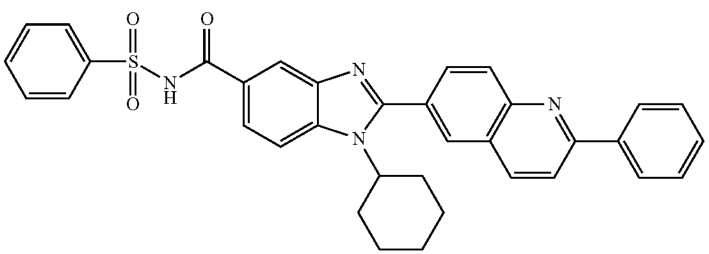 | phenyl | Methyl | quinolin-6-yl | N-[1-cyclohexyl-2-(2-phenyl-quinolin-6-yl)-1H-benzoimidazol-5-ylcarbonyl]-N-(phenylsulfonyl)amine |
| 285 | 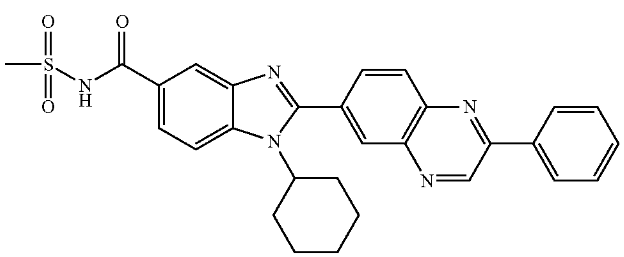 | methyl | Phenyl | Quinoxalin-6-yl | N-[1-cyclohexyl-2-(2-phenyl-quinoxalin-6-yl)-1H-benzoimidazol-5-ylcarbonyl]-N-(methylsulfonyl)amine |

TABLE IV-continued

| Cmpd # | Structure | R4 | Y | Het | Name |
|---|---|---|---|---|---|
| 286 | 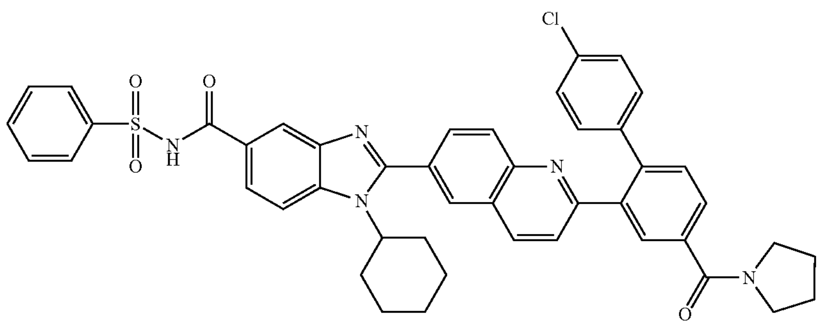 | phenyl | 4'-chloro-4-(pyrrolidine-1-carbonyl)-biphen-2-yl- | quinolin-6-yl | N-[1-cyclohexyl-2-(2-[4'-chloro-4-(pyrrolidine-1-carbonyl)-biphen-2-yl]-quinoxalin-6-yl)-1H-benzomimdazol-5-ylcarbonyl]-N-(phenylsulfonyl)amine |
| 287 | 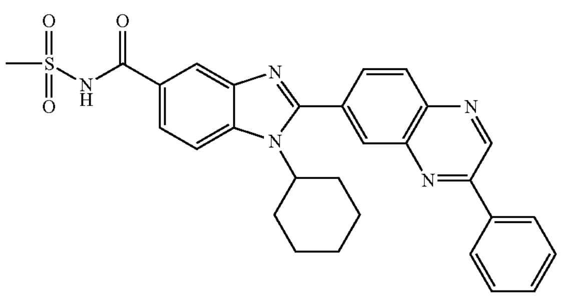 | methyl | phenyl | Quinoxalin-6-yl | N-[1-cyclohexyl-2-(3-phenyl-quinoxalin-6-yl)-1H-benzomimdazol-5-ylcarbonyl]-N-(methylsulfonyl)amine |

TABLE IV-continued

| Cmpd # | Structure | R⁴ | Y | Het | Name |
|---|---|---|---|---|---|
| 288 | 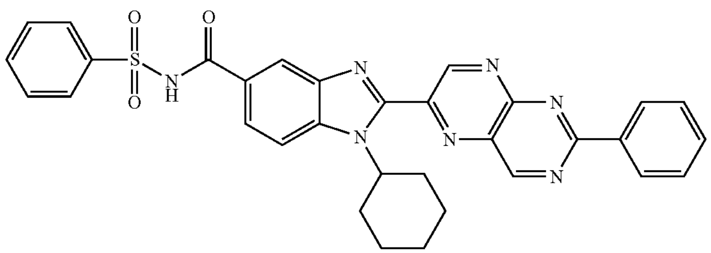 | phenyl | phenyl | pteridin-6-yl | N-[1-cyclohexyl-2-(2-phenyl-pteridin-6-yl)-1H-benzoimidazol-5-ylcarbonyl]-N-(phenylsulfonyl)amine |
| 289 | 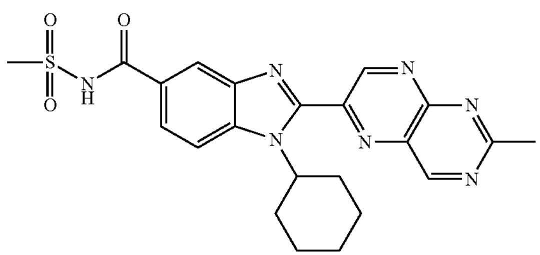 | methyl | methyl | pteridin-6-yl | N-[1-cyclohexyl-2-(2-methyl-pteridin-6-yl)-1H-benzoimidazol-5-ylcarbonyl]-N-(methylsulfonyl)amine |
| 290 | 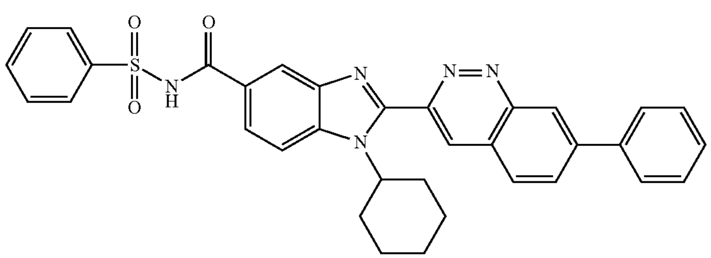 | phenyl | phenyl | cinnolin-3-yl | N-[1-cyclohexyl-2-(7-phenyl-cinnolin-3-yl)-1H-benzoimidazol-5-ylcarbonyl]-N-(phenylsulfonyl)amine |

TABLE IV-continued

| Cmpd # | Structure | R⁴ | Y | Het | Name |
|---|---|---|---|---|---|
| 291 | 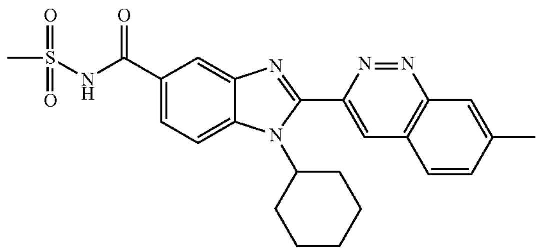 | methyl | methyl | cinnolin-3-yl | N-[1-cyclohexyl-2-(7-methyl-cinnolin-3-yl)-1H-benzoimidazol-5-ylcarbonyl]-N-(methylsulfonyl)amine |
| 292 | 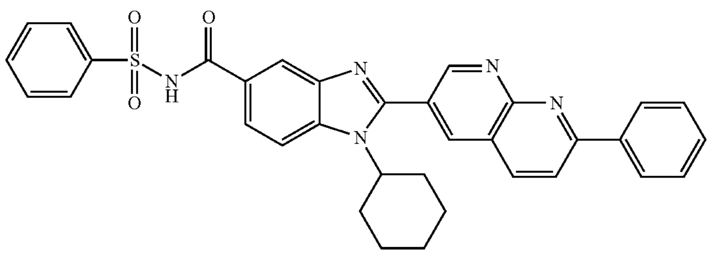 | phenyl | phenyl | [1,8]naphthyridin-3-yl | N-[1-cyclohexyl-2-phenyl-[1,8]naphthyridin-3-yl)-1H-benzoimidazol-5-ylcarbonyl]-N-(phenylsulfonyl)amine |
| 293 | 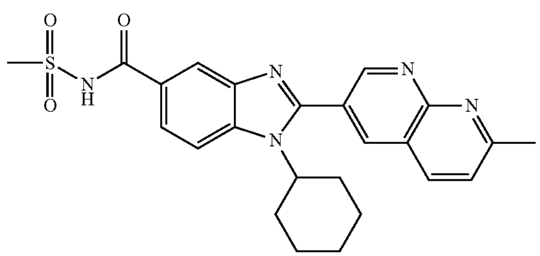 | methyl | methyl | [1,8]naphthyridin-3-yl | N-[1-cyclohexyl-2-(7-methyl-[1,8]naphthyridin-3-yl)-1H-benzoimidazol-5-ylcarbonyl]-N-(methylsulfonyl)amine |

TABLE IV-continued

| Cmpd # | Structure | R⁴ | Y | Het | Name |
|---|---|---|---|---|---|
| 294 | 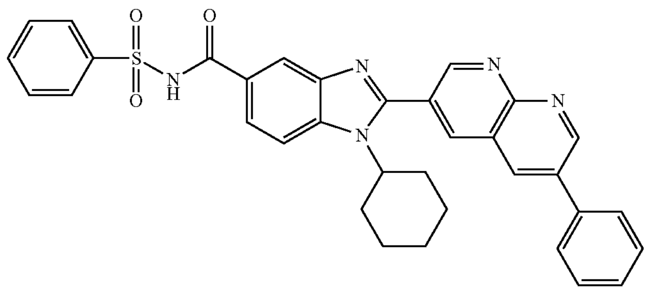 | phenyl | phenyl | [1,8]naphthyridin-3-yl | N-[1-cyclohexyl-2-(6-phenyl-[1,8]naphthyridin-3-yl)-1H-benzoimidazol-5-ylcarbonyl]-N-(phenylsulfonyl)amine |
| 295 | 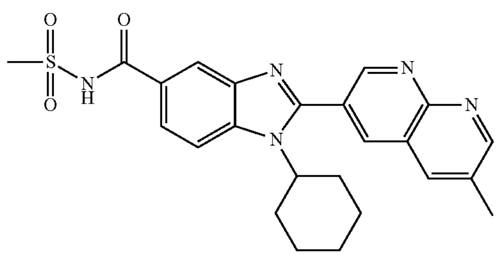 | methyl | methyl | [1,8]naphthyridin-3-yl | N-[1-cyclohexyl-2-(6-methyl-[1,8]naphthyridin-3-yl)-1H-benzoimidazol-5-ylcarbonyl]-N-(methylsulfonyl)amine |
| 296 | 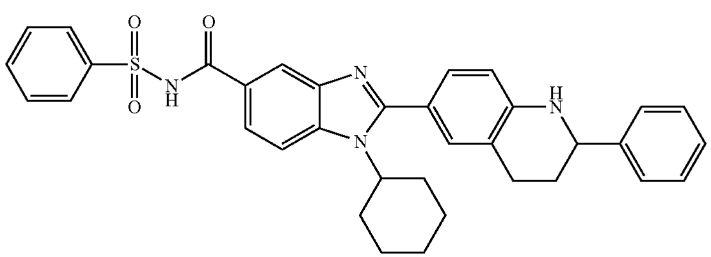 | phenyl | phenyl | 1,2,3,4-tetrahydroquinolin-6-yl | N-[1-cyclohexyl-2-(2-phenyl-1,2,3,4-tetrahydroquinolin-6-yl)-1H-benzoimidazol-5-ylcarbonyl]-N-(phenylsulfonyl)amine |

TABLE IV-continued

| Cmpd # | Structure | R⁴ | Y | Het | Name |
|---|---|---|---|---|---|
| 297 | 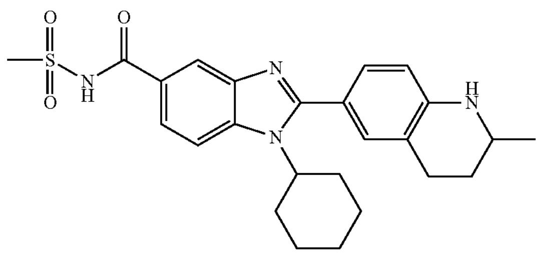 | methyl | methyl | 1,2,3,4-tetrahydroquinolin-6-yl | N-[1-cyclohexyl-2-(2-methyl-1,2,3,4-tetrahydroquinolin-6-yl)-1H-benzoimidazol-5-ylcarbonyl]-N-(methylsulfonyl)amine |
| 298 | 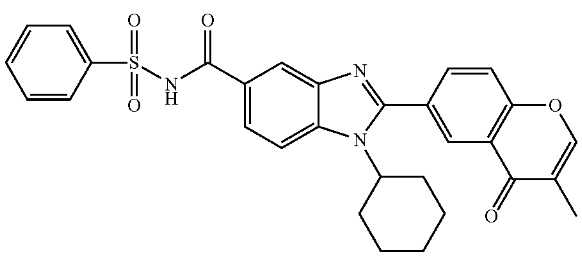 | phenyl | methyl | 4-oxo-2H-chromen-6-yl | N-[1-cyclohexyl-2-(3-methyl-4-oxo-2H-chromen-6-yl)-1H-benzoimidazol-5-ylcarbonyl]-N-(phenylsulfonyl)amine |
| 299 | 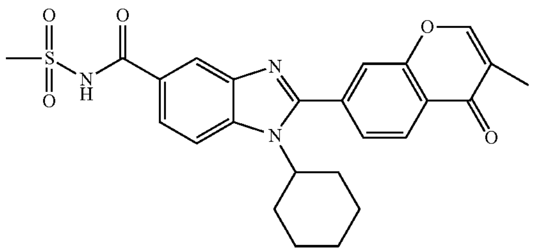 | methyl | methyl | 2-oxo-2H-chromen-7-yl | N-[1-cyclohexyl-2-(3-methyl-2-oxo-2H-chromen-7-yl)-1H-benzoimidazol-5-ylcarbonyl]-N-(methylsulfonyl)amine |

TABLE IV-continued

| Cmpd # | Structure | R⁴ | Y | Het | Name |
|---|---|---|---|---|---|
| 300 | 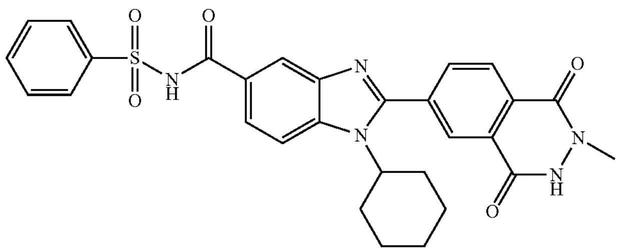 | phenyl | methyl | 1,4-dioxo-1,2,3,4-tetrahydro-phthalazin-6-yl | N-[1-cyclohexyl-2-(2-methyl-1,4-dioxo-1,2,3,4-tetrahydro-phthalazin-6-yl)-1H-benzoimidazol-5-ylcarbonyl]-N-(phenylsulfonyl)amine |
| 301 | 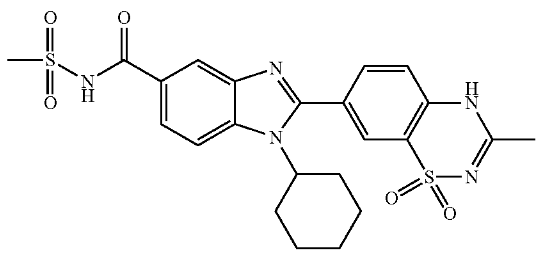 | methyl | methyl | 1,1-dioxo-1,4-dihydro-1λ6-benzo[1,2,4]thiadiazin-7-yl | N-[1-cyclohexyl-2-(3-methyl-1,1-dioxo-1,4-dihydro-benzo[1,2,4]thiadiazol-5-ylcarbonyl]-N-(methylsulfonyl)amine |
| 302 | 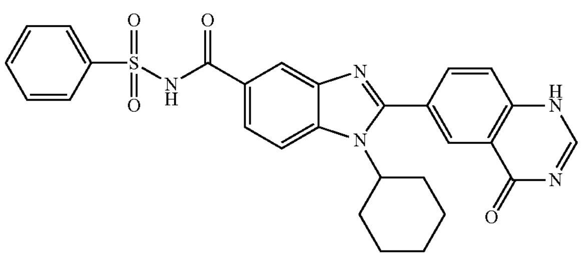 | phenyl | | 4-oxo-1,4-dihydro-quinazolin-6-yl | N-[1-cyclohexyl-2-(4-oxo-1,4-dihydro-quinazolin-6-yl)-1H-benzoimidazol-5-ylcarbonyl]-N-(phenylsulfonyl)amine |

TABLE IV-continued

| Cmpd # | Structure | R⁴ | Y | Het | Name |
|---|---|---|---|---|---|
| 303 | 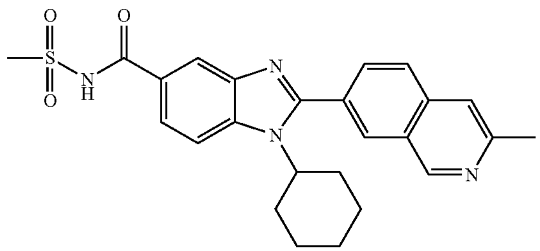 | methyl | methyl | isoquinolin-6-yl | N-[1-cyclohexyl-2-(3-methyl-isoquinolin-6-yl)-1H-benzoimidazol-5-ylcarbonyl]-N-(methylsulfonyl)amine |
| 304 | 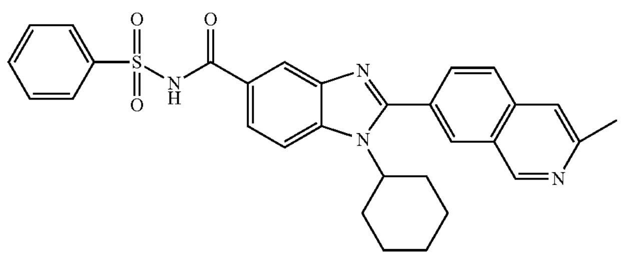 | phenyl | methyl | 1,4-dihydro-isoquinolin-6-yl | N-[1-cyclohexyl-2-(3-methyl-1,4-dihydroisoquinolin-6-yl)-1H-benzoimidazol-5-ylcarbonyl]-N-(phenylsulfonyl)amine |
| 305 | 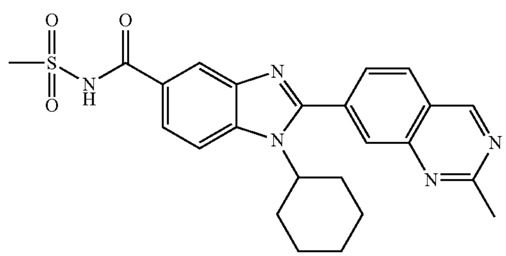 | methyl | methyl | Quinazolin-7-yl | N-[1-cyclohexyl-2-(2-methyl-quinazolin-7-yl)-1H-benzoimidazol-5-ylcarbonyl]-N-(methylsulfonyl)amine |

TABLE IV-continued

| Cmpd # | Structure | R⁴ | Y | Het | Name |
|---|---|---|---|---|---|
| 306 | 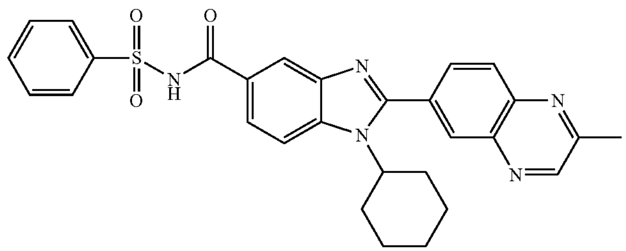 | phenyl | methyl | Quinoxalin-6-yl | N-[1-cyclohexyl-2-(2-methyl-quinoxalin-6-yl)-1H-benzoimidazol-5-ylcarbonyl]-N-(phenylsulfonyl)amine |
| 307 | 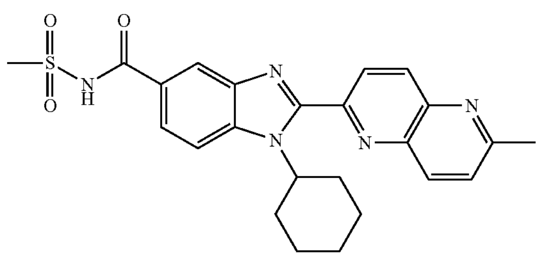 | methyl | methyl | [1,5]naphthyridin-2-yl | N-[1-cyclohexyl-2-(6-methyl-[1,5]naphthyridin-2-yl)-1H-benzoimidazol-5-ylcarbonyl]-N-(methylsulfonyl)amine |

TABLE IV-continued

| Cmpd # | Structure | R⁴ | Y | Het | Name |
|---|---|---|---|---|---|
| 308 | 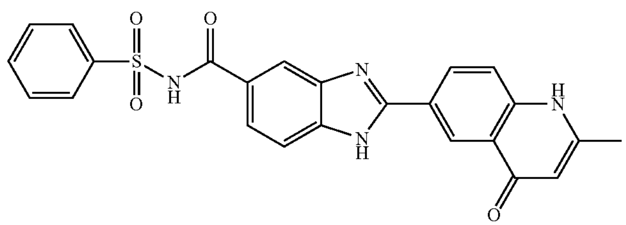 | phenyl | methyl | 4-oxo-1,4-dihydroquinolin-6-yl | N-[1-cyclohexyl-2-(2-methyl-4-oxo-1,4-dihydroquinolin-6-yl)-1H-benzoimidazol-5-ylcarbonyl]-N-(phenylsulfonyl)amine |
| 309 | 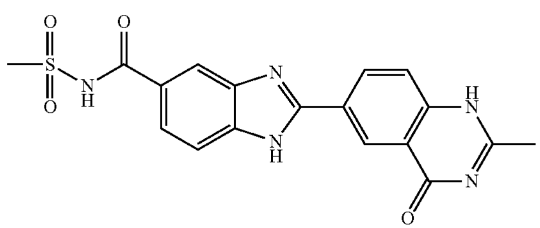 | methyl | methyl | 4-oxo-1,4-dihydroquinazolin-6-yl | N-[1-cyclohexyl-2-(2-methyl-4-oxo-1,4-dihydroquinazolin-6-yl)-1H-benzoimidazol-5-ylcarbonyl]-N-(methylsulfonyl)amine |

TABLE V

| Cmpd # | Structure | R² | R²' | Y | Het-Y | Name |
|---|---|---|---|---|---|---|
| 310 | 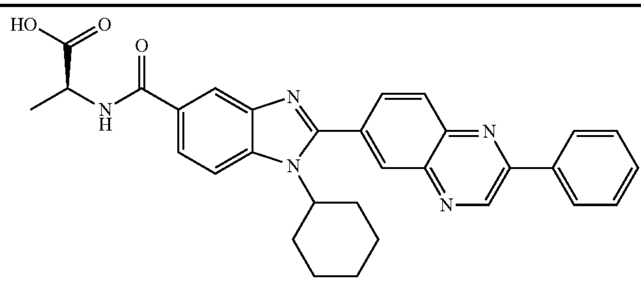 | methyl | H | phenyl | quinoxalin-6-yl | 2-[(2-(2-phenyl-quinoxalin-6-yl)-1-cyclohexyl-1H-benzoimidazole-5-carbonyl)-amino]-propionic acid |
| 311 | 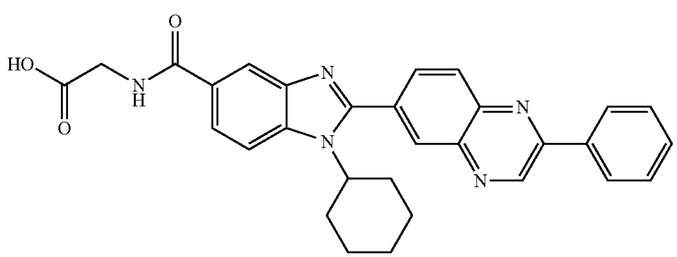 | H | H | phenyl | quinoxalin-6-yl | {[1-cyclohexyl-2-(2-phenyl-quinoxalin-6-yl)-1H-benzoimidazole-5-carbonyl]-amino}-acetic acid |

TABLE V-continued

| Cmpd # | Structure | R² | R²' | Y | Het-Y | Name |
|---|---|---|---|---|---|---|
| 312 | 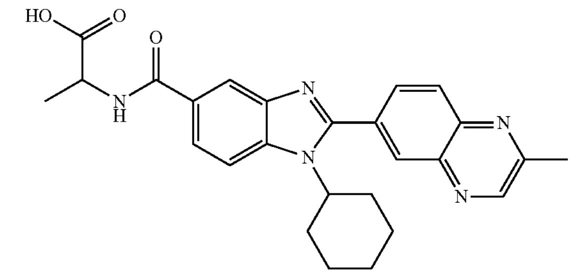 | methyl | H | methyl | quinoxalin-6-yl | 2-[(2-(2-methyl-quinoxalin-6-yl)-1-cyclohexyl-1H-benzoimidazole-5-carbonyl)-amino]-propionic acid |
| 313 | 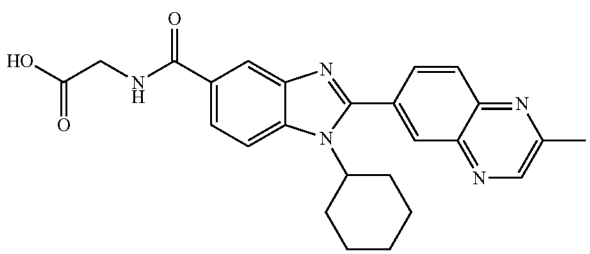 | H | H | methyl | quinoxalin-6-yl | {[1-cyclohexyl-2-(2-methyl-quinoxalin-6-yl)-1H-benzoimidazole-5-carbonyl]-amino}-acetic acid |
| 314 | 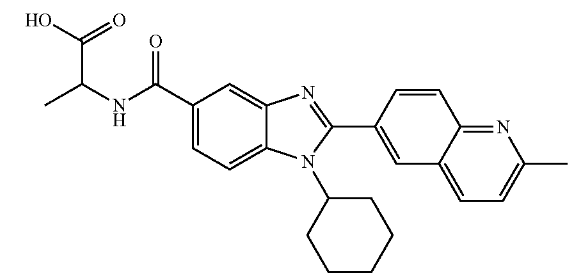 | methyl | H | methyl | quinolin-6-yl | 2-[(2-(2-methyl-quinolin-6-yl)-1-cyclohexyl-1H-benzoimidazole-5-carbonyl)-amino]-propionic acid |

TABLE V-continued

| Cmpd # | Structure | R² | R²' | Y | Het-Y | Name |
|---|---|---|---|---|---|---|
| 315 | 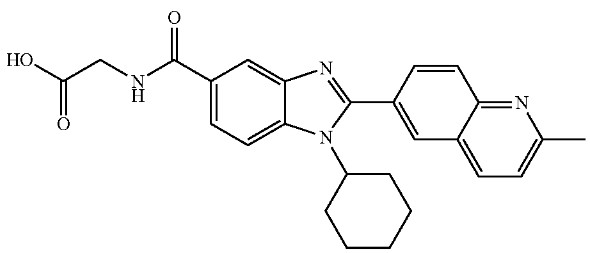 | H | H | methyl | quinolin-6-yl | {[1-cyclohexyl-2-(2-methyl-quinolin-6-yl)-1H-benzoimidazole-5-carbonyl]-amino}-acetic acid |
| 316 | 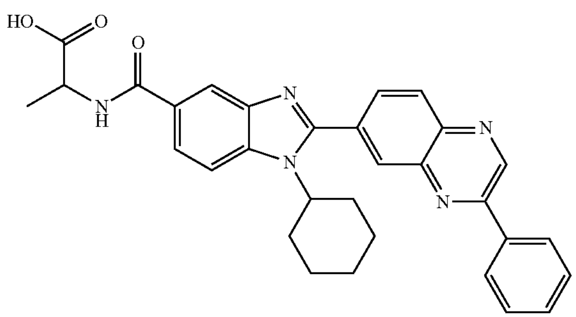 | methyl | H | phenyl | quinoxalin-6-yl | 2-{[2-(3-phenyl-quinoxalin-6-yl)-1-cyclohexyl-1H-benzoimidazole-5-carbonyl)-amino]-propionic acid |

TABLE V-continued

| Cmpd # | Structure | R² | R²' | Y | Het-Y | Name |
|---|---|---|---|---|---|---|
| 317 | 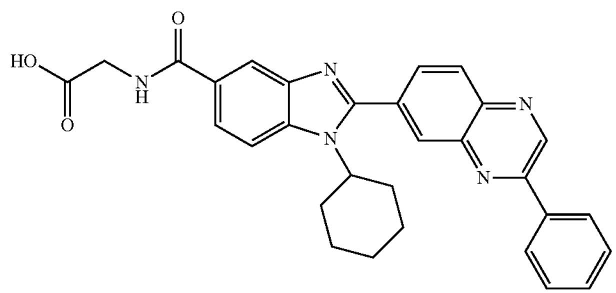 | H | H | phenyl | quinoxalin-6-yl | {[1-cyclohexyl-2-(3-phenyl-quinoxalin-6-yl)-1H-benzoimidazole-5-carbonyl]-amino}-acetic acid |
| 318 | 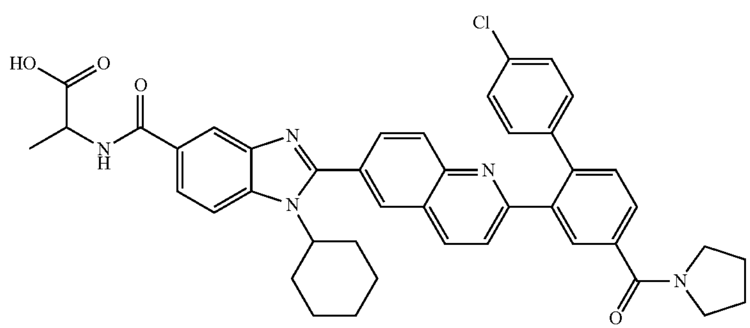 | methyl | H | 4'-chloro-4-(pyrrolidin-1-ylcarbonyl)-biphen-2-yl | quinolin-6-yl | 2-[(2-{2-[4'-chloro-4-(pyrrolidine-1-carbonyl)-biphen-2-yl]-quinolin-6-yl}-1-cyclohexyl-1H-benzoimidazole-5-carbonyl)-amino]-propionic acid |

TABLE V-continued
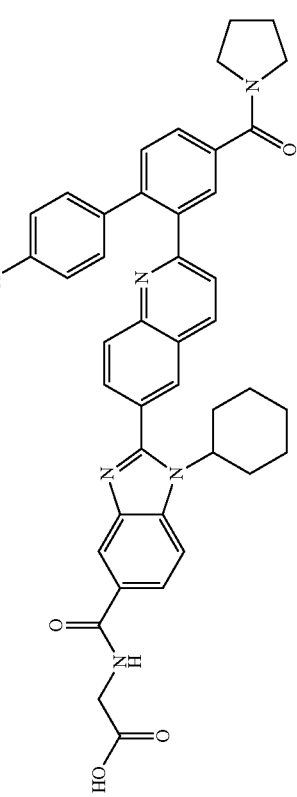
| Cmpd # | Structure | R² | R²' Y | Het-Y | Name |
|---|---|---|---|---|---|
| 319 | 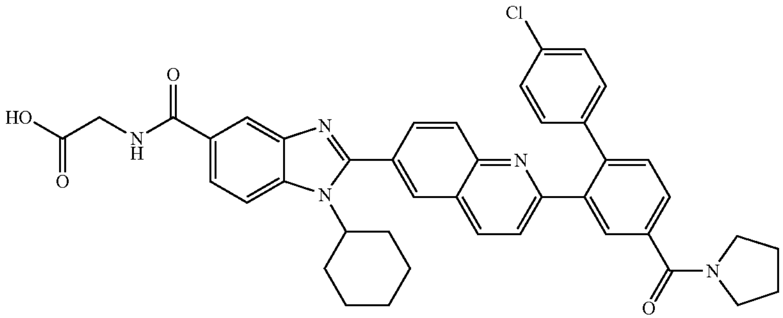 | H | H 4'-chloro-3-(pyrrolidin-1-ylcarbonyl)-biphen-2-yl | quinolin-6-yl | 2-[(2-{2-[(4'-chloro-4-(pyrrolidine-1-carbonyl)-biphen-2-yl]-quinolin-6-yl}-1-cyclohexyl-1H-benzoimidazole-5-carbonyl)-amino]-acetic acid |

TABLE VI

| Cmpd # | R⁶-COOH | Y | Het | Name |
|---|---|---|---|---|
| 320 | 1-phenyl-1H-pyrazole-4-carboxylic acid-5-yl | phenyl | quinolin-6-yl | 5-{[1-cyclohexyl-2-(2-phenyl-quinolin-6-yl)-1H-benzoimidazole-5-carbonyl]-amino}-1-phenyl-1H-pyrazole-4-carboxylic acid |
| 321 | nicotinic acid-6-yl | phenyl | quinolin-6-yl | 5-{[1-cyclohexyl-2-(2-phenyl-quinolin-6-yl)-1H-benzoimidazole-5-carbonyl]-amino}-nicotinic acid |

TABLE VI-continued

| Cmpd # | R⁶-COOH | Y | Het | Name |
|---|---|---|---|---|
| 322 | naphthalene-2-carboxylic acid-6-yl | phenyl | quinolin-6-yl | 6-{[1-cyclohexyl-2-(2-phenyl-quinolin-6-yl)-1H-benzoimidazole-5-carbonyl]-amino}-naphthalene-2-carboxylic acid |
| 323 | phenylacetic acid-4-yl | phenyl | quinolin-6-yl | 4-{[1-cyclohexyl-2-(2-phenyl-quinolin-6-yl)-1H-benzoimidazole-5-carbonyl]-amino}-phenylacetic acid |

TABLE VI-continued

| Cmpd # | R⁶-COOH | Y | Het | Name |
|---|---|---|---|---|
| 324 | phthalic acid-4-yl | phenyl | quinolin-6-yl | 4-{[1-cyclohexyl-2-(2-phenyl-quinolin-6-yl)-1H-benzoimidazole-5-carbonyl]-amino}-phthalic acid |
| 325 | pyrazine-2-carboxylic acid-3-yl | phenyl | quinolin-6-yl | 3-{[1-cyclohexyl-2-(2-phenyl-quinolin-6-yl)-1H-benzoimidazole-5-carbonyl]-amino}-pyrazine-2-carboxylic acid |

TABLE VI-continued

| Cmpd # | R⁶-COOH | Y | Het | Name |
|---|---|---|---|---|
| 326 | 2-hydroxy-benzoic acid-5-yl | phenyl | quinolin-6-yl | 5-{[1-cyclohexyl-2-(2-phenyl-quinolin-6-yl)-1H-benzoimidazole-5-carbonyl]-amino}-2-hydroxy-benzoic acid |
| 327 | benzoic acid-5-yl | phenyl | quinolin-6-yl | 5-{[1-cyclohexyl-2-(2-phenyl-quinolin-6-yl)-1H-benzoimidazole-5-carbonyl]-amino}-benzoic acid |

TABLE VI-continued

| Cmpd # | | $R^6$-COOH | Y | Het | Name |
|---|---|---|---|---|---|
| 328 | | thiophene-3-carboxylic acid-2-yl | phenyl | quinolin-6-yl | 2-{[1-cyclohexyl-2-(2-phenyl-quinolin-6-yl)-1H-benzoimidazole-5-carbonyl]-amino}-thiophene-3-carboxylic acid |
| 526 | | naphthalene-2-carboxylic acid | phenyl | Quinoxalin-6-yl | 6-{[1-cyclohexyl-2-(2-phenyl-quinoxalin-6-yl)-1H-benzoimidazole-5-carbonyl]-amino}-naphthalene-2-carboxylic acid |

TABLE VII

| Cmpd # | Structure | W | R⁷ | R | Y | Het | Name |
|---|---|---|---|---|---|---|---|
| 527 | 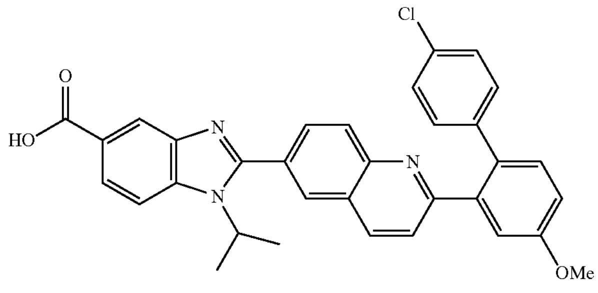 | CH | H | isopropyl | 4'-chloro-4-methoxy-biphen-2-yl | quinolin-6-yl | 2-[2-(4'-chloro-4-methoxy-biphen-2-yl)-quinolin-6-yl]-1-isopropyl-1H-benzoimidazole-5-carboxylic acid |
| 528 | 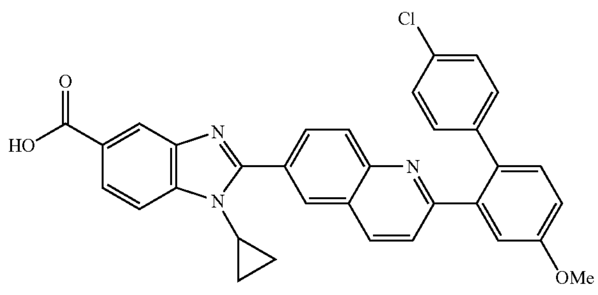 | CH | H | Cyclopropyl | 4'-chloro-4-methoxy-biphen-2-yl | quinolin-6-yl | 2-[2-(4'-chloro-4-methoxy-biphen-2-yl)-quinolin-6-yl]-1-cyclopropyl-1H-benzoimidazole-5-carboxylic acid |

TABLE VII-continued

| Cmpd # | Structure | W | R[7] | R | Y | Het | Name |
|---|---|---|---|---|---|---|---|
| 529 | 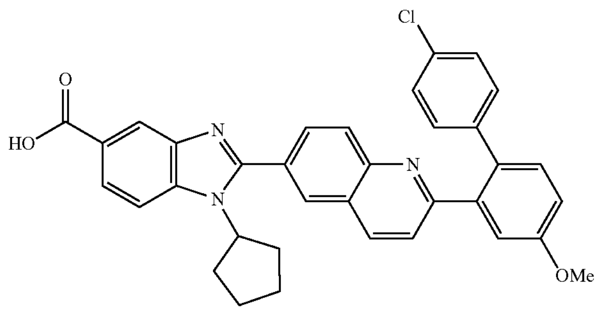 | CH | H | Cyclopentyl | 4'-chloro-4-methoxy-biphen-2-yl | quinolin-6-yl | 2-[2-(4'-chloro-4-methoxy-biphen-2-yl)-quinolin-6-yl]-1-cyclopentyl-1H-benzoimidazole-5-carboxylic acid |
| 530 | 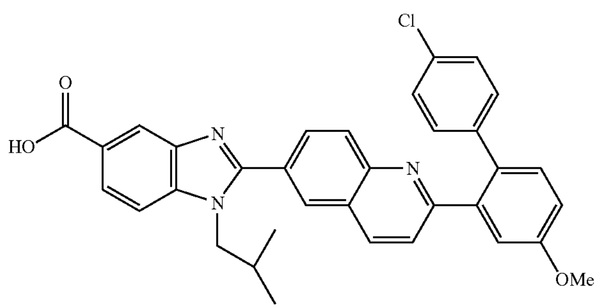 | CH | H | isobutyl | 4'-chloro-4-methoxy-biphen-2-yl | quinolin-6-yl | 2-[2-(4'-chloro-4-methoxy-biphen-2-yl)-quinolin-6-yl]-1-isobutyl-1H-benzoimidazole-5-carboxylic acid |

TABLE VII-continued
| Cmpd # | Structure | W | R⁷ | R | Y | Het | Name |
|---|---|---|---|---|---|---|---|
| 531 | 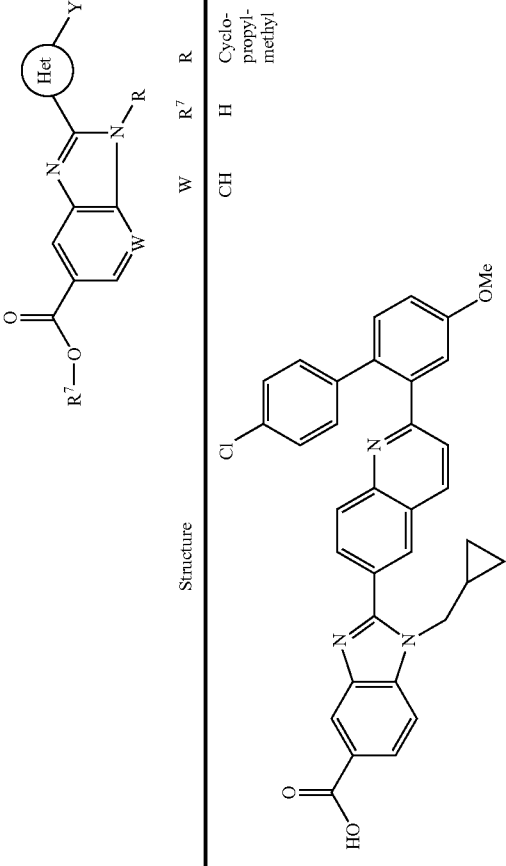 | CH | H | Cyclopropyl-methyl | 4'-chloro-4-methoxy-biphen-2-yl | quinolin-6-yl | 2-[2-(4'-chloro-4-methoxy-biphen-2-yl)-quinolin-6-yl]-1-cyclopropylmethyl-1H-benzoimidazole-5-carboxylic acid |
| 532 | 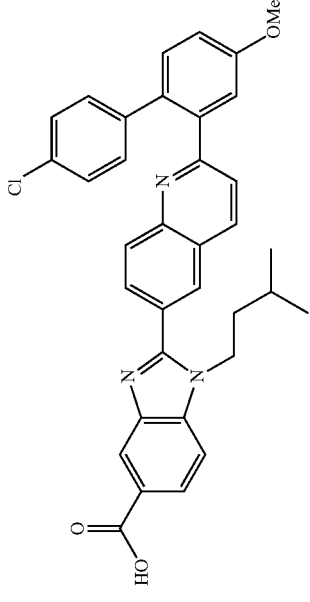 | CH | H | 2-methyl-butyl | 4'-chloro-4-methoxy-biphen-2-yl | quinolin-6-yl | 2-[2-(4'-chloro-4-methoxy-biphen-2-yl)-quinolin-6-yl]-1-(3-methyl-butyl)-1H-benzoimidazole-5-carboxylic acid |

TABLE VII-continued

| Cmpd # | Structure | W | R⁷ | R | Y | Het | Name |
|---|---|---|---|---|---|---|---|
| 533 | 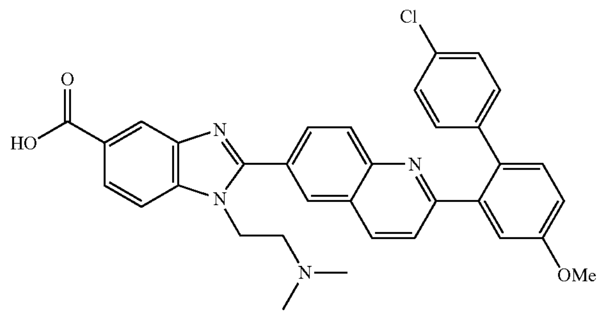 | CH | H | 2-(N,N-dimethyl)-ethyl | 4'-chloro-4-methoxy-biphen-2-yl | quinolin-6-yl | 2-[2-(4'-chloro-4-methoxy-biphen-2-yl)-quinolin-6-yl]-1-(2-dimethylamino-ethyl)-1H-benzoimidazole-5-carboxylic acid |
| 534 | 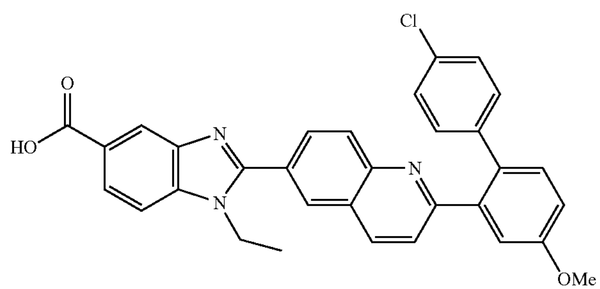 | CH | H | ethyl | 4'-chloro-4-methoxy-biphen-2-yl | quinolin-6-yl | 2-[2-(4'-chloro-4-methoxybiphenyl-2-yl)-quinolin-6-yl)-1-ethyl-1H-benzoimidazole-5-carboxylic acid |

TABLE VII-continued

| Cmpd # | Structure | W | R[7] | R | Y | Het | Name |
|---|---|---|---|---|---|---|---|
| 535 | 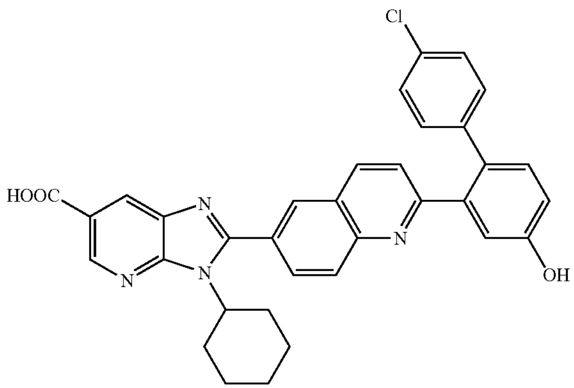 | N | H | Cyclohexyl | 4'-chloro-4-methoxy-biphen-2-yl | quinolin-6-yl | 2-[2-(4'-chloro-4-hydroxy-biphen-2-yl)-quinolin-6-yl]-3-cyclohexyl-3H-imidazo[4,5-b]pyridine-6-carboxylic acid |
| 536 | 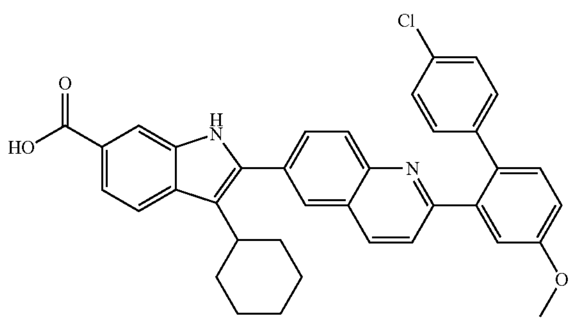 | CH | H | Cyclohexyl | 4'-chloro-4-methoxy-biphen-2-yl | quinolin-6-yl | 2-[2-(4'-chloro-4-methoxy-biphen-2-yl)-quinolin-6-yl]-3-cyclohexyl-1H-indole-6-carboxylic acid |

TABLE VII-continued

| Cmpd # | Structure | W | R[7] | R | Y | Het | Name |
|---|---|---|---|---|---|---|---|
| 537 | 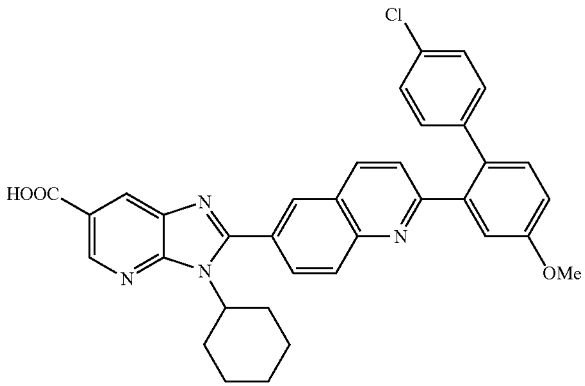 | N | H | Cyclo-hexyl | 4'-chloro-4-methoxy-biphen-2-yl | quinolin-6-yl | 2-[2-(4'-chloro-4-methoxy-biphen-2-yl)-quinolin-6-yl]-3-cyclohexyl-3H-imidazo[4,5-b]pyridine-6-carboxylic acid |
| 538 | 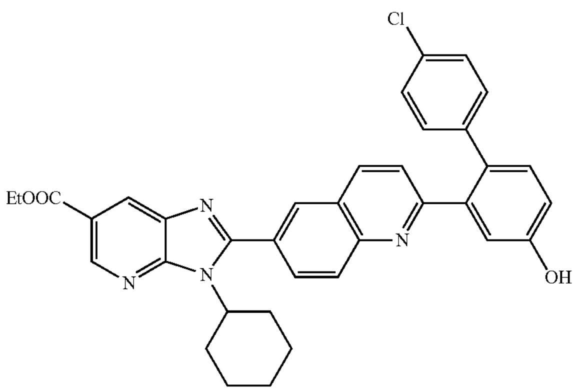 | N | ethyl | Cyclo-hexyl | 4'-chloro-4-methoxy-biphen-2-yl | quinolin-6-yl | 2-[2-(4'-chloro-4-hydroxy-biphen-2-yl)-quinolin-6-yl]-3-cyclohexyl-3H-imidazo[4,5-b]pyridine-6-carboxylic acid ethyl ester |

TABLE VII-continued

| Cmpd # | Structure | W | R⁷ | R | Y | Het | Name |
|---|---|---|---|---|---|---|---|
| 539 | 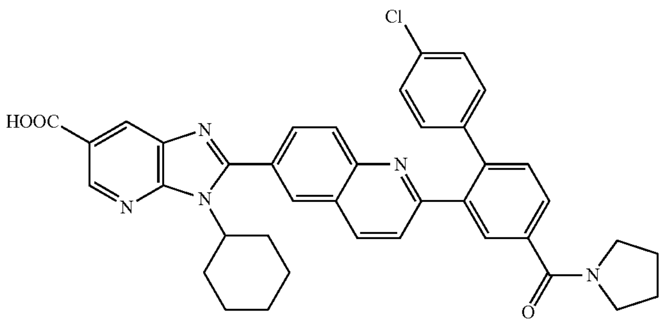 | N | H | Cyclohexyl | 4'-chloro-4-(pyrrolidin-1-ylcarbonyl)-biphen-2-yl | quinolin-6-yl | 2-{2-[4'-chloro-4-(pyrrolidine-1-carbonyl)-biphen-2-yl]-quinolin-6-yl}-3-cyclohexyl-3H-imidazo[4,5-b]pyridine-6-carboxylic acid |
| 571 | 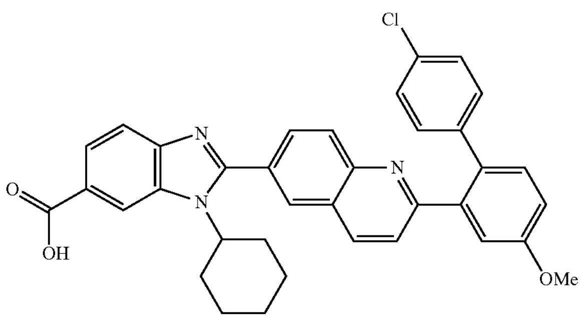 | CH | H | Cyclohexyl | 4'-chloro-4-methoxy-biphen-2-yl | quinolin-6-yl | 2-[2-(4'-chloro-4-methoxybiphen-2-yl)-quinolin-6-yl]-3-cyclohexyl-3H-benzoimidazole-5-carboxylic acid |

TABLE VII-continued
| Cmpd # | Structure | W | R⁷ | R | Y | Het | Name |
|---|---|---|---|---|---|---|---|
| 572 | 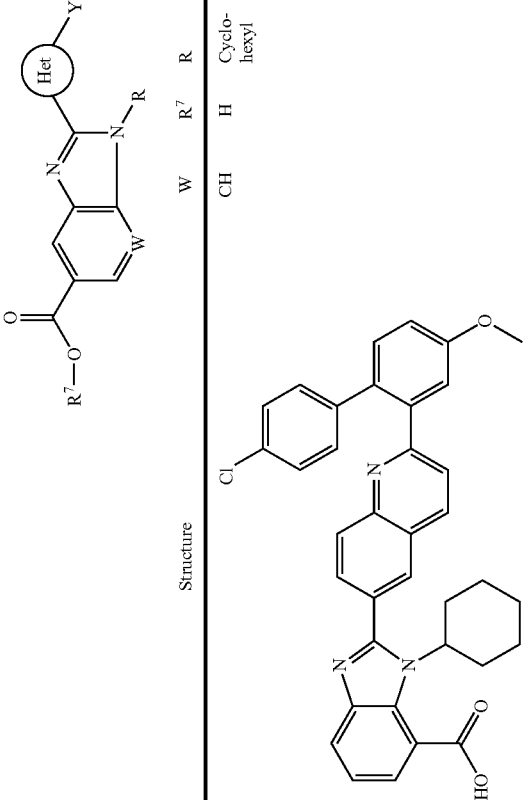 | CH | H | Cyclohexyl | 4'-chloro-4-methoxy-biphen-2-yl | quinolin-6-yl | 2-(4'-chloro-4-methoxybiphen-2-yl)-quinolin-6-yl]-3-cyclohexyl-3H-benzoimidazole-4-carboxylic acid |
| 402a | 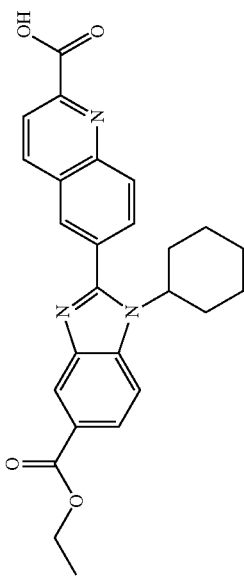 | CH | Et | Cyclohexyl | carboxylic acid | quinolin-6-yl | 6-(1-cyclohexyl-5-ethoxycarbonyl-1H-benzimidazol-2-yl)quinoline-2-carboxylic acid |

TABLE VII-continued

| Cmpd # | Structure | W | R⁷ | R | Y | Het | Name |
|---|---|---|---|---|---|---|---|
| 578 | (structure) | CH | H | trans-2-hydroxycyclohexyl | phenyl | Quinoxalin-6-yl | 1-(trans-2-hydroxycyclohexyl)-2-(2-phenyl-quinoxalin-6-yl)-1H-benzoimidazole-5-carboxylic acid |
| 579 | (structure) | CH | H | trans-4-hydroxycyclohexyl | phenyl | Quinoxalin-6-yl | 1-(trans-4-hydroxycyclohexyl)-2-(2-phenyl-quinoxalin-6-yl)-1H-benzoimidazole-5-carboxylic acid |

TABLE VIII

| Cmpd # | Structure | W | R[7] | R | Y | Het | Name |
|---|---|---|---|---|---|---|---|
| 540 | 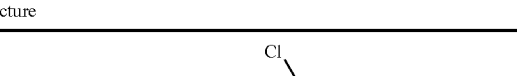 | CH | H | cyclo-hexyl | 4'-chloro-4-(pyrrolidine-1-carbonyl)-biphen-2-yl | quin-olin-6-yl | {4'-chloro-2-[6-(1-cyclohexyl-1H-benzoimidazol-2-yl)-quinolin-2-yl]-biphen-4-yl}-pyrrolidin-1-yl-methadone |

In still another embodiment the present invention is contemplated to include the following compounds N-[1-cyclohexyl-2-(4-oxo-1,4-dihydro-quinazolin-6-yl)-1H-benzoimidazol-5-ylcarbonyl]-N-(phenylsulfonyl)amine;

6-[1-cyclohexyl-5-(1H-tetrazol-5-yl)-1H-benzimidazol-2-yl]-4-oxo-1,4-dihydro-quinazoline;

1-cyclohexyl-2-(4-oxo-1,4-dihydro-quinazolin-6-yl)-1H-benzoimidazole-5-carboxylic acid; and pharmaceutically acceptable tautomers and salts thereof.

This invention is also directed to pharmaceutical compositions comprising a pharmaceutically acceptable diluent and a therapeutically effective amount of one of the compounds described herein or mixtures of one or more of such compounds.

This invention is still further directed to methods for treating a viral infection mediated at least in part by a virus in the flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of one of the compounds described herein or mixtures of one or more of such compounds.

In yet another embodiment of the invention, methods of treating or preventing viral infections in mammals are provided where in the compounds of this invention are administered in combination with the administration of a therapeutically effective amount of one or more agents active against HCV. Active agents against HCV include ribavirin, levovirin, thymosin alpha-1, an inhibitor of NS3 serine protease, and inhibitor of inosine monophosphate dehydrogenase, interferon-alpha, pegylated interferon-alpha, alone or in combination with ribavirin or levovirin. Prefereably the additional agent active against HCV is interferon-alpha or pegylated interferon-alpha alone or in combination with ribavirin or levovirin.

DETAILED DESCRIPTION OF THE INVENTION

The invention is directed to compounds, compositions and methods for treating Flaviviridae family viral infections. However, prior to describing this invention in detail, the following terms will first be defined.

Definitions

Before the present invention is described in detail, it is to be understood that, unless otherwise indicated, this invention is not limited to any particular composition or pharmaceutical carrier, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "pharmaceutically acceptable diluent" in a composition includes two or more pharmaceutically acceptable diluents, and so forth.

In this specification and in the claims that follow, reference will be made to a number of terms that shall be defined to have the following meanings:

As used herein, "alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy ester, cycloalkyl, substituted cycloalkyl, heteroaryl, substituted heteroaryl, heterocyclic, and substituted heterocyclic.

As used herein, "alkylene" refers to straight chain and branched divalent alkyl groups having from 1 to 10 carbon atoms, preferably from 1 to 5 carbon atoms and more preferably 1 to 3 carbon atoms. This term is exemplified by groups such as methylene, ethylene, propylene, butylene, and the like.

"Substituted alkylene" refers to an alkylene group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy ester, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NR$^{20}$R$^{21}$ where R$^{20}$ and R$^{21}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R$^{20}$ and R$^{21}$ are joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Alkenyl" refers to alkenyl group having from 2 to 10 carbon atoms, preferably having from 2 to 6 carbon atoms, and more preferably 2 to 4 carbon atoms and having at least 1 and preferably from 1-2 sites of alkenyl unsaturation.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy ester, cycloalkyl, substituted cycloalkyl, heteroaryl, substituted heteroaryl, heterocyclic, and substituted heterocyclic.

"Alkynyl" refers to alkynyl group having from 2 to 10 carbon atoms, preferably having from 2 to 6 carbon atoms, and more preferably 2 to 3 carbon atoms and having at least 1 and preferably from 1-2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy ester, cycloalkyl, substituted cycloalkyl, heteroaryl, substituted heteroaryl, heterocyclic, and substituted heterocyclic.

"Amino" refers to the group —NH$_2$.

"Substituted amino" refers to the group —NR$^{22}$R$^{23}$ where R$^{22}$ and R$^{23}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R$^{22}$ and R$^{23}$ are joined, together with the nitrogen bound thereto to form a heterocyclic or substituted heterocyclic group provided that R$^{22}$ and R$^{23}$ are both not hydrogen. When R$^{22}$ is hydrogen and R$^{23}$ is alkyl, the substituted amino group is sometimes referred to herein as alkylamino. When R$^{22}$ and R$^{23}$ are alkyl, the substituted amino group is sometimes referred to herein as dialkylamino.

"Aminoacyl" refers to the groups —NR$^{24}$C(O)alkyl, —NR$^{24}$C(O)substituted alkyl, —NR$^{24}$C(O)-cycloalkyl, —NR$^{24}$C(O)substituted cycloalkyl, —NR$^{24}$C(O)alkenyl, —NR$^{24}$C(O)substituted alkenyl, —NR$^{24}$C(O)alkynyl, —NR$^{24}$C(O)substituted alkynyl, —NR$^{24}$C(O)aryl, —NR$^{24}$C(O)substituted aryl, —NR$^{24}$C(O)heteroaryl, —NR$^{24}$C(O)substituted heteroaryl, —NR$^{24}$C(O)heterocyclic, and —NR$^{24}$C(O)substituted heterocyclic where R$^{24}$ is hydrogen or alkyl.

The term "aminocarbonylamino" refers to the group —NR$^{25}$C(O)NR$^{26}$R$^{27}$ where R$^{25}$ is hydrogen or alkyl and R$^{26}$ and R$^{27}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R$^{26}$ and R$^{27}$ are joined, together with the nitrogen bound thereto to form a heterocyclic or substituted heterocyclic group.

The term "aminocarbonyloxy" refers to the group —NR$^{28}$C(O)OR$^{29}$ where R$^{28}$ is hydrogen or alkyl and R$^{29}$ is selected from the group consisting of alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic and substituted heterocyclic.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is to an aromatic ring atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxy, carboxy esters, cyano, thiol, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxy" refers to —COOH or salts thereof.

"Carboxy esters" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic. Preferred carboxy esters are —C(O)O-alkyl, —C(O)O-substituted alkyl, —C(O)O-aryl, and —C(O)O-substituted aryl.

"Cycloalkyl" refers to cyclic alkyl groups of from 3 to 10 carbon atoms having single or multiple cyclic rings optionally comprising 1 to 3 exo carbonyl or thiocarbonyl groups. Suitable cycloalkyl groups include, by way of example, adamantyl, cyclopropyl, cyclobutyl, cyclopentyl, cyclohexyl, cyclooctyl, 3-oxocyclohexyl, and the like. In multiple condensed rings, one or more of the rings may be other than cycloalkyl (e.g., aryl, heteroaryl or heterocyclic) provided that the point of attachment is to a carbon ring atom of the cycloalkyl group. In one embodiment, the cycloalkyl group does not comprise 1 to 3 exo carbonyl or thiocarbonyl groups. In another embodiment, the cycloalkyl group does comprise 1 to 3 exo carbonyl or thiocarbonyl groups. It is understood, that the term "exo" refers to the attachment of a carbonyl or thiocarbonyl to a carbon ring atom of the cycloalkyl group.

In a preferred embodiment, cycloalkyl includes alkyl groups of from 3 to 10 carbon atoms having single or multiple cyclic rings including, by way of example, adamantyl, cyclopropyl, cyclobutyl, cyclopentyl, cyclooctyl, and the like.

"Cycloalkenyl" refers to cyclic alkenyl groups of from 4 to 10 carbon atoms having single or multiple cyclic rings and further having at least 1 and preferably from 1 to 2 internal sites of ethylenic (>C=C<) unsaturation optionally comprising 1 to 3 exo carbonyl or thiocarbonyl groups. Suitable cycloalkenyl groups include, by way of example, cyclopentenyl, cyclohexenyl, cyclooctenyl, 3-oxocyclohex-1,2-enyl, and the like. In one embodiment, the cycloalkenyl group does not comprise 1 to 3 exo carbonyl or thiocarbonyl groups. In a preferred embodiment, the cycloalkenyl group does comprise 1 to 3 exo carbonyl or thiocarbonyl groups. It is understood, that the term "exo" refers to the attachment of a carbonyl or thiocarbonyl to a carbon ring atom of the cycloalkenyl group.

"Substituted cycloalkyl" and "substituted cycloalkenyl" refers to an cycloalkyl or cycloalkenyl group, having from 1 to 5 substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy esters, cycloalkyl, substituted cycloalkyl, heteroaryl, substituted heteroaryl, heterocyclic, and substituted heterocyclic. Preferred substituted cycloalkyl and substituted cycloalkenyl include cycloalkyl or cycloalkenyl group, having from 1 to 5 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

The term "guanidino" refers to the group —NHC(=NH)NH$_2$ and the term substituted "guanidino" refers to —NR$^{30}$C(=NR$^{30}$)N(R$^{30}$)$_2$ where each R$^{30}$ is independently hydrogen or alkyl.

"Halo" or "halogen" refers to fluoro, chloro, bromo and iodo and preferably is fluoro or chloro.

"Haloalkyl" refers to an alkyl group substituted with at least one halogen such that a monohaloalkyl, a polyhaloalkyl or a perhaloalkyl are encompassed by the term haloalkyl.

"Heteroaryl" refers to an aromatic group of from 1 to 15 carbon atoms, preferably from 1 to 10 carbon atoms, and 1 to 4 heteroatoms selected from the group consisting of oxygen, nitrogen, sulfur, —S(O)—, and —S(O)$_2$— within the ring. Preferably, such heteroaryl groups are aromatic groups of from 1 to 15 carbon atoms, preferably from 1 to 10 carbon atoms, and 1 to 4 heteroatoms selected from the group consisting of oxygen, nitrogen, and sulfur within the ring. Such heteroaryl groups can have a single ring (e.g., pyridyl or furyl) or multiple condensed rings (e.g., indolizinyl or benzothienyl).

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur, —S(O)—, —S(O)$_2$— or oxygen within the ring which ring may optionally comprise 1 to 3 exo carbonyl or thiocarbonyl groups. Preferably, such heterocyclic groups are saturated or unsaturated group having a single ring or multiple condensed rings, from 1 to 10 carbon atoms and from 1 to 4 hetero atoms selected from the group consisting of nitrogen, sulfur, or oxygen within the ring.

In multiple condensed rings, one or more of the rings may be other than heterocyclic (e.g., aryl, heteroaryl or cycloalkyl) provided that the point of attachment is to a heterocyclic ring atom. In one embodiment, the heterocyclic group does not comprise 1 to 3 exo carbonyl or thiocarbonyl groups. In a preferred embodiment, the heterocyclic group does comprise 1 to 3 exo carbonyl or thiocarbonyl groups. It is understood, that the term "exo" refers to the attachment of a carbonyl or thiocarbonyl to a carbon ring atom of the heterocyclic group.

"Substituted heterocyclic" refers to heterocycle groups that are substituted with from 1 to 3 of the same substituents as defined for substituted cycloalkyl. Preferred substituents for substituted heterocyclic groups include heterocyclic groups having from 1 to 5 having substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxy, carboxy esters, cycloalkyl, substituted cycloalkyl, heteroaryl, substituted heteroaryl, heterocyclic, and substituted heterocyclic.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

The term "oxycarbonylamino" refers to the group —O(CO)NR31R32 where R31 and R32 are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R$^{31}$ and R$^{32}$ are joined, together with the nitrogen bound thereto to form a heterocyclic or substituted heterocyclic group.

The term "oxycarbonyloxy" refers to the group —OC(O)OR$^{33}$ where R$^{33}$ is selected from the group consisting of alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic and substituted heterocyclic.

The term "thiol" refers to the group —SH.

The term "thioalkyl" refers to the group —S-alkyl and the term "substituted thioalkyl" refers to the group —S-substituted alkyl.

The term "amino acid" refers to β-amino acids or to α-amino acids of the formula $HR^{34}NCH(R^2)COOH$ where $R^2$ is as defined above and $R^{34}$ is hydrogen, alkyl, substituted alkyl or aryl. Preferably, the α-amino acid is one of the twenty naturally occurring L amino acids.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The following synthetic protocols illustrate the general manner for preparing the compounds described herein.

Scheme I. General Synthesis of 4-amino-3-formyl-benzoic acid methyl ester 7.

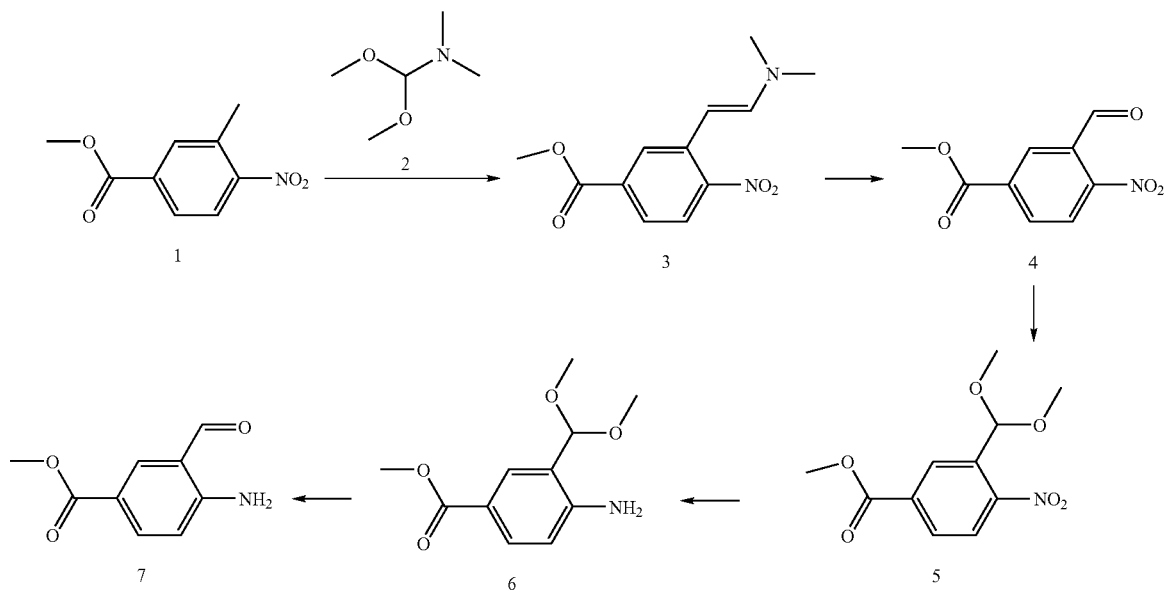

General Synthetic Methods

The compounds of this invention can be prepared from readily available starting materials using the following general methods and procedures. It will be appreciated that where Scheme I illustrates the conventional preparation of 4-amino-3-formyl-benzoic acid methyl ester, compound 7, which is a starting material in the preparation of quinoline or substituted quinoline groups, i.e., Het-Y. Specifically, in Scheme I, commercially available 3-methyl-4-nitrobenzoic acid methyl ester, compound 1, is contacted with at least a stoichiometric equivalent of commercially available dimethoxymethyl-dimethyl-amine, also known as N,N-dimethylformamide dimethylacetal, compound 2, under conditions to form 3-(2-dimethylamino-vinyl)-4-nitro-benzoic acid methyl ester, compound 3. The reaction is preferably conducted in an inert diluent such as N,N-dimethylformamide at an elevated temperature of from about 100 to 160° C. for a period of time to effect substantial completion of the reaction which typically occurs within 12 to 48 hours. After reaction completion, the resulting product, compound 3, can be isolated by conventional techniques such as extraction, filtration, chromatography, and the like; or, alternatively, used in the next step without purification and/or isolation.

3-(2-dimethylamino-vinyl)-4-nitro-benzoic acid methyl ester, 3, is subsequently converted to the formaldehyde by contact with at least a stoichiometric amount of oxidant, under conditions appropriate, to form 3-formyl-4-nitro-benzoic acid methyl ester 4. The reaction is conducted in a suitable solvent, such as THF, in the presence of water. Preferably, the reaction is conducted at a temperature of from room temperature to 50° C. The reaction is continued until it is substantially complete which typically occurs within about 0.5 to 2 hours. Suitable oxidants are well known in the art and include, for example, sodium periodate, NaIO$_4$. While Compound 4 may be prepared in this manner, the compound is also commercially available.

The formyl group of 3-formyl-4-nitro-benzoic acid methyl ester 4 is protected with a suitable protecting group, for example, as the acetal to form 3-dimethoxymethyl-4-nitro-benzoic acid methyl ester 5. Other protecting groups are well known in the art and may also be used. In the acetal reaction, compound 4 is contacted with an acidic solution in methanol, under conditions appropriate to form compound 5. The reaction is preferably conducted at an elevated temperature of from 80 to 100° C. The reaction is continued until it is substantially complete which typically occurs within about 10 to 30 minutes. Upon reaction completion, the 3-dimethoxymethyl-4-nitro-benzoic acid methyl ester, compound 5, can be recovered by conventional techniques such as extraction, precipitation, chromatography, filtration and the like; or, alternatively, used in the next step without purification and/or isolation.

The nitro group of 3-dimethoxymethyl-4-nitro-benzoic acid methyl ester, compound 5 is then converted to the primary amine by conventional reducing procedures to provide 4-amino-3-dimethoxymethyl-benzoic acid methyl ester, compound 6. Conventional reducing procedures include, but are not limited to, hydrogenation utilizing Pd/C. The reaction is preferably conducted in a suitable vessel such as a Parr apparatus, at room temperature for a time sufficient to provide substantial reaction completion, which typically occurs in from 15 minutes to 1.5 hours. Compound 6 can be recovered by conventional techniques such as extraction, precipitation, chromatography, filtration and the like; or, alternatively, used in the next step without purification and/or isolation.

4-Amino-3-formyl-benzoic acid methyl ester, compound 7, is obtained by conventional deprotection of the protecting group. Preferably, the acetal of compound 6 is hydrolyzed under standard reaction conditions. Acetal hydrolysis conditions are well known in the art and may be achieved by treating compound 6 with, for example, an acidic aqueous solution. The reaction is preferably conducted at room temperature and continued until it is substantially complete which typically occurs within about 15 to 30 minutes. Upon reaction completion, the product 4-amino-3-formyl-benzoic acid methyl ester, compound 7, can be recovered by conventional techniques such as extraction, precipitation, chromatography, filtration and the like.

Alternatively, Compound 7 may be prepared directly from Compound 4 by reduction with iron sulfate and ammonium hydroxide.

Scheme II. General synthesis of 3-amino-4-cyclohexylamino-benzoic acid ethyl ester 11.

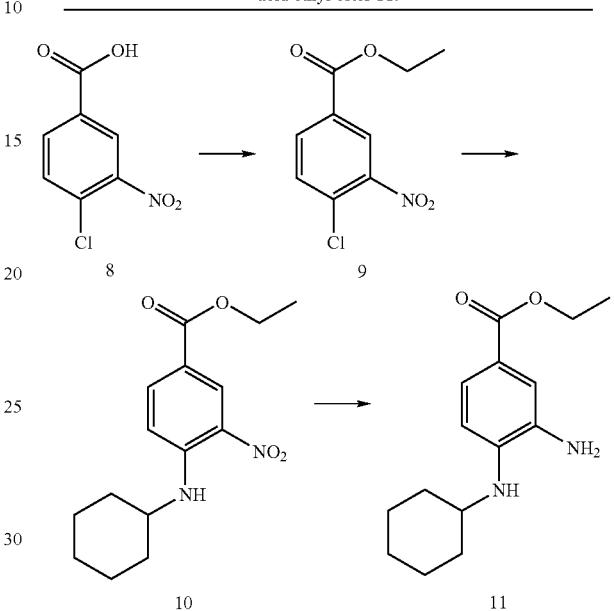

Scheme II illustrates the general synthesis of 3-amino-4-cyclohexylamino-benzoic acid ethyl ester, compound 11, which is used as a starting material in the preparation of 2-Het-Y substituted 1-cyclohexyl-1H-benzoimidazole-5-carboxylic acids. It is understood that the cyclohexyl group in Scheme II is only for illustrative purposes and that other R groups can be prepared using the protocols described herein merely by replacing the cyclohexylamine with other suitable amines.

Specifically, in Scheme II, commercially available 4-chloro-3-nitro-benzoic acid, compound 8, is converted to the corresponding ethyl ester using conventional alkylation protocols. In one preferred method, compound 8 is contacted with a molar excess of the appropriate alcohol (ethanol) in the presence of an acid at an elevated temperature. The reaction is maintained at an elevated temperature, preferably at the reflux temperature of the alcohol solvent/reactant, until reaction completion, which is typically achieved in about 10 to 24 hours. Upon reaction completion, the resulting 4-chloro-3-nitro-benzoic acid ethyl ester, compound 9, can be recovered by conventional techniques such as extraction, precipitation, chromatography, filtration and the like; or, alternatively, used in the next step without purification and/or isolation.

4-chloro-3-nitro-benzoic acid ethyl ester, compound 9 is then aminated to provide 4-cyclohexylamino-3-nitro-benzoic acid ethyl ester, compound 10. In this reaction, compound 9 is treated with cyclohexylamine in the presence of TEA. The reaction is preferably conducted in an inert diluent such as acetonitrile, at an elevated temperature, preferably at the reflux temperature of the solvent, for a period of time to effect substantial completion of the reaction which typically occurs within 10 to 48 hours. After reaction completion, the resulting product, compound 10, can be isolated by conventional techniques such as extraction, filtration, chromatography, and the like; or, alternatively, used in the next step without purification and/or isolation.

3-Amino-4-cyclohexylamino-benzoic acid ethyl ester, compound 11, is provided by reducing the nitro functionality of compound 10. Reduction protocols are well known in the art and include, for example, hydrogenation with Pd/C. The reaction is preferably conducted at room temperature in a suitable inert solvent such as ethyl acetate and is continued until a substantial amount of product is obtained, which typically occurs in about 2 to 8 hours. The resulting 3-amino-4-cyclohexylamino-benzoic acid ethyl ester, compound 11, can be recovered by conventional techniques such as extraction, precipitation, chromatography, filtration and the like.

Tetrazolyl-substituted compounds are similarly obtained using 4-chloro-3-nitro-benzonitrile, as shown in Scheme IIa below.

Initially, commercially available 2-chloro-5-cyano-nitrobenzene, compound 125, is aminated as described above with cyclohexylamine, compound 126 to provide for compound 127. As before, cyclohexylamine is representative of suitable amines which can be used in this protocol. Conversion of the cyano group of the 2-cyclohexylamino-5-cyano-nitrobenzene, compound 127, to the corresponding tetrazolyl derivative, compound 128, proceeds via conventional conditions such as contacting compound 127 with trimethyltin azide in the presence of refluxing toluene. An aqueous acid is then added and acidic hydrolysis proceeds for several hours at room temperature to provide for compound 128 which can be recovered by conventional techniques such as extraction, precipitation, chromatography, filtration and the like; or, alternatively, used in the next step without purification and/or isolation.

Scheme IIa.
General synthesis of 1-cyclohexyl-5-(tetrazol-2-yl)-
2-(3-phenylquinoxalin-6-yl)benzoimidazole 131.

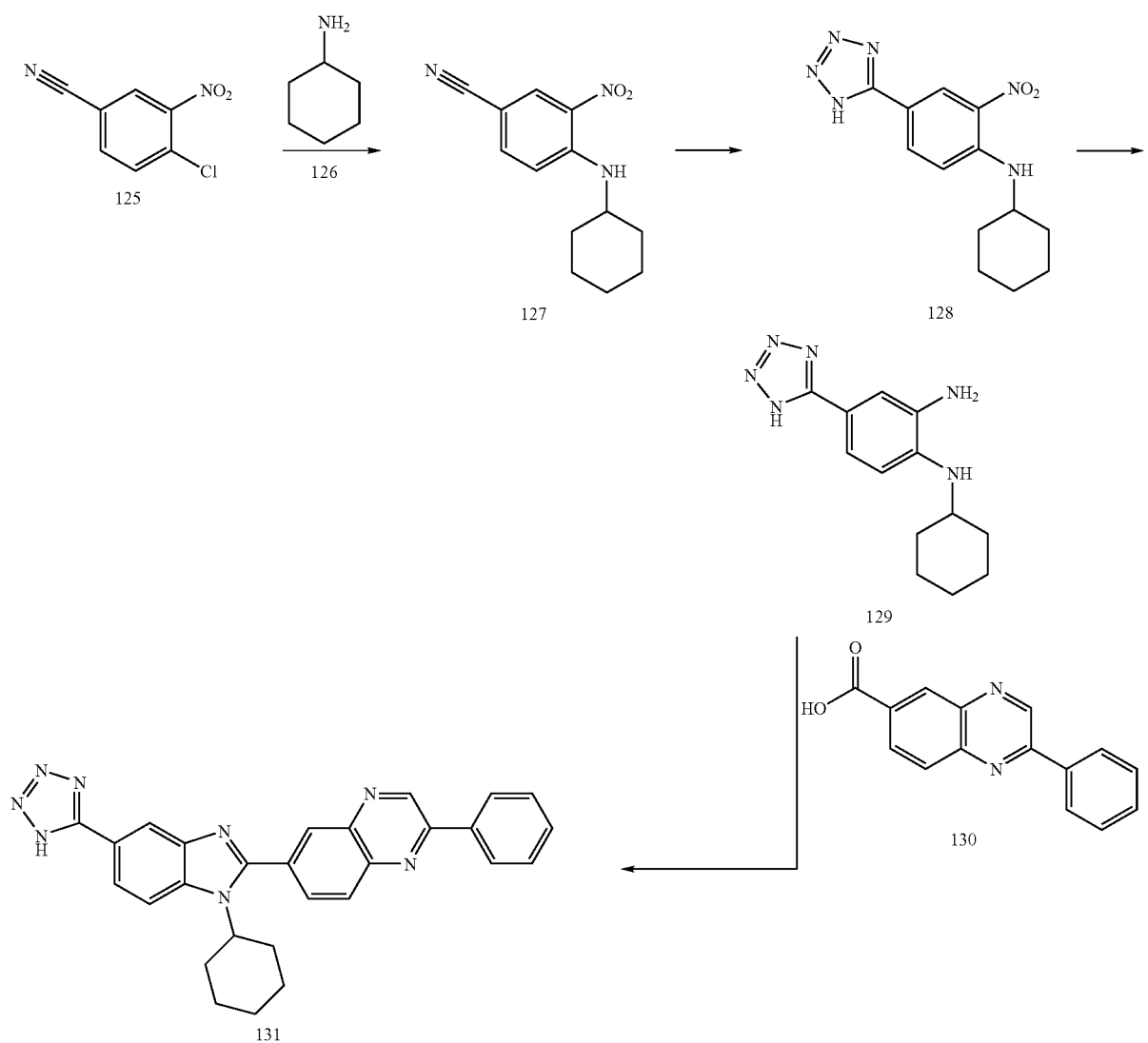

The nitro group of compound 128 is then converted to the primary amine by conventional reducing procedures to provide for compound 129. Conventional reducing procedures include, but are not limited to, hydrogenation utilizing Pd/C. The reaction is preferably conducted in a suitable vessel such as a Parr apparatus, at room temperature for a time sufficient to provide substantial reaction completion, which typically occurs in from 15 minutes to 1.5 hours. Compound 129 can be recovered by conventional techniques such as extraction, precipitation, chromatography, filtration and the like; or, alternatively, used in the next step without purification and/or isolation.

Subsequent conventional coupling of compound 129 with 2-phenyl-6-carboxyquinoxaline, compound 130, provides for compound 131.

elevated temperature, preferably at the solvent reflux temperature, for a time sufficient to effect substantial completion of the reaction which typically occurs within 10 to 48 hours. After reaction completion, the resulting 2-Y-quinoline-6-carboxylic acid, compound 13, can be isolated by conventional techniques such as extraction, filtration, chromatography, and the like; or, alternatively, used in the next step without purification and/or isolation.

The carboxylic acid moiety of compound 13 is then converted to an acyl chloride by treating 13 with a suitable chlorinating agent. Chlorinating agents are well known in the art, and preferable chlorinating agents include thionyl chloride, oxalyl chloride, phosphorus trichloride, and the like. The reaction is subjected to conventional reaction conditions.

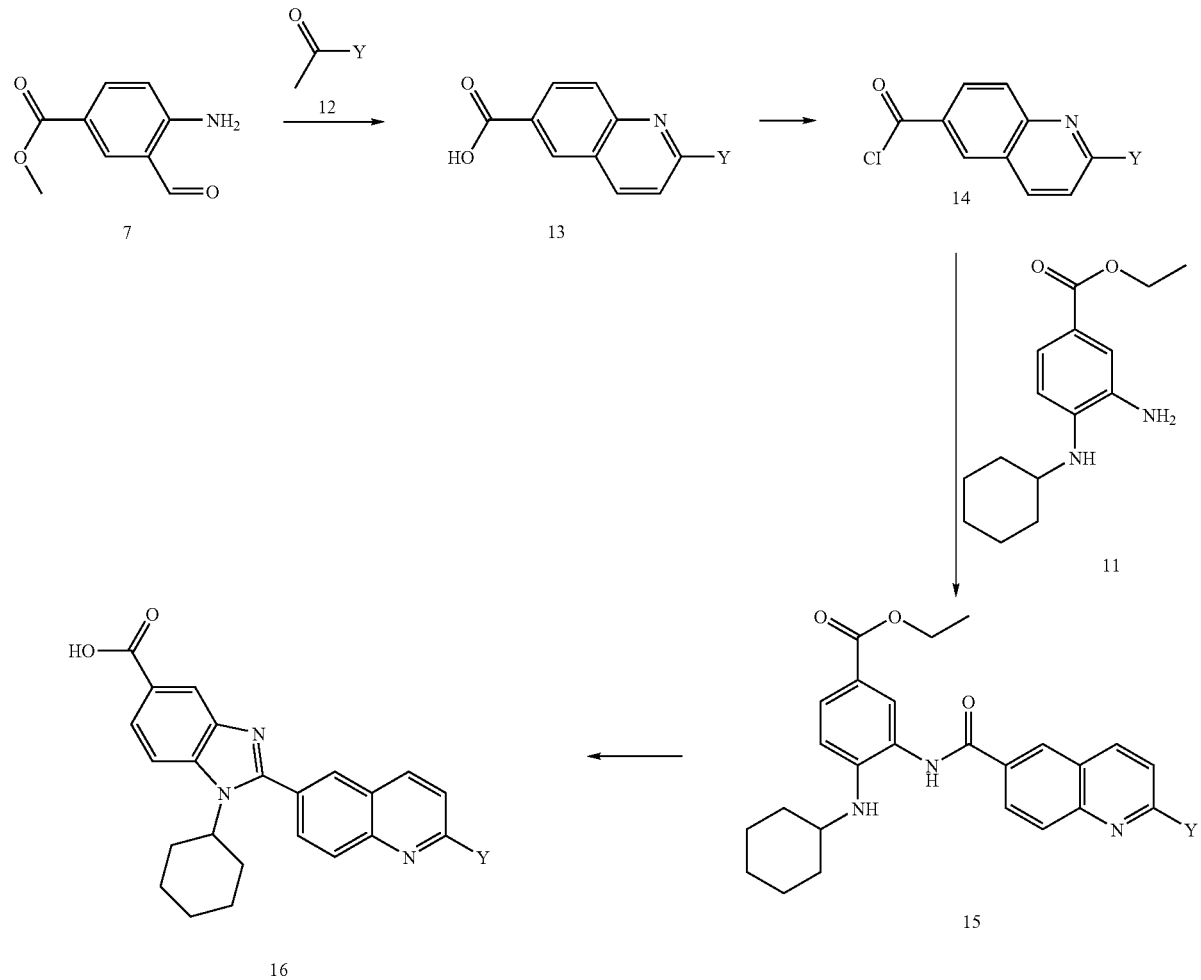

Scheme III. General synthesis of 1-cyclohexyl-2-(2-"Y"-quinolin-6-yl)-1H-Benzoimidazole-5-carboxylic acid.

Compound 7 as prepared above is combined with a suitable ketone, such as acetophenone (where Y=phenyl or substituted phenyl), in a basic alcohol solvent system such as KOH/EtOH to provide the aromatized product, 2-Y-quinoline-6-carboxylic acid, compound 13. Y may be an aryl group such as phenyl, substituted phenyl or an alkyl group such as methyl or other suitable functionality such as those particularly disclosed herein. Preferably, the reaction is allowed to proceed at an Preferably, compound 13 is treated with thionyl chloride and the reaction is run neat, in the absence of other solvents, until substantial reaction completion. Typically, the reaction requires elevated temperatures such as the reflux temperature of thionyl chloride, for a time sufficient to produce substantial product, usually about 1 to 2 hours. After reaction completion, the resulting acyl chloride, compound 14, can be isolated by conventional techniques such as extraction, filtration, chromatography, and the like; or, alternatively, used in the next step without purification and/or isolation.

2-Y-quinoline-6-carbonyl chloride, compound 14 undergoes aminolysis with compound 11, as provided above, to produce the intermediate 4-cyclohexylamino-3-[(2-Y-quinoline-6-carbonyl)-amino]-benzoic acid ethyl ester, compound 15. The aminolysis reaction is preferably conducted in the presence of an inert solvent such as DMF and requires at least a stoichiometric amount of compound 11. The reaction is preferably conducted for a time sufficient for substantial reaction completion. Compound 15 can be isolated by conventional techniques such as extraction, filtration, chromatography, and the like and is used in the subsequent step without further purification.

Compound 15 is then treated with acetic acid to affect cyclization and provide 1-cyclohexyl-2-(2-Y-quinolin-6-yl)-1H-benzoimidazole-5-carboxylic acid ethyl ester (not shown). Cyclization is preferably performed at elevated temperatures, typically reflux temperatures of the solvent which usually occurs between 130 to 145° C., for a time sufficient to provide substantial reaction completion, which typically occurs in 2 to 5 hours. Upon reaction completion, the resulting compound can be recovered by conventional techniques such as neutralization, extraction, precipitation, chromatography, filtration and the like; or, alternatively, may be used in the next step without purification and/or isolation. An alternate cyclization protocol involves treating 15 with 10% TFA in 1,2-dichloroethane at the reflux temperature of the solution for a time sufficient to affect substantial reaction completion, which typically occurs between 3 to 10 hours. Upon reaction completion, the resulting compound can be recovered by conventional techniques such as neutralization, extraction, precipitation, chromatography, filtration and the like; or, alternatively, may be used in the next step without purification and/or isolation. The ethyl ester is subsequently deprotected under basic reaction conditions in an appropriate aqueous alcoholic solvent such as ethanol. Preferably, the ethyl ester is treated with a base such as aqueous NaOH at an elevated temperature, such as the reflux temperature of the solvent. The reaction is allowed to continue for a time sufficient to effect substantial reaction completion, typically from 1 to 3 hours to provide compound 16. Upon reaction completion, the resulting compound can be recovered by conventional techniques such as neutralization, extraction, precipitation, chromatography, filtration and the like; or additionally, purified 16 may be converted to the acid salt by treatment with HCl or other acid salt in an appropriate solvent, such as dioxane and ether, for a time sufficient to provide substantial salt formation, followed by conventional recovery techniques.

Scheme IV. General synthesis of 5-"Q"-1-cyclohexyl-2-(2-"Y"-quinolin-6-yl)-1H-benzoimidazole-5-carboxylic acid, compound 17.

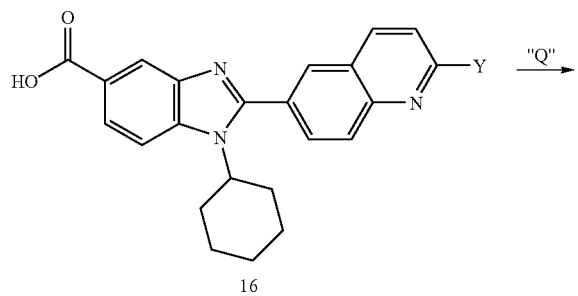

16

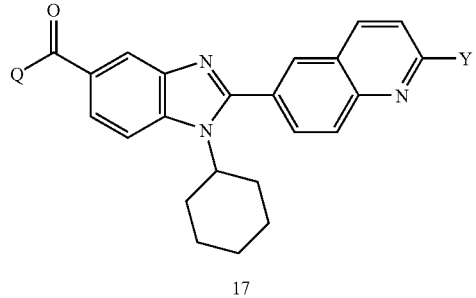

17

Compound 16 is further derivatized with a suitable moiety, Q. Preferred Q groups include those which give rise to Z groups as recited for the compounds of Formula I when Z is as defined in Formula I subset (b), (c —C(O)NHSO$_2$R$^4$) or (d). Preferably, compound 16 is coupled with Q wherein Q is a heteroatom containing group, preferably an amino or substituted amino group including, for example, substituted amino acids such as L-5-hydroxytryptophane. Suitable amino groups are well known in the art and include a variety of commercially available primary or secondary amines, and preferably, an amino acid or substituted amino acid derived from an L isomer of an amino acid. Compound 16 is activated by conventional means, such as treatment with HBTU and DIEA at room temperature for a time sufficient to promote activation, typically from 5 to 20 minutes. Activated 16 is then treated with Q, for example, a nitrogen containing group, in an inert diluent such as N,N-dimethylformamide at room temperature for a period of time to effect substantial completion of the reaction which typically occurs within 30 minutes to 1 hour. After reaction completion, the resulting product, compound 17, can be isolated by conventional techniques such as extraction, filtration, chromatography, and the like. The purified product may also be converted to the acid salt by treatment of 17 with an appropriate acid salt, such as TFA, for a time sufficient for substantial reaction completion.

Scheme V. General synthetic scheme for the synthesis of 2-[4'-chloro-4-(pyrrolidine-1-carbonyl)-biphen-2-yl]-quinolin-6-yl derivatives.

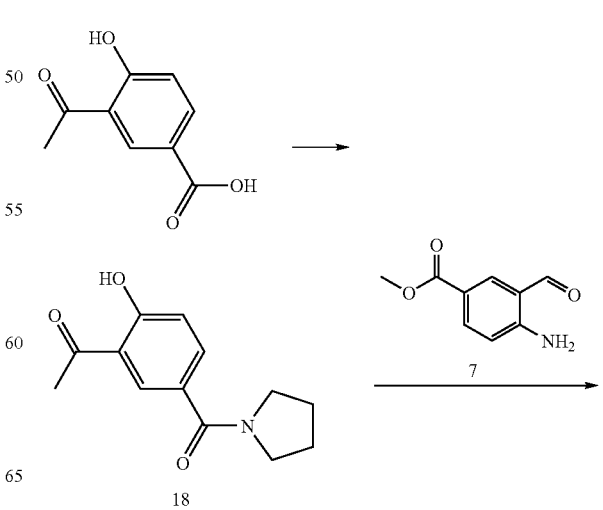

18

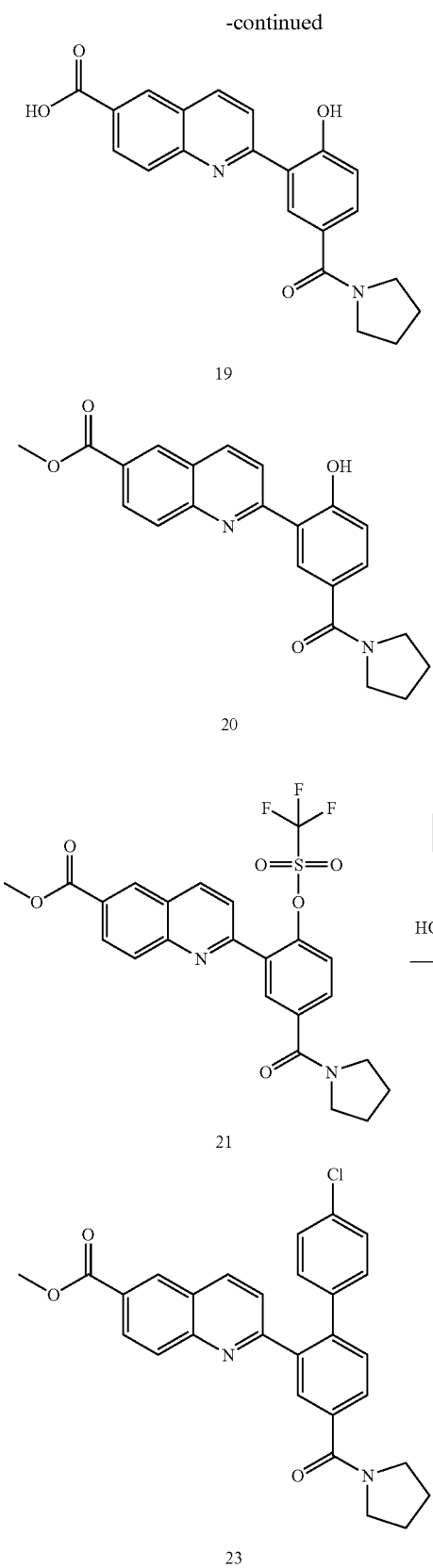

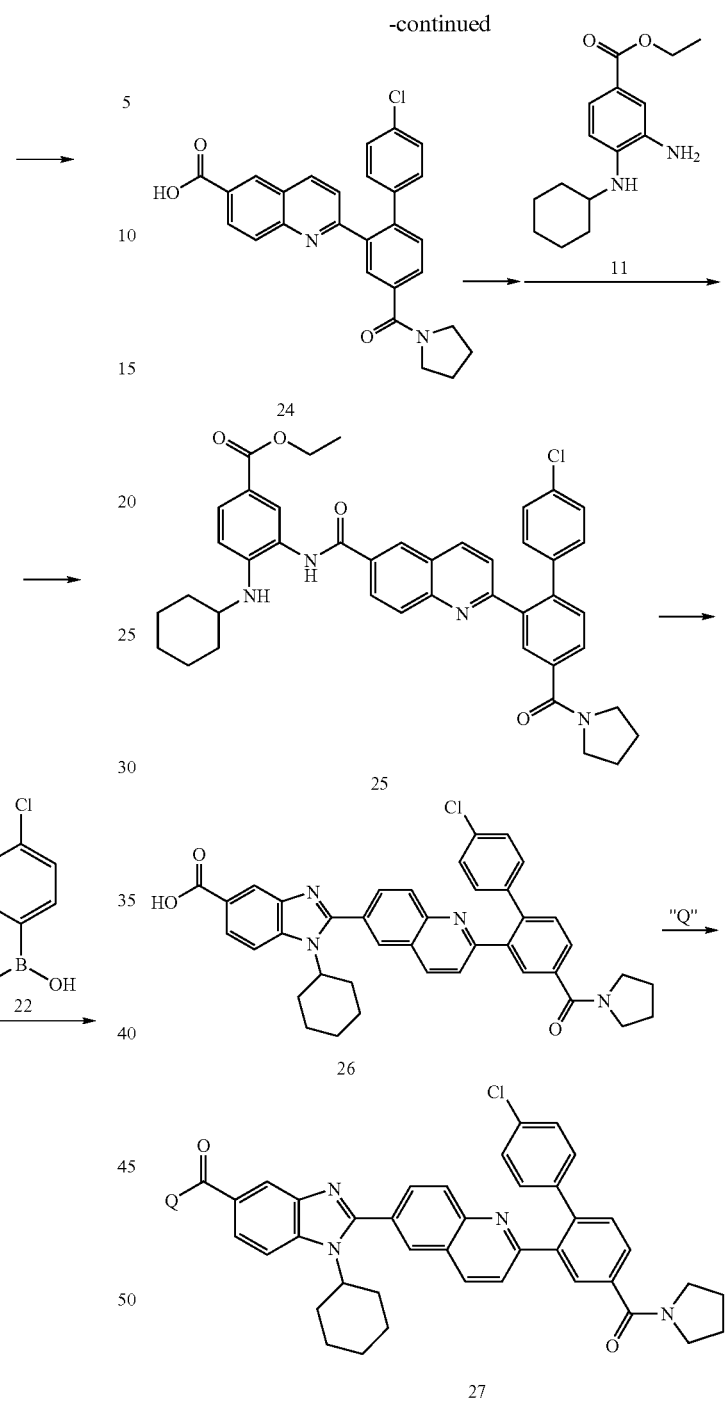

Scheme V illustrates the general synthetic scheme for the synthesis of 2-[4'-chloro-4-(pyrrolidine-1-carbonyl)-biphen-2-yl]-quinolin-6-yl derivatives of the title compounds. Specifically, the carboxylic acid moiety of commercially available 3-acetyl-4-hydroxy-benzoic acid is converted to an amide by coupling with pyrrolidine. Other basic nitrogen containing compounds may be used in this reaction if other primary or secondary amide moieties are desired. The reaction is preferably conducted in the presence of an inert solvent such as DMF, and is performed at room temperature for a time sufficient to provide substantial conversion to the product, 1-[2-hydroxy-5-(pyrrolidine-1-carbonyl)-phenyl]ethanone 18 which typically occurs in from 30 minutes to 2 hours. After reaction completion, the resulting product can be isolated by conventional techniques such as extraction, filtration, chromatography, and the like; or, alternatively, may be used in subsequent reaction without further purification.

Compound 18 is treated with compound 7, which is produced as shown above, in an alcohol solvent. Treatment of the mixture with a base under inert atmosphere provides conditions appropriate for cyclization and affords compound 19. Cyclization is preferably performed at elevated temperatures for a time sufficient to provide substantial reaction completion, which typically occurs in 10 to 48 hours. A suitable base/solvent can be, for example, KOH/ethanol, although other bases and solvents may also be used. Upon reaction completion, the resulting compound 19 can be recovered by conventional techniques such as neutralization, extraction, precipitation, chromatography, filtration and the like; or, alternative, may be used in subsequent synthetic steps without purification and/or isolation.

The carboxylic acid of compound 19 is protected as a methyl ester by treatment of 19 with acidic methanol under conventional reaction conditions. Preferably, the reaction is performed at elevated temperature, from 50 to 80° C. for a time such that substantial conversion of starting material to the methyl ester has occurred, which typically is 12 to 24 hours. The corresponding methyl ester, 20, once obtained, can be recovered by conventional techniques such as neutralization, extraction, precipitation, chromatography, filtration and the like; or, alternatively, may be used in subsequent synthetic steps without purification and/or isolation.

The phenol of 20 is subsequently converted to the corresponding triflate or other good leaving group by treatment of 20 with, for example, triflic anhydride. The reaction is preferably conducted in an inert solvent, such as DCM in the presence of base, such as DMAP or pyridine. The reaction is typically conducted at room temperature for a time sufficient to provide substantial reaction completion, which typically occurs in about 10 to 48 hours. Compound 21 can be recovered by conventional techniques such as neutralization, extraction, precipitation, chromatography, filtration and the like; or, alternative, may be used in subsequent synthetic steps without purification and/or isolation.

Compound 21 is coupled with a suitable boronic acid, such as para-chlorophenylboronic acid 22 to provide the biphenyl derivative, 23. Other boronic acids may be used if other substituents or substitution patterns are desired. The reaction is conducted under conventional coupling reaction conditions, such as in the presence of a lithium salt and palladium catalyst in dioxane under an inert atmosphere. The reaction is preferably conducted at elevated temperatures, such as the reflux temperature of the solvent, for a time sufficient to allow substantial completion of the reaction, which typically occurs in 10 to 48 hours. Compound 23 can be recovered by conventional techniques such as neutralization, extraction, precipitation, chromatography, filtration and the like; or, alternatively, may be used in subsequent synthetic steps without purification and/or isolation.

The methyl ester of compound 23 is then removed under basic conditions to provide compound 24, which may be used in a subsequent synthetic step without purification and/or isolation. Deprotection protocols are well known in the art and preferably, the reaction involves treating 23 with a suitable base, such as aqueous sodium hydroxide, in an alcohol solvent at reflux temperature for about 1 to 3 hours to provide the quinolin carboxylic acid 24.

The carboxylic acid of 24 is subsequently treated with compound 11, which is prepared above, under conditions suitable to effect an amide linkage. Preferably, compound 24 is activated with, for example, HATU and DIEA at room temperature for a time of from 10 to 30 minutes and is then treated with compound 11 at room temperature for a time sufficient to effect substantial reaction completion, typically between 10 to 48 hours. The resulting amide 25 may be recovered by conventional techniques such as neutralization, extraction, precipitation, chromatography, filtration and the like; or, alternatively, may be used in subsequent synthetic steps without purification and/or isolation.

Compound 25 is then treated with acetic acid to affect cyclization and provide the benzoimidazole-5-carboxylic acid ethyl ester (not shown). Cyclization is preferably performed at elevated temperatures, typically reflux temperature of the solution which usually occurs between 130 to 145° C., for a time sufficient to provide substantial reaction completion, which typically occurs in 2 to 5 hours. Upon reaction completion, the resulting compound can be recovered by conventional techniques such as neutralization, extraction, precipitation, chromatography, filtration and the like; or, alternatively, may be used in the next step without purification and/or isolation. The ethyl ester is subsequently deprotected under basic reaction conditions in an appropriate alcoholic solvent such as ethanol. Preferably, the ethyl ester is treated with a base such as aqueous NaOH at an elevated temperature, such as the reflux temperature of the solvent. The reaction is allowed to continue for a time sufficient to effect substantial reaction completion, typically from 1 to 3 hours to provide compound 26. Upon reaction completion, the resulting compound can be recovered by conventional techniques such as neutralization, extraction, precipitation, chromatography, filtration and the like; or additionally, purified compound 26 may be converted to the acid salt by treatment with HCl or other acid salt in an appropriate solvent, such as dioxane and ether, for a time sufficient to provide substantial salt formation, followed by conventional recovery techniques.

Compound 26 is further derivatized with any suitable Q moiety as recited above. Preferably, compound 26 is coupled with a substituted amino group, preferably a substituted amino acid such as L-5-hydroxytryptophane. Suitable amino groups are well known in the art and include a variety of commercially available primary or secondary amines, and preferably, an amino acid or substituted amino acid derived from an L isomer of an amino acid. Compound 26 is activated by conventional means, such as treatment with HBTU and DIEA at room temperature for a time sufficient to promote activation, typically from 5 to 20 minutes. Activated compound 26 is then coupled with Q, such as, for example, an amino group, in an inert diluent such as N,N-dimethylformamide at room temperature for a period of time to effect substantial completion of the reaction which typically occurs within 30 minutes to 1 hour. After reaction completion, the resulting product, compound 27, can be isolated by conventional techniques such as extraction, filtration, chromatography, and the like. The purified product may also be converted to the acid salt by treatment of compound 27 with an appropriate acid salt, such as HCl, for a time sufficient for substantial reaction completion.

Compound 26 is shown in the tables as Compound 204.

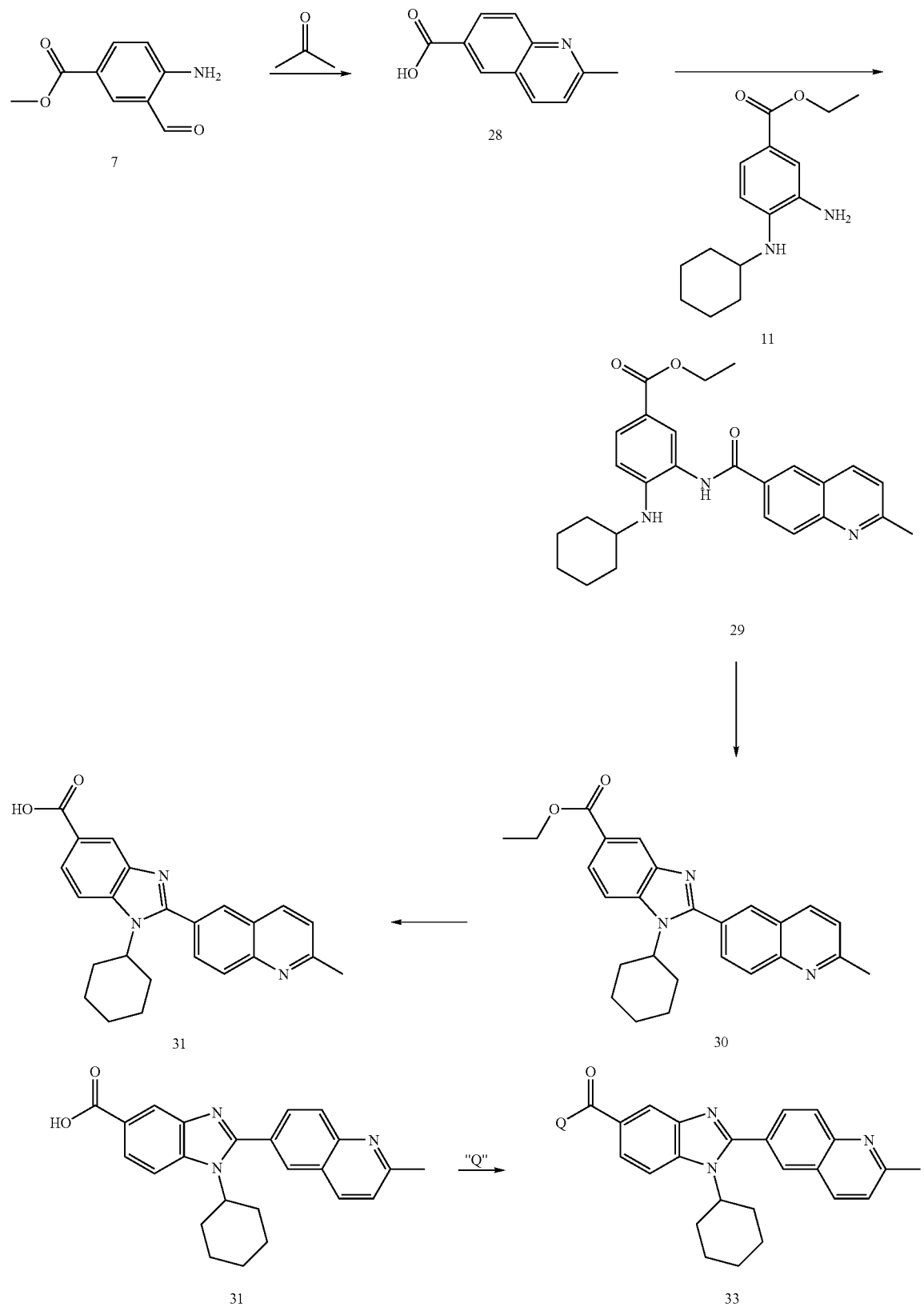
Scheme VI. General synthetic scheme for methyl substituted quinoline derivatives.

Scheme VI illustrates a synthetic scheme for producing methyl substituted quinoline derivatives of the title compounds utilizing the protocols provided in Schemes III and IV above.

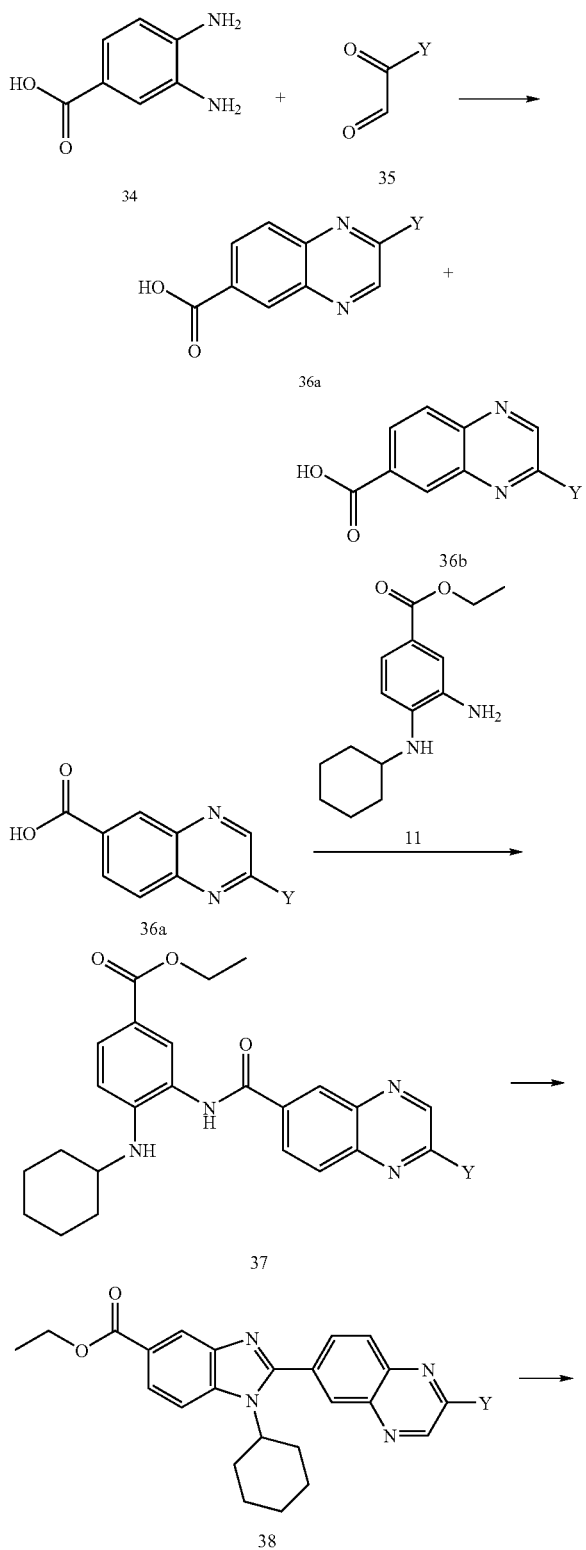

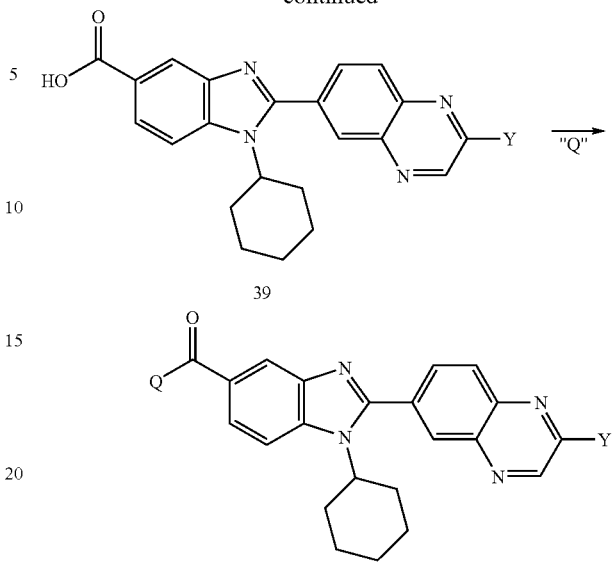

Scheme VII illustrates the conventional preparation of substituted quinoxaline derivates of the title compounds. Specifically, in Scheme VII, commercially available 3,4-diaminobenzoic acid is treated with a readily available dione, such as phenyl glyoxal (where Y=phenyl) under reaction conditions appropriate to effect cyclization to the quinoxaline. Preferably, the reaction is conducted under inert atmosphere under acidic reaction conditions, such as in acetic acid. The reaction is allowed to proceed at an elevated temperature, typically the reflux temperature of the solution, for a time sufficient to effect substantial cyclization, which typically occurs in about 1 to 4 hours. The resulting quinoxaline isomers, 36a and 36b can be separated by conventional techniques such as by chromatography. Alternatively, the major isomer, compound 36a, may be prepared using an alcoholic solvent such as ethanol at reduced temperatures such as 0° C. for a time sufficient to effect substantial cyclization, typically 10 to 48 hours. The major isomer is then obtained by conventional separation techniques, such as, for example, filtration.

Compound 36a is subsequently coupled with compound 11 as formed above to provide the intermediate amide product, compound 37. Preferably, the reaction is conducted in an inert solvent, such as DMF, and compound 36a is activated, for example, by treatment with HATU and DIEA for a time such that activation occurs, typically 5 to 30 minutes. Preferably, compound 11 is added to the reaction mixture under conditions appropriate to afford the amide product. Preferably, the reaction is conducted at around room temperature for a time sufficient to establish substantial product, compound 37, which typically occurs in about 10 to 24 hours. Upon reaction completion, the resulting amide can be isolated by conventional techniques such as extraction, filtration, chromatography, and the like; or, alternatively, used in the next step without purification and/or isolation.

The amide, compound 37, is subsequently cyclized by treatment with acid at elevated reaction temperatures. Preferably, the reaction is conducted at, for example, reflux temperature of the solution, for a time sufficient to promote substantial cyclization, which typically occurs in from 2 to 6 hours. Preferably, the reaction is run neat in glacial acetic acid. The resulting product, compound 38, may be isolated by conventional techniques such as extraction, filtration, chromatography, and the like; or, alternatively, used in the next step without purification and/or isolation.

The ethyl ester of compound 38 is subsequently removed by treatment with an aqueous base in an appropriate alcoholic solvent. Preferably, the reaction is conducted at elevated temperatures in the presence of a base such as NaOH for a time sufficient to afford substantial deprotection and production of the corresponding carboxylic acid, compound 39. The resulting product, compound 39, may be isolated by conventional techniques such as extraction, filtration, chromatography, and the like; or, alternatively, used in the next step without purification and/or isolation.

Compound 39 is optionally derivatized with any suitable amino or substituted amino moiety shown as "Q". Amino groups are well known in the art and it is apparent that readily available amines may be used in this reaction. Preferably, compound 39 is treated with a substituted amino acid such as L-5-hydroxytryptophane. The reaction is preferably conducted in an inert diluent such as DMF at room temperature for a portion of time to effect substantial completion of the reaction which typically occurs within 30 minutes to 1 hour. After reaction completion, the resulting product, 40 can be isolated by conventional techniques such as extraction, filtration, chromatography, and the like; or, alternatively, used in the next step without purification and/or isolation.

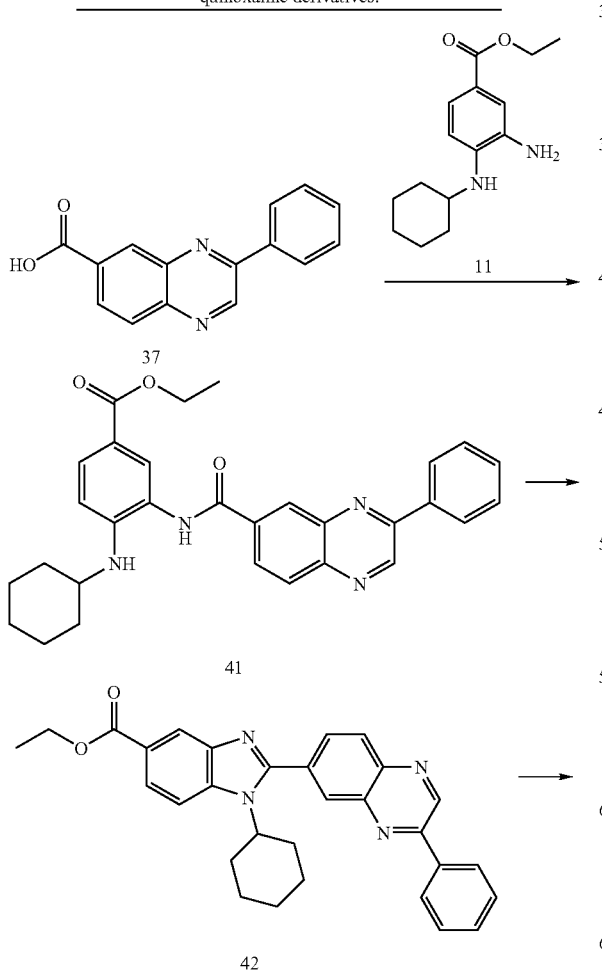

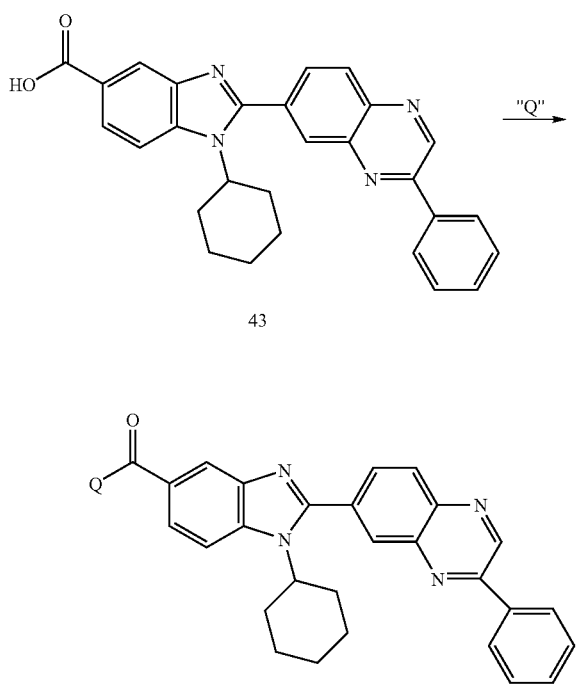

Scheme VIIa illustrates the conventional preparation of 3-substituted quinoxaline derivates of the title compounds. More specifically, the phenyl-substituted derivative is exemplified above, although this group is readily substituted with, for example, a methyl group as has been shown with the previous examples. Compound 37 as obtained above, is aminated with compound 11 under conventional protocols, such as those described above, to afford the quinoxaline derivative 41. Similarly to the above synthetic schemes, compound 41 may undergo cyclization under acidic reaction conditions to afford the cyclized product 42. Hydrolysis of the ethyl ester protecting group, as in the above Schemes, provides compound 43. Optional derivatization with an amino group, represented by "Q" affords product 44. The synthetic protocols in this Scheme may be inferred from the examples depicted in the Schemes above.

In addition to the foregoing Schemes, the following examples illustrate Het-Y groups that are within the scope of the present invention. Specifically, illustrative compounds I-A to I-W below optionally may be further derivatized with functional groups, for example, with amino, substituted alkyl, heteroaryl, sulfonamido, or other suitable functional groups. It is recognized throughout that further derivatization may require the use of protecting groups and protecting group strategies such that selective reactions may be pursued. Accompanying the illustrative examples below are preferred synthetic protocols which are useful in obtaining the the compounds of formula I-A to I-W. In the illustrations below, $R^{50}$, which is selected from hydrogen, Y or X', denotes an optional substituent on HET (when $R^{50}$ is not hydrogen) where X' and Y are as defined above.

3-Substituted Quinoline Het-Y

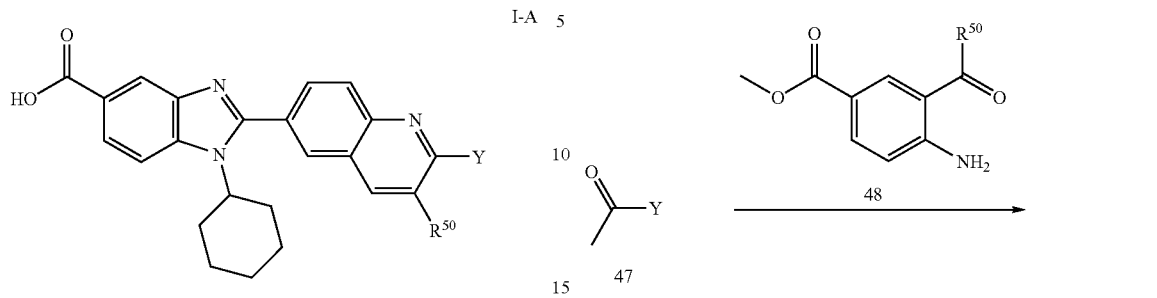

I-A may be obtained by the protocols above using the intermediate 46 the synthesis is as described below. The preferred intermediate 46 is to be synthesized as described for 19 except 18 is replaced with the analogues alkyl-aryl-ketone, 45, whose synthesis is described in R. P. Thummel, S. Chirayl, C. Hery, J-L. Lim, T-L Wang, J.Org.Chem.,, 1993, 58, 1666-1671.

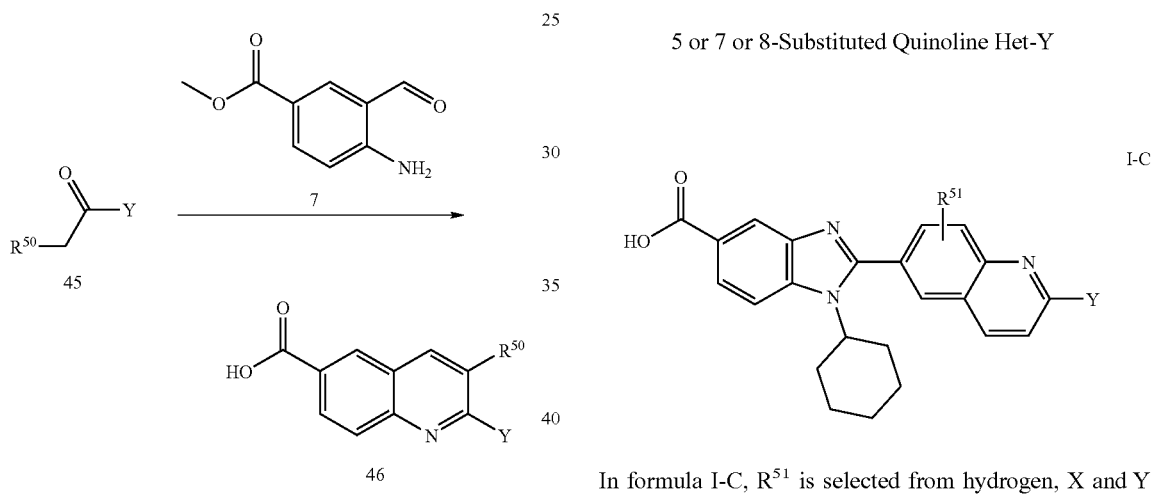

4-Substituted Quinoline Het-Y

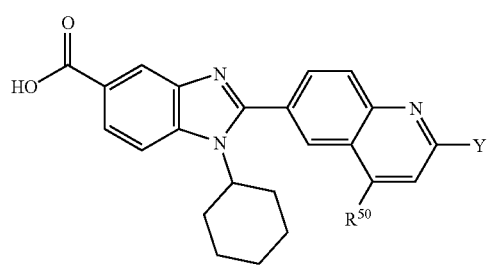

I-B may be optionally further modified as per the above Schemes to afford title compounds with a 4-substituted quinolin Het-Y moiety. I-B may be obtained as shown above, using compound 49 as an intermediate the synthesis of which is described below. The preferred compound 49 is to be synthesized as described for compound 19 except compound 7 is replaced with alkyl-aryl-ketone, compound 47, whose synthesis is described in R. P. Thummel, S. Chirayl, C. Hery, J-L. Lim, T-L Wang, J.Org.Chem., 1993, 58, 1666-1671.

5 or 7 or 8-Substituted Quinoline Het-Y

In formula I-C, $R^{51}$ is selected from hydrogen, X and Y where X and Y are as defined above. I—C may be optionally further modified as per the above Schemes to afford the title compounds with a 5 or 7 or 8-substituted quinoline Het-Y moiety. I—C may be obtained from the intermediate 51 the synthesis of which is described below. The preferred intermediate is to be synthesized as described for 19 except 7 is replaced with the analogues alkyl-substituted amino-aldehyde, 50, synthesized as described in R. P. Thummel, S. Chirayl, C. Hery, J-L. Lim, T-L Wang, J.Org.Chem., 1993, 58, 1666-1671.

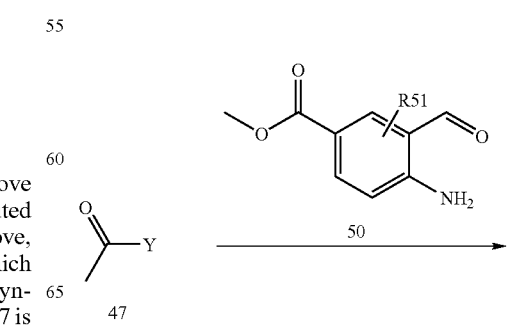

-continued

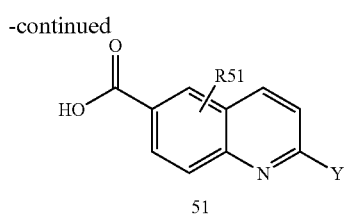

51

3,7-Quinoline Het-Y

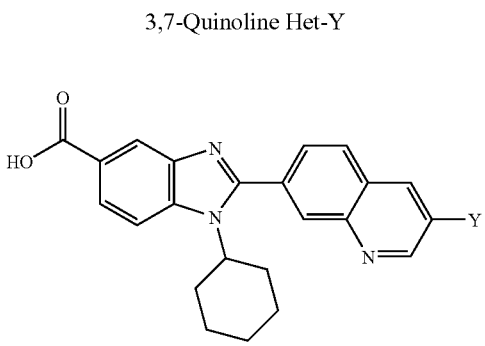

I-D

I-D may be optionally further modified as per the above Schemes to afford the title compounds with a 3,7-quinoline Het-Y moiety. I-D may be obtained from the intermediate 54 the synthesis of which is described below. The preferred intermediate is to be synthesized as described for 19 except 7 and 18 are replaced with 53 and 52, respectively, synthesized as described in R. P. Thummel, S. Chirayl, C. Hery, J-L. Lim, T-L Wang, J.Org.Chem., 1993, 58, 1666-1671.

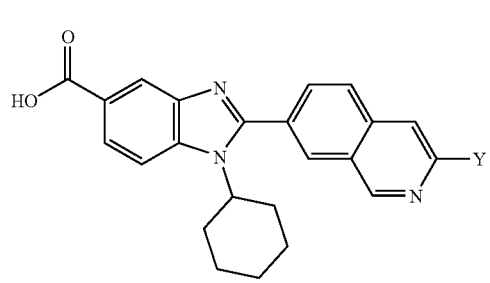

3,7-Isoquinoline Het-Y

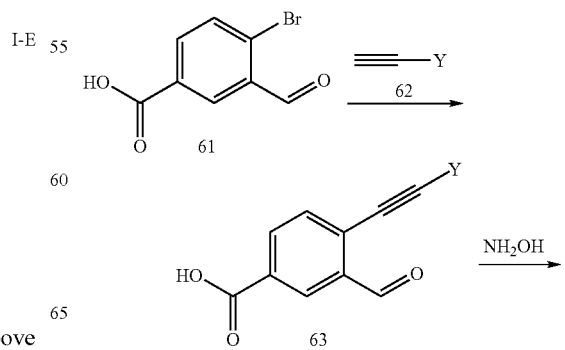
I-E

I-E may be optionally further modified as per the above Schemes to afford the title compounds with a 3,7-isoquino- line Het-Y moiety. I-E may be obtained from the intermediate 60 the synthesis of which is described below. The preferred 3,7-isoquinoline intermediate 60 is synthesized by a modification of the Pomeranz-Fritsch reaction described in Gensler, W.J., Organic Reactions, 1951, 6, 191 and Kucznierz, R. et al., Synth. Commun., 1999, 29, 1617 and shown directly below with numerical indicators 55 to 60.

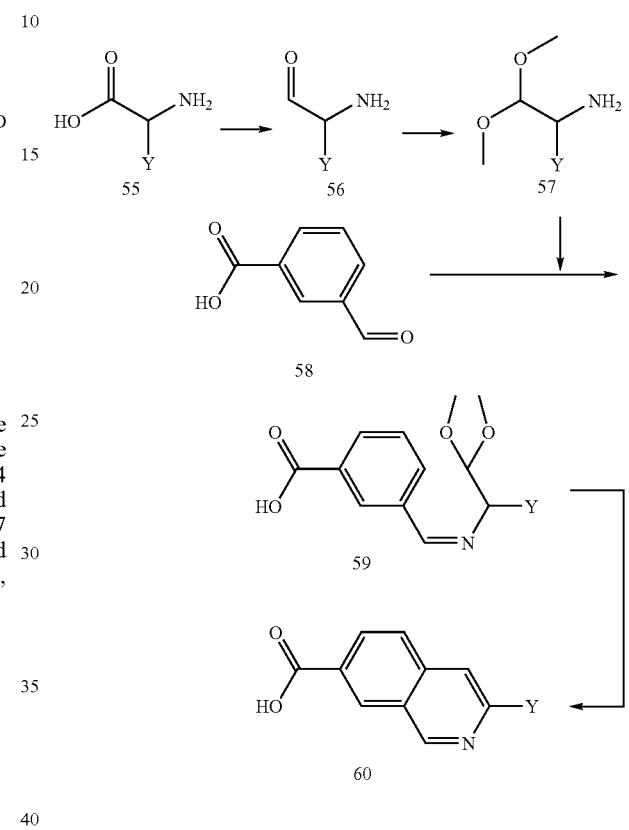

Alternatively, another preferred protocol is utilized to synthesize the key 3,7-isoquinoline intermediate by modification of the procedure described in Numata, A., et al., Synthesis, 1999, 306, followed by reduction of the isoquinoline N-oxide with triphenylphospine as described in Katrizky, A. R., Lam, J. N., Heterocycles, 1992, 33, 1011, as shown directly below with the compounds numbered 61 to 65. Note that the alternative procedure provides the same preferred intermediate above, with the numerical indicator 65 illustrating the second reaction protocol. Thus, 60 is the same intermediate as 65.

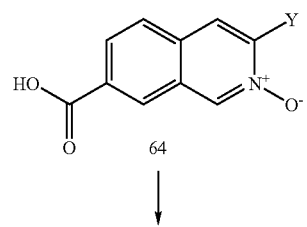

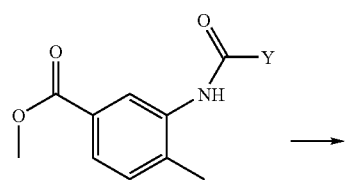

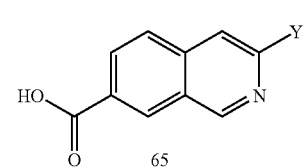

Quinazoline Het-Y

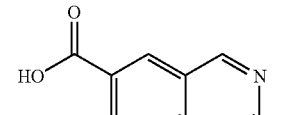

To form the preferred intermediate, 67 is first acylated with 66 using a standard coupling reagent (e.g. HATU). The resulting amide, 68 is to be heated with alcoholic ammonia as described by A. Biscler et al., Berichte, 1895, 28 to afford the intermediate 69.

Reverse 2,6-Quinoline linker Het-Y

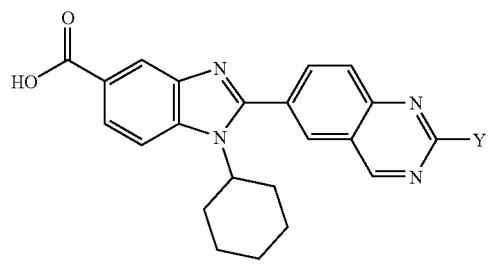

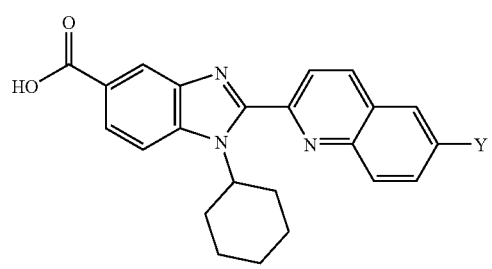

I-F may be optionally further modified as per the above Schemes to afford the title compounds with a 3,7-isoquinoline Het-Y moiety. I-F may be obtained from the intermediate 69 the synthesis of which is provided as shown below.

I-G may be optionally further modified as per the above Schemes to afford the title compounds with a 2,6-quinoline Het-Y moiety. I-G may be obtained from the intermediate 72 which is provided as shown below.

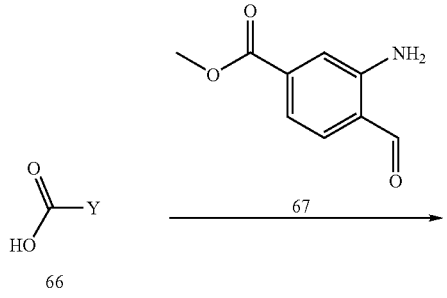

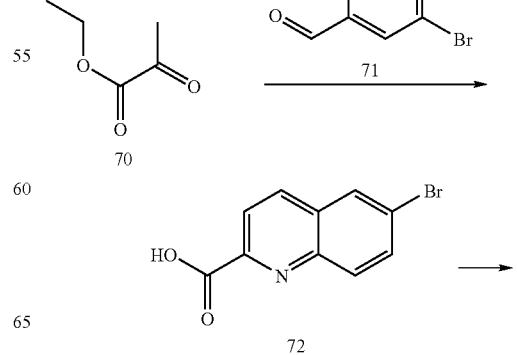

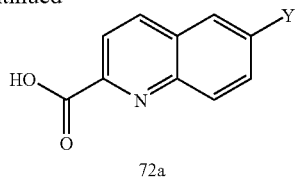

72a

The preferred intermediate is to be synthesized as described for 19 except 7 and 18 are replaced with ethylpyruvate, 70, and 71, respectively as described in R. P. Thummel, S. Chirayl, C. Hery, J-L. Lim, T-L Wang, J.Org.Chem., 1993, 58, 1666-1671. 72 may be further derivatized with the substituted aryl moiety by using standard coupling procedures, such as Suzuki conditions using the appropriately substituted aryl boronic acid to provide for intermediate 72a.

3,7-Isoquinoline Het-Y

The preferred "reversed" 3,7-isoquinoline intermediate is synthesized by reaction of commercial 5-bromosalicylaldehyde 73 with the appropriate aryl boronic acid under Suzuki conditions. The product, 74, is then converted to the triflate, 75, using standard conditions (triflic anhydride, 2,6-lutidine in dichloromethane). This intermediate and commercial ethyl propynoate, 76, are then used to synthesize the desired isoquinoline by modification of the procedure described in Numata, A., et al., Synthesis, 1999, 306, followed by reduction of the isoquinoline N-oxide with triphenylphospine as described in Katrizky, A. R., Lam, J. N., Heterocycles, 1992, 33, 1011 to afford the intermediate 78.

Reverse 3,7-Quinoline Linker

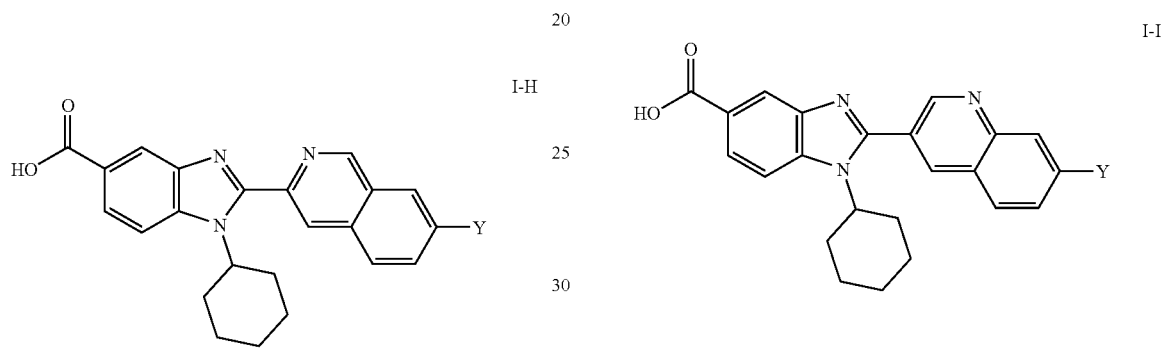

I-H may be optionally further modified as per the above Schemes to afford the title compounds with a 3,7-isoquinoline Het-Y moiety. I-H may be obtained from the intermediate 78 which is provided as shown below.

I-I may be optionally further modified as per the above Schemes to afford the title compounds with a reverse 3,7-quinoline Het-Y moiety. I-I may be obtained from the intermediate 81 which is provided as shown below.

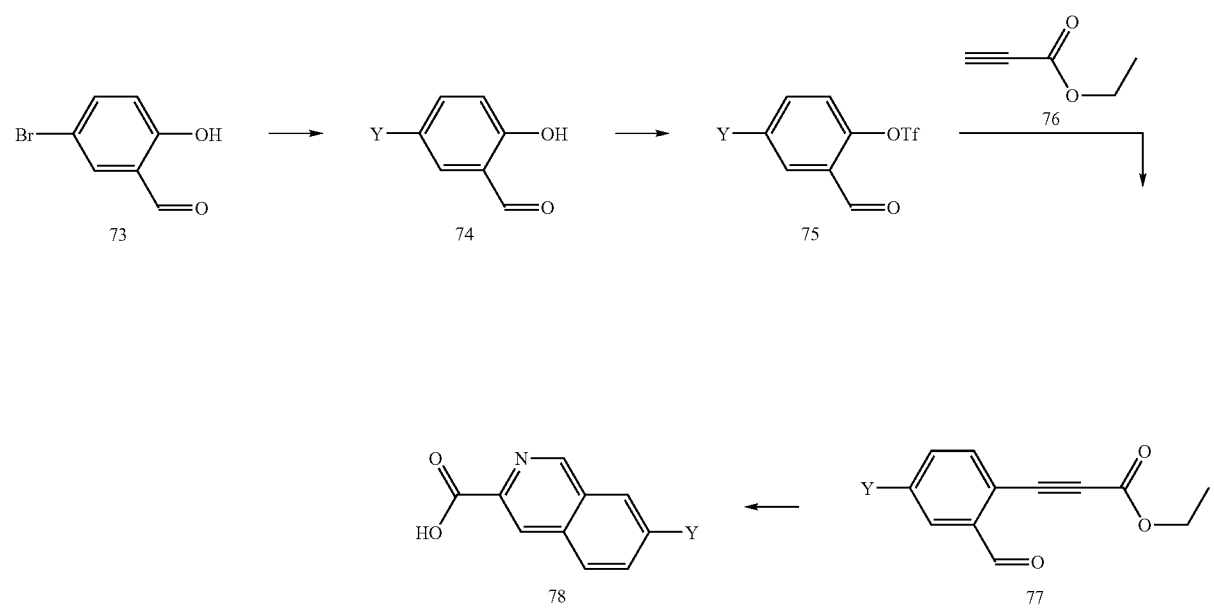

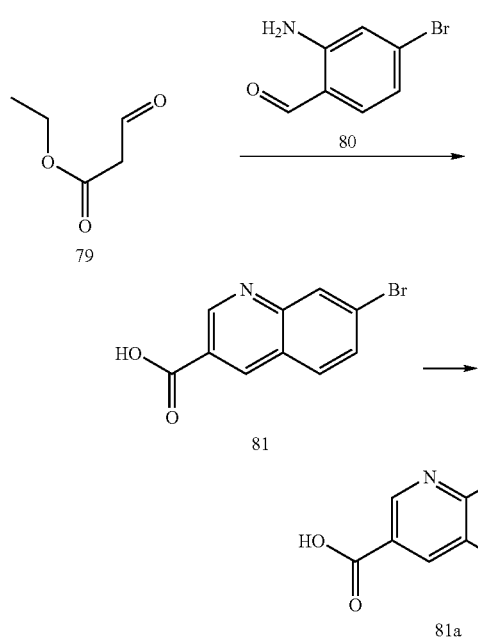

The preferred intermediate, 81, is to be synthesized as described for 19 except 7 and 18 are replaced with 79 and 80, respectively, as described in R. P. Thummel, S. Chirayl, C. Hery, J-L. Lim, T-L Wang, J.Org.Chem., 1993, 58, 1666-1671 which is then coupled using Suzuki conditions to the appropriately substituted aryl boronic acid to provide the aryl substituted product 81a.

Reverse Quinoxaline Het-Y

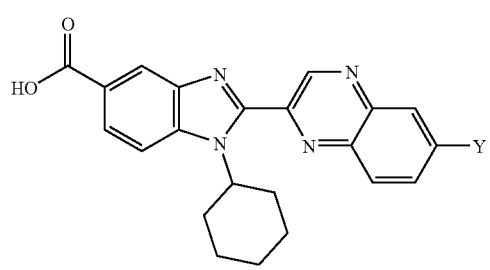

I-J may be optionally further modified as per the above Schemes to afford the title compounds with a reverse quinoxaline Het-Y moiety. I-J may be obtained from the intermediate 85 which is provided as shown below.

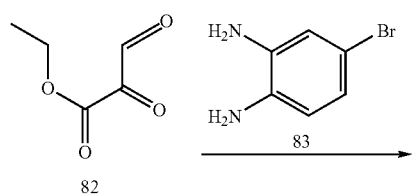

The preferred intermediate is to be synthesized as described for 36 and 37 except 3,4-diaminobenzoic acid, 34, and phenylglyoxal, 35, are replaced with 82 and 83, respectively as described in F. Roubinek, V. Bydzovsky and Z. Budesinsky, Coll. Czech. Chem. Commun., 49, 285, 1984. The resulting isomers, compounds 84 and 85 are then resolved and then coupled using Suzuki conditions to the appropriate substituted aryl boronic acid to provide the aryl substituted reverse quinoxaline, compounds 84a and 85a.

[1,5]-Naphthyridine Het-Y

I-K may be optionally further modified as per the above Schemes to afford the title compounds with a [1,5]-Naphthyridine Het-Y moiety. I-K may be obtained from the intermediate 88 which is provided as shown below:

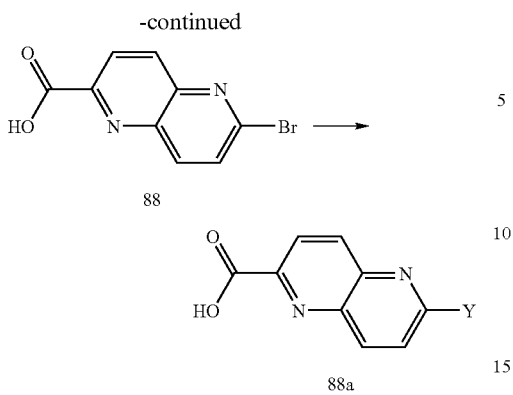

The preferred intermediate, compound 88, is to be synthesized using the procedure described by X. Li, Z. Xu, E. F. Erin, M. C. Kozlowski, Tetrahedron Lett., 43(20), 3747 (2002) utilizing 87 (synthesis described in V. S. Binz, Chem. Ber., 68, 1935; 315;321) and 86. This is then coupled using Suzuki conditions to the appropriate substituted aryl boronic acid to provide the aryl substituted [1,5]-naphthyridine product, compound 88a.

3,7-Substituted [1,8]-Naphthyridine Het-Y

The preferred intermediate, compound 91, is synthesized using the procedure described by H. Bock, T. T. H. Van, H. Schoedel, Monatsh. Chem., 127; 4; 1996; 391-396 utilizing 89 (described in Coleman, Glattfeld, J. Am. Chem. Soc., 66, 1944; 1183; 1186) and 90. The bromo-substituted product is then coupled using Suzuki conditions to the appropriate substituted aryl boronic acid to afford the aryl substituted 3,7-substituted [1,8]-naphthyridine product compound 91a.

3,6-Substituted [1,8]-Naphthyridine Het-Y

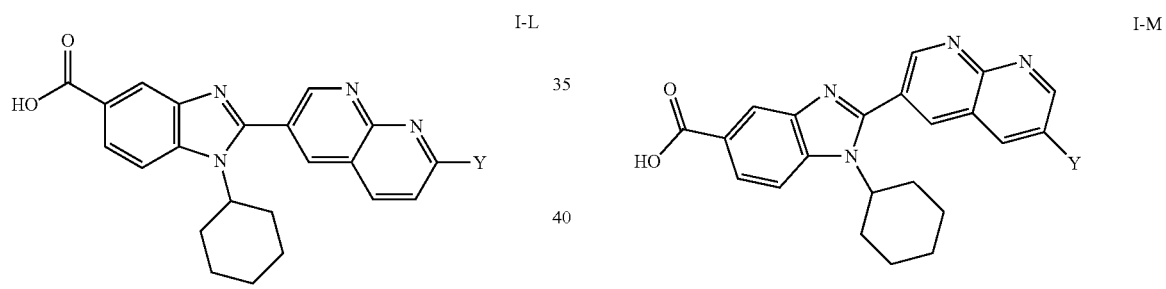

I-L may be optionally further modified as per the above Schemes to afford the title compounds with a 3,7-substituted [1,8]-naphthyridine Het-Y moiety. I-L may be obtained from the intermediate 91 which is provided as shown below:

I-M may be optionally further modified as per the above Schemes to afford the title compounds with a 3,6-Substituted [1,8]-Naphthyridine Het-Y moiety. I-M may be obtained from the intermediate 94 which is provided as shown below:

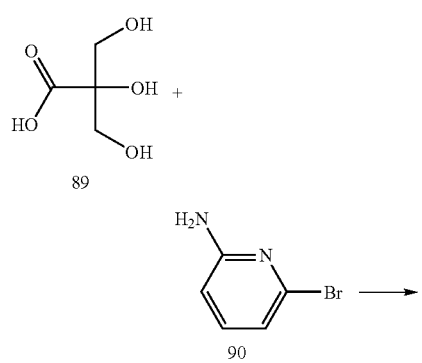

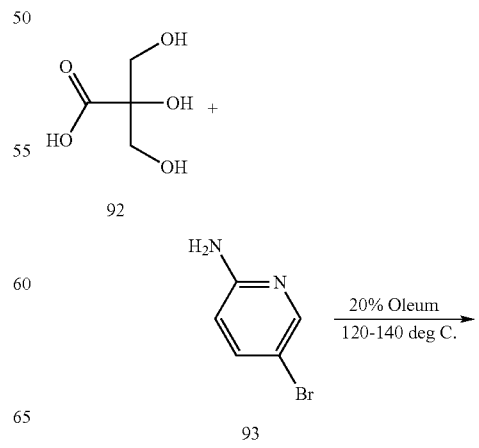

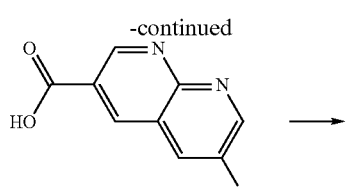

Suzuki conditions to the appropriate substituted aryl boronic acid to provide the aryl substituted 3,6-Substituted [1,8]-naphthyridine product, 94a.

3,7-Cinnoline Het-Y

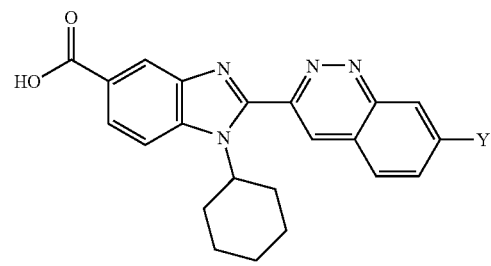

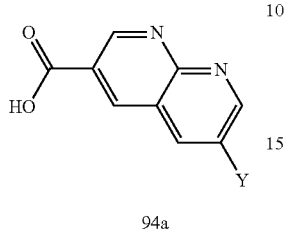

The preferred intermediate, 94, is synthesized using the procedure described by H. Bock, T. T. H. Van, H. Schoedel, *Monatsh. Chem.*, 127; 4; 1996; 391-396 utilizing 93 (whose synthesis is described in Coleman, Glattfeld, *J. Am. Chem. Soc.*, 66, 1944; 1183; 1186) and 92. This is then coupled using I-N may be optionally further modified as per the above Schemes to afford the title compounds with a 3,7-Cinnoline Het-Y moiety. I-N may be obtained from the intermediate 102 which is provided as shown below:

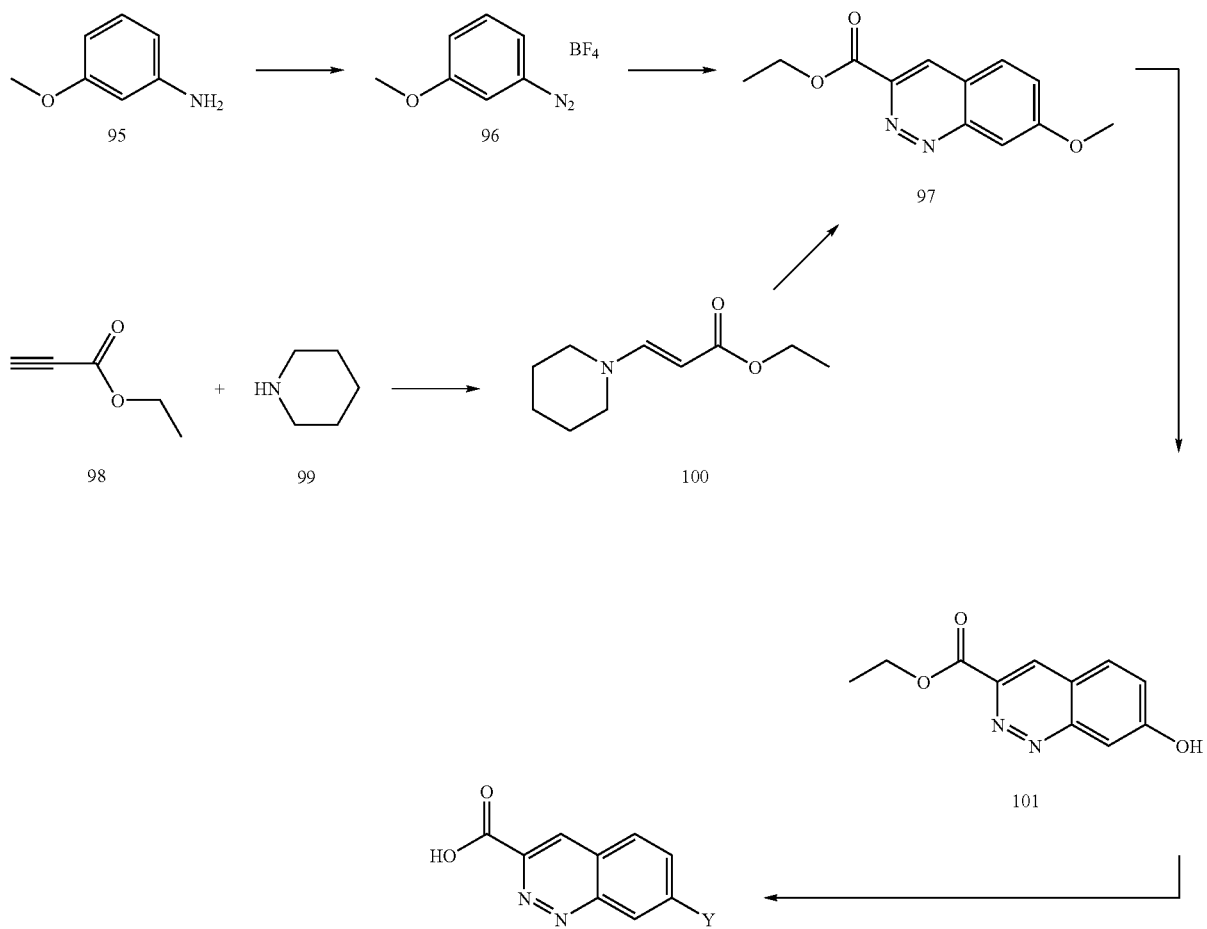

The preferred 3,7-cinnoline intermediate, 102, is synthesized by conversion of commercial anisidine 95 to its diazo form 96 (synthesis described in Hanson, P. et al., J. Chem. Soc. Perkin Trans. 2, 2002, 6, 1135.) and then coupled with ethyl (E)-3-piperidinoacrylate 100 to yield the 3-carboxyethyl-7-methoxy-cinnoline 97 as described in Kanner, C. B., Pandit, U. K., Tetrahedron, 1982, 38,3597. The methoxy group is deprotected to the phenol 101 using standard BBr₃ conditions. Intermediate 101 is then converted to the triflate (not shown) using standard conditions (triflic anhydride, 2,6-lutidine in dichloromethane) and finally converted to the preferred intermediate 102 via a Suzuki reaction with the appropriately substituted aryl boronic acid. 2,6-1H-Quinolin-4-one Het-Y:

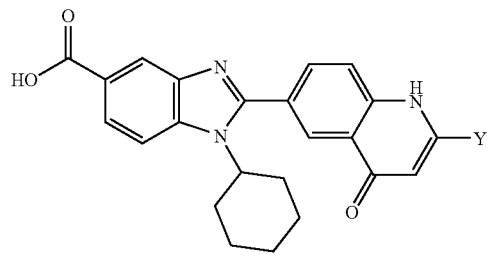

I-O may be optionally further modified as per the above Schemes to afford the title compounds with a 2,6-1H-Quinolin-4-one Het-Y moiety. I-O may be obtained from the intermediate 107 which is provided as shown below:

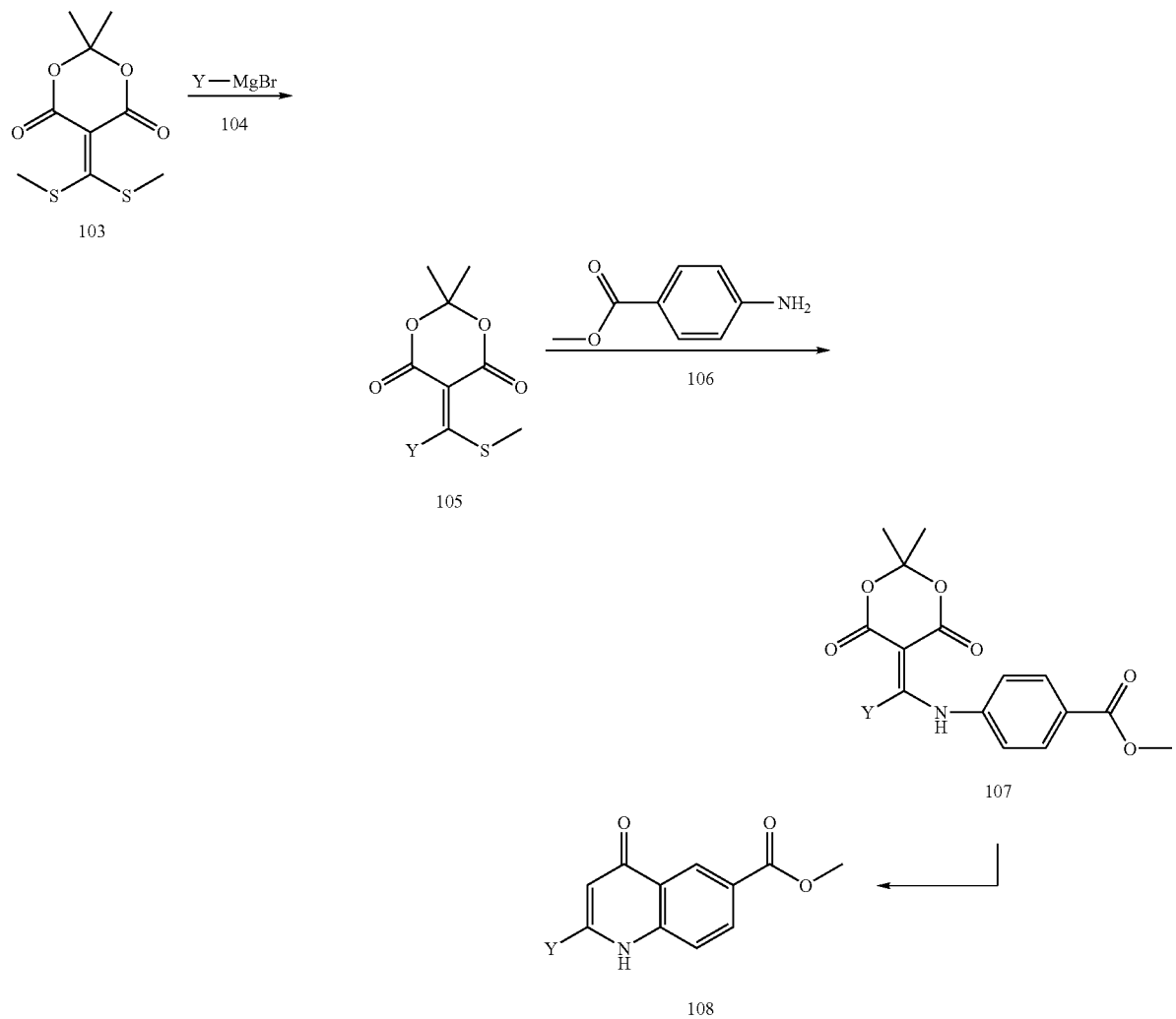

The key intermediate 108 is synthesized by a variation of the Conrad-Limpach-Knorr synthesis. Commercial starting material 103 is reacted with the appropriate aromatic Grignard-reagent, Compound 104, (or other appropriate organometallic) to yield compound 105 as described in J. Chem. Soc. Perkin Trans. 110, 1995; 1209-{214. Subsequent nucleophilic attack of amine 106 yields compound 107 as described in Synthesis 1987, 5, 482-483. 107 is then heated in Dowtherm A at 240° C. to yield compound 108 as described in J.Med. Chem. 38; 22; 1995; 4439-4445 or Eur. J. Med. Chem. Chim. Ther. 32; 7-8; 1997; 547-570.

2,6-Chromen-4-one Het-Y

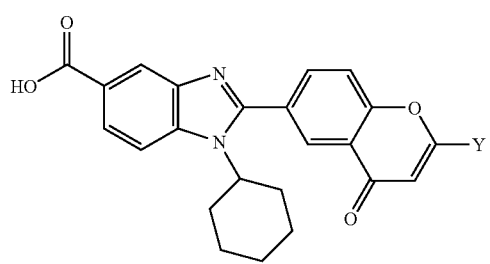

I-P

I-P may be optionally further modified as per the above Schemes to afford the title compounds with a 2,6-chromen-4-one Het-Y moiety. I-P may be obtained from the intermediate 112 which is provided as shown below.

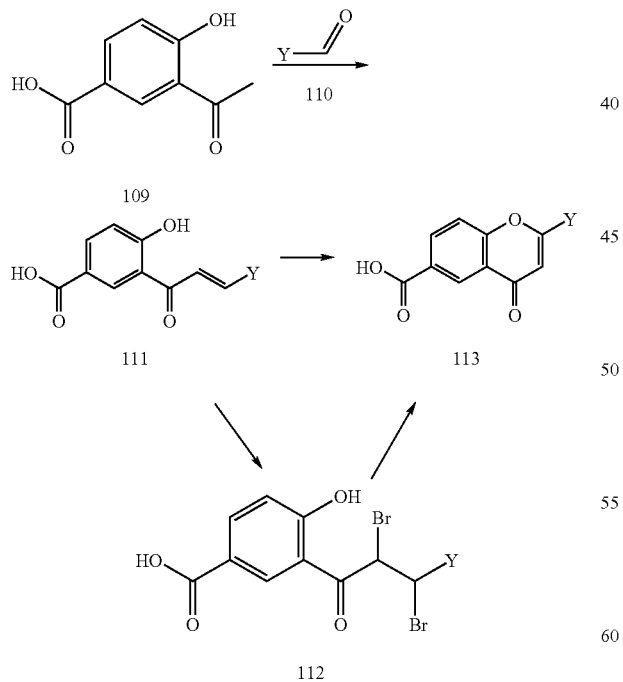

The preferred intermediate is synthesized by an aldol condensation performed on starting material 109 with the appropriate substituted aldehyde 110 with sodium hydroxide in ethanol, as described in Eur. J. Med. Chem. Chim. Ther. 31; 11;1996; 861-874 or J. Med. Chem. 23;3;1980; 335-338. Subsequent cyclization to 113 is accomplished using selenium dioxide in amyl alcohol at 150° C. or DDQ as described in JACS 77; 1955; 2223 or Eur. J. Med. Chem. Chim. Ther. 13; 1978; 33-39. Alternatively the double-bond of enone 111 is brominated to give 112, which in turn is cyclized to give 113, using aqueous potassium hydroxide as catalyst, as described in J. Med. Chem. 23;3;1980; 335-338.

3,7-Isochromen-1-one Het-Y

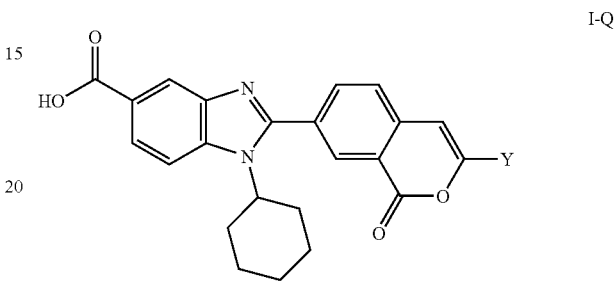

I-Q

I-Q may be optionally further modified as per the above Schemes to afford the title compounds with a 3,7-isochromen-1-one Het-Y moiety. I-Q may be obtained from the intermediate 119 which is provided as shown below.

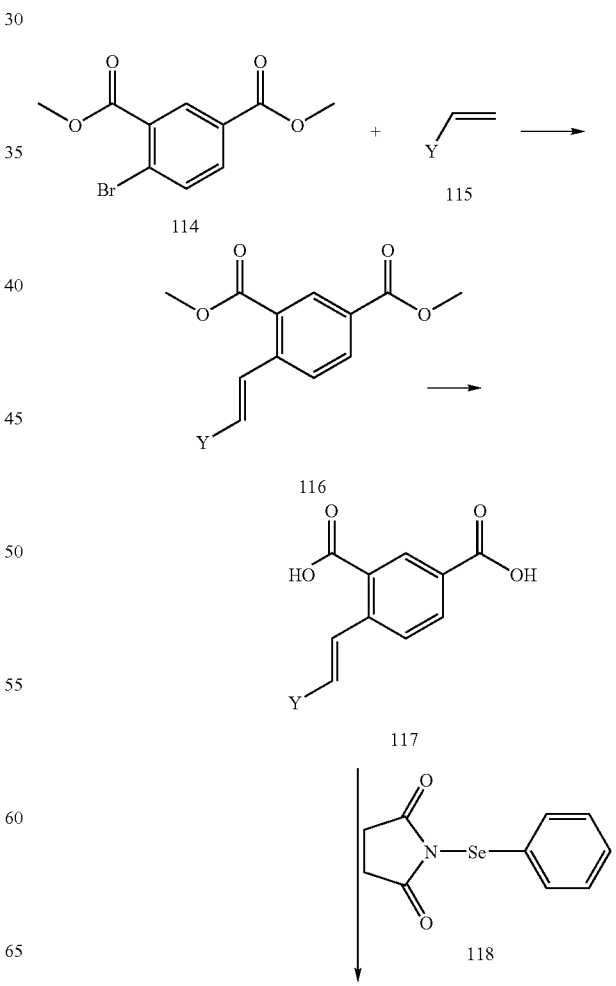

-continued

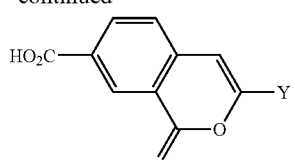
119

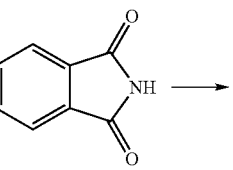
120

The preferred intermediate 119 is synthesized via a modification of Izumi, et al., Heterocycl. Chem. 31;1;1994;145-152. Starting material 114 (described in J. Heterocycl. Chem. 31;1;1994;145-152) is coupled via standard Heck reaction conditions to the appropriate styrene 115 to give 116. Hydrolysis of the methyl esters of 116 with sodium hydroxide gives the free acid 117, which is then oxidatively cyclized using selenium reagent 118 to give intermediate 119.

2,6-(2,3-Dihydrophthalazine-1,4-dione) Het-Y

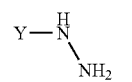
121

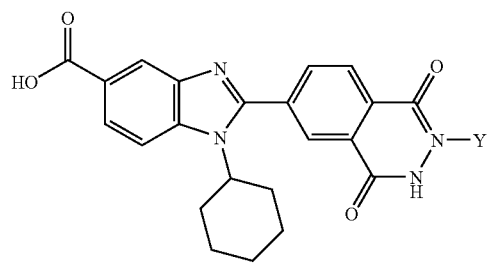
I-R

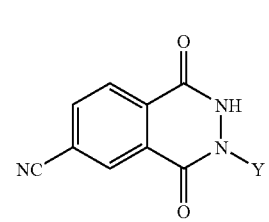
123

+

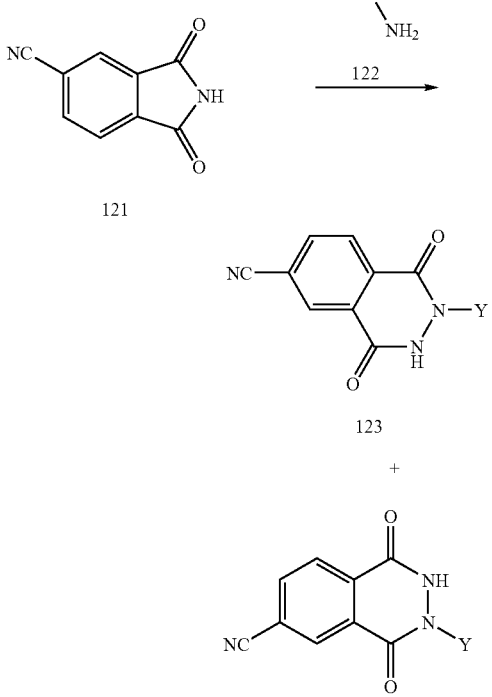
124

I-R may be optionally further modified as per the above Schemes to afford the title compounds with a 2,6-(2,3-Dihydrophthalazine-1,4-dione) Het-Y moiety. I-R may be obtained from the intermediate 124 which is provided as shown below:

2,7-(2,3-Dihydrophthalazine-1,4-dione) Het-Y

The preferred intermediates are synthesized via a modification of the procedure described by Watanabe, N., et al., J. Med. Chem. 1998, 41, 3367-3372. Amine 120 is converted to 121 by formation and subsequent nucleophilic displacement with cyanide of the diazonium salt. 121 is then reacted with the appropriate substituted hydrazine 122 to give a mixture of 123 and 124. This mixture is then resolved via chromatography or crystallization into its pure forms. Intermediate 123 is then utilized to synthesize I-R and intermediate 124 is used to synthesize I-S.

3,7-tetrahydroquinoline (I-T) and Reversed 3,7-tetrahydroquinoline (I-T) Het-Y

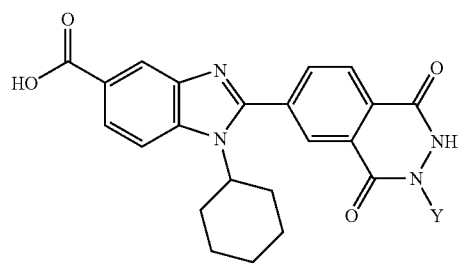
I-S

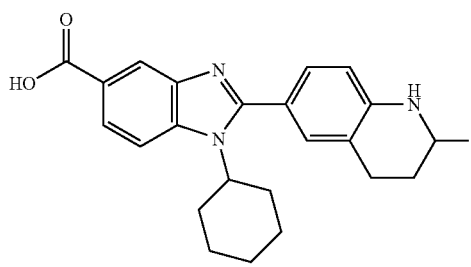
I-T

I-S may be optionally further modified as per the above Schemes to afford the title compounds with a 2,7-(2,3-Dihydrophthalazine-1,4-dione) Het-Y moiety. I-S may be obtained from the intermediate 124 which is provided as shown below.

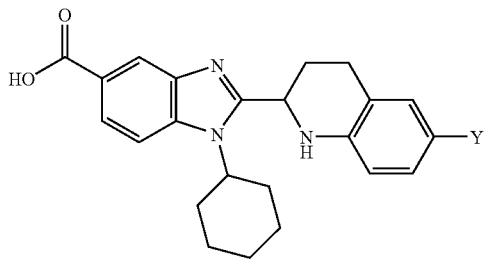

I-U

I-T and I-U may be optionally further modified as per the above Schemes to afford the title compounds with a 3,7-tetrahydroquinoline (I-T) and reversed 3,7-tetrahydroquinoline (I-T) Het-Y moiety. I-T and I-U may be obtained from by selective catalytic reduction of the aromatic Het-Y molecule with PtO$_2$ utilizing a modification of the procedure described in Maillard, M. C., et al., J. Med. Chem., 1998, 41, 3048.

3,7-tetrahydroisoquinoline and Reversed
3,7-tetrahydroisoquinoline Het-Y

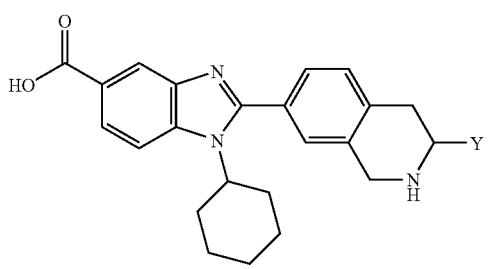

I-V

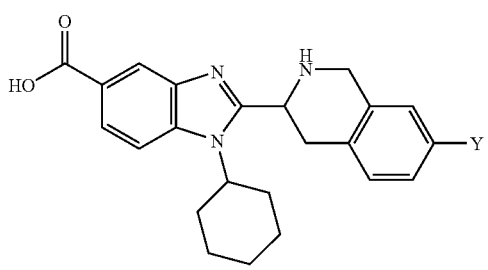

I-W

I-V and I-W may be used in the above Schemes to afford the title compounds with a 3,7-tetrahydroisoquinoline (I-V) and reversed 3,7-tetrahydroisoquinoline (I-W) Het-Y moiety. I-V and I-W may be obtained from selective catalytic reduction of the aromatic Het-Y molecule with PtO$_2$ utilizing a modification of the procedure described in Maillard, M. C., et al., J. Med. Chem., 1998, 41, 3048.

Utility

The present invention provides novel compounds possessing antiviral activity, including Flaviviridae family viruses such as hepatitis C virus. The compounds of this invention inhibit viral replication by inhibiting the enzymes involved in replication, including RNA dependent RNA polymerase. They may also inhibit other enzymes utilized in the activity or proliferation of Flaviviridae viruses.

Compounds of this invention maybe used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula I may range from approximately 0.1 to 20 mg per kilogram body weight of the recipient per day, more preferably from about 0.1 to 10 mg/kg/day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract, in particular for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula I in combination with at least one pharmaceutically acceptable excipient. Acceptable excipients are non-toxic, aid administration, and do not adversely affect the therapeutic benefit of the compound of formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of formula I, Ia, IIb, II, or III based on the total formulation, with the balance being one or more suitable pharmaceutical excipients. Preferably, the compound is present at a level of about 1-80 wt %. Representative pharmaceutical formulations containing a compound of formula I, Ia, Ib, II, or III are described below.

EXAMPLES

In the examples below and the synthetic schemes above, the following abbreviations have the following meanings. If an abbreviation is not defined, it has its generally accepted meaning.

| | |
|---|---|
| µL = | microliters |
| µM = | micromolar |
| µg = | micrograms |
| NMR = | nuclear magnetic resonance |
| AcOH = | acetic acid |
| aq. = | aqueous |
| boc = | t-butoxycarbonyl |
| br = | broad peak |
| cm = | centimeters |
| CSA = | camphorsulfonic acid |
| d = | doublet |
| δ = | chemical shift |
| DCM = | dichloromethane |
| dd = | doublet of doublets |
| DIEA = | diisopropylethylamine |
| DMAP = | 4-N,N-dimethylaminopyridine |
| DMEM = | Dulbeco's Modified Eagle's Medium |
| DMF = | N,N-dimethylformamide |
| DMSO = | dimethylsulfoxide |
| dppp = | 1,3-bis(diphenylphosphino)propane |
| DTT = | dithiothreotol |
| EDTA = | ethylenediaminetetraacetic acid |
| eq. = | equivalents |
| ESI = | electrospray ionization |
| EtOAc = | ethyl acetate |
| EtOH = | ethanol |
| Fmoc = | 9-fluorenylmethoxycarbonyl |
| g = | gram |
| h = | hours |
| HATU = | O-(7-Azabenzotriazol-1-yl)-N,N,N',N'-tetramethyluronium hexafluorophosphate |
| HBTU = | O-Benzotriazol-1-yl-N,N,N',N'-tetramethyluronium hexafluorophosphate |
| HCV = | hepatitis C virus |
| HPLC = | high performance liquid chromatography |
| Hz = | hertz |
| IPTG = | isopropyl-β-D-thiogalactopyranoside |
| IU = | International Units |
| $IC_{50}$ = | inhibitory concentration at 50% inhibition |
| J = | coupling constant |
| L = | liters |
| m = | multiplet |
| M = | molar |
| $M + H^+$ = | parent mass spectrum peak plus $H^+$ |
| $M - H^+$ = | parent mass spectrum peak minus $H^+$ |
| MeOH = | methanol |
| MeCN = | methylcyanide |
| mg = | milligram |
| min. = | minutes |
| mL = | milliliter |
| mM = | millimolar |
| mmol = | millimole |
| MS = | mass spectrum |
| N = | normal |
| nm = | nanometer |
| nM = | nanomolar |
| ng = | nanogram |
| NMP = | 1-methyl-2-pyrrolidinone |
| NTA = | nitrilotriacetic acid |
| NTP = | nucleoside triphosphate |
| PCR = | Polymerase chain reaction |
| Pfp = | pentafluorophenyl radical |
| Ph or ø = | phenyl |
| ppm = | parts per million |
| psi = | pounds per square inch |
| PyBroP = | Bromotris(pyrrolidine)phosphonium hexafluorophosphate |
| q = | quartet |
| Rp-HPLC = | reversed phase high performance liquid chromatography |
| s = | singlet |
| t = | triplet |
| dt = | Doublet of triplets |
| t-Bu = | tertiary-butyl protecting group |
| TBTU = | O-(Benzotriazol-1-yl)-N,N,N',N'-tetramethyluronium tetrafluoroborate |
| $TC_{50}$ = | Toxic concentration at 50% cell toxicity |
| TEA = | triethylamine |
| tetrakis or tetrakis palladium = | tetrakis(triphenylphosphine)palladium(0) |
| $Tf_2O$ = | Trifluorosulfonic anhydride |
| TFMSA = | Trifluoromethanesulfonic acid |
| TFA = | trifluoroacetic acid |
| THF = | tetrahydrofuran |
| TLC = | Thin layer chromatography |
| Tris = | Tris(hydroxymenthyl)aminomethane |
| UTP = | uridine triphosphate |
| v/v = | Volume to volume ratio |
| w/v = | Weight to volume ratio |

Set forth in the examples below are compounds and intermediates useful for making compounds of the present invention. An overview of the synthetic protocols employed to prepare these compounds is set forth above.

Unless indicated otherwise the HPLC methods referred to in the Examples correspond to the following procedures.

HPLC Procedure A
  Buffer A consists of 0.1% TFA in purified water
  Buffer B consists of 0.1% TFA in acetonitrile
  Vydac C18 Protein and Peptide column (250×4.6 mm)
  The column uses a flow rate of 1 mL per minute with a gradient of 20% B to 99% B over 20 minutes.
  (c18 column)

HPLC Procedure B
  Buffer A consists of 0.1% TFA in purified water
  Buffer B consists of 0.1% TFA in acetonitrile
  Vydac C18 Protein and Peptide column (250×4.6 mm)
  The column uses a flow rate of 2 mL per minute with a gradient of 20% B to 99% B over 10 minutes.
  (C18 column)

HPLC Procedure C
  Buffer A consists of 0.1% TFA in purified water
  Buffer B consists of 0.1% TFA in acetonitrile
  Merck KGaA Chromolith Performance RP-18e column (100×4.6 mm)
  The column uses a flow rate of 4 mL per minute with a gradient of 20% B to 99% B over 5 minutes.
  (Monolithic column)

Example 1

Preparation of 1-Cyclohexyl-2-(2-phenyl-quinolin-6-yl)-1H-benzoimidazole-5-carboxylic-acid (Compound 201)

Step 1: trans-3-(2-Dimethylamino-vinyl)-4-nitro-benzoic acid methyl ester (Compound 3)

A 100 mL flask fitted with a 15 cm Vigreux head was charged with 10 g (49.7 mmol) of 3-methyl-4-nitro-benzoic acid methyl ester, 12.5 mL of DMF and 14.8 g (124.2 mmol) of N,N-dimethylformamide dimethylacetal. The reaction vessel was immersed in a 140° C. oil bath for 18 h under argon while the forming methanol distilled away. Upon cooling to room temperature the dark red content of the flask solidified. The solid was transferred to a 250 mL flask using DMF which was removed by evaporation. The residue was triturated with petroleum ether to give 11.81 g of enamine as dark red solid.

MS: 251.10 (M+H$^+$); H$^1$-NMR (CDCl$_3$): δ (ppm) 8.11 (d, 1H, Ar—H$^2$), 7.80 (d, 1H, Ar—H$^5$), 7.53-7.50 (dd, 1H, Ar—H$^6$), 7.06 (d, 1H, CH=), 5.76 (d, 1H, CH=), 3.93 (s, 3H, OCH$_3$), 2.93 (s, 6H, (CH$_3$)$_2$N).

Step 2: 3-Formyl-4-nitro-benzoic acid methyl ester (Compound 4)

Compound 3 (11.81 g 47.2 mmol) and NaIO$_4$ (30.3 g 141.6 mmol) was dissolved in 250 mL THF/H$_2$O 1:1 at room temperature. The dark red solution was warmed to about 40° C. while heavy precipitation occurred and the color changed to light brown. After 1 h the precipitate was removed by filtration and washed with 200 mL ethyl acetate. The organic layer was washed three times with saturated NaHCO$_3$, once with brine and dried with Na$_2$SO$_4$. The solution was evaporated to dryness and the resulting oil was purified on a silicagel pad eluting with DCM-hexane gradient (30% to 60% DCM) to yield after evaporation yellow Compound 4.

H$^1$-NMR (CDCl$_3$): δ (ppm) 10.39 (s, 1H, CHO), 8.57 (d, 1H, J=2.1 Hz, Ar—H$^2$) 8.40-8.36 (dd, 1H, J=2.1 Hz and 8.4 Hz, Ar—H$^6$), 8.14 (d, 1H, J=8.4 Hz, Ar—H$^5$), 4.00 (s, 3H, OCH$_3$).

Step 3: 3-Dimethoxymethyl-4-nitro-benzoic acid methyl ester (Compound 5)

To a solution of Compound 4 (1 g, 4.78 mmol) in 20 mL methanol, 0.5 mL 4N HCL/dioxane was added and the mixture was kept at 90° C. for 10 minutes. The reaction mixture was then evaporated to dryness. The white solid material was dissolved in 20 mL methanol and was treated with 0.5 mL 4N HCl again in the same way. The solid was dried under high vacuum overnight to give compound 5 in quantitative yield.

H$^1$-NMR (CDCl$_3$): δ (ppm) 8.40 (d, 1H, J=1.8 Hz, Ar—H$^2$), 8.14-8.10 (dd, 1H, J=8.1 Hz and 1.8 Hz, Ar—H$^6$), 7.81 (d, 1H, J=8.1 Hz, Ar—H$^5$), 5.89 (s, 1H, Ar—CH), 3.96 (s, 3H, ester CH$_3$), 3.40 (s, 6H, acetal CH$_3$);

Step 4: 4-Amino-3-dimethoxymethyl-benzoic acid methyl ester (Compound 6)

100 mg 10% Pd/C and 1 g Mg$_2$SO$_4$ were suspended in 20 mL methanol and were hydrogenated in a Parr apparatus at 30 psi for 15 minutes. The apparatus was opened, and 1.22 g (4.78 mmol) of Compound 5 dissolved in 40 mL methanol was added, followed by 2 mL TEA. The mixture was hydrogenated at 30 psi for 30 minutes, the catalyst was removed by means of filtration and the solution was evaporated to dryness. The solid material was dried over P$_2$O$_5$/H$_3$PO$_4$ overnight to give Compound 6.

H$^1$-NMR (DMSO): δ (ppm) 7.80 (d, 1H, J=2.1 Hz, Ar—H 2), 7.62-7.58 (dd, 1H, J=8.4 Hz and 2.1 Hz, Ar—H$^6$), 6.64 (d, 1H, J=8.4 Hz, Ar—H$^5$), 5.84 (s, 2H, NH2), 5.32 (s, 1H, Ar—CH), 3.72 (s, 3H, ester CH$_3$), 3.20 (s, 6H, acetal CH$_3$).

Step 5: 4-Amino-3-formyl-benzoic acid methyl ester (Compound 7)

Compound 6 (0.95 g, 4.2 mmol) was dissolved at room temperature in 15 mL of a solvent mixture composed of EtOH-acetic acid-water 2:2:1. The strongly colored yellow solution became pale yellow in 5 minutes. The mixture was let stand for an additional 15 minutes before it was evaporated to dryness and further dried in high vacuum overnight to get Compound 7 as a yellow powder.

MS: 180.05 (M+H$^+$); H$^1$-NMR (CDCl$_3$): δ (ppm) 9.88 (s, 1H, CHO), 8.23 (d, 1H, J=2.1 Hz, Ar—H 2), 7.96-7.91 (dd, 1H, J=8.7 Hz and 2.1 Hz, Ar—H 6), 6.64 (d, 1H, J=8.4 Hz, Ar—H$^5$), 3.88 (s, 1H, CH$_3$).

Step 6: 4-Chloro-3-nitro-benzoic acid ethyl ester (Compound 9)

4-chloro-3-nitrobenzoic acid (100 g) was dissolved in 500 mL anhydrous ethanol and 35 mL concentrated sulfuric acid was added dropwise over a period of 5 minutes. The mixture was refluxed overnight then poured on 1 L ice. The precipitate was separated by filtration, washed four times with water and was then air dried. Recrystallization from 275 mL ethanol afforded a pale yellow product.

H$^1$-NMR (CDCl$_3$): δ (ppm) 8.49 (d, 1H, J=2.1 Hz, Ar—H 2), 8.17-8.13 (dd, 1H, J=8.8 and 2.1 Hz), Ar—H$^6$), 7.63 (d, 1H, J=8.1 Hz, Ar—H$^5$), 4.42 (q, 2H, J=7.5 Hz, CH$_2$), 1.42 (t, 3H, J=7.5 Hz, CH$_3$);

Step 7: 4-Cyclohexylamino-3-nitro-benzoic acid ethyl ester (Compound 10)

A solution of Compound 9 (22.96 g, 100 mmol), cyclohexylamine (15.31 g, 154 mmol) and TEA (13.57 g, 134 mmol) in 100 mL acetonitrile was refluxed overnight. The reaction mixture was poured into icy water and the precipitated crystals were collected by means of filtration, washed three times with water then was dried over phosphorous pentoxide in high vacuum to yield Compound 10.

MS: 293.16 (M+H$^+$); H$^1$-NMR (CDCl$_3$): δ (ppm) 8.85 (d, 1H, J=2.1 Hz, Ar—H$^2$), 8.40 (d, br, 1H, J=6.9 Hz, NH), 8.01-7.97 (dd, 1H, J=9.0 and 2.1 Hz), Ar—H$^6$), 6.86 (d, 1H, J=9.0 Hz, Ar—H$^5$), 4.34 (q, 2H, J=7.5 Hz, CH$_2$), 3.56 (m, 1H, —CH═), 2.05 (m, 2H), 1.81 (m, 2H), 1.65 (m, 2H), 1.44 (m, 4H), 1.38 (t, 3H, J=7.5 Hz, CH$_3$);

Step 8: 3-Amino-4-cyclohexylamino-benzoic acid ethyl ester (Compound 11)

To a solution of 5.84 g (20 mmol) of Compound 10 in 50 mL ethyl acetate and 30 mL methanol, 100 mg of 10% Pd/C was added, and the mixture was hydrogenated at 30 psi for 6 h. The catalyst was removed by filtration through a pad of Celite, the solvent was evaporated to dryness resulting in a dark purple solid which was recrystallized from ether-hexane. The mother liquid was evaporated, and the resulting solid was suspended in hexane and filtered to give additional yield of Compound 11

MS: 263.18 (M+H$^+$); H$^1$-NMR (CDCl$_3$): δ (ppm) 7.57-7.54 (dd, 1H, J=8.7 and 2.1 Hz, Ar—H$^6$), 7.39 (d, 1H, J=2.1 Hz, Ar—H$^2$), 6.57 (d, 1H, J=9.0 Hz, Ar—H$^5$), 4.29 (q, 2H, J=7.2 Hz, CH$_2$), 3.32 (m, 1H, —CH═), 2.05 (m, 2H), 1.77 (m, 2H), 1.66 (m, 2H), 1.42-1.20 (m, 7H);

Step 9: 2-Phenyl-quinoline-6-carboxylic acid (Compound 13, Y=phenyl)

To a solution of 100 mg (0.56 mmol) of Compound 7 and 67 mg (0.56 mmol) of acetophenone in 7 mL ethanol, 420 μL of a 10% KOH/ethanol (0.75 mmol) solution was added and the mixture was refluxed under argon overnight. The product partially precipitated as bright yellow crystals which were not filtered off. The whole mixture was evaporated to dryness, the residue was triturated with ether to give the product as potassium salt. The acid was liberated by dissolving in 10 mL water and acidification to pH 4 (about 500 μL 1M HCl). The precipitate was collected by filtration, washed twice with water and dried over phosphorous pentoxide in high vacuum to yield Compound 13.

MS: 250.10 (M+H$^+$); H$^1$-NMR (DMSO): δ (ppm) 8.51-8.48 (m, 2H), 8.22-8.08 (m, 4H), 7.96 (d, 1H, J=8.4 Hz), 7.50-7.40 (m, 3H);

Step 10: 2-Phenyl-quinoline-6-carbonyl chloride (Compound 14, Y=phenyl)

Compound 13 (100 mg, 0.4 mmol) was suspended in 15 mL of thionyl chloride and refluxed for 1 hr. The mixture was evaporated to dryness and the residue co-evaporated twice with toluene to give Compound 14 as a yellow solid in quantitative yield which was used immediately without further purification.

Step 11: 1-Cyclohexyl-2-(2-phenyl-quinolin-6-yl)-1H-benzoimidazole-5-carboxylic-acid (Compound 201 or Compound 16, Y=phenyl))

Compound 14, prepared from 100 mg (0.4 mmol) of Compound 13, was dissolved in 4 mL of DMF. Then 105.2 mg (0.4 mmol) Compound 11 was added as a solid, followed by 69 μL (0.4 mmol) of DIEA. The mixture was then evaporated to dryness and the residue dissolved in 30 mL of glacial acetic acid. The solution was refluxed for 3 h and evaporated to dryness. The yellow solid was dissolved again in 15 mL methanol, and 4 mL 1N NaOH was added with stirring at 80° C. for 1 h. The reaction mixture was cooled in an ice bath, acidified with 4 mL 1N HCl and evaporated to dryness to give an oil which was dissolved in 20 mL DMF-water 1:1 containing 0.1% TFA. The solution was applied on a RP-HPLC column to give the pure Compound 201.

Conversion to HCl salt: The purified title compound was dissolved in 4 mL methanol, 500 μL 4M HCl in dioxane was added followed by 40 mL ether. The white precipitate was separated by filtration and dried in high vacuum overnight.

MS: 448.20 (M+H$^+$); H$^1$-NMR (DMSO-d$_6$): δ (ppm) 8.70 (m, 1H), 8.47 (s, 1H), 8.33 (m, 5H), 8.22 (m, 1H), 8.09 (m, 1H), 8.00 (m, 2H), 7.58 (m, 3H), 4.44 (m, 1H), 4.23 (br, 4H), 2.33 (m, 2H), 2.10 (m, 2H), 1.85 (m, 2H), 1.61 (m, 1H), 1.36 (m, 3H);

Example 2

Preparation of 2-{[1-Cyclohexyl-2-(2-phenyl-quinolin-6-yl)-1H-benzoimidazole-5-carbonyl]-amino}-3-(5-hydroxy-1H-indol-3-yl)-propionic acid (Compound 229)

To a solution of 45 mg (0.1 mmol) Compound 201 in 500 μL DMF 22.8 μL (0.13 mmol) TFA-OPfp and 23 μL (0.13 mmol) DIEA was added. The mixture was stirred at room temperature for 30 minutes. 29.1 mg (0.13 mmol) L-5-hydroxytryptophane dissolved in 500 μL DMF was added to the activated ester solution followed by 40 μL DIEA. The reaction was complete in 1 h. The DMF was evaporated and the residual oil which was dissolved in 20 mL DMF-water 1:1 containing 0.1% TFA. The solution was applied on a RP-HPLC column to give the pure Compound 229 as TFA salt.

Conversion to HCl salt: The purified Compound 229 was dissolved in 4 mL methanol, 1 mL 4M HCl in dioxane was added followed by 40 mL ether. The off-white precipitate was separated by filtration and dried in high vacuum overnight.

MS: 650.29 (M+H$^+$); H$^1$-NMR (DMSO-d$_6$): δ (ppm) 10.52 (d, 1H), 8.93 (d, 1H), 8.71 (d, 1H), 8.49 (d, 1H), 8.35-8.24 (m, 5H), 8.23 (d, 1H), 8.09 (dd, 1H), 7.97 (dd, 1H), 7.63-7.54 (m, 3H), 7.12-7.08 (m, 2H), 6.90 (d, 1H), 6.57 (dd, 1H), 4.46 (m, 1H), 4.44 (m, 1H), 3.32 (m, 2H), 2.33 (m, 2H), 2.10 (m,2H), 1.85 (m, 2H), 1.60 (m, 1H), 1.32 (m, 3H);

Example 3

Preparation of 1-(trans-4-Hydroxy-cyclohexyl)-2-(2-phenyl-quinoxalin-6-yl)-1H-benzoimidazole-5-carboxylic acid (Compound 579)

Step 1: 3-Nitro-4-(trans-4-hydroxy-cyclohexylamino)-benzoic acid ethyl ester (Compound 579a)

Compound 9 (689 mg, 3 mmol) was suspended in acetonitrile (5 mL) and then triethylamine was added (1.3 mL, 9 mmol). trans-4-aminocyclohexanol hydrochloride (682 mg, 4.5 mmol) was then added and the reaction refluxed for 12 hours, 2 mL methanol was then added and the reaction further refluxed for another 24 hours. Water (100 mL) was added and the resulting precipitate filtered, washed 3 times with water and air-dried. The product was used without further characterization in the next step MS: 309.3 (M+H$^+$).

Step 2: 3-Amino-4-(trans-4-hydroxy-cyclohexylamino)-benzoic acid ethyl ester (Compound 579b)

The product from the previous step (3 mmol) was dissolved in ethyl acetate (60 mL) and methanol (40 mL) and 10% Pd/C (100 mg) was added. The reaction was hydrogenated on a Parr-shaker at 35 psi for 6½ hours at ambient temperature. The Pd/C was filtered and the filtrate concentrated. Chromatography (SiO₂, methanol/dichloromethane 3:97 v/v) to yield the title intermediate (265 mg, 0.95 mmol) MS: 279.2 (M+H⁺).

Step 3: 1-(trans-4-Hydroxy-cyclohexyl)-2-(2-phenyl-quinoxalin-6-yl)-1H-benzoimidazole-5-carboxylic acid (Compound 579)

Compound 36A Y=Phenyl, (200 mg, 0.8 mmol) was activated in 8 mL DMF with TBTU (282 mg, 0.88 mmol) and DIEA (0.285 mL, 1.6 mmol) for 30 minutes at room temperature. This solution was then added to Compound 579b (265 mg, 0.95 mmol) and stirred at ambient temperature for 20 hours. The reaction was concentrated to a residue in-vacuo and then dissolved in acetic acid (20 mL) and refluxed overnight. In the morning, the acetic acid was removed in-vacuo and the crude residue dissolved in a mixture of THF (20 mL), methanol (16 mL) and 2 M NaOH (4 mL) and the solution heated at 60 C. overnight. The solution was then concentrated in-vacuo to an aqueous solution and concentrated HCl added until the pH was 5. The resulting precipitate was filtered, washed with water and purified using RP-HPLC column to give the pure title compound.

Conversion to HCl salt: The HPLC purified product was dissolved in 4 mL methanol, 500 µL 4M HCl in dioxane was added followed by 40 mL ether. The resulting precipitate was separated by filtration and dried in high vacuum overnight. Yield: 15.7 mg.

MS: 465.21 (M+H⁺); H$^1$-NMR (DMSO-d$_6$): δ (ppm) 9.72 (s, 1H), 8.45 (s, 1H), 8.41-8.32 (m, 5H), 8.19-8.12 (m, 2H), 7.98 (d, 1H, 8.4 Hz), 7.62 (m, 3H), 4.27 (t, 1H, 12 Hz), 2.53-2.36 (m, 3 H), 2.06-1.93 (m, 4 H), 1.29-1.22 (m, 2 H).

Example 4

Preparation of 2-{[1-Cyclohexyl-2-(2-methyl-quinolin-6-yl)-1H-benzoimidazole-5-carbonyl]-amino}-3-(5-hydroxy-1H-indol-3-yl)-propionic acid (Compound 230)

Step 1: 2-Methyl-quinoline-6-carboxylic acid (Compound 28)

Compound 28 was synthesized as described for Compound 13, using acetone in place of acetophenone.
MS: 188.06 (M+H⁺); H$^1$-NMR (DMSO-d$_6$): δ (ppm) 8.88 (d, 1H, J=8.4 Hz), 8.78 (s, 1H), 8.37-8.26 (m, 2H), 7.83-7.80 (m, 1H), 2.88 (s, 3H).

Step 2: 4-Cyclohexylamino-3-[(2-methyl-quinoline-6-carbonyl)-amino]-benzoic acid ehyl ester (Compound 29)

Compound 29 was synthesized from Compound 28 as described for Compound 25 with quantitative yield.

Step 3: 1-Cyclohexyl-2-(2-methyl-quinolin-6-yl)-1H-benzoimidazole-5-carboxylic acid ethyl ester (Compound 30)

Compound 30 was synthesized from Compound 29 as described for Compound 23 with quantitative yield. MS: 414.24 (M+H⁺).

Step 4: 1-Cyclohexyl-2-(2-methyl-quinolin-6-yl)-1H-benzoimidazole-5-carboxylic acid (Compound 31)

Compound 31 was synthesized from Compound 30 as described for Compound 204. Yield: 77%.

MS: 386.21 (M+H⁺); H$^1$-NMR (DMSO-d$_6$): δ (ppm) 8.99 (d, 1H, J=8.7 Hz), 8.57 (d, 1H, J=1.8 Hz), 8.52 (d, 1H, J=8.7 Hz), 8.27-8,23 (m, 2H), 8.085 (d, 1H, J=9.0 Hz), 7.92-7.88 (m, 2H), 4.28 (m, 1H), 2.94 (s, 3H), 2.30-2.18 (m, 2H), 1.99 (m, 2H), 1.78 (m, 2H), 1.56 (m, 1H), 1.36-1.20 (m, 3H).

Step 4: 2-{[1-Cyclohexyl-2-(2-methyl-quinolin-6-yl)-1H-benzoimidazole-5-carbonyl]-amino}-3-(5-hydroxy-1H-indol-3-yl)-propionic acid (Compound 230)

Compound 230 was synthesized from Compound 31 as described for Compound 235 Yield: 32%.

MS: 588.29 (M+H⁺); H$^1$-NMR (DMSO-d$_6$): δ (ppm) 10.47 (s, 1H), 8.92 (d, 1H, J=9.0 Hz), 8.79 (d, 1H, J=7.5 Hz) 8.56 (s, 1H), 8.41 (d, 1H, J=8.7 Hz), 8.28-8.21 (m, 2H), 8.10 (d, 1H, J=8.7 Hz), 7.88 (d, 2H, J=8.7 Hz), 7.08-7.04 (m, 2H), 6.86 (d, 1H, J=1.8 Hz), 6.55-6.51 (dd, 1H, J=2.1 Hz, 8.7 Hz), 4.61 (m, 1H), 4.31 (m, 1H), 2.91 (s, 3H), 2.28-2.24 (m, 2H), 2.01 (m, 2H), 1.80 (m, 2H), 1.56 (m, 1H), 1.32-1.19 (m, 3H).

Example 5

Preparation of 2-{[1-Cyclohexyl-2-(2-phenyl-quinolin-6-yl)-1H-benzoimidazole-5-carbonyl]-amino}-3-hydroxy-propionic acid (Compound 231)

Compound 231 was synthesized from Compound 201 as described for Compound 235, except L-serine was used instead of L-5-hydroxytryptophane. Yield: 36%.

MS: 535.26 (M+H⁺); H$^1$-NMR (DMSO-d$_6$): δ (ppm) 8.93 (d, 1H, J=7.2 Hz), 8.73 (d, 1H, J=8.4 Hz), 8.54 (d, 1H, J=2.1 Hz), 8.46 (s, 1H), 8.38-8.29 (m, 5H), 8.15-8.11 (m, 2H), 7.73-7.55 (m, 3H), 4.50 (m, 2H), 3.85 (d, 1H, J=5.4 Hz), 2.37-2.32 (m, 2H), 2.15 (m, 2H), 1.86 (m, 2H), 1.61 (m, 1H), 1.39-1.30 (m, 3H).

Example 6

Preparation of 6-Amino-2-{[1-cyclohexyl-2-(2-phenyl-quinolin-6-yl)-1H-benzoimidazole-5-carbonyl]-amino}-hexanoic acid (Compound 232)

Compound 232 was synthesized from Compound 201 as described for Compound 235, except H-Lys(Boc)-OtBu was used instead of L-5-hydroxytryptophane. In the 3rd step the protected intermediate was treated with a mixture of TFA-anisol 8:2 for 2 hours then the product was precipitated with ether and purified on RP-HPLC. Yield 15%.

MS: 576.33 (M+H⁺); H$^1$-NMR (DMSO-d$_6$): δ (ppm) 8.90 (d, 1H, J=7.8 Hz), 8.71 (d, 1H, J=8.7 Hz), 8.48 (d, 1H, J=1.8 Hz), 8.41 (d, 1H), 8.35-8.32 (m, 4H), 8.22 (d, 1H, J=9.6 Hz), 8.12-8.08 (dd, 1H, J=1.8 Hz, 8.7 Hz), 8.02 (d, 1H, J=8.7 Hz), 7.86 (br, 3H), 7.60-7.54 (m, 3H), 4.42 (m, 2H), 2.78 (m, 2H), 2.36-2.27 (m, 2H), 2.11 (m, 2H), 1.90-1.83 (m, 4H), 1.62 (m, 3H), 1.53-1.25 (m, 6H).

Example 7

Preparation of 1-[1-Cyclohexyl-2-(2-phenyl-quinolin-6-yl)-1H-benzoimidazole-5-carbonyl]-pyrrolidine-2-carboxylic acid (Compound 233)

Compound 233 was synthesized from Compound 201 as described for Compound 235, except L-proline was used instead of L-5-hydroxytryptophane. Yield: 15%.

MS: 545.28 (M+H⁺); H$^1$-NMR (DMSO-d$_6$): δ (ppm) 8.71 (d, 1H), J=9.0 Hz), 8.49 (d, 1H), 8.36-8.32 (m, 4H, 8.26 (d, 1H, J=8.7 Hz), 8.12-8.08 (dd, 1H, J=1.5 Hz, 8.7 Hz), 7.95 (m, 1H), 7.65-7.53 (m, 2H), 4.44 (m, 1H), 3.56 (m,1H), 2.30 (m, 3H), 2.11 (m, 2H), 1.92-1.83 (m, 6H), 1.65 (m,1H), 1.37-1.32 (m, 4H).

Example 8

Preparation of 1-Cyclohexyl-2-(2-phenyl-quinoxalin-6-yl)-1H-benzoimidazole-5-carboxylic acid (Compound 203 or Compound 39, Y=phenyl)

Step 1: 2-Phenyl-quinoxaline-6-carboxylic acid (compound 36A, Y=phenyl) and 3-Phenyl-quinoxaline-6-carboxylic acid (Compound 36B, Y=phenyl)

To a solution of Compound 34 (850.75 mg, 5 mmol) and 3,4-diaminobenzoic acid in 50 mL of acetic acid, Compound 35 (670.7 mg, 5 mmol) phenylglyoxal was added and was refluxed under argon for 2.5 h. The reaction mixture was evaporated to dryness. The resulting grey solid containing the two isomers in about 2:1 ration was separated by HPLC resulting in 230 mg (19%) Compound 36A and 140 mg (12%) Compound 36B.

The major component (Compound 36A) was also prepared in an alternate manner. Ethanol was used as a solvent in place of acetic acid and the reaction mixture was stirred overnight at 0° C. The precipitate formed during the reaction was filtered off, washed with cold ethanol and dried to provide Compound 36A. Yield (78%).

Compound 36A: MS: 251.10 (M+H$^+$); H$^1$-NMR (DMSO): δ (ppm) 13.5 (s, 1H), 9.67 (s, 1H,), 8.60 (d, 1H, J=1.5 Hz), 8.38-8.34 (m, 2H), 8.31-8.27 (dd, 1H, J=8.7 Hz and 2.1 Hz), 8.20 (d, 1H, J=9 Hz), 7.65-7.59 (m, 3H);

Compound 36B: MS: 251.10 (M+H$^+$); H$^1$-NMR (DMSO): δ (ppm) 13.5 (s, 1H), 9.63 (s, 1H,), 8.30 (d, 1H, J=1.2 Hz), 8.38-8.34 (m, 2H), 8.28-8.24 (dd, 1H, J=8.7 Hz and 1.8 Hz), 8.18 (d, 1H, J=8.7 Hz), 7.63-7.57 (m, 3H);

Step 2: 4-Cyclohexylamino-3-[(2-phenyl-quinoxaline-6-carbonyl)-amino]-benzoic acid ethyl ester (compound 37, Y=phenyl)

The suspension of 250 mg (1 mmol) of Compound 36 in 4 mL of DMF was activated by treatment with 418 mg (1.1 mmol) of HATU and 383 μL (2.2 mmol) of DIEA for 10 minutes at room temperature during which time it remains a suspension. Compound 11 (289 mg, 1.1 mmol) was added and the mixture was stirred at room temperature overnight, becoming a clear solution. The DMF was evaporated and the resulting oil was triturated with water. The solidified material was filtered, washed with water (3×) and dried to give Compound 37 as a yellow solid which was used without further purification. MS: 495.27 (M+H$^+$);

Step 3: 1-Cyclohexyl-2-(2-phenyl-quinoxalin-6-yl)-1H-benzoimidazole-5-carboxylic acid ethyl ester (Compound 38, Y=phenyl)

Compound 37 (1 mmol) from the previous step was dissolved in 80 mL glacial acetic acid and was refluxed for 4 h. The acetic acid was evaporated and the resulting oil was dried overnight under high vacuum to give Compound 38 as a semisolid which was used without further purification. MS: 477.25 (M+H$^+$);

Step 4: 1-Cyclohexyl-2-(2-phenyl-quinoxalin-6-yl)-1H-benzoimidazole-5-carboxylic acid (Compound 203)

To the solution of 1 mmol of Compound 38 in 40 mL ethanol, 10 mL of 1 M NaOH was added and the mixture was refluxed for 1 h. The reaction mixture was then cooled and evaporated to dryness. The residue was dissolved in 50 mL of water and acidified with 1M HCl to pH 4. The precipitate was filtered off, washed with water (4×) and dried to give the title compound.

MS: 449.23 (M+H$^+$); H$^1$-NMR (DMSO): δ (ppm) 9.73 (s, 1H), 8.51 (d, 1H, J=1.5 Hz), 8.42-8.35 (m, 4H), 8.24-8.16 (m, 2H), 8.03-7.99 (dd, 1H, J=9 Hz and 1.5 Hz), 7.65-7.61 (m, 3H), 4.41 (m, 1H), 4.5-3.9 (br, 2H), 2.31 (m, 2H), 2.10 (m, 2H), 1.85 (m, 2H), 1.61 (m, 1H), 1.40-1.20 (m, 3H);

Example 9

Preparation of 2-{[1-Cyclohexyl-2-(2-phenyl-quinoxalin-6-yl)-1H-benzoimidazole-5-carbonyl]-amino}-3-(5-hydroxy-1H-indol-3-yl)-propionic acid (Compound 234)

Compound 203 (100 mg, 0.22 mmol) was activated in 2 mL DMF with 92 mg (0.24 mmol) HBTU and 85 μL DIEA for 10 minutes at room temperature. 56 mg 5-hydroxy-L-tryptophane, dissolved in 1 mL DMF was added followed by 44 μL DIEA. The mixture was stirred at room temperature for 1 h, then evaporated to dryness. The oil was purified using RP-HPLC column to give Compound 234.

Conversion to HCl salt: The purified Compound 234 was dissolved in 4 mL methanol, 500 μL of 4M HCl in dioxane was added followed by 40 mL of ether. The yellow precipitate was separated by filtration and dried in high vacuum overnight. Yield: 76 mg (58%) off yellow solid.

MS: 651.28 (M+H$^+$); H$^1$-NMR (DMSO-d$_6$): δ (ppm) 10.49 (d, 1H), 9.71 (s, 1H), 8.73 (d, 1H), 8.41-8.31 (m, 5H), 8.18-8.14 (dd, 1H, J=8.4 Hz and 1.8 Hz), 8.05 (d, 1H, J=9 Hz), 7.85 (dd, 1H, J=9 Hz and 1.8 Hz), 7.67-7.61 (m, 3H), 7.13-7.08 (m, 2H), 6.90 (d, 1H, J=2.1 Hz), 6.59-6.55 (dd, 1HH, J=8.7 Hz and 2.4 Hz), 4.65 (m, 1H), 4.41 (m, 1H), 3.20 (m, 2H), 2.32 (m, 2H), 2.04 (m, 2H), 1.85 (m, 2H), 1.61 (m, 1H), 1.44-1.22 (m, 3H).

Example 10

Preparation of 2-{2-[4'-Chloro-4-(pyrrolidine-1-carbonyl)-biphen-2-yl]-quinolin-6-yl}-1-cyclohexyl-1H-benzoimidazole-5-carboxylic acid (Compound 204)

Step 1: 1-[2-Hydroxy-5-(pyrrolidine-1-carbonyl)-phenyl]-ethanone (Compound 18)

To a solution of 500 mg (2.8 mmol) of 3-acetyl-4-hydroxybenzoic acid in 5 mL of DMF, 721.6 μL (4.2 mmol) of TFA-OPfp and 731.5 μL (4.2 mmol) of DIEA were added. The clear solution was stirred at room temperature for 15 minutes, then 467.5 μL (5.6 mmol) of pyrrolidine was added. The mixture was stirred for another hour and was then evaporated to dryness. The oily residue was taken up in 50 mL water-50 mL ethyl acetate mixture, the EtOAc phase was separated, washed twice with 1 M HCl, water, saturated NaHCO$_3$, brine and was dried with Na$_2$SO$_4$. The EtOAc was evaporated and the oil was purified on an open silica gel column using a toluene/ethyl acetate gradient containing 5% acetic acid to yield 410 mg (51%) Compound 18.

MS: 232.12 (M−H$^+$); H$^1$-NMR (DMSO-d$_6$): δ (ppm) 12.02 (s, 1H), 7.99 (d, 1H, J=2.1 Hz), 7.69-7.65 (dd, 1H, J=2.1 Hz, 8.7 Hz), 6.97 (d, 1H, J=8.7 Hz), 3.47-3.32 (m, 4H), 2.65 (s, 3H), 1.90-1.83 (br, 4H).

Step 2: 2-[2-Hydroxy-5-(pyrrolidine-1-carbonyl)-phenyl]-quinoline-6-carboxylic acid (Compound 19)

Compound 18 (410 mg, 1.75 mmol) and Compound 7 (315 mg, 1.75 mmol) were dissolved in 30 mL of ethanol, 2.45 mL of a 10% KOH/ethanol solution was added and the mixture was refluxed overnight under argon. The ethanol was evaporated, the residue dissolved in water, and acidified with 3 mL of 1M HCl. The formed gel was solidified by addition of 30 mL of ethyl acetate and 30 mL of a saturated NaCl solution. The solid was filtered, awashed with water, and dried. Yield 302 mg (48%) Compound 19.

MS: 363.15 (M+H$^+$); H$^1$-NMR (DMSO-d$_6$): δ (ppm) 13.28 (br, 1H), 8.72 (m, 2H), 8.50 (m, 1H), 8.37 (s, 1H), 8.25 (m, 1H), 8.14 (d, 1H, J=8.7 Hz), 7.58 (m, 1H), 7.02 (d, 1H, J=8.7 Hz), 3.51 (m, 4H), 1.85 (m, 4H).

Step 3: 2-[2-Hydroxy-5-(pyrrolidine-1-carbonyl)-phenyl]-quinoline-6-carboxylic acid methyl ester (Compound 20)

To the solution of 295 mg (0.81 mmol) of Compound 19 in 3 mL of methanol, 1 mL of 4M HCl/dioxane was added, and the mixture was heated at 60° C. overnight. The reaction mixture was then evaporated to dryness to give Compound 20 in quantitative yield. MS: 377.18 (M+H$^+$).

Step 4: 2-[5-(Pyrrolidine-1-carbonyl)-2-trifluoromethanesulfonyloxy-phenyl]-quinoline-6-carboxylic acid methyl ester (Compound 21)

Compound 20 described in the previous step (0.81 mmol) and 10 mg of DMAP were dissolved in 10 mL of DCM. Then 1 mL of pyridine was added, followed by 450 μL (2.67 mmol) of triflic anhydride (drop-wise), and the mixture was stirred overnight. The reaction mixture was evaporated and purified on silicagel using toluene-ethyl acetate (10-50%) gradient. Yield: 320 mg (77%) Compound 21.

MS: 509.11 (M+H$^+$); H$^1$-NMR (DMSO-d$_6$): δ (ppm) 8.78-8.74 (m, 2H), 8.29-8.25 (dd, 1H, J=2.1 Hz, 9.0 Hz), 8.18 (d, 1H, J=8.7 Hz), 8.1 (d, 1H, J=2.1 Hz), 8.03 (d, 1H, J=8.7 Hz), 7.85-7.81 (dd, 1H, J=2.1 Hz, J=2.1 Hz, 8.4 Hz), 7.67 (d, 1H, J=8.4 Hz), 3.94 (s, 3H), 3.51-3.41 (m, 4H), 1.9-1.82 (m, 4H); F$^{19}$-NMR: δ -74.58.

Step 5: 2-[4'-Chloro-4-(pyrrolidine-1-carbonyl)-biphen-2-yl]-quinoline-6-carboxylic acid methyl ester (Compound 23)

Compound 21 (320 mg, 0.63 mmol), 4-chloro-phenylboronic acid (Compound 22, 148 mg, 0.94 mmol), 500 mg (2.35 mmol) of K$_3$PO$_4$, 27 mg (0.63 mmol) of LiCl and 36.5 mg (0.031 mmol) of Pd(PPh$_3$)$_4$ were dissolved in 30 mL dioxane (degassed). The mixture was refluxed under argon overnight. The black solution was filtered through a Celite pad, and evaporated to dryness to give Compound 23 as yellow oil which was used without further purification. MS: 471.16 (M+H$^+$).

Step 6: 2-[4'-Chloro-4-(pyrrolidine-1-carbonyl)-biphen-2-yl]-quinoline-6-carboxylic acid (Compound 24)

Compound 23 from the previous step (0.63 mmol) was dissolved in 15 mL methanol, and 5 mL of 1M NaOH were added. The solution was refluxed for 2 hours, then evaporated. The residue was then dissolved in water, acidified with 5 mL of 1M HCl, and the precipitate was filtered off, washed three times with water and dried to yield 276 mg (96%) of Compound 24.

MS: 455.12 (M+H$^+$); H$^1$-NMR (DMSO-d$_6$): δ (ppm) 13.1 (br, 1H), 8.59 (d, 1H, J=1.8 Hz), 8.33 (d, 1H, J=8.4 Hz), 8.20-8.17 (dd, 1H, J=2.1 Hz, 9.0 Hz), 8.04 (d, 1H, J=8.7 Hz), 7.87 (d, 1H, J=1.8 Hz), 7.74-7.71 (dd, 1H, J=1.8 Hz, 8.1 Hz), 7.55-7.51 (d, 1H, J=8.4 Hz), 7.32-7.3 (m, 2H), 7.17-7.13 (m, 3H), 3.51-3.47 (m, 4H), 1.88-1.83 (m, 4H).

Step 7: 3-({2-[4'-Chloro-4-(pyrrolidine-1-carbonyl)-biphen-2-yl]-quinoline-6-carbonyl}-amino)-4-cyclohexylamino-benzoic acid ethyl ester (Compound 25)

Compound 24 (270 mg, 0.59 mmol) in 4 mL of DMF was activated with 246.6 mg (0.65 mmol) of HATU and 226 μL (1.30 mmol) of DIEA at room temperature for 15 minutes. Compound 11 (170 mg, 0.65 mmol) was added as solid and the mixture was stirred overnight. The DMF was evaporated; the remaining oil was solidified by trituration with water. The solid Compound 25 was filtered off, dried and used without further purification. MS: 701.34 (M+H$^+$).

Step 8: 2-{2-[4'-Chloro-4-(pyrrolidine-1-carbonyl)-biphen-2-yl]-quinolin-6-yl)-1-cyclohexyl-1H-benzoimidazole-5-carboxylic acid ethyl ester (Compound 27 Q=ethyl)

The compound from the previous step (0.59 mmol) was dissolved in 80 mL acetic acid and refluxed for 2.5 hours. The acetic acid was evaporated, the residue was dried to give Compound 204 in quantitative yield. MS: 683.33 (M+H$^+$).

Step 9: 2-{2-[4'-Chloro-4-(pyrrolidine-1-carbonyl)-biphen-2-yl]-quinolin-6-yl}-1-cyclohexyl-1H-benzoimidazole-5-carboxylic acid (Compound 204)

Compound 27 Q=ethyl (0.59 mmol), from the previous step, was dissolved in a mixture of 25 mL of ethanol and 5 mL of 1M NaOH and was refluxed for 2 hours. The reaction mixture was then evaporated to dryness. The residue was dissolved in 30 mL water, acidified with 1M HCl to pH 4. The precipitate that formed was filtered off, washed four times with water and dried. Yield 315 mg (73%). The title compound maybe further purified using RP-HPLC.

Conversion to HCl salt: The purified Compound 204 was dissolved in 4 mL methanol, 1 mL 4M HCl in dioxane was added followed by 40 mL ether. The off-white precipitate was separated by filtration and dried in high vacuum overnight. Yield: 28.3 mg solid.

MS: 655.26 (M+H$^+$); H$^1$-NMR (DMSO-d$_6$): δ (ppm) 8.41-8.38 (m, 2H), 8.32 (d, 1H, J=1.5 Hz), 8.27-8.19 (m, 2H), 8.10-8.06 (dd, 1H, J=1.8 Hz, 8.7 Hz), 8.02-7.98 (dd, 1H, J=1.5 Hz, 8.7 Hz), 7.92 (d, 1H, J=1.8 Hz), 7.77-7.74 (dd, 1H, J=2.1 Hz, 8.1 Hz), 7.58 (d, 1H, J=7.8 Hz), 7.36-7.33 (m, 2H), 7.25-7.19 (m, 3H), 4.43 (m, 1H), 3.51 (m, 4H), 3.33 (m, 2H), 2.08 (m, 2H), 1.87 (m, 6H), 1.61 (m, 1H), 1.32 (m, 3H).

Example 11

Preparation of 1-Cyclohexyl-2-(3-phenyl-quinoxalin-6-yl)-1H-benzoimidazole-5-carboxylic acid (Compound 205)

Step 1: 4-Cyclohexylamino-3-[(3-phenyl-quinoxaline-6-carbonyl)-amino]-benzoic acid ethyl ester (Compound 41)

The solution of 238 mg (0.95 mmol) Compound 37 in 5 mL DMF was activated by treatment with 398 mg (1.05 mmol) HATU and 365 μL (2.1 mmol) DIEA for 10 minutes at room temperature. Compound 11 (275 mg, 1.1 mmol) was added and the mixture was stirred at room temperature overnight.

The DMF was evaporated, the resulting oil was triturated with water, the solidified material filtered off, washed with water (3×) and dried to give Compound 41 as a 92% pure yellow solid which was used without further purification. MS: 495.26 (M+H$^+$);

Step 2: 1-Cyclohexyl-2-(3-phenyl-quinoxalin-6-yl)-1H-benzoimidazole-5-carboxylic acid ethyl ester (Compound 42)

Compound 41 (0.95 mmol) from the previous step was refluxed in 80 mL acetic acid for 3.5 h. The mixture was then evaporated to dryness and dried overnight under high vacuum to yield Compound 42 in quantitative yield. It was not further purified before saponification.

Step 3: 1-Cyclohexyl-2-(3-phenyl-quinoxalin-6-yl)-1H-benzoimidazole-5-carboxylic acid (Compound 205)

To the solution of Compound 42 (0.95 mmol) in 25 mL ethanol 5 mL, 1 M NaOH was added and the mixture was refluxed for 1 h. It was then cooled and evaporated to dryness. The residue was dissolved in 50 mL water, acidified with 1M HCl to pH 4. The precipitate was filtered off, washed with water (4×) and dried to give 345 mg (81%) of the title compound which maybe further purified by RP-HPLC.

MS: 448.19 (M–H$^+$); H$^1$-NMR (DMSO-): δ (ppm) 9.72 (s, 1H), 8.48 (d, 1H, J=1.8 Hz), 8.39-8.34 (m, 4H), 8.20-8.11 (m, 2H), 8.01-7.97 (dd, 1H, J=8.7 Hz and 1.5 Hz), 7.63-7.60 (m, 3H), 4.41 (m, 1H), 4.5-3.9 (br, 2H), 2.31 (m, 2H), 2.10 (m, 2H), 1.85 (m, 2H), 1.60 (m, 1H), 1.40-1.20 (m, 3H);

Example 12

Preparation of 2-[(2-{2-[4'-Chloro-4-(pyrrolidine-1-carbonyl)-biphen-2-yl]-quinolin-6-yl}-1-cyclohexyl-1H-benzoimidazole-5-carbonyl)-amino]-3-(5-hydroxy-1H-indol-3-yl)-propionic acid (Compound 235)

Compound 204 (100 mg, 0.15 mmol) in 2 mL DMF was activated with 64 mg (0.17 mmol) HBTU and 58 μL (0.33 mmol) DIEA at room temperature for 10 minutes. Then 40 mg (0.18 mmol) 5-hydroxytryptophane and 32 μL (0.25 mmol) DIEA, dissolved in 1 mL DMF, was added and the mixture was stirred for 1 h. The DMF was evaporated; the residue was purified with RP-HPLC.

Conversion to HCl salt: The purified Compound 235 was dissolved in 4 mL methanol, 1 mL 4M HCl in dioxane was added followed by 40 mL ether. The off-white precipitate was separated by filtration and dried in high vacuum overnight. Yield: 44.1 mg (32%).

MS: 856.23 (M+H$^+$); H$^1$-NMR (DMSO-d$_6$): δ (ppm) 10.51 (d, 1H, J=1.8 Hz), 8.89 (d, 1H, J=4.8 Hz), 8.41-8.38 (m, 2H), 8.33 (d, 1H, J=1.5 Hz), 8.28-8.19 (m, 2H), 8.10-8.07 (dd, 1H, J=1.5 Hz, 8.1 Hz), 7.96-7.91 (m, 2H), 7.78-7.74 (dd, 1H, J=1.8 Hz, 8.1 Hz), 7.58 (d, 1H, J=7.8 Hz), 7.37-7.34 (m, 2H), 7.26-7.19 (m, 3H), 7.10 (m, 2H), 6.89 (d, 1H, J=1.8 Hz), 6.58-6.55 (dd, 1H, J=2.1 Hz, 8.7 Hz), 4.65 (m. 1H), 4.43 (m, 1H), 3.51 (m,4H), 2.33 (m, 2H), 2.08 (m, 2H), 1.87 (m, 6H), 1.61 (m, 1H), 1.32 (m, 3H).

Example 13

Preparation of 2-{[1-Cyclohexyl-2-(3-phenyl-quinoxalin-6-yl)-1H-benzoimidazole-5-carbonyl]-amino}-3-(5-hydroxy-1H-indol-3-yl)-propionic acid (Compound 236)

Compound 205 (100 mg, 0.22 mmol) was activated in 2 mL of DMF with 92 mg (0.24 mmol) of HBTU and 85 μL of DIEA for 10 minutes at room temperature. 5-hydroxy-L-tryptophane (56 mg) dissolved in 1 mL DMF was added, followed by 44 μL of DIEA. The mixture was stirred at room temperature for 1 h, then was evaporated to dryness. The oil was purified using RP-HPLC column to give the pure Compound 236.

Conversion to HCl salt: The purified Compound 236 was dissolved in 4 mL methanol, 500 μL 4M HCl in dioxane was added followed by 40 mL ether. The dark gray precipitate was separated by filtration and dried in high vacuum overnight. Yield: 87 mg (55%) of grayish brown solid.

MS: 649.22 (M–H$^+$); H$^1$-NMR (DMSO-d$_6$): δ (ppm) 10.54 (d, 1H, J-2.1 HZ), 9.75 (s, 1H), 8.99 (d, 1H, J=7.5 Hz), 8.58 (d, 1H, J=1.8 Hz), 8.41-8.36 (m, 4H), 8.28-8.25 (d, 1H, J=9.0 Hz), 8.18-8.14 (dd, 1H, J=1.8 Hz, 8.7 Hz), 8.02-7.99 (dd, 1H, 1.8 Hz, 8.7 Hz), 7.65-7.60 (m, 3H), 7.12-7.08 (m, 2H), 6.90 (m, 1H), 6.59-6.55 (dd, 1H, J=2.4 Hz, 8.7 Hz), 4.67 (m, 1H), 4.44 (m, 1H), 3.22 (m, 2H), 2.30 (m, 2H), 2.12 (m, 2H), 1.85 (m, 2H), 1.58 (m, 1H), 1.36-1.25 (m, 3H);

Example 14

Preparation of 2-{[1-Cyclohexyl-2-(2-phenyl-quinolin-6-yl)-1H-benzoimidazole-5-carbonyl]-amino}-pentanedioic acid (Compound 237)

Compound 237 was synthesized from Compound 201 as described for Compound 235, using L-glutamic acid dimethylester in place of L-5-hydroxytryptophane. In the 3rd step the protected intermediate was treated with aqueous sodium hydroxide for a 15% yield of the title compound MS: 577.17 (M+H$^+$); H$^1$-NMR (DMSO d$_6$): δ (ppm) 8.72-8.64 (m, 2H), 8.38-8.25 (m, 6H), 8.06-8.02 (m, 2H), 7.89-7.86 (dd, 1H, J=1.5 Hz, 8.7 Hz), 7.60-7.53 (m, 3H) 4.48-4.38 (m, 2H), 2.42-2.28 (m, 4H), 2.16-1.96 (m, 4H), 1.88-1.83 (m, 2H), 1.62 (m, 1H), 1.4-1.22 (m, 3H).

Example 15

Preparation of 1-Cyclohexyl-2-(3-phenyl-quinolin-6-yl)-1H-benzoimidazole-5-carboxylic acid (Compound 206)

Step 1: 3-Phenyl-quinoline-6-carboxylic acid (Compound 206a)

The title intermediate was synthesized as described for Compound 13, using phenylacet-aldehyde instead of acetophenone. Yield: 68%.

MS: 248.09 (M–H$^+$); H$^1$-NMR (DMSO-d$_6$): δ (ppm) 9.20 (s, 1H), 8.79 (d, 2H), 8.20-8.00 (m, 2H), 7.95-7.00 (m, 5H).

Step 2: 4-Cyclohexylamino-3-[(3-phenyl-quinoline-6-carbonyl)-amino]-benzoic acid ethyl ester (Compound 206b)

The title intermediate was synthesized from the product of the previous step as described for Compound 25 with quantitative yield.

Step 3: 1-Cyclohexyl-2-(3-phenyl-quinolin-6-yl)-1H-benzoimidazole-5-carboxylic acid ethyl ester (Compound 206c)

The title intermediate was synthesized from the product of the previous step as described for compound 27 Q=ethyl with quantitative yield. MS: 476.26 (M+H$^+$).

Step 4: 1-Cyclohexyl-2-(3-phenyl-quinolin-6-yl)-1H-benzoimidazole-5-carboxylic acid The title compound was synthesized from the product of the previous step as described for Compound 204. Yield: 91%.

MS: 448.22 (M+H$^+$); H$^1$-NMR (DMSO-d$_6$): δ (ppm) 9.50 (d, 1H, J=2.4 Hz), 9.05 (d, 1H, J=1.8 Hz), 8.55 (d, 1H, J=1.5 Hz), 8.39-8.34 (m, 2H), 8.24-8.21 (d, 1H, J=8.7 Hz), 8.16-8.12 (dd, 1H, J=9.0 Hz, 1.5 Hz), 8.03-7.94 (m, 3H), 7.61-7.47 (m, 3H), 4.44 (m, 1H), 2.35-2.26 (m, 2H), 2.16-2.08 (m, 2H), 1.86-1.82 (m, 2H), 1.60 (m, 1H), 1.43-1.25 (m, 3H).

Example 16

Preparation of 2-{[1-Cyclohexyl-2-(3-phenyl-quinolin-6-yl)-1H-benzoimidazole-5-carbonyl]-amino}-3-(5-hydroxy-1H-indol-3-yl)-propionic acid (Compound 238)

The title compound was synthesized from Compound 206 as described for Compound 235 Yield: 19%.

MS: 650-31 (M+H$^+$); H$^1$-NMR (DMSO-d$_6$): δ (ppm) 10.52 (s, 1H), 9.49 (d, 1H, J=1.8 Hz), 9.01 (s, 1H), 8.95-8.92 (d, 1H, J=7.5 Hz), 8.56 (s, 1H), 8.39-8.33 (m, 2H), 8.25-8.22 (d, 1H, J=9.0 Hz), 8.15-8.12 (d, 1H, J=8.7 Hz), 7.99-7.94 (m, 3H), 7.61-7.47 (m, 3H), 7.11-7.03 (m, 2H), 6.89 (m, 1H), 6.58-6.55 (m, 1H), 4.70-4.62 (m, 1H), 4.44 (m, 2H), 3.21 (m, 1H), 2.34-2.31 (m, 2H), 2.10 (m, 2H), 1.86-1.82 (m, 2H), 1.59 (m, 1H), 1.45-1.30 (m, 3H).

Example 17

Preparation of 2-[(2-(2-phenyl-quinoxalin-6-yl)-1-cyclohexyl-1H-benzoimidazole-5-carbonyl)-amino]-propionic acid (Compound 310)

The general procedure described for Compound 242 was used with Fmoc-Ala Wang resin (167 mg, 0.6 mmol/g), producing 10.2 mg of the title compound. (10% yield). MS: 520.26 (M+H$^+$) HPLC Procedure A, retention time=12.52 min.

Example 18

Preparation of 3-{[1-Cyclohexyl-2-(2-phenyl-quinoxalin-6-yl)-1H-benzoimidazole-5-carbonyl]-amino}-propionic acid (Compound 239)

The general procedure described for Compound 242 was used with with Fmoc-β-Ala Wang resin (167 mg, 0.6 mmol/g), producing 21 mg of the title compound (39% yield).

MS: 520.26 (M+H$^+$) HPLC Procedure A, retention time=12.25 min.

Example 19

Preparation of 3-Biphenyl-4-yl-2-{[1-cyclohexyl-2-(2-phenyl-quinoxalin-6-yl)-1H-benzoimidazole-5-carbonyl]-amino}propionic acid (Compound 240)

The general procedure described for Compound 242 was used with Fmoc-Bip Wang resin (125 mg, 0.8 mmol/g), producing 33 mg of the title compound (51% yield).

MS: 672.33 (M+H$^+$) HPLC Procedure A, retention time=16.33 min.

Example 20

Preparation of 3-(4-Benzoyl-phenyl)-2-{[1-cyclohexyl-2-(2-phenyl-quinoxalin-6-yl)-1H-benzoimidazole-5-carbonyl]-amino}-propionic acid (Compound 241)

The general procedure described for Compound 242 was used with Fmoc-Bpa Wang resin (125 mg, 0.8 mmol/g), producing 37 mg of the title compound (50% yield).

MS: 700.32 (M+H$^+$) HPLC Procedure A, retention time=15.46 min.

Example 21

Preparation of 3-Cyclohexyl-2-{[1-cyclohexyl-2-(2-phenyl-quinoxalin-6-yl)-1H-benzoimidazole-5-carbonyl]-amino}-propionic acid (Compound 242)

Fmoc protected amino acids on Wang resins (0.1 mmol) were added to a reaction vessel. The resin was then stirred for 1 hour with a 20% solution of piperidine in DMF. The resins were rinsed 6 times with DMF. A solution of Compound 203 (0.5 mmol in 6 mL DMF), preactivated with HATU (0.496 mmol) and DIEA (1.0 mmol), was added to the resin and mixed for 16 hours. The resins were then washed with DMF (5 mL 3 times), dichloromethane (5 mL 3 times), and diethylether (5 mL 3 times). The desired compound was cleaved from the resin with 2% water in TFA and converted to the HCl salt by dissolving in 0.8 mL methanol and adding 1 mL 4M HCl in dioxane followed by 40 mL ether. The compound was centrifuged down, the solvent decanted off, and the solid dried to yield the final compound.

This general procedure was followed with Fmoc-Cys Wang resin (167 mg, 0.6 mmol/g), producing 25 mg of the title compound (46% yield). MS: 600.29 (M−H+) HPLC Procedure A, retention time=15.76 min.

Example 22

Preparation of Cyclohexyl-{[1-cyclohexyl-2-(2-phenyl-quinoxalin-6-yl)-1H-benzoimidazole-5-carbonyl]-amino}-acetic acid (Compound 243)

The general procedure described for Compound 242 was used with Fmoc-Cha Wang resin (250 mg, 0.4 mmol/g), producing 29 mg of the title compound (48% yield). MS: 586.27 (M−H$^+$) HPLC Procedure A, retention time=14.94 min.

Example 23

Preparation of 2-{[1-Cyclohexyl-2-(2-phenyl-quinoxalin-6-yl)-1H-benzoimidazole-5-carbonyl]-amino}-succinic acid (Compound 244)

The general procedure described for Compound 242 was used with Fmoc-Asp Wang resin (125 mg, 0.8 mmol/g), producing 28 mg of the title compound (50% yield). MS: 562.20 (M−H$^+$) HPLC Procedure A, retention time=12.08 min.

Example 24

Preparation of 2-{[1-Cyclohexyl-2-(2-phenyl-quinoxalin-6-yl)-1H-benzoimidazole-5-carbonyl]-amino}-pentanedioic acid (Compound 245)

The general procedure described for Compound 242 was used with Fmoc-Glu Wang resin (111 mg, 0.9 mmol/g), producing 25 mg of the title compound (44% yield). MS: 576.22 (M−H$^+$) HPLC Procedure A, retention time=12.14 min.

Example 25

Preparation of 2-{[1-Cyclohexyl-2-(2-phenyl-quinoxalin-6-yl)-1H-benzoimidazole-5-carbonyl]-amino}-3-phenyl-propionic acid (Compound 246)

The general procedure described for Compound 242 was used with Fmoc-Phe Wang resin (167 mg, 0.6 mmol/g), producing 26 mg of the title compound (44% yield). MS: 594.24 (M−H$^+$) HPLC Procedure A, retention time=14.58 min.

Example 26

Preparation of {[1-Cyclohexyl-2-(2-phenyl-quinoxalin-6-yl)-1H-benzoimidazole-5-carbonyl]-amino}-acetic acid (Compound 311)

The general procedure described for Compound 242 was used with Fmoc-Gly Wang resin (125 mg, 0.8 mmol/g), producing 30 mg of the title compound (55% yield). MS: 504.21 (M−H$^+$) HPLC Procedure A, retention time=12.32 min.

Example 27

Preparation of 2-{[1-Cyclohexyl-2-(2-phenyl-quinoxalin-6-yl)-1H-benzoimidazole-5-carbonyl]-amino}-3-(1H-imidazol-4-yl)-propionic acid (Compound 247)

The general procedure described for Compound 242 was used with Fmoc-His Wang resin (250 mg, 0.4 mmol/g), producing 30 mg of the title compound (51% yield). MS: 584.24 (M−H$^+$) HPLC Procedure A, retention time=11.16 min.

Example 28

Preparation of 1-[1-Cyclohexyl-2-(2-phenyl-quinoxalin-6-yl)-1H-benzoimidazole-5-carbonyl]-4-hydroxy-pyrrolidine-2-carboxylic acid (Compound 248)

The general procedure described for Compound 242 was used with Fmoc-Hyp Wang resin (143 mg, 0.7 mmol/g), producing 23 mg of the title compound (50% yield). MS: 560.23 (M−H$^+$) HPLC Procedure A, retention time=11.58 min.

Example 29

Preparation of 2-{[1-Cyclohexyl-2-(2-phenyl-quinoxalin-6-yl)-1H-benzoimidazole-5-carbonyl]-amino}-3-methyl-pentanoic acid (Compound 249)

The general procedure described for Compound 242 was used with Fmoc-Ile Wang resin (250 mg, 0.4 mmol/g), producing 23 mg of the title compound (54% yield). MS: 560.26 (M−H$^+$) HPLC Procedure A, retention time=14.34 min.

Example 30

Preparation of 2-{[1-Cyclohexyl-2-(2-phenyl-quinoxalin-6-yl)-1H-benzoimidazole-5-carbonyl]-amino}-4-methyl-pentanoic acid (Compound 513)

The general procedure described for Compound 242 was used with Fmoc-Leu Wang resin (111 mg, 0.9 mmol/g), producing 8.1 mg of the title compound (14% yield). MS: 560.25 (M−H$^+$) HPLC Procedure A, retention time=17.17 min.

Example 31

Preparation of 2-{[1-Cyclohexyl-2-(2-phenyl-quinoxalin-6-yl)-1H-benzoimidazole-5-carbonyl]-amino}-4-methylsulfanyl-butyric acid (Compound 515)

The general procedure described for Compound 242 was used with Fmoc-Met Wang resin (111 mg, 0.9 mmol/g), producing 21 mg of the title compound (36% yield). MS: 578.21 (M−H$^+$) HPLC Procedure A, retention time=15.08 min.

Example 32

Preparation of 2-{[1-Cyclohexyl-2-(2-phenyl-quinoxalin-6-yl)-1H-benzoimidazole-5-carbonyl]-amino}-succinamic acid (Compound 518)

The general procedure described for Compound 242 was used with Fmoc-Asn Wang resin (167 mg, 0.6 mmol/g), producing 22 mg of the title compound (36% yield). MS: 561.21 (M−H$^+$) HPLC Procedure A, retention time=15.04 min.

Example 33

Preparation of 4-Carbamoyl-2-{[1-cyclohexyl-2-(2-phenyl-quinoxalin-6-yl)-1H-benzoimidazole-5-carbonyl]-amino}-butyric acid (Compound 541)

The general procedure described for Compound 242 was used with Fmoc-Gln Wang resin (167 mg, 0.6 mmol/g), producing 27 mg of the title compound (47% yield). MS: 575.22 (M−H$^+$) HPLC Procedure A, retention time=15.02 min.

Example 34

Preparation of 2-{[1-Cyclohexyl-2-(2-phenyl-quinoxalin-6-yl)-1H-benzoimidazole-5-carbonyl]-amino}-5-guanidino-pentanoic acid (Compound 523)

The general procedure described for Compound 242 was used with Fmoc-Arg Wang resin (200 mg, 0.5 mmol/g), producing 53 mg of the title compound (87% yield). MS: 605.35 (M+H$^+$) HPLC Procedure A, retention time=14.84 min.

Example 35

Preparation of 2-{[1-Cyclohexyl-2-(2-phenyl-quinoxalin-6-yl)-1H-benzoimidazole-5-carbonyl]-amino}-3-hydroxy-butyric acid (Compound 512)

The general procedure described for Compound 242 was used with Fmoc-Thr Wang resin (200 mg, 0.5 mmol/g), producing 26 mg of the title compound (47% yield). MS: 548.22 (M−H$^+$) HPLC Procedure A, retention time=15.45 min.

Example 36

Preparation of 2-[1-Cyclohexyl-2-(2-phenyl-quinoxalin-6-yl)-1H-benzoimidazole-5-carbonyl]-1,2,3,4-tetrahydro-isoquinoline-3-carboxylic acid (Compound 520)

The general procedure described for Compound 242 was used with Fmoc-Tic Wang resin (143 mg, 0.7 mmol/g), producing 25 mg of the title compound (41% yield). MS: 606.22 (M−H$^+$) HPLC Procedure A, retention time=17.18 min.

Example 37

Preparation of 2-{[1-Cyclohexyl-2-(2-phenyl-quinoxalin-6-yl)-1H-benzoimidazole-5-carbonyl]-amino}-3-methyl-butyric acid (Compound 517)

The general procedure described for Compound 242 was used with Fmoc-Val Wang resin (250 mg, 0.4 mmol/g), producing 16 mg of the title compound (29% yield). MS: 546.23 (M–H$^+$) HPLC Procedure A, retention time=16.59 min.

Example 38

Preparation of 2-{[1-Cyclohexyl-2-(2-phenyl-quinoxalin-6-yl)-1H-benzoimidazole-5-carbonyl]-amino}-3-(4-hydroxy-phenyl)-propionic acid (Compound 519)

The general procedure described for Compound 242 was used with Fmoc-Tyr Wang resin (125 mg, 0.8 mmol/g), producing 22 mg of the title compound (36% yield). MS: 610.22 (M–H$^+$) HPLC Procedure A, retention time=16.14 min.

Example 39

Preparation of 2-[2-(4'-Chloro-biphen-2-yl)-quinolin-6-yl]-1-cyclohexyl-1H-benzoimidazole-5-carboxylic acid (Compound 387)

Compound 352 (150 mg, 0.28 mmol), 4-chlorophenyl boronic acid (134 mg, 0.86 mmol), potassium phosphate (452 mg, 2.14 mmol), lithium chloride (12.1 mg, 0,28 mmol) and tetrakis(triphenylphosphine) palladium(0) (34 mg, 0.028 mmol) were combined in 15 mL degassed dioxane and the mixture was refluxed under argon overnight. The dark mixture was filtered through a Celite pad, was evaporated and purified using RP-HPLC to give 31 mg (17%) of the title compound.

MS: 558.24 (M+H$^+$); H$^1$-NMR (DMSO-d$_6$): δ (ppm) 8.49-8.40 (m, 3H), 8.34-8.30 (m, 2H), 8.17-8.14 (dd, 1H, J=8.4 Hz &1.5 Hz), 8.10-8.07 (dd, 1H, J=8.4 Hz & 1.2 Hz), 7.87-7.84 (m, 1H), 7.68-7.56 (m, 3H), 7.39-7.36 (m, 2H), 7.30-7.27 (d, 1H, J=8.4 Hz), 7.24-7.21 (m, 2H), 4.50 (m, 1H), 2.35 (m, 2H), 2.15 (m, 2H), 1.90 (m, 2H), 1.65 (m, 1H), 1.49-1.26 (m, 3H).

Example 40

Preparation of 1-Cyclohexyl-2-[2-(2-pyrid-4-yl-phenyl)-quinolin-6-yl]-1H-benzoimidazole-5-carboxylic acid (Compound 369)

The title compound was synthesized as described for Compound 387 except pyridine-4-boronic acid was used instead of 4-chlorophenyl-boronic acid.

MS: 525.26 (M+H$^+$); H$^1$-NMR (DMSO-d$_6$): δ (ppm) 8.75 (m, 2H), 8.61-8.58 (d, 1H, J=8.4 Hz), 8.41 (d, 1H, 1.5 Hz), 8.32 (d, 1H, 1.5 Hz), 8.13-8.10 (d, 1H, J=8.4 Hz), 8.05-7.90 (m, 4H), 7.82-7.71 (m, 6H), 4.42 (m, 1H), 2.35 (m, 2H), 2.08 (m, 2H), 1.90 (m, 2H), 1.65 (m, 1H), 1.40-1.26 (m, 3H).

Example 41

Preparation of 1-Cyclohexyl-2-{2-[3-(pyrrolidine-1-carbonyl)-phenyl]-quinolin-6-yl}-1H-benzoimidazole-5-carboxylic acid (Compound 370)

Step 1:
1-[3-(Pyrrolidine-1-carbonyl)-phenyl]-ethanone (Compound 370a)

The title intermediate was synthesized as described for Compound 18 except 3-acetylbenzoic acid was used instead of 3-acetyl-4-hydroxy benzoic acid.

H$^1$-NMR (DMSO-d$_6$): δ (ppm) 8.06-8.02 (m, 2H), 7.80-7.77 (m, 1H), 7.63-7.58 (m, 1H), 3.51 (t, 2H, J=6.6 Hz), 3.40 (t, 2H, J=6.3 Hz), 2.65 (s, 3H), 1.94-1.83 (m, 4H).

Step 2: 1-Cyclohexyl-2-{2-[3-(pyrrolidine-1-carbonyl)-phenyl]-quinolin-6-yl}-1H-benzoimidazole-5-carboxylic acid (Compound 370)

The title compound was synthesized in four steps as described for Compound 13, Compound 25, Compound 27 Q=ethyl and Compound 204, respectively, except the product of the previous step was used in the first step, instead of acetophenone.

MS: 545.28 (M+H$^+$); H$^1$-NMR (DMSO-d$_6$): δ (ppm) 8.78-8.75 (d, 1H, J=8.4 Hz), 8.55 (d, 1H, J=1.5 Hz), 8.50 (s, 1H), 8.47-8.38 (m, 4H), 8.33-8.30 (d, 1H), J=9.0 Hz), 8.17-8.14 (dd, 1H, J=8.7 Hz & 1.5 Hz), 8.10-8.06 (dd, 1H, J=8.7 Hz & 1.8 Hz), 7.74-7.66 (m, 2H), 4.50 (m, 1H), 2.36 (m, 2H), 2.15 (m, 2H), 1.90 (m, 6H), 1.65 (m, 1H), 1.44-1.20 (m, 3H).

Example 42

Preparation of 2-[2-(2-Bromo-phenyl)-4-methyl-quinolin-6-yl]-1-cyclohexyl-1H-benzoimidazole-5-carboxylic acid (Compound 471)

Step 1: 4-{[1-(2-Bromo-phenyl)-meth-(E)-ylidene]-amino}-benzoic acid methyl ester (Compound 471a)

4-aminobenzoic acid methyl ester (1.51 g, 10 mmol) and 2-bromobenzaldehyde (1.45 mL, 12.5 mmol) were dissolved in 15 mL of methanol. The mixture was let stand overnight. A white precipitate formed and the crystals were filtered off, washed with cold methanol (2×) and dried.

MS: 318.03 & 320.03 (M+H$^+$); H$^1$-NMR (DMSO-d$_6$): δ (ppm) 8.81 (s, 1H), 8.22-8.19 (dd, 1H, J=7.8 &1.8 Hz), 8.09-8.05 (m, 2H), 7.63-7.60 (dd, 1H, J=7.8&1.2 Hz), 7.43-7.30 (m, 2H), 7.24-7.2 (m, 2H), 3.92 (s, 3H), 1.62 (s. 1H).

Step 2: 2-(2-Bromo-phenyl)-4-methyl-quinoline-6-carboxylic acid methyl ester (Compound 471b)

A suspension of 1.97 g (6.1 mmol) of the product of the previous step in 20 mL acetonitrile and a solution of 385 mg (0.61 mmol) of ytterbium-triflate in 20 mL acetonitrile were combined and stirred at room temperature for 10 minutes. Then 1.46 mL (15.3 mmol) of 2-methoxy-propene were added in one portion. The suspension immediately cleared. The mixture was stirred at room temperature overnight. The next day the reaction was quenched by the addition of 20 mL of 2.5 M HCl. The resulting mixture was evaporated and the product purified on a silica pad using hexane-ethyl acetate 10%-30% step gradient to yield 500 mg (23%) (See also, Y. Makioka, T. Shindo, Y. Taniguchi, K Takaki, Y. Fujiwara, *Synthesis*, 1995.) MS: 356.05 & 358.05 (M+H$^+$).

Step 3: 2-(2-Bromo-phenyl)-4-methyl-quinoline-6-carboxylic acid (Compound 471c)

Compound 471b (500 mg, 1.4 mmol) was refluxed in a mixture of 15 mL dioxane and 15 mL 1M aqueous NaOH for 1 h then it was evaporated to dryness, the residue dissolved in 50 mL water and acidified with 1M HCl solution to pH 4. The precipitate was filtered off, washed four times with water and dried. Yield: 361 mg (75%).

MS: 344.02 & 342.03 (M+H$^+$); H$^1$-NMR (DMSO-d$_6$): δ (ppm) 7.65-7.62 (dd, 1H, J=8.1 & 0.9 Hz), 7.60-7.51 (m, 4H), 7.46-41 (m, 1H), 7.27-7.25 (m, 2H), 1.98 (s, 3H).

Step 4: 2-[2-(2-Bromo-phenyl)-4-methyl-quinolin-6-yl]-1-cyclohexyl-1H-benzoimidazole-5-carboxylic acid (Compound 471)

The title compound was synthesized in a one-pot reaction sequence of three steps starting with the product of the previous step as described for Compound 25, Compound 27 Q=ethyl and Compound 204, respectively. Yield: 91%.

MS: 540.13 & 542.14 (M+H$^+$); H$^1$-NMR (DMSO-d$_6$): δ (ppm) 8.639 (s, 1H), 8.4-8.34 (m, 2H), 8.3-8.27 (d, 1H, J=8.7 Hz), 8.21-8.13 (d, 1H, J=8.7 Hz), 8.08-8.05 (d, 1H, J=9.0 Hz), 7.88-7.83 (m, 2H), 7.7-7.67 (dd, 1H, J=7.2 & 1.5 Hz), 7.64-7.59 (m, 1H), 7.54-7.48 (m, 1H), 4.57 (m, 1H), 2.89 (s, 1H), 2.39 (m, 2H), 2.15 (m, 2H), 1.90 (m, 2H), 1,67 (m, 1H), 1.44 (m, 3H).

Example 43

Preparation of 2-[2-(4'-Chloro-biphen-2-yl)-4-methyl-quinolin-6-yl]-1-cyclohexyl-1H-benzoimidazole-5-carboxylic acid (Compound 485) and 1-Cyclohexyl-2-(4-methyl-2-phenyl-quinolin-6-yl)-1H-benzoimidazole-5-carboxylic acid (Compound 498)

Compound 471 was treated as described for Compound 23. The reaction resulted in two products that were separated using preparative RP-HPLC.

Compound 485: MS: 572.21 (M+H$^+$); H$^1$-NMR (DMSO-d$_6$): δ (ppm) 8.38 (s, 1H), 8.3 (d, 1H, J=1.2 Hz), 8.17-8.05 (m, 3H), 7.96-7.92 (dd, 1H, J=9.0 & 1.5 Hz), 7.78-7.74 (m, 1H), 7.63-7.51 (m, 3H), 7.34-7.31 (m, 2H), 7.21-7.18 (m, 3H), 4.46 (m, 1H), 2.59 (s, 3H), 2.33 (m, 2H), 2.05 (m, 2H), 1.85 (m, 2H), 1.62 (m, 1H), 1.34 (3H).

Compound 498: MS: 462.22 (M+H$^+$); H$^1$-NMR (DMSO-d$_6$): δ (ppm) 8.49 (m, 1H), 8.35-8.30 (m, 4H), 8.23 (s, 1H), 8.19-8.16 (d, 1H, J=8.7 Hz), 8.13-8.09 (dd, 1H, J=8.7 & 1.8 Hz), 8.00-7.97 (dd, 1H, J=8.7 Hz), 7.63-7.55 (m, 3H), 4.48 (m, 1H), 2.86 (s, 1H), 2.34 (m, 2H), 2.10 (m, 2H), 1.86 (m, 2H), 1.62 (m, 1H), 1.35 (m, 3H).

Example 44

Preparation of 2-[2-(4'-Chloro-biphen-2-yl)-quinolin-6-yl]-1H-benzoimidazole-5-carboxylic acid (Compound 353)

Step 1: 2-(2-Bromo-phenyl)-quinoline-6-carboxylic acid (Compound 353a)

The title intermediate was synthesized as described for Compound 13, Y=phenyl except 2' bromoacetophenone was used instead of acetophenone.

MS: 326.00 & 328.00 (M+H$^+$); H$^1$-NMR (DMSO-d$_6$): δ (ppm) 8.72 (d, 1H, J=1.2 Hz), 8.65-8.62 (d, 1H, J=8.4 Hz), 8.25-8.21 (dd, 1H, J=9.0 Hz & 1.8 Hz), 8.11-8.09 (d, 1H, J=8.7 Hz), 7.83-7.77 (m, 2H), 7.64-7.61 (m, 1H), 7.56-7.51 (m, 1H), 7.46-7.40 (m, 1H).

Step 2: 2-(4'-Chloro-biphen-2-yl)-quinoline-6-carboxylic acid (Compound 353b)

The title intermediate was synthesized from the product of the previous step, compound 353a, as described for compound 387.

MS: 358.09 (M+H$^+$); H$^1$-NMR (DMSO-d$_6$): δ (ppm) 8.62 (d, 1H, J=1.2 Hz), 8.36-8.33 (d, 1H, J=8.4 Hz), 8.24-8.21 (dd, 1H, J=9.0 Hz & 1.8 Hz), 8.08-8.05 (d, 1H, J=9 Hz), 7.81-7.78 (dd, 1H, J=6.3 hz & 2.1 Hz), 7.14-7.12 (d, 1H, J=8.7 Hz), 7.64-7.52 (m, 3H), 7.34-7.31 (m, 2H), 7.18-7.15 (m, 2H).

Step 3: 2-[2-(4'-Chloro-biphen-2-yl)-quinolin-6-yl]-[H-benzoimidazole-5-carboxylic acid (Compound 353)

The title compound was synthesized from Compound 353b in two steps as described for Compound 25 and 27 Q=ethyl, respectively.

MS: 476.11 (M+H$^+$); H$^1$-NMR(DMSO-d$_6$): δ (ppm) 9.03 (m, 1H), 8.71-8.69 (dd, 1H, J=7 .Hz), 8.43-8.29 (m, 3H), 8.1-8.07 (dd, 1H, J=7.5 Hz), 7.93-7.84 (m, 2H), 7.68-7.57 (m, 3H), 7.38-7.2 (m, 5H).

Example 45

Preparation of 2-[2-(4'-Chloro-biphen-2-yl)-7-fluoro-quinolin-6-yl]-1-cyclohexyl-1H-benzoimidazole-5-carboxylic acid (Compound 408)

The title compound was synthesized using the procedures described in Examples 42 to 43 except in step 1 of Example 424-aminobenzoic acid methyl ester was replaced by 4-amino-2-fluorobenzoic acid methyl ester and in the second step methyl-vinyl ether was used.

MS: 576.19 (M+H$^+$); H$^1$-NMR (DMSO-d$_6$): δ (ppm) 8.42-8.40 (d, 1H, J=7.8 Hz), 8.34-8.31 (m, 2H), 8.13-8.3 (m, 2H), 7.97-7.94 (dd, 1H, J=8.4 & 1.5 Hz), 7.81-7.78 (m, 1H), 7.63-7.51 (m, 3H), 7.35-7.32 (m, 2H), 7.19-7.12 (m, 3H), 4.14 (m, 1H), 2.26 (m, 2H), 1.95 (m, 2H), 1.82 (m, 2H), 1.60 (m, 1H), 1.33 (m, 3H). F$^{19}$-NMR (DMSO-d$_6$): δ (ppm) −112.33 (t).

Example 46

Preparation of 2-(2-Biphen-2-yl-7-fluoro-quinolin-6-yl)-1-cyclohexyl-1H-benzoimidazole-5-carboxylic acid (Compound 388)

The title compound was collected as a side product of the synthesis of Compound 408.

MS: 541.22 (M+H$^+$); H$^1$-NMR (DMSO-d$_6$): δ (ppm) 8.39-8.36 (d, 1H, J=7.5 Hz), 8.30 (d, 1H, J=1.5 Hz), 8.26-8.23 (d, 1H, J=8.7 Hz), 8.10-8.04 (m, 2H), 7.96-7.78 (m, 1H), 7.65-7.51 (m, 3H), 7.30-7.26 (m, 3H), 7.18-7.15 (m, 2H), 7.08-7.05 (d, 1H, J=8.7 Hz), 4.14 (m, 1H), 2.26 (m, 2H), 1.95 (m, 2H), 1.82 (m, 2H), 1.60 (m, 1H), 1.32 (m, 3H). F$^{19}$-NMR (DMSO-d$_6$): δ (ppm) −112.51 (t).

Example 47

Preparation of 2-[2-(4'-Chloro-biphen-2-yl)-8-methyl-quinolin-6-yl]-1-cyclohexyl-1H-benzoimidazole-5-carboxylic acid (Compound 417)

The title compound was synthesized using the procedures described in Examples 42 to Example 43 except in step 1 of Example 42 4-aminobenzoic acid methyl ester was replaced by 4-amino-3-methylbenzoic acid methyl ester and in the second step methyl-vinyl ether was used.

MS: 572.21 (M+H$^+$); H$^1$-NMR (DMSO-d$_6$): δ (ppm) 8.43 (d, 1H, J=8.4 Hz), 8.30 (d, 1H, J=1.5 Hz), 8.20-8.17 (m, 2H), 7.99 (dd, 1H, J=8.7 and 1.2 Hz), 7.88-7.83 (m, 2H), 7.62-7.59 (m, 2H), 7.53-7.50 (m, 1H0, 7.46 (d, 1H, J=8.7 Hz), 7.33-7.30 (m, 2H), 7.17-7.14 (m, 2H), 4.46 (m, 1H), 2.51 (s, 3H), 2.35-1.28 (m 10H).

Example 48

Preparation of 2-(2-Biphen-2-yl-8-methyl-quinolin-6-yl)-1-cyclohexyl-1H-benzoimidazole-5-carboxylic acid (Compound 379)

The title compound was collected as a side product of the synthesis of Compound 417.

MS: 538.27 (M+H$^+$); H$^1$-NMR (DMSO-d$_6$): δ (ppm) 8.33-8.27 (m, 2H), 8.12-8.10 (m, 2H), 7.95 (dd, 1H, J=8.7 Hz), 7.86-7.83 (m, 2H), 7.60-7.50 (m, 3H), 7.34 (d, 1H, J=8.7 Hz), 7.26-7.13 (m, 5H), 4.44 (m, 1H), 2.62 (s, 3H), 2.35-1.23 (m 10H).

Example 49

Preparation of 1-Cyclohexyl-2-(8-methyl-2-phenyl-quinolin-6-yl)-1H-benzoimidazole-5-carboxylic acid (Compound 397)

The title compound was collected as a side product of the synthesis of Compound 417.

MS: 462.22 (M+H$^+$); H$^1$-NMR (DMSO-d$_6$): δ (ppm) 8.64 (d, 1H, J=8.7 Hz), 8.38-8.36 (m, 2H), 8.32-8.29 (m, 2H), 8.21 (m, 1H), 8.13 (d, 1H, J=8.1 Hz), 7.97-7.94 (m, 2H), 7.62-7.53 (m, 3H), 4.45 (m, 1H), 2.92 (s, 3H), 2.35-1.23 (m 10H);

Example 50

Preparation of {2-[2-(4'-Chloro-biphen-2-yl)-7-fluoro-quinolin-6-yl]-1-cyclohexyl-1H-benzoimidazol-5-yl}-(4-methyl-piperazin-1-yl)-methanone (Compound 521)

The title compound was synthesized from Compound 408 and N-methyl-piperazine using standard HBTU activation.

MS: 329.63 (M+2H$^+$)/2; H$^1$-NMR (DMSO-d$_6$): δ (ppm) 10.95 (s, 1H), 8.34-8.28 (m, 2H), 8.06-8.00 (m, 2H), 7.85 (d, 1H, J=1.8 Hz), 7.80-7.77 (m,1H), 7.62-7.50 (m, 3H), 7.43-7.39 (dd, 1H, J=8.1 Hz & 1.5 Hz), 7.35-7.32 (m, 2H), 7.20-7.10 (m, 3H), 4.09 (, 1H), 3.38 (m, 5H), 3.12 (m, 3H), 2.78 (d, 3H, J=4.2 Hz), 2.28 (m, 2H), 1.93-1.80 (m, 4H), 1,59 (m, 1H), 1.33 (m, 3H); F$^{19}$-NMR (DMSO-d$_6$): δ (ppm)-112.71 (t).

Example 51

Preparation of {2-[2-(4'-Chloro-biphen-2-yl)-7-fluoro-quinolin-6-yl]-1-cyclohexyl-1H-benzoimidazol-5-yl}-(4-hydroxy-piperidin-1-yl)-methanone (Compound 514)

The title compound was synthesized from Compound 408 and 4-hydroxypiperidine using standard HBTU activation.

MS: 659.31 (M+H$^+$); H$^1$-NMR (DMSO-d$_6$): δ (ppm) 8.44-8.36 (m, 2H), 8.11-8.08 (m, 2H), 7.89-7.86 (m, 1H), 7.80 (d, 1H, J-1.2 Hz), 7.70-7.67 (m, 2H), 7.62-7.59 (m, 1H), 7.43-7.41 (m, 3H), 7.24-7.18 (, 3H), 4.17 (m, 1H), 3.83 (m, 1H), 3.3 (m, 1H), 2.37 (, 2H), 2.37-1.41 (m, 15H); ); F$^{19}$-NMR (DMSO-d$_6$): δ (ppm)-112.67 (t).

Example 52

Preparation of [2-(2-Biphen-2-yl-7-fluoro-quinolin-6-yl)-1-cyclohexyl-1H-benzoimidazol-5-yl]-(4-methyl-piperazin-1-yl)-methanone (Compound 522)

The title compound was isolated as a side product of Compound 521 synthesis.

MS: 312.65 (M+2H$^+$)/2; H$^1$-NMR (DMSO-d$_6$): δ (ppm) 10.76 (s, 1H), 8.30 (d, 1H, J=7.8 Hz), 8.22 (d, 1H), J=8.7 Hz), 8.05-8.01 (m, 2H), 7.84 (d, 1H, J=1.2 Hz), 7.80-7.77 (m, 2H), 7.61-7.50 (m, 3H), 7.42-7.39 (dd, 1H), J=6.9 Hz & 1.2 Hz), 7.28-7.25 (m, 3H), 7.18-7.14 (m. 2H), 7.05 (d, 1H, J=8.7 Hz), 4.1 (m, 1H), 3.38 (m, 2H), 3.12 (m, 3H), 2.79 (d, 3H, J=4.2 Hz), 2.28-1.22 (m, 13H); F$^{19}$-NMR (DMSO-d$_6$): δ (ppm)-112.77 (t).

Example 53

Preparation of 2-(2-Biphen-2-yl-7-fluoro-quinolin-6-yl)-1-cyclohexyl-1H-benzoimidazol-5-yl]-(4-hydroxy-piperidin-1-yl)-methanone (Compound 410)

The title compound was isolated as a side product of Compound 514 synthesis.

MS: 625.34 (M+H$^+$); H$^1$-NMR (DMSO-d$_6$): δ (ppm) 8.32 (d, 1H0, J=8.4 Hz), 8.21 (d, 1H, J=8.4 Hz), 8.04-8.97 (m, 2H), 7.79 (m, 1H0, 7.71 (d, 1H, J=1.2 Hz), 7.63-7.50 (m, 3H), 7.32 (dd, 1H0, J=8.4 Hz & 1.5 Hz), 7.28-7.14 (m, 2H), 7.03 (d, 1H, J=8.7 Hz), 4.09 (m, 1H), 3.73 (m, 1H), 3.20 (m, 2H), 2.25-1.33 (m, 16H). F$^{19}$-NMR (DMSO-d$_6$): δ (ppm) –112.81 (t).

Example 54

Preparation of 2-[2-(5-Bromo-2-hydroxy-phenyl)-quinolin-6-yl]-1-cyclohexyl-1H-benzoimidazole-5-carboxylic acid (Compound 354)

Step 1: 3-Dimethoxymethyl-4-nitro-benzoic acid (Compound 354a)

To a solution of 5.49 g (21.5 mmol) of Compound 5 in 200 mL of methanol, 50 mL of 1M NaOH were added and the mixture was stirred at room temperature for 2 h. The reaction mixture was then evaporated to dryness, the residue was dissolved in 100 mL water, acidified with 1 M HCl to pH 3-4. The precipitate was then filtered off, washed with water (4×), and dried. Yield: 4.96 g (95%).

MS: 240.08 (M+H$^+$); H$^1$-NMR (DMSO-d$_6$): δ (ppm) 8.49 (d, 1H, J=1.8 Hz), 8.21-8.18 (dd, 1H, J=8.4 & 1.8 Hz), 7.85-7.82 (d, 1H, J=8.4 Hz), 5.90 (s, 1H), 3.41 (s, 6H).

Step 2: 4-Cyclohexylamino-3-(3-dimethoxymethyl-4-nitro-benzoylamino)-benzoic acid ethyl ester (Compound 354b)

The title intermediate was synthesized from the product of the previous step as described for Compound 25.

MS: 486.23 (M+H$^+$); H$^1$-NMR (DMSO-d$_6$): δ (ppm) 8.93 (s, 1H), 8.23-8.15 (m, 2H), 8.05-8.02 (d, 1H, J=8.1 Hz), 7.70-7.67 (m, 2H), 6.78-6.75 (d, 1H, J=8.4 Hz), 5.83 (s, 1H), 5.54-5.51 (d, 1H, J=7.5 Hz), 4.22 (q, 2H, J=7.2 Hz), 3.39-3.34 (m, 7H), 1.92 (m, 2H), 1.73-1.58 (m, 3H), 1.38-1.12 (m, 8H).

Step 3: 1-Cyclohexyl-2-(3-dimethoxymethyl-4-nitro-phenyl)-1H-benzoimidazole-5-carboxylic acid ethyl ester (Compound 354c)

To a solution of 1.53 g (3.15 mol) the product of the previous step in 75 mL acetic acid 1.5 g 4A molecular sieves was added and the mixture was refluxed for 2 h. TLC indicated a complete and clean reaction. The mixture was evaporated to dryness, dried under high vacuum and was used without further purification.

Step 4: 2-(4-Amino-3-dimethoxymethyl-phenyl)-1-cyclohexyl-1H-benzoimidazole-5-carboxylic acid ethyl ester (Compound 354d)

In 20 mL methanol 100 mg of 10% Pd-C was pre-hydrogenated in the presence of 1 g MgSO$_4$ at 30 psi for 15 minutes. Compound 354c (100 mg) dissolved in a solution of 20 mL of methanol containing 2 mL triethylamine, was added to the catalyst and the hydrogenation was continued for 30 minutes. The catalyst and the magnesium sulfate were filtered using Celite. The solution was evaporated to dryness and the oily residue was used immediately in the following step.

Step 5: 2-(4-Amino-3-formyl-phenyl)-1-cyclohexyl-1H-benzoimidazole-5-carboxylic acid ethyl ester (compound 354e)

The oily product of the previous step was dissolved in 25 mL ethanol-acetic acid-water 2:2:1 mixture and was let stand for 15 minutes at room temperature. It was evaporated to dryness to get the solid title intermediate, which was pure enough to use in the next step without further purification. MS: 392.25 (M+H$^+$).

Step 6: 2-[2-(5-Bromo-2-hydroxy-phenyl)-quinolin-6-yl]-1-cyclohexyl-1H-benzoimidazole-5-carboxylic acid (Compound 354)

The title compound was synthesized from the product of the previous step as described for Compound 19, followed by purification on RP-HPLC.

MS: 542.15 (M+H$^+$); H$^1$-NMR (DMSO-d$_6$): δ (ppm) 12.81 (s, 1H), 8.77-8.74 (d, 1H, J=8.7 Hz), 8.56-8.53 (d, 1H, J=9.0 Hz), 8.41 (m, 2H), 8.30-8.27 (m, 2H), 8.10-8.07 (dd, 1H, J=8.7 & 2.1 Hz), 8.03-8.00 (d, 1H, J=8.7 Hz), 7.90-7.87 (dd, 2H, J=8.7 & 1.5 Hz), 7.57-7.53 (dd, 1H, J=9.0 & 2.4 Hz), 7.02-6.99 (d, 1H, J=9.0 Hz), 4.39 (m, 1H), 2.33 (m, 2H), 2.02 (m, 2H), 1.85 (m, 2H), 1.61 (m, 1H), 1.32 (m, 3H).

Example 55

Preparation of 2-[2-(4'-Chloro-4-methoxy-biphen-2-yl)-quinolin-6-yl]-1-cyclohexyl-1H-benzoimidazole-5-carboxylic acid (Compound 356)

The title compound was synthesized in seven steps as described for Compound 204 except 2-hydroxy-5-methoxy acetophenone was used instead of Compound 18.

MS: 588.23 (M+H$^+$); H$^1$-NMR (DMSO-d$_6$): δ (ppm) 8.38-8.35 (m, 2H), 8.30 (d, 1H, J=1.5 Hz), 8.23 (d, 1H, J=8, 7 Hz), 8.15 (d, 1H, J=8.7 Hz), 8.05 (dd, 1H, J=8.7 Hz & 1.5 Hz), 7.97 (dd, 1H, J=9 Hz & 1.5 Hz), 7.45 (d, 1H, J=8.4 Hz), 7.31-7.27 (m, 3H), 7.21-7.17 (m, 2H), 7.13-7.10 (m, 2H), 4.41 (m, 1H), 3.87 (s, 3H), 2.34-1.28 (m, 10H);

Example 56

Preparation of 1-Cyclohexyl-2-[2-(4-methoxy-biphen-2-yl)-quinolin-6-yl]-1H-benzoimidazole-5-carboxylic acid (Compound 499)

The title compound was isolated as side product of the synthesis of Compound 356.

MS: 554.26 (M+H$^+$); H$^1$-NMR (DMSO-d$_6$): δ (ppm) 8.34-8.24 (m, 4H), 8.13 (d, 1H, J=8.4 Hz), 8.05 (dd, 1H, J=9 Hz), 7.95 (dd, 1H, J=8.4 Hz & 1.2 Hz), 7.46 (d, 1H, J=8.4 Hz), 7.33 (d, 1H, J=2.4 Hz), 7.24-7.10 (m, 7H), 4.42 (m, 1H), 3.88 (s, 3H), 2.34-1.28 (m, 10H).

Example 57

Preparation of 1-Cyclohexyl-2-[2-(3-methoxy-phenyl)-quinolin-6-yl]-1H-benzoimidazole-5-carboxylic acid (Compound 486)

The title compound was isolated as side product of the synthesis of Compound 356.

MS: 478.22 (M+H$^+$); H$^1$-NMR (DMSO-d$_6$): δ (ppm) 8.68 (d, 1H, J=8.7 Hz), 8.43 (d, 1H, J=1.8 Hz), 8.33-8.29 (m, 3H), 8.15 (d, 1H, J=9 Hz), 8.06 (dd, 1H, J=8.7 Hz &1.5 Hz), 7.97 (dd, 1H, J=8.7 Hz & 1.5 Hz), 7.91-7.87 (m, 2H), 7.53-7.48 (m, 1H), 7.12 (dd, 1H, J=8.4 Hz, 2.4 Hz), 4.43 (m, 1H), 3.89 (s, 3H), 2.35-1.28 (m, 10H).

Example 58

Preparation of 2-[2-(4'-Chloro-4-hydroxy-biphen-2-yl)-quinolin-6-yl]-1-cyclohexyl-1H-benzoimidazole-5-carboxylic acid (Compound 500) and 1-Cyclohexyl-2-[2-(3-hydroxy-phenyl)-quinolin-6-yl]-1H-benzoimidazole-5-carboxylic acid (Compound 474) and 1-Cyclohexyl-2-[2-(4-hydroxy-biphen-2-yl)-quinolin-6-yl]-1H-benzoimidazole-5-carboxylic acid (Compound 487)

To a cold solution of 2.3 g (3.7 mmol) of Compound 500a in 90 mL DCM, 37.2 mL (37.2 mmol) of a solution of 1M PBr$_3$ in DCM was added. The mixture was stirred overnight then was quenched by addition of 110 mL of methanol. The reaction mixture was evaporated to dryness and triturated with water to give the title compound which was purified by RP-HPLC. After trituration, Compound 500 was sufficient to use in subsequent reactions without further purification. Two side-products (Compound 487) and (Compound 474) were also separated and identified from the reaction mixture.

(Compound 500): MS: 574.21 (M+H$^+$); H$^1$-NMR (DMSO-d$_6$): δ (ppm) 8.38-8.31 (m, 3H), 8.25 (d, 1H, J=8.7 Hz), 8.18 (d, 1H, J=8.7 Hz), 8.08 (dd, 1H, J=8.7 & 2.1 Hz), 7.99 (dd, 1H, J=8.4 & 1.5 Hz), 7.35 (d, 1H, J=8.7 Hz), 7.28 (m, 2H), 7.21 (d, 1H, J=2.7 Hz), 7.16 (d, 1H, J=8.7 Hz), 7.10 (m. 2H), 7.01 (dd, 1H, J=8.4 & 2.1 Hz), 4.44 (m, 1H), 2.35-1.03 (m, 10H);

(Compound 474): MS: 464.21 (M+H$^+$); H$^1$-NMR (DMSO-d$_6$): δ (ppm) 8.68 (d, 1H, J=8.7 Hz), 8.47 (d, 1H, J=1.8 Hz), 8.34-8.22 (m, 4H), 8.10 (dd, 1H, J=8.7 & 1.8 Hz), 8.03 (dd, 1H, J=8.7 & 1.5 Hz), 7.76-7.70 (m, 2H), 7.41-7.35 (m, 1H), 6.97-6.94 (m, 1H), 4.44 (m, 1H), 2.35-1.23 (m, 10H);

(Compound 487): MS: 540.25 (M+H$^+$); H$^1$-NMR (DMSO-d$_6$): , (ppm) 8.34-8.24 (m, 4H), 8.15 (d, 1H), 8.05 (dd, 1H), 7.98 (dd, 1H), 7.34 (d, 1H, J=8.7 Hz), 7.21 (m, 4H), 7.11-7.08 (m, 3H), 7.01 (dd, 1H, J=8.1 & 2.7 Hz), 5.43 (m, 1H), 2.35-1.33 (m, 10H);

Example 59

Preparation of 2-{2-[4'-Chloro-4-(2-methoxy-ethoxy)-biphen-2-yl]-quinolin-6-yl}-1-cyclohexyl-1H-benzoimidazole-5-carboxylic acid (Compound 475)

Step 1: 2-[2-(4'-Chloro-4-hydroxy-biphen-2-yl)-quinolin-6-yl]-1-cyclohexyl-1H-benzoimidazole-5-carboxylic acid methyl ester (Compound 475a)

To a solution of 2.15 g (3.745 mmol) of Compound 500 in 100 mL methanol, 25 mL of 4M HCl in dioxane were added and the mixture was heated at 55 C° for 3 hours. The reaction mixture was then evaporated to dryness and the residual oil triturated with water and dried to yield 1.97 g (89%) of the title intermediate, which was used without further purification.

Step 2: 2-{2-[4'-Chloro-4-(2-methoxy-ethoxy)-biphen-2-yl]-quinolin-6-yl}-1-cyclohexyl-1H-benzoimidazole-5-carboxylic acid (Compound 475)

Compound 475a (100 mg, 0.162 mmol) was dissolved in 2 mL of DMF and treated with 16.8 mg (0.7 mmol) of NaH for 30 min. 1-bromo-2-methoxy ethane (30.5 μL) was added and the mixture was agitated overnight. The next day the reaction mixture was evaporated to dryness, the oily residue dissolved in 3 mL methanol followed by the addition of 1 mL 1M NaOH. The mixture was refluxed for 2 h before it was evaporated to dryness. The product was purified by RP-HPLC for a yield of 19.3 mg of the title compound.

MS: 632.24 (M+H$^+$); H$^1$-NMR (DMSO-d$_6$): δ (ppm) 8.40-8.34 (m, 2H), 8.32 (d, 1H, J=1.2 Hz), 8.23 (d, 1H, J=8.7 Hz), 8.15 (d, 1H, J=9.0 Hz), 8.07 (dd, 1H, J=9.0 and 1.8 Hz), 7.48 (dd, 1H, J=8.4 and 1.2 Hz), 7.45 (d, 1H, J=8.4 Hz), 7.33-7.29 (m, 3H), 7.23-7.14 (m, 2H), 7.14-7.11 (m, 2H), 4.43 (m, 1H), 4.24 (m, 3H), 3.71 (m, 2H), 3.37 (m, 3H), 2.35-1.30 (m. 10H);

Example 60

Preparation of 1-Cyclohexyl-2-{2-[4-(2-methoxy-ethoxy)-biphen-2-yl]-quinolin-6-yl}-1H-benzoimidazole-5-carboxylic acid (Compound 461)

The title compound was isolated as a side product of the synthesis of Compound 475.

MS: 598.29 (M+H$^+$); H$^1$-NMR (DMSO-d$_6$): δ (ppm) 8.33-8.28 (m, 3H), 8.23 (d, 1H, J=9.0 Hz), 8.13-8.03 (m, 2H), 7.95 (dd, 1H, J=8.7 Hz, 1.2 Hz), 7.45 (d, 1H, J=8.4 Hz), 7.34 (d, 1H, J=2.7 Hz), 7.24-7.18 (m, 4H), 7.14-7.10 (m, 3H), 4.41 (m, 1H), 4.22 (m, 2H), 3.5-3.3 (m, 5H offset by water), 2.34-1.23 (m, 10H);

Example 61

Preparation of 1-Cyclohexyl-2-{2-[3-(2-methoxy-ethoxy)-phenyl]-quinolin-6-yl}-1H-benzoimidazole-5-carboxylic acid (Compound 445)

The title compound was isolated as a side product of the synthesis of Compound 475.

MS: 522.24 (M+H$^+$); H$^1$-NMR (DMSO-d$_6$): δ (ppm) 8.69 (d, 1H, J=8.7 Hz), 8.44 (d, 1H, J=1.8 Hz), 8.35-8.29 (m, 3H), 8.17 (d, 1H, J=8.7 Hz), 8.08 (dd, 1H, J=8.7 and 1.8 Hz), 8.98 (dd, 1H, J=9.0 and 1.8 Hz), 7.92-7.89 (m, 2H), 7.52-7.47 (m, 1H), 7.15-7.12 (m, 1H), 4.43 (m, 1H), 4,24 (m, 2H), 3.73 (m, 2H), 3.41-3.34 (m, 3H), 2.36-1.2 (m, 10H);

Example 62

Preparation of 2-{2-[4'-Chloro-4-(2-ethoxy-ethoxy)-biphen-2-yl]-quinolin-6-yl}-1-cyclohexyl-1H-benzoimidazole-5-carboxylic acid (Compound 507)

The title compound was synthesized as described for Compound 475, except 1-bromo-2-ethoxy ethane was used for alkylation instead of 1-bromo-2-methoxy ethane.

MS: 646.29 (M+H$^+$); H$^1$-NMR (DMSO-d$_6$): δ (ppm) 8.34-8.22 (m, 3H), 8.18 (d, 1H, J=9.0 Hz), 8.08 (d, 1H, J=8.4 Hz), 8.01 (dd, 1H, J=8.4 and 1.5 Hz), 7.91 (dd, 1H, 8.4 and 1.2 Hz), 7.40 (m, 1H), 7.29-7.07 (m, 7H), 4.37 (m, 1H), 4,18 (m, 2H), 3.70 (m, 2H), 3.50 (q, 2H, J=1.2 Hz), 2.30-1.24 (m, 10H), 1.10 (t, 3H, J=1.2 Hz);

Example 63

Preparation of 2-[2-(4-Carboxymethoxy-4'-chloro-biphen-2-yl)-quinolin-6-yl]-1-cyclohexyl-1H-benzoimidazole-5-carboxylic acid (Compound 393)

The title compound was synthesized as described for Compound 475, except tert-butyl bromoacetate was used for alkylation instead of 1-bromo-2-methoxy ethane. The tert-butyl group was removed in a separate step before saponification by a 1 h treatment with TFA.

MS: 630.16 (M–H$^+$); H$^1$-NMR (DMSO-d$_6$): δ (ppm) 8.41-8.38 (m, 2H), 8.32 (d, 1H, J=1.5 Hz), 8.25-8.18 (m, 2H), 8.09 (dd, 1H, J=8.4 and 1.8 Hz), 8.00 (dd, 1H, J=8.7 and 1.5 hz), 7.47 (d, 1H, J=8.4 Hz), 7.32-7.29 (m, 3H), 7.23-7.11 (m, 4H), 4.83 (s, 2H), 4.44 (m, 1H), 2.35-1.3 (m, 10H);

Example 64

Preparation of 2-[2-(4-Carboxymethoxy-biphen-2-yl)-quinolin-6-yl]-1-cyclohexyl-1H-benzoimidazole-5-carboxylic acid (Compound 375)

The title compound was isolated as a side product of the synthesis of Compound 393.

MS: 596.20 (M–H$^+$); H$^1$-NMR (DMSO-d$_6$): δ (ppm) 8.35-8.29 (m, 3H), 8.25 (d, 1H, J=8.7 Hz), 8.15 (dd, 1H, J=9.0 Hz), 8.07 (dd, 1H, J=9.0 Hz), 7.97 (dd, 1H, 7.2 and 1.8 Hz), 7.46 (d, 1H, J=8.4 Hz), 7.31 (d, 1H, J=2.7 Hz), 7.25-7.11 (m, 8H), 4.82 (s, 2H), 4.42 (m, 1H), 2.43-1.30 (m, 10H);

Example 65

Preparation of 2-[2-(3-Carboxymethoxy-phenyl)-quinolin-6-yl]-1-cyclohexyl-1H-benzoimidazole-5-carboxylic acid (Compound 359)

The title compound was isolated as a side product of the synthesis of Compound 393.

MS: 520.17 (M–H$^+$); H$^1$-NMR (DMSO-d$_6$): δ (ppm) 8.70 (d, 1H, J=8.7 Hz), 8.45 (d, 1H), 8.32 (m, 3H), 8.19 (d, 1H, J=9.0 Hz), 8.09 (dd, 1H), 8.00-7.87 (m, 3H), 7.50 (m, 1H), 7.11 (m, 1H), 4.83 (s, 2H), 4.44 (m, 1H), 2.35-1.30 (m, 10H);

Example 66

Preparation of 2-{2-[4'-Chloro-4-(3-pyrrolidin-1-yl-propoxy)-biphen-2-yl]-quinolin-6-yl}-1-cyclohexyl-1H-benzoimidazole-5-carboxylic acid (Compound 447)

The title compound was synthesized as described for Compound 475, except 1,3-dibromopropane was used for alkylation instead of 1-bromo-2-methoxy ethane. The resulting 3-bromopropyl derivative was treated in situ with an excess of pyrrolidine to give the final product.

MS: 685.34 (M+H$^+$); H$^1$-NMR (DMSO-d$_6$): δ (ppm) 10.74 (m, 1H), 8.39-8.36 (m, 2H), 8.32 (d, 1H, J=1.5 Hz), 8.25 (d, 1H, J=8.7 Hz), 8.18 (d, 1H, J=8.7 Hz), 8.07 (dd, 1H, J=8.4 and 1.8 Hz), 8.98 (dd, 1H, J=9.0 and 1.6 Hz), 7.47 (d, 1H, J=8.7 Hz), 7.35-7.29 (m, 3H), 7.23-7.18 (m 2H), 7.14-7.11 (m, 2H), 4.42 (m, 1H), 4.21 (m, 2H), 3.56 (m, 2H), 3.33 (m, 2H), 3.02 (m, 2H), 2.35-1.28 (m, 16H);

Example 67

Preparation of 1-Cyclohexyl-2-{2-[4-(3-pyrrolidin-1-yl-propoxy)-biphen-2-yl]-quinolin-6-yl}-1H-benzoimidazole-5-carboxylic acid (Compound 430)

The title compound was isolated as a side product of the synthesis of Compound 447.

MS: 651.36 (M+H$^+$); H$^1$-NMR (DMSO-d$_6$): δ (ppm) 10.70 (m, 1H), 8.34-8.23 (m, 4H), 8.13 (d, 1H, J=8.4 Hz), 8.06 (dd, 1H, J=8.7 and 1.8 Hz), 7.96 (dd, 1H, J=8.7 and 1.5 Hz), 7.47 (d, 1H, J=8.7 Hz), 7.35 (d, 1H, J=2.7 Hz), 7.26-7.18 (m, 4H), 7.14-7.09 (m, 3H), 4.41 (m, 1H), 4.21 (m, 2H), 3.58 (m, 2H), 3.34 (m, 2H), 3.02 (m, 2H), 2.35-1.23 (m, 16H);

Example 68

Preparation of 1-Cyclohexyl-2-{2-[3-(3-pyrrolidin-1-yl-propoxy)-phenyl]-quinolin-6-yl}-1H-benzoimidazole-5-carboxylic acid (Compound 414)

The title compound was isolated as a side product of the synthesis of Compound 447.

MS: 575.32 (M+H$^+$); H$^1$-NMR (DMSO-d$_6$): δ (ppm) 10.70 (m, 1H), 8.68 (d, 1H, J=8.7 Hz), 8.42 (d, 1H), 8.30 (m, 3H), 8.14 (d, 1H, J=8.4 Hz), 8.07 (dd, 1H, J=8.4 Hz), 7.97-7.90 (m, 3H), 7.71 (m, 1H), 7.13 (m, 1H), 4.41 (m, 1H), 4.22 (m, 2H), 3.59 (m, 2H), 3.36 (m, 2H), 3.042 (m, 2H), 2.43-1.23 (m, 16H);

Example 69

Preparation of 2-{2-[4'-Chloro-4-(2-oxo-2-pyrrolidin-1-yl-ethoxy)-biphen-2-yl]-quinolin-6-yl}-1-cyclohexyl-1H-benzoimidazole-5-carboxylic acid (Compound 376)

The title compound was synthesized as described for Compound 475, except 2-bromo-1-pyrrolidin-1-yl-ethanone was used for alkylation instead of 1-bromo-2-methoxy ethane.

MS: 685.34 (M+H$^+$); H$^1$-NMR (DMSO-d$_6$): δ (ppm) 8.37-8.34 (m, 3H), 8.20 (d, 1H, J=8.4 Hz), 8.12-8.03 (m, 2H), 7.94 (dd, 1H, J=8.7 and 1.2 Hz), 7.43 (d, 1H, J=8.7 Hz), 7.31-7.28 (m, 3H), 7.20-7.11 (m, 4H), 4.87 (s, 2H), 4.41 (m, 1H), 3.49 (m, 2H), 3.33 (m, 2H), 2.35-1.23 (m, 14H);

Example 70

Preparation of 1-cyclohexyl-2-{2-[4-(2-oxo-2-pyrrolidin-1-yl-ethoxy)-biphen-2-yl]-quinolin-6-yl}-1H-benzoimidazole-5-carboxylic acid (Compound 360)

The title compound was isolated as a side product of the synthesis of Compound 376.

MS: 651.34 (M+H$^+$); H1-NMR (DMSO-d$_6$): δ (ppm) 8.30-8.25 (m, 3H), 8.20 (d, 1H, J=8.4 Hz), 8.05 (m, 2H), 7.192 (dd, 1H, J=8.4 and 1.5 Hz), 7.43 (d, 1H, J=8.4 Hz), 7.30 (d,1H, J=2.7 Hz), 7.24-7.08 (m, 8H), 4.87 (s, 2H), 4.40 (m, 1H), 3.49 (m, 2H), 3.34 (m, 2H), 2.34-1.23 (m, 14H);

Example 71

Preparation of 1-cyclohexyl-2-{2-[3-(2-oxo-2-pyrrolidin-1-yl-ethoxy)-phenyl]-quinolin-6-yl}-1H-benzoimidazole-5-carboxylic acid (Compound 503)

The title compound was isolated as a side product of the synthesis of Compound 376.

MS: 575.29 (M+H$^+$); H$^1$-NMR (DMSO-d$_6$): δ (ppm) 8.66 (d, 1H, J=8.7 hz), 8.41 (d, 1H, J=1.8 Hz), 8.30-8.26 (m, 3H), 8.12-8.04 (m, 2H), 7.96-7.87 (m, 3H), 7.49 (m, 1H), 7.10 (dd, 1H, J=7.8 and 2.1 Hz), 4.87 (s, 2H), 4.42 (m, 1H), 3.41 (m, 2H), 3.35 (m, 2H), 2.35-1.23 (m, 14H);

Example 72

Preparation of 2-[2-(4-Carboxy-4'-chloro-biphen-2-yl)-quinolin-6-yl]-1-cyclohexyl-1H-benzoimidazole-5-carboxylic acid (Compound 415)

Step 1: 2-[2-(4'-Chloro-4-trifluoromethanesulfonyloxy-biphen-2-yl)-quinolin-6-yl]-1-cyclohexyl-1H-benzoimidazole-5-carboxylic acid methyl ester (Compound 415a)

To a solution of 1 g (1.7 mmol) of Compound 475a in 20 mL of DCM, 550 μL (6.8 mmol) of pyridine, and 21 mg (0.17 mmol) of DMAP were added and the entire mixture was cooled to 0° C. Dropwise, 860 μL of Tf$_2$O was added. The reaction was then stirred at room temperature for 1 h. Finally the reaction mixture was evaporated, and the product dissolved in ethyl acetate, washed with cold water (2×), brine (2×), dried with Na$_2$SO$_4$ and evaporated again to give the title intermediate as a white solid foam in quantitative yield.

Step 2: 2-[2-(4-Carboxy-4'-chloro-biphen-2-yl)-quinolin-6-yl]-1-cyclohexyl-1H-benzoimidazole-5-carboxylic acid methyl ester (Compound 415b)

A mixture of 1.334 g (1.85 mmol) of the product from the previous step, 350 μL of acetic anhydride, 288 mg (5.55 mmol) of LiO(O)CH, 235 mg (5.55 mmol) of LiCl, 644 μL (3.7 mmol) of DIEA and 54 mg (92.5 μmol) of Pd Cl$_2$(dppp) in DMF was heated under Ar at 80° C. overnight. The solvent was evaporated and the residue triturated with water to give 1 g of the crude title intermediate, which was not isolated and was used as is in the following steps.

Step 3: 2-[2-(4-Carboxy-4'-chloro-biphen-2-yl)-quinolin-6-yl]-1-cyclohexyl-1H-benzoimidazole-5-carboxylic acid (Compound 415)

The crude product from the previous step (250 mg) was saponified with 5 eq. of aq. 1M NaOH in methanol for 1 h at 55° C. The reaction mixture was evaporated and the product purified with RP-HPLC to give the title compound as a yellow solid.

MS: 600.14 (M−H$^+$); H$^1$-NMR (DMSO-d$_6$): δ (ppm) 8.41-8.38 (m, 2H), 8.34-8.28 (m, 3H), 8.23 (d, 1H, J=8.4 Hz), 8.14 (dd, 1H, J=8.1 and 1.8 Hz), 8.09 (dd, 1H, J=8.4 and 1.8 Hz), 8.00 (dd, 1H, J=7.2 Hz), 7.67 (d, 1H, J=7.8 Hz), 7.37 (m, 2H), 7.26-7.20 (m, 3H), 4.43 (m 1H), 2.31-1.32 (m, 10H).

Example 73

Preparation of 2-{2-[4'-Chloro-4-(2-dimethylamino-ethylcarbamoyl)-biphen-2-yl]-quinolin-6-yl}-1-cyclohexyl-1H-benzoimidazole-5-carboxylic acid (Compound 491)

Crude Compound 415b (250 mg, 0.4 mmol) in 2 mL DMF was pre-activated with 193 mg (0.5 mmol) of HATU and 174 μL (1 mmol) of DIEA for 15 min at room temperature. N$^1$,N$^1$-dimethyl-ethane-1,2-diamine (100 μL, 0.9 mmol) was added and stirred overnight. The next day the reaction mixture was evaporated to dryness and triturated with water. The wet solid was dissolved in 5 mL methanol and was saponified as described for Compound 415 to give, after RP-HPLC purification, 8.5 mg of the title compound.

MS: 672.28 (M+H$^+$); H$^1$-NMR (DMSO-d$_6$): δ (ppm) 10.10 (m, 1H), 9.04 (m, 1H), 8.40-8.36 (m, 2H), 8.31-8.29 (m, 2H), 8.23 (d, 1H, J=8.7 Hz), 8.16-8.04 (m, 3H), 7.94 (dd, 1H, J=8.7 and 1.2 Hz), 7.65 (d, 1H, J=7.8 Hz), 7.36 (m, 2H), 7.22 (m, 3H), 4.41 (m, 1H), 3.69 (m, 2H), 3.31 (m, 2H), 2.84 (s, 6H), 2.36-1.23 (m, 10H).

Example 74

Preparation of 1-Cyclohexyl-2-{2-[4-(2-dimethylamino-ethylcarbamoyl)-biphen-2-yl]-quinolin-6-yl}-1H-benzoimidazole-5-carboxylic acid (Compound 504)

The title compound was isolated as a side product of the synthesis of Compound 491.

MS: 638.31 (M+H$^+$); H$^1$-NMR (DMSO-d$_6$): δ (ppm) 9.99 (m, 1H), 9.00 (m, 1H), 8.33-8.28 (m, 4H), 8.25 (d, 1H, J=8.7 Hz), 8.14-8.04 (m, 3H), 7.94 (dd, 1H, J=9.0 Hz), 7.66 (d, 1H, J=8.1 Hz), 7.30-7.27 (m, 3H), 7.21-1.13 (m, 3H), 4.41 (m, 1H), 3.68 (m, 2H), 3.31 (m, 2H), 2.83 (s, 6H), 2.35-1.23 (m, 10H).

Example 75

Preparation of 2-{2-[4-(Carbamoylmethyl-carbamoyl)-4'-chloro-biphen-2-yl]-quinolin-6-yl}-1-cyclohexyl-1H-benzoimidazole-5-carboxylic acid (Compound 361)

The title compound was synthesized as described for Compound 491, except glycine-amide was used instead of N$^1$,N$^1$-dimethyl-ethane-1,2-diamine.

MS: 658.24 (M+H$^+$); H$^1$-NMR (DMSO-d$_6$): δ (ppm) 8.92 (m, 1H), 8.41-8.23 (m, 5H), 8.14-8.04 (m, 3H), 7.95 (dd, 1H, J=8.4 and 1.5 Hz), 7.65 (d, 1H, J=8.4 Hz), 7.43-7.35 (m, 3H), 7.26-7.20 (m, 3H), 7.06 (m, 1H), 4.42 (m, 1H), 3.86 (m, 2H), 2.35-1.23 (m, 10H).

Example 76

Preparation of 2-{2-[4-(Carbamoylmethyl-carbamoyl)-biphen-2-yl]-quinolin-6-yl}-1-cyclohexyl-1H-benzoimidazole-5-carboxylic acid (Compound 377)

The title compound was isolated as a side product of the synthesis of Compound 361.

MS: 624.24 (M+H$^+$); H$^1$-NMR (DMSO-d$_6$): δ (ppm) 8.90 (m, 1H), 8.33-8.25 (m, 4H), 8.12-8.04 (m, 3H), 7.95 (d, 1H, J=9.0 Hz), 7.64 (d, 1H, J=8.1 Hz), 7.42 (m, 1H), 7.28 (m, 2H), 7.22-7.06 (m, 3H), 4.42 (m, 1H), 3.87 (m, 2H), 2.35-1.23 (m, 10H).

Example 77

Preparation of 2-[2-(4'-chloro-4-methylcarbamoyl-biphen-2-yl)-quinolin-6-yl]-1-cyclohexyl-1H-benzoimidazole-5-carboxylic acid (Compound 378)

The title compound was synthesized as described for Compound 491, except methyl amine was used instead of N$^1$,N$^1$-dimethyl-ethane-1,2-diamine.

MS: 615.25 (M+H$^+$); H$^1$-NMR (DMSO-d$_6$): δ (ppm) 8.70 (d, 1H, J=9.3 Hz), 8.46 (d, 1H, J=1.5 Hz), 8.39 (m, 1H), 8.34-8.31 (m, 3H), 8.27-8.19 (m, 2H), 8.10-7.99 (m, 3H), 7.64-7.55 (m, 3H), 7.35 (d, 1H, J=8.4 Hz), 7.27-7.19 (m, 1H), 4.44 (m, 1H), 2.83 (d, 3H), 2.35-1.23 (m, 10H).

Example 78

Preparation of 1-cyclohexyl-2-[2-(4-methylcarbamoyl-biphen-2-yl)-quinolin-6-yl]-1H-benzoimidazole-5-carboxylic acid (Compound 362)

The title compound was isolated as a side product of the synthesis of Compound 378.

MS: 581.28 (M+H$^+$); H$^1$-NMR (DMSO-d$_6$): δ (ppm) 8.65 (m, 1H), 8.36-8.25 (m, 5H), 8.15 (d, 1H, J=9.0 Hz), 8.08-8.04 (m, 2H0, 7.97 (dd, 1H, J=8.7 and 1.8 Hz), 7.62 (d, 1H, J=7.8 Hz), 7.30-7.15 (m, 6H), 4.43 (m, 1H), 2.84 (d, 3H), 2.35-1.23 (m, 10H).

Example 79

Preparation of 2-(2-biphen-2-yl-quinolin-6-yl)-1-cyclohexyl-1H-benzoimidazole-5-carboxylic acid (Compound 395)

The title compound was isolated as a side product of the synthesis of Compound 378.

MS: 524.22 (M+H$^+$); H$^1$-NMR (DMSO-d$_6$): δ (ppm) 8.40 (d, 1H, J=1.8 Hz), 8.34-8.28 (m, 3H), 8.23 (d, 1H, J=8.7 Hz), 8.10 (dd, 1H, J=8.4 and 1.7 Hz), 8.02 (dd, 1H, J=8.7 and 1.2 Hz), 7.81 (dd, 1H, J=7.8 and 1.5 Hz), 7.63-7.52 (m, 3H), 7.28-7.14 (m, 6H), 4.44 (m, 1H), 2.35-1.29 (m, 10H).

Example 80

Preparation of Cyclohexyl-2-(2,3-diphenylquinoxalin-6-yl)-1H-benzimidazole-5-carboxylic acid (Compound 406)

Step 1: 3,4-Bis-tert-butoxycarbonylaminobenzoic acid (Compound 406a)

A solution of 2 g (13.15 mmol) of 3,4-diaminobenzoic acid, 8.61 g (39.45 mmol) of $(BOC)_2O$, and 2.04 g (15.78 mmol) of DIEA in 15 mL anhydrous DMF was stirred at room temperature overnight and then poured into 150 mL $H_2O$. The pH of the mixture was adjusted to pH 5 or 6 followed by extraction with 3×100 mL EtOAc. The organic layer was washed with 300 mL $H_2O$, dried ($Na_2SO_4$) and the solvent was evaporated. The residue was purified on silica gel using hexane and EtOAc to yield 3 g white solid. MS: 351.17 ($M-H^+$).

Step 2: 1-Cyclohexyl-2-(3,4-diaminophenyl)-1H-benzimidazole-5-carboxylic acid (Compound 406b)

A solution of 1 g (2.84 mmol) of the product of the previous step, 0.91 g (2.84 mmol) of TBTU and 0.73 g (5.68 mmol) of DIEA in 10 mL anhydrous DMF was allowed to stand at room temperature for 15 min. To this solution was added 0.90 g (3.41 mmol) of Compound 11, and the solution was allowed to stand at room temperature overnight. The solution was then poured into 100 mL $H_2O$, stirred for 30 min, filtered and dried. The solution of the solids thus obtained, in 50 mL 1M HCl and 25 mL EtOH, was refluxed at 110° C. overnight. The solvents were removed and the residue was treated with 14 mL 2 M NaOH in 70 mL of MeOH at 60° C. overnight. The MeOH was evaporated, the residue was diluted with 70 mL $H_2O$ and acidified to pH 6. The precipitate was filtered, washed with $H_2O$ and dried yielding 0.95 g brown solid. MS: 351.20 ($M+H^+$).

Step 3: 1-Cyclohexyl-2-(2,3-diphenylquinoxalin-6-yl)-1H-benzimidazole-5-carboxylic acid (Compound 406)

A solution of 100 mg (0.29 mmol) of Compound 406b and 74 mg (0.35 mmol) of benzil was stirred at room temperature overnight. The solvent was evaporated and the residue was purified on preparative HPLC yielding 10 mg.

MS: 523.25 ($M-H^+$); $^1$H-NMR (DMSOd$_6$): δ (ppm) 8.44-8.32 (m, 3H), 8.18-8.12 (m, 2H), 7.97-7.90 (m, 2H), 7.79 (t, 1H, J=7.5 Hz), 7.77-7.60 (m, 1H), 7.53-7.50 (m, 3H), 7.44-7.35 (m, 4H), 4.42 (m, 1H), 2.40-2.20 (m, 2H), 2.09-2.06 (m, 2H), 1.86 (m, 2H), 1.62 (m, 2H), 1.39-1.23 (m, 3H).

Example 81

Preparation of 2-[2,3-Bis-(4-bromophenyl)quinoxalin-6-yl]-1-cyclohexyl-1H-benzimidazole-5-carboxylic acid (Compound 371)

Prepared as described for Compound 406 using 4,4'-dibromobenzil in place of benzil.

MS: 683.04 ($M+H^+$); $^1$H-NMR (DMSOd$_6$): δ (ppm) 8.42-8.30 (m, 3H), 7.88-7.81 (m, 3H), 7.65-7.60 (m, 4H), 7.49-7.44 (m, 4H), 4.38 (m, 1H), 2.34-2.27 (m, 2H), 2.08-2.04 (m, 2H), 1.91-1.83 (m, 2H), 1.61 (m, 1H), 1.42-1.23 (m, 3H).

Example 82

Preparation of 1-Cyclohexyl-2-(2,3-di-p-tolylquinoxalin-6-yl)-1H-benzimidazole-5-carboxylic acid (Compound 389)

Prepared as described for Compound 406 using 4,4'-dimethylbenzil in place of benzil.

MS: 553.26 ($M+H^+$); $^1$H-NMR (DMSOd$_6$): δ (ppm) 8.38-8.31 (m, 3H), 8.10 (t, 2H, J=10.55 Hz), 7.93 (d, 1H, J=8.4 Hz), 7.42 (dd, 4H, J=2.7 Hz and 7.8 Hz), 7.19 (d, 4H, J=7.8 Hz) 4.40 (m, 1H), 2.41-2.31 (m, 8H), 2.07 (m, 2H), 1.83 (m, 2H), 1.61 (m, 1H), 1.23 (m, 3H).

Example 83

Preparation of 2-[2,3-Bis-(4-fluorophenyl)quinoxalin-6-yl]-1-cyclohexyl-1H-benzimidazole-5-carboxylic acid (Compound 409)

Prepared as described for Compound 406 using 4,4'-difluorobenzil in place of benzil.

MS: 561.19 ($M+H^+$); $^1$H-NMR (DMSOd$_6$): δ (ppm) 8.44 (s, 1H), 8.35 (t, 2H, J=9 Hz), 8.15 (m, 2H), 7.59-7.54 (m, 4H), 7.28-7.22 (m, 4H), 4.40 (m, 1H), 2.30 (m, 2H), 2.07 (m, 2H), 1.85 (m, 2H), 1.62 (m, 1H), 1.43-1.23 (m, 3H).

Example 84

Preparation of 2-[2,3-Bis-(3-methoxyphenyl)quinoxalin-6-yl]-1-cyclohexyl-1H-benzimidazole-5-carboxylic acid (Compound 425)

Prepared as described for Compound 406 using 3,3'-dimethoxybenzil in place of benzil.

MS: 585.25 ($M+H^+$); $^1$H-NMR (DMSOd$_6$): δ (ppm) 8.40-8.31 (m, 4H), 8.15 (d, 1H, J=8.4 Hz), 8.06 (d, 1H, J=4.2 Hz), 7.92 (d, 1H, J=8.4 Hz), 7.30 (t, 2H, J=8.1 Hz), 7.07(m, 3H), 6.99 (d, 2H, J=8.1 Hz), 4.39 (m, 1H), 3.67 (s, 3H), 3.66(s, 3H), 2.35-2.26(m, 2H), 2.08-2.04 (m, 2H), 1.87-1.84 (m, 2H), 1.62 (m, 1H), 1.34-1.23 (m, 3H).

Example 85

Preparation of 2-[2,3-Bis-(4-methoxyphenyl)quinoxalin-6-yl]-1-cyclohexyl-1H-benzimidazole-5-carboxylic acid (Compound 441)

Prepared as described for Compound 406 using 4,4'-dimethoxybenzil in place of benzil.

MS: 585.25 ($M+H^+$); $^1$H-NMR (DMSOd$_6$): δ (ppm) 8.39 (s, 1H), 8.32 (d, 2H, J=9H), 8.13 (m, 2H), 7.96 (m, 1H), 7.84 (dd, 1H, J=0.9 Hz and 9 Hz), 7.51 (m, 4H), 6.96 (dd, 4H, J=3 Hz, 9 Hz), 4.42 (m, 1H), 3.80 (s, 3H), 3.79 (s, 3H), 2.35-2.27 (m, 2H), 2.09-2.06 (m, 2H), 1.87-1.83 (m, 2H), 1.65-1.61 (m, 1H), 1.38-1.23 (m, 3H).

Example 86

Preparation of 2-[2,3-Bis-(4-dimethylaminotphenyl)quinoxalin-6-yl]-1-cyclohexyl-1H-benzimidazole-5-carboxylic acid (Compound 458)

Prepared as described for Compound 406 using 4,4'-dimethylaminobenzil in place of benzil.

MS: 306.17 ($M/2+H^+$); $^1$H-NMR (DMSOd$_6$): δ (ppm) 8.32 (m, 2H), 8.22-8.15 (m, 3H), 8.02-7.96 (m, 3H), 7.49-7.44 (m, 4H), 6.73 (d, 4H, J=9 Hz), 4.43 (m, 1H), 2.97 (s, 6H), 2.96 (s, 6H), 2.35-2.27 (m, 2H), 2.09-2.06 (m, 2H), 1.91-1.83 (m, 2H), 1.61 (m, 1H), 1.38-1.23 (m, 3H).

Example 87

Preparation of 1-Cyclohexyl-2-{2-[3',4'-dimethoxy-4-(pyrrolidine-1-carbonyl)biphen-2-yl]quinolin-6-yl}-1H-benzimidazole-5-carboxylic acid (Compound 419)

Step 1: 3-Acetyl-4-iodobenzoic acid methyl ester (Compound 419a)

A suspension of 1.45 g (7.56 mmol) of 3-acetyl-4-aminobenzoic acid methyl ester in 15 mL of 6N HCl and 3 mL MeOH was stirred and cooled to 0° C. (See Padwa, A.; et al. *J. Org Chem.* 1997, 62, 4088-4096). A solution of 0.63 g (9.07 mmol) of $NaNO_2$ in 5 mL $H_2O$ was added dropwise to the suspension while stirring. The resulting solution was stirred at 0° C. for 15 min. A solution of 3.77 g of KI in 25 mL $H_2O$ was added dropwise to this solution. The flask was removed from the cooling bath and stirred overnight. The mixture was extracted with 3×50 mL EtOAc. The organic layer was washed with 10% $Na_2S_2O_3$ solution until all $I_2$ was removed. A pale yellow solution was obtained which was dried ($Na_2SO_4$) and concentrated. The residue was purified on silica gel using hexane and EtOAc as eluent yielding 2 g yellow solid.

Step 2: 3-Acetyl-4-iodobenzoic acid (Compound 419b)

A solution of 2 g of the product from the previous step (6.58 mmol) in a mixture of 66 mL MeOH and 33 mL 2 N aqueous NaOH was heated at 60° C. overnight. The MeOH was evaporated and the residue was acidified by the addition of 70 mL of 1 N aqueous HCl. The resulting emulsion was extracted with 3×50 mL EtOAc, the organic layer was washed with 50 mL of $H_2O$, dried ($Na_2SO_4$) and the solvent was evaporated to yield 1.92 g of a yellow solid.

Step 3: 1-[2-Iodo-5-(pyrrolidine-1-carbonyl)phenyl]ethanone (Compound 419c)

A solution of 1.92 g (6.62 mmol) of the product from the previous step, 1.61 g (15.88 mmol) of $Et_3N$ and 3.01 g (7.94 mmol) of HBTU in 10 mL anhydrous DMF was allowed to stand at room temperature for 15 min. Pyrrolidine (2 mL) was added and the solution was allowed to stand at room temperature overnight. The volatiles were removed and the residue was purified on silica gel using hexane and EtOAc as eluent yielding 1.6 g yellow oil. MS: 343.99 (M+H$^+$)

Step 4: 1-Cyclohexyl-2-{2-[iodo-5-(pyrrolidine-1-carbonyl)phenyl]quinolin-6-yl}-1H-benzimidazole-5-carboxylic acid ethyl ester (Compound 419d)

A mixture of 1.03 g (3 mmol) compound 419c 1.41 g (3.6 mmol) Compound 354e and 5.1 mL 10% KOH in EtOH in 50 mL anhydrous EtOH was heated at 55° C. for 30 min. The solvent was evaporated, the residue was dissolved in 50 mL $H_2O$ and the solution was extracted with 3×50 mL EtOAc. The organic layers were washed with 50 mL $H_2O$, dried over $Na_2SO_4$ and the solvent was evaporated. The residue was purified on silica gel using first hexane/EtOAc and then $CH_2Cl_2$/MeOH as the eluent to yield 1.09 g yellow solid. MS: 699.22 (M+H$^+$).

Step 5: 1-Cyclohexyl-2-{2-[3',4'-dimethoxy-4-(pyrrolidine-1-carbonyl)biphen-2-yl]quinolin-6-yl}-1H-benzimidazole-5-carboxylic acid (Compound 419)

A mixture of 50 mg (0.07 mmol)) of the product from the previous step, 20 mg (0.11 mmol) of 3,4-dimethoxyphenylboronic acid, 8 mg (0.007 mmol) of Pd(PPh$_3$)$_4$ and 1.25 mL of saturated aqueous $NaHCO_3$ in 2.5 mL degassed toluene was stirred at 80° C., under Ar, overnight. The mixture was filtered through Celite, the solvents were evaporated and the residue was hydrolyzed in 2.5 mL MeOH and 0.35 mL 2 N aqueous NaOH at 65° C. for 2.5 h. The mixture was acidified with 1 mL 4 N HCl in dioxane and the solvents were removed. The residue was purified by HPLC yielding 10 mg.

MS: 681.31 (M+H$^+$); $^1$H-NMR (DMSOd$_6$): δ (ppm) 8.47-8.30 (m, 4H), 8.16-8.08 (m, 2H), 7.91 (d, 1H, J=1.5 Hz), 7.75 (m, 1H), 7.63 (d, 1H, J=8.1 Hz), 7.24 (d, 1H, J=8.7 Hz), 6.87-6.80 (m, 3H), 6.68 (m, 1H), 4.40 (m, 1H), 3.56 (s, 3H), 3.55 (m, 4H), 3.54 (s, 3H), 2.30 (m, 2H), 2.17 (m, 2H), 1.88 (m, 4H), 1.59 (s, 1H), 1.25 (m, 3H).

Example 88

Preparation of 1-cyclohexyl-2-{2-[4'-nitro-4-(pyrrolidine-1-carbonyl)biphen-2-yl]quinolin-6-yl}-1H-benzimidazole-5-carboxylic acid (Compound 435)

The title compound (5.2 mg yield) was prepared as described for Compound 419 using 4-nitrophenylboronic acid in place of 3,4-dimethoxyphenylboronic acid.

MS: 666.27 (M+H$^+$); $^1$H-NMR (DMSOd$_6$): δ (ppm) 8.46 (m, 3H), 8.35 (d, 1H, J=1.2 Hz), 8.26 (d, 1H), 8.20-7.98 (m, 5H), 7.81 (m, 1H), 7.48 (d, 2H, J=9 Hz), 7.40 (d, 1H, J=8.7 Hz), 3.55 (m, 4H), 2.38 (m, 2H), 2.15 (m, 2H), 1.89 (m, 4H), 1.63 (m, 1H), 1.30 (m, 3H).

Example 89

Preparation of 6-(5-carboxy-1-cyclohexyl-1H-benzimidazol-2-yl)quinoline-2-carboxylic acid (Compound 402)

Step 1: 6-(1-Cyclohexyl-5-ethoxycarbonyl-1H-benzimidazol-2-yl)quinoline-2-carboxylic acid (Compound 402a)

A solution of 500 mg (1.28 mmol) of Compound 354e, 255 mg (2.56 mmol) of pyruvic acid and 436 mg (5.16 mmol) of piperidine in 25 mL anhydrous MeOH was heated at 55° C. overnight. The solvent was evaporated, the residue was dissolved in $H_2O$ and neutralized. The precipitate was filtered, washed with $H_2O$ and dried yielding 600 mg white solid.

MS: 442.18 (M−H$^+$); $^1$H-NMR (DMSOd$_6$): δ (ppm) 8.76 (d, 1H, J=8.4 Hz), 8.50 (d, 1H, J=1.5 Hz), 8.38-8.32 (m, 2H), 8.22 (d, 1H, J=8.4 Hz), 8.16-8.13 (m, 2H), 7.95 (dd, 1H, J=1.8 Hz and 9 hz), 4.36 (q, 2H, J=7.2 Hz), 2.31 (m, 2H), 2.07 (m, 2H), 1.84 (m, 2H), 1.61 (m, 1H), 1.37 (t, 3H, J=6.9 Hz), 1.32 (m, 3H).

Step 2: 6-(5-Carboxy-1-cyclohexyl-1H-benzimidazol-2-yl)quinoline-2-carboxylic acid (Compound 402)

A solution of 90 mg (0.2 mmol) of Compound 402a and 1 mL 2 N aq. NaOH in 4 mL MeOH was heated overnight at 55° C. The solvent was evaporated, the residue was dissolved in $H_2O$ and neutralized. The precipitate was filtered, washed with $H_2O$ and dried. The product was purified by HPLC to yield 34 mg.

MS: 416.17 (M+H$^+$); $^1$H-NMR (DMSOd$_6$): δ (ppm) 9.23 (s, 1H), 8.76 (d, 1H, J=8.7 Hz), 8.48 (s, 1H), 8.36 (d, 1H, J=8.7 Hz), 8.30-8.21 (m, 2H), 8.12 (t, 2H, J=8.4 Hz), 8.95 (m, 1H, J=8.7 Hz), 4.32 (m, 1H), 2.30 (m, 2H), 2.06 (m, 2H), 1.85 (m, 2H), 1.63 (m, 1H), 1.35 (m, 3H).

Example 90

Preparation of 2-[2-(1-Carbamoylethylcarbamoyl)quinolin-6-yl]-1-cyclohexyl-1H-benzimidazole-5-carboxylic acid (Compound 497)

Step 1: 2-[2-(1-Carbamoylethylcarbamoyl)quinolin-6-yl]-1-cyclohexyl-1H-benzimidazole-5-carboxylic acid ethyl ester (Compound 497a)

A solution of 100 mg (0.23 mmol) of Compound 402a, 86 mg (0.69 mmol) of L-alaninamide, 322 mg (0.69 mmol) of PyBroP, 84 mg (0.69 mmol) DMAP and 89 mg (0.69 mmol) DIEA in 5 mL anhydrous CH$_2$Cl$_2$ was stirred at room temperature for 24 h. To this solution was added 214 mg (0.92 mmol) of CSA. The solution was stirred for another 24 h, diluted with 10 mL CH$_2$Cl$_2$ and washed with 10 mL H$_2$O. The solvent was dried and evaporated. The residue was chromatographed on silica gel using first hexane/EtOAc then CH$_2$Cl$_2$/MeOH as eluent yielding 50 mg yellow oil. MS: 514.28 (M+H$^+$).

Step 2: 2-[2-(1-Carbamoylethylcarbamoyl)quinolin-6-yl]-1-cyclohexyl-1H-benzimidazole-5-carboxylic acid (Compound 497)

A solution of 50 mg (0.1 mmol) of the product from the previous step in 2.5 mL THF, 2 mL MeOH and 0.5 mL 2 N aq. NaOH was allowed to stand at room temperature overnight. The solvents were removed, the residue was dissolved in 1 mL H$_2$O, and the solution was neutralized with 1 M aq. HCl. The precipitate was purified by HPLC to yield 7 mg of the title compound.

MS: 486.24 (M+H$^+$); $^1$H-NMR (CD$_3$OD): δ (ppm) 8.76 (d, 1H, J=8.4 Hz), 8.61-8.51 (m, 3H), 8.40-8.32 (m, 3H), 8.20 (d, 1H, J=8.4 Hz), 4.70 (m, 2H), 2.47 (m, 2H), 2.67 (m, 2H), 2.00 (m, 2H), 1.75 (m, 1H), 1.60 (d, 3H, J=6.9 Hz), 1.45 (m, 3H).

Example 91

Preparation of 2-[2-(1-Carbamoyl-2-methylpropylcarbamoyl)quinolin-6-yl]-1-cyclohexyl-1H-benzimidazole-5-carboxylic acid (Compound 511)

The title compound (5 mg yield) was prepared as described for Compound 497a using L-valinamide in place of L-alaninamide, and hydrolyzed as described for Compound 497.

MS: 514.28 (M+H$^+$); $^1$H-NMR (CD$_3$OD): δ (ppm) 8.72 (d, 1H, J=9 Hz), 8.52-8.47 (m, 3H), 8.40-8.36 (m, 1H), 8.19-8.14 (m, 2H), 7.99 (d, 1H, J=8.4 Hz), 4.58 (m, 2H), 2.44 (m, 2H), 2.29 (m, 1H), 2.19 (m, 2H), 2.02 (m, 3H), 1.74 (m, 1H), 1.44 (m, 3H), 1.10 (m, 6H).

Example 92

Preparation of 2-{2-[1-Carbamoyl-2-(1H-imidazol-2-yl)ethylcarbamoyl]quinolin-6-yl}-1-cyclohexyl-1H-benzimidazole-5-carboxylic acid (Compound 368)

The title compound (8 mg yield) was prepared as described for Compound 497a using L-histidinamide in place of L-alaninamide and hydrolyzed as described for Compound 497.

MS: 552.25 (M+H$^+$); $^1$H-NMR (CD$_3$OD): δ (ppm) 8.80 (d, 1H, J=1.5 Hz), 8.71 (d, 1H, J=8.7 Hz), 8.49-8.45 (m, 3H), 8.32 (d, 1H, J=8.7 Hz), 8.21 (m, 2H), 8.15 (dd, 1H, J=1.8 Hz and 8.7 Hz), 7.97 (s, 1H), 7.40 (d, 1H, J=1.2 Hz), 5.05-5.01 (m, 1H), 4.53 (m, 1H), 3.54 (dd, 1H, J=5.4 Hz and 15.3 Hz), 3.52 (t, 1H, J=8.4 Hz), 2.46 (m, 2H), 2.17 (m, 2H), 1.98 (m, 2H), 1.74 (m, 1H), 1.45-1.36 (m, 3H).

Example 93

Preparation of 2-[2-(1-Carbamoyl-2-hydroxyethylcarbamoyl)quinolin-6-yl]-1-cyclohexyl-1H-benzimidazole-5-carboxylic acid (Compound 385)

The title compound (5 mg yield) was prepared as described for Compound 497a using L-serinamide in place of L-alaninamide and hydrolyzed as described for Compound 497.

MS: 502.23 (M+H$^+$); $^1$H-NMR (CD$_3$OD): δ (ppm) 8.73 (d, 1H, J=8.4 Hz), 8.51 (m, 2H,), 8.40 (d, 1H, J=8.7 Hz), 8.26 (s, 2H), 8.17 (d, 1H, J=9.3), 7.97 (s, 1H), 4.72 (t, 1H, J=4.5 Hz), 4.59 (m, 1H), 4.02 (m, 2H), 3.00 (s, 1H), 2.86 (s, 1H), 2.46 (m, 2H), 2.20 (m, 2H), 1.98 (m, 2H), 1.75 (m, 1H), 1.43 (m, 3H).

Example 94

Preparation of 2-[2-(1-Carbamoyl-2-phenylethylcarbamoyl)quinolin-6-yl]-1-cyclohexyl-1H-benzimidazole-5-carboxylic acid (Compound 542)

The title compound (5 mg yield) was prepared as described for Compound 497a using L-phenylalaninamide in place of L-alaninamide and hydrolyzed as described for Compound 497.

MS: 562.27 (M+H$^+$); $^1$H-NMR (CD$_3$OD): δ (ppm) 9.06 (d, 1H, J=8.1 Hz), 8.72 (d, 1H, J=8.4 Hz), 8.50 (m, 2H), 8.32 (m, 2H), 8.17 (dd, 1H, J=1.8 Hz and 8.7 Hz), 7.34-7.19 (m, 5H), 4.61 (m, 1H), 3.34 (d, 2H, obscured by residual solvent), 3.22 (m, 1H), 2.46 (m, 2H), 2.25 (m, 2H), 2.00 (m, 2H), 1.77 (m, 1H), 1.44 (m, 3H).

Example 95

Preparation of 2-[2-(4-Chlorophenylcarbamoyl)quinolin-6-yl]-1-cyclohexyl-1H-benzimidazole-5-carboxylic acid (Compound 510)

Step 1: 2-[2-(4-Chlorophenylcarbamoyl)quinolin-6-yl]-1-cyclohexyl-1H-benzimidazole-5-carboxylic acid ethyl ester (Compound 510a)

The title compound was prepared as described for Compound 497a using 4-chloroaniline in place of L-alaninamide yielding 91 mg yellow solid. MS: 553.23 (M+H$^+$).

Step 2: 2-[2-(4-Chlorophenylcarbamoyl)quinolin-6-yl]-1-cyclohexyl-1H-benzimidazole-5-carboxylic acid (Compound 510)

The 91 mg of the product from the previous step was hydrolyzed as described for Compound 497 yielding 16 mg of the title compound.

MS: 525.18 (M+H$^+$); $^1$H-NMR (DMSOd$_6$): δ (ppm) 10.97 (s, 1H), 8.83 (d, 1H, J=8.7), 8.46 (m, 2H), 8.32 (m, 2H), 8.19 (dd, 1H, J=1.8 Hz and 8.7 Hz), 8.10 (d, 1H, J=8.7 Hz), 8.02 (m, 2H), 7.94 (dd, 1H, J=1.5 Hz and 8.4 Hz), 7.48 (m, 1H), 4.41 (m, 1H), 2.32 (m, 2H), 2.06 (m, 2H), 1.85 (m, 2H), 1.62 (m, 1H), 1.36 (m, 3H).

Example 96

Preparation of 2-[2-(4'-Chloro-4-methoxy-biphen-2-yl)-quinolin-6-yl]-3-cyclohexyl-1H-indole-6-carboxylic acid (Compound 536)

Step 1: 2-Amino-5-bromo-benzaldehyde (Compound 536a)

The title intermediate was synthesized as described for Compound 7 in five steps starting from 5-bromo-2-nitrotoluene instead of 3-methyl-4-nitrobenazoic acid methyl ester. MS: 199.97 & 201.97 (M+H$^+$); H$^1$-NMR (CDCl$_3$): δ (ppm) 9.75 (s, 1H), 7.71 (s, 1H), 7.39 (d, 1H, J=9.3 Hz), 7.22 (s, 2H), 6.72 (d, 1H, J=9.3 Hz);

Step 2: 6-Bromo-2-(4'-chloro-4-methoxy-biphen-2-yl)-quinoline (Compound 536c)

The title intermediate was synthesized from the product of the previous reaction and Compound 525a using the procedure described for Compound 13 (y=phenyl) in 44% yield.
MS: 424.03 & 426.03 (M+H$^+$); H$^1$-NMR (CDCl$_3$): δ (ppm) 8.20 (d, 1H, J=2.1 Hz), 8.10 (d, 11H, J=9.0 Hz), 7.93-7.83 (m, 2H), 7.40 (d, 1H, J=8.4 Hz), 7.26-7.23 (m, 3H0, 7.16-7.03 (m, 4H), 3.85 (s, 3H);

Step 3: 2-Boronic acid derivative of 3-Cyclohexyl-1H-indole-6-carboxylic acid methyl ester (Compound 536e)

Compound 536d (1 g, 3 mmol) (See International Patent Application Publication Number WO 03/010141), 890 mg (9 mmol) of potassium acetate, 105 mg (0.15 mmol) of dichloro [1,1'-bis(diphenylphosphino)ferrocene]palladium (II) dichloromethane adduct and 6.7 g (30 mmol) of bis(neopentyl glycolato)diboron were dissolved in 20 mL of DMSO and the mixture was heated overnight at 95° C. The crude product was precipitated by addition of 30 mL water. It was purified on a silicagel pad using toluene-ethyl acetate solvent gradient elution to yield 391 mg (43%) of the title compound.
H$^1$-NMR (CDCl$_3$): δ (ppm) 11.06 (s, 1H), 8.01 (d, 1H, J=1.5 Hz), 7.78 (d, 1H, J=8.4 Hz), 7.47 (dd, 1H, J=8.4 and 1.8 Hz), 3.81 (s, 3H), 1.98-1.33 (m, 11H).

Step 4: 2-[2-(4'-Chloro-4-methoxy-biphen-2-yl)-quinolin-6-yl]-3-cyclohexyl-1H-indole-6-carboxylic acid (Compound 536)

A mixture of 106 g (0.25 mmol) of Compound 536c, 180 mg (0.6 mmol) of Compound 536e, 58 mg (0.05 mmol) of tetrakis-(triphenylphosphino) palladium, 6 mL of toluene, 1.5 mL of methanol and 600 μL of saturated sodium bicarbonate was heated under Ar overnight at 80° C. The reaction mixture was then evaporated to dryness, the semi-solid dissolved in 5 mL ethanol, 3 mL 1M NaOH was added and was heated at 85° C. for 30 minutes. The reaction mixture was then evaporated to dryness. The pure title compound was isolated using RP-HPLC to yield 27.5 mg (19%) yellow solid.
MS: 587.23 (M+H$^+$); H$^1$-NMR (CDCl$_3$): δ (ppm) 11.66 (s, 1H), 8.39 (d, 1H, J=8.4 Hz), 8.20 (d, 1H, J=8.7 Hz), 8.12 (d, 1H, J=1.5 Hz), 8.00-7.95 (m, 2H), 7.86 (d, 1H, J=8.4 Hz), 7.59 (, dd, 1H, J=8.7 and 1.5 Hz), 4.47 (d, 1H, J=8.7 Hz), 7.34-7.28 (m, 3H), 7.22-7.18 (m, 2H), 7.14-7.11 (m, 2H), 3.88 (s, 3H), 2.96 (m, 1H), 2.05-1.22 (m, 10H).

Example 97

Preparation of 1-Cyclohexyl-2-(2-phenyl-quinolin-7-yl)-1H-benzoimidazole-5-carboxylic acid (Compound 405)

Step 1: 4-methyl-3-nitro-benzoic acid methyl ester (Compound 405a)

4-Methyl-3-nitro benzoic acid (12.5 g, 69 mmol) was dissolved in anhydrous methanol (500 mL) in a 1 L flask. HCl gas was then bubbled through the solution until saturation (3 h). The HCl source was then removed, and the reaction was stirred at room temperature overnight. The reaction was then concentrated to dryness and dried over phosphorus pentoxide overnight to yield 13.34 g (99%) of product which was 99% pure by QC HPLC.
H$^1$-NMR (CDCl$_3$): δ (ppm) 8.59 (d, 1H, Ar—H$^2$), 8.13 (dd, 1H, Ar—H$^6$), 7.43 (d, 1H, Ar—H$^5$), 3.96 (s, 3H, OCH$_3$), 2.67 (s, 3H, CH$_3$)

Step 2: trans-4-(2-Dimethylamino-vinyl)-3-nitro-benzoic acid methyl ester (Compound 405b)

A 100 mL flask fitted with a 15 cm Vigreux head was charged with 10 g (49.7 mmol) of the product from the previous step, 16.9 mL of DMF, and 21.2 g (196.0 mmol) of N,N-dimethylformamide dimethylacetal. The reaction vessel was immersed in a 140 C° oil bath for 18 h under Ar while the forming methanol was distilled away. Upon cooling to room temperature the dark red content of the flask solidified. The solid was transferred to a 250 mL flask using DMF, which was subsequently removed by evaporation. The residue was triturated with petroleum ether to give 16.16 g (95%) enamine as dark red solid which was 98.4% pure based on QC HPLC.
H$^1$-NMR (CDCl$_3$): δ (ppm) 8.48 (d, 1H, Ar—H$^2$), 7.88 (dd, 1H, Ar—H$^6$), 7.45 (d, 1H, Ar—H$^5$), 7.15 (d, 1H, CH=), 5.91 (d, 1H, CH=), 3.90 (s, 3H, OCH$_3$), 2.95 (s, 6H, (CH$_3$)$_2$N)

Step 3: 4-Formyl-3-nitro-benzoic acid methyl ester (Compound 405c)

The product from the previous step (16.10 g, 64.3 mmol) and NaIO$_4$ (41 g, 191.7 mmol) was dissolved in 250 mL of 1:1 THF/H$_2$O at room temperature. The dark red solution was warmed to about 40° C. while heavy precipitation occurred and the solution color changed to light brown. After 1 h, the precipitate was removed by filtration and was washed with 400 mL ethyl acetate. The organic layer was washed three times with saturated NaHCO$_3$, once with brine and dried with Na$_2$SO$_4$. The solution was evaporated to dryness and the resulting oil was purified on a silicagel pad eluting with ethyl acetate-hexane gradient (30% to 40% ethyl acetate) to yield 11.07 g (83%) of the title intermediate as a yellow solid after evaporation.
H$^1$-NMR (CDCl$_3$): δ (ppm) 10.45 (s, 1H, CHO), 8.75 (d, 1H, Ar—H2) 8.41 (dd, 1H, Ar—H$^6$), 8.01 (d, 1H, Ar—H$^5$), 4.02 (s, 3H, OCH$_3$)

Step 4: 4-Dimethoxymethyl-3-nitro-benzoic acid methyl ester (Compound 405d)

To a solution of 1 g (52.6 mmol) of the product from the previous step in 220 mL methanol 5.5 mL 4N HCL/dioxane was added. The mixture was kept at 90° C. for 10 minutes before it was evaporated to dryness. The white solid material was dissolved in 20 mL methanol again and was treated with 5.5 mL 4N HCl in the same way 2 more times. The solid was dried in high vacuum overnight to give 12.46 g (93%) reddish oil of the title intermediate (76%).

H$^1$-NMR (CDCl$_3$): δ (ppm) 8.43 (d, 1H, Ar—H$^2$), 8.23 (dd, 1H, Ar—H$^6$), 7.87 (d, 1H, Ar—H$^5$), 5.93 (s, 1H, Ar—CH), 3.97 (s, 3H, ester CH$_3$), 3.41 (s, 6H, acetal CH$_3$)

Step 5: 3-Amino-4-dimethoxymethyl-benzoic acid methyl ester (Compound 405e)

Mg$_2$SO$_4$ (1 g) and 100 mg of 10% Pd/C were suspended in 20 mL methanol and were hydrogenated in a Parr apparatus at 30 psi for 20 minutes. The apparatus was opened and 1.22 g (4.78 mmol) of the product from the previous step dissolved in 20 mL methanol was added followed by 2 mL TEA. The mixture was hydrogenated at 30 psi for 45 minutes, the catalyst was removed by filtration and the solution was evaporated to dryness. The solid material was dried over P$_2$O$_5$ overnight to give 84 mg (95.4%) of the title intermediate.

H$^1$-NMR (CDCl$_3$): δ (ppm) 7.37 (d, 2H, Ar—H$^{5+6}$), 7.31 (d, 1H, Ar—H$^2$), 5.34 (s, 1H, Ar—CH), 4.36 (s, 2H, NH2), 3.88 (s, 3H, ester CH$_3$), 3.33 (s, 6H, acetal CH$_3$)

Step 6: 3-Amino-4-formyl-benzoic acid methyl ester (Compound 53)

The product from the previous step (100 mg, 0.44 mmol) was dissolved at room temperature in a 15 mL solvent mixture composed of 2:2:1 EtOH-acetic acid-water. The strong yellow solution became pale yellow in 5 minutes. The mixture was let stand for an additional 15 minutes then was evaporated to dryness and was further dried in high vacuum overnight to get 75 mg (94%) of the title intermediate as a yellow powder.

H$^1$-NMR (CDCl$_3$): δ (ppm) 9.92 (s, 1H, CHO), 7.55 (d, 1H, Ar—H$^2$), 7.34 (m, 2H, Ar—H$^{5+6}$), 3.91 (s, 1H, CH$_3$)

Step 7: 2-Phenyl-quinoline-7-carboxylic acid (Compound 405f)

To a solution of 500 mg (2.8 mmol) of the product from the previous step, 340 mg (2.8 mmol) of acetophenone in 20 mL ethanol, 2.1 mL of a 10% KOH/ethanol solution was added and the mixture was refluxed under argon overnight. The product partially precipitated as dull tan crystals which were not filtered off. The whole mixture was evaporated to dryness; the residue was triturated with ether to give the product as a potassium salt. The acid was obtained by dissolving the potassium salt in 25 mL water and acidifying to pH 4. The precipitate was collected by filtration, washed twice with water and dried over phosphorous pentoxide in high vacuum to yield 261 mg (54%) the title intermediate MS: 250.32 (M+H$^+$).

Step 8: 4-Cyclohexylamino-3-[(2-phenyl-quinoline-7-carbonyl)-amino]-benzoic acid ethyl ester (Compound 405 g)

To a solution of 250 mg (1.0 mmol) of the product from the previous step and 418 mg HATU (1.1 mmol) in DMF (5 mL), 0.383 mL (2.2 mmol) of DIEA was added. The reaction was stirred at room temperature for 15 minutes before 289 mg (1.1 mmol) of Compound 11 was added. The reaction was complete after stirring at room temperature for 1 hour. After being evaporated to dryness, the reaction mixture was dissolved in ethyl acetate, and washed with water (2×100 mL), brine (1×100 mL), dried over sodium sulfate, and evaporated to an oil residue which was then dried over phosphorus pentoxide overnight to produce 200 mg (46% yield) of the title intermediate.

Step 9: 1-Cyclohexyl-2-(2-phenyl-quinolin-7-yl)-1H-benzoimidazole-5-carboxylic acid (Compound 405)

The product from the previous step (200 mg, 0.4 mmol) was dissolved in 30 mL of glacial acetic acid. The solution was refluxed for 4 h, then evaporated to dryness. The yellow solid was dissolved again in 20 mL ethanol, and 4 mL 1N NaOH was added with stirring at 80° C. for 1 h. The reaction mixture was then evaporated to dryness. The solid was dissolved in 20 mL water, cooled in an ice bath, acidified with 4 mL 1N HCl after which the precipitate was filtered and washed with water. The solid was dried over phosphorus pentoxide overnight to yield 25 mg of the title compound.

MS: 448.27 (M+H$^+$); H$^1$-NMR (DMSO-d$_6$): δ (ppm) 8.64 (d, 1H), 8.44 (s, 1H), 8.30 (m, 5H), 8.18 (d, 1H), 7.95 (dd, 1H), 7.90 (dd, 1H), 7.55 (m, 3H), 3.40 (m, 4H), 2.32 (dd, 2H), 2.08 (d, 2H), 1.85 (d, 2H), 1.62 (d, 1H)

Example 98

Preparation of 1-cyclohexyl-2-(3-phenyl-quinolin-7-yl)-1H-benzoimidazole-5-carboxylic acid (Compound 351)

Step 1: 3-Phenyl-quinoline-7-carboxylic acid (Compound 351a)

Following the same reaction procedure and workup for Compound 405f, 500 mg (2.8 mmol) of Compound 53 was reacted with 340 mg (2.8 mmol) phenylacetaldehyde to produce 603 mg (87% yield) of the title intermediate.

MS: 250.17 (M+H$^+$); H$^1$-NMR (DMSO): δ (ppm) 9.35 (d, 1H), 8.72 (s, 1H), 8.58 (s, 1H), 8.12 (m, 2H); 7.90 (d, 2H), 7.55 (m, 3H);

Step 2: 4-Cyclohexylamino-3-[(3-phenyl-quinoline-7-carbonyl)-amino]-benzoic acid ethyl ester (Compound 351b)

Following the same reaction procedure and workup as for Compound 405 g, 250 mg (1 mmol) of the product from the previous step was reacted with 289 mg (1.1 mmol) of Compound 11, using 418 mg (1.1 mmol) of HATU and 0.383 mL of DIEA to produce 448 mg (91% yield) of the title intermediate. MS: 494.29 (M+H$^+$).

Step 3: 1-Cyclohexyl-2-(3-phenyl-quinolin-7-yl)-1H-benzoimidazole-5-carboxylic acid (Compound 351)

Following the same reaction procedure and workup as for Compound 405, 450 mg (0.9 mmol) of the product from the previous step was cyclized with 40 mL acetic acid and saponified with 35 mL EtOH and 7 mL 1M NaOH to produce 70 mg (17% yield) of the title compound.

MS: 448.23 (M+H$^+$); H$^1$-NMR (DMSO-d$_6$): δ (ppm) 9.49 (d, 1H), 9.0 (d, 1H), 8.56 (s, 1H), 8.39 (m, 2H), 8.26 (d, 1H), 8.05 (m, 5H), 7.55 (m, 3H), 2.30 (m, 3H), 2.12 (d, 3H), 1.86 (d, 3H), 1.62 (d, 2H), 1.34 (m, 5H)

Example 99

Preparation of 2-{[1-cyclohexyl-2-(3-phenyl-quinolin-7-yl)-1H-benzoimidazole-5-carbonyl]-amino}-3-(5-hydroxy-1H-indol-3-yl)-propionic acid (Compound 516)

To a solution of 50 mg (0.11 mmol) of Compound 351 in 2 mL DMF, 46 mg (0.12 mmol) of HATU and 40 µL (0.24 mmol) of DIEA were added. The mixture was stirred at room temperature for 30 minutes and 27 mg (0.12 mmol) of L-5-hydroxytryptophane was added to the activated ester solution. The reaction was complete in 1 h. The DMF was evaporated and the residual oil which was dissolved in 20 mL 1:1 DMF-water containing 0.1% TFA. The solution was applied on a RP-HPLC column to give the pure title compound as TFA salt.

Conversion to HCl salt: The purified Compound 516 was dissolved in 0.8 mL methanol, 1 mL 4M HCl in dioxane was added followed by 40 mL ether. The off-white precipitate was centrifuged down and the ether was decanted off. Yield: 15 mg (25%) beige solid.

MS: 648.24 (M−H$^+$); H$^1$-NMR (DMSO-d$_6$): δ (ppm) 10.50 (d, 1H), 9.45 (s, 1H), 8.92 (s, 1H), 8.52 (s, 1H), 8.39-8.30 (m, 3H), 8.23 (m, 1H), 7.98 (m, 4H), 7.54 (m, 3H), 7.08 (m, 3H), 6.87 (m, 3H), 6.56 (d, 1H), 4.65 (m, 1H), 4.36 (m, 1H), 2.32 (m, 2H), 2.10 (m,2H), 1.84 (d, 2H), 1.95(m, 1H), 1.29 (m, 4H);

Example 100

Preparation of 1-cyclohexyl-2-(2-phenyl-quinoxalin-6-yl)-1H-benzoimidazole-5-carboxylic acid morpholin-4-ylamide (Compound 574)

A solution of Compound 203 (0.25 mmol) in 3 mL DMF was preactivated with HATU (0.246 mmol) and DIEA (0.5 mmol). To the solution, the desired amine was added (0.1 mmol) and the reaction was stirred for 16 hours. The completed reaction was then purified via RP-HPLC, and converted to the HCl salt by evaporating to dryness, dissolving in 0.8 mL methanol and adding 1 mL 4M HCl in dioxane followed by 40 mL ether. The compound was centrifuged down, the solvent decanted off, and the solid dried to yield the final compound.

Using this general procedure with morpholin-4-ylamine (9.8 ul), produced 15 mg of the title compound (58% yield). MS: 533.32 (M+H$^+$) HPLC Procedure A, retention time=12.87 min.

Example 101

Preparation of 2-1 [1-Cyclohexyl-2-(2-phenyl-quinoxalin-6-yl)-1H-benzoimidazole-5-carbonyl]-amino}-ethanesulfonic acid (Compound 524)

The general procedure described for Compound 574 was used with 2-amino-ethanesulfonic acid (12.5 mg), producing 28 mg of the title compound (98% yield). MS: 556.28 (M+H$^+$) HPLC Procedure A, retention time=11.36 min.

Example 102

Preparation of 1-Cyclohexyl-2-(2-phenyl-quinoxalin-6-yl)-1H-benzoimidazole-5-carboxylic acid (7-hydroxy-naphthalen-1-yl)-amide (Compound 575)

The general procedure described for Compound 574 was used with 8-amino-naphthalen-2-ol (15.9 mg), producing 5 mg of the title compound (20% yield). MS: 590.25 (M+H$^+$) HPLC Procedure A, retention time=15.31 min.

Example 103

Preparation of 1-Cyclohexyl-2-(2-phenyl-quinoxalin-6-yl)-1H-benzoimidazole-5-carboxylic acid (5-hydroxy-naphthalen-1-yl)-amide (Compound 576)

The general procedure described for Compound 574 was used with 5-amino-naphthalen-1-ol (15.9 mg), producing 7 mg of the title compound (25% yield). MS: 590.24 (M+H$^+$) HPLC Procedure A, retention time=15.26 min.

Example 104

Preparation of 6-{[1-Cyclohexyl-2-(2-phenyl-quinoxalin-6-yl)-1H-benzoimidazole-5-carbonyl]-amino}-naphthalene-2-carboxylic acid (Compound 526)

The general procedure described for Compound 574 was used with 6-amino-naphthalene-2-carboxylic acid (18.7 mg), producing 15 mg of the title compound (53% yield). MS: 618.30 (M+H$^+$) HPLC Procedure A, retention time=16.24 min.

Example 105

Preparation of 1-Cyclohexyl-2-(2-phenyl-quinoxalin-6-yl)-1H-benzoimidazole-5-carboxylic acid (4-methyl-2-oxo-2H-chromen-7-yl)-amide (Compound 577)

The general procedure described for Compound 574 was used with 7-Amino-4-methyl-chromen-2-one (17.5 mg), producing 8 mg of the title compound (27% yield). MS: 606.29 (M+H$^+$) HPLC Procedure A, retention time=19.22 min.

Example 106

Preparation of 1-Cyclohexyl-2-(2-phenyl-1,2,3,4-tetrahydro-quinolin-6-yl)-1H-benzoimidazole-5-carboxylic acid (Compound 215)

A solution of Compound 203 (100 mg, 0.23 mmol) and platinum oxide (12 mg, 0.048 mmol) in methanol (5 mL) was hydrogenated at 40 psi for 3 h. The reaction was evaporated to dryness, and purified via HPLC. The resulting compound was then converted to the HCl salt using the standard method, yielding 40 mg (37% yield) of the title compound.

MS: 452.25 (M+H$^+$); H$^1$-NMR (DMSO-d$_6$): δ (ppm) 8.31 (d, 1H, J=9), 8.22 (d, 1H, J=1.5), 8.044 (dd, 1H, J=9.1,1.5), 7.36 (m, 7H), 6.865 (d, 1H, J=9), 4.58 (m, 2H), 2.86 (m, 1H), 2.66 (m, 1H), 2.33 (m, 2H), 2.07 (m, 3H), 1.90 (m, 3H), 1.66 (m, 1H), 1.41 (m, 3H).

Example 107

Preparation of 2-[2-(2-Bromo-phenyl)-3-phenyl-quinolin-6-yl]-1-cyclohexyl-1H-benzoimidazole-5-carboxylic acid (Compound 424)

Step 1: 1-(2-Bromo-phenyl)-2-phenyl-ethanol (Compound 424a)

A mixture of 2-bromobenzaldehyde (1 mL, 5.4 mmol) in diethylether (2 mL) was added to a flame dried flask, and flushed with argon. The temperature was reduced to −10° C. and benzylmagnesium chloride was slowly added to the flask via syringe. The reaction was stirred at −10° C. for 1 hour and then stirred at room temperature for 16 hours. The reaction was the poured over ice and acidified to pH 3. It was then extracted with ether (3×40 mL). The organic layers were combined, evaporated, and the resulting residue was purified via silica gel chromatography to produce 520 mg (33% yield) of the title intermediate.

$H^1$-NMR (CDCl$_3$): δ (ppm) 7.54 (dd, 2H), 7.33 (m, 1H), 7.25 (m, 3H), 7.12 (m, 2H), 5.22 (m, 1H), 3.18 (dd, 3.18, J=2.7,13.8), 2.715 (dd, 1H, J=13.8, 9)

Step 2: 1-(2-Bromo-phenyl)-2-phenyl-ethanone (Compound 424b)

To a flame dried flask, Dess-Martin periodinane (1.23 g, 2.9 mmol) and dichloromethane (30 mL) were added. The mixture was cooled to 0° C., and the product of the previous reaction (520 mg, 1.8 mmol) was added and stirred for 1 hour at the reduced temperature before being stirred for 48 hours at room temperature. The reaction was then evaporated to an oil, and purified on silica gel to produce the title intermediate (385 mg, 78% yield).

$H^1$-NMR (CDCl$_3$): δ (ppm) 7.58 (m, 1H), 7.26 (m, 8H), 4.23 (s, 2H)

Step 3: 3-(2-Bromo-phenyl)-2-phenyl-quinoline-6-carboxylic acid (Compound 424c)

Following the same reaction procedure and workup as for Compound 405f (235 mg, 1.31 mmol) of Compound 53 was reacted with the product of the previous reaction, Compound 424b (360 mg, 1.31 mmol), in ethanol (12 mL) using 10% w/v KOH in ethanol (1.1 mL) to produce the title compound (210 mg, 40% yield).

MS: 403.22 (M−H$^+$); $H^1$-NMR (DMSO-d$_6$): δ (ppm) 8.69 (s, 1H), 8.28 (d, 1H, J=8.7), 8.04 (s, 1H, J=8.7), 7.93 (s, 1H); 7.542 (d, 1H, J=7.2), 7.40 (m, 3H), 7.25 (m, 4H)

Step 4: 3-{[2-(2-Bromo-phenyl)-3-phenyl-quinoline-6-carbonyl]-amino}-4-cyclohexylamino-benzoic acid Ethyl Ester (Compound 424d)

Using the same reaction procedure and workup as for Compound 405 g, the product of the previous reaction, Compound 424c (200 mg, 0.495 mmol), HATU (207 mg, 0.545 mmol), DIEA (141 mg, 1.09 mmol), Compound 11 (143 mg, 0.545 mmol) and DMF (4 mL) were used to produce of the title intermediate (250 mg, 78% yield). MS 649.57 (M+H$^+$).

Step 5: 2-[2-(2-Bromo-phenyl)-3-phenyl-quinolin-6-yl]-1-cyclohexyl-1H-benzoimidazole-5-carboxylic acid (Compound 424)

Using the same reaction procedure and workup as for Compound 405, the product of the previous reaction (250 mg, 0.39 mmol) was reacted with acetic acid (30 mL), and 1M NaOH (4 mL) to produce the title compound (60 mg, 25% yield).

MS 602.15; $H^1$-NMR (DMSO-d$_6$): δ (ppm) 8.71 (s, 1H), 8.53 (s, 1H), 8.31 (m, 2H), 8.13 (m, 2H), 7.98 (dd, 1H, J=1.5, 8.4), 7.585 (d, 1H, J=7.8), 7.46 (m, 2H), 7.3 (m, 6H), 4.47 (m, 1H), 2.35 (m, 3H), 2.09 (m, 2H), 1.86 (m, 2H), 1.63 (m, 1H), 1.37 (m, 3H)

Example 108

Preparation of 2-[2-(4'-Chloro-biphen-2-yl)-3-phenyl-quinolin-6-yl]-1-cyclohexyl-1H-benzoimidazole-5-carboxylic acid (Compound 440)

Compound 424 (50 mg, 0.083 mmol), 4-chlorophenylboronic acid (20 mg, 0.125 mmol), and CsF (143 mg, 0.94 mmol) were added to degassed dioxane (6 mL). A solution of 2-(dicyclohexylphosphino)biphenyl (5 mg, 0.0125 mmol) and palladium acetate (2 mg, 0.0083 mmol) in degassed dioxane (3 mL) was added to the reaction solution. The reaction was then refluxed under argon for 3 hours. The reaction was then evaporated to dryness and purified via HPLC resulting in the title compound (4 mg, 10% yield).

MS 634.18; $H^1$-NMR (DMSO-d$_6$): δ (ppm) 8.40 (d, 2H, J=4.8), 8.30 (d, 2H, J=8.7), 8.09 (m, 2H), 7.9 (d, 1H, J=8.7), 7.3 (d, 1H, J=7.2), 7.54 (m, 2H), 7.20 (m, 2H), 7.08 (dd, 4H, J=13.8, 7.8), 6.61 (d, 2H, J=6.9), 6.47 (d, 2H, J=8.4), 2.34 (m, 2H), 2.05 (m, 2H), 1.85 (m, 2H), 1.62 (m, 1H), 1.38 (m, 3H)

Example 109

Preparation of 2-(2-biphenyl-4-yl-quinolin-6-yl)-1-cyclohexyl-1H-benzoimidazole-5-carboxylic acid (Compound 390)

Following the procedure and workup for Compound 354, Compound 354e (100 mg, 0.256 mmol) was reacted with 1-biphenyl-4-yl-ethanone (51 mg, 0.256 mmol) in ethanol (2 mL) using 10% w/v KOH in ethanol (506 μL, 0.64 mmol) to produce the title compound (15 mg, 10% yield).

MS: 524.24 (M+H$^+$); $H^1$-NMR (DMSO-d$_6$): δ (ppm) 8.71 (d, 1H, J=9), 8.39 (m, 6H), 8.2 (d, 1H, J=8.7), 8.19 (d, 1H, J=9), 8.0 (d, 1H, J=9), 7.9 (d, 2H, J=8.1), 7.79 (d, 2H, J=7.5), 7.52 (m, 2H), 7.42 (m, 1H), 3.56 (s, 1H), 2.45 (m, 2H), 2.10 (m, 2H), 1.86 (m, 2H), 1.62 (s, 1H), 1.34 (m, 3H)

Example 110

Preparation of 1-cyclohexyl-2-[2-(2,4-dimethyl-thiazol-5-yl)-quinolin-6-yl]-1H-benzoimidazole-5-carboxylic acid (Compound 426)

Following the procedure and workup for Compound 354, Compound 354e (100 mg, 0.256 mmol) was reacted with 1-(2,4-dimethyl-thiazol-5-yl)-ethanone (40 mg, 0.256 mmol) in ethanol (2 mL) using 10% w/v KOH in ethanol (506 μL, 0.64 mmol) to produce the title compound (14 mg, 12% yield).

MS: 483.19 (M+H$^+$); $H^1$-NMR (DMSO-d$_6$): 8.61 (m, 1H), 8.37 (m, 1H), 8.26 (m, 1H), 8.0 (m, 5H), 4.38 (s, 1H), 2.72 (s, 3H), 2.66 (s, 3H), 2.28 (m, 2H), 2.02 (m, 2H), 1.82 (m, 2H), 1.62 (m, 1H), 1.30 (m, 3H)

Example 111

Preparation of 1-cyclohexyl-2-(2-pyrazin-2-yl-quinolin-6-yl)-1H-benzoimidazole-5-carboxylic acid (Compound 442)

Following the procedure and workup for Compound 354, Compound 354e (100 mg, 0.256 mmol) was reacted with 1-pyrazin-2-yl-ethanone (32 mg, 0.256 mmol) in ethanol (2 mL) using 10% w/v KOH in ethanol (506 μL, 0.64 mmol) to produce the title compound (15 mg, 10% yield).

MS: 450.20 (M+H$^+$); $H^1$-NMR (DMSO-d$_6$): 9.79 (d, 1H, J=1.5), 8.84 (m, 3H), 8.62 (d, 1H, J=8.7), 8.53 (d, 1H, J=1.5), 8.40 (d, 1H, J=8.4), 8.34 (d, 1H, J=1.5), 8.22 (d, 1H, J=8.7), 8.15 (dd, 1H, J=9, 2.1), 8.01 (dd, 1H, J=8.4, 1.2), 2.33 (m, 2H), 2.10 (m, 2H), 1.85 (m, 2H), 1.61 (m, 1H), 1.35 (m, 3H)

Example 112

Preparation of 1-cyclohexyl-2-[2-(5-methyl-2-phenyl-thiophen-3-yl)-quinolin-6-yl]-1H-benzoimidazole-5-carboxylic acid (Compound 472)

Following the procedure and workup for Compound 354, Compound 354e (100 mg, 0.256 mmol) was reacted with 1-(5-methyl-2-phenyl-thiophen-3-yl)-ethanone (56 mg, 0.256 mmol) in ethanol (2 mL) using 10% w/v KOH in ethanol (506 μL, 0.64 mmol) to produce the title compound (8 mg, 6% yield). MS: 544.27 (M+H$^+$) HPLC Procedure A, retention time=17.05 min.

Example 113

Preparation of 1-cyclohexyl-2-(2-pyridin-3-yl-quinolin-6-yl)-1H-benzoimidazole-5-carboxylic acid (Compound 355)

Following the procedure and workup for Compound 354, Compound 354e (100 mg, 0.256 mmol) was reacted with 1-pyridin-3-yl-ethanone (0.256 mmol) in ethanol (2 mL) using 10% w/v KOH in ethanol (506 μL, 0.64 mmol) to produce the title compound (19 mg, 17% yield). MS: 449.21 (M+H$^+$) HPLC Procedure A, retention time=7.96 min.

Example 114

Preparation of 2-[2-(4-amino-3-bromo-phenyl)-quinolin-6-yl]-1-cyclohexyl-1H-benzoimidazole-5-carboxylic acid (Compound 372)

Following the procedure and workup for Compound 354, Compound 354e (100 mg, 0.256 mmol) was reacted with N-(4-acetyl-2-bromo-phenyl)-acetamide (0.256 mmol) in ethanol (2 mL) using 10% w/v KOH in ethanol (506 μL, 0.64 mmol) to produce the title compound (16 mg, 15% yield).
MS: 541.15 (M+H$^+$); H$^1$-NMR (DMSO-d$_6$): 8.80 (d, 1H, J=9), 8.53 (m, 3H), 8.35 (m, 2H), 8.28 (d, 1H, J=9), 8.17 (m, 2H), 8.04 (dd, 1H, J=8.7, 1.2), 6.98 (d, 1H, J=8.7), 4.44 (m, 1H), 2.30 (m, 2H), 2.12 (m, 2H), 1.85 (m, 2H), 1.62 (m, 1H), 1.35 (m, 3H)

Example 115

Preparation of 2-[2-(2-amino-4-methyl-thiazol-5-yl)-quinolin-6-yl-1-cyclohexyl-1H-benzoimidazole-5-carboxylic acid (Compound 391)

Following the procedure and workup for Compound 354, Compound 354e (100 mg, 0.256 mmol) was reacted with 1-(2-amino-4-methyl-thiazol-5-yl)-ethanone (0.256 mmol) in ethanol (2 mL) using 10% w/v KOH in ethanol (506 μL, 0.64 mmol) to produce the title compound (8 mg, 9% yield). MS: 484.19 (M+H$^+$); HPLC Procedure A, retention time=8.57 min.

Example 116

Preparation of 1-cyclohexyl-2-[2-(7-hydroxy-benzofuran-2-yl)-quinolin-6-yl]-1H-benzoimidazole-5-carboxylic acid (Compound 411)

Following the procedure and workup for Compound 354, Compound 354e (100 mg, 0.256 mmol) was reacted with 1-(7-hydroxy-benzofuran-2-yl)-ethanone (0.256 mmol) in ethanol (2 mL) using 10% w/v KOH in ethanol (506 μL, 0.64 mmol) to produce the title compound (19 mg, 20% yield). MS: 504.22 (M+H$^+$); HPLC Procedure A, retention time=12.20 min.

Example 117

Preparation of 1-cyclohexyl-2-(2-pyridin-2-yl-quinolin-6-yl)-1H-benzoimidazole-5-carboxylic acid (Compound 427)

Following the procedure and workup for Compound 354, Compound 354e (100 mg, 0.256 mmol) was reacted with 1-pyridin-2-yl-ethanone (0.256 mmol) in ethanol (2 mL) using 10% w/v KOH in ethanol (506 μL, 0.64 mmol) to produce the title compound (66 mg, 61% yield). MS: 449.19 (M+H$^+$); HPLC Procedure A, retention time=9.85 min.

Example 118

Preparation of 1-cyclohexyl-2-(2-pyridin-4-yl-quinolin-6-yl)-1H-benzoimidazole-5-carboxylic acid (Compound 443)

Following the procedure and workup for Compound 354, Compound 354e (100 mg, 0.256 mmol) was reacted with 1-pyridin-4-yl-ethanone (0.256 mmol) in ethanol (2 mL) using 10% w/v KOH in ethanol (506 μL, 0.64 mmol) to produce the title compound (68 mg, 62% yield). MS: 449.19 (M+H$^+$); HPLC Procedure A, retention time=7.98 min.

Example 119

Preparation of 1-cyclohexyl-2-[2-(5,6,7,8-tetrahydro-naphthalen-2-yl)-quinolin-6-yl]-1H-benzoimidazole-5-carboxylic acid (Compound 459)

Following the procedure and workup for Compound 354, Compound 354e (100 mg, 0.256 mmol) was reacted with 1-(5,6,7,8-tetrahydro-naphthalen-2-yl)-ethanone (0.256 mmol) in ethanol (2 mL) using 10% w/v KOH in Ethanol (506 μL, 0.64 mmol) to produce the title compound (65 mg, 60% yield).
MS: 502.26 (M+H$^+$); H$^1$-NMR (DMSO-d$_6$): 8.76 (m, 1H), 8.54 (s, 1H), 8.39 (m, 4H), 8.10 (m, 4H), 7.36 (m, 1H), 4.45 (m, 1H), 2.84 (m, 4H), 2.35 (m, 2H), 2.14 (m, 2H), 1.80 (m, 6H), 1.62 (m, 1H), 1.34 (m, 3H)

Example 120

Preparation of 1-cyclohexyl-2-[2-(4-imidazol-1-yl-phenyl)-quinolin-6-yl]-1H-benzoimidazole-5-carboxylic acid (Compound 473)

Following the procedure and workup for Compound 354, Compound 354e (100 mg, 0.256 mmol) was reacted with 1-(4-imidazol-1-yl-phenyl)-ethanone (0.256 mmol) in ethanol (2 mL) using 10% w/v KOH in ethanol (506 μL, 0.64 mmol) to produce the title compound (75 mg, 59% yield). MS: 514.23 (M+H$^+$); HPLC Procedure A, retention time=8.40 min.

Example 121

Preparation of 2-(2-benzo[1,3]dioxol-5-yl-quinolin-6-yl)-1-cyclohexyl-1H-benzoimidazole-5-carboxylic acid (Compound 412)

Following the procedure and workup for Compound 354, Compound 354e (100 mg, 0.256 mmol) was reacted with 1-benzo[1,3]dioxol-5-yl-ethanone (0.256 mmol) in ethanol (2 mL) using 10% w/v KOH in ethanol (506 μL, 0.64 mmol) to produce the title compound (30 mg, 24% yield).
MS: 492.21 (M+H$^+$); H$^1$-NMR (DMSO-d$_6$): 8.68 (m, 1H), 8.42 (s, 1H), 8.28 (m, 4H), 8.05 (m, 2H), 7.92 (m, 2H), 7.13

(m, 1H), 6.15 (s, 2H), 2.33 (m, 2H), 2.10 (m, 2H), 1.85 (m, 2H), 1.62 (m, 1H), 1.35 (m, 3H)

Example 122

Preparation of 1-cyclohexyl-2-[2-(4-phenoxy-phenyl)-quinolin-6-yl]-1H-benzoimidazole-5-carboxylic acid (Compound 428)

Following the procedure and workup for Compound 354, Compound 354e (100 mg, 0.256 mmol) was reacted with 1-(4-phenoxy-phenyl)-ethanone (0.256 mmol) in ethanol (2 mL) using 10% w/v KOH in Ethanol (506 µL, 0.64 mmol) to produce the title compound (42 mg, 31% yield).
MS: 540.25 (M+H$^+$); H$^1$-NMR (DMSO-d$_6$): 8.68 (d, 1H), 8.46 (d, 1H), 8.30 (m, 6H), 8.04 (dd, 2H), 7.44 (m, 2H), 7.16 (m, 5H), 4.45 (m, 1H), 2.32 (m, 2H), 2.10 (m, 2H), 1.85 (m, 2H), 1.65 (m, 1H), 1.35 (m, 3H)

Example 123

Preparation of 1-cyclohexyl-2-[2-(6-methyl-naphthalen-2-yl)-quinolin-6-yl]-1H-benzoimidazole-5-carboxylic acid (Compound 444)

Following the procedure and workup for Compound 354, Compound 354e (100 mg, 0.256 mmol) was reacted with 1-(6-methyl-naphthalen-2-yl)-ethanone (0.256 mmol) in ethanol (2 mL) using 10% w/v KOH in ethanol (506 µL, 0.64 mmol) to produce the title compound (23 mg, 18% yield).
MS: 512.26 (M+H$^+$); H$^1$-NMR (DMSO-d$_6$): 8.85 (s, 1H), 8.73 (d, 1H), 8.46 (d, 3H), 8.34 (m, 2H), 8.20 (d, 1H), 8.10 (dd, 1H), 8.02 (m, 3H), 7.57 (s, 1H), 7.44 (1H), 2.32 (m, 2H), 2.08 (m, 2H), 1.85 (m, 2H), 1.64 (m, 1H), 1.36 (m, 3H)

Example 124

Preparation of 1-cyclohexyl-2-[2-(2-hydroxy-naphthalen-1-yl)-quinolin-6-yl]-1H-benzoimidazole-5-carboxylic acid (Compound 460)

Following the procedure and workup for Compound 354, Compound 354e (100 mg, 0.256 mmol) was reacted with 1-(2-hydroxy-naphthalen-1-yl)-ethanone (0.256 mmol) in ethanol (2 mL) using 10% w/v KOH in ethanol (506 µL, 0.64 mmol) to produce the title compound (7 mg, 6% yield). MS: 514.23 (M+H$^+$); HPLC Procedure A, retention time=12.20 min.

Example 125

Preparation of 1-cyclohexyl-2-(2-naphthalen-1-yl-quinolin-6-yl)-1H-benzoimidazole-5-carboxylic acid (Compound 357)

Following the procedure and workup for Compound 354, Compound 354e (100 mg, 0.256 mmol) was reacted with 1-naphthalen-1-yl-ethanone (0.256 mmol) in ethanol (2 mL) using 10% w/v KOH in ethanol (506 µL, 0.64 mmol) to produce the title compound (4 mg, 4% yield).
MS: 498.24 (M+H$^+$); H$^1$-NMR (DMSO-d$_6$): 8.82 (d, 1H), 8.59 (d, 1H), 8.36 (m, 2H), 8.24 (d, 1H), 8.10 (m, 6H), 7.81 (d, 1H), 7.70 (m, 1H), 7.57 (m, 2H), 4.49 (m, 1H), 3.55 (s, 1H), 2.31 (m, 2H), 2.10 (m, 2H), 1.82 (m, 2H), 1.62 (m, 1H), 1.36 (m, 3H)

Example 126

Preparation of 1-cyclohexyl-2-[2-(4-piperazin-1-yl-phenyl)-quinolin-6-yl]-1H-benzoimidazole-5-carboxylic acid (Compound 488)

Following the procedure and workup for Compound 354, Compound 354e (100 mg, 0.256 mmol) was reacted with 1-(4-piperazin-1-yl-phenyl)-ethanone (0.256 mmol) in ethanol (2 mL) using 10% w/v KOH in ethanol (506 µL, 0.64 mmol) to produce the title compound (120 mg, 91% yield). MS: 532.21 (M+H$^+$); HPLC Procedure A, retention time=7.78 min.

Example 127

Preparation of 2-[2-(4-acetylamino-phenyl)-quinolin-6-yl]-1-cyclohexyl-1H-benzoimidazole-5-carboxylic acid (Compound 501)

Following the procedure and workup for Compound 354, Compound 354e (100 mg, 0.256 mmol) was reacted with N-(4-acetyl-phenyl)-acetamide (0.256 mmol) in ethanol (2 mL) using 10% w/v KOH in ethanol (506 µL, 0.64 mmol) to produce the title compound (19 mg, 15% yield). MS: 505.26 (M+H$^+$); HPLC Procedure A, retention time=9.94 min.

Example 128

Preparation of 2-[2-(4-amino-phenyl)-quinolin-6-yl]-1-cyclohexyl-1H-benzoimidazole-5-carboxylic acid (Compound 358)

Following the procedure and workup for Compound 354, Compound 354e (100 mg, 0.256 mmol) was reacted with 1-(4-amino-phenyl)-ethanone (0.256 mmol) in ethanol (2 mL) using 10% w/v KOH in ethanol (506 µL, 0.64 mmol) to produce the title compound (14 mg, 10% yield). MS: 463.23 (M+H$^+$); HPLC Procedure A, retention time=8.62 min.

Example 129

Preparation of 2-[2-(3-carbamoyl-4-hydroxy-phenyl)-quinolin-6-yl]-1-cyclohexyl-1H-benzoimidazole-5-carboxylic acid (Compound 374)

Following the procedure and workup for Compound 354, Compound 354e (100 mg, 0.256 mmol) was reacted with 5-acetyl-2-hydroxy-benzamide (0.256 mmol) in ethanol (2 mL) using 10% w/v KOH in Ethanol (506 µL, 0.64 mmol) to produce the title compound (13 mg, 10% yield). MS: 507.24 (M+H$^+$); HPLC Procedure A, retention time=10.36 min.

Example 130

Preparation of 1-Cyclohexyl-2-[2-(3-hydroxy-propyl)-quinolin-6-yl]-1H-benzoimidazole-5-carboxylic acid (Compound 392)

Following the procedure and workup for Compound 354, Compound 354e (100 mg, 0.256 mmol) was reacted with 5-hydroxy-pentan-2-one (0.256 mmol) in ethanol (2 mL) using 10% w/v KOH in ethanol (506 µL, 0.64 mmol) to produce the title compound (96 mg, 90% yield). MS: 430.23 (M+H$^+$); HPLC Procedure A, retention time=6.84 min, 82.48% purity.

Example 131

Preparation of 2-(2-benzofuran-2-yl-quinolin-6-yl)-1-cyclohexyl-1H-benzoimidazole-5-carboxylic acid (Compound 413)

Following the procedure and workup for Compound 354, Compound 354e (100 mg, 0.256 mmol) was reacted with 1-benzofuran-2-yl-ethanone (0.256 mmol) in ethanol (2 mL) using 10% w/v KOH in ethanol (506 µL, 0.64 mmol) to produce the title compound (75 mg, 62% yield). MS: 488.22 (M+H$^+$); HPLC Procedure A, retention time=14.35 min.

Example 132

Preparation of 1-cyclohexyl-2-[2-(4-morpholin-4-yl-phenyl)-quinolin-6-yl]-1H-benzoimidazole-5-carboxylic acid (Compound 429)

Following the procedure and workup for Compound 354, Compound 354e (100 mg, 0.256 mmol) was reacted with 1-(4-morpholin-4-yl-phenyl)-ethanone (0.256 mmol) in ethanol (2 mL) using 10% w/v KOH in ethanol (506 µL, 0.64 mmol) to produce the title compound (37 mg, 30% yield). MS: 533.28 (M+H$^+$); HPLC Procedure A, retention time=10.39 min.

Example 133

Preparation of 2-[6-(2-Nitro-phenyl)-quinolin-6-yl]-1H-benzoimidazole-5-carboxylic acid (Compound 446)

Following the procedure and workup for Compound 354, Compound 354e (100 mg, 0.256 mmol) was reacted with 1-(2-nitro-phenyl)-ethanone (0.256 mmol) in ethanol (2 mL) using 10% w/v KOH in ethanol (506 µL, 0.64 mmol) to produce the title compound (11 mg, 10% yield). MS: 493.21 (M+H$^+$); HPLC Procedure A, retention time=12.72 min.

Example 134

Preparation of 2-[2-(4-benzyloxy-2-hydroxy-3-methyl-phenyl)-quinolin-6-yl]-1-cyclohexyl-1H-benzoimidazole-5-carboxylic acid (Compound 462)

Following the procedure and workup for Compound 354, Compound 354e (100 mg, 0.256 mmol) was reacted with 1-(4-benzyloxy-2-hydroxy-3-methyl-phenyl)-ethanone (0.256 mmol) in ethanol (2 mL) using 10% w/v KOH in ethanol (506 µL, 0.64 mmol) to produce the title compound (73 mg, 10% yield). MS: 584.29 (M+H$^+$); HPLC Procedure A, retention time=18.27 min.

Example 135

Preparation of 1-cyclohexyl-2-[2-(2-pyrazol-1-yl-ethyl)-quinolin-6-yl]-1H-benzoimidazole-5-carboxylic acid (Compound 476)

Following the procedure and workup for Compound 354, Compound 354e (100 mg, 0.256 mmol) was reacted with 4-pyrazol-1-yl-butan-2-one (0.256 mmol) in ethanol (2 mL) using 10% w/v KOH in Ethanol (506 µL, 0.64 mmol) to produce the title compound (14 mg, 50% yield). MS: 466.27 (M+H$^+$); HPLC Procedure A, retention time=8.41 min.

Example 136

Preparation of 1-cyclohexyl-2-(2-dipropylaminomethyl-quinolin-6-yl)-1H-benzoimidazole-5-carboxylic acid (Compound 489)

Following the procedure and workup for Compound 354, Compound 354e (100 mg, 0.256 mmol) was reacted with 1-dipropylamino-propan-2-one (0.256 mmol) in ethanol (2 mL) using 10% w/v KOH in ethanol (506 µL, 0.64 mmol) to produce the title compound (70 mg, 58% yield). MS: 485.34 (M+H$^+$); HPLC Procedure A, retention time=9.20 min.
H$^1$-NMR (DMSO-d$_6$): 8.70 (d, 1H), 8.44 (d, 1H), 8.25 (m, 2H), 8.10 (m, 2H), 7.92 (dd, 1H), 7.95 (d, 1H), 4.8 (m, 2H), 3.4 (m, 4H), 3.25 (m, 2H), 2.30 (m, 1H), 2.00 (m, 1H), 1.85 (m, 5H), 1.6 (m, 1H), 1.35 (m, 3H), 0.89 (m, 6H)

Example 137

Preparation of 2-[2-(3-carboxymethyl-2,2-dimethyl-cyclobutyl)-quinolin-6-yl]-1-cyclohexyl-1H-benzoimidazole-5-carboxylic acid (Compound 502)

Following the procedure and workup for Compound 354, Compound 354e 100 mg, 0.256 mmol) was reacted with (3-acetyl-2,2-dimethyl-cyclobutyl)-acetic acid (0.256 mmol) in ethanol (2 mL) using 10% w/v KOH in ethanol (506 µL, 0.64 mmol) to produce the title compound (21 mg, 16% yield). MS: 512.31 (M+H$^+$); HPLC Procedure A, retention time=9.07 min.

Example 138

Preparation of 2-[2-(7-bromo-5-methoxy-benzofuran-2-yl)-quinolin-6-yl]-1-cyclohexyl-1H-benzoimidazole-5-carboxylic acid (Compound 394)

Following the procedure and workup for Compound 354, Compound 354e (100 mg, 0.256 mmol) was reacted with 1-(7-bromo-5-methoxy-benzofuran-2-yl)-ethanone (0.256 mmol) in ethanol (2 mL) using 10% w/v KOH in ethanol (506 µL, 0.64 mmol) to produce the title compound, 17% yield).
MS: 596.12 (M+H$^+$); H$^1$-NMR (DMSO-d$_6$): 8.75 (d, 1H), 8.51 (d, 1H), 8.34 (m, 2H), 8.3 (m, 2H), 8.13 (dd, 1H), 8.05 (dd, 1H), 7.96 (s, 1H), 7.31 (m, 2H), 4.40 (m, 1H), 3.83 (s, 1H), 2.30 (m, 2H), 2.15 (m, 2H), 1.85 (m, 2H), 1.62 (m, 1H), 1.35 (m, 3H)

Example 139

Preparation of 2-{2-[1-(2-chloro-pyridin-3-yl)-2,4-dioxo-1,2,3,4-tetrahydro-pyrimidin-5-yl]-quinolin-6-yl}-1-cyclohexyl-1H-benzoimidazole-5-carboxylic acid (Compound 431)

Following the procedure and workup for Compound 354, Compound 354e (100 mg, 0.256 mmol) was reacted with 5-acetyl-1-(2-chloro-pyridin-3-yl)-1H-pyrimidine-2,4-dione (0.256 mmol) in ethanol (2 mL) using 10% w/v KOH in ethanol (506 µL, 0.64 mmol) to produce the title compound 45 mg, 31% yield). MS: 593.17 (M+H$^+$); HPLC Procedure A, retention time=10.02 min.

Example 140

Preparation of 2-[2-(5-benzyloxy-2-methyl-benzofuran-3-yl)-quinolin-6-yl]-1-cyclohexyl-1H-benzoimidazole-5-carboxylic acid (Compound 448)

Following the procedure and workup for Compound 354, Compound 354e (100 mg, 0.256 mmol) was reacted with 1-(5-benzyloxy-2-methyl-benzofuran-3-yl)-ethanone (0.256 mmol) in ethanol (2 mL) using 10% w/v KOH in ethanol (506 µL, 0.64 mmol) to produce the title compound (75 mg, 49% yield). MS: 608.25 (M+H$^+$); HPLC Procedure A, retention time=17.24 min.

Example 141

Preparation of 2-[2-(6-chloro-9-methyl-9H-carbazol-3-yl)-quinolin-6-yl]-1-cyclohexyl-1H-benzoimidazole-5-carboxylic acid (Compound 463)

Following the procedure and workup for Compound 354, Compound 354e (100 mg, 0.256 mmol) was reacted with 1-(6-chloro-9-methyl-9H-carbazol-3-yl)-ethanone (0.256 mmol) in ethanol (2 mL) using 10% w/v KOH in ethanol (506 µL, 0.64 mmol) to produce the title compound (18 mg, 12% yield). MS: 585.21 (M+H$^+$); HPLC Procedure A, retention time=16.25 min.

Example 142

Preparation of 1-cyclohexyl-2-[2-(2,3-dihydro-benzofuran-5-yl)-quinolin-6-yl]-1H-benzoimidazole-5-carboxylic acid (Compound 478)

Following the procedure and workup for Compound 354, Compound 354e (100 mg, 0.256 mmol) was reacted with 1-(2,3-dihydro-benzofuran-5-yl)-ethanone (0.256 mmol) in ethanol (2 mL) using 10% w/v KOH in Ethanol (506 µL, 0.64 mmol) to produce the title compound (34 mg, 28% yield). MS: 490.19 (M+H$^+$); HPLC Procedure A, retention time=11.50 min.

Example 143

Preparation of 1-cyclohexyl-2-[2-(1-phenyl-1H-pyrazol-4-yl)-quinolin-6-yl]-1H-benzoimidazole-5-carboxylic acid (Compound 449)

Following the procedure and workup for Compound 354, Compound 354e (100 mg, 0.256 mmol) was reacted with 1-(1-phenyl-1H-pyrazol-4-yl)-ethanone (0.256 mmol) in ethanol (2 mL) using 10% w/v KOH in ethanol (506 µL, 0.64 mmol) to produce the title compound (69 mg, 51% yield). MS: 514.23 (M+H$^+$); HPLC Procedure B, retention time=6.36 min.

Example 144

Preparation of 1-cyclohexyl-2-[2-(3,5-dimethyl-1-phenyl-1H-pyrazol-4-yl)-quinolin-6-yl]-1H-benzoimidazole-5-carboxylic acid (Compound 464)

Following the procedure and workup for Compound 354, Compound 354e (100 mg, 0.256 mmol) was reacted with 1-(3,5-dimethyl-1-phenyl-1H-pyrazol-4-yl)-ethanone (0.256 mmol) in ethanol (2 mL) using 10% w/v KOH in ethanol (506 µL, 0.64 mmol) to produce the title compound (47 mg, 37% yield).

MS: 542.27 (M+H$^+$); H$^1$-NMR (DMSO-d$_6$): 8.73 (d, 1H), 8.49 (d, 1H), 8.32 (m, 2H), 8.23 (d, 1H), 8.12 (dd, 1H), 8.02 (dd, 1H), 7.93 (d, 1H), 7.57 (m, 4H), 7.47 (m, 1H), 4.45 (m, 1H), 2.58 (s, 3H), 2.34 (m, 2H), 2.32 (s, 3H), 2.10 (m, 2H), 1.85 (m, 2H), 1.62 (m, 1H), 1.36 (m, 3H)

Example 145

Preparation of 1-cyclohexyl-2-{2-[3-(3,4-dichloro-phenyl)-isoxazol-5-yl]-quinolin-6-yl}-1H-benzoimidazole-5-carboxylic acid (Compound 479)

Following the procedure and workup for Compound 354, Compound 354e (100 mg, 0.256 mmol) was reacted with 1-[3-(3,4-dichloro-phenyl)-isoxazol-5-yl]-ethanone (0.256 mmol) in ethanol (2 mL) using 10% w/v KOH in ethanol (506 µL, 0.64 mmol) to produce the title compound (21 mg, 15% yield). MS: 583.16 (M+H$^+$); HPLC Procedure B, retention time=8.77 min.

Example 146

Preparation of 2-{2-[2-chloro-4-(4-chloro-phenoxy)-phenyl]-quinolin-6-yl}-1-cyclohexyl-1H-benzoimidazole-5-carboxylic acid (Compound 492)

Following the procedure and workup for Compound 354, Compound 354e (100 mg, 0.256 mmol) was reacted with 1-[2-chloro-4-(4-chloro-phenoxy)-phenyl]-ethanone (0.256 mmol) in ethanol (2 mL) using 10% w/v KOH in ethanol (506 µL, 0.64 mmol) to produce the title compound (75 mg, 49% yield). MS: 608.17 (M+H$^+$); HPLC Procedure B, retention time=8.44 min.

Example 147

Preparation of 2-{2-[5-(4-chloro-phenyl)-2-methyl-furan-3-yl]-quinolin-6-yl}-1-cyclohexyl-1H-benzoimidazole-5-carboxylic acid (Compound 505)

Following the procedure and workup for Compound 354, Compound 354e (100 mg, 0.256 mmol) was reacted with 1-[5-(4-chloro-phenyl)-2-methyl-furan-3-yl]-ethanone (0.256 mmol) in ethanol (2 mL) using 10% w/v KOH in ethanol (506 µL, 0.64 mmol) to produce the title compound (83 mg, 59% yield). MS: 562.21 (M+H$^+$); HPLC Procedure B, retention time=8.99 min.

Example 148

Preparation of 2-{2-[3-(4-chloro-phenyl)-5-methyl-isoxazol-4-yl]-quinolin-6-yl}-1-cyclohexyl-1H-benzoimidazole-5-carboxylic acid (Compound 396)

Following the procedure and workup for Compound 354, Compound 354e (100 mg, 0.256 mmol) was reacted with 1-[3-(4-chloro-phenyl)-5-methyl-isoxazol-4-yl]-ethanone (0.256 mmol) in ethanol (2 mL) using 10% w/v KOH in ethanol (506 µL, 0.64 mmol) to produce the title compound (16 mg, 12% yield).

MS: 563.20 (M+H$^+$); H$^1$-NMR (DMSO-d$_6$): 8.59 (d, 1H), 8.46 (d, 1H), 8.35 (d, 1H), 8.24 (m, 2H), 8.06 (m, 2H), 7.53 (s,

4H), 7.46 (d, 1H), 4.48 (m, 1H), 3.55 (s, 1H), 2.72 (s, 3H), 2.30 (m, 2H), 2.10 (m, 2H), 1.83 (m, 2H), 1.62 (m, 1H), 1.34 (m, 3H)

Example 149

Preparation of 2-{2-[2-(4-chloro-phenyl)-4-methyl-thiazol-5-yl]-quinolin-6-yl}-1-cyclohexyl-1H-benzoimidazole-5-carboxylic acid (Compound 416)

Following the procedure and workup for Compound 354, Compound 354e (100 mg, 0.256 mmol) was reacted with 1-[2-(4-chloro-phenyl)-4-methyl-thiazol-5-yl]-ethanone (0.256 mmol) in ethanol (2 mL) using 10% w/v KOH in ethanol (506 µL, 0.64 mmol) to produce the title compound (27 mg, 19% yield). MS: 580.19 (M+H$^+$); HPLC Procedure B, retention time=9.18 min.

Example 150

Preparation of 1-cyclohexyl-2-[2-(1H-pyrrol-3-yl)-quinolin-6-yl]-1H-benzoimidazole-5-carboxylic acid (Compound 432)

Following the procedure and workup for Compound 354, Compound 354e (100 mg, 0.256 mmol) was reacted with 1-(1H-pyrrol-3-yl)-ethanone (0.256 mmol) in ethanol (2 mL) using 10% w/v KOH in ethanol (506 µL, 0.64 mmol) to produce the title compound (10 mg, 8% yield).
MS: 437.20 (M+H$^+$); H$^1$-NMR (DMSO-d$_6$): 12.22 (s, 1H), 8.95 (d, 1H), 8.89 (d, 1H), 8.55 (m 2H), 8.42 (d, 1H), 8.31 (m, 2H), 8.15 (d, 1H), 7.90 (d, 1H), 7.49 (s, 1H), 7.15 (s, 1H), 4.39 (m, 1H), 3.55 (s, 1H), 2.32 (m, 2H), 2.05 (m, 2H), 1.85 (m, 2H), 1.66 (m, 1H), 1.35 (m, 3H)

Example 151

Preparation of 1-Cyclohexyl-2-[2-(1H-pyrrol-2-yl)-quinolin-6-yl]-1H-benzoimidazole-5-carboxylic acid (Compound 450)

Following the procedure and workup for Compound 354, Compound 354e (100 mg, 0.256 mmol) was reacted with 1-(1H-pyrrol-2-yl)-ethanone (0.256 mmol) in ethanol (2 mL) using 10% w/v KOH in ethanol (506 µL, 0.64 mmol) to produce the title compound (11 mg, 9% yield).
MS: 437.16 (M+H$^+$); H$^1$-NMR (DMSO-d$_6$): 12.12 (s, 1H), 8.80 (d, 1H), 8.49 (m, 2H), 8.31 (m, 2H), 8.18 (m, 2H), 7.95 (d, 1H), 7.63 (m, 1H), 7.43 (s, 1H), 6.45 (m, 1H), 4.40 (m, 1H), 3.51 (s, 1H), 2.30 (m, 2H), 2.08 (m, 2H), 1.85 (m, 2H), 1.65 (m, 1H), 1.35 (m, 3H)

Example 152

Preparation of 1-cyclohexyl-2-[2-(3-oxo-3,4-dihydro-2H-benzo[1,4]oxazin-6-yl)-quinolin-6-yl]-1H-benzoimidazole-5-carboxylic acid (Compound 465)

Following the procedure and workup for Compound 354, Compound 354e (100 mg, 0.256 mmol) was reacted with 6-acetyl-4H-benzo[1,4]oxazin-3-one (0.256 mmol) in ethanol (2 mL) using 10% w/v KOH in ethanol (506 µL, 0.64 mmol) to produce the title compound (11 mg, 8% yield).
MS: 519.21 (M+H$^+$); H$^1$-NMR (DMSO-d$_6$): 10.95 (s, 1H), 8.67 (d, 1H), 8.49 (s, 1H), 8.25 (m, 4H), 8.05 (m, 2H), 7.95 (d, 1H), 7.85 (m, 1H), 7.12 (d, 1H), 4.68 (s, 2H), 4.45 (m, 1H), 2.31 (m, 2H), 2.11 (m, 2H), 1.83 (m, 2H), 1.60 (m, 1H), 1.31 (m, 3H)

Example 153

Preparation of 2-[2-(3-amino-5-phenyl-thiophen-2-yl)-quinolin-6-yl]-1-cyclohexyl-1H-benzoimidazole-5-carboxylic acid (Compound 480)

Following the procedure and workup for Compound 354, Compound 354e (100 mg, 0.256 mmol) was reacted with 1-(3-amino-5-phenyl-thiophen-2-yl)-ethanone (0.256 mmol) in ethanol (2 mL) using 10% w/v KOH in ethanol (506 µL, 0.64 mmol) to produce the title compound (19 mg, 14% yield). MS: 545.24 (M+H$^+$); HPLC Procedure B, retention time=8.25 min.

Example 154

Preparation of 1-cyclohexyl-2-[2-(5-methoxy-benzofuran-3-yl)-quinolin-6-yl]-1H-benzoimidazole-5-carboxylic acid (Compound 493)

Following the procedure and workup for Compound 354, Compound 354e (100 mg, 0.256 mmol) was reacted with 1-(5-methoxy-benzofuran-3-yl)-ethanone (0.256 mmol) in ethanol (2 mL) using 10% w/v KOH in ethanol (506 µL, 0.64 mmol) to produce the title compound (10 mg, 8% yield). MS: 518.24 (M+H$^+$); HPLC Procedure B, retention time=7.60 min.

Example 155

Preparation 1-(trans-2-Hydroxy-cyclohexyl)-2-(2-phenyl-quinoxalin-6-yl)-1H-benzoimidazole-5-carboxylic acid (Compound 578)

Step 1: 3-Nitro-4-(trans-2-hydroxy-cyclohexylamino)-benzoic acid Ethyl Ester (Compound 578a)

Compound 9 (689 mg, 3 mmol) was suspended in acetonitrile (5 mL) and then triethylamine was added (1.3 mL, 9 mmol). trans-2-aminocyclohexanol hydrochloride (682 mg, 4.5 mmol) was then added and the reaction refluxed for 12 hours, 2 mL methanol was then added and the reaction further refluxed for another 24 hours. Water (100 mL) was added and the resulting precipitate filtered, washed 3 times with water and air-dried. The product was used without further characterization in the next step. MS: 309.3 (M+H$^+$)

Step 2: 3-Amino-4-(trans-2-hydroxy-cyclohexylamino)-benzoic acid Ethyl Ester (Compound 578b)

The product from the previous step (3 mmol) was dissolved in ethyl acetate (60 mL) and methanol (40 mL) and 10% Pd/C (100 mg) was added. The reaction was hydrogenated on a Parr-shaker at 35 psi for 6½ hours at ambient temperature. The Pd/C was filtered and the filtrate concentrated. Chromatography (SiO$_2$, ethyl acetate/toluene 6:4 v/v) to yield the title intermediate (230 mg, 0.83 mmol) MS: 279.2 (M+H$^+$)

Step 3: 1-(trans-2-Hydroxy-cyclohexyl)-2-(2-phenyl-quinoxalin-6-yl)-1H-benzoimidazole-5-carboxylic acid (Compound 578)

Compound 36A Y=Phenyl, (200 mg, 0.8 mmol) was activated in 8 mL DMF with TBTU (282 mg, 0.88 mmol) and DIEA (0.285 mL, 1.6 mmol) for 30 minutes at room temperature. This solution was then added to Compound 578b (230 mg, 0.83 mmol) and stirred at ambient temperature for 20 hours. The reaction was concentrated to a residue in-vacuo and then dissolved in acetic acid (20 mL) and refluxed overnight. In the morning, the acetic acid was removed in-vacuo and the crude residue dissolved in a mixture of THF (20 mL), methanol (16 mL) and 2 M NaOH (4 mL) and the solution heated at 60 C overnight. The solution was then concentrated in-vacuo to an aqueous solution and concentrated HCl added until the pH was 5. The resulting precipitate was filtered, washed with water and purified using RP-HPLC column to give the pure title compound.

Conversion to HCl salt: The HPLC purified product was dissolved in 4 mL methanol, 500 µL 4M HCl in dioxane was added followed by 40 mL ether. The resulting precipitate was separated by filtration and dried in high vacuum overnight. Yield: 18.3 mg.

MS: 465.21 (M+H$^+$); H$^1$-NMR (DMSO-d$_6$): δ (ppm) 9.71 (s, 1H), 8.68 (s, 1H), 8.41-8.32 (m, 5H), 8.2 (d, 1H, J=8.7 Hz), 7.98 (d, 1H, 8.7 Hz), 7.62 (m, 3H), 4.33 (m, 2H), 2.36 (m, 1H), 2.06 (m, 2H), 1.77-1.55 (m, 2H), 1.29-1.22 (m, 2H).

Example 156

Preparation of 2-[2-(4-amino-3,5-dichloro-phenyl)-quinolin-6-yl]-1-cyclohexyl-1H-benzoimidazole-5-carboxylic acid (Compound 363)

Following the procedure and workup for Compound 354, Compound 354e (100 mg, 0.256 mmol) was reacted with 1-(4-amino-3,5-dichloro-phenyl)-ethanone (0.256 mmol) in ethanol (2 mL) using 10% w/v KOH in ethanol (506 µL, 0.64 mmol) to produce the title compound (31 mg, 25% yield).

MS: 531.15 (M+H$^+$); H$^1$-NMR (DMSO-d$_6$): 8.68 (d, 1H), 8.49 (d, 1H), 8.34 (m, 6H), 8.09 (m, 2H), 4.48 (m, 1H), 3.55 (s, 1H), 2.30 (m, 2H), 2.12 (m, 2H), 1.82 (m, 2H), 1.60 (m, 1H), 1.30 (m, 3H)

Example 157

Preparation of 2-[2-(3-bromo-phenyl)-quinolin-6-yl]-1-cyclohexyl-1H-benzoimidazole-5-carboxylic acid (Compound 482)

Following the procedure and workup for Compound 354, Compound 354e (100 mg, 0.256 mmol) was reacted with 1-(3-bromo-phenyl)-ethanone (0.256 mmol) in ethanol (2 mL) using 10% w/v KOH in ethanol (506 µL, 0.64 mmol) to produce the title compound (15 mg, 12% yield).

MS: 526.12 (M+H$^+$); H$^1$-NMR (DMSO-d$_6$): 8.72 (d, 1H), 8.53 (m, 1H), 8.48 (d, 1H), 8.35 (m, 4H), 8.23 (d, 1H), 8.10 (dd, 1H), 8.01 (dd, 1H), 7.74 (m, 1H), 7.55 (m, 1H), 4.45 (m, 1H), 3.51 (s, 1H), 2.30 (m, 2H), 2.10 (m, 2H), 1.83 (m, 2H), 1.64 (m, 1H), 1.33 (m, 3H)

Example 158

Preparation of 1-cyclohexyl-2-[2-(3,5-dimethoxy-phenyl)-quinolin-6-yl]-1H-benzoimidazole-5-carboxylic acid (Compound 495)

Following the procedure and workup for Compound 354, Compound 354e (100 mg, 0.256 mmol) was reacted with 1-(3,5-dimethoxy-phenyl)-ethanone (0.256 mmol) in ethanol (2 mL) using 10% w/v KOH in ethanol (506 µL, 0.64 mmol) to produce the title compound (44 mg, 35% yield).

MS: 508.23 (M+H$^+$); H$^1$-NMR (DMSO-d$_6$): 8.74 (d, 1H), 8.55 (d, 1H), 8.37 (m, 4H), 8.10 (m, 2H), 7.47 (d, 2H), 6.70 (m, 1H), 4.43 (m, 1H), 3.85 (s, 6H), 3.51 (s, 1H), 2.30 (m, 2H), 2.13 (m, 2H), 1.82 (m, 2H), 1.60 (m, 1H), 1.32 (m, 3H)

Example 159

Preparation of 1-cyclohexyl-2-[2-(3,4-dichloro-phenyl)-quinolin-6-yl]-1H-benzoimidazole-5-carboxylic acid (Compound 508)

Following the procedure and workup for Compound 354, Compound 354e (100 mg, 0.256 mmol) was reacted with 1-(3,4-dichloro-phenyl)-ethanone (0.256 mmol) in ethanol (2 mL) using 10% w/v KOH in ethanol (506 µL, 0.64 mmol) to produce the title compound (12 mg, 10% yield).

MS: 516.14 (M+H$^+$); H$^1$-NMR (DMSO-d$_6$): 8.74 (d, 1H), 8.58 (d, 1H), 8.49 (d, 1H), 8.40 (d, 1H), 8.34 (m, 3H), 8.25 (d, 1H), 8.11 (dd, 1H), 8.03 (dd, 1H), 7.85 (d, 1H), 4.45 (m, 1H), 3.51 (s, 1H), 2.32 (m, 2H), 2.10 (m, 2H), 1.84 (m, 2H), 1.62 (m, 1H), 1.33 (m, 3H)

Example 160

Preparation of 1-cyclohexyl-2-[2-(2,4-dihydroxy-phenyl)-quinolin-6-yl]-1H-benzoimidazole-5-carboxylic acid (Compound 364)

Following the procedure and workup for Compound 354, Compound 354e (100 mg, 0.256 mmol) was reacted with 1-(2,4-dihydroxy-phenyl)-ethanone (0.256 mmol) in ethanol (2 mL) using 10% w/v KOH in ethanol (506 µL, 0.64 mmol) to produce the title compound (9.5 mg, 8% yield).

MS: 480.21 (M+H$^+$); H1-NMR (DMSO-d$_6$): 8.72 (d, 1H), 8.46 (d, 1H), 8.35 (m, 2H), 8.26 (dd, 2H), 8.15 (dd, 1H), 8.03 (d, 2H), 6.47 (dd, 1H), 6.42 (d, 1H), 4.44 (m, 1H), 3.51 (s, 1H), 2.30 (m, 2H), 2.10 (m, 2H), 1.84 (m, 2H), 1.64 (m, 1H), 1.35 (m, 3H)

Example 161

Preparation of 1-cyclohexyl-2-[2-(3,5-dihydroxy-phenyl)-quinolin-6-yl]-1H-benzoimidazole-5-carboxylic acid (Compound 381)

Following the procedure and workup for Compound 354, Compound 354e (100 mg, 0.256 mmol) was reacted with 1-(3,5-dihydroxy-phenyl)-ethanone (0.256 mmol) in ethanol (2 mL) using 10% w/v KOH in ethanol (506 µL, 0.64 mmol) to produce the title compound (22 mg, 18% yield).

MS: 480.21 (M+H$^+$); H$^1$-NMR (DMSO-d$_6$): 8.66 (d, 1H), 8.46 (d, 1H), 8.32 (m, 1H), 8.25 (m, 2H), 8.11 (m, 2H), 8.01 (m, 1H), 7.15 (d, 2H), 6.41 (m, 1H), 4.46 (m, 1H), 3.51 (s, 1H), 2.32 (m, 2H), 2.15 (m, 2H), 1.84 (m, 2H), 1.62 (m, 1H), 1.32 (m, 3H)

Example 162

Preparation of 1-cyclohexyl-2-[2-(2-hydroxy-5-methyl-3-nitro-phenyl)-quinolin-6-yl]-1H-benzoimidazole-5-carboxylic acid (Compound 418)

Following the procedure and workup for Compound 354, Compound 354e (100 mg, 0.256 mmol) was reacted with 1-(2-hydroxy-5-methyl-3-nitro-phenyl)-ethanone (0.256 mmol) in ethanol (2 mL) using 10% w/v KOH in ethanol (506 µL, 0.64 mmol) to produce the title compound (40 mg, 31% yield).

MS: 523.24 (M+H⁺); H¹-NMR (DMSO-d₆): 8.870 (d, 1H, J=9.3), 8.61 (d, 1H, J=9.3), 8.49 (s, 2H), 8.41 (d, 1H, J=8.7), 8.30 (s, 1H), 8.15 (d, 2H, J=7.8), 7.97 (d, 1H, J=9.3), 7.89 (s, 1H), 4.20 (m, 1H), 3.55 (s, 1H), 2.42 (s, 3H), 2.32 (m, 2H), 2.08 (m, 2H), 1.84 (m, 2H), 1.62 (m, 1H), 1.37 (m, 3H)

Example 163

Preparation of 1-cyclohexyl-2-[2-(2-hydroxy-6-methoxy-phenyl)-quinolin-6-yl]-1H-benzoimidazole-5-carboxylic acid (Compound 434)

Following the procedure and workup for Compound 354, Compound 354e (100 mg, 0.256 mmol) was reacted with 1-(2-hydroxy-6-methoxy-phenyl)-ethanone (0.256 mmol) in ethanol (2 mL) using 10% w/v KOH in ethanol (506 µL, 0.64 mmol) to produce the title compound (75 mg, 69% yield).

MS: 494.24 (M+H⁺); H¹-NMR (DMSO-d₆): 9.03 (d, 1H, J=9.3), 8.63 (s, 1H), 8.42 (d, 1H, J=8.1), 8.26 (m, 3H), 8.15 (d, 1H, J=8.4), 7.97 (d, 1H, J=9), 7.40 (m, 1H), 6.74 (m, 2H), 4.42 (m, 1H), 3.81 (s, 3H), 3.55 (s, 1H), 2.32 (m, 2H), 2.07 (m, 2H), 1.86 (m, 2H), 1.61 (m, 1H), 1.36 (m, 3H)

Example 164

Preparation of 1-cyclohexyl-2-[2-(2-hydroxy-4,6-dimethoxy-phenyl)-quinolin-6-yl]-1H-benzoimidazole-5-carboxylic acid (Compound 452)

Following the procedure and workup for Compound 354, Compound 354e (100 mg, 0.256 mmol) was reacted with -(2-hydroxy-4,6-dimethoxy-phenyl)-ethanone (0.256 mmol) in ethanol (2 mL) using 10% w/v KOH in ethanol (506 µL, 0.64 mmol) to produce the title compound (85 mg, 65% yield).

MS: 524.25 (M+H⁺); H¹-NMR (DMSO-d₆): 8.98 (d, 1H, J=8.1), 8.59 (s, 1H), 8.40 (d, 1H, J=8.7), 8.33 (m, 2H), 8.24 (d, 1H, J=9), 8.15 (d, 1H, J=8.7), 7.97 (d, 1H, J=8.7), 6.31 (m, 2H), 4.40 (m, 1H), 3.86 (s, 3H), 3.84 (s, 3H), 3.55 (s, 1H), 2.32 (m, 2H), 2.08 (m, 2H), 1.83 (m, 2H), 1.62 (m, 1H), 1.37 (m, 3H)

Example 165

Preparation of 2-[2-(4'-chloro-biphenyl-3-yl)-quinolin-6-yl]-1-cyclohexyl-1H-benzoimidazole-5-carboxylic acid (Compound 483)

In dried vial with a Teflon lined screw cap, a solution of Compound 482 (156 mg, 0.31 mmol), 4-chlorophenylboronic acid (73 mg, 0.465 mmol), and Palladium Tetrakis (37 mg, 0.031 mmol) in toluene (9 mL), methanol (2 mL), and saturated sodium bicarbonate in water (900 µL) was degassed, flushed with argon, and sealed. The reaction was stirred for 16 h at 90° C. The completed reaction was then evaporated to dryness, purified via HPLC, and converted to the HCl salt using the standard procedure (as described in Compound 516) to produce the title compound (73 mg, 42% yield).

MS: 559.23 (M+H⁺); Hf-NMR (DMSO-d₆): 8.76 (d, 1H, J=9), 8.53 (m, 3H), 8.34 (m, 4H), 8.13 (dd, 1H, J=8.7, 1.8), 8.05 (dd, 1H, J=8.7, 1.5), 7.86 (m, 3H), 7.70 (t, 1H, J=7.8), 7.57 (m, 2H), 4.47 (m, 1H), 3.55 (s, 1H), 2.33 (m, 2H), 2.13 (m, 2H), 1.85 (m, 2H), 1.61 (m, 1H), 1.36 (m, 3H)

Example 166

Preparation of 2-[2-(4'-cyano-4-methoxy-biphen-2-yl)-quinolin-6-yl]-1-cyclohexyl-1H-benzoimidazole-5-carboxylic acid (Compound 365)

Step 1: 2-[2-(2-Bromo-5-methoxy-phenyl)-quinolin-6-yl]-1-cyclohexyl-1H-benzoimidazole-5-carboxylic acid (Compound 365a)

Following the procedure and workup for Compound 354, Compound 354e (2.28 g, 5.83 mmol) was reacted with 1-(2-bromo-5-methoxy-phenyl)-ethanone (1.335 g, 5.83 mmol) (the ethanone was prepared by reacting 1-(2-bromo-5-methoxy)benzoic acid with thionyl chloride to give 1-(2-bromo-5-methoxy) benzoyl chloride which is further reacted with dimethyl zinc to give the ethanone) in ethanol (45 mL) using 10% w/v KOH in ethanol (11.57 m, 17.5 mmol) to the title intermediate (2.80 g, 86% yield).

MS: 557.14 (M+H⁺); HPLC Procedure C, retention time=2.82 min.

Step 2: 2-[2-(2-Bromo-5-methoxy-phenyl)-quinolin-6-yl]-1-cyclohexyl-1H-benzoimidazole-5-carboxylic acid Methyl Ester (Compound 365b)

In a flame dried flask with stir bar, the product of the previous reaction (1.35 g, 2.43 mmol) was dissolved in anhydrous methanol (70 mL) and 4N HCl in dioxane (10 mL) was added. The reaction was refluxed at 60° C. overnight. The completed reaction was then evaporated to an oil, coevaporated 3 times with 50 mL anhydrous methanol, and foamed from acetonitrile to produce the title intermediate (1.38 g, 99% yield).

MS: 573.12 (M+H⁺); HPLC Procedure C, retention time=3.25 min.

Step 3: 2-[2-(4'-Cyano-4-methoxy-biphen-2-yl)-quinolin-6-yl]-1-cyclohexyl-1H-benzoimidazole-5-carboxylic acid (Compound 365)

In a flame dried vial with a Teflon lined screw cap, a solution of the product of the previous reaction (100 mg, 0.175 mmol), 4-cyanophenylboronic acid (31 mg, 0.2625 mmol), and Palladium Tetrakis (20 mg, 0.0175 mmol) in toluene (6.5 mL), methanol (1.6 mL), and saturated sodium bicarbonate in water (800 ul) was degassed, flushed with argon, and sealed. The reaction was stirred for 16 hours at 90° C. The vial was then cooled to room temperature and 10% w/v KOH in methanol (2 mL, 3.5 mmol) was added. The reaction was resealed and stirred at 70° C. for 1 hour. The completed reaction was then evaporated to dryness, purified via HPLC, and converted to the HCl salt using the standard procedure (as described for Compound 516) to produce the title compound.

MS: 579.29 (M+H⁺); H¹-NMR (DMSO-d₆): δ (ppm) 8.44-8.41 (m, 2H), 8.33 (s, 1H), 8.24-8.18 (m, 2H), 8.09-8.00 (m, 2H), 7.7-7.68 (m, 2H), 7.50 (d, 1H, J=8.7 Hz), 7.35-7.21 (m, 5H), 4.42 (m, 1H), 3.89 (s, 3H), 2.33-1.28 (m 10H)

Example 167

Preparation of 2-[2-(4'-carbamoyl-4-methoxy-biphen-2-yl)-quinolin-6-yl]-1-cyclohexyl-1H-benzoimidazole-5-carboxylic acid (Compound 382)

In a flame dried vial with a Teflon lined screw cap, a solution of Compound 365b (100 mg, 0.175 mmol), 4-amidophenylboronic acid (31 mg, 0.2625 mmol), and Palladium Tetrakis (20 mg, 0.0175 mmol) in toluene (6.5 mL), methanol (1.6 mL), and saturated sodium bicarbonate in water (800 ul) was degassed, flushed with argon, and sealed. The reaction was stirred for 16 hours at 90° C. The vial was then cooled to room temperature and 10% w/v KOH in methanol (2 mL, 3.5 mmol) was added. The reaction was resealed and stirred at 70° C. for 1 hour. The completed reaction was then evaporated to dryness, purified via HPLC, and converted to the HCl salt using the standard procedure (as described for Compound 516) to produce the title compound.

MS: 597.30 (M+H$^+$); H$^1$-NMR (DMSO-d$_6$): δ (ppm) 8.39-8.19 (m, 5H), 8.09 (d, 1H, J=9.3 Hz), 7.99 (d, 1H, J=8.4 Hz), 7.91 (m, 1H), 7.74-7.71 (m, 2H), 7.50 (d, 1H, J=8.1 Hz), 7.33-7.31 (m, 2H), 7.23-7.17 (4H), 4.43 (m, 1H), 3.88 (s, 3H), 2.33-1.33 (m 10H)

Example 168

Preparation of 2-[2-(3'-chloro-4'-fluoro-4-methoxy-biphen-2-yl)-quinolin-6-yl]-1-cyclohexyl-1H-benzoimidazole-5-carboxylic acid (Compound 366)

In dried vial with a Teflon lined screw cap, a solution of Compound 365b (100 mg, 0.175 mmol), 4-fluoro-3-chlorophenylboronic acid (61 mg, 0.2625 mmol), and Palladium Tetrakis (20 mg, 0.0175 mmol) in toluene (6.5 mL), methanol (1.6 mL), and saturated sodium bicarbonate in water (800 ul) was degassed, flushed with argon, and sealed. The reaction was stirred for 16 hours at 90° C. The vial was then cooled to room temperature and 10% w/v KOH in methanol (2 mL, 3.5 mmol) was added. The reaction was resealed and stirred at 70° C. for 1 hour. The completed reaction was then evaporated to dryness, purified via HPLC, and converted to the HCl salt using the standard procedure (as described for Compound 516) to produce the title compound (7 mg, 7% yield).

MS: 606.20 (M); H$^1$-NMR (DMSO-d$_6$): 8.40 (m, 2H), 8.31 (s, 1H), 8.19 (m, 2H), 8.05 (d, 1H, J=9), 7.96 (d, 1H, J=8.1), 7.49 (d, 1H, J=8.4), 7.37 (m, 1H), 7.30 (m, 2H), 7.20 (m, 2H), 6.98 (s, 1H), 4.40 (m, 1H), 3.75 (s, 3H), 3.55 (s, 1H), 2.30 (m, 2H), 2.05 (m, 2H), 1.85 (m, 2H), 1.63 (m, 1H), 1.30 (m, 3H)

Example 169

Preparation of 1-cyclohexyl-2-[2-(4-methoxy-4'-nitro-biphen-2-yl)-quinolin-6-yl]-1H-benzoimidazole-5-carboxylic acid (Compound 383)

Following the full procedure and workup for Compound 366, Compound 365b (100 mg, 0.175 mmol) was reacted with 4-nitrophenylboronic acid (62 mg, 0.2625 mmol) to produce the title compound (15 mg, 14% yield).

MS: 599.26 (M+H$^+$); H$^1$-NMR (DMSO-d$_6$): 8.40 (m, 2H), 8.29 (s, 1H), 8.10 (m, 5H), 7.97 (m, 1H), 7.53 (d, 1H, J=8.4), 7.36 (m, 4H), 7.24 (m, 1H), 4.40 (s, 1H), 3.90 (s, 3H), 3.55 (s, 1H), 2.30 (m, 2H), 2.06 (m, 2H), 1.84 (m, 2H), 1.62 (s, 1H), 1.32 (m, 3H)

Example 170

Preparation of 1-cyclohexyl-2-[2-(4'-dimethylamino-4-methoxy-biphen-2-yl)-quinolin-6-yl]-1H-benzoimidazole-5-carboxylic acid (Compound 401)

Following the full procedure and workup for Compound 366, Compound 365b (100 mg, 0.175 mmol) was reacted with 4-dimethylaminophenylboronic acid (44 mg, 0.2625 mmol) to produce the title compound (27 mg, 26% yield).

MS: 597.32 (M+H$^+$); H$^1$-NMR (DMSO-d$_6$): 8.34 (m, 4H), 8.16 (d, 1H, J=9.6), 8.06 (d, 1H, J=9.3), 7.96 (m, 1H), 7.42 (d, 1H, J=9), 7.30 (s, 1H), 7.17 (m, 3H), 7.07 (m, 3H), 4.40 (m, 1H), 3.87 (s, 3H), 2.92 (s, 6H), 2.31 (m, 2H), 2.08 (m, 2H), 1.82 (m, 2H), 1.16 (m, 1H), 1.36 (m, 3H)

Example 171

Preparation of 1-cyclohexyl-2-[2-(4-methoxy-3'-nitro-biphen-2-yl)-quinolin-6-yl]-1H-benzoimidazole-5-carboxylic acid (Compound 420)

Following the full procedure and workup for Compound 366, Compound 365b (100 mg, 0.175 mmol) was reacted with 3-nitrophenylboronic acid (44 mg, 0.2625 mmol) to produce the title compound (7 mg, 7% yield).

MS: 599.26 (M+H$^+$); H$^1$-NMR (DMSO-d$_6$): 8.36 (m, 3H), 8.13 (d, 2H, J=9), 8.02 (m, 4H), 7.58 (d, 1H, J=9), 7.50 (m, 2H), 7.37 (m, 2H), 7.24 (m, 1H), 4.37 (m, 1H), 3.90 (s, 3H), 3.55 (s, 1H), 2.28 (m, 2H), 2.06 (m, 2H), 1.85 (m, 2H), 1.61 (m, 1H), 1.34 (m, 3H)

Example 172

Preparation of 1-cyclohexyl-2-[2-(4-methoxy-4'-trifluoromethyl-biphen-2-yl)-quinolin-6-yl]-1H-benzoimidazole-5-carboxylic acid (Compound 436)

Following the full procedure and workup for Compound 366, Compound 365b (100 mg, 0.175 mmol) was reacted with 4-trifluoromethylphenylboronic acid (50 mg, 0.2625 mmol) to produce the title compound (14 mg, 12% yield).

MS: 622.27 (M+H$^+$); H$^1$-NMR (DMSO-d$_6$): 8.40 (m, 2H), 8.32 (s, 1H), 8.21 (d, 2H, J=8.4), 8.06 (dd, 1H, J=8.7, 1.5), 8.00 (d, 1H, J=8.7), 7.58 (d, 2H, J=8.7), 7.51 (d, 1H, J=8.4), 7.32 (m, 4H), 7.22 (m, 2H), 4.45 (m, 1H), 3.89 (s, 3H), 3.55 (s, 1H), 2.32 (m, 2H), 2.07 (m, 2H), 1.84 (m, 2H), 1.06 (m, 1H), 1.35 (m, 3H)

Example 173

Preparation of 1-cyclohexyl-2-[2-(2-furan-2-yl-5-methoxy-phenyl)-quinolin-6-yl]-1H-benzoimidazole-5-carboxylic acid (Compound 454)

Following the full procedure and workup for Compound 366, Compound 365b (100 mg, 0.175 mmol) was reacted with 2-furanboronic acid (30 mg, 0.2625 mmol) to produce the title compound (5 mg, 5% yield).

MS: 544.25 (M+H$^+$); H$^1$-NMR (DMSO-d$_6$): 8.51 (d, 1H, J=8.4), 8.42 (s, 1H), 8.28 (m, 2H), 8.09 (m, 2H), 7.92 (m, 2H), 7.68 (d, 1H, J=7.8), 7.48 (s, 1H), 7.40 (d, 1H, J=8.4), 7.17 (m, 1H), 6.40 (s, 1H), 6.06 (m, 1H), 4.45 (m, 1H), 3.86 (s, 3H), 2.34 (m, 2H), 2.08 (m, 2H), 1.85 (m, 2H), 1.62 (m, 1H), 1.34 (m, 3H)

Example 174

Preparation of 1-cyclohexyl-2-[2-(4,4'-dimethoxy-biphen-2-yl)-quinolin-6-yl]-1H-benzoimidazole-5-carboxylic acid (Compound 468)

Following the full procedure and workup for Compound 366, Compound 365b (100 mg, 0.175 mmol) was reacted with 4-methoxyphenylboronic acid (40 mg, 0.2625 mmol) to produce the title compound (15 mg, 15% yield).

MS: 584.29 (M+H$^+$); H$^1$-NMR (DMSO-d$_6$): 8.37 (m, 4H), 8.20 (d, 1H, J=9.6), 8.10 (d, 1H, J=8.1), 8.00 (d, 1H, J=9), 7.42 (d, 1H, J=8.4), 7.30 (d, 1H, J=1.5), 7.17 (m, 2H), 7.03 (d, 2H, J=8.1), 6.81 (d, 2H, J=8.7), 4.43 (m, 1H), 3.88 (s, 3H), 3.68 (s, 3H), 3.55 (s, 1H), 2.32 (m, 2H), 2.08 (m, 2H), 1.84 (m, 2H), 1.61 (m, 1H), 1.34 (m, 3H)

Example 175

Preparation of 2-[2-(4'-carboxy-4-methoxy-biphen-2-yl)-quinolin-6-yl]-1-cyclohexyl-1H-benzoimidazole-5-carboxylic acid (Compound 421)

Following the full procedure and workup for Compound 366, Compound 365b (100 mg, 0.175 mmol) was reacted with methyl 4-boronic acid benzoate (47 mg, 0.2625 mmol) to produce the title compound (22 mg, 21% yield).

MS: 598.26 (M+H$^+$); H$^1$-NMR (DMSO-d$_6$): 8.32 (m, 2H), 8.21 (d, 1H, J=8.7), 8.13 (d, 1H, J=8.7), 8.03 (m, 2H), 7.95 (m, 1H), 7.84 (d, 1H, J=8.7), 7.76 (d, 2H, J=8.4), 7.50 (d, 1H, J=8.4), 7.33 (d, 1H, J=2.4), 7.21 (m, 3H), 4.41 (m, 1H), 3.89 (s, 3H), 3.55 (s, 1H), 2.29 (m, 2H), 2.05 (m, 2H), 1.83 (m, 2H), 1.61 (m, 1H), 1.32 (m, 3H)

Example 176

Preparation of 2-[2-(3'-carboxy-4-methoxy-biphen-2-yl)-quinolin-6-yl]-1-cyclohexyl-1H-benzoimidazole-5-carboxylic acid (Compound 437

Following the full procedure and workup for Compound 366, Compound 365b (100 mg, 0.175 mmol) was reacted with ethyl 3-boronic acid benzoate (51 mg, 0.2625 mmol) to produce the title compound (26 mg, 23% yield).

MS: 598.27 (M+H$^+$); H$^1$-NMR (DMSO-d$_6$): 8.31 (m, 2H), 8.20 (d, 1H, J=8.7), 8.11 (d, 1H, J=9), 8.03 (m, 1H), 7.93 (m, 1H), 7.74 (m, 2H), 7.49 (d, 1H, J=8.7), 7.31 (m, 3H), 7.19 (m, 3H), 4.40 (m, 1H), 3.89 (s, 3H), 3.55 (s, 1H), 2.29 (m, 2H), 2.04 (m, 2H), 1.84 (m, 2H), 1.61 (m, 1H), 1.31 (m, 3H)

Example 177

Preparation of 1-Cyclohexyl-2-[2-(4'-fluoro-4-methoxy-biphen-2-yl)-quinolin-6-yl]-1H-benzoimidazole-5-carboxylic acid (Compound 455) and Ethyl 1-Cyclohexyl-2-[2-(4'-fluoro-4-methoxy-biphen-2-yl)-quinolin-6-yl]-1H-benzoimidazole-5-carboxylic acid (Compound 554)

Following the full procedure and workup for Compound 366, Compound 365b (100 mg, 0.175 mmol) was reacted with 4-fluorophenylboronic acid (37 mg, 0.2625 mmol) to produce both the title compound (9 mg, 8% yield), as well as the ester of the same, Compound 554.

Compound 516: MS: 572.27 (M+H$^+$); H$^1$-NMR (DMSO-d$_6$): 8.36 (m, 2H), 8.30 (d, 1H, J=1.8), 8.24 (d, 1H, J=8.7), 8.17 (d, 1H, J=9), 8.07 (dd, 1H, J=8.7, 1.8), 7.98 (dd, 1H, J=8.7, 1.5), 7.45 (d, 1H, J=8.7), 7.31 (d, 1H, J=2.7), 7.13 (m, 6H), 4.41 (m, 1H), 3.87 (s, 3H), 3.55 (s, 1H), 2.33 (m, 2H), 2.06 (m, 2H), 1.84 (m, 2H), 1.62 (m, 1H), 1.32 (m, 3H)

Compound 554: MS: 586.30 (M+H$^+$); H$^1$-NMR (DMSO-d$_6$): 8.35 (m, 3H), 8.25 (d, 1H, J=8.7), 8.16 (d, 1H, J=8.7), 8.06 (dd, 1H, J=8.7, 1.8), 7.97 (dd, 1H, J=8.4, 1.5), 7.45 (d, 1H, J=8.7), 7.31 (d, 1H, J=3), 7.14 (m, 6H), 4.41 (m, 1H), 3.90 (s, 3H), 3.87 (s, 3H), 3.55 (s, 1H), 2.29 (m, 2H), 2.05 (m, 2H), 1.84 (m, 2H), 1.61 (m, 1H), 1.34 (m, 3H)

Example 178

Preparation of 1-cyclohexyl-2-[2-(4'-hydroxy-4-methoxy-biphen-2-yl)-quinolin-6-yl]-1H-benzoimidazole-5-carboxylic acid (Compound 469)

Following the full procedure and workup for Compound 366, Compound 365b (100 mg, 0.175 mmol) was reacted with 4-phenolboronic acid (36 mg, 0.2625 mmol) to produce the title compound (10 mg, 8% yield).

MS: 570.27 (M+H$^+$); H$^1$-NMR (DMSO-d$_6$): 8.36 (m, 3H), 8.21 (d, 1H, J=9), 8.10 (dd, 1H, J=8.4, 1.2), 8.00 (dd, 1H, J=8.7, 1.5), 7.56 (m, 1H), 7.40 (d, 1H, J=8.7), 7.31 (d, 1H, J=2.7), 7.15 (m, 2H), 6.90 (d, 2H, J=8.7), 6.62 (d, 2H, J=8.4), 4.45 (m, 1H), 3.86 (s, 3H), 3.54 (s, 1H), 2.31 (m, 2H), 2.08 (m, 2H), 1.84 (m, 2H), 1.60 (m, 1H), 1.35 (m, 3H)

Example 179

Preparation of 1-cyclohexyl-2-[2-(3',4'-dichloro-4-methoxy-biphen-2-yl)-quinolin-6-yl]-1H-benzoimidazole-5-carboxylic acid (Compound 403)

Following the full procedure and workup for Compound 366, Compound 365b (100 mg, 0.175 mmol) was reacted with 3,4-dichlorophenylboronic acid (50 mg, 0.2625 mmol) to produce the title compound (5 mg, 4% yield).

MS: 622.20 (M+H$^+$); H$^1$-NMR (DMSO-d$_6$): 8.40 (d, 1H, J=9), 8.34 (m, 1H), 8.27 (m, 1H), 8.17 (d, 1H, J=8.4), 8.06 (m, 2H), 7.93 (m, 1H), 7.50 (d, 1H, J=8.4), 7.42 (m, 2H), 7.31 (m, 2H), 7.19 (dd, 1H, J=9, 2.7), 6.96 (dd, 1H, J=8.1, 1.2), 4.45 (m, 1H), 3.88 (s, 3H), 2.29 (m, 2H), 2.05 (m, 2H), 1.84 (m, 2H), 1.61 (m, 1H), 1.31 (m, 3H)

Example 180

Preparation of 2-[2-(3'-chloro-4-methoxy-biphen-2-yl)-quinolin-6-yl]-1-cyclohexyl-1H-benzoimidazole-5-carboxylic acid (Compound 422)

Following the full procedure and workup for Compound 366, Compound 365b (100 mg, 0.175 mmol) was reacted with 3-chlorophenylboronic acid (41 mg, 0.2625 mmol) to produce the title compound (20 mg, 17% yield).

MS: 588.23 (M+H$^+$); H$^1$-NMR (DMSO-d$_6$): 8.39 (m, 2H), 8.30 (d, 1H, J=1.8), 8.20 (m, 2H), 8.06 (dd, 1H, J=8.7, 1.8), 7.98 (dd, 1H, J=8.4, 1.5), 7.49 (d, 1H, J=7.5), 7.31 (d, 1H, J=2.7), 7.24 (m, 6H), 6.99 (m, 1H), 4.41 (m, 1H), 3.88 (s, 3H), 3.55 (s, 1H), 2.31 (m, 2H), 2.06 (m, 2H), 1.84 (m, 2H), 1.60 (m, 1H), 1.31 (m, 3H)

Example 181

Preparation of 1-cyclohexyl-2-[2-(4-methoxy-4'-methyl-biphen-2-yl)-quinolin-6-yl]-1H-benzoimidazole-5-carboxylic acid (Compound 438)

Following the full procedure and workup for Compound 366, Compound 365b (100 mg, 0.175 mmol) was reacted with p-tolylboronic acid (36 mg, 0.2625 mmol) to produce the title compound (12 mg, 12% yield).

MS: 568.30 (M+H$^+$); H$^1$-NMR (DMSO-d$_6$): 8.32 (m, 4H), 7.16 (d, 1H, J=9), 8.07 (dd, 1H, J=8.7, 2.1), 7.97 (dd, 1H, J=8.7, 1.8), 7.42 (d, 1H, J=8.7), 7.30 (d, 1H, J=2.7), 7.15 (m,

2H), 7.02 (m, 4H), 4.42 (m, 1H), 3.87 (s, 3H), 3.54 (s, 1H), 2.30 (m, 2H), 2.24 (s, 3H), 2.06 (m, 2H), 1.84 (m, 2H), 1.63 (m, 1H), 1.32 (m, 3H)

Example 182

Preparation of 1-cyclohexyl-2-[2-(4-methoxy-3'-methyl-biphen-2-yl)-quinolin-6-yl]-1H-benzoimidazole-5-carboxylic acid (Compound 367)

Following the full procedure and workup for Compound 366, Compound 365b (100 mg, 0.175 mmol) was reacted with m-tolylboronic acid (36 mg, 0.2625 mmol) to produce the title compound (27 mg, 27% yield).

MS: 568.29 (M+H$^+$); H$^1$-NMR (DMSO-d$_6$): 8.30 (m, 4H), 8.16 (d, 1H, J=8.7), 8.07 (dd, 1H, J=8.4, 1.8), 7.97 (dd, 1H, J=9, 1.8), 7.44 (d, 1H, J=8.4), 7.32 (d, 1H, J=2.7), 7.16 (m, 2H), 7.04 (m, 3H), 6.78 (d, 1H, J=7.2), 4.41 (m, 1H), 3.87 (s, 3H), 3.55 (s, 1H), 2.29 (m, 2H), 2.20 (s, 3H), 2.06 (m, 2H), 1.84 (m, 2H), 1.61 (m, 1H), 1.31 (m, 3H)

Example 183

Preparation of 2-[2-(4'-aminomethyl-4-methoxy-biphen-2-yl)-quinolin-6-yl]-1-cyclohexyl-1H-benzoimidazole-5-carboxylic acid (Compound 384)

Following the full procedure and workup for Compound 366, Compound 365b (100 mg, 0.175 mmol) was reacted with 4-aminomethylphenylboronic acid (49 mg, 0.2625 mmol) to produce the title compound (48 mg, 46% yield).

MS: 583.31 (M+H$^+$); H$^1$-NMR (DMSO-d$_6$): 8.31 (m, 3H), 8.14 (d, 1H, J=8.7), 8.05 (dd, 1H, J=8.4, 1.8), 7.95 (dd, 1H, J=8.4, 1.2), 7.70 (m, 1H), 7.58 (m, 1H), 7.43 (d, 1H, J=8.4), 7.45 (d, 2H, J=8.4), 7.28 (d, 1H, J=2.4), 7.17 (m, 4H), 4.40 (m, 1H), 3.87 (s, 3H), 3.55 (s, 1H), 2.30 (m, 2H), 2.05 (m, 2H), 1.83 (m, 2H), 1.64 (m 1H), 1.33 (m, 3H)

Example 184

Preparation of 1-cyclohexyl-2-[2-(4'-ethoxy-4-methoxy-biphen-2-yl)-quinolin-6-yl]-1H-benzoimidazole-5-carboxylic acid (Compound 456)

Following the full procedure and workup for Compound 366, Compound 365b (100 mg, 0.175 mmol) was reacted with 4-ethoxyphenylboronic acid (44 mg, 0.2625 mmol) to produce the title compound (17 mg, 16% yield).

MS: 598.32 (M+H$^+$); H$^1$-NMR (DMSO-d$_6$): 8.35 (m, 4H), 8.23 (d, 1H, J=8.4), 8.12 (d, 1H, J=9), 8.02 (d, 1H, J=8.7), 7.42 (d, 1H, J=8.7), 7.32 (m, 1H), 7.16 (m, 2H), 7.02 (d, 2H, J=8.7), 6.78 (m, 2H), 4.43 (m, 1H), 3.94 (m, 2H), 3.86 (s, 3H), 3.54 (s, 1H), 2.32 (m, 2H), 2.08 (m, 2H), 1.84 (m, 2H), 1.61 (m, 1H), 1.34 (m, 3H), 1.27 (m, 3H)

Example 185

Preparation of 1-cyclohexyl-2-[2-(5-methoxy-2-thiophen-2-yl-phenyl)-quinolin-6-yl]-1H-benzoimidazole-5-carboxylic acid (Compound 470)

Following the full procedure and workup for Compound 366, Compound 365b (100 mg, 0.175 mmol) was reacted with 2-thiopheneboronic acid (34 mg, 0.2625 mmol) to produce the title compound (26 mg, 27% yield).

MS: 598.32 (M+H$^+$); H$^1$-NMR (DMSO-d$_6$): 8.48 (m, 2H), 8.34 (m, 2H), 8.27 (d, 1H, J=8.7), 8.12 (d, 1H, J=8.7), 8.04 (d, 1H, J=9), 7.56 (d, 1H, J=8.4), 7.40 (m, 2H), 7.30 (d, 1H, J=2.7), 7.17 (dd, 1H, J=8.4, 2.7), 6.91 (m, 1H), 6.77 (d, 1H, 2.7), 4.46 (m, 1H), 3.86 (s, 3H), 3.55 (s, 1H), 2.31 (m, 2H), 2.11 (m, 2H), 1.84 (m, 2H), 1.61 (m, 1H), 1.33 (m, 3H)

Example 186

Preparation of 1-cyclohexyl-2-{2-[2-(2,4-dimethoxy-pyrimidin-5-yl)-5-methoxy-phenyl]-quinolin-6-yl}-1H-benzoimidazole-5-carboxylic acid (Compound 484)

Following the full procedure and workup for Compound 366, Compound 365b (100 mg, 0.175 mmol) was reacted with 2,4-dimethoxypyrimidine-5-boronic acid (34 mg, 0.2625 mmol) to produce the title compound (8 mg, 7% yield).

MS: 616.30 (M+H$^+$); H$^1$-NMR (DMSO-d$_6$): 8.55 (d, 1H, J=9), 8.43 (s, 1H), 8.32 (d, 1H, J=0.9), 8.21 (d, 1H, J=8.7), 8.16 (s, 1H), 8.09 (m, 2H), 8.00 (m, 1H), 7.56 (d, 1H, J=8.7), 7.39 (m, 2H), 7.18 (dd, 1H, J=8.7, 2.7), 4.40 (m, 1H), 3.87 (m, 6H), 3.55 (s, 1H), 3.84 (s, 3H), 2.30 (m, 2H), 2.10 (m, 2H), 1.84 (m, 2H), 1.60 (m, 1H), 1.32 (m, 3H)

Example 187

Preparation of 2-[2-(2-bromo-phenyl)-quinolin-6-yl]-3-cyclohexyl-3H-imidazo[4,5-b]pyridine-6-carboxylic acid (Compound 477)

Step 1: 6-Hydroxy-5-nitronicotinic acid (Compound 477a)

A solution of 6-hydroxynicotinic acid (10 g, 71.89 mmol) in fuming nitric acid (100 mL) was stirred at 50° C. for 4 h. After evaporation of extra nitric acid, the solid was obtained and it was directly used in the next step reaction. MS: 185.02 (M+H$^+$).

Step 2: Ethyl 6-chloro-5-nitronicotinic Ester (Compound 477b)

A mixture of 6-hydroxy-5-nitronicotinic acid (Compound 477a) (1.5 g, 8.15 mmol), phosphorus pentachloride (3 g) and phosphoryl chloride (5 mL) was stirred at 100° C. for 2 h. Excess of phosphoryl chloride was removed under reduced pressure and to the residue was added anhydrous EtOH (2 mL) at 0° C. Water (50 mL) was added. The mixture was extracted with EtOAc. The combined organic phase was washed with water, dried over anhydrous Na$_2$SO$_4$ and evaporated to give the title intermediate (1.24 g, 66%). MS: 230.03 (M+H$^+$).

Step 3: 6-Cyclohexylamino-5-nitro-nicotinic acid Ethyl Ester (Compound 477c)

A mixture of ethyl 6-chloro-5-nitronicotinic ester (Compound 477b)(0.83 g, 3.60 mmol), DIEA (0.32 mL, 18.0 mmol) and cyclohexylamine (1.25 mL, 10.93 mmol) in MeCN (15 mL) was stirred at reflux under Ar overnight. After removal of solvent, the residue was purified by chromatography using CHCl$_3$-hexane (2:1) as the eluent to give the title intermediate (1.0 g, 95%). MS: 294.13 (M+H$^+$).

Step 4: 2-[2-(2-Bromo-phenyl)-quinolin-6-yl]-3-cyclohexyl-3H-imidazo[4,5-b]pyridine-6-carboxylic acid Ethyl Ester (Compound 477d)

(1) A mixture of Compound 477c (0.18 g, 0.614 mmol) and 5% Pd/C (20 mg) in MeOH was shaken under 40 psi of $H_2$ for 30 min. The mixture was filtered through Celite and washed with MeOH and DMF. The combined filtrate was evaporated to dryness to give the amine.

(2) A mixture of Compound 353a (0.217 g, 0.661 mmol), HBTU (0.26 g, 0.686 mmol) and DIEA (0.267 mL, 1.53 mmol) in DMF (10 mL) was stirred at room temperature for 30 min and then transferred to above amine. The resulting reaction mixture was stirred at room temperature for 6 h and evaporated to dryness.

(3) To this residue was added AcOH (8 mL) and the solution was stirred at reflux for 2 h. After removal of solvent by evaporation, the residue was purified by chromatography using $CHCl_3$-hexane (10:1) and $CHCl_3$-MeOH (100:1) as the eluents to give the title intermediate. Total yield was 69%. MS: 557.17 (M+H$^+$).

Step 5: 2-[2-(2-Bromo-phenyl)-quinolin-6-yl]-3-cyclohexyl-3H-imidazo[4,5-b]pyridine-6-carboxylic acid (Compound 477)

Compound 477d (0.139 g, 0.25 mmol) was dissolved in MeOH (3 mL) and 2 N aqueous NaOH (1.5 mL) was added. The mixture was stirred at 55° C. for 2 h and then neutralized with 5 N HCl to pH 3 at 0° C. The precipitates formed was collected by filtration and purified by RP HPLC (15% of buffer B to 95% of buffer B) to give the title compound. Yield 96%.

MS: 527.17, 529.17 (M+H$^+$); $^1$H NMR (DMSO-d$_6$) δ (ppm) 8.97 (d, 1H, J=2.1 Hz), 8.67 (d, 1H, J=8.1 Hz), 8.55 (d, 1H, J=1.5 Hz), 8.46 (d, 1H, J=1.5 Hz), 8.26 (d, 1H, J=8.7 Hz), 8.10 (dd, 1H, J=1.8, 8.7 Hz), 7.87 (d, 1H, J=8.4 Hz), 7.81 (dd, 1H, J=1.2, 8.1 Hz), 7.66 (d, 1H, J=2.1, 7.5 Hz), 7.57 (dt, 1H, J=1.2, 7.5 Hz), 7.45 (dt, 1H, J=1.2, 7.7 Hz), 4.42 (m, 1H), 2.72-2.68 (m, 2H), 2.07-2.00 (m, 2H), 1.83 (m, 5H), 1.65 (m, 1H), 1.30 (m, 4H).

Example 188

Preparation of 2-[2-(4'-chloro-biphen-2-yl)-quinolin-6-yl]-3-cyclohexyl-3H-imidazo[4,5-b]pyridine-6-carboxylic acid (Compound 490)

A mixture of Compound 477d (0.139 g, 0.25 mmol), 4-chlorobenzeneboronic acid (78 mg, 0.50 mmol) and Pd(PPh$_3$)$_4$ (20 mg) in toluene (8 mL), MeOH (2 mL) and saturated NaHCO$_3$ (0.8 mL) was stirred under Ar at 70° C. for 16 h. After evaporation of solvent, the residue was dissolved in CHCl$_3$ (30 mL) and filtered. The filtrate was evaporated to dryness. MS: 587.25 (M+H$^+$).

The residue was hydrolyzed with 2 N aqueous NaOH in MeOH according to procedure described in Compound 477. Purification was achieved by RP HPLC (15% of buffer B to 95% of buffer B) to give the title compound (0.116 g, 83%).

MS: 559.22 (M+H$^+$); $^1$H NMR (DMSO-d$_6$) δ (ppm) 8.97 (d, 1H, J=1.8 Hz), 8.54 (d, 1H, J=2.1 Hz), 8.43 (d, 1H, J=8.4 Hz), 8.39 (d, 1H, J=1.8 Hz), 8.25 (d, 1H, J=8.7 Hz), 8.11 (dd, 1H, J=1.8, 9.0 Hz), 7.81 (dd, 1H, J=2.1, 6.9 Hz), 7.65-7.60 (m, 2H), 7.54 (dd, 1H, J=2.4, 6.6 Hz), 7.33 (d, 2H, J=8.4 Hz), 7.24 (d, 1H, J=8.4 Hz), 7.19 (d, 2H, J=8.4 Hz), 4.40 (m, 1H), 2.72-2.67 (m, 2H), 2.03-1.99 (m, 2H), 1.83 (m, 5H), 1.65 (m, 1H), 1.29 (m, 4H).

Example 189

Preparation of (4'-chloro-2-{6-[1-cyclohexyl-5-(1H-tetrazol-5-yl)-1H-benzoimidazol-2-yl]-quinolin-2-yl}-biphenyl-4-yl)-pyrrolidin-1-yl-methanone (Compound 259)

Step 1: 1-[4'-Chloro-4-(pyrrolidine-1-carbonyl)-biphen-2-yl]-ethanone (Compound 259a)

A mixture of Compound 419c (0.29 g, 0.845 mmol), 4-chlorobenzeneboronic acid (0.159 g, 1.02 mmol)) and Pd(PPh$_3$)$_4$ (97 mg) in toluene (25 mL), MeOH (6 mL) and saturated NaHCO$_3$ (2.5 mL) was stirred under Ar at 70° C. for 16 h. After evaporation of solvent, the residue was dissolved in CHCl$_3$ (30 mL) and filtered. The filtrate was evaporated to dryness. The residue was purified by chromatography using CHCl$_3$-MeOH (80:1 to 30:1) as the eluent to give an oil (0.266 g, 96%). MS: 328.08 (M+H$^+$).

Step 2: 2-[4'-Chloro-4-(pyrrolidine-1-carbonyl)-biphen-2-yl]-quinoline-6-carboxylic acid (Compound 259e)

To a mixture of Compound 259a (0.388 g, 1.184 mmol) and Compound 7 (0.223 g, 1.243 mmol) was added a solution of KOH (0.234 g, 3.55 mmol) in EtOH (18 mL). The reaction mixture was stirred under Ar at 75° C. for 16 h. EtOH (10 mL) was added to make a clean solution, which was neutralized by adding 4 N HCl in dioxane (about 1 mL) to pH 3. After evaporation of solvent, H$_2$O (15 mL) was added and the precipitates were collected by filtration, washed with water and dried. Yield 0.125 g, 89%. MS: 457.12, 458.13 (M+H$^+$).

Step 3: (4'-Chloro-2-{6-[1-cyclohexyl-5-(1H-tetrazol-5-yl)-1H-benzoimidazol-2-yl]-quinolin-2-yl}-biphenyl-4-yl)-pyrrolidin-1-yl-methanone (Compound 259)

Compound 128 (91 mg, 0.316 mmol) was reduced to the corresponding amine by hydrogenation according to procedures used in the preparation of Compound 477d.

The amine was reacted with Compound 259e (0.125 g, 0.274 mmol) in the presence of HBTU (0.114 g, 0.30 mmol), followed cyclization in AcOH according to procedures described for the preparation of Compound 477d. Separation by RP HPLC (from 10% of buffer B to 85% of buffer B) gave the title compound (42 mg, 23%).

MS: 679.30 (M+H$^+$); $^1$H NMR (DMSO-d$_6$) δ (ppm) 8.45 (d, 1H, J=1.2 Hz), 8.40-8.37 (m, 2H), 8.29 (d, 1H, J=8.7 Hz), 8.24 (d, 1H, J=9.0 Hz), 8.10-8.06 (m, 2H), 7.92 (d, 1H, J=1.8 Hz), 7.76 (dd, 1H, J=1.8, 8.1 Hz), 7.59 (d, 1H, J=7.8 Hz), 7.35 (d, 2H, J=8.4 Hz), 7.24-7.20 (m, 3H), 4.44 (m, 1H), 3.55-3.49 (m, 4H), 2.43-2.2.28 (m, 2H), 2.09-2.06 (m, 2H), 1.92-1.85 (m, 5H), 1.68-1.62 (m, 1H), 1.45-1.29 (m, 4H).

Example 190

Preparation of 2-{2-[4'-chloro-4-(pyrrolidine-1-carbonyl)-biphen-2-yl]-quinolin-6-yl}-3-cyclohexyl-3H-imidazo[4,5-b]pyridine-6-carboxylic acid (Compound 539)

Compound 477c (0.104 g, 0.355 mmol) was hydrogenated over 5% Pd/C (11 mg) according to procedure (1) in the preparation of Compound 477d.

The amine was then reacted with Compound 259e (0.13 g, 0.284 mmol) in the presence of HBTU (0.135 g, 0.356 mmol), followed cyclization in AcOH and purification according to procedure (2) and (3) in the preparation of Compound 477d, resulting in the precursor ester of Compound 539.

Hydrolysis of the ester with 2N aqueous NaOH/MeOH to the acid and purification by HPLC to give the title compound (23 mg, 13%).

MS: 656.30 (M+H$^+$); $^1$H NMR (DMSO-d$_6$) δ (ppm) 8.96 (d, 1H, J=1.8 Hz), 8.53 (d, 1H, J=2.1 Hz), 8.37-8.34 (m, including d, 2H, J=8.1 Hz), 8.20 (d, 1H, J=8.7 Hz), 8.06 (dd, 1H, J=1.8, 8.4 Hz), 7.90 (d, 1H, J=1.8 Hz), 7.75 (dd, 1H, J=1.8, 7.8 Hz), 7.58 (d, 1H, J=7.5 Hz), 7.36 (d, 2H, J=8.4 Hz), 7.22-7.18 (m, 3H), 4.40 (m, 1H), 3.51-3.41 (m, 4H), 2.72-2.68 (m, 2H), 2.02-1.98 (m, 2H), 1.87 (m, 5H), 1.65 (m, 1H), 1.29-1.23 (m, 4H).

Example 191

Preparation of 14'-chloro-2-[6-(1-cyclohexyl-1H-benzoimidazol-2-yl)-quinolin-2-yl]-biphenyl-4-yl]-pyrrolidin-1-yl-methanone (Compound 540)

Compound 259e (50 mg, 0.109 mmol) was reacted with HBTU (62 mg, 0.163 mmol) in DMF (1.5 mL) in the presence of DIEA (38 μL, 0.219 mmol) at room temperature for 30 min. N-cyclohexyl-benzene-1,2-diamine (31.2 mg, 0.164 mmol), (prepared in the manner described for Compound 11 starting with 2-chloro-nitrobenzene instead of 4-chloro-3 nitro benzoic acid) was added and the mixture was stirred at room temperature for 16 h. After evaporation of solvent, to the residue was added AcOH (5 mL) and the mixture was stirred at reflux for 2 h. The solvent was evaporated and the residue was separated by RP HPLC (from 10% of buffer B to 85% of buffer B) to give the title compound (26 mg, 39%).

MS: 611.28 (M+H$^+$); $^1$H NMR (DMSO-d$_6$) δ (ppm) 8.47 (s, 1H), 8.40 (d, 1H, J=8.7 Hz), 8.31-8.28 (m, including d, 2H, J=8.7 Hz), 8.12 (d, 1H, J=8.4 Hz), 7.92-7.89 (m, 2H), 7.77 (dd, 1H, J=1.5, 8.1 Hz), 7.65-7.58 (m, 3H), 7.36 (d, 2H, J=8.1 Hz), 7.27 (d, 1H, J=8.1 Hz), 7.21 (d, 2H, J=8.7 Hz), 4.47 (m, 1H), 3.55-3.49 (m, 4H), 2.37-2.29 (m, 2H), 2.15-2.12 (m, 2H), 1.92-1.83 (m, 5H), 1.68-1.61 (m, 1H), 1.46-1.23 (m, 4H).

Example 192

Preparation of 2-(4'-chloro-4-methoxy-biphen-2-yl)-6-[1-cyclohexyl-5-(1H-tetrazol-5-yl)-1H-benzoimidazol-2-yl]-quinoline (Compound 525)

Step 1:1-(4'-Chloro-4-methoxy-biphen-2-yl)-ethanone (Compound 525a)

1-(2-Bromo-5-methoxyphenyl)ethanone (prepared as described in Step 1 of Example 166) (12 g, 52.39 mmol) was reacted with 4-chlorobenzeneboronic acid (9.02, 57.68 mmol) and the catalyst Pd(PPh$_3$)$_4$ (0.605 g) as described for Compound 477e. Purification by chromatography using CHCl$_3$-MeOH (80:1) as the eluent gave the title intermediate (12.67 g, 93%). MS: 261.08 (M+H$^+$), 283.07 (M+Na$^+$).

Step 2: 2-(4'-Chloro-4-methoxy-biphen-2-yl)-quinoline-6-carboxylic acid (Compound 525c)

Compound 7 (3.06 g. 11.72 mmol) was reacted with compound 525a (2.1 g, 11.72 mmol) and KOH (2.32 g, 35.16 mmol) in EtOH (150 mL) according to the procedure in the preparation of Compound 259e. Purification by chromatography using CHCl$_3$-MeOH (7:1) as the eluent gave the title intermediate (3.1 g, 91%). MS: 388.07 (M+H$^+$).

Step 3: Preparation of 2-(4'-Chloro-4-methoxy-biphen-2-yl)-6-[1-cyclohexyl-5-(1H-tetrazol-5-yl)-1H-benzoimidazol-2-yl]-quinoline (Compound 525)

Compound 128 (98 mg, 0.34 mmol) was reduced to the corresponding amine by hydrogenation according to procedure (1) in the preparation of Compound 477d.

The amine was reacted with compound 525c (0.11 g, 0.34 mmol) in the presence of HBTU (0.135 g, 0.356 mmol), followed by cyclization in AcOH according to procedure (2) in the preparation of Compound 477d. Separation by RP HPLC (from 20% of buffer B to 99% of buffer B) gave the title compound (51 mg, 25%).

MS: 612.26 (M+H$^+$). $^1$H NMR (DMSO-d$_6$) δ (ppm) 8.54 (d, 1H, J=1.6 Hz), 8.44-8.37 (m, 3H), 8.29 (d, 1H, J=8.7 Hz), 8.19 (d, 1H, J=9.0 Hz), 8.12 (d, 1H, J=8.7 Hz), 7.48-7.42 (m, 2H), 7.33-7.19 (m, 5H), 7.12 (d, 1H, J=8.4 Hz), 4.46 (m, 1H), 3.88 (s, 1H), 2.38-2.34 (m, 2H), 2.13-2.09 (m, 2H), 1.88-1.84 (m, 2H), 1.62 (m, 1H), 1.47-1.30 (m, 3H).

Example 193

Preparation of 2-[2-(4'-chloro-4-methoxy-biphen-2-yl)-quinolin-6-yl]-3-cyclohexyl-3H-imidazo[4,5-b]pyridine-6-carboxylic acid (Compound 537)

Step 1: 2-[2-(4'-Chloro-4-methoxy-biphen-2-yl)-quinolin-6-yl]-3-cyclohexyl-3H-imidazo[4,5-b]pyridine-6-carboxylic acid Ethyl Ester (Compound 537a)

Compound 477c (0.225 g, 0.767 mmol) was reduced to the corresponding amine by hydrogenation according to procedure (1) in the preparation of Compound 477d.

The amine was reacted with Compound 525c (0.314 g, 0.805 mmol) in the presence of HBTU (0.32 g, 0.844 mmol) and DIEA (0.47 mL, 2.68 mmol) in DMF (10 mL), followed cyclization in AcOH (10 mL) according to procedure (2) and (3) in the preparation of Compound 477d. Separation by RP HPLC (from 20% of buffer B to 99% of buffer B) gave the title intermediate (0.19 g, 40%).

Step 2: 2-[2-(4'-Chloro-4-methoxy-biphen-2-yl)-quinolin-6-yl]-3-cyclohexyl-3H-imidazo[4,5-b]pyridine-6-carboxylic acid (Compound 537)

Hydrolysis of the product from the previous reaction (63 mg, 0.102 mmol) with 2N aqueous NaOH/MeOH and purification by HPLC was accomplished using the procedures described for Compound 477 giving the title compound (31 mg, 52%).

MS: 589.24 (M+H$^+$); $^1$H NMR (DMSO-d$_6$) δ (ppm) 8.96 (d, 1H, J=1.8 Hz), 8.53 (d, 1H, J=2.1 Hz), 8.36-8.33 (m, 2H), 8.20 (d, 1H, J=8.4 Hz), 8.06 (dd, 1H, J=1.8, 9.0 Hz), 7.45 (d, 1H, J=8.4 Hz), 7.31-7.28 (m, 3H), 7.20-7.11 (m, 4H), 4.44-4.36 (m, 1H), 3.88 (s, 3H), 2.72-2.67 (m, 2H), 2.01-1.97 (m, 2H), 1.82 (m, 2H), 1.65 (m, 1H), 1.29-1.22 (m, 3H).

Example 194

Preparation of 2-[2-(4'-chloro-4-hydroxy-biphen-2-yl)-quinolin-6-yl]-3-cyclohexyl-3H-imidazo[4,5-b]pyridine-6-carboxylic acid (Compound 535) and 2-[2-(4'-chloro-4-hydroxy-biphen-2-yl)-quinolin-6-yl]-3-cyclohexyl-3H-imidazo[4,5-b]pyridine-6-carboxylic acid Ethyl Ester (Compound 538)

Compound 537a (71.8 mg) was dissolved in anhydrous CH$_2$Cl$_2$ (8 mL) and 1.0 M BBr$_3$ in CH$_2$Cl$_2$ (4 mL) was added dropwise at −70° C. The mixture was stirred at −70° C. for 1 h and at room temperature overnight. The mixture was cooled down to −70° C. again and MeOH (2 mL) was added dropwise. To the mixture was added 2 N aqueous NaOH (1 mL) at room temperature and neutralized with 5 N HCl to pH 3. After evaporation of solvent, the dry residue was dissolved in MeOH (10 mL) and filtered off insoluble precipitates. The filtrate was evaporated to dryness. Separation by RP HPLC (form 20% buffer B to 99% buffer B) gave the title compounds.

Compound 535: (25.8 mg) MS: 575.22 (M+H$^+$); $^1$H NMR (DMSO-d$_6$) δ (ppm) 9.88 (br s, 1H), 8.96 (d, 1H, J=1.8 Hz), 8.53 (d, 1H, J=1.8 Hz), 8.33-8.30 (m, 2H), 8.20 (d, 1H, J=9.0 Hz), 8.06 (dd, 1H, J=2.1, 9.0 Hz), 7.33 (d, 1H, J=8.1 Hz), 7.29-7.25 (m, 2H), 7.19 (d, 1H, J=2.4 Hz), 7.13-7.08 (m, 3H), 6.99 (dd, 1H, J=2.7, 8.4 Hz), 4.41 (m, 1H), 3.88 (s, 3H), 2.72-2.68 (m, 2H), 2.01-1.98 (m, 2H), 1.83 (m, 2H), 1.66 (m, 1H), 1.30 (m, 3H).

Compound 538: (10.6 mg): MS: 603.25 (M+H$^+$); $^1$H NMR (DMSO-d$_6$) δ (ppm) 8.98 (d, 1H, J=1.8 Hz), 8.55 (d, 1H, J=2.1 Hz), 8.33-8.30 (m, 2H), 8.20 (d, 1H, J=8.7 Hz), 8.06 (dd, 1H, J=1.8, 8.7 Hz), 7.32 (d, 1H, J=8.1 Hz), 7.30-7.25 (m, 3H), 7.19 (d, 1H, J=2.4 Hz), 7.13-7.08 (m, 3H), 6.99 (dd, 1H, J=2.4, 8.4 Hz), 4.42-4.34 (m, 3H), 2.72-2.67 (m, 2H), 2.02-1.98 (m, 2H), 1.83 (m, 2H), 1.67 (m, 1H), 1.37 (t, 3H, J=7.2 Hz), 1.29-1.23 (m, 3H).

Example 195

Preparation of 2-[2-(4'-chloro-4-methoxy-biphen-2-yl)-quinolin-6-yl]-3-cyclohexyl-3H-benzoimidazole-5-carboxylic acid (Compound 571)

Step 1: 3-Cyclohexylamino-4-nitro-benzoic acid (Compound 571a)

A mixture of 3-fluoro-4-nitrobenzoic acid (0.35 g, 1.891 mmol) and cyclohexylamine (2.17 mL, 18.91 mmol) in NMP (10 mL) was stirred under Ar at 85° C. for 6 h. The solvent was evaporated under high vacuum. The residue was purified by chromatography using CH$_3$Cl-MeOH (10:1) as the eluent to give the title intermediate in a quantitative yield. MS: 263.11 (M−H$^+$).

Step 2: 3-Cyclohexylamino-4-nitro-benzoic acid Ethyl Ester (Compound 571b)

A solution of the product of the previous step (0.4 g) in anhydrous EtOH (50 mL) was gently bubbled with anhydrous HCl gas for 4 h and the solution was left at room temperature for 16 h. The solvent was evaporated to dryness to give the title intermediate in a quantitative yield. MS: 293.14 (M+H$^+$).

Step 3: 2-[2-(4'-Chloro-4-methoxy-biphen-2-yl)-quinolin-6-yl]-3-cyclohexyl-3H-benzoimidazole-5-carboxylic acid (Compound 571)

The product from the previous step (0.14 g, 0.479 mmol) was reduced to the corresponding amine by hydrogenation according to the preparation of Compound 477d.

The amine was reacted with Compound 525c (0.215 g, 0.552 mmol) in the presence of HBTU (0.22 g, 0.58 mmol) and DIEA (0.17 mL, 0.976 mmol) in DMF (10 mL), followed cyclization in AcOH (10 mL) according to procedure (2) and (3) in the preparation of Compound 477d.

Hydrolysis of above ester with 2 N aqueous NaOH/MeOH and purification by HPLC was accomplished as described for Compound 477 to give the title compound (43.2 mg, 15%).

MS: 588.24 (M+H$^+$); $^1$H NMR (DMSO-d$_6$) δ (ppm) 8.48 (s, 1H), 8.42-8.38 (m, 2H), 8.27 (d, 1H, J=9.0 Hz), 8.10 (dd, 1H, J=1.8, 9.0 Hz), 8.03 (dd, 1H, J=1.5, 8.7 Hz), 7.89 (d, 1H, J=8.7 Hz), 7.46 (d, 1H, J=8.7 Hz), 7.32 (d, 1H, J=2.7 Hz), 7.29 (d, 2H, J=8.7 Hz), 7.25-7.19 (m, 2H), 7.13 (d, 2H, J=8.7 Hz), 4.52-4.45 (m, 1H), 3.87 (s, 3H), 2.27-2.12 (m, 4H), 1.86 (br s, 2H), 1.67 (br s, 1H), 1.34 (br, 3H).

Example 196

Preparation of 2-[2-(4'-chloro-4-methoxy-biphen-2-yl)-quinolin-6-yl]-1-ethyl-1H-benzoimidazole-5-carboxylic acid (Compound 534)

Step 1: Loading the resin with 4-chloro-3-nitrobenzoic acid (Resin 534a)

To a solution of 4-chloro-3-nitrobenzoic acid (0.605 g, 3 mmol) in ethanol (15 mL) and water (5 mL) was added dropwise 10% aqueous Cs$_2$CO$_3$ to adjust the solution to pH 7. The resulting mixture was evaporated to dryness and co-evaporated with toluene (20 mL) four times. The residue was then dried over P$_2$O$_5$ under high vacuum.

A mixture in anhydrous DMF (8 mL) of Merrifield resin HL (Nova Biochem, 100-200 mesh, loading: 1.34 mmol/g, 1.04 g) and the dry Cs-salt prepared above was gently agitated at 50° C. overnight. The solution was drained and the resin was washed with DMF (5 mL×5), DMF/H$_2$O (9:1 v/v, 5 mL×5), DMF (5 mL×5), and MeOH (5 mL×5). The resin was dried under high vacuum. Based on the increase of the resin weight, the loading of substitution was calculated to be 1.30 mmol/g.

Step 2: Amine Addition

A mixture of Resin 534a (0.308 g, 0.40 mmol), a 2.0 M solution of ethylamine in MeOH (3.9 mL, 7.8 mmol), and DIEA (0.82 mL, 4.68 mmol) in NMP (10 mL) was shaken for 16 h at room temperature. The solution was drained and the resin was washed with DMF (5 mL×5), MeOH (5 mL×5), and CH$_2$Cl$_2$ (5 mL×5). The resins was dried under high vacuum.

Step 3: Reduction of the Nitro Group

The resin was then suspended in DMF (10 mL) and SnCl$_2$.2H$_2$O (5.42 g, 24 mmol) was added. The mixture was shaken under Ar at room temperature for 32 h. The solution was drained and the resin was washed with DMF (5 mL×5), MeOH (5 mL×5), and CH$_2$Cl$_2$ (5 mL×5). The resin was dried under high vacuum.

Step 4: Formation of the Benzimidazole Ring

Compound 525c (0.38 g, 0.97 mmol) was reacted with HBTU (0.444 g, 1.2 mmol) in anhydrous DMF (5 mL) in the presence of DIEA (0.41 mL, 2.35 mmol) for 30 min. The mixture was then transferred to a suspension of amine-resin in DMF (5 mL). The reaction mixture was shaken at room temperature overnight. The solution was drained and the resin was washed with DMF (5 mL×5), MeOH (5 mL×5), and CH$_2$Cl$_2$ (5 mL×5). The resin was dried under high vacuum.

Step 5: Cleavage of the Resin

To the resin was added AcOH (10 mL) and the mixture was refluxed for 3 h. After evaporation of AcOH, TFA (3 mL) and TFMSA (0.3 mL) were added to the dry resin. The mixture was left at room temperature for 2 h. The resin was filtered off and washed with TFA (3 mL×3) and MeOH (3 mL×2). The filtrate was evaporated and the residue was neutralized with ammonium solution. The product was purified by reverse phase HPLC from 20% of Buffer B to 99% of Buffer A.

MS: 534.16 (M+H$^+$); $^1$H NMR (DMSO-d$_6$) δ (ppm) 8.50 (s, 1H), 8.42-8.34 (m, including d, 2H, J=8.4 Hz), 8.29-8.20 (m, including d, 2H, J=8.4 Hz), 8.08 (d, 1H, J=8.4 Hz), 8.02 (d, 1H, J=9.0 Hz), 7.46 (d, 1H, J=8.0 Hz), 7.33-7.07 (m, 7H), 4.53 (q, 2H, J=6.9 Hz), 3.88 (s, 3H), 1.45 (t, 3H, J=5.7 Hz).

Example 197

Preparation of 2-[2-(4'-chloro-4-methoxy-biphen-2-yl)-quinolin-6-yl]-1-cyclopropyl-1H-benzoimidazole-5-carboxylic acid (Compound 528)

The title compound was prepared from Resin 534a and cyclopropylamine according to the procedure described in the preparation of Compound 534.

MS: 546.16 (M+H$^+$); $^1$H NMR (DMSO-d$_6$) δ (ppm) 8.70 (s, 1H), 8.46-8.39 (m, 2H), 8.31 (s, 1H), 8.23 (d, 1H, J=9.0 Hz), 8.05 (d, 1H, J=8.4 Hz), 7.90 (d, 1H, J=2.1, 8.7 Hz), 7.48-7.42 (m, 2H), 7.35-7.28 (m, 2H), 7.25-7.07 (m, 4H), 4.12 (m, 1H), 3.88 (s, 3H), 1.19 (d, 2H, J=6.6 Hz), 0.76 (br s, 2H).

Example 198

Preparation of 2-[2-(4'-chloro-4-methoxy-biphen-2-yl)-quinolin-6-yl]-1-isopropyl-1H-benzoimidazole-5-carboxylic acid (Compound 527)

The title compound was prepared from Resin 534a and isopropylamine according to the procedure described in the preparation of Compound 534.

MS: 548.19 (M+H$^+$); $^1$H NMR (DMSO-d$_6$) δ (ppm) 8.38 (s, 1H), 8.36 (d, 1H, J=7.0 Hz), 8.32 (d, 1H, J=1.5 Hz), 8.24 (d, 1H, J=8.7 Hz), 8.14 (d, 1H, J=9.0 Hz), 8.09 (dd, 1H, J=2.1, 8.7 Hz), 7.99 (dd, 1H, J=1.5, 8.7 Hz), 7.46 (d, 1H, J=8.7 Hz), 7.32-7.27 (m, 3H), 7.22-7.18 (m, 2H), 7.14-7.11 (m, 2H), 4.89 (t, 1H, J=7.2 Hz), 3.88 (s, 3H), 1.69 (d, 6H, J=7.2 Hz).

Example 199

Preparation of 2-[2-(4'-chloro-4-methoxy-biphen-2-yl)-quinolin-6-yl]-1-(2-dimethylamino-ethyl)-1H-benzoimidazole-5-carboxylic acid (Compound 533)

The title compound was prepared from Resin 534a and N,N-dimethylethyleneamine according to the procedure described in the preparation of Compound 534.

MS: 577.22 (M+H$^+$); $^1$H NMR (DMSO-d$_6$) δ (ppm) 10.77 (br s, 1H), 8.47 (s, 1H), 8.42 (d, 1H, J=8.7 Hz), 8.32 (d, 1H, J=0.9 Hz), 8.26-8.21 (m, 2H), 8.00 (s, 2H), 7.45 (d, 2H, J=8.4 Hz), 7.32-7.26 (m, 2H), 7.22-7.17 (m, 2H), 7.14-7.11 (m, 2H), 4.88 (t, 2H, J=7.8 Hz), 3.88 (s, 3H), 3.83 (s, 6H), 3.61 (m, 2H).

Example 200

Preparation of 2-[2-(4'-chloro-4-methoxy-biphen-2-yl)-quinolin-6-yl]-1-cyclopentyl-1H-benzoimidazole-5-carboxylic acid (Compound 529)

The title compound was prepared from Resin 534a and cyclopentylamine according to the procedure described in the preparation of Compound 534.

MS: 574.21 (M+H$^+$); $^1$H NMR (DMSO-d$_6$) δ (ppm) 8.39 (d, 1H, J=8.7 Hz), 8.38 (s, 1H), 8.32 (d, 1H, J=1.5 Hz), 8.24 (d, 1H, J=8.7 Hz), 8.10 (dd, 1H, J=2.1, 8.8 Hz), 8.00 (dd, 1H, J=1.5, 8.7 Hz), 7.90 (d, 1H, J=8.4 Hz), 7.45 (d, 1H, J=8.4 Hz), 7.31-7.28 (m, 3H), 7.23-7.18 (m, 2H), 7.15-7.11 (m, 2H), 5.03 (q, 1H, J=9.3 Hz), 3.88 (s, 3H), 2.23 (m, 4H), 2.02 (m, 2H), 1.72-1.69 (m, 2H).

Example 201

Preparation of 2-[2-(4'-Chloro-4-methoxy-biphen-2-yl)-quinolin-6-yl]-1-isobutyl-1H-benzoimidazole-5-carboxylic acid (Compound 530)

The title compound was prepared from Resin 534a and isobutylamine according to the procedure described in the preparation of Compound 534.

MS: 562.22 (M+H$^+$); $^1$H NMR (DMSO-d$_6$) δ (ppm) 8.51 (s, 1H), 8.35 (d, 1H, J=9.0 Hz), 8.32 (s, 1H), 8.22 (br s, 2H), 8.03-7.95 (m, 2H), 7.45 (d, 1H, J=8.4 Hz), 7.34 (d, 1H, J=2.7 Hz), 7.29 (d, 2H, J=8.7 Hz), 7.20 (d, 1H, J=8.4 Hz), 7.18 (d, 1H, J=8.4 Hz), 7.12 (d, 2H, J=8.7 Hz), 4.41 (d, 2H, J=7.8 Hz), 3.88 (s, 3H), 1.98-1.93 (m, 1H), 0.68 (d, 6H, J=6.9 Hz).

Example 202

Preparation of 2-[2-(4'-chloro-4-methoxy-biphen-2-yl)-quinolin-6-yl]-1-(3-methyl-butyl)-1H-benzoimidazole-5-carboxylic acid (Compound 532)

The title compound was prepared from Resin 534a and isoamylamine according to the procedure described in the preparation Compound 534.

MS: 576.24 (M+H$^+$); $^1$H NMR (DMSO-d$_6$) δ (ppm) 8.49 (s, 1H), 8.37 (d, 1H, J=8.7 Hz), 8.32 (d, 1H, J=1.2 Hz), 8.25-8.17 (m, 2H), 8.03 (dd, 1H, J=1.3, 8.4 Hz), 7.94 (d, 1H, J=8.7 Hz), 7.46 (d, 1H, J=8.7 Hz), 7.33 (d, 1H, J=2.7 Hz), 7.28-7.18 (m, including d, 4H, J=8.4 Hz), 7.10 (d, 2H, J=8.4 Hz), 4.49 (t, 2H, J=7.2 Hz), 3.88 (s, 3H), 1.71-1.64 (m, 2H), 1.55-1.46 (m, 1H), 0.78 (d, 6H, J=6.6 Hz).

Example 203

Preparation of 2-[2-(4'-Chloro-4-methoxy-biphen-2-yl)-quinolin-6-yl]-1-(1-ethyl-propyl)-1H-benzoimidazole-5-carboxylic acid (Compound 564)

The title compound was prepared from Resin 534a and 1-ethylpropylamine according to the procedure described in the preparation of Compound 534.

MS: 576.25 (M+H$^+$); $^1$H NMR (DMSO-d$_6$) δ (ppm) 8.39 (d, 1H, J=8.4 Hz), 8.35-8.32 (m, 2H), 8.27 (d, 1H, J=8.7 Hz), 8.09-8.02 (m, 2H), 7.98 (d, 1H, J=9.0 Hz), 7.46 (d, 1H, J=8.7 Hz), 7.33 (d, 1H, J=3.0 Hz), 7.30 (d, 2H, J=8.4 Hz), 7.22-7.18 (m, including d, 2H, J=8.7 Hz), 7.13 (d, 2H, J=8.4 Hz), 4.35-4.30 (m, 1H), 3.88 (s, 3H), 2.25-2.15 (m, 2H), 2.05-1.96 (m, 2H), 0.70 (t, 6H, J=7.2 Hz).

Example 204

Preparation of 2-[2-(4'-chloro-4-methoxy-biphen-2-yl)-quinolin-6-yl]-1-cyclopropylmethyl-1H-benzoimidazole-5-carboxylic acid (Compound 531)

The title compound was prepared from Resin 534a and cyclopropylmethylamine according to the procedure described in the preparation of Compound 534.

MS: 560.21 (M+H$^+$); $^1$H NMR (DMSO-d$_6$) δ (ppm) 8.29 (s, 1H), 8.13 (d, 1H, J=8.4 Hz), 8.11 (d, 1H, J=1.2 Hz), 8.01 (m, 2H), 7.81-7.73 (m, 2H), 7.25 (d, 1H, J=8.4 Hz), 7.46 (d, 1H, J=8.7 Hz), 7.33 (d, 1H, J=2.7 Hz), 7.09 (d, 2H, J=8.7 Hz), 7.00 (d, 1H, J=8.4 Hz), 6.98 (d, 1H, J=8.4 Hz), 6.92 (d, 2H, J=8.7 Hz), 4.23 (d, 2H, J=6.9 Hz), 3.88 (s, 3H), 0.89 (m, 1H), 0.23-0.169 (m, 2H), 0.03-0.02 (m, 2H).

Example 205

Preparation of 2-[2-(4'-chloro-4-methoxy-biphen-2-yl)-quinolin-6-yl]-1-(tetrahydrofuran-2-yl-methyl)-1H-benzoimidazole-5-carboxylic acid (Compound 566)

The title compound was prepared from Resin 534a and tetrahydrofurfurylamine according to the procedure described in the preparation of Compound 534.
MS: 590.22 (M+H$^+$); $^1$H NMR (DMSO-d$_6$) δ (ppm) 8.49 (s, 1H), 8.31 (d, 1H, J=9.0 Hz), 8.29 (s, 1H), 8.22-8.15 (m, 2H), 7.97-7.89 (m, 2H), 7.45 (d, 1H, J=8.4 Hz), 7.31 (d, 1H, J=2.4 Hz), 7.28 (d, 2H, J=8.4 Hz), 7.19 (d, 1H, J=8.4 Hz), 7.17 (d, 1H, J=8.4 Hz), 7.11 (d, 2H, J=8.4 Hz), 4.61-4.42 (m, 2H), 4.22-4.18 (m, 1H), 3.88 (s, 3H), 1.99-1.90 (m, 2H), 1.77-1.1.67 (m, 2H), 1.58-1.49 (m, 2H).

Example 206

Preparation of 1-bicyclo[2.2.1]hept-2-yl-2-[2-(4'-chloro-4-methoxy-biphen-2-yl)-quinolin-6-yl]1H-benzoimidazole-5-carboxylic acid (Compound 568)

The title compound was prepared from Resin 534a and 2-aminonorbornane according to the procedure described in the preparation of Compound 534.
MS: 600.22 (M+H$^+$); $^1$H NMR (DMSO-d$_6$) δ (ppm) 8.39 (d, 1H, J=1.8 Hz), 8.34 (d, 1H, J=8.7 Hz), 8.29 (s, 1H), 8.20 (d, 1H, J=8.7 Hz), 8.12 (dd, 1H, J=1.8, 8.7 Hz), 8.00 (br s, 2H), 7.46 (d, 1H, J=8.4 Hz), 7.33 (d, 1H, J=2.7 Hz), 7.29 (d, 2H, J=8.7 Hz), 7.22-7.18 (m, 2H), 7.15-7.11 (m, 2H), 4.98-4.93 (m, 1H), 3.88 (s, 3H), 3.73-3.65 (m, 2H), 3.49-3.45 (m, 1H), 2.31 (br s, 1H), 2.04-1.93 (m, 1H), 1.86-1.77 (m, 1H), 1.56-1.45 (m, 3H), 1.33-1.30 (m, 1H).

Example 207

Preparation of 2-[2-(4'-chloro-4-methoxy-biphen-2-yl)-quinolin-6-yl]-1-(4-methyl-cyclohexyl)-1H-benzoimidazole-5-carboxylic acid (Compound 543) (Cis or Trans)

The title compound was prepared from Resin 534a and a mixture of cis and trans 4-methylcyclohexyl-amine according to the procedure described in the preparation of Compound 534.
MS: 602.25 (M+H$^+$); $^1$H NMR (DMSO-d$_6$) δ (ppm) 8.36-8.32 (m, 2H), 8.29 (d, 1H, J=1.5 Hz), 8.19 (d, 1H, J=8.7 Hz), 8.04 (dd, 1H, J=1.8, 8.7 Hz), 7.98 (dd, 1H, J=1.5, 8.7 Hz), 7.91 (d, 1H, J=8.4 Hz), 7.45 (d, 1H, J=8.4 Hz), 7.31-7.27 (m, including d, 3H, J=8.4 Hz), 7.20-7.17 (m, 2H), 7.12 (d, 2H, J=8.4 Hz), 4.42-4.33 (m, 1H), 3.88 (s, 3H), 2.44-2.34 (m, 2H), 1.97-1.94 (m, 1H), 1.86-1.83 (m, 2H), 1.62 (m, 4H), 1.13 (d, 3H, J=7.2 Hz).

Example 208

Preparation of 2-[2-(4'-chloro-4-methoxy-biphen-2-yl)-quinolin-6-yl]-1-(4-methyl-cyclohexyl)-1H-benzoimidazole-5-carboxylic acid (Compound 547) (Trans or Cis)

The title compound was prepared from Resin 534a and a mixture of cis and trans 4-methylcyclohexyl-amine according to the procedure described in the preparation of Compound 534.
MS: 602.25 (M+H$^+$); $^1$H NMR (DMSO-d$_6$) δ (ppm) 8.36-8.32 (m, 2H), 8.27 (d, 1H, J=1.5 Hz), 8.19 (d, 1H, J=8.7 Hz), 8.07-8.01 (m, 2H), 7.92 (dd, 1H, J=1.5, 8.7 Hz), 7.45 (d, 1H, J=8.4 Hz), 7.31-7.27 (m, including d, 3H, J=9.0 Hz), 7.20-7.17 (m, 2H), 7.12 (d, 2H, J=8.7 Hz), 4.42-4.33 (m, 1H), 3.88 (s, 3H), 2.44-2.36 (m, 2H), 2.03-1.99 (m, 2H), 1.82-1.78 (m, 2H), 1.62 (m, 2H), 1.06-1.02 (m, 1H), 0.89 (d, 3H, J=6.6 Hz).

Example 209

Preparation of 2-[2-(4'-chloro-4-methoxy-biphen-2-yl)-quinolin-6-yl]-1-(3,3,5-trimethyl-cyclohexyl)-1H-benzoimidazole-5-carboxylic acid (Compound 555)

The title compound was prepared from Resin 534a and 3,3,5-trimethylcyclohexylamine according to the procedure described in the preparation of Compound 534.
MS: 630.28 (M+H$^+$); $^1$H NMR (DMSO-d$_6$) δ (ppm) 8.35-8.32 (m, 2H), 8.29 (d, 1H, J=1.2 Hz), 8.19 (d, 1H, J=8.7 Hz), 8.10 (d, 1H, J=9.0 Hz), 8.05 (dd, 1H, J=1.5, 8.7 Hz), 7.93 (dd, 1H, J=1.5, 8.7 Hz), 7.45 (d, 1H, J=8.4 Hz), 7.32 (d, 1H, J=2.7 Hz), 7.27 (d, 2H, J=8.7 Hz), 7.23-7.17 (m, 2H), 7.09 (d, 2H, J=8.4 Hz), 4.71-4.62 (m, 1H), 3.88 (s, 3H), 2.25-2.15 (m, 1H), 1.94-1.87 (m, 2H), 1.63 (br s, 1H), 1.36-1.32 (m, 1H), 1.23-1.08 (m, 2H), 1.03 (s, 3H), 0.89 (d, 3H, J=7.2 Hz), 0.87 (s, 3H).

Example 210

Preparation of cyclohexyl-2-(4-oxo-2-phenyl-4H-chromen-6-yl)-1H-benzoimidazole-5-carboxylic acid (Compound 407)

Step 1: 4-Hydroxy-3-(3-phenyl-acryloyl)-benzoic acid (Compound 407a)

3-Acetyl-4-hydroxy-benzoic acid was prepared as described in J. Pfister et al. in *J. Med. Chem.* (1980), 23, 335-338. To an ice cooled solution of 3-acetyl-4-hydroxy-benzoic acid (4 g, 22.2 mmol) and benzaldehyde (2.44 mL, 24 mmol, 1.08 eq.) in 60 mL ethanol was added 20 mL of an 40% KOH solution. The resulting dark red solution was stirred under argon at ambient temperature until the reaction was complete as judged by TLC (2 days). Thereafter, the mixture was slowly poured into excess 6N HCl, and the resulting yellow precipitate was filtered off, washed with water and dried. The crude materials were recrystallized from THF-EtOH to yield 2.43 g of a yellow/brown solid (88% yield).
MS: 267.10 (M–H$^+$); H$^1$-NMR (d6-DMSO): δ (ppm) 12.88 (br s, 1H), 12.46 (s, 1H), 8.50 (d, 1H, J=2.1 Hz), 8.03 (dd, 1H, J=2.1 HZ, J=8.8 Hz), 7.85-7.93 (m, 3H), 7.77 (d, 1H, J=15.5 Hz), 7-44-7.48 (m, 3H), 7.08 (d, 1H, J=8.8 Hz)

Step 2: 4-Oxo-2-phenyl-4H-chromene-6-carboxylic acid (Compound 407b)

Bromine (216 μL, 1.13 eq.) was added to 4-hydroxy-3-(3-phenyl-acryloyl)-benzoic acid (1 g, 3.72 mmol) in acetic acid (37.5 mL). After the solution was stirred at ambient temperature for 1 day, 10% aqueous NaHSO$_3$ (62.5 mL) was added slowly. The resulting precipitate was filtered off, washed with water and suspended in ethanol (25 mL). MS: 426.93 (M+H$^+$).

Potassium hydroxide (861 mg, 3.5eq., 13.05 mmol) dissolved in water (12.5 mL) was added and stirring was continued for 4h. The reaction mixture was acidified with 2N HCL, and the precipitate formed was filtered off, washed with water, died and recrystallized to give 621 mg (62%) of product.

MS: 265.08 (M−H$^+$); H$^1$-NMR (d6-DMSO): δ (ppm) 8.57 (d, 1H, J=2.1 Hz), 8.30 (dd, 1H, J=2.1 Hz, J=8.5 Hz), 8.11-8.14 (m, 2H), 7.87 (d, 1H, 8.7 Hz), 7.58-7.89 (m, 3H), 7.12 (s, 1H).

Step 3: 1-Cyclohexyl-2-(4-oxo-2-phenyl-4H-chromen-6-yl)-1H-benzoimidazole-5-carboxylic acid (Compound 407)

4-Oxo-2-phenyl-4H-chromene-6-carboxylic acid (280 mg, 1.05 mmol) was dissolved in DMF (5 mL), and HATU (418 mg, 1.1 eq.) and diisopropyl ethylamine (402 μL) were added. After stirring at room temperature for 15 minutes, 3-amino-4-cyclohexylamino-benzoic acid ethyl ester (303 mg, 1.1 eq.) dissolved in 2 mL DMF was added. After stirring overnight, the reaction was evaporated, dissolved in ethyl acetate and washed with water and brine, dried with sodium sulfate, evaporated and dried overnight. The product was then refluxed in acetic acid for 4h, evaporated to dryness, and coevaporated 2 more times with toluene. Saponification proceeds by dissolving the residue in ethanol (10 mL), adding 10 eq. of 1N NaOH solution and stirring at 40° C. for 4 hr. The ethanol was evaporated, water was added and acidified. The resulting precipitate was purified via reverse-phase HPLC. Yield: 58 mg MS: 465.20 (M+H$^+$); H$^1$-NMR (MeOD): δ (ppm) 8.64 (d, 1H, J=2.3 Hz), 8.49 (s, 1H), 8.30-8.38 (m, 2H), 8.24 (dd, 1H, J=2.3 Hz, J=8.8 Hz), 8.12-8.17 (m, 3H), 7.59-7.66 (m, 3H), 7.10 (s, 1H), 4.55-4.63 (m, 1H), 2.42-2.50 (m,2H), 2.20-2.24 (m, 2H), 2.00-2.03 (m, 2H), 1.77-1.81 (m, 1H), 1.42-1.49 (m, 3H).

Example 211

Preparation of 1-cyclohexyl-2-(4-oxo-2-phenyl-1,4-dihydro-quinolin-6-yl)-1H-benzoimidazole-5-carboxylic acid (Compound 373)

4-Oxo-2-phenyl-1,4-dihydro-quinoline-6-carboxylic acid (298.5 mg, 1.05 mmol), (Compound 481c), was dissolved in DMF (5 mL), and HATU (440 mg, 1.1 eq.) and diisopropyl ethylamine (402 μL) were added. After stirring at room temperature for 15 minutes, 3-amino-4-cyclohexylamino-benzoic acid ethyl ester (303 mg, 1.1 eq.) dissolved in 2 mL DMF was added. After stirring overnight, the reaction was evaporated, dissolved in ethyl acetate and washed with water and brine, dried with sodium sulfate, evaporated and dried overnight. The product was then refluxed in acetic acid for 4 hr, evaporated to dryness, and coevaporated 2 more times with toluene. Saponification proceeded by dissolving the residue in ethanol (10 mL), adding 10 eq. of 1N NaOH solution and stirring at 40° C. for 4 hr. The ethanol was evaporated, and water was added and acidified. The resulting precipitate is purified via reverse-phase HPLC. Yield: 47 mg.

MS: 464.19 (M+H$^+$); H$^1$-NMR (MeOD): δ (ppm) 8.71 (s, 1H), 8.44 (s, 1H), 8.22-8.25 (m, 2H), 8.15 (s, 1H), 7.86-7.89 (m,2H), 7.61-7.64 (m, 2H), 6.79 (s, 1H), 4.55-4.64 (m, 1H), 2.45-2.53 (m, 2H), 2.19-2.23 (m, 2H), 1.99-2.02 (m, 2H), 1.76-1.80 (m, 2H), 1.41-1.48 (m, 3H).

Example 212

Preparation of 1-cyclohexyl-2-(4-dimethylamino-2-phenyl-quinolin-6-yl)-1H-benzoimidazole-5-carboxylic acid (Compound 481)

Step 1: 4-Oxo-2-phenyl-1,4-dihydro-quinoline-6-carboxylic acid Ethyl Ester (Compound 481b)

4-Amino-benzoic acid ethyl ester (66 g, 0.4 mol) and 3-oxo-3-phenyl-propionic acid ethyl ester (0.4 mol, 1 eq.) were dissolved in 500 mL cyclohexane and refluxed for 2 days using a Dean-Stark trap. The solution was filtered, the solvent evaporated and the residue recrystallized to give 4-(2-ethoxycarbonyl-1-phenyl-ethylideneamino)-benzoic acid ethyl ester (Compound 481a) MS: 340.18 (M+H$^+$). 4-(2-Ethoxycarbonyl-1-phenyl-ethylideneamino)-benzoic acid ethyl ester was dissolved in diphenyl-methanone (250 mL) and heated to 250° C. for 4 hr. The resulting solution was diluted with diethyl ether and filtered to give 48.6 g of the title intermediate as a white crystalline solid.

MS: 294.13 (M+H$^+$); H$^1$-NMR (d6-DMSO): δ (ppm) 11.98 (br s, 1H), 8.69 (d, 1H, J=1.1 Hz), 8.16 (dd, 1H, J=2.0 Hz, J=8.5 Hz), 7.82-7.86 (m, 3H), 7.56-7.61 (m, 3H), 6.42 (s, 1H), 4.35 (q, 2H, J=7.0 Hz), 1.36 (t, 3H, J=7.0 Hz)

Step 2: 4-Oxo-2-phenyl-1,4-dihydro-quinoline-6-carboxylic acid (Compound 481c)

Saponification proceeded with dissolving 26.5 g (0.1 mol) 4-oxo-2-phenyl-1,4-dihydro-quinoline-6-carboxylic acid ethyl ester in ethanol (100 mL), adding 10 eq. of 1N NaOH solution and stirring at 40° C. for 4 hr. The ethanol was evaporated, water was added and acidified, and the precipitate filtered. The white product was dried over P$_2$O$_5$ to give quantitative amounts of 4-oxo-2-phenyl-1,4-dihydro-quinoline-6-carboxylic acid.

MS: 266.10 (M+H$^+$); H$^1$-NMR (d$_6$-DMSO): δ (ppm) 12.29 (s, 1H), 8.14 (dd, 1H, J-2.0 Hz, J=8.8 Hz), 7.94 (d, 1H, J-8.8 Hz), 7.84-7.89 (m, 2H), 7.55-7.59 (m, 3H), 6.46 (s, 1H).

Step 3: 1-Cyclohexyl-2-(4-oxo-2-phenyl-1,4-dihydro-quinolin-6-yl)-1H-benzoimidazole-5-carboxylic acid Ethyl Ester acid (Compound 481d)

4-Oxo-2-phenyl-1,4-dihydro-quinoline-6-carboxylic acid (2.78 g, 1.05 mmol) was dissolved in DMF (50 mL), and HATU (1.1 eq.) and diisopropyl ethylamine (2.2 eq, 402 μL) were added. After stirring at room temperature for 15 minutes, 3-amino-4-cyclohexylamino-benzoic acid ethyl ester (2.89 g, 1.1 eq.) dissolved in 20 mL DMF was added. After stirring overnight, the reaction was evaporated, dissolved in ethyl acetate and washed with water and brine, dried with sodium sulfate, evaporated and dried overnight. The product was then refluxed in acetic acid for 4 hr, evaporated to dryness, and coevaporated 2 more times with toluene. The product was recrystallized from methanol to give 4.13 g of product.

MS: 492.25 (M+H$^+$); H$^1$-NMR (d6-DMSO): δ (ppm) 11.98 (s, 1H), 8.35 (d, 1H, J=1.5 Hz), 8.27 (d, 1H, 1.7 Hz), 7.95-8.02 (m, 3H), 7.82-7.88 (m, 3H), 7.57-7.69 (m, 3H), 6.43 (s, 1H), 4.29-4.38 (m, 3H), 2.26-2.37 (m, 2H), 1.95-1.99 (m, 2H), 1.84-1.89 (m, 2H), 1.62-1.66 (m, 1H), 1.24-1.42 (m, 6H).

Step 4: 2-(4-Chloro-2-phenyl-quinolin-6-yl)-1-cyclohexyl-1H-benzoimidazole-5-carboxylic acid Ethyl Ester (Compound 481e)

1-Cyclohexyl-2-(4-oxo-2-phenyl-1,4-dihydro-quinolin-6-yl)-1H-benzoimidazole-5-carboxylic acid ethyl ester acid (4 g, 8.14 mmol) was dissolved in phosphorous oxy chloride and heated at 100° C. overnight. After evaporation of the solvent the product was recrystallized from methanol/water to give 3.96 g of crude product. Silica gel purification of the title compound proved to be unsatisfactory due to degradation of the product on the column. MS: 510.22 (M+H$^+$).

Step 5: Preparation of 1-Cyclohexyl-2-(4-dimethylamino-2-phenyl-quinolin-6-yl)-1H-benzoimidazole-5-carboxylic acid (Compound 481)

2-(4-Chloro-2-phenyl-quinolin-6-yl)-1-(1-cyclohexyl)-1H-benzoimidazole-5-carboxylic acid ethyl ester was dissolved in 5 mL NMP and 1.1 eq of nucleophile is added. The reaction mixture was heated to 80° C. overnight, and subsequently evaporated. Saponification proceeded with dissolving the residue in ethanol (10 mL), adding 10 eq. of 1N NaOH solution and stirring at 40° C. for 4 hr. The ethanol was evaporated, and the residue purified via reverse-phase HPLC.

In the synthesis of the title compound 51 mg (0.1 mmol) of crude 2-(4-chloro-2-phenyl-quinolin-6-yl)-1-cyclohexyl-1H-benzoimidazole-5-carboxylic acid ethyl ester were used. The nucleophile used was neat DMF. No NMP was used in this reaction. Yield: 11 mg.

MS: 491.26 (M+H$^+$); H$^1$-NMR (MeOD): δ (ppm) 8.69 (s, 1H), 8.41 (s, 1H), 8.12-8.30 (m, 2H), 7.87-8.08 (m,4H), 7.62-7.74 (m,3H), 7.20 (s, 1H), 4.40-4.48 (m, 1H), 3.67 (s, 6H), 2.44-2.48 (m, 2H), 1.96-1.99 (m, 2H), 1.75-1.79 (m, 1H), 1.30-1.42 (m, 3H).

Example 213

Preparation of 1-cyclohexyl-2-(4-ethoxy-2-phenyl-quinolin-6-yl)-1H-benzoimidazole-5-carboxylic acid (Compound 494)

The title compound was isolated as a side product from the reaction sequence used for the preparation of Compound 481. Yield: 4 mg.

MS: 492.22 (M+H$^+$); H$^1$-NMR (MeOD): δ (ppm) 8.80 (s, 1H), 8.36-8.46 (m, 3H), 8.12-8.17 (m, 4H), 7.71-97 (m, 4H), 4.75 (q, 1H, J=7.0 Hz), 4.46-4.57 (m, 1H), 2.42-2.55 (m 2H), 2.13-2.17 (m, 2H), 1.94-1.99 (m, 2H), 1.71-1.76 (m, 1H), 1.69 (t, 3H, J=7.0 Hz), 1.38-1.45 (m, 3H)

Example 214

Preparation of 2-[4-(4-chloro-phenylamino)-2-phenyl-quinolin-6-yl]-1-cyclohexyl-1H-benzoimidazole-5-carboxylic acid (Compound 380)

The title compound was prepared using the method described for Compound 481. In this reaction 102 mg (0.2 mmol) of crude 2-(4-chloro-2-phenyl-quinolin-6-yl)-1-cyclohexyl-1H-benzoimidazole-5-carboxylic acid ethyl ester were used. The nucleophile used wasp-chlorophenylamine. Yield: 89 mg.

MS: 573.22 (M+H$^+$); H$^1$-NMR (MeOD): δ (ppm) 8.98 (d, 1H, J=1.4 Hz), 8.27-8.38 (m, 3H), 8.08-8.16 (m, 2H), 7.86-7.96 (m, 2H), 7.54-7.72 (m, 7H), 7.13 (s, 1H), 4.45 (t t, 1H, J=8.0 Hz, J=4.3 Hz), 2.37-2.48 (m, 2H), 2.13-2.17 (m, 2H), 1.94-1.99 (m, 2H), 1.74-1.78 (m, 1H), 1.37-1.49 (m, 3H)

Example 215

Preparation of 1-cyclohexyl-2-[4-(4-hydroxy-butylamino)-2-phenyl-quinolin-6-yl]-1H-benzoimidazole-5-carboxylic acid (Compound 398)

In this reaction 102 mg (0.2 mmol) of crude 2-(4-chloro-2-phenyl-quinolin-6-yl)-1-cyclohexyl-1H-benzoimidazole-5-carboxylic acid ethyl ester were used in the same reaction sequence as that used for Compound 481. The nucleophile used was 4-amino-butan-1-ol. Yield: 59 mg.

MS: 535.28 (M+H$^+$); H$^1$-NMR (MeOD): δ (ppm) 8.75 (s, 1H), 8.43 (s, 1H), 8.15-8.24 (m, 2H), 8.07-8.10 (dd, 1H, J=0.9 Hz, J=8.8 Hz), 7.98-8.03 (m, 3H), 7.67-7.73 (m, 3H), 7.15 (s,1H), 4.34 (m, 1H), 3.75 (tr, 2H, 7.0 Hz), 3.67 (tr, 2H, J=5.9 Hz), 2.37-2.45 (m, 2H), 2.07-2.11 (m, 2H), 1.90-1.97 (m, 4H), 1.70-1.79 (m, 3H), 1.28-1.45 (m, 3H)

Example 216

Preparation of 1-cyclohexyl-2-(2-phenyl-4-phenylamino-quinolin-6-yl)-1H-benzoimidazole-5-carboxylic acid (Compound 433)

In this reaction 102 mg (0.2 mmol) of crude 2-(4-chloro-2-phenyl-quinolin-6-yl)-1-cyclohexyl-1H-benzoimidazole-5-carboxylic acid ethyl ester were used in the same reaction sequence as that used for Compound 481. The nucleophile used was aniline. Yield: 143 mg.

MS: 571.30 (M+H$^+$), 539.26; H$^1$-NMR (d6-DMSO): δ (ppm) 11.10 (bs, 1H), 9.11 (s, 1H), 8.25-8.36 (m, 3H), 8.05 (d,1H, 8.8 Hz), 7.88-7.93 (m, 3H), 7.57-7.67 (m, 7H), 7.39-7.45 (m, 1H), 7.03 (s, 1H), 4.24-4.29 (m, 1H), 2.31-2.37 (m, 2H), 2.02-2.04 (m, 2H), 1.84-1.88 (m, 2H), 1.62-1.66 (m, 1H), 1.21-1.43 (m, 3H)

Example 217

Preparation of 1-cyclohexyl-2-[4-(3-imidazol-1-yl-propylamino)-2-phenyl-quinolin-6-yl]-1H-benzoimidazole-5-carboxylic acid (Compound 451)

In this reaction 102 mg (0.2 mmol) of crude 2-(4-chloro-2-phenyl-quinolin-6-yl)-1-cyclohexyl-1H-benzoimidazole-5-carboxylic acid ethyl ester were used in the same reaction sequence as that used for Compound 481. The nucleophile used was 3-imidazol-1-yl-propylamine. Yield: 31 mg.

MS: 571.30 (M+H$^+$), 286.12 ((M+2H$^+$)/2); H$^1$-NMR (MeOD): δ (ppm) 9.03 (s, 1H), 8.91 (s, 1H), 8.46 (s, 1H), 8.09-8.30 (m, 5H), 8.01-8.04 (m, 2H), 7.68-7.74 (m, 4H), 7.56-7.58 (m, 1H), 7.17 (s, 1H), 4.49 (tr, 2H, J=7.0 Hz), 4.37-4.47 (m, 1H), 3.83 (tr, 2H, J=6.7 Hz), 2.42-2.51 (m, 2H), 2.12-2.16 (2H, m, 2H), 1.95-1.99 (m, 2H), 1.74-1.78 m, 1H), 1.35-1.42 (m, 3H)

Example 218

Preparation of 1-cyclohexyl-2-(4-phenoxy-2-phenyl-quinolin-6-yl)-1H-benzoimidazole-5-carboxylic acid (Compound 496)

In this reaction 51 mg (0.1 mmol) of crude 2-(4-chloro-2-phenyl-quinolin-6-yl)-1-cyclohexyl-1H-benzoimidazole-5-carboxylic acid ethyl ester were used in the same reaction sequence as that used for Compound 481. The nucleophile used was phenol. Yield: 19 mg.

MS: 540.25 (M+H$^+$); H$^1$-NMR (MeOD): δ (ppm) 8.97 (s, 1H), 8.45-8.50 (m, 2H), 8.32 (d, 1H, J=8.5 Hz), 8.18 (s, 2H), 7.91-7.94 (m, 2H), 7.54-7.65 (m, 5H), 7.41-7.49 (m, 3H), 7.19 (s, 1H), 4.58-4.66 (m, 1H), 2.42-2.49 (m, 2H), 2.17-2.21 (m, 2H), 1.95-2.01 (m, 2H), 1.72-1.84 (m, 1H), 1.41-1.52 (m, 3H).

Example 219

Preparation of 1-cyclohexyl-2-[4-(7-hydroxy-naphthalen-2-yloxy)-2-phenyl-quinolin-6-yl]-1H-benzoimidazole-5-carboxylic acid (Compound 509)

In this reaction 51 mg (0.1 mmol) of crude 2-(4-chloro-2-phenyl-quinolin-6-yl)-1-cyclohexyl-1H-benzoimidazole-5-carboxylic acid ethyl ester were used in the same reaction sequence as that used for Compound 481. The nucleophile used was naphthalene-2,7-diol. Yield: 6.2 mg.

MS: 606.28 (M+H$^+$); H$^1$-NMR (d6-DMSO): δ (ppm) 8.66 (s, 1H), 8.29-8.34 (m, 2H), 8.15-8.18 (m, 1H), 8.03-8.11 (m, 3H), 7.91-7.97 (m, 2H), 7.83 (d, 1H, J=8.8 Hz), 7.65 (bs, 1H), 7.47-7.49 (m, 3H), 7.34 (s, 1H), 7.27-7.31 (m, 1H), 7.14 (bs, 1H), 7.07-7.11 (m, 1H), 4.47-4.49 (m, 2H, OH and CH), 2.32 (q, 2H, J=12.6 Hz), 2.01-2.04 (m, 2H), 1.81-1.84 (m, 2H), 1.58-1.62 (m, 1H), 1.22-1.41 (m, 3H).

Example 220

Preparation of 1-Cyclohexyl-2-(2-phenyl-4-phenylsulfanyl-quinolin-6-yl)-1H-benzoimidazole-5-carboxylic acid (Compound 467)

In this reaction 51 mg (0.1 mmol) of crude 2-(4-chloro-2-phenyl-quinolin-6-yl)-1-cyclohexyl-1H-benzoimidazole-5-carboxylic acid ethyl ester were used in the same reaction sequence as that used for Compound 481. The nucleophile used was benzenethiol. Yield: 36 mg.

MS: 556.21 (M+H$^+$); H$^1$-NMR (d6-DMSO): δ (ppm) 8.48 (s, 1H), 8.28-8.31 (m, 2H), 8.16 (d, 1H, J=8.8 Hz), 8.05 (d, 1H, J=8.8 Hz), 7.89-7.97 (m,3H), 7.66-7.70 (m,2H), 7.55-7.57 (m, 3H), 7.48-7.53 (m, 4H), 4.43-4.49 (m,1H), 2.30-2.40 (m, 2H), 2.00-2.04 (m, 2H), 1.85-1.88 (m, 2H), 1.62-1.66 (m, 1H), 1.22-1.37 (m, 3H).

Example 221

Preparation of 1-cyclohexyl-2-[2-(2-ethoxy-5-nitrophenyl)-quinolin-6-yl]-1H-benzoimidazole-5-carboxylic acid (Compound 404)

1-(2-Bromo-5-nitro-phenyl)-ethanone (61 mg, 0.25 mmol) prepared similarly to the procedure described in Meisenheimer, J., Zimmermann P., and v. Kummer, U. *Ann. der. Chem.* 446, pp. 205-228) and 2-(4-amino-3-formyl-phenyl)-1-cyclohexyl-1H-benzoimidazole-5-carboxylic acid ethyl ester (98 mg, 0.25 mmol) were dissolved in 500 µL ethanol and 500 µL 10% ethanolic KOH were added. The reaction was stirred at 75° C. overnight. The reaction was acidified with 4N hydrochloric acid, extracted three times with ethyl acetate, the organic extracts were dried with sodium sulfate and then evaporated. Purification via reverse-phase HPLC gave 16 mg (97.33% pure) of product.

MS: 537.23 (M+H$^+$); H$^1$-NMR (d6-DMSO): δ (ppm) 8.71 (d, 1H, J=2.9 Hz), 8.62 (d, 1H, J=8.8 Hz), 8.41 (d, 1H, J=2.7 Hz), 8.37 (dd, 1H, J=3.0 Hz, J=9.0 Hz), 8.29-8.33 (m, 2 Hz), 8.18 (d, 1H, J=8.5 Hz), 8.04-8.08 (m, 2H), 7.92 (1H, dd, J=1.8 Hz, J=8.5 Hz), 7.44 (d, 1H, 8.4 Hz), 4.31-4.44 (m, 3H), 2.26-2.34 (m,2H), 2.02-2.05 (m, 2H), 1.83-1.86 (m, 2H), 1.61-1.65 (m, 1H), 1.28-1.43 (m, 6H).

Example 222

Preparation of 2-[2,4']biquinolinyl-6-yl-1-cyclohexyl-1H-benzoimidazole-5-carboxylic acid (Compound 423)

Methylmagnesium bromide in diethyl ether (2.4 mL of 3.0M solution) was dropped onto solid quinoline-4-carboxylic acid (250 mg). After stirring for an additional 15 min. the reaction was quenched by addition of methanol. The solution was separated between ethyl acetate and water, the water extracted two more times with ethyl acetate, the organic phases were dried with sodium sulfate and then evaporated. The crude product (1-quinolin-4-yl-ethanone was used without further purification in the next step.

MS: 172.07 (M+H$^+$); H$^1$-NMR (CDCl$_3$): δ (ppm) 9.01 (d, 1H, J=4.5 Hz), 8.42 (d, 1H, J=9 Hz), 8.14 (d, 1H, J=9 Hz), 7.72-7.78 (m, 1H), 7.59-7.64 (m, 2H), 2.75 (s, 3H))

(1-Quinolin-4-yl-ethanone (43 mg, 0.25 mmol) and 2-(4-amino-3-formyl-phenyl)-1-cyclohexyl-1H-benzoimidazole-5-carboxylic acid ethyl ester (98 mg, 0.25 mmol) were dissolved in 500 µL ethanol and 500 µL 10% ethanolic KOH were then added. The reaction was stirred at 75° C. overnight. The reaction was acidified with 4N hydrochloric acid, extracted three times with ethyl acetate, and the organic extracts were dried with sodium sulfate and then evaporated. Purification via reverse-phase HPLC gave 24 mg product.

MS: 499.23 (M+H$^+$); H$^1$-NMR (MeOD): δ (ppm) 9.33 (d, 1H, J=5.5 Hz), 8.87 (d, 1H, J=8.5 Hz), 8.65 (d, 1H, J=1.8 Hz), 8.55 (d, 1H, 8.8 Hz), 8.48-8.52 (m, 2H), 8.37 (d, 1H, 8.5 Hz), 8.30 (d, 5.5 Hz), 8.16-8.27 (m, 5H), 7.94-7.99(m, 1H), 4.62 (t,t, 1H, J=8.5 Hz, J=3.9 Hz), 2.43-2.54 (m (like br q), 2H), 2.22-2.26 (m, 2H), 1.99-2.03 (m, 2H), 1.76-1.80 (m, 1H), 1.40-1.53 (m, 3H).

Example 223

Preparation of 2-[2-(4'-chloro-4-nitro-biphen-2-yl)-quinolin-6-yl]-1-cyclohexyl-1H-benzoimidazole-5-carboxylic acid (Compound 439)

1-(2-Bromo-5-nitro-phenyl)-ethanone (1 g, 4 mmol; prepared similarly to the procedure described in Meisenheimer, J., Zimmermann P., and v. Kummer, U. *Ann. der. Chem.* 446, pp. 205-228), p-Chlorophenylboronic acid (768 mg, 1.2 eq.), and tetrakis(triphenylphosphine)-palladium(0) (473 mg, 0.1 eq.), were dissolved in 25 mL toluene, 6 mL methanol and 2.5 mL sat. sodium bicarbonate solution. After degassing/sonicating the solution, the sealed reaction vessel was heated to 80° C. overnight. The cooled solution was separated between ethyl acetate and water; the aqueous phase extracted two more times with ethyl acetate, and the organic fractions were combined, dried with sodium sulfate and evaporated. Silica gel chromatography (4:1 hexanes/ethyl acetate) gave 1-(4'-chloro-4-nitro-biphen-2-yl)-ethanone (962 mg).

1-(4'-Chloro-4-nitro-biphen-2-yl)-ethanone (69 mg, 0.25 mmol) and 2-(4-amino-3-formyl-phenyl)-1-cyclohexyl-1H-benzoimidazole-5-carboxylic acid ethyl ester (98 mg, 0.25 mmol) were dissolved in 500 µL ethanol and 500 µL 10% ethanolic KOH were added. The reaction was stirred at 75° C. overnight. The reaction was acidified with 4N hydrochloric acid, extracted three times with ethyl acetate, the organic extracts were dried with sodium sulfate and then evaporated. Purification via reverse-phase HPLC gave 34 mg product.

MS: 603.20 (M+H$^+$); H$^1$-NMR (d6-DMSO): δ (ppm) 8.57 (d, 1H, J=2.3 Hz), 8.38-8.45 (m, 2H), 8.34 (d, 1H, J=1.8 Hz), 8.24-8.28 (m, 2H), 8.05-8.08 (m, (like d), 2H), 7.91 (dd, 1H, J=1.5, J=8.8 Hz), 7.82 (d, 1H, J=8.5 Hz), 7.38-7.43 (m, 2 Hz), 7.20-7.27 (m, 3H), 4.34-4.43 (m, 1H), 2.26-2.34 (m, 2H), 2.01-2.05 (m, 2H), 1.83-1.87 (m, 2H), 1.62-1.75 (m, 2H), 1.32-1.43 (m, 3H).

Example 224

Preparation of 6-[1-cyclohexyl-5-(1H-tetrazol-5-yl)-1H-benzimidazol-2-yl]-2-phenylquinoxaline (Compound 258)

Step 1: 4-Cyclohexylamino-3-nitrobenzonitrile (Compound 127)

A solution of 1 g (5.48 mmol) 4-chloro-3-nitrobenzonitrile, Compound 126, and 1.14 g (11.51 mmol) of cyclohexylamine were heated overnight in 5 mL anhydrous DMF. After cooling to room temperature, the solution was added dropwise into 100 mL H$_2$O stirring vigorously. The solids were collected by filtration and dried under vacuum yielding 1.34 g (100%) bright yellow solids which were used as such without analysis in the next step.

Step 2: Cyclohexyl-[2-nitro-4-(1H-tetrazol-5-yl)-phenyl]amine (Compound 128)

A solution of 1.10 g (4.49 mmol) of 4-cyclohexylamino-3-nitrobenzonitrile, Compound 127, and 1.11 g (5.39 mmol) of Me$_3$SnN$_3$ in 50 mL toluene was refluxed overnight. The crystals were collected by filtration, washed with toluene, dried, and treated with 50 mL 4M HCl in dioxane for 4 h. The solids were collected by filtration, washed with dioxane, and dried yielding 1.14 g (88%) red solids. MS: 289.15 (M+H$^+$).

Step 3: N-1-Cyclohexyl-4-(1H-tetrazol-5-yl)-benzene-1,2-diamine (Compound 129)

The title intermediate was prepared from 1.20 g (4.16 mmol) Compound 128 as described for Compound 11 to yield 0.9 g (83%). MS: 259.18 (M+H$^+$).

Step 4: 6-[1-Cyclohexyl-5-(1H-tetrazol-5-yl)-1H-benzimidazol-2-yl]-2-phenylquinoxaline (Compound 258)

The title compound was prepared from 100 mg (0.39 mmol) of Compound 129 and Compound 36A Y=phenyl as described for compound 38 Y=phenyl to yield 21 mg.

MS: 473.25 (M+H$^+$); $^1$H-NMR (DMSOd$_6$): δ (ppm) 9.73 (s, 1H), 8.46 (d, 2H, J=1.2 Hz), 8.42-8.36 (m, 4H), 8.29 (d, 1H, J=5.6 Hz), 8.19 (dd, 1H, J=1.2 Hz and 5.6 Hz), 8.09 (dd, 1H, J=1 Hz and 5.8 Hz), 7.63 (m, 5H), 4.45 (m, 1H), 2.44-2.35 (m, 2H), 2.12-2.08 (m, 2H), 1.90-1.85 (m, 2H), 1.62 (m, 1H), 1.50-1.29 (m, 3H).

Example 225

Preparation of 1-cyclohexyl-2-(2,3-diphenyl-quinolin-6-yl)-1H-benzoimidazole-5-carboxylic acid (Compound 386)

The title compound was synthesized in four steps as described for Compound 13, Compound 25, Compound 27 Q=ethyl and Compound 204, respectively, except deoxybenzoin was used in the first step instead of acetophenone.

MS: 524.29 (M+H$^+$); H$^1$-NMR (DMSO-d$_6$): δ (ppm) 8.73 (s, 1H), 8.57 (s, 1H), 8.40-8.37 (m, 2H), 8.31-8.28 (d, 1H, J=8.4 Hz), 8.17-8.14 (d,1H, J=8.4 Hz), 8.07-8.04 (d, 1H, J=8.4 Hz), 7.45-7.29 (m, 10H), 4.46 (m, 1H), 2.34-2.26 (m, 2H), 2.14-2.10 (m, 2H), 1.86-1.82 (m, 2H), 1.60 (m, 1H), 1.43-1.21 (m, 3H).

Example 226

Preparation of 2-(2-benzhydryl-quinolin-6-yl)-1-cyclohexyl-1H-benzoimidazole-5-carboxylic acid (Compound 457)

The title compound was synthesized in four steps as described for Compound 13, Compound 25, Compound 27, Q=ethyl and Compound 204, respectively, except 1,1-diphenylacetone was used in the first step, instead of acetophenone.

MS: 538.30 (M+H$^+$); H$^1$-NMR (DMSO-d$_6$): δ (ppm) 8.63-8.60 (d, 1H, J=9.0 Hz), 8.47 (d, 1H, J=1.5 Hz), 8.34 (d, 1H, J=1.2 Hz), 8.29-8.24 (m, 2H), 8.10-8.02 (m, 2H), 7.66-7.63 (d, 1H), J=8.7 Hz), 7.36-7.20 (m, 10H), 6.05 (s, 1H), 4.45-4.41 (m, 1H), 2.33-2.28 (m, 2H), 2.1-2.06 (m, 2H), 1.84-1.79 (m 2H), 1.58 (m, 1H), 1.38-1.20 (m, 3H).

Example 227

Preparation of 2-[2-(2-bromo-phenyl)-quinolin-6-yl]-1-cyclohexyl-1H-benzoimidazole-5-carboxylic acid (Compound 352)

The title compound was synthesized in four steps as described for Compound 13, Compound 25, Compound 27 Q=ethyl and Compound 204, respectively, except 2'-bromoacetophenon was used in the first step instead of acetophenone.

MS: 526.14 (M+H$^+$); H$^1$-NMR (DMSO-d$_6$): δ (ppm) 8.75-8.72 (d, 1H, J=8.7 Hz), 8.55 (d, 1H, J=1.5 Hz), 8.38 (d, 1H, J=1.2 Hz), 8.36-8.33 (d, 1H, J=8.7 Hz), 8.26-8.8.22 (d, 1H, J=8.7 Hz), 8.17-8.13 (dd, 1H, J=8, 7 Hz and 1.8 Hz), 8.06-8.02 (dd, 1H, J=8.4 Hz and 1.5 Hz), 7.96-7.93 (d, 1H, J=8.4 Hz), 7.87-7.84 (dd, 1H, J=7.8 Hz and 0.9 Hz), 7.73-7.69 (dd, 1H, J=7.5 Hz and 1.8 Hz), 7.64-7.59 (m, 1H), 7.53-7.47 (m 1H), 4.49 (m, 1H), 2.40-2.32 (m, 2H), 2.15-2.11 (m, 2H), 1.91-1.87 (m, 2H), 1.66 (m, 1H), 1.42-1.34 (m, 3H).

Example 228

Preparation of 2-{2-[(4-Chlorophenyl)methyl carbamoyl]quinolin-6-yl}-1-cyclohexyl-1H-benzimidazole-5-carboxylic acid (Compound 546)

Step 1: (4-Chlorophenyl)isopropylamine (Compound 546a)

A mixture of 1 g (7.84 mmol) of 4-chloroaniline, 0.91 g (15.68 mmol) of acetone, 0.99 g (15.68 mmol) of NaCNBH$_3$, 4 g of MgSO$_4$ in 99 mL anhydrous EtOH and 1 mL AcOH was stirred at room temperature overnight, filtered and the solvent was removed. The residue was dissolved in 50 mL EtOAc, washed with 50 mL H$_2$O, dried (Na$_2$SO$_4$) and evaporated. The residue was purified on silica gel using hexane/EtOAc as eluent to yield 0.86 g colorless oil. MS: 170.08 (M+H$^+$).

Step 2: (4-Chlorophenyl)cyclohexylamine (Compound 546b)

Prepared as described above using cyclohexanone in place of acetone to yield 1.11 g colorless crystals. MS: 210.12 (M+H$^+$).

Step 3: 2-{2-[(4-Chlorophenyl)methyl carbamoyl] quinolin-6-yl}-1-cyclohexyl-1H-benzimidazole-5-carboxylic acid Ethyl Ester (Compound 546c)

A solution of 100 mg (0.23 mmol) Compound 402a in 1 mL SOCl$_2$ was allowed to stand at room temperature for 10 min and SOCl$_2$ was removed. The residue was dissolved in 5 mL anhydrous CH$_2$Cl$_2$; 89 mg (0.69 mmol) DIEA, 84 mg (0.69 mmol) DMAP, 98 mg (0.69 mmol) 4-chloro-N-methylaniline were added; and the solution was vortexed and allowed to stand at room temperature overnight. The solvent was removed and the residue was chromatographed on silica gel using hexane/EtOAc as the eluent to yield 63 mg of yellow oil. MS: 576.24 (M+H$^+$).

Step 4: 2-{2-[(4-Chlorophenyl)methyl carbamoyl] quinolin-6-yl}-1-cyclohexyl-1H-benzimidazole-5-carboxylic acid (Compound 546)

A solution of 63 mg (0.11 mmol) of Compound 546c in 0.55 mL THF, 0.44 mL of EtOH and 0.11 mL of 2 N aq. NaOH was allowed to stand at room temperature overnight. The reaction was quenched with 0.22 mL 1 M aq. HCl. The solvents were removed and the residue was purified by HPLC to yield 6 mg of the title compound.
MS: 539.21 (M+H$^+$); $^1$H-NMR (CD$_3$OD): δ (ppm) 8.47 (m, 3H), 8.31 (m, 2H), 8.10 (m, 2H), 7.84 (m, 1H), 7.23 (m, 4H), 4.58 (m, 1H), 3.58 (s, 3H), 2.45 (m, 2H), 2.19 (m, 2H), 1.98 (m, 2H), 1.74 (m, 1H), 1.46-1.30 (m, 3H).

Example 229

Preparation of 2-{2-[(4-Chlorophenyl)isopropyl carbamoyl]quinolin-6-yl}-1-cyclohexyl-1H-benzimidazole-5-carboxylic acid (Compound 550)

Step 1: 2-{2-[(4-Chlorophenyl)isopropyl carbamoyl] quinolin-6-yl}-1-cyclohexyl-1H-benzimidazole-5-carboxylic acid Ethyl Ester (Compound 550a)

The title compound was prepared as described for Compound 546c using Compound 546a in place of 4-chloro-N-methylaniline. MS: 595.27 (M+H$^+$).

Step 2: 2-{2-[(4-Chlorophenyl)isopropyl carbamoyl] quinolin-6-yl}-1-cyclohexyl-1H-benzimidazole-5-carboxylic acid (Compound 550)

The title compound was prepared as described for Compound 546 heating the solution at 50° C. for 4 h instead of standing overnight.
MS: 567.25 (M+H$^+$); $^1$H-NMR (CD$_3$OD): δ (ppm) 8.45 (m, 2H), 8.36 (s, 1H), 8.24 (m, 2H), 8.15 (d, 1H, J=9 Hz), 8.04 (d, 1H, J=8.4 Hz), 7.71 (d, 1H, J=8.4 Hz), 7.24 (dd, 4H, J=8.4 Hz and 18.3 Hz), 5.12 (m, 1H), 4.53 (m, 1H), 2.41 (m, 2H), 2.15 (m, 2H), 1.95 (m, 2H), 1.73 (m, 1H) 1.41 (m, 3H), 1.31 (d, 6H, J=6.6 Hz).

Example 230

Preparation of 2-{2-[(4-Chlorophenyl)cyclohexyl carbamoyl]quinolin-6-yl}-1-cyclohexyl-1H-benzimidazole-5-carboxylic acid (Compound 551)

Step 1: 2-{2-[(4-Chlorophenyl)cyclohexyl carbamoyl]quinolin-6-yl}-1-cyclohexyl-1H-benzimidazole-5-carboxylic acid Ethyl Ester (Compound 551a)

The title compound was prepared as described for Compound 546c using Compound 546b in place of 4-chloro-N-methylaniline. MS: 635.31 (M+H$^+$).

Step 2: 2-{2-[(4-Chlorophenyl)cyclohexyl carbamoyl]quinolin-6-yl}-1-cyclohexyl-1H-benzimidazole-5-carboxylic acid (Compound 551)

The title compound was prepared as described for Compound 550 using 5 eq. of 2 N aq NaOH in place of 1 eq.
MS: 607.28 (M+H$^+$); $^1$H-NMR (DMSO-d$_6$): δ (ppm) 8.46 (d, 1H, J=8.4 Hz), 8.25 (s, 2H), 7.96 (m, 3H), 7.68 (d, 1H, J=8.4 Hz), 7.26 (s, 4H), 4.61 (m, 1H), 4.34 (m, 1H), 2.29-0.96 (m, 10H).

Example 231

Preparation of 1-Cyclohexyl-2-[2-(4'-ethyl-4-methoxy-biphen-2-yl)-quinolin-6-yl]-1H-benzoimidazole-5-carboxylic acid (Compound 557)

Following the full procedure and workup for Compound 366, Compound 365b (100 mg, 0.175 mmol) was reacted with 4-ethylphenylboronic acid (39 mg, 0.2625 mmol) to produce the title compound (48 mg, 48% yield).
MS: 582.32 (M+H$^+$); H$^1$-NMR (DMSO-d$_6$): 8.38 (d, 1H, J=1.5), 8.31 (m, 3H), 8.17 (d, 1H, J=8.7), 8.07 (dd, 1H, J=8.7, 1.8), 7.98 (dd, 1H, J=8.4, 1.2), 7.43 (d, 1H, J=8.7), 7.31 (d, 1H, J=2.7), 7.17 (m, 2H), 7.05 (m, 4H0, 4.42 (m, 1H), 3.87 (s, 3H), 2.53 (m, 2H), 2.31 (m, 2H), 2.07 (m, 2H), 1.84 (m, 2H), 1.61 (m, 1H), 1.32 (m, 3H), 1.12 (m, 3H)

Example 232

Preparation of 1-Cyclohexyl-2-[2-(3',4'-difluoro-4-methoxy-biphen-2-yl)-quinolin-6-yl]-1H-benzoimidazole-5-carboxylic acid (Compound 560)

Following the full procedure and workup for Compound 366, Compound 365b (100 mg, 0.175 mmol) was reacted with 3,4-difluorophenylboronic acid (42 mg, 0.2625 mmol) to produce the title compound (26 mg, 25% yield).
MS: 590.26 (M+H$^+$); H$^1$-NMR (DMSO-d$_6$): 8.46 (m, 2H), 8.36 (s, 1H), 8.29 (d, 2H, J=9), 8.11 (dd, 1H, J=8.7, 1.8), 8.05 (dd, 1H, J=9, 1.5), 7.49 (d, 1H, J=8.4), 7.27 (m, 5H), 6.84 (m, 1H), 4.44 (m, 1H), 3.88 (s, 3H), 3.54 (s, 1H), 2.30 (m, 2H), 2.11 (m, 2H), 1.84 (m, 2H), 1.61 (m, 1H), 1.35 (m, 3H)

Example 233

Preparation of 1-Cyclohexyl-2-[2-(3',5'-dichloro-4-methoxy-biphen-2-yl)-quinolin-6-yl]-1H-benzoimidazole-5-carboxylic acid (Compound 562)

Following the full procedure and workup for Compound 366, Compound 365b (100 mg, 0.175 mmol) was reacted with 3,5-dichlorophenylboronic acid (50 mg, 0.2625 mmol) to produce the title compound (17 mg, 15% yield).
MS: 622.20 (M+H$^+$); H$^1$-NMR (DMSO-d$_6$): 8.48 (d, 1H, J=8.4), 8.44 (s, 1H), 8.32 (s, 1H), 8.22 (m, 2H), 8.05 (m, 2H), 7.53 (d, 1H, J=8.4), 7.42 (m, 2H), 7.33 (d, 1H, J=2.7), 7.20 (dd, 1H, H=8.7, 2.7), 7.11 (m, 2H), 4.40 (m, 1H), 3.89 (s, 3H), 2.30 (m, 2H), 2.08 (m, 2H), 1.84 (m, 2H), 1.60 (m, 1H), 1.32 (m, 3H)

Example 234

Preparation of 1-Cyclohexyl-2-[2-(4'-fluoro-4-methoxy-biphen-2-yl)-quinolin-6-yl]-1H-benzoimidazole-5-carboxylic acid Amide (Compound 570)

Compound 455 (50 mg, 0.087 mmol) was dissolved in ammonia saturated methanol (50 mL) and placed in a 100 mL glass bomb. The reaction was argon flushed, sealed, and stirred at 70° C. for 8 days. The reaction was then evaporated to dryness and purified via HPLC to produce the title compound (9 mg, 18% yield).

MS: 571.27 (M+H$^+$); H$^1$-NMR (DMSO-d$_6$): 8.37 (m, 3H), 8.29 (m, 2H), 8.09 (m, 2H), 7.55 (s, 1H), 7.46 (2, 1H, J=8.4), 7.32 (d, 1H, J=2.7), 7.20 (m, 2H), 7.12 (m, 4H), 4.44 (s, 1H), 3.88 (s, 3H), 3.55 (s, 1H), 2.34 (m, 2H), 2.10 (m, 2H), 1.84 (m, 2H), 1.60 (m, 1H), 1.35 (m, 3H)

Example 235

Preparation of 1-Cyclohexyl-2-[2-(2'-fluoro-4-methoxy-biphen-2-yl)-quinolin-6-yl]-1H-benzoimidazole-5-carboxylic acid (Compound 544)

Following the full procedure and workup for Compound 366, Compound 365b (100 mg, 0.175 mmol) was reacted with 2-fluorophenylboronic acid (37 mg, 0.2625 mmol) to produce the title compound (9 mg, 25% yield).

MS: 572.26 (M+H$^+$); H$^1$-NMR (DMSO-d$_6$): 8.40 (m, 2H), 8.34 (m, 1H), 8.24 (d, 1H, J=8.7), 8.17 (d, 1H, J=9), 8.04 (m, 2H), 7.41 (m, 2H), 7.29 (m, 3H), 7.20 (m, 2H), 7.03 (m, 1H), 4.43 (m, 1H), 3.90 (s, 3H), 3.55 (s, 1H), 2.30 (m, 2H), 2.10 (m, 2H), 1.84 (m, 2H), 1.61 (m, 1H), 1.35 (m, 3H)

Example 236

Preparation of 2-(2-Biphenyl-4-yl-quinolin-6-yl)-1-cyclohexyl-1H-benzoimidazole-5-carboxylic acid (Compound 548)

Step 1: 1-(4-Methoxy-2'-methyl-biphen-2-yl)-ethanone (Compound 548a)

Following the procedure and workup (without the potassium hydroxide addition) for Compound 366, 2-bromo, 5-methoxyacetophenone (80 mg, 0.35 mmol) was reacted with o-tolylboronic acid (71 mg, 0.525 mmol) to produce the title intermediate (42 mg, 50% yield). HPLC Procedure C, retention time=2.84 min.

Step 2: 2-(2-Biphenyl-4-yl-quinolin-6-yl)-1-cyclohexyl-1H-benzoimidazole-5-carboxylic acid (Compound 562)

Following the procedure and workup for Compound 354 (68 mg, 0.17 mmol) was reacted with Compound 548a (42 mg, 0.17 mmol) in ethanol (3 mL) using 10% w/v KOH in Ethanol (506 µL, 0.64 mmol) to produce the title compound 29 mg, 28% yield).

MS: 568.28 (M+H$^+$); H$^1$-NMR (DMSO-d$_6$): δ (ppm) 8.43 (d, 1H, J=1.8), 8.34 (m, 4H), 8.09 (m, 2H), 7.43 (d, 1H, J=2.4), 7.32 (d, 1H, J=8.4), 7.14 (m, 6H), 4.45 (m, 1H), 3.90 (s, 3H), 3.55 (s, 1H), 2.30 (m, 2H), 2.11 (m, 2H), 1.96 (s, 3H), 1.83 (m, 2H), 1.60 (m, 1H), 1.30 (m, 3H)

Example 237

Preparation of 1-Cyclohexyl-2-[2-(4,2'-dimethoxy-biphen-2-yl)-quinolin-6-yl]-1H-benzoimidazole-5-carboxylic acid (Compound 552) Step 1:1-(4,2'-Dimethoxy-biphen-2-yl)-ethanone (Compound 552a)

Following the procedure and workup (without the potassium hydroxide addition) for Compound 366, 2-bromo, 5-methoxyacetophenone (80 mg, 0.35 mmol) was reacted with 2-methoxyphenylboronic acid (80 mg, 0.525 mmol) to produce Compound 552a (40 mg, 48% yield). HPLC Procedure C, retention time=2.37 min.

Step 2: 1-Cyclohexyl-2-[2-(4,2'-dimethoxy-biphen-2-yl)-quinolin-6-yl]-1H-benzoimidazole-5-carboxylic acid (Compound 552)

Following the procedure and workup for Compound 354 (68 mg, 0.17 mmol) was reacted with Compound 552a (40 mg, 0.17 mmol) in ethanol (3 mL) using 10% w/v KOH in Ethanol (506 µL, 0.64 mmol) to produce the title compound (12 mg, 10% yield).

MS: 584.28 (M+H$^+$); H$^1$-NMR (DMSO-d$_6$): δ (ppm) 8.50 (m, 2H), 8.37 (m, 2H), 8.27 (d, 1H, J=9), 8.17 (m, 1H), 8.04 (m, 1H), 7.40 (m, 2H), 7.24 (m, 4H), 6.94 (m, 1H), 6.82 (d, 1H, J=8.4), 4.41 (m, 1H), 3.90 (s, 3H), 3.55 (s, 1H), 3.23 (s, 3H), 2.29 (m, 2H), 2.10 (m, 2H), 1.84 (m, 2H), 1.60 (m, 1H), 1.32 (m, 3H)

Example 238

Preparation of 1-Cyclohexyl-2-[2-(2-cyclohexyl-5-methoxy-phenyl)-quinolin-6-yl]-1H-benzoimidazole-5-carboxylic acid (Compound 545)

Step 1: 1-(2-Cyclohexyl-5-methoxy-phenyl)-ethanone (Compound 545a)

2-bromo-5-methoxyacetophenone (500 mg, 2.185 mmol), Pd(P(t-Bu)$_3$)$_2$ (100 mg, 0.219 mmol), and NMP (15 mL) were added to a 25 mL, flame dried, Argon filled flask. The flask was sealed and, while stirring, cyclohexyl zinc bromide (5.5 mL, 0.5M in THF) was added dropwise. The reaction was stirred at 90° C. for 20h. The reaction was then evaporated to dryness and purified via RP-HPLC to produce the title intermediate (50 mg, 10% yield). HPLC Procedure C, retention time=3.12 min.

Step 2: 1-Cyclohexyl-2-[2-(2-cyclohexyl-5-methoxy-phenyl)-quinolin-6-yl]-1H-benzoimidazole-5-carboxylic acid (Compound 545)

Following the procedure and workup for Compound 354, Compound 354e (86 mg, 0.22 mmol) was reacted with Compound 545a (50 mg, 0.22 mmol) in ethanol (3 mL) using 10% w/v KOH in Ethanol (436 µL, 0.66 mmol) to produce the title compound (26 mg, 21% yield).

MS: 560.30 (M+H$^+$); H$^1$-NMR (DMSO-d$_6$): δ (ppm) 8.78 (d, 1H, J=8.7), 8.59 (s, 1H), 8.31 (m, 3H), 8.17 (m, 1H), 8.04 (d, 1H, J=8.7), 7.85 (d, 1H, J=8.7), 7.41 (d, 1H, J=8.7), 7.06 (m, 2H), 4.48 (m, 1H), 3.78 (s, 3H), 3.55 (m, 2H), 2.7 (m, 1H), 2.34 (m, 2H), 2.12 (m, 2H), 1.87-1.04 (m, 14H)

Example 239

Preparation of 1-Cyclohexyl-2-{2-[4'-fluoro-4-(pyrrolidine-1-carbonyl)biphen-2-yl]quinolin-6-yl}-1H-benzimidazole-5-carboxylic acid (Compound 549)

Step 1: 1-Cyclohexyl-2-{2-[4'-fluoro-4-(pyrrolidine-1-carbonyl)biphen-2-yl]quinolin-6-yl}-1H-benzimidazole-5-carboxylic acid Ethyl Ester (Compound 549a)

A mixture of 200 mg (0.29 mmol) Compound 419d 62 mg (0.44 mmol) 4-fluorophenyl-boronic acid, 32 mg (0.029 mmol) Pd(PPh$_3$)$_4$ and 2 mL sat. NaHCO$_3$ in 16 mL degassed MeOH was heated at 90° C. under Ar overnight. The mixture was evaporated to dryness, the residue was taken up in CH$_2$Cl$_2$ and purified on silica gel using CH$_2$Cl$_2$¦MeOH as eluent to yield 197 mg orange solid.

Step 2: 1-Cyclohexyl-2-{2-[4'-fluoro-4-(pyrrolidine-1-carbonyl)biphen-2-yl]quinolin-6-yl}-1H-benzimidazole-5-carboxylic acid (Compound 549)

A solution of 197 mg (0.30 mmol) Compound 549a in 3.75 mL THF, 3 mL MeOH and 0.75 mL 2 N NaOH was stirred at room temperature overnight and then heated at 50° C. for 1.5 h. After the addition of 1.5 mL 1 M HCl, the solution was evaporated to dryness and the residue was purified on HPLC to yield 66 mg yellow solid.

MS: 639.40 (M+H$^+$); $^1$H-NMR (DMSOd$_6$): δ (ppm) 8.43-8.35 (m, 2H), 8.31-8.25 (m, 2H), 8.11 (dd, 1H, J=9 Hz and 1.8 Hz), 8.04 (dd, 1H, J=8.7 Hz and 1.5 Hz), 7.93 (d, 1H, J=1.5 Hz), 7.76 (dd, 1H, J=8.1 Hz and 1.8 Hz), 7.61-7.55 (m, 4H), 7.24 (m, 2H), 7.14 (m, 2H), 4.45 (m, 1H), 3.52 (m, 4H), 2.31 (m, 2H), 2.12 (m, 2H), 1.88 (m, 6H), 1.62 (m, 1H), 1.33 (m, 3H).

Example 240

Preparation of 1-Cyclohexyl-2-{2-[4'-methoxy-4-(pyrrolidine-1-carbonyl)biphen-2-yl]quinolin-6-yl}-1H-benzimidazole-5-carboxylic acid (Compound 561)

Step 1: 1-Cyclohexyl-2-{2-[4'-methoxy-4-(pyrrolidine-1-carbonyl)biphen-2-yl]quinolin-6-yl}-1H-benzimidazole-5-carboxylic acid Ethyl Ester (Compound 561a)

Prepared as described for Compound 549a using 4-methoxyphenylboronic acid instead of 4-fluorophenylboronic acid.

Step 2: 1-Cyclohexyl-2-{2-[4'-methoxy-4-(pyrrolidine-1-carbonyl)biphen-2-yl]quinolin-6-yl}-1H-benzimidazole-5-carboxylic acid (Compound 561)

Prepared as described for Compound 549 using Compound 561a instead Compound 549a.

MS: 651.32 (M+H$^+$); $^1$H-NMR (DMSOd$_6$): δ (ppm): 8.35-8.27 (m, 3H), 8.15-8.05 (m, 2H), 7.96 (d, 1H, J=8.7 Hz), 8.90 (d, 1H, J=1.2 Hz), 7.73 (dd, 1H, J=7.8 Hz and 1.2 Hz), 7.55 (d, 2H, J=8.1 Hz), 7.15-7.11 (m, 3H), 6.86 (d, 2H, J=8.4 Hz), 4.43 (m, 1H), 3.72 (s, 3H), 3.52 (m, 4H), 2.31 (m, 2H), 2.07 (m, 2H), 1.87 (m, 6H), 1.62 (m, 1H), 1.33 (m, 3H).

Example 241

Preparation of 2-[2-(4'-Chloro-4-fluoro-biphen-2-yl)-quinolin-6-yl]-1-cyclohexyl-1H-benzoimidazole-5-carboxylic acid (Compound 563)

1-(2-Bromo-5-fluoro-phenyl)-ethanone (868 mg, 4 mmol), p-chlorophenylboronic acid (768 mg, 1.2 eq.), and tetrakis (triphenylphosphine)palladium(0) (473 mg, 0.1 eq.), were dissolved in 25 mL toluene, 6 mL methanol and 2.5 mL sat. sodium bicarbonate solution. After degassing/sonicating the solution, the sealed reaction vessel was heated to 80° C. overnight. The cooled solution was separated between ethyl acetate and water; the aqueous phase extracted two more times with ethyl acetate, and the organic fractions were combined, dried with sodium sulfate and evaporated. Silica gel chromatography (5:1 hexanes/ethyl acetate) gave 1-(4'-chloro-4-fluoro-biphen-2-yl)-ethanone (821 mg).

1-(4'-Chloro-4-fluoro-biphen-2-yl)-ethanone (62 mg, 0.25 mmol) and 2-(4-amino-3-formyl-phenyl)-1-cyclohexyl-1H-benzoimidazole-5-carboxylic acid ethyl ester (98 mg, 0.25 mmol) were dissolved in 500 μL ethanol and 500 μL 10% ethanolic KOH were added. The reaction was stirred at 75° C. overnight. The reaction was acidified with 4N hydrochloric acid, extracted three times with ethyl acetate, the organic extracts were dried with sodium sulfate and then evaporated. Purification via reverse-phase HPLC gave 84 mg product.

MS: 576.20 (M+H$^+$); $^1$H-NMR (d6-DMSO): δ (ppm) 8.27-8.35 (m, 3H), 8.18 (8d, 1H, J=8.8 Hz), 8.07 (d, 1H, J=8.5 Hz), 8.01 (dd, 1H, J=2.1 Hz, 8.8 Hz), 8.92 (dd, 1H, J=1.4 Hz, 8.5 Hz), 7.84 (dd, 1H, J=5.9 Hz, 8.5 Hz), 7.38-7.47 (m, 2H), 7.31-7.36 (m, 2H), 7.18-7.22 (m,2H), 7.15 (d, 1H, 8.5 Hz) 4.36-4.45 (m, 1H), 2.26-2.35 (m, 2H), 2.01-2.05 (m, 2H), 1.83-1.87 (m, 2H), 1.62-1.75 (m,1H), 1.28-1.43 (m, 3H)

Example 242

Preparation of 2-[2-(4-amino-4'-chloro-biphen-2-yl)-quinolin-6-yl]-1-cyclohexyl-1H-benzoimidazole-5-carboxylic acid (Compound 569)

1-(4'-Chloro-4-nitro-biphen-2-yl)-ethanone (69 mg, 0.25 mmol) and 2-(4-amino-3-formyl-phenyl)-1-cyclohexyl-1H-benzoimidazole-5-carboxylic acid ethyl ester (98 mg, 0.25 mmol) were dissolved in 500 μL ethanol and 500 μL 10% ethanolic KOH were added. The reaction was stirred at 75° C. for 3 days. The reaction was acidified with 4N hydrochloric acid, extracted three times with ethyl acetate, the organic extracts were dried with sodium sulfate and then evaporated. Purification via reverse-phase HPLC gave 18 mg product.

MS: 563.22 (M+H$^+$); H$^1$-NMR (d$_6$-acetone): δ (ppm) 8.51-8.59 (m,2H), 8.12-8.34 (m, 5H), 7.90-7.99 (m, 1H), 7.73 (d, 1H, 8.5 Hz), 7.61-7.68 (m, 1H), 7.15-7.36 (m, 5H), 4.70-4.75 (m, 1H), 2.46-2.58 (m, 2H), 2.22-2.30 (m, 2H), 1.92-2.00 (m, 2H), 1.72-1.75 (m, 1H), 1.46-1.55 (m, 3H)

Example 243

Preparation of 1-cyclohexyl-2-[2-(4,4'-dichloro-biphen-2-yl)-quinolin-6-yl]-1H-benzoimidazole-5-carboxylic acid (Compound 567)

Step 1: 1-(4'-chloro-4-chloro-biphen-2-yl)-ethanone (Compound 567a)

1-(2-Bromo-5-chloro-phenyl)-ethanone (467 mg, 2 mmol; synthesized similarly as described in Example 166 from 2-Bromo-5-chloro-benzoic acid), p-chlorophenylboronic acid (384 mg, 1.2 eq.), and tetrakis (triphenylphosphine)palladium(0) (237 mg, 0.1 eq.), were dissolved in 12.5 mL toluene, 3 mL methanol and 1.3 mL sat. sodium bicarbonate solution. After degassing/sonicating the solution, the sealed reaction vessel was heated to 80° C. overnight. The cooled solution was separated between ethyl acetate and water; the aqueous phase extracted two more times with ethyl acetate, and the organic fractions were combined, dried with sodium sulfate and evaporated. Silica gel chromatography (5:1 hexanes/ethyl acetate) gave the title intermediate (438 mg).

Step 2: The Title Compound 1-(4'-Chloro-4-chloro-biphen-2-yl)-ethanone (132 mg, 0.5 mmol) and 2-(4-amino-3-formyl-phenyl)-1-cyclohexyl-1H-benzoimidazole-5-carboxylic acid ethyl ester (98 mg, 0.25 mmol) were dissolved in 500 μL ethanol and 500 μL 10% ethanolic KOH were added. The reaction was stirred at 75° C. overnight. The reaction was acidified with 4N hydrochloric acid, extracted three times with ethyl acetate, the organic extracts were dried with sodium sulfate and then evaporated. Purification via reverse-phase HPLC gave 132 mg product.

MS: 592.17 (M+H$^+$); H$^1$-NMR (d$_6$-acetone): δ (ppm) 8.54-8.55 (m, 2H), 8.19-8.32 (m, 4H), 8.10 (dd, 1H, J=1.0 Hz, 8.5 Hz), 7.88 (d, 1H, 2.0 Hz), 7.62 (dd, 1H, J=2.3 Hz, 8.3 Hz), 7.55 (d, 1H, 8.2 Hz), 7.22-7.33 (m, 5H), 4.73-4.82 (m, 1H), 2.46-2.54 (m, 2H), 2.28-2.32 (m, 2H), 1.94-1.97 (m, 2H), 1.71-1.75 (m, 1H), 1.46-1.55 (m, 3H)

Example 244

Preparation of 2-{2-[8-(4-chloro-phenyl)-3,4-dihydro-2H-benzo[b][1,4]dioxepin-7-yl]-quinolin-6-yl}-1-cyclohexyl-1H-benzoimidazole-5-carboxylic acid (Compound 565)

Step 1: 1-[8-(4-Chloro-phenyl)-3,4-dihydro-2H-benzo[b][1,4]dioxepin-7-yl]-ethanone (Compound 565a)

1-(8-Bromo-3,4-dihydro-2H-benzo[b][1,4]dioxepin-7-yl)- (1.08 g, 4 mmol), p chlorophenylboronic acid (768 mg, 1.2 eq.), and tetrakis (triphenylphosphine)palladium(0) (473 mg, 0.1 eq.), were dissolved in 25 mL toluene, 6 mL methanol and 2.5 mL of saturated sodium bicarbonate solution. After degassing/sonicating the solution, the sealed reaction vessel was heated to 80 C overnight. The cooled solution was separated between ethyl acetate and water; the aqueous phase extracted two more times with ethyl acetate, and the organic fractions were combined, dried with sodium sulfate and evaporated. Silica gel chromatography (5:1 hexanes/ethyl acetate) was used for purification.

Step 2: The Title Compound

1-[8-(4-Chloro-phenyl)-3,4-dihydro-2H-benzo[b][1,4]dioxepin-7-yl]-ethanone (76 mg, 0.25 mmol) and 2-(4-amino-3-formyl-phenyl)-1-cyclohexyl-1H-benzoimidazole-5-carboxylic acid ethyl ester (98 mg, 0.25 mmol) were dissolved in 500 μL ethanol and 500 μL 10% ethanolic KOH were added. The reaction was stirred at 75° C. overnight. The reaction was acidified with 4N hydrochloric acid, extracted three times with ethyl acetate, the organic extracts were dried with sodium sulfate and then evaporated. Purification via reverse-phase HPLC gave 132 mg of the title compound.

MS: 630.23 (M+H$^+$); H$^1$-NMR (d6-DMSO): δ (ppm) 8.27-8.32 (m, 3H), 8.17 (d, 1H, J=8.8 Hz), 8.07 (d, 1H, 8.5 Hz), 8.02 (dd, 1H, 1.8 Hz, 9.1 Hz), 7.41 (s, 1H), 7.29-7.32 (m, 2H), 7.09-7.15 (m, 4H), 4.36-4.45 (m, 1H), 4.22-4.30 (m,2H), 2.26-2.34 (m,2H), 2.17-2.21 (m, 2H), 2.01-2.05 (m, 2H), 1.83-1.86 (m, 2H), 1.62-1.75 (m, 1H), 1.28-1.35 (m, 3H)

Example 245

Preparation of 2-[4-(2-tert-butoxycarbonylamino-ethylamino)-2-phenyl-quinolin-6-yl]-1-cyclohexyl-1H-benzoimidazole-5-carboxylic acid (Compound 399)

In this reaction 51 mg (0.1 mmol) of crude 2-(4-chloro-2-phenyl-quinolin-6-yl)-1-cyclohexyl-1H-benzoimidazole-5-carboxylic acid ethyl ester were used. The nucleophile used was (2-amino-ethyl)-carbamic acid tert-butyl ester. Yield: 21 mg.

MS: 606.32 (M+H$^+$); H$^1$-NMR (CD$_3$OD): δ (ppm) 8.72 (s,1H), 8.45 (s, 1H), 8.04-8.27 (m, 6H), 7.68-7.76 (m, 4H), 7.33 (s, 1H), 4.36-4.45 (m, 1H), 3.81 (tr, 2H, 5.6 Hz), 3.49 (tr, 2H, 5.6 Hz), 2.42-2.48 (m, 2H), 2.14-2.16 (m, 2H), 1.96-2.99 (m, 2H), 1.74-1.80 (m, 1H), 1.35-1.45 (m, 3H), 1.25 (s, 9H)

Example 246

Preparation of 1-Cyclohexyl-2-(4-hydrazino-2-phenyl-quinolin-6-yl)-1H-benzoimidazole-5-carboxylic acid (Compound 466)

In this reaction 102 mg (0.2 mmol) of crude 2-(4-chloro-2-phenyl-quinolin-6-yl)-1-cyclohexyl-1H-benzoimidazole-5-carboxylic acid ethyl ester was reacted with hydrazine as the nucleophile as described for the preparation of Compound 481. Yield: 3.7 mg.

MS: 478.20 (M+H$^+$); H$^1$-NMR (CD$_3$OD): δ (ppm) 8.74 (s,1H), 8.38-8.44 (m,2H), 8.28-8.31 (m, 1H), 8.05-8.18 (m, 4H), 7.71-7.77 (m, 4H), 4.36-4.45 (m, 1H), 2.44-2.48 (m,2H), 2.10-2.14 (m, 2H), 1.97-2.01 (m, 2H), 1.83-1.86 (m, 2H), 1.75-1.80 (m, 1H), 1.35-1.42 (m, 3H)

Example 247

Preparation of 1-Benzyl-2-[2-(4'-chloro-4-methoxy-biphen-2-yl)-quinolin-6-yl]-1H-benzoimidazole-5-carboxylic acid (Compound 559)

The title compound was prepared from resin 534a and benzylamine according to the procedure described in the preparation of Compound 534.

MS (ESI) 596.19 (M+H$^+$); $^1$H NMR (DMSO-d$_6$) δ (ppm) 8.45 (s, 1H), 8.35 (s, 1H), 8.26 (d, 1H, J=8.7 Hz), 8.17 (s, 2H), 7.95 (dd, 1H, J=1.5, 8.4 Hz), 7.72 (d, 1H, J=8.7 Hz), 7.45 (d, 1H, J=7.5 Hz), 7.32-7.26 (m, 6H), 7.18 (d, 2H, J=8.4 Hz), 7.10 (d, 2H, J=8.4 Hz), 7.04 (d, 2H, J=8.41 Hz), 5.81 (s, 2H), 3.87 (s, 3H).

Example 248

Preparation of 2-[2-(4'-Chloro-4-methoxy-biphen-2-yl)-quinolin-6-yl]-3-cyclohexyl-3H-benzoimidazole-4-carboxylic acid (Compound 572)

Step 1. 2-Cyclohexylamino-3-nitro-benzoic acid Ethyl Ester

To a solution of 2-chloro-3-nitrobenzoic acid (0.85 g, 4.22 mmol) in anhydrous EtOH (50 mL) was bubbled with dry hydrogen chloride for 2 h at room temperature and the mixture was then stirred at room temperate overnight. After evaporation of solvent, water (100 mL) was added and the precipitates were collected by filtration and dried to give 2-chloro-3-nitro-benzoic acid ethyl ester.

The crude 2-chloro-3-nitro-benzoic acid ethyl ester was dissolved in acetonitrile (100 mL) and cyclohexylamine (2.5 mL, 21.83 mmol) was added. The mixture was stirred at reflux overnight. After evaporation of solvent, water (100 mL) was added and the precipitates were collected by filtration and dried to give 2-cyclohexylamino-3-nitro-benzoic acid ethyl ester (1.168 g, 95%). MS: 293.16 (M+H$^+$).

Step 2. 2-[2-(4'-Chloro-4-methoxy-biphen-2-yl)-quinolin-6-yl]-3-cyclohexyl-3H-benzoimidazole-4-carboxylic acid Compound 572)

2-Cyclohexylamino-3-nitro-benzoic acid ethyl ester (0.165 g, 0.564 mmol) by hydrogenation according to procedure (1) in the preparation of Compound 477d.

The amine was reacted with Compound 525c (0.23 g, 0.592 mmol) in the presence of HBTU (0.135 g, 0.356 mmol), followed cyclization in AcOH according to procedure (2) in the preparation of Compound 477d. Separation by RP HPLC (from 20% of buffer B to 99% of buffer B) gave the title compound (36 mg, 11%).

MS: 588.23 (M+H$^+$); $^1$H NMR (DMSO-d$_6$) δ (ppm) 8.38 (d, 1H, J=1.5 Hz), 8.35 (d, 1H, J=9.0 Hz), 8.21 (d, 1H, J=8.7 Hz), 8.08 (dd, 1H, J=1.5, 8.5 Hz), 7.95 (dd, 1H, J=1.1, 8.0 Hz), 7.77 (d, 1H, J=7.5 Hz), 7.53 (d, 1H, J=7.5 Hz), 7.46 (d, 1H, J=8.7 Hz), 7.36 (d, 1H, J=2.4 Hz), 7.29-7.25 (m, 2H), 7.22-7.19 (m, 2H), 7.10 (d, 2H, J=8.1 Hz), 4.74-4.65 (m, 1H), 3.88 (s, 3H), 2.11-2.08 (m, 2H), 1.70-1.66 (m, 2H), 1.55-1.48 (m, 2H), 1.23-1.16 (m, 2H), 0.82-0.73-1.23 (m, 2H).

Example 249

Preparation of 2-[2-(4'-Chloro-4-methoxy-biphen-2-yl)-quinolin-6-yl]-1-(2-methyl-cyclohexyl)-1H-benzoimidazole-5-carboxylic acid (Compound 556)

The title compound was prepared from resin 534a and 2-methylcyclopropylamine (a mixture of cis and trans) according to the procedure described in the preparation of Compound 534. This product is a mixture of cis and trans isomers.

MS: 602.24 (M+H$^+$).

Example 250

Preparation of 2-[2-(4'-Chloro-4-methoxy-biphen-2-yl)-quinolin-6-yl]-1-piperidin-4-yl-1H-benzoimidazole-5-carboxylic acid (Compound 558)

The title compound was prepared from resin 534a and 4-amino-cyclohexanecarboxylic acid tert-butyl ester according to the procedure described in the preparation of Compound 534.

MS: 589.22 (M+H$^+$); $^1$H NMR (DMSO-d$_6$) δ (ppm) 8.36 (d, 1H, J=8.7 Hz), 8.33-8.29 (m, 3H), 8.20 (d, 1H, J=8.7 Hz), 8.08 (dd, 2H, J=2.1, 8.7 Hz), 7.95 (dd, 1H, J=1.2, 8.4 Hz), 7.46 (d, 1H, J=8.4 Hz), 7.32-7.28 (m, 3H), 7.22-7.12 (m, 4H), 4.85 (m, 1H), 3.88 (s, 3H), 3.16-3.03 (m, 3H), 2.92-2.82 (m, 3H), 2.24-2.20 (m, 2H).

Example 251

Preparation of 1-Cyclohexyl-2-{2-[5-(pyrrolidine-1-carbonyl)-2-thiophen-2-yl]quinoline-6-yl}-1H-benzimidazole-5-carboxylic acid (Compound 400)

Step 1: 1-Cyclohexyl-2-{2-[5-(pyrrolidine-1-carbonyl)-2-thiophen-2-yl]quinoline-6-yl}-1H-benzimidazole-5-carboxylic acid Ethyl Ester (Compound 400a)

Prepared as described for Compound 402a using 4-tiopheneboronic acid instead of 4-fluorophenylboronic acid.

Step 2: 1-Cyclohexyl-2-{2-[5-(pyrrolidine-1-carbonyl)-2-thiophen-2-yl]quinoline-6-yl}-1H-benzimidazole-5-carboxylic acid (Compound 400)

Prepared as described for Compound 402 using Compound 400a instead of Compound 402a.

MS: 627.25 (M+H$^+$); $^1$H-NMR (DMSOd$_6$): δ (ppm): 8.52-8.49 (m, 2H), 8.38-8.29 (m, 3H), 8.16-8.04 (m, 2H), 7.81-7.69 (m, 3H), 7.54-7.44 (m, 2H), 7.00-6.93 (m, 2H), 4.40 (m, 1H), 3.51 (m, 4H), 2.30 (m, 2H), 2.15 (m, 2H), 1.87 (m, 6H), 1.62 (m, 1H), 1.38 (m, 3H).

Example 252

Preparation of 2-{2-[4'-Carboxy-4-(pyrrolidine-1-carbonyl)biphen-2-yl]quinolin-6-yl}-1-cyclohexyl-1H-benzimidazole-5-carboxylic acid (Compound 453)

Step 1: 2-{2-[4'-Carboxy-4-(pyrrolidine-1-carbonyl)biphen-2-yl]quinolin-6-yl}-1-cyclohexyl-1H-benzimidazole-5-carboxylic acid Ethyl Ester (Compound 453a)

Prepared as described for Compound 549a using 4-carboxyphenylboronic acid instead of 4-fluorophenylboronic acid.

Step 2: 2-{2-[4'-Carboxy-4-(pyrrolidine-1-carbonyl)biphen-2-yl]quinolin-6-yl}-1-cyclohexyl-1H-benzimidazole-5-carboxylic acid (Compound 453)

Prepared as described for Compound 549 using Compound 453a instead of Compound 549a.

MS: 665.26 (M+H$^+$); $^1$H-NMR (DMSOd$_6$): δ (ppm): 8.47-8.28 (m, 6H), 8.14-8.06 (m, 2H), 7.97 (d, J=1.8 Hz), 7.85-7.78 (m, 2H), 7.68-7.62 (m, 2H), 7.34-7.26 (m, 2H), 4.47 (m, 1H), 3.39 (m, 4H), 2.47 (m, 2H), 2.12 (m, 2H), 1.88 (m, 6H), 1.62 (m, 1H), 1.34 (m, 3H).

BIOLOGICAL EXAMPLES

Example A

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al. *Jnl. of Vir.*, 73:1649-1654, 1999; Ishii et al., *Hepatology*, 29:1227-1235, 1999; Lohmann et al., *Jnl of Bio. Chem.*, 274:10807-10815, 1999; and Yamashita et al., *Jnl. of Bio. Chem.*, 273:15479-15486, 1998.

WO 97/12033, filed on Sep. 27, 1996, by Emory University, listing C. Hagedom and A. Reinoldus as inventors, which claims priority to U.S. Ser. No. 60/004,383, filed on September 1995, describes an HCV polymerase assay that can be used to evaluate the activity of the of the compounds described herein. Another HCV polymerase assay has been reported by Bartholomeusz, et. al., Hepatitis C Virus (HCV) RNA polymerase assay using cloned HCV non-structural proteins; Antiviral Therapy 1996:1 (Supp 4) 18-24.

Screens that measure reductions in kinase activity from HCV drugs are disclosed in U.S. Pat. No. 6,030,785, to Katze et al., U.S. Pat. No. 6,228,576, to Delvecchio et al., and U.S. Pat. No. 5,759,795 to Jubin et al. Screens that measure the protease inhibiting activity of proposed HCV drugs are disclosed in U.S. Pat. No. 5,861,267 to Su et al., U.S. Pat. No. 5,739,002 to DeFrancesco et al., and U.S. Pat. No. 5,597,691 to Houghton et al.

Example B

Replicon Assay

A cell line, ET (Huh-lucubineo-ET) was used for screening of compounds of the present invention for HCV replication. The ET cell line was stably transfected with RNA transcripts harboring a I$_{389}$luc-ubi-neo/NS3-3'/ET replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They are all available through Life Technologies (Bethesda, Md.). The cells were plated at 0.5-1.0×10$^4$ cells/well in the 96 well plates and incubated for 24 h before adding test compounds. Then the compounds each at 5 and 50 µM were added to the cells. Luciferase activity was measured 48-72 hours later by adding a lysis buffer and the substrate (Catalog number Glo-lysis buffer E2661 and Bright-Glo leuciferase system E2620 Promega, Madison, Wis.). Cells should not be too confluent during the assay. Percent inhibition of replication was plotted relative to no compound control. Under the same condition, cytotoxicity of the compounds was determined using cell proliferation reagent, WST-1 (Roche, Germany). The compounds showing antiviral activities, but no significant cytotoxicities were chosen to determine $IC_{50}$ and $TC_{50}$.

Example C

Cloning and Expression of Recombinant HCV-NS5b

The coding sequence of NS5b protein was cloned by PCR from pFKI$_{389}$luc/NS3-3'/ET as described by Lohmann, V., et al. (1999) Science 285, 110-113 using the following primers:

(SEQ. ID. NO. 1)
aggacatggatccgcggggtcgggcacgagacag (SEQ. ID. NO. 2)
aaggctggcatgcactcaatgtcctacacatggac The cloned fragment was missing the C terminus 21 amino acid residues. The cloned fragment was inserted into an IPTG-inducible expression plasmid that provided an epitope tag $(His)_6$ at the carboxy terminus of the protein.

The recombinant enzyme was expressed in XL-1 cells and after induction of expression, the protein was purified using affinity chromatography on a nickel-NTA column. Storage condition was 10 mM Tris-HCl pH 7.5, 50 mM NaCl, 0.1 mM EDTA, 1 mM DTT, 20% glycerol at −20° C.

Example D

HCV-NS5b Enzyme Assay

The polymerase activity was assayed by measuring incorporation of radiolabeled UTP into a RNA product using a biotinylated, heteropolymeric template, which included a portion of the HCV genome. Typically, the assay mixture (50 µL) contained 10 mM Tris-HCl (pH 7.5), 5 mM $MgCl_2$, 0.2 mM EDTA, 10 mM KCl, 1 unit/µL RNAsin, 1 mM DTT, 10 µM each of NTP, including [$^3$H]-UTP, and 10 ng/µL heteropolymeric template. Test compounds were initially dissolved in 100% DMSO and further diluted in aqueous buffer containing 5% DMSO. Typically, compounds were tested at concentrations between 1 nM and 100 µM. Reactions were started with addition of enzyme and allowed to continue at 37° C. for 2 hours. Reactions were quenched with 8 µL of 100 mM EDTA and reaction mixtures (30 µL) were transferred to streptavidin-coated scintillation proximity microtiter plates (FlashPlates) and incubated at 4° C. overnight. Incorporation of radioactivity was determined by scintillation counting.

Shown in Table IX below are the values for enzyme inhibition measured at compound concentrations of 100 and 33 uM, (% inh@199 and % inh@33, respectively). The percent inhibition values are calculated from the differential incorporation of radioactivity compared to a control reaction without compound:

% inhibition=100−[(Counts$_{INH}$−Counts$_{BKG}$)/Counts$_{CTRL}$−Counts$_{BKG}$)×100 where Counts$_{INH}$ is the signal of the testwell with inhibitor, Counts$_{BKG}$ is the background signal and Counts$_{CTRL}$ is the signal of a testwell without inhibitor.

TABLE IX

Percent Inhibition Data

| Cmpd # | % inh@100 | % inh@33 |
|---|---|---|
| 203 | 97.54 | 74.98 |
| 204 | 100.95 | 99.68 |
| 205 | 98.95 | 84.42 |
| 206 | 96.87 | 94.16 |
| 215 | 100.88 | 99.25 |
| 230 | 98.22 | 92.74 |
| 231 | 97.54 | 66.96 |
| 232 | 80.22 | 60.45 |
| 233 | 88.16 | 49.99 |
| 234 | 100.11 | 98.59 |
| 235 | 99.50 | 99.07 |
| 236 | 99.25 | 99.19 |
| 237 | 95.62 | 79.74 |
| 238 | 98.40 | 97.60 |
| 239 | 70.15 | 49.12 |
| 240 | 96.08 | 95.74 |
| 241 | 98.41 | 98.00 |
| 242 | 97.00 | 97.40 |
| 243 | 98.12 | 95.99 |
| 244 | 97.02 | 75.71 |
| 245 | 97.38 | 73.22 |
| 246 | 96.40 | 95.92 |
| 247 | 94.24 | 66.78 |
| 248 | 86.78 | 47.36 |
| 249 | 97.15 | 94.51 |
| 258 | 97.99 | 97.03 |
| 259 | 99.36 | 99.71 |
| 310 | 98.33 | 83.24 |
| 311 | 93.27 | 83.02 |
| 351 | 98.13 | 94.87 |
| 352 | 98.82 | 94.18 |
| 353 | 67.52 | 67.33 |
| 354 | 100.55 | 97.99 |
| 355 | 89.31 | 72.35 |
| 356 | 100.47 | 101.08 |
| 357 | 100.55 | 98.79 |
| 358 | 95.33 | 85.08 |
| 359 | 99.60 | 97.29 |
| 360 | 97.86 | 97.56 |
| 361 | 98.71 | 100.00 |
| 362 | 98.43 | 100.52 |
| 363 | 100.53 | 98.36 |
| 364 | 100.54 | 98.60 |
| 365 | 102.60 | 102.25 |
| 366 | 99.38 | 97.62 |
| 367 | 100.85 | 102.67 |
| 368 | 79.47 | 51.25 |
| 369 | 98.80 | 96.18 |
| 370 | 99.67 | 97.76 |
| 372 | 98.17 | 98.12 |
| 373 | 83.79 | 39.89 |
| 374 | 98.32 | 97.62 |
| 376 | 97.19 | 97.42 |
| 377 | 99.42 | 99.20 |
| 378 | 100.93 | 100.39 |
| 379 | 97.78 | 93.32 |
| 380 | 101.16 | 97.59 |
| 381 | 98.05 | 94.33 |
| 382 | 100.73 | 101.35 |
| 384 | 99.26 | 95.54 |
| 385 | 76.24 | 42.63 |
| 386 | 99.90 | 100.34 |
| 387 | 98.68 | 99.05 |
| 388 | 98.58 | 98.73 |
| 389 | 99.55 | 99.92 |
| 390 | 92.52 | 79.87 |
| 391 | 97.45 | 94.13 |
| 392 | 93.53 | 83.75 |
| 393 | 96.94 | 97.56 |
| 394 | 100.04 | 98.90 |
| 395 | 101.21 | 100.10 |
| 396 | 100.24 | 100.13 |
| 397 | 99.28 | 95.57 |
| 398 | 92.05 | 59.65 |
| 399 | 101.52 | 95.64 |

TABLE IX-continued

Percent Inhibition Data

| Cmpd # | % inh@100 | % inh@33 |
|---|---|---|
| 401 | 101.01 | 100.40 |
| 403 | 99.93 | 99.42 |
| 404 | 101.17 | 102.42 |
| 405 | 98.89 | 90.50 |
| 406 | 98.06 | 97.29 |
| 408 | 98.86 | 99.29 |
| 409 | 99.86 | 97.88 |
| 410 | 88.64 | 84.34 |
| 411 | 91.45 | 78.12 |
| 412 | 100.15 | 98.44 |
| 413 | 100.19 | 95.50 |
| 414 | 96.83 | 93.43 |
| 415 | 101.59 | 101.27 |
| 416 | 102.51 | 100.70 |
| 417 | 97.98 | 97.75 |
| 418 | 102.87 | 103.58 |
| 419 | 101.14 | 100.67 |
| 420 | 98.26 | 98.26 |
| 421 | 100.12 | 100.02 |
| 422 | 99.18 | 98.76 |
| 423 | 101.62 | 102.46 |
| 424 | 99.09 | 98.70 |
| 425 | 98.18 | 96.17 |
| 426 | 101.61 | 96.59 |
| 427 | 98.37 | 93.85 |
| 428 | 99.57 | 98.85 |
| 429 | 100.88 | 96.25 |
| 430 | 96.65 | 98.02 |
| 431 | 96.38 | 95.34 |
| 432 | 96.37 | 88.94 |
| 433 | 100.50 | 92.47 |
| 434 | 102.40 | 104.83 |
| 435 | 101.42 | 102.36 |
| 436 | 99.29 | 98.82 |
| 437 | 100.51 | 100.29 |
| 438 | 99.60 | 98.71 |
| 439 | 97.03 | 99.19 |
| 440 | 97.75 | 99.15 |
| 441 | 98.75 | 97.35 |
| 442 | 98.23 | 92.50 |
| 443 | 98.70 | 87.01 |
| 444 | 100.55 | 99.55 |
| 445 | 99.64 | 96.88 |
| 446 | 100.99 | 96.61 |
| 447 | 94.86 | 97.83 |
| 448 | 96.03 | 94.57 |
| 449 | 101.33 | 99.77 |
| 450 | 99.70 | 96.48 |
| 451 | 95.64 | 76.27 |
| 452 | 102.35 | 102.39 |
| 454 | 100.56 | 98.26 |
| 455 | 99.79 | 100.03 |
| 456 | 99.69 | 100.26 |
| 457 | 98.33 | 98.21 |
| 458 | 103.55 | 100.15 |
| 459 | 99.82 | 99.54 |
| 460 | 101.72 | 100.53 |
| 461 | 96.65 | 97.89 |
| 462 | 101.29 | 98.24 |
| 463 | 97.17 | 95.99 |
| 464 | 100.35 | 99.74 |
| 465 | 100.83 | 98.78 |
| 466 | 100.12 | 92.92 |
| 467 | 100.48 | 96.33 |
| 468 | 99.12 | 99.33 |
| 469 | 98.24 | 94.22 |
| 470 | 99.37 | 100.78 |
| 471 | 99.81 | 97.79 |
| 472 | 98.07 | 97.10 |
| 473 | 97.41 | 99.22 |
| 474 | 100.57 | 96.95 |
| 475 | 95.91 | 97.50 |
| 476 | 97.06 | 97.35 |
| 477 | 95.91 | 92.43 |
| 478 | 97.15 | 95.80 |
| 479 | 102.24 | 99.64 |
| 480 | 103.84 | 101.37 |
| 481 | 96.74 | 76.46 |
| 482 | 100.85 | 100.12 |
| 483 | 99.39 | 101.50 |
| 484 | 98.30 | 99.62 |
| 485 | 99.54 | 98.59 |
| 486 | 97.89 | 93.46 |
| 487 | 101.00 | 101.69 |
| 488 | 97.17 | 91.81 |
| 489 | 96.01 | 87.01 |
| 490 | 94.33 | 95.94 |
| 491 | 99.95 | 98.35 |
| 492 | 100.37 | 99.19 |
| 493 | 99.96 | 101.32 |
| 494 | 99.18 | 94.82 |
| 495 | 100.98 | 99.76 |
| 496 | 101.35 | 101.25 |
| 497 | 88.47 | 65.45 |
| 498 | 100.08 | 98.48 |
| 499 | 99.74 | 100.97 |
| 500 | 100.96 | 101.33 |
| 501 | 96.82 | 90.61 |
| 502 | 100.17 | 99.04 |
| 503 | 96.99 | 95.76 |
| 504 | 99.97 | 98.26 |
| 505 | 101.67 | 99.73 |
| 506 | 99.12 | 98.92 |
| 507 | 100.68 | 100.80 |
| 508 | 98.89 | 98.94 |
| 509 | 100.70 | 100.44 |
| 510 | 100.14 | 99.45 |
| 511 | 94.96 | 78.44 |
| 512 | 97.87 | 78.89 |
| 513 | 95.91 | 93.18 |
| 514 | 91.87 | 89.64 |
| 515 | 88.31 | 81.94 |
| 516 | 100.07 | 99.30 |
| 517 | 97.78 | 81.02 |
| 518 | 97.84 | 75.95 |
| 519 | 99.11 | 96.88 |
| 520 | 98.89 | 94.81 |
| 521 | 91.41 | 84.85 |
| 522 | 74.23 | 76.67 |
| 523 | 94.97 | 87.14 |
| 524 | 93.58 | 74.09 |
| 525 | 100.63 | 100.83 |
| 526 | 98.99 | 96.84 |
| 527 | 100.64 | 99.42 |
| 528 | 101.32 | 100.28 |
| 529 | 99.75 | 99.20 |
| 530 | 98.15 | 98.17 |
| 531 | 99.26 | 99.98 |
| 532 | 98.77 | 99.64 |
| 533 | 89.85 | 56.75 |
| 534 | 101.02 | 90.07 |
| 535 | 100.49 | 100.97 |
| 536 | 98.87 | 97.55 |
| 537 | 99.76 | 100.24 |
| 538 | 72.78 | 56.60 |
| 539 | 102.41 | 104.03 |
| 540 | 95.05 | 91.13 |
| 541 | 98.14 | 76.08 |
| 542 | 98.58 | 81.13 |
| 543 | 101.90 | 102.06 |
| 544 | 100.09 | 101.67 |
| 545 | 101.02 | 99.18 |
| 546 | 101.72 | 95.35 |
| 547 | 101.82 | 102.71 |
| 548 | 100.68 | 102.77 |
| 549 | 102.09 | 100.38 |
| 550 | 101.72 | 99.13 |
| 551 | 95.68 | 87.53 |
| 552 | 100.63 | 101.29 |
| 554 | 82.03 | 64.68 |

TABLE IX-continued

Percent Inhibition Data

| Cmpd # | % inh@100 | % inh@33 |
|---|---|---|
| 555 | 100.85 | 101.06 |
| 556 | 102.27 | 102.72 |
| 557 | 101.41 | 102.52 |
| 558 | 77.35 | 32.53 |
| 559 | 101.13 | 101.11 |
| 560 | 100.73 | 101.03 |
| 562 | 101.41 | 101.94 |
| 563 | 100.87 | 100.69 |
| 564 | 101.39 | 102.31 |
| 565 | 100.47 | 102.26 |
| 566 | 100.49 | 99.17 |
| 567 | 97.65 | 100.79 |
| 568 | 100.49 | 100.99 |
| 569 | 100.78 | 100.86 |

FORMULATION EXAMPLES

The following are representative pharmaceutical formulations containing a compound of formula I.

Formulation Example 1

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Formulation Example 3

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4

Injectable Formulation

The following ingredients are mixed to form an injectable formulation.

| Ingredient | Amount |
|---|---|
| compound of this invention | 0.2 mg-20 mg |
| sodium acetate buffer solution, 0.4 M | 2.0 mL |
| HCl (1 N) or NaOH (1 N) | q.s. to suitable pH |
| water (distilled, sterile) | q.s. to 20 mL |

Formulation Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
|---|---|
| Compound of the invention | 500 mg |
| Witepsol ® H-15 | balance |

What is claimed is:

1. A compound according to formula II:

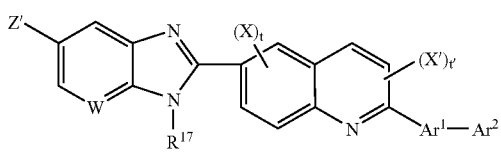

wherein:

W is CH;

Z' is selected from the group consisting of carboxy and carboxy ester, $R^{17}$ is selected from the group consisting of cycloalkyl and cycloalkyl substituted with 1 to 3 alkyl groups;

X and X' are independently selected from the group consisting of alkyl, substituted alkyl, alkoxy, substituted alkoxy, halo, hydroxy, and nitro;

$A^1$ is selected from the group consisting of aryl, and substituted aryl;

and $Ar^2$ is selected from the group consisting of aryl, substituted aryl, cycloalkyl, substituted cycloalkyl, heteroaryl, substituted heteroaryl, heterocyclic and substituted heterocyclic;

t is an integer equal to 0, 1 or 2; and t' is an integer equal to 0 or 1;

and pharmaceutically acceptable salts thereof.

2. The compound according to claim 1, wherein $R^{17}$ is cycloalkyl.

3. The compound according to claim 2, wherein $R^{17}$ is cyclohexyl.

4. The compound according to claim 1, wherein —$Ar^1$—$Ar^2$ are selected from the group consisting of -aryl-aryl, -aryl-substituted aryl, -substituted aryl-aryl, and -substituted aryl-substituted aryl.

5. The compound according to claim 2, wherein —$Ar^1$—$Ar^2$ are selected from the group consisting of biphen-2-yl, biphen-4-yl, 4-amino-4'-chlorobiphen-2-yl, 4'-aminomethyl-4-methoxybiphen-2-yl, 4-carbamoyl-4'-methoxybiphen-2-yl, 4-carbamoyl-4'-fluorobiphen-2-yl, 4-carbamoyl-4'-methoxybiphen-2-yl, 4-carbamoyl-4'-nitrobiphen-2-yl, 4-(carbamoylmethy-carbamoyl)biphen-2-yl, 4-(carbamoylmethylcarbamoyl)-4'chlorobiphen-2-yl, 4-carboxy-4'-chlorobiphen-2-yl, 3-carboxy-4'-methoxybiphen-2-yl, 4-carboxy-4'-methoxybiphen-2-yl, 4'-carboxy-4-(pyrrolidin-1-ylcarbonyl)biphen-2-yl, 4-carboxymethoxybiphen-2-yl, 4-carboxymethoxy-4'-chlorobiphen-2-yl, 4'-chlorobiphen-2-yl, 4'-chloro-4-chlorobiphen-2-yl, 4'-chloro-4-(dimethylaminocthylcarbamoyl)biphen-2-yl, 4'-chloro-4-(2-ethoxyethoxy)biphen-2-yl, 3'-chloro-4'-fluoro-4-methoxybiphen-2-yl, 4'-chloro-4-fluorobiphen-2-yl, 4'-chloro-4-hydroxybiphen-2-yl, 3'-chloro-4-methoxybiphen-2-yl, 4'-chloro-4-methylcarbamoylbiphen-2-yl, 4'-chloro-4-methoxybiphen-2-yl, 4'-chloro-4-(2-methoxyethoxy)biphen-2-yl, 4'-chloro-4-nitrobiphen-2-yl, 4'-chloro-4-(2-oxo-2-pyrrolidin-1-ylethoxy)biphen-2-yl, 4'-chloro-4-(pyrrolidin-1-ylcarbonyl)biphen-2-yl, 4' chloro-4-(3-pyrrolidin-1-ylpropoxy)biphen-2-yl, 4'-cyano-4-methoxybiphen-2-yl, 3',4' dichloro-4-methoxybiphen-2-yl, 4,4'-dimethoxybiphen-2-yl, 3',4'-dimethoxy-4-(pyrrolidin-1-ylcarbonyl)biphen-2-yl, 4'-dimethylamino-4-methoxybiphen-2-yl, 4-(2-dimethylaminoethylcarbamoyl)biphen-2-yl, 4'-ethoxy-4-methoxybiphen-2-yl, 4'-fluoro-4-methoxybiphen-2-yl, 4-hydroxybiphenyl, 4-methoxybiphenyl, 4-methoxy-4'-hydroxybiphen-2-yl, 4-(2-methoxyethoxy)biphen-2-yl, 4-methoxy-4'-methylbiphen-2-yl, 4-methoxy-3'-nitrobiphen-2-yl, 4-methoxy-4'-nitrobiphen-2-yl, 4-methylcarbamoylbiphen-2-yl, 3'-methyl-4-methoxybiphen-2-yl, 4'-nitro-4-(pyrrolidin-1-ylcarbonyl)biphen-2-yl, 4-(2-oxo-2-pyrrolidin-1-ylethoxy)biphen-2-yl, 4-(3-pyrrolidin-1-ylpropoxy)biphen-2-yl, and 4'-trifluoromethyl-4-methoxybiphen-2-yl.

6. The compound according to claim 1, wherein —$Ar^1$—$Ar^2$ are selected from the group consisting of -aryl-heteroaryl, -aryl-substituted heteroaryl, -substituted aryl-heteroaryl, and -substituted aryl-substituted heteroaryl.

7. The compound according to claim 6, wherein —$Ar^1$—$Ar^2$ are selected from the group consisting of 2-furan-2-yl-5-methoxyphenyl, 4-(imidazol-1-yl)phenyl, 5-methoxy-2-thiophen-2-ylphenyl, 2-(2,4-dimethoxypyrimidin-5-yl)4-methoxyphenyl, and 2-(pyrid-4-yl)phenyl.

8. The compound according to claim 1, wherein —$Ar^1$—$Ar^2$ are selected from the group consisting of -aryl-cycloalkyl, -aryl-substituted cycloalkyl, -substituted aryl-cycloalkyl, -substituted aryl-substituted cycloalkyl, -arylheterocyclic, aryl-substituted heterocyclic, substituted aryl-heterocyclic, and substituted aryl-substituted heterocyclic.

9. The compound according to claim 8, wherein —$Ar^1$—Ar2 are selected from the group consisting of(4-piperazin-1-yl)phenyl, 2-cyclohexyl-5-methoxyphenyl, and 4-morpholinophenyl.

10. A compound selected from the group consisting of

2-{2-[4'-chloro-4-(pyrrolidine-1-carbonyl)-biphen-2-yl]quinolin-6-yl}-1-cyclohexyl-1H-benzoimidazole-5-carboxylic acid;

2-[2-(4'-chloro-4-methoxy-biphen-2-yl)quinolin-6-yl]1-cyclohexyl-1H-benzoimidazole-5-carboxylic acid;

1-cyclohexyl-2-{2-[4-(2-oxo-2-pyrrolidin-1-yl-ethoxy)-biphen-2-yl]-quinolin-6-yl}-1H-benzoimidazole-5-carboxylic acid;

2-{2-[4-(carbamoylmethyl-carbamoyl)-4'-chloro-biphen-2-yl]-quinolin-6-yl}-1-cyclohexyl-1H-benzoimidazole-5-carboxylic acid;

1-cyclohexyl-2-[2-(4-methylcarbamoyl-biphen-2-yl)quinolin-6-yl]1H-benzoimidazole-5-carboxylic acid;

2-[2-(4'-cyano-4-methoxy-biphen-2-yl)-quinolin-6-yl]-1-cyclohexyl-1H-benzoimidazole-5-carboxylic acid;
2-[2-(3'-chloro-4'-fluoro-4-methoxy-biphen-2yl)-quinolin-6-yl]1-cyclohexyl-1H-benzoimidazole-5-carboxylic acid;
1-cyclohexyl-2-[2-(4-methoxy-3'-methyl-biphen-2-yl)-quinolin-6-yl]1H-benzoimidazole-5-carboxylic acid;
1-cyclohexyl-2[2-(2-pyridin-4-yl-phenyl)quinolin-6-yl]-1H-benzoimidazole-5-carboxylic acid;
2-[2-(4-carboxymethoxy-biphen-2-yl)-quinolin-6-yl]-1-cyclohexyl-1H-benzoimidazole-5-carboxylic acid;
2-{2-[4'-chloro-4-(2-oxo-2-pyrrolidin-1-yl-ethoxy)-biphen-2-yl]-quinolin-6-yl}-1-cyclohexyl-1H-benzoimidazole-5-carboxylic acid;
2-{2-[4-(carbamoylmethyl-carbamoyl)-biphen-2-yl]-quinolin-6-yl}-1-cyclohexyl-1H-benzoimidazole-5-carboxylic acid;
2-[2-(4'-chloro-4-methylcarbamoyl-biphen-2-yl)-quinolin-6-yl]1-cyclohexyl-1H-benzoimidazole-5-carboxylic acid;
2-(2-biphen-2-yl-8-methyl-quinolin-6-yl)-1-cyclohexyl-1H-benzoimidazole-5-carboxylic acid;
2-[2-(4'-carbamoyl-4-methoxy-biphen-2-yl)-quinolin-6-yl]-1-cyclohexyl-1H-benzoimidazole-5-carboxylic acid;
1-cyclohexyl-2-[2-(4-methoxy-4'-nitro-biphen-2-yl)-quinolin-6-yl]-1H-benzoimidazole-5-carboxylic acid;
2-[2-(4'-aminomethyl-4-methoxy-biphen-2-yl)-quinolin-6-yl]-1-cyclohexyl-1H-benzoimidazole-5-carboxylic acid;
2-[2-(4'-chloro-biphen-2-yl)-quinolin-6-yl]1-cyclohexyl-1H-benzoimidazole-5-carboxylic acid;
2-(2-biphen-2-yl-7-fluoro-quinolin-6-yl)-1-cyclohexyl-1H-benzoimidazole-5-carboxylic acid;
2-(2-biphenyl-4-yl-quinolin-6-yl)-1-cyclohexyl-1H-benzoimidazole-5-carboxylic acid;
2-(2-biphen-2-yl-quinolin-6yl)-1-cyclohexyl-1H-benzoimidazole-5-carboxylic acid;
1-cyclohexyl-2-[2-(4'-dimethylamino-4-methoxy-biphen-2-yl)-quinolin-6-yl]1H-benzoimidazole-5-carboxylic acid;
1-cyclohexyl-2-[2-(3',4'-dichloro-4-methoxy-biphen-2-yl)-quinolin-6-yl]-1H-benzoimidazole-5-carboxylic acid;
2-[2-(4'-chloro-biphen-2-yl)-7-fluoro-quinolin-6-yl]-1-cyclohexyl-1H-benzoimidazole-5-carboxylic acid;
2-[2-(4-carboxy-4'-chloro-biphen-2-yl)-quinolin-6-yl]-1-cyclohexyl-1H-benzoimidazole-5-carboxylic acid;
2-[2-(4'-chloro-biphen-2-yl)-8-methyl-quinolin-6-yl]-1-cyclohexyl-1H-benzoimidazole-5-carboxylic acid;
1-cyclohexyl-2-{2-[3',4'-dimethoxy-4-(pyrrolidine-1-carbonyl)biphen-2-yl]quinolin-6-yl}-1H-benzimidazole-5-carboxylic acid;
1-cyclohexyl-2-[2-(4-methoxy-3'-nitro-biphen-2-yl)-quinolin-6-yl]-1H-benzoimidazole-5-carboxylic acid;
2-[2-(4'-carboxy-4-methoxy-biphen-2-yl)-quinolin-6-yl]-1-cyclohexyl-1H-benzoimidazole-5-carboxylic acid;
2-[2-(3'-chloro-4-methoxy-biphen-2-yl)-quinolin-6-yl]-1-cyclohexyl-1H-benzoimidazole-5-carboxylic acid;
1-cyclohexyl-2-[2-(4-morpholin-4-yl-phenyl)-quinolin-6-yl]-1H-benzoimidazole-5-carboxylic acid;
1-cyclohexyl-2-{2-[4-(3-pyrrolidin-1-yl-propoxy)-biphen-2-yl]-quinolin-6-yl}-1H-benzoimidazole-5-carboxylic acid;
1-cyclohexyl-2-{2-[4'-nitro-4-(pyrrolidine-1-carbonyl)biphen-2-yl]quinolin-6-yl}-1H-benzimidazole-5-carboxylic acid;
1-cyclohexyl-2-[2-(4-methoxy-4'-trifluoromethyl-biphen-2-yl)-quinolin-6-yl]-1H-benzoimidazole-5-carboxylic acid;
2-[2-(3'-carboxy-4-methoxy-biphen-2-yl)-quinolin-6-yl]-1-cyclohexyl-1H-benzoimidazole-5-carboxylic acid;
1-cyclohexyl-2-[2-(4-methoxy-4'-methyl-biphen-2-yl)-quinolin-6-yl]-1H-benzoimidazole-5-carboxylic acid;
2-[2-(4'-chloro-4-nitro-biphen-2-yl)-quinolin-6-yl]-1-cyclohexyl-1H-benzoimidazole-5-carboxylic acid;
2-[2-(4'-chloro-biphen-2-yl)-3-phenyl-quinolin-6-yl]-1-cyclohexyl-1H-benzoimidazole-5-carboxylic acid;
2-{2-[4'-chloro-4-(3-pyrrolidin-1-yl-propoxy)-biphen-2-yl]-quinolin-6-yl}-1-cyclohexyl-1H-benzoimidazole-5-carboxylic acid;
2-{2-[4'-carboxy-4-(pyrrolidine-1-carbonyl)biphen-2-yl]quinolin-6-yl}-1-cyclohexyl-1H-benzimidazole-5-carboxylic acid;
1-cyclohexyl-2-[2-(2-furan-2-yl-5-methoxy-phenyl)-quinolin-6-yl]-1H-benzoimidazole-5-carboxylic acid;
1-cyclohexyl-2-[2-(4'-fluoro-4-methoxy-biphen-2-yl)-quinolin-6-yl]1H-benzoimidazole-5-carboxylic acid;
1-cyclohexyl-2-[2-(4'-ethoxy-4-methoxy-biphen-2-yl)-quinolin.-6-yl]-1H-benzoimidazole-5-carboxylic acid;
1-cyclohexyl-2-{2-[4-(2-methoxy-ethoxy)-biphen-2-yl]-quinolin-6-yl}-1H-benzoimidazole-5-carboxylic acid;
1-cyclohexyl-2-[2-(4,4'-dimethoxy-biphen-2-ylquinolin-6-yl]-1H-benzoimidazole-5-carboxylic acid;
1-cyclohexyl-2-[2-(4'-hydroxy-4-methoxy-biphen-2-yl)-quinolin-6-yl]-1H-benzoimidazole-5-carboxylic acid;
1-cyclohexyl-2-[2-(5-methoxy-2-thiophen-2-yl-phenyl)-quinolin-6-yl]-1H-benzoimidazole-5-carboxyhc acid;
1-cyclohexyl-2-[2-(4-imidazol-1-yl-phenyl)-quinolin-6-yl]-1H-benzoimidazole-5-carboxylic acid;
2-{2-[4'-chloro-4-(2-methoxy-ethoxy)-biphen-2-yl]-quinolin-6-yl}-1-cyclohexyl-1H-benzoiinidazole-5-carboxylic acid;
2-[2-(4'-chloro-biphenyl-3-yl)-quinolin-6-yl]-1-cyclohexyl-1H-benzoimidazole-5-carboxylic acid;
1-cyclohexyl-2-{2-[2(2,4-dimethoxy-pyrimidin-5-yl)-5-methoxy-phenyl]-quinolin-6-yl}-1H-benzoimidazole-5-carboxylic acid;
2-[2-(4'-chloro-biphen-2-yl)-4-methyl-quinolin-6-yl]1-cyclohexyl-1H-benzoimidazole-5-carboxylic acid;
1-cyclohexyl-2-[2-(4-hydroxy-biphen-2-yl)-quinolin-6-yl]-1H-benzoimidazole-5-carboxylic acid;
1-cyclohexyl-2-[2-(4-piperazin-1-yl-phenyl)-quinolin-6-yl]-1H-benzoimidazole-5-carboxylic acid;
2-{2-[4'-chloro-4-(2-dimethylamino-ethylcarbamoyl)-biphen-2-yl]quinolin-6-yl}-1-cyclohexyl-1H-benzoimidazole-5-carboxylic acid;
1-cyclohexy-2-2-[2-(4-methoxy-biphen-2-yl)-quinolin-6-yl]-1H-benzoimidazole-5-carboxylic acid;
2-[2-(4'-chloro-4-hydroxy-biphen-2-yl)-quinolin-6-yl]-1-cyclohexyl-1H-benzoimidazole-5-carboxylic acid;
1-cyclohexyl-2-{2-[4-(2-dimethylamino-ethylcarbamoyl)-biphen-2-yl]-quinolin-6-yl}-1H-benzoimidazole-5-carboxylic acid;
2-{2-[4'-chloro-4-(2-ethoxy-ethoxy)-biphen-2-yl]-quinolin-6-yl}-1-cyclohexyl-1H-benzoimidazole-5-carboxylic acid;
2-[2-(4'-chloro-4-methoxy-biphen-2-yl)-quinolin-6-yl]-1-(4-methyl-cyclohexyl)-1H-benzoimidazole-5-carboxylic acid;
1-cyclohexyl-2-[2-(2'-fluoro-4-methoxy-biphen-2-yl)-quinolin-6-yl]1H-benzoimidazole-5-carboxylic acid;
1-cyclohexyl-2-[2-(2-cyclohexyl-5-methoxy-phenyl)-quinolin-6-yl]-1H-benzoimidazole-5-carboxylic acid;
2-[2-(4'-chloro-4-methoxy-biphen-2-yl)-quinolin-6-yl]-1-(4-methyl-cyclohexyl)-1H-benzoimidazole-5-carboxylic acid;
2-(2-biphenyl-4-yl-quinolin-6-yl)-1-cyclohexyl-1H-benzoimidazole-5-carboxylic acid;

1-cyclohexyl-2-{2-[4'-fluoro-4-(pyrrolidine-1-carbonyl)biphen-2-yl]quinolin-6-yl}-1H-benzimidazole-5-carboxylic acid;

1-cyclohexyl-2-[2-(4,2'-dimethoxy-biphen-2-yl)-quinolin-6-yl]-1H-benzoimidazole-5-carboxylic acid;

Ethyl 1-cyclohexyl-2-[2-(4'-fluoro-4-methoxy-biphen-2-yl)-quinolin-6-yl]1H-benzoimidazole-5-carboxylic acid;

2-[2-(4'-chloro-4-methoxy-biphen-2-yl)-quinolin-6-yl]1-(3,3,5-trimethyl-cyclohexyl)-1H-benzoimidazole-5-carboxylic acid;

2-[2-(4'-chloro-4-methoxy-biphen-2-yl)-quinolin-6-yl]-1-(2-methyl-cyclohexyl)-1H-benzoimidazole-5-carboxylic acid;

1-cyclohexyl-2-[2-(4'-ethyl-4-methoxy-biphen-2-yl]-1H-benzoimidazole-5-carboxylic acid;

1-cyclohexyl-2-[2-(3',4'-difluoro-4-methoxy-biphen-2-yl)-quinolin-6-yl]-1H-benzoimidazole-5-carboxylic acid;

1-cyclohexyl-2-{2-[4'-methoxy-4-(pyrrolidine-1-carbonyl)biphen-2-yl]quinolin-6-yl}-1H-benzimidazole-5-carboxylic acid;

1-cyclohexyl-2-[2-(3',5'-dichloro-4-methoxy-biphen-2-yl)-quinolin-6-yl]-1H-benzoimidazole-5-carboxylic acid;

2-[2-(4'-chloro-4-fluoro-biphen-2-yl)-quinolin-6-yl]-1-cyclohexyl-1H-benzoimidazole-5-carboxylic acid;

2-{2-[8-(4-chloro-phenyl)-3,4-dihydro-2H-benzo[b][1,4]dioxepin-7-yl]-quinolin-6-yl}-1-cyclohexyl-1H-benzoimidazole-5-carboxylic acid;

1-cyclohexyl-2-[2-(4,4'-dichloro-biphen-2-yl)-quinolin-6-yl]-1H-benzoimidazole-5-carboxylic acid;

1-bicyclo[2.2.1]hept-2-yl-2-[2-(4'-chloro-4-methoxy-biphen-2-yl)-qulnolin-6-yl]1H-benzoimidazole-5-carboxylic acid;

2-[2-(4-amino-4'-chloro-biphen-2-yl)-quinolin-6-yl]-1-cyclohexyl-1H-benzoimidazole-5-carboxylic acid;

2-[2-(4'-chloro-4-methoxy-biphen-2-yl)-quinolin-6-yl]-1-cyclopropyl-1H-benzoimidazole-5-carboxylic acid;

2-[2-(4'-chloro-4-methoxy-biphen-2-yl)-quinolin-6-yl]-1-cyclopentyl-1H-benzoimidazole-5-carboxylic acid;

1-cyclohexyl-2-(2-(4-methoxy-2'-methylbiphenyl-2-yl)-quinolin-6-yl)-1H-benzoimidazole-5-carboxylic acid; and 2-[2-(4-carbamoyl-5-hydroxy-4'-nitro-biphen-2-yl)-7-fluoro-quinolin-6-yl]-1-cyclohexyl-1H-benzoimidazole-5-carboxylic acid; and pharmaceutically acceptable tautomers or salts thereof.

11. A pharmaceutical composition comprising a pharmaceutically acceptable diluent and a therapeutically effective amount of a compound of any of claims 1, 2-9 and 10 or a mixture of two or more of such compounds.

* * * * *

UNITED STATES PATENT AND TRADEMARK OFFICE
CERTIFICATE OF CORRECTION

PATENT NO.       : 7,511,145 B2
APPLICATION NO.  : 10/909758
DATED            : March 31, 2009
INVENTOR(S)      : Franz Ulrich Schmitz et al.

It is certified that error appears in the above-identified patent and that said Letters Patent is hereby corrected as shown below:

Claim 1, at Column 385, Line 37, please replace "$A^1$ is selected from the group consisting of aryl, and sub-" with -- $Ar^1$ is selected from the group consisting of aryl, and sub- --.

Claim 1, at Column 385, Line 39, please replace "stituted arvl, cycloalkyl, substituted cvcloalkyl, het-" with -- stituted aryl, cycloalkyl, substituted cycloalkyl, het- --.

Claim 5, at Column 385, Line 58, please replace "4-(carbamoylmethy-carbamoyl)biphen-2-yl, 4-(carbamoyl-" with -- 4-(carbamoylmethyl-carbamoyl)biphen-2-yl, 4-(carbamoyl- --.

Claim 5, at Column 385, Line 59, please replace "methylcarbamoyl)-4'chlorobiphen-2-yl, 4-carboxy-4'-chlo-" with -- methylcarbamoyl)-4'-chlorobiphen-2-yl, 4-carboxy-4'-chlo- --.

Claim 5, at Column 385, Line 64-65, please replace "dimethylaminocthylcarbamoylbiphen-2-yl," with -- dimethylaminoethylcarbamoylbiphen-2-yl, --.

Claim 7, at Column 386, Line 43, please replace "2-(2,4-dimethoxypyrimidin-5-yl)4-" with -- 2-(2,4-dimethoxypyrimidin-5-yl)-4- --.

Claim 9, at Column 386, Line 51, please replace "Ar2 are selected from the group consisting of(4-piperazin-1-" with -- $Ar^2$ are selected from the group consisting of (4-piperazin-1- --.

Claim 10, at Column 386, Line 58, please replace "2-[2-(4'-chloro-4-methoxy-biphen-2-yl)quinolin-6-yl]1-" with -- 2-[2-(4'-chloro-4-methoxy-biphen-2-yl)-quinolin-6-yl]-1- --.

Claim 10, at Column 386, Line 66, please replace "1-cyclohexyl-2-[2-(4-methylcarbamoyl-biphen-2-yl)" with -- 1-cyclohexyl-2-[2-(4-methylcarbamoyl-biphen-2-yl)- --.

UNITED STATES PATENT AND TRADEMARK OFFICE
CERTIFICATE OF CORRECTION

PATENT NO. : 7,511,145 B2
APPLICATION NO. : 10/909758
DATED : March 31, 2009
INVENTOR(S) : Franz Ulrich Schmitz et al.

It is certified that error appears in the above-identified patent and that said Letters Patent is hereby corrected as shown below:

Claim 10, at Column 386, Line 67, please replace "quinolin-6-yl]1H-benzoimidazole-5-carboxylic acid;" with -- quinolin-6-yl]-1H-benzoimidazole-5-carboxylic acid; --.

Claim 10, at Column 387, Line 3, please replace "2-[2-(3'-chloro-4'-fluoro-4-methoxy-biphen-2yl)-quino-" with -- 2-[2-(3'-chloro-4'-fluoro-4-methoxy-biphen-2-yl)-quino- --.

Claim 10, at Column 387, Line 4, please replace "lin-6-yl]1-cyclohexyl-1H-benzoimidazole-5-carboxy-" with -- lin-6-yl]-1-cyclohexyl-1H-benzoimidazole-5-carboxylic acid; --.

Claim 10, at Column 387, Line 7, please replace "quinolin-6-yl]1H-benzoimidazole-5-carboxylic acid;" with -- quinolin-6-yl]-1H-benzoimidazole-5-carboxylic acid --.

Claim 10, at Column 387, Line 8, please replace "1-cyclohexyl-2[2-(2-pyridin-4-yl-phenyl)quinolin-6-y1]-" with -- 1-cyclohexyl-2-[2-(2-pyridin-4-yl-phenyl)-quinolin-6-yl]- --.

Claim 10, at Column 387, Line 18, please replace "lin-6-yl]1-cyclohexyl-1H-benzoimidazole-5-carboxy-" with -- lin-6-yl]-1-cyclohexyl-1H-benzoimidazole-5-carboxy- --.

Claim 10, at Column 387, Line 29, please replace "2-[2-(4'-chloro-biphen-2-yl)-quinolin-6-yl]1-cyclohexyl-" with -- 2-[2-(4'-chloro-biphen-2-yl)-quinolin-6-yl]-1-cyclohexyl- --.

Claim 10, at Column 387, Line 35, please replace "2-(2-biphen-2-yl-quinolin-6yl)-1-cyclohexyl-1H-ben-" with -- 2-(2-biphen-2-yl-quinolin-6-yl)-1-cyclohexyl-1H-ben- --.

UNITED STATES PATENT AND TRADEMARK OFFICE
CERTIFICATE OF CORRECTION

PATENT NO. : 7,511,145 B2
APPLICATION NO. : 10/909758
DATED : March 31, 2009
INVENTOR(S) : Franz Ulrich Schmitz et al.

It is certified that error appears in the above-identified patent and that said Letters Patent is hereby corrected as shown below:

Claim 10, at Column 387, Line 38, please replace "2-yl)-quinolin-6-yl]1H-benzoimidazole-5-carboxylic" with -- 2-yl)-quinolin-6-yl]-1H-benzoimidazole-5-carboxylic --.

Claim 10, at Column 388, Line 17, please replace "quinolin-6-yl]1H-benzoimidazole-5-carboxylic acid;" with -- quinolin-6-yl]-1H-benzoimidazole-5-carboxylic acid; --.

Claim 10, at Column 388, Line 19, please replace "quinolin.-6-yl]-1H-benzoimidazole-5-carboxylic acid;" with -- quinolin-6-yl]-1H-benzoimidazole-5-carboxylic acid; --.

Claim 10, at Column 388, Line 22, please replace "1-cyclohexyl-2-[2-(4,4'-dimethoxy-biphen-2-ylyquino-" with -- 1-cyclohexyl-2-[2-(4,4'-dimethoxy-biphen-2-yl)-quino- --.

Claim 10, at Column 388, Line 27, please replace "quinolin-6-yl]-1H-benzoimidazole-5-carboxyhc acid;" with -- quinolin-6-yl]-1H-benzoimidazole-5-carboxylic acid; --.

Claim 10, at Column 388, Line 31, please replace "quinolin-6-yl}-1-cyclohexyl-1H-benzoiinidazole-5-" with -- quinolin-6-yl}-1-cyclohexyl-1H-benzoimidazole-5- --.

Claim 10, at Column 388, Line 35, please replace "1-cyclohexyl-2-{2-[2(2,4-dimethoxy-pyrimidin-5-yl)-5-" with -- 1-cyclohexyl-2-{2-[2-(2,4-dimethoxy-pyrimidin-5-yl)-5- --.

Claim 10, at Column 388, Line 38, please replace "2-[2-(4'-chloro-biphen-2-yl)-4-methyl-quinolin-6-yl]1-" with -- 2-[2-(4'-chloro-biphen-2-yl)-4-methyl-quinolin-6-yl]-1- --.

Claim 10, at Column 388, Line 45, please replace "phen-2-yl]quinolin-6-yl}-1-cyclohexyl-1H-benzoimi-" with -- phen-2-yl]-quinolin-6-yl}-1-cyclohexyl-1H-benzoimi- --.

UNITED STATES PATENT AND TRADEMARK OFFICE
CERTIFICATE OF CORRECTION

PATENT NO. : 7,511,145 B2
APPLICATION NO. : 10/909758
DATED : March 31, 2009
INVENTOR(S) : Franz Ulrich Schmitz et al.

It is certified that error appears in the above-identified patent and that said Letters Patent is hereby corrected as shown below:

Claim 10, at Column 388, Line 47, please replace "1-cyclohexy-2-2-[2-(4-methoxy-biphen-2-yl)-quinolin-6-" with -- 1-cyclohexyl-2-[2-(4-methoxy-biphen-2-yl)-quinolin-6- --.

Claim 10, at Column 388, Line 60, please replace "quinolin-6-yl]1H-benzoimidazole-5-carboxylic acid;" with -- quinolin-6-yl]-1H-benzoimidazole-5-carboxylic acid; --.

Claim 10, at Column 389, Line 7, please replace "yl)-quinolin-6-yl]1H-benzoimidazole-5-carboxylic" with -- yl)-quinolin-6-yl]-1H-benzoimidazole-5-carboxylic --.

Claim 10, at Column 389, Line 9, please replace "2-[2-(4'-chloro-4-methoxy-biphen-2-yl)-quinolin-6-yl]1-" with -- 2-[2-(4'-chloro-4-methoxy-biphen-2-yl)-quinolin-6-yl]-1- --.

Claim 10, at Column 389, Line 14, please replace "1-cyclohexyl-2-[2-(4'-ethyl-4-methoxy-biphen-2-yl]-1H-" with -- 1-cyclohexyl-2-[2-(4'-ethyl-4-methoxy-biphen-2-yl)-quinolin-6-yl]-1H- --.

Claim 10, at Column 390, Line 7, please replace "phen-2-yl)-qulnolin-6-yl]1H-benzoimidazole-5-car-" with -- phen-2-yl)-quinolin-6-yl]1H-benzoimidazole-5-car- --.

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,511,145 B2 |
| APPLICATION NO. | : 10/909758 |
| DATED | : March 31, 2009 |
| INVENTOR(S) | : Franz Ulrich Schmitz |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by (497) days Delete the phrase "by 497 days" and insert -- by 1020 days --

Signed and Sealed this

Sixth Day of July, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggacatgga tccgcggggt cgggcacgag acag                              34
```

```
<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggctggca tgcactcaat gtcctacaca tggac                              35
```